US012570640B2

(12) United States Patent
Acton, III et al.

(10) Patent No.: US 12,570,640 B2
(45) Date of Patent: Mar. 10, 2026

(54) 2-AMINOQUINAZOLINES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: John J. Acton, III, Cranford, NJ (US); Ryan Chau, Somerville, MA (US); Peter H. Fuller, Ashland, MA (US); Anmol Gulati, Watertown, MA (US); Rebecca Elizabeth Johnson, Oakland, CA (US); Solomon Kattar, Wakefield, MA (US); Mitchell H. Keylor, Malden, MA (US); Derun Li, West Roxbury, MA (US); Kaila A. Margrey, Cambridge, MA (US); Gregori J. Morriello, Randolph, NJ (US); Xin Yan, Newton Highlands, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 457 days.

(21) Appl. No.: 18/041,849

(22) PCT Filed: Sep. 1, 2021

(86) PCT No.: PCT/US2021/048620

§ 371 (c)(1),
(2) Date: Feb. 16, 2023

(87) PCT Pub. No.: WO2022/051337

PCT Pub. Date: Mar. 10, 2022

(65) Prior Publication Data

US 2023/0303540 A1 Sep. 28, 2023

Related U.S. Application Data

(60) Provisional application No. 63/073,500, filed on Sep. 2, 2020.

(51) Int. Cl.

| | |
|---|---|
| *C07D 405/14* | (2006.01) |
| *C07D 403/12* | (2006.01) |
| *C07D 403/14* | (2006.01) |
| *C07D 417/14* | (2006.01) |
| *C07D 471/08* | (2006.01) |
| *C07D 487/04* | (2006.01) |
| *C07D 487/10* | (2006.01) |
| *C07D 491/107* | (2006.01) |
| *C07D 498/08* | (2006.01) |

(52) U.S. Cl.

CPC ......... *C07D 405/14* (2013.01); *C07D 403/12* (2013.01); *C07D 403/14* (2013.01); *C07D 417/14* (2013.01); *C07D 471/08* (2013.01); *C07D 487/04* (2013.01); *C07D 487/10* (2013.01); *C07D 491/107* (2013.01); *C07D 498/08* (2013.01)

(58) Field of Classification Search

CPC .. C07D 405/14; C07D 403/12; C07D 403/14; C07D 417/14; C07D 471/08; C07D 487/04; C07D 487/10; C07D 491/107; C07D 498/08

See application file for complete search history.

(56) References Cited

U.S. PATENT DOCUMENTS

| | | | |
|---|---|---|---|
| 2003/0073668 | A1 | 4/2003 | Booth et al. |
| 2010/0311965 | A1 | 12/2010 | Sawa et al. |

FOREIGN PATENT DOCUMENTS

| | | | |
|---|---|---|---|
| WO | 2007149798 | A2 | 12/2007 |
| WO | 2012044090 | A2 | 4/2012 |
| WO | 2014036015 | A1 | 3/2014 |
| WO | 2016036586 | A1 | 3/2016 |
| WO | 2020119606 | A1 | 6/2020 |

(Continued)

OTHER PUBLICATIONS

Ding, Xiao et al., Leucine-rich repeat kinase 2 inhibitors: a patent review (2014-present), Expert Opinion on Therapeutic Patents, 30:4, 275-286, 2020.

(Continued)

*Primary Examiner* — Brandon J Fetterolf

(74) *Attorney, Agent, or Firm* — Sylvia A. Ayler; Catherine Fitch

(57) ABSTRACT

The present invention is directed to certain 2-aminoquinzaoline derivatives of Formula (I): and pharmaceutically acceptable salts thereof, wherein $R^1$, $R^3$, $R^4$, $X^1$, and $X^2$ are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of such diseases in which LRRK-2 kinase is involved.

(I)

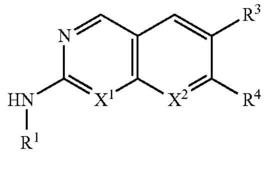

20 Claims, No Drawings

(56) References Cited

FOREIGN PATENT DOCUMENTS

| | | | |
|---|---|---|---|
| WO | 2020149925 | A1 | 7/2020 |
| WO | WO2021080929 | A1 * | 4/2021 |

OTHER PUBLICATIONS

Aasly, J.O. et al., Clinical Features of LRRK2-Associated Parkinson's Disease in Central Norway, Ann Neurol, 2005, 762-765, 57(5).

Adams, J.R. et al., PET in LRRK2 mutations: comparison to sporadic Parkinson's disease and evidence for presymptomatic compensation, Brain, 2005, 2777-2785, 128.

Agalliu, I. et al., Higher Frequency of Certain Cancers in LRRK2 G2019S Mutation Carriers With Parkinson Disease, JAMA Neurology, 2015, 58-65, 72(1).

Bailey, R.M. et al., LRRK2 phosphorylates novel tau epitopes and promotes tauopathy, Acta Neuropathol, 2013, 809-827, 126.

Bingham, A.L., et al.,, "Over One Hundred Solvates of sulfathiazole", Chem. Commun., 2001, pp. 603-604.

Caira, M.R., et al.,, "Preparation and Crystal Characterization of a Polymorph, a Monohydrate, and an Ethyl Acetate Solvate of the Antifungal Fluconazole", J. Pharmaceutical Sci., 2004, pp. 601-611, vol. 93, No. 3.

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1q32 and STAT3 with Ankylosing Spondylitis Suggests Genetic Overlap with Crohn's Disease, PLoS Genetics, 2010, 1-5, 6(12):e1001195.

Engel, P. et al., Therapeutic Targeting of B Cells for Rheumatic Autoimmune Diseases, Pharmacological Reviews, 2011, 127-156, 63(1).

Gilks, W.P. et al., A common LRRK2 mutation in idiopathic Parkinson's disease, Lancet, 2005, 415-416, 365.

Goedert, M. et al., Mutations causing neurodegenerative tauopathies, Biochimica et Biophysica Acta, 2005, 240-250, 1739.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS One, 2012, 1-9, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G Bac transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Pubmed Compound Record for CID 123649375, '[[4-(4-Methoxy-6-methylcyclohexa-2,4-dien-1-yl)pyrrolidin-3-ylidene] amino]-[3-[(2-methyl pyrazol-3-yl)aminolisoquinolin-6-yl]-oxoazanium', U.S. National Library of Medicine, Jan. 25, 2017 (Jan. 25, 2017), pp. 1-7 (https://pubchem.ncbi.nlm.nih.gov/compound/123649375); p2 (7 pages).

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. 1, Article 12, US.

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, 2006, 1-9, 1:17.

Zimprich, A. et al., Mutations in LRRK2 Cause Autosomal-Dominant Parkinsonism with Pleomorphic Pathology, Neuron, 2004, 601-607, 44(4).

* cited by examiner

2-AMINOQUINAZOLINES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2021/048620 filed Sep. 1, 2021, which claims priority from U.S. 63/073,500, filed Sep. 2, 2020.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5): 1602-11). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscluar disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain 2-aminoquinzaoline derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of Formula (I), each of which possess a 2-aminoquinzaoline moiety, the amino substituent attached to a carbon atom of a five-member heteroaryl group selected from pyrazolyl and thiazolyl, exhibit excellent LRRK2 inhibitory activity. In some embodiments, the compounds of the invention exhibit unexpectedly superior potency as inhibitors of LRRK2 kinase, as evidenced by the data reported herein. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

(I)

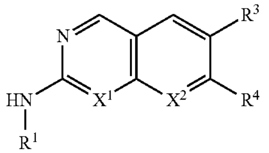

or a pharmaceutically acceptable salt thereof, wherein:

$X^1$ is N or CH;

$X^2$ is N or $CR^2$;

$R^1$ is selected from:

(i)

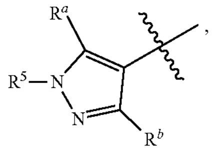

-continued (ii)

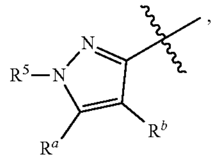

(iii)

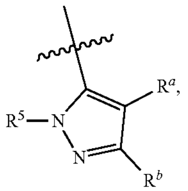

(iv)

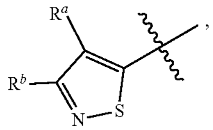

(v)

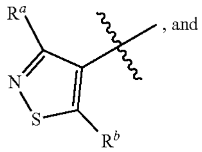

, and (vi)

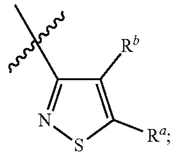

$R^2$ is absent or is selected from H, $C_{1-6}$ alkyl, and Cl, $R^3$ is selected from H, Cl, CN, and $C_{1-6}$ alkyl;

$R^4$ represents NRR', or an N-linked $C_{4-10}$ heterocyclyl, said heterocyclyl optionally substituted with 1 to 3 groups of $R^d$;

each R represents H, or $C_{1-6}$ alkyl;

R' is selected from H, $C_{1-6}$ alkyl, $C_{3-6}$ cycloalkyl, and $C_{4-10}$ heterocyclyl, said alkyl, cycloalkyl and heterocyclyl optionally substituted with 1 to 3 groups of $R^e$;

$R^5$ is selected from hydrogen, $C_{1-6}$ alkyl, $C_{1-6}$ alkylOR, $C_{1-3}$ haloalkyl, $-(CH_2)_nC_{4-10}$ heterocyclyl, $-(CH_2)_nC_{3-10}$cycloalkyl, $-(CH_2)_nC_{5-10}$ heteroaryl, said alkyl, cycloalkyl, heteroaryl, and heterocyclyl optionally substituted with 1 to 3 groups of $R^c$;

$R^a$ and $R^b$ are independently selected from hydrogen, halogen, $C_{1-6}$ alkyl, $C_{1-3}$ haloalkyl, $-(CH_2)_nC_{5-10}$ heteroaryl, and $C_{3-6}$cycloalkyl, provided $R^a$ and $R^b$ are not the same when $R^1$; or $R^5$ and $R^a$ in (i) and (ii) of $R^1$ can combine with the nitrogen and carbon atoms to which they are attached, respectively, to form a five or six membered ring;

$R^c$ is selected from OR, halogen, $(CH_2)_nCN$, $C_{1-3}$ haloalkyl, $C_{1-6}$ alkyl, $C_{1-6}$ alkylOR, $C_{1-3}$ haloalkyl, and $C_{4-10}$ heterocyclyl, said alkyl and heterocyclyl optionally substituted with 1 to 3 groups of $C_{1-6}$ alkyl or CN;

$R^d$ is selected from oxo, OR, $C_{1-6}$ alkyl, $C_{1-6}$ alkylOR, $CH_2CF_3$, $C_{4-10}$ heterocyclyl, $-(CH_2)_nC_{3-10}$cycloalkyl, $C(O)C_{1-6}$ alkyl, and NRR, said alkyl, heterocyclyl and cycloalkyl optionally substituted with 1 to 3 groups of $R^e$;

$R^e$ is selected from OR, $C_{1-6}$ alkyl, CN, and fluorine; and

Each n is independently 1, 2, 3, or 4.

An embodiment of this invention is realized when $X^1$ is CH. A subembodiment of this aspect of the invention is realized when $X^1$ is CH and $X^2$ is C—$R^2$.

Another embodiment of this invention is realized when $X^1$ is N. A subembodiment of this aspect of the invention is realized when $X^1$ is N, $X^2$ is C—$R^2$.

An embodiment of this invention is realized when $X^2$ is N. A subembodiment of this aspect of the invention is realized when $X^1$ is N, and $X^2$ is N. Another subembodiment of this aspect of the invention is realized when $X^1$ is CH, $X^2$ is N.

Another embodiment of this invention is realized when R' is selected H. Another embodiment of this invention is realized when R' is optionally substituted $C_{1-6}$ alkyl. Another embodiment of this invention is realized when R' is optionally substituted cycloalkyl. Another embodiment of this invention is realized when R' is optionally substituted $C_{4-10}$ heterocyclyl.

Another embodiment of this invention is realized when $R^1$ is structural formula (i).

Another embodiment of this invention is realized when $R^1$ is structural formula (ii).

Another embodiment of this invention is realized when $R^1$ is structural formula (iii).

Another embodiment of this invention is realized when $R^1$ is structural formula (iv).

Another embodiment of this invention is realized when $R^1$ is structural formula (v).

Another embodiment of this invention is realized when $R^1$ is structural formula (vi).

Another embodiment of this invention is realized when adjacent $R^5$ and $R^a$ in (i) and (ii) of $R^1$ is combined with the nitrogen and carbon atoms to which they are attached, respectively, to form a five or six membered ring. An example of this aspect of the invention is realized when adjacent $R^5$ and $R^a$ combine and are represented by structural formula (vii) and (viii):

(vii)

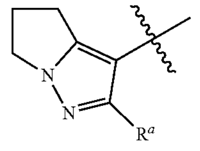

(viii)

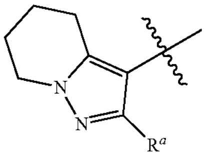

Yet another embodiment of this invention is realized when $R^5$ of $R^1$ is selected from the group consisting of $CH_3$, $CD_3$, $CH_2CH_3$, $CH_2CHF_2$, $(CH_2)_2F$, $CH_2CF_3$, $CHF_2$, $(CH_2)_nC(CH_3)_3$, $CH_2C(CH_3)_2OH$, $CH_2CH(OH)CH_2C(CH_3)_2OH$, $C(CH_3)_2CN$, $(CH_2)_2CN$, $(CH_2)_n$cyclopropyl, $(CH_2)_n$cyclobutyl, $(CH_2)_n$cyclopentyl, $(CH_2)_n$cyclohexyl, $(CH_2)_n$oxetanyl, azetidinyl, piperazinyl, piperidinyl, oxanyl, bicyclopentanyl, dihydropyrrolopyrazolo, azaspiroheptanyl, and tetrahydropyrazolopyridinyl, said cyclopropyl, cyclobutyl, cyclopentyl, cyclohexyl, oxetanyl, azetidinyl, piperazinyl, piperidinyl, oxanyl, bicyclopentanyl, dihydropyrrolopyrazolo, azaspiroheptanyl, and tetrahydropyrazolopyridinyl optionally substituted with 1 to 3 groups of $R^c$. A subembodiment of this aspect of the invention is realized when $R^5$ of $R^1$ is selected from $CH_3$, $CH_2CH_3$, $(CH_2)_2F$, $CH_2CF_3$, $CHF_2$, $CH_2C(CH_3)_2OH$, $(CH_2)_n$cyclopropyl, $(CH_2)_n$oxetanyl, piperazinyl, piperidinyl, and bicyclopentanyl, said cyclopropyl, oxetanyl, piperazinyl, piperidinyl, and bicyclopentanyl optionally substituted with 1 to 3 groups of $R^c$. Yet another subembodiment of this aspect of the invention is realized when $R^5$ of $R^1$ is $CH_3$, $CH_2CH_3$ or $CH_2C(CH_3)_2OH$. Another subembodiment of this aspect of the invention is realized when $R^5$ of $R^1$ is $(CH_2)_2F$, $CH_2CF_3$, or $CHF_2$. Another subembodiment of this aspect of the invention is realized when $R^5$ of $R^1$ is optionally substituted $(CH_2)_n$cyclopropyl. Another subembodiment of this aspect of the invention is realized when $R^5$ of $R^1$ is optionally substituted $(CH_2)_n$oxetanyl. Another subembodiment of this aspect of the invention is realized when $R^5$ of $R^1$ is optionally substituted piperazinyl. Another subembodiment of this aspect of the invention is realized when $R^5$ of $R^1$ is optionally substituted piperidinyl. Another subembodiment of this aspect of the invention is realized when $R^5$ of $R^1$ is optionally substituted bicyclopentanyl. Still another subembodiment of this aspect of the invention is realized when the substituent $R^c$ is selected from methyl, $CF_3$, $CH_2OCH_3$, $CH_2(CH_3)OH$, fluorine, oxetanyl, said oxetanyl optionally substituted with 1 to 3 groups of $C_{1-6}$ alkyl, fluorine, or CN.

Another embodiment of this invention is realized when $R^2$ is hydrogen.

Another embodiment of this invention is realized when $R^2$ is $C_{1-6}$ alkyl. A subembodiment of this aspect of the invention is realized when $R^2$ is methyl.

Another embodiment of this invention is realized when $R^2$ is chlorine.

Another embodiment of this invention is realized when $X^2$ is C. A subembodiment of this aspect of the invention is realized when $X^2$ is C and $R^2$ is hydrogen.

Another embodiment of this invention is realized when $R^3$ is chlorine.

Another embodiment of this invention is realized when $R^3$ is fluorine.

Another embodiment of this invention is realized when $R^3$ is bromine.

Another embodiment of this invention is realized when $R^3$ is H.

Another embodiment of this invention is realized when $R^4$ is an N-linked $C_{4-10}$ heterocyclyl. A subembodiment of this aspect of the invention is realized when $R^4$ is selected from the group consisting of optionally substituted N-linked piperazinyl, piperidinyl, pyrrolidinyl, azetidinyl, diazaspirononanyl, azabicyclohexanyl, dihydrotriazolopyrazinyl, diazabicycloheptanyl, azabicycloheptanyl, azabicyclooctanyl, oxaazabicyclooctanyl, octahydropyrrolopyridinyl, oxazolidinonyl, oxa-azaspirodecanyl, azaspirodecanonyl, azabicycloheptanonyl, azaspiroheptanyl, diazaspiroheptanyl, tetrahydropyrazolopyridinyl, and azabicycloheptanonyl. A subembodiment of this aspect of the invention is realized when $R^4$ is selected from the group consisting of optionally substituted N-linked piperazinyl, piperidinyl, pyrrolidinyl, oxazolidinonyl, azabicycloheptanonyl, azaspiroheptanyl, azabicycloheptanyl, azabicyclooctanyl, and azaspirodecanyl. A subembodiment of this aspect of the invention is realized when $R^4$ is substituted with 1 to 3 groups of $R^d$. Another subembodiment of this aspect of the invention is realized when $R^d$ is selected from $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl optionally substituted with 1 to 3 groups of $R^e$. Another subembodiment of this aspect of the invention is realized when $R^e$ is selected from $C_{1-6}$ alkyl, OH, $OCH_3$, CN, and fluorine.

Another embodiment of this invention is realized when $R^4$ is optionally substituted piperazinyl. A subembodiment of this aspect of the invention is realized when the piperazinyl is represented as (a):

(a)

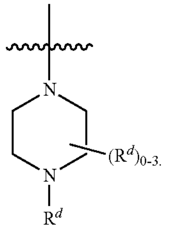

Another embodiment of this invention is realized when $R^4$ is optionally substituted piperidinyl. A subembodiment of this aspect of the invention is realized when the piperidinyl is represented as (b):

(b)

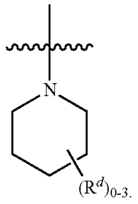

Another embodiment of this invention is realized when $R^4$ is optionally substituted pyrrolidinyl. A subembodiment of this aspect of the invention is realized when the pyrrolodinyl is represented as (c)

(c)

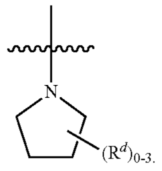

Another embodiment of this invention is realized when $R^4$ is optionally substituted azetidinyl. A subembodiment of this aspect of the invention is realized when the azetidinyl is represented as (d)

(d)

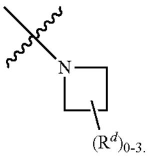

Another embodiment of this invention is realized when $R^4$ is optionally substituted diazaspirononanyl. A subembodiment of this aspect of the invention is realized when the diazaspirononanyl is represented as (e)

(e)

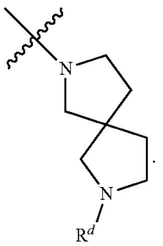

Another embodiment of this invention is realized when $R^4$ is optionally substituted oxa-azaspirononanyl. A subembodiment of this aspect of the invention is realized when the oxa-azaspirononanyl is represented as (f):

(f)

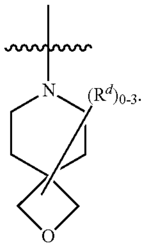

Another embodiment of this invention is realized when $R^4$ is optionally substituted azabicyclohexanyl. A subembodiment of this aspect of the invention is realized when the azabicyclohexanyl is represented as (g):

(g)

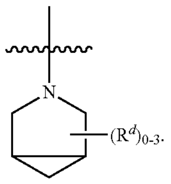

Another embodiment of this invention is realized when $R^4$ is optionally substituted dihydrotriazolopyrazinyl. A subembodiment of this aspect of the invention is realized when the dihydrotriazolopyrazinyl is represented as (h):

(h)

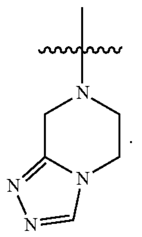

Another embodiment of this invention is realized when $R^4$ is optionally substituted diazabicycloheptanyl. A subembodiment of this aspect of the invention is realized when the diazabicycloheptanyl is represented as (i):

(i)

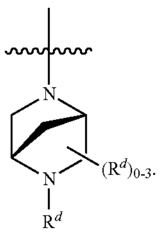

Another embodiment of this invention is realized when $R^4$ is optionally substituted azabicycloheptanyl. A subembodiment of this aspect of the invention is realized when the azabicycloheptanyl is represented as (j):

(j)

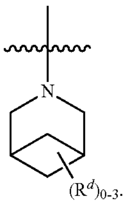

Another embodiment of this invention is realized when $R^4$ is optionally substituted azabicyclooctanyl. A subembodiment of this aspect of the invention is realized when the azabicyclooctanyl is represented as (k):

(k)

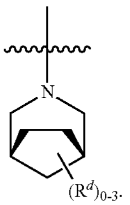

Another embodiment of this invention is realized when $R^4$ is optionally substituted oxa-azabicyclooctanyl. A subembodiment of this aspect of the invention is realized when the oxa-azabicyclooctanyl is represented as (l):

(l)

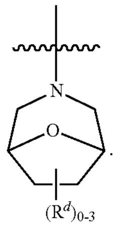

Another embodiment of this invention is realized when $R^4$ is optionally substituted octahydropyrrolopyridinyl. A subembodiment of this aspect of the invention is realized when the octahydropyrrolopyridinyl is represented as (m):

(m)

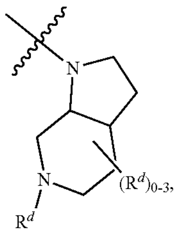

Another embodiment of this invention is realized when $R^4$ is optionally substituted oxazolidinonyl. A subembodiment of this aspect of the invention is realized when the oxazolidinonyl is represented as (n):

(n)

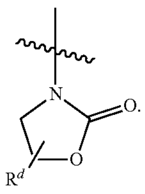

Another embodiment of this invention is realized when $R^4$ is optionally substituted oxa-azaspirodecanyl. A subembodiment of this aspect of the invention is realized when the azaspirodecanyl is represented as (o) and (o'):

(o)

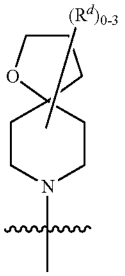

and (o')

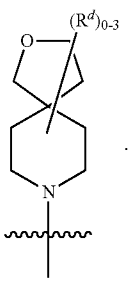

Another embodiment of this invention is realized when $R^4$ is optionally substituted tetrahydropyrazolopyridinyl. A subembodiment of this aspect of the invention is realized when the tetrahydropyrazolopyridinyl is represented as (p):

(p)

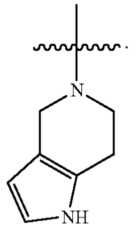

Another embodiment of this invention is realized when $R^4$ is optionally substituted azabicycloheptanonyl. A subembodiment of this aspect of the invention is realized when the azabicycloheptanonyl is represented as (q):

(q)

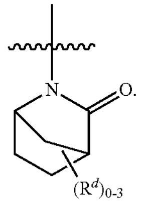

Another embodiment of this invention is realized when $R^4$ is optionally substituted azaspiroheptanyl. A subembodiment of this aspect of the invention is realized when the azaspiroheptany is represented as (r):

(r)

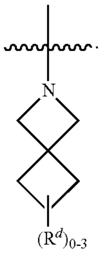

Another embodiment of this invention is realized when $R^4$ is optionally substituted diazaspiroheptanyl. A subembodiment of this aspect of the invention is realized when the diazaspiroheptanyl is represented as (s):

(s)

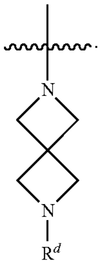

Still another embodiment of this invention is realized when $R^4$ represents NRR. Still another embodiment of this invention is realized when $R^4$ represents NRR provided R and R' are not both hydrogen. A subembodiment of this aspect of this invention is realized when NRR' is selected from $N(CH_3)_2$, $NHCH_3$, $NHCH_2CH_3$, $NHCH(CH_3)_2$, $NHCH_2$cyclopropyl, and $N(CH_3)$oxetanyl.

N. Another subembodiment of the invention of Formula II is realized when $R^3$ is chlorine. Another subembodiment of the invention of Formula II is realized when $R^3$ is hydrogen. A subembodiment of the invention of Formula II is realized when $R^4$. is selected from the group consisting of a1

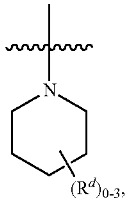

a2

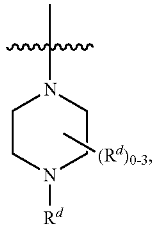

a3

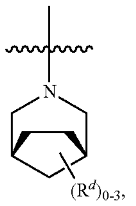

a4

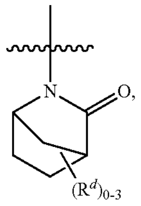

a5

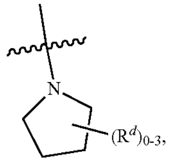

a6

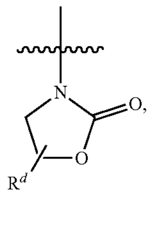

and

-continued a7

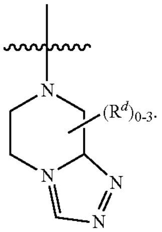

A subembodiment of the invention Formula II is realized when $R^4$ is substituted with 0 to 3 groups of $R^d$ selected from $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl optionally substituted with 1 to 3 groups of $R^e$ selected from $C_{1-6}$ alkyl, OH, $OCH_3$, CN, and fluorine. A subembodiment of the invention of Formula II is realized when $R^5$ is selected from the group consisting of $CH_3$, $CH_2CH_3$, $(CH_2)_2F$, $CH_2CF_3$, $CHF_2$, $CH_2C(CH_3)_2OH$, $(CH_2)_n$cyclopropyl, $(CH_2)_n$oxetanyl, piperazinyl, piperidinyl, and bicyclopentanyl, said cyclopropyl, oxetanyl, piperazinyl, piperidinyl, and bicyclopentanyl optionally substituted with 1 to 3 groups of $R^c$. Another subembodiment of the invention of Formula II is realized when the substituent $R^c$ is selected from methyl, $CF_3$, $CH_2OCH_3$, $CH_2(CH_3)OH$, fluorine, oxetanyl, said oxetanyl optionally substituted with 1 to 3 groups of $C_{1-6}$ alkyl, fluorine, or CN. A subembodiment of the invention of formula II is realized when $R^4$ is a1. Another subembodiment of the invention of Formula II is realized when $R^4$ is a2. A subembodiment of the invention of formula II is realized when $R^4$ is a3. A subembodiment of the invention of formula II is realized when $R^4$ is a4. A subembodiment of the invention of formula II is realized when $R^4$ is a5. A subembodiment of the invention of formula II is realized when $R^4$ is a6. A subembodiment of the invention of formula II is realized when $R^4$ is a7.

Another embodiment of this invention is represented by structural Formula III:

Formula III

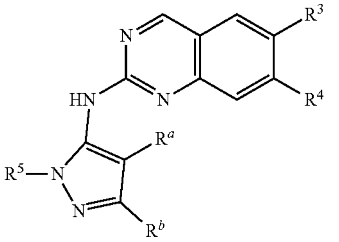

or a pharmaceutically acceptable salt thereof, wherein $R^a$, $R^b$, $R^3$, $R^4$ and $R^5$ are as described herein. A subembodiment of the invention of Formula III is realized when $R^a$ and $R^b$ are independently selected from hydrogen, chlorine, methyl, $CF_3$, $CHF_2$, and cyclopropyl. Another subembodiment of the invention of Formula III is realized when $R^3$ is $CH_3$, chlorine, hydrogen, and CN. Another subembodiment of the invention of Formula III is realized when $R^3$ is chlorine. Another subembodiment of the invention of Formula III is realized when $R^3$ is hydrogen. A subembodiment of the invention of Formula III is realized when $R^4$. is selected from the group consisting of a1

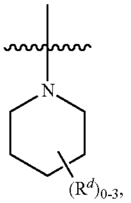

a2

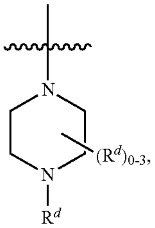

a3

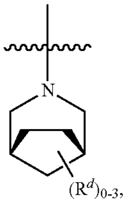

a4

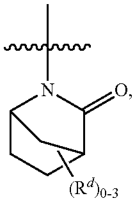

a5

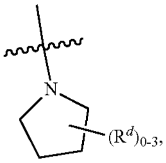

a6

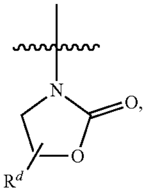

and a7

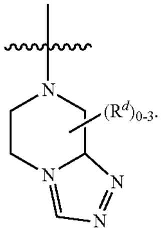

A subembodiment of the invention Formula II is realized when $R^4$ is substituted with 0 to 3 groups of $R^d$ selected from $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl optionally substituted with 1 to 3 groups of $R^e$ selected from $C_{1-6}$ alkyl, OH, $OCH_3$, CN, and fluorine. A subembodiment of the invention of Formula III is realized when $R^5$ is selected from the group consisting of $CH_3$, $CH_2CH_3$, $(CH_2)_2F$, $CH_2CF_3$, $CHF_2$, $CH_2C(CH_3)_2OH$, $(CH_2)_n$cyclopropyl, $(CH_2)_n$oxetanyl, piperazinyl, piperidinyl, and bicyclopentanyl, said cyclopropyl, oxetanyl, piperazinyl, piperidinyl, and bicyclopentanyl optionally substituted with 1 to 3 groups of R'. Another subembodiment of the invention of Formula III is realized when the substituent R' is selected from methyl, $CF_3$, $CH_2OCH_3$, $CH_2(CH_3)OH$, fluorine, oxetanyl, said oxetanyl optionally substituted with 1 to 3 groups of $C_{1-6}$ alkyl, fluorine, or CN. A subembodiment of the invention of formula III is realized when $R^4$ is a1. Another subembodiment of the invention of Formula III is realized when $R^4$ is a2. A subembodiment of the invention of formula III is realized when $R^4$ is a3. A subembodiment of the invention of formula III is realized when $R^4$ is a4. A subembodiment of the invention of formula III is realized when $R^4$ is a5. A subembodiment of the invention of formula III is realized when $R^4$ is a6. A subembodiment of the invention of formula III is realized when $R^4$ is a7.

Another embodiment of this invention is represented by structural Formula IV:

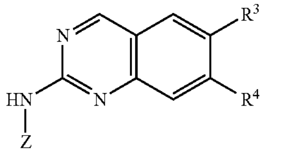

Z is

Formula IV (v)

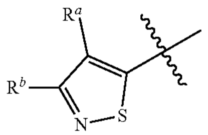

(vi)

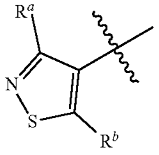

or (vii)

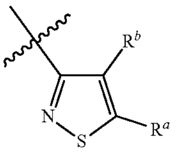

or a pharmaceutically acceptable salt thereof, wherein $R^a$, $R^b$, $R^3$, and $R^4$ are as described herein. A subembodiment of the invention of Formula IV is realized when $R^a$ and $R^b$ are independently selected from hydrogen, chlorine, methyl, $CF_3$, $CHF_2$, and cyclopropyl. Another subembodiment of the invention of Formula IV is realized when $R^3$ is $CH_3$, chlorine, hydrogen, and CN. Another subembodiment of the invention of Formula IV is realized when $R^3$ is chlorine. Another subembodiment of the invention of Formula IV is realized when $R^3$ is hydrogen. A subembodiment of the invention of Formula IV is realized when $R^4$ is selected from the group consisting of a1

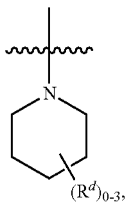

a2

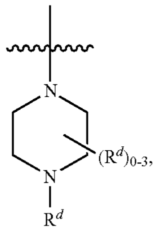

a3

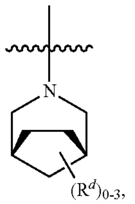

a4

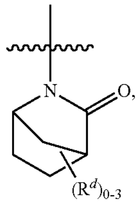

a5

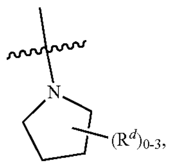

a6

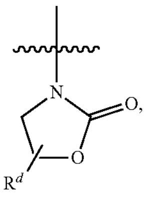

and

-continued a7

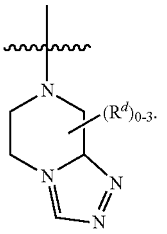

A subembodiment of the invention Formula IV is realized when $R^4$ is substituted with 1 to 3 groups of $R^d$ selected from $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl optionally substituted with 1 to 3 groups of $R^e$ selected from $C_{1-6}$ alkyl, OH, $OCH_3$, CN, and fluorine. A subembodiment of the invention of formula IV is realized when $R^4$ is a1. Another subembodiment of the invention of Formula IV is realized when $R^4$ is a2. A subembodiment of the invention of formula IV is realized when $R^4$ is a3. A subembodiment of the invention of formula IV is realized when $R^4$ is a4. A subembodiment of the invention of formula IV is realized when $R^4$ is a5. A subembodiment of the invention of formula IV is realized when $R^4$ is a6. A subembodiment of the invention of formula IV is realized when $R^4$ is a7.

In another embodiment, the compounds of the invention have the structural Formula V:

V

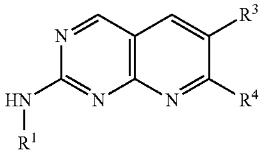

or a pharmaceutically acceptable salt thereof, wherein $R^1$, $R^3$, and $R^4$ are as defined herein. Another subembodiment of the invention of Formula V is realized when $R^3$ is $CH_3$, chlorine, hydrogen, and CN. Another subembodiment of the invention of Formula V is realized when $R^3$ is chlorine. Another subembodiment of the invention of Formula V is realized when $R^3$ is hydrogen. A subembodiment of the invention of Formula V is realized when $R^4$. is selected from the group consisting of a1

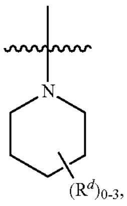

-continued a2

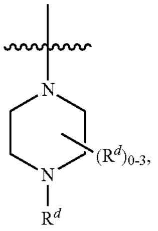

a3

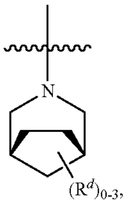

a4

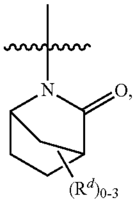

a5

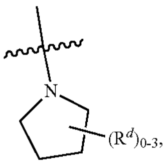

a6

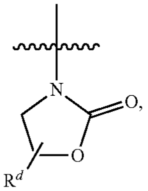

and a7

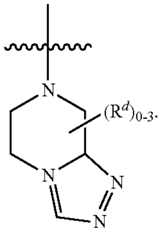

A subembodiment of the invention Formula V is realized when $R^4$ is substituted with 0 to 3 groups of $R^d$ selected from $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl optionally substituted with 1 to 3 groups of $R^e$ selected from $C_{1-6}$ alkyl, OH, $OCH_3$, CN, and fluorine. A subembodiment of the invention of formula V is realized when $R^4$ is a1. Another subembodiment of the invention of Formula V is realized when $R^4$ is a2. A subembodiment of the invention of formula V is realized when $R^4$ is a3. A subembodiment of the invention of formula V is realized when $R^4$ is a4. A subembodiment of the invention of formula V is realized when $R^4$ is a5. A subembodiment of the invention of formula V is realized when $R^4$ is a6. A subembodiment of the invention of formula V is realized when $R^4$ is a7.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

DETAILED DESCRIPTION OF THE INVENTION

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formulae I, II, III, IV, and V, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulae I, II, III, IV, and V. For example, different isotopic forms of hydrogen (H) include protium (H) and deuterium (H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulae I, II, III, IV, and V can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $—CH_2C(O)—$ groups (keto forms) may undergo tautomerism to form hydroxyl $—CH{=}C(OH)—$ groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the methyl group is emerging from the plane of the paper and the ethyl group is descending into the plane of the paper with the cyclohexene ring in the plane of the paper.

Illus-I

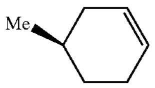

Illus-2

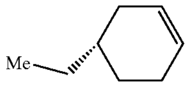

Illus-3

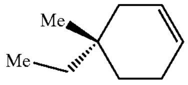

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents appended to a compound substrate, for example, a halogen or a moiety appended to a portion of a structure replacing a hydrogen, means that one substituent of the group of substituents specified is present, and more than one of said substituents may be bonded to any of the defined or chemically accessible bonding points of the substrate.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula I, Formula II, Formula III, Formula IV, or Formula V that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula I through Formula VI to a compound of Formula I, Formula II, Formula III, Formula IV, or Formula V or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

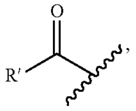

equally, with no differentiation implied using any or all of these representations;

"alkyl" (including the alkyl portions of other moieties, such as trifluoromethyl-alkyl- and alkoxy-) means a straight or branched aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "cycloalkyl" means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term "cycloalkyl" also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamantly; and the like;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

where a structural formula represents bonding between a moiety and a substrate using a the bonding line that terminates in the middle of the structure, for example the following representations:

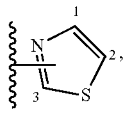 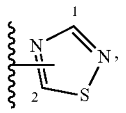 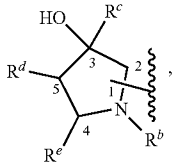

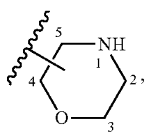 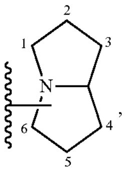

whether or not numbered the structure indicates that unless otherwise defined the moiety may be bonded to the substrate through any of available ring atom, for example, the numbered atoms of the example moieties;

"heterocyclyl" (or heterocycloalkyl) means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain 5 to 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected substituents;

the nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl

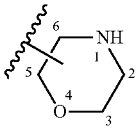

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

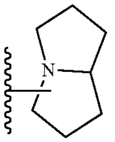 and 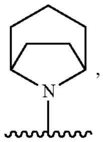, and the like.

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means $—CF_3$;

"hydroxyl" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

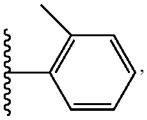, indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, J Pharmaceutical Sci., 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, AAPS PharmSciTech., 5(11, article 12 (2004); and A. L. Bingham et al, Chem. Commun., 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula I, Formula II, Formula III, Formula IV, and Formula V and of the salts, solvates and prodrugs of the compounds of Formula I, Formula II, Formula III, Formula IV, or Formula V, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

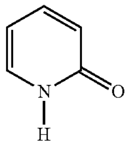 and 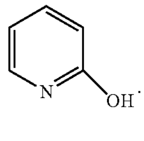.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of Formula I, Formula II, Formula III, Formula IV, and Formula V, or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I, Formula II, Formula III, Formula IV, or Formula V is used contemporaneously with one or more other drugs, a pharmaceutical composition in unit dosage form containing such other drugs and the compound of Formula I, Formula II, Formula III, Formula IV, or Formula V is preferred. However, the combination therapy may also include therapies in which the compound of Formula I, Formula II, Formula III, Formula IV, or Formula V, and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I, Formula II, Formula III, Formula IV, or Formula V.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or acetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above-mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

Preparative Examples

The compounds of the present invention can be prepared according to the following schemes and specific examples, or modifications thereof, using readily available starting materials, reagents and conventional synthesis procedures. It is also possible to make use of variants which are themselves known to those of ordinary skill in this art but are not mentioned in detail. The general procedures for making the compounds claimed in this invention can be readily understood by one skilled in the art from viewing the following schemes and descriptions. Abbreviations used in the experimental may include, but are not limited to the following:

| | |
|---|---|
| 2-MeTHF | 2-Methyltetrahydrofuran |
| AcOH | Acetic Acid |
| Aq. | Aqueous |
| $BH_3$—$Me_2S$ | Borane dimethylsulfide |
| BHT | 3,5-Di-tert-4-butylhydroxytoluene |
| BINAP | (2,2'-bis(diphenylphosphino)-1,1'-binaphthyl) |
| BrettPhos Pd G3 | BrettPhos-Pd-G3,[(2-Di-cyclohexylphosphino-3,6-dimethoxy-2',4',6'-triisopropyl-1,1'-biphenyl)-2-(2'-amino-1,1'-biphenyl)]palladium(II) methanesulfonate 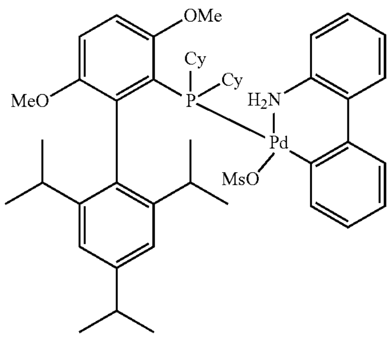 |
| BTMG | 2-tert-Butyl-1,1,3,3-tetramethylguanidine |
| CataCXium ® A Pd G3 | [Di(1-adamantyl)-butylphosphine)-2-(2'-amino-1,1'-biphenyl)]palladium(II) methanesulfonate |

-continued

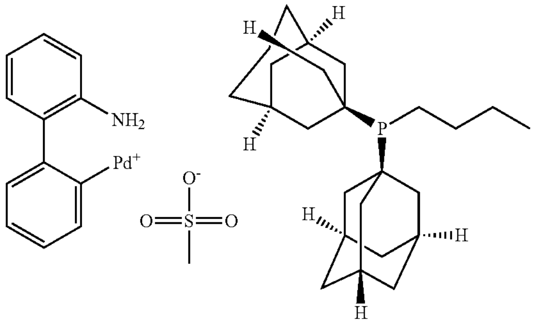

| | |
|---|---|
| $C_2Cl_6$ | Hexachloroethane |
| Cy | Cyclohexyl |
| DAST | Diethylaminosulfur trifluoride |
| DCE | Dichloroethane |
| DCM | Dichloromethane |
| DIAD | Diisopropyl azodicarboxylate |
| DIBAL-H | Diisobutylaluminum hydride |
| DIPEA | N,N-Diisopropylethylamine |
| DMA | Dimethylacetamide |
| DMAP | 4-Dimethylaminopyridine |
| DMCDA | trans-N,N'-dimethylcyclohexane-1,2-diamine |
| DMF | Dimethylformamide |
| DMP | Dess-Martin periodinane |
| DMSO | Dimethyl sulfoxide |
| DPPF Pd G3 | Methanesulfonato 1,1-ferrocenediyl-bis(diphenylphosphino) (2'-amino-1,1'-biphenyl-2-yl)palladium(II) |

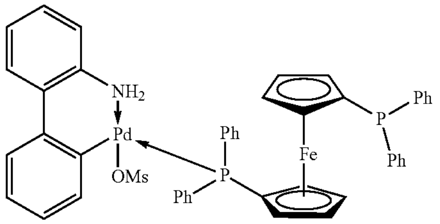

| | |
|---|---|
| EDTA | Ethylenediaminetetraacetic acid |
| EGTA | Ethylene glycol-bis(β-aminoethyl ether)-N,N,N',N'-tetraacetic acid |
| Et | Ethyl |
| EtOAc | Ethyl acetate |
| EtOH | Ethanol |
| $Et_3N$ | Triethylamine |
| $Et_2N$ | Diethyl zinc |
| EI | Electron impact |
| ESI | Electrospray ionization |
| h | Hour(s) |
| $^1$H-NMR | Proton nuclear magnetic resonance |
| HPLC | High performance liquid chromatography |
| IPA | Isopropyl alcohol |
| iPr | Isopropyl |
| LCMS | Liquid chromatography-mass spectrometry |
| LDA | Lithium diisopropylamide |
| LHMDS | Lithium bis(trimethylsilyl)amide |
| Me | Methyl |
| MeCN | Acetonitrile |
| MeOH | Methanol |
| Min | Minutes |
| MS | Mass spectrometry |
| MTBE | Methyl tert-butyl ether |
| m/z | Mass to charge ratio |
| $NaBH(OAc)_3$ | Sodium triactoxyborohydride |
| nBuLi | n-butyllithium |
| NCS | N-chlorosuccinimide |
| NIS | N-iodosuccinimide |
| NBS | N-bromosuccinimide |

-continued

| | |
|---|---|
| NHP | N-hydroxyphthalimide |
| NMP | N-Methyl-2-pyrrolidone |
| Palau'Chor ® | 2-Chloro-1,3-bis(methoxycarbonyl)guanidine |
| $Pd(amphos)Cl_2$ | Bis(di-tert-butyl(4-dimethylaminophenyl)phosphine)dichloropalladium(II) 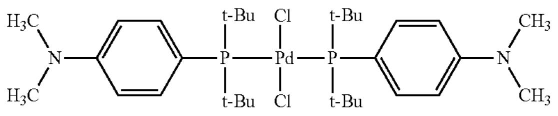 |
| Pd/C | Palladium on Carbon |
| Pd-PEPPSI ™ -IPen | Dichloro[1,3-bis(2,6-Di-3-pentylphenyl)imidazol-2-ylidene](3-chloropyridyl)palladium(II) 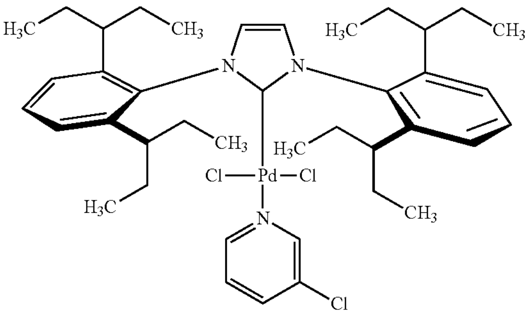 |
| PE | Petroleum ether |
| psi | Pounds per square inch |
| Py | Pyridine |
| PTSA | p-Toluenesulfonic acid |
| RT | Room termperature |
| RuPhos | 2-Dicyclohexylphosphino-2',6'-diisopropoxybiphenyl 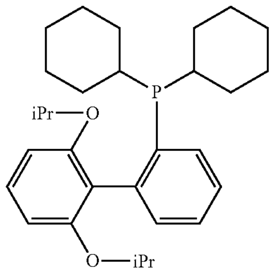 [SMILES: CC(C)Oc1cccc(OC(C)C)c1-c1ccccc1P(C1CCCCC1)C1CCCCC1] |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate 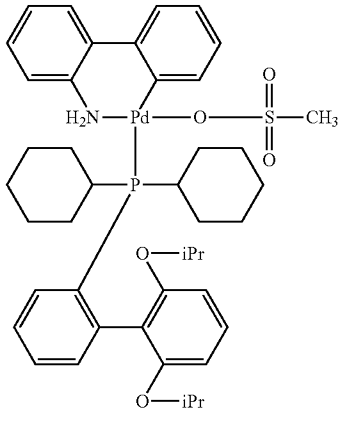 |

-continued

| | |
|---|---|
| RuPhos Pd G4 | (2-Dicyclohexylphosphino-2',6'-diisopropoxy-1,1'-biphenyl)[2-(2'-amino-1,1'-biphenyl)]palladium(II) methanesulfonate |
| Sat. | Saturated |
| SFC | Supercritical Fluid Chromatography |
| STAB | Sodium Triacetoxyborohydride |
| TBAF | Tetra-n-butylammonium fluoride |
| TBDPSCI | tert-Butyl(chloro)diphenylsilane |
| tBu | Tert-butyl |
| tBu BrettPhos Pd G3 | tert-BuBrettPhos-Pd-G3, [(2-Di-tert-butylphosphino-3,6-dimethoxy-2',4',6'-triisopropyl-1,1'-biphenyl)-2-(2'-amino-1,1'-biphenyl]palladium(II) methanesulfonate |
| TFA | Trifluoroacetic acid |
| THF | Tetrahydrofuran |
| TLC | Thin Layer Chromatography |
| $t_R$ | Retention time |
| TsCl | 4-Toluenesulfonyl chloride |
| Xantphos Pd G3 | [(4,5-Bis(diphenylphosphino)-9,9-dimethylxanthene)-2-(2'-amino-1,1'-biphenyl)]palladium(II) methanesulfonate<br>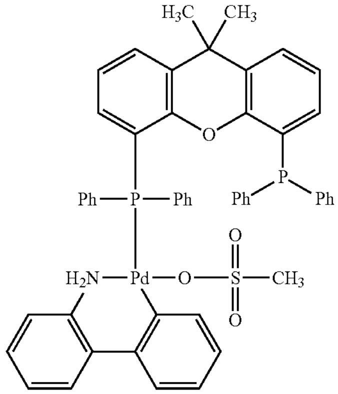 |
| Xphos Pd G3 | (2-Dicyclohexylphosphino-2',4',6'-triisopropyl-1,1'-biphenyl)[2-(2'-amino-1,1'-biphenyl)]palladium(II) methanesulfonate<br>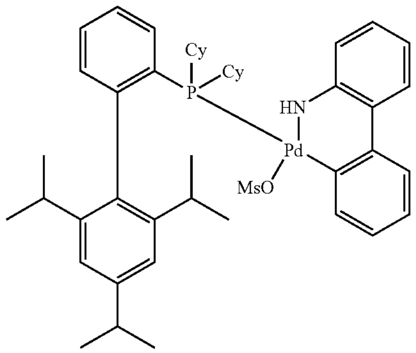 |

General Experimental Information:

Unless otherwise noted, all reactions are magnetically stirred. Unless otherwise noted, when diethyl ether is used in the experiments described below, it is Fisher ACS certified material and is stabilized with BHT. Unless otherwise noted, "concentrated" and/or "solvent removed under reduced pressure" means evaporating the solvent from a solution or mixture using a rotary evaporator or vacuum pump. Unless otherwise noted, flash chromatography is carried out on a Teledyne Isco (Lincoln, NE), Analogix (Burlington, WI), or Biotage (Stockholm, SWE) automated chromatography system using a commercially available cartridge as the column. Columns may be purchased from Teledyne Isco, Analogix, Biotage, Varian (Palo Alto, CA), or Supelco (Bellefonte, PA) and are usually filled with silica gel as the stationary phase. Reverse phase prep-HPLC conditions, where used, can be found at the end of each experimental section. Aqueous solutions were concentrated on a Genevac (Ipswich, ENG) or by freeze-drying/lyophilization. Unless otherwise noted, all LRRK2 $pIC_{50}$ data presented in tables refers to the LRRK2 G2019S $K_m$ ATP LanthaScreen™ assay (Life Technologies Corp., Carlsbad, CA) that is described in the Biological Assay section.

Synthesis of Common Intermediates

Scheme 1. Synthesis of 7-bromo-6-chloroquinazolin-2-amine

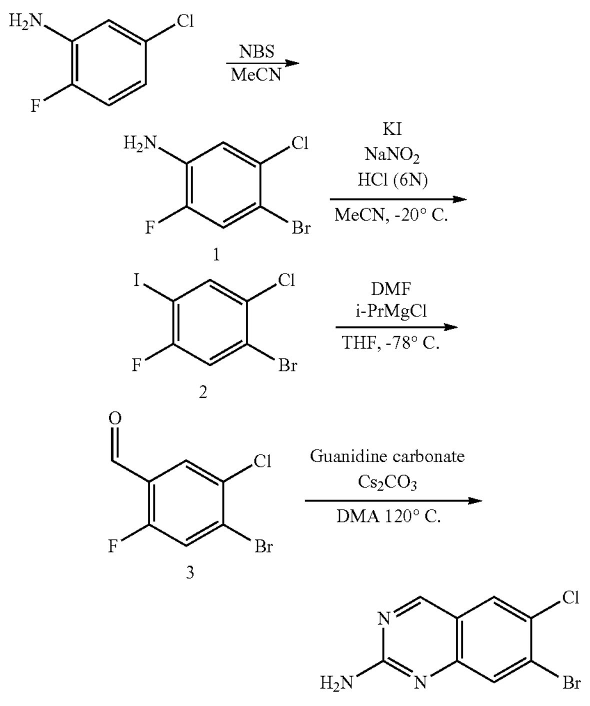

1
2
3
4

4-Bromo-5-chloro-2-fluoroaniline (1)

A 5 L, 4-necked round-bottom flask was charged with 5-chloro-2-fluoroaniline (215 g, 1.48 mol) under inert atmosphere. MeCN (2.15 L) was added, followed by the portionwise addition of NBS (263 g, 1.48 mol) at RT, and the resultant solution was stirred for 2 h at RT. Solvent was then removed under reduced pressure, and the crude residue was diluted with EtOAc (1.5 L). This mixture was washed with water (3×500 mL), then brine (1×500 mL), then dried over anhydrous $Na_2SO_4$. The solution was filtered, and solvent removed from the collected filtrate under reduced pressure to afford the title compound 11.

1-Bromo-2-chloro-5-fluoro-4-iodobenzene (2)

A 10 L, 4-necked round-bottom flask was charged with 4-bromo-5-chloro-2-fluoroaniline 1 (300 g, 1.34 mol) under inert atmosphere. MeCN (4.5 L) was added, followed by the addition of 6 N HCl (aqueous, 223 mL, 1.34 mol) at RT and stirred for 1.5 h. The mixture was then cooled to −20° C., and sodium nitrite (96.8 g, 1.40 mol) in water (300 mL) was added dropwise over 15 min, then stirred for 30 min. The mixture was maintained at −20° C. and treated with an aqueous (1.3 L) solution of potassium iodide (665 g, 4.01 mol) dropwise with stirring over 20 min. The resultant mixture was allowed to warm to RT and stirred for 1 h. The mixture was then extracted with EtOAc (2×3 L), and the combined organic phases were washed with sat. aq. $Na_2S_2O_3$ (4×1.5 L) and brine (1×1.5 L). Solvent was removed under reduced pressure and the resultant crude residue was purified by flash chromatography on silica gel (100% PE) to afford the title compound 2.

4-Bromo-5-chloro-2-fluorobenzaldehyde (3)

A 10 L, 4-necked round-bottom flask was charged with 1-bromo-2-chloro-5-fluoro-4-iodobenzene 2 (374 g, 1.12 mol) under inert atmosphere. To the flask was added THF (4 L), and the mixture was cooled to −78° C. Isopropylmagnesium chloride (2 M in THF, 614 mL, 1.23 mol) was added dropwise with stirring, and the resultant mixture was stirred for 1 h at −78° C. DMF (245 g, 3.35 mol) was added dropwise with stirring at −78° C., and the mixture was allowed to warm to RT and stirred for 2 h. After quenching with 2 L of water/ice, the mixture was extracted with EtOAc (2×2 L). The organic phase was washed with brine (1×2 L), and the solvent removed under reduced pressure. The residue was slurried with PE (500 mL) to afford the title compound 3.

7-Bromo-6-chloroquinazolin-2-amine (4)

A 10 L 4-necked round-bottom flask was charged with 4-bromo-5-chloro-2-fluorobenzaldehyde 3 (200 g, 842 mmol), $Cs_2CO_3$ (823 g, 2.53 mol), and guanidine carbonate (152 g, 842 mmol) under inert atmosphere. DMA (4 L) was added, and the resultant solution was stirred for 12 h at 120° C. On cooling, the mixture was diluted with 15 L of water/ice. Solids were collected by filtration and slurried with EtOAc (700 mL) to afford the title compound 4. MS (ESI): m/z calc'd for $C_8H_6BrClN_3$ $[M+H]^+$: 258, found 258; $^1H$ NMR (300 MHz, DMSO-$d_6$, 25° C.) δ: 9.11 (s, 1H), 8.07 (s, 1H), 7.78 (s, 1H), 7.17 (s, 2H).

Scheme 2. Synthesis of N,N-bis (tert-butyloxycarbonyl)-7-bromo-6-chloroquinazolin-2-amine

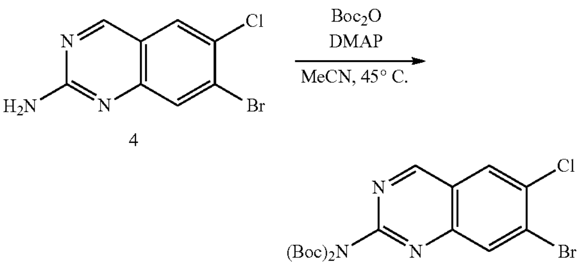

4
5

N,N-bis(tert-butyloxycarbonyl)-7-bromo-6-chloroquinazolin-2-amine (5)

A 5 L 4-necked round-bottom flask was charged with 7-bromo-6-chloroquinazolin-2-amine 4 (168 g, 650 mmol) and DMAP (79 g, 650 mmol) under inert atmosphere. MeCN (1.7 L) was added, and to the stirring mixture was added di-tert-butyl dicarbonate (426 g, 1.95 mol) dropwise with stirring at 45° C. The resultant solution was stirred for 1 h at 45° C. The reaction was removed from the heat, diluted with water (1 L), and extracted with EtOAc (2×1 L). Solvent was removed under reduced pressure and the crude residue was purified by flash chromatography on silica gel (EtOAc/PE, 10-30%) to afford the title compound 5. MS (ESI): m/z calc'd for $C_{18}H_{22}BrClN_3O_4$ $[M+H]^+$: 458, found 458; $^1H$ NMR (400 MHz, $CDCl_3$, 25° C.) δ: 9.35 (m, 1H), 8.38 (s, 1H), 8.09 (s, 1H), 1.49 (s, 18H).

Scheme 3. Synthesis of 7-bromo-2,6-dichloroquinazoline

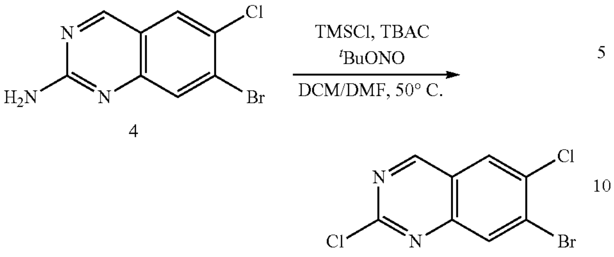

4

6

7-Bromo-2,6-dichloroquinazoline (6)

A 500-mL 4-necked round-bottom flask was charged with 7-bromo-6-chloroquinazolin-2-amine 4 (6.0 g, 23 mmol) under inert atmosphere. A solution of TMSCl (9.8 g, 90 mmol) in DCM (60 mL) was added to the flask, followed by DMF (6 mL). The solution was stirred at RT for 1 h. Tetrabutylammonium chloride (7.78 g, 28 mmol) was then added, and the resultant mixture was warmed to 50° C. To the stirring mixture at 50° C., tert-butyl nitrite (7.14 g, 69 mmol) was added dropwise, and on complete addition the mixture was stirred at this temperature for 1 h. The reaction was then quenched by the addition of sat. aq. $NH_4Cl$ (200 mL). This mixture was extracted with DCM (2×100 mL), and the combined organic layers washed with brine (1×50 mL). The organic phase was dried over $Na_2SO_4$, filtered, and the solvent removed under reduced pressure. The crude residue was then purified by flash chromatography over silica gel (EtOAc/PE, 25%) to afford the title compound 6. MS (ESI): m/z calc'd for $C_8H_4BrCl_2N_2$ $[M+H]^+$: 277, found 277; $^1H$ NMR (300 MHz, DMSO-$d_6$, 25° C.) δ: 9.61 (s, 1H), 8.61 (s, 1H), 8.52 (s, 1H).

Scheme 4. Synthesis of 7-bromo-6-chloro-N-(5-chloro-1-cyclopropyl-1H-pyrazol-4-yl)quinazolin-2-amine

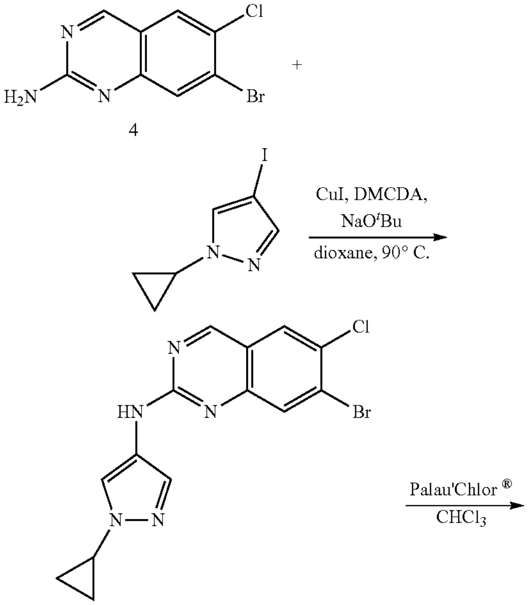

4

7

-continued

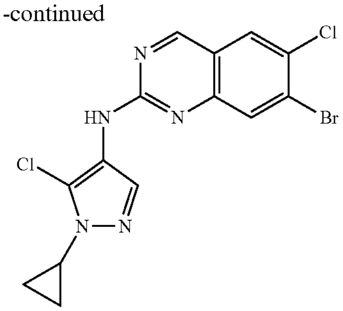

8

7-Bromo-6-chloro-N-(1-cyclopropyl-1H-pyrazol-4-yl)quinazolin-2-amine (7)

A 10-L 4-necked round-bottom flask was charged with DMCDA (39.5 g, 278 mmol) and copper (I) iodide (35.2 g, 185 mmol) under inert atmosphere. Dioxane (7 L) was added and the headspace degassed under vacuum. The mixture was stirred at RT for 5 min, at which point 7-bromo-6-chloroquinazolin-2-amine 4 (240 g, 925 mmol), 1-cyclopropyl-4-iodo-1H-pyrazole (239 g, 925 mmol), and NaO$^t$Bu (178 g, 1.85 mol) were added in sequence. The flask was degassed again and the resultant mixture was heated to 90° C. and maintained at this temperature for 8 h with stirring under inert atmosphere. Upon cooling to RT, the mixture was diluted with EtOAc (5 L) and washed successively with sat. aq. $NH_4Cl$ (1.5 L) and brine (1.5 L). The organic layer was dried over anhydrous magnesium sulfate, filtered, and solvent was removed from the collected filtrate under reduced pressure. The resultant crude residue was subjected to purification by flash chromatography over silica gel (MeOH/DCM, 0-20%) to afford the title compound 7.

7-Bromo-6-chloro-N-(5-chloro-1-cyclopropyl-1H-pyrazol-4-yl)quinazolin-2-amine (8)

A 5-L 4-necked round-bottom flask was charged with intermediate 7 (110 g, 302 mmol) under inert atmosphere. Chloroform (2.75 L) was added, and to the stirring mixture at RT was added Palau'Chlor® (70 g, 332 mmol). The resultant mixture was stirred at 25° C. for 2 h, at which point the reaction was quenched by the addition of sat. aq. sodium thiosulfate solution (110 mL, 1 V) at RT. Phases were separated and the aqueous phase was extracted with DCM (3x2L). The combined organic layers were washed successively with 1 N HCl (2×1.5 L) and brine (1.5 L), dried over $MgSO_4$, filtered, and solvent was removed from the collected filtrate under reduced pressure. The resultant crude product was upgraded by slurry overnight in PE/EtOAc (1:1, 1.1 L). The solid was collected by vacuum filtration to afford the title compound 8. MS (ESI): m z calc'd for $C_{14}H_{11}BrCl_2N_5$ $[M+H]^+$: 398, found 398; $^1H$ NMR (400 MHz, DMSO-$d_6$, 25° C.) δ: 9.41 (s, 1H), 9.24 (s, 1H), 8.21 (s, 1H), 7.97 (s, 1H), 7.87 (s, 1H), 3.61 (m, 1H), 1.15-1.02 (m, 4H).

Scheme 5. Synthesis of N,N-bis(tert-butyloxycarbonyl)-6-chloro-7-iodoquinazolin-2-amine

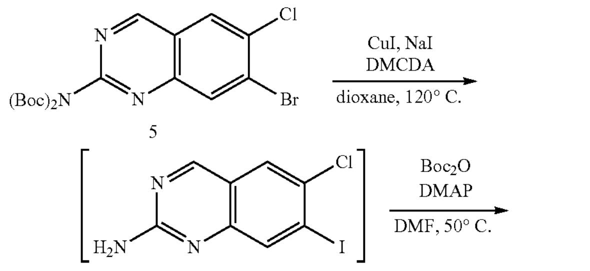

5

9

10

N,N-bis(tert-cutyloxycarbonyl)-6-chloro-7-iodoquinazolin-2-amine (10)

A 5-L 4-necked round-bottom flask was charged with N,N-bis(tert-butyloxycarbonyl)-7-bromo-6-chloroquinazolin-2-amine 5 (250 g, 545 mmol), copper(I) iodide (10.3 g, 54 mmol), trans-N,N'-dimehtylcyclohexane-1,2-diamine (DMCDA) (15.5 g, 109 mmol), and sodium iodide (405 g, 2.70 mol) under inert atmosphere. The mixture was then dissolved/suspended in dioxane (2.5 L) and heated to reflux overnight with stirring. Upon cooling, the mixture was diluted with ice water (5 L), and precipitated solids were collected by filtration to afford the crude 6-chloro-7-iodoquinazolin-2-amine 9, a fraction of which was carried on directly to the subsequent step. A 3-L 4-necked round-bottom flask was charged with the crude intermediate 9 (120 g, 393 mmol) and DMAP (48 g, 393 mmol) under inert atmosphere. MeCN (1 L) was added, followed by the portionwise addition of di-tert-butyl decarbonate (429 g, 1.97 mol) at 50° C. The resultant solution was stirred for 2 h at this temperature. Solvent was removed under reduced pressure, and the crude residue was purified by flash chromatography over silica gel (EtOAc/hexanes, 5%) to afford the title compound 9. MS (ESI): m/z calc'd for $C_{18}H_{22}ClIN_3O_4$ $[M+H]^+$: 506, found 506; $^1H$ NMR (400 MHz, $CDCl_3$, 25° C.) δ: 9.33 (s, 1H), 8.65 (s, 1H), 8.04 (s, 1H), 1.47 (s, 18H).

Scheme 6. Synthesis of 5-chloro-1-(2,2-difluoroethyl)-1H-pyrazol-4-amine

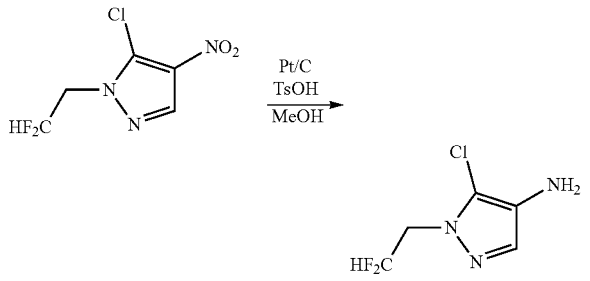

11

5-Chloro-1-(2,2-difluoroethyl)-1H-pyrazol-4-amine (11)

A 3-L pressure tank reactor purged and maintained with an inert atmosphere of $H_2$, was charged with 5-chloro-1-(2,2-difluoroethyl)-4-nitropyrazole (200.0 g, 945 mmol), 2-methyltetrahydrofuran (1.6 L), MeOH (1.6 L), para-toluene sulfonate (163 g, 946 mmol), and Pt/C (40.0 g, 10.3 mmol, 5%). The resultant mixture was stirred at 25° C. for 18 h. The solids were filtered out. The resulting mixture was concentrated, and the solids were collected by filtration and washed with EtOAc (1 L) to afford the title compound 11

Scheme 7. Synthesis of 6-chloro-N-(5-chloro-1-(2,2-difluoroethyl)-1H-pyrazol-4-yl)-7-iodoquinazolin-2-amine

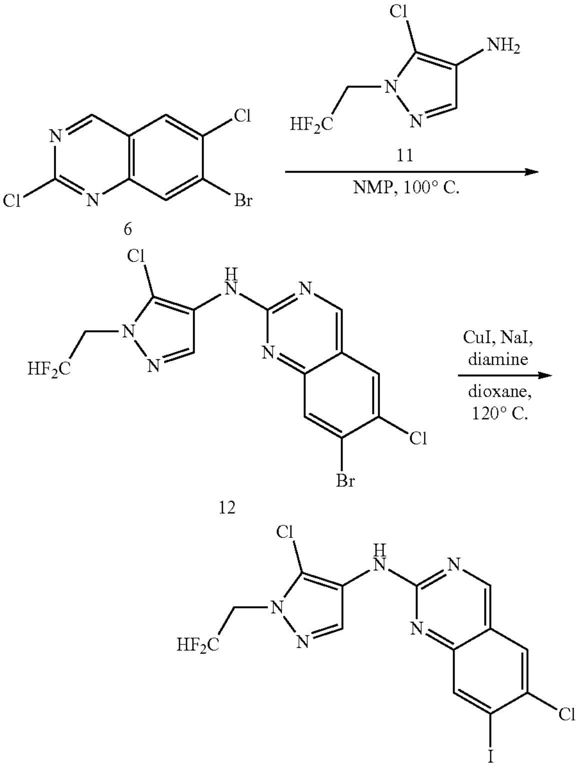

11

6

12

13

7-Bromo-6-chloro-N-(5-chloro-1-(2,2-difluoroethyl)-1H-pyrazol-4-yl)quinazolin-2-amine (12)

A 3-L 4-necked round-bottom flask purged and maintained with an inert atmosphere of nitrogen was charged with 7-bromo-2,6-dichloroquinazoline 6 (150 g, 539 mmol), 5-chloro-1-(2,2-difluoroethyl)pyrazol-4-amine 11 (200 g, 565 mmol). NMP (1.50 L) was added and the resultant solution was stirred at 100° C. for 2 h. The reaction mixture was cooled to RT with a water/ice bath and was then quenched by the addition of ice water (2 L). The solids were collected by filtration to afford the title compound 12.

6-Chloro-N-(5-chloro-1-(2,2-difluoroethyl)-1H-pyrazol-4-yl)-7-iodoquinazolin-2-amine (13)

A 2-L 4-necked round-bottom flask purged and maintained with an inert atmosphere of nitrogen, was charged with 7-bromo-N-[5-chloro-1-(2,2-difluoroethyl)pyrazol-4-yl]quinazolin-2-amine 12 (100 g, 257 mmol), copper(I) iodide (4.90 g, 25.7 mmol), sodium iodide (194 g, 1290 mmol), and (1R,2R)-N1,N2-dimethylcyclohexane-1,2-diamine (7.3 g, 51 mmol). Dioxane (1.00 L) was added and the resultant mixture was stirred at 120° C. for 18 h. The reaction was then quenched by the addition of ice water (2 L). The solids were collected by filtration. The crude product was purified by reversed phase HPLC eluting with water (0.1% $NH_4OH$)-MeCN to afford the title compound 13. MS (ESI): m/z calc'd for $C_{13}H_8Cl_2F_2IN_5$ $[M+H]^+$: 470, found 470; $^1H$ NMR: (400 MHz, $CDCl_3$, 25° C.): δ 9.45 (s, 1H), 9.24 (s, 1H), 8.20 (s, 1H), 8.15 (s, 1H), 8.06 (s, 1H), 6.56-6.27 (m, 1H), 4.65 (m, 2H).

Scheme 8. Synthesis of 6-chloro-7-fluoroquinazolin-2-amine

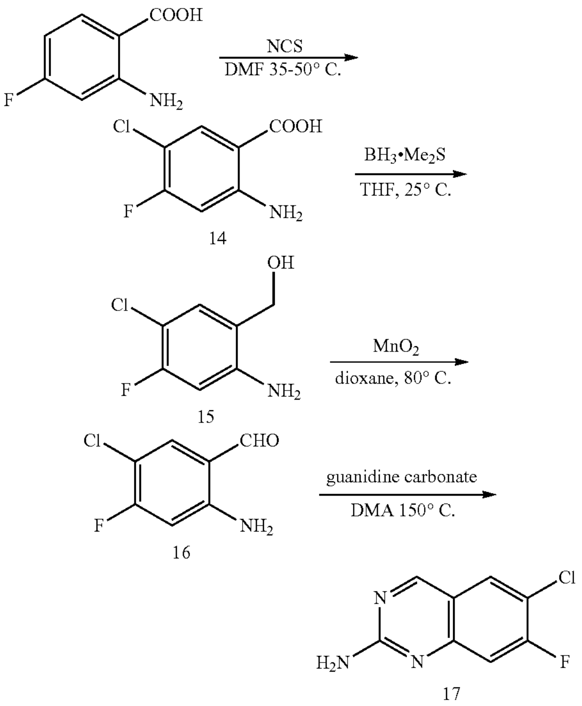

2-Amino-5-chloro-4-fluorobenzoic acid (14)

A 5 L three-necked round bottom flask was charged with 2-amino-4-fluorobenzoic acid (468 g, 3.02 mol) and the contents were dissolved in DMF (2.8 L). NCS (382 g, 2.87 mol) was added to the reaction and the resultant solution was stirred for 12 h at 35° C. and then for 3 h at 50° C. After quenching the reaction by the addition of 20 L of water/ice, the aqueous layer was extracted with ethyl acetate (3×2 L). The combined organic phases were washed with brine (1×2 L) and the solvent removed under reduced pressure. The crude product was triturated with DCM (1 L) to obtain compound 14. MS (ESI): m/z calc'd for $C_7H_5ClFNO_2$ $[M+H]^+$: 190, found 190.

(2-Amino-5-chloro-4-fluorophenyl)methanol (15)

A 5 L three-necked round bottom flask was charged with compound 14 (314 g, 1.66 mol) in THF (2.4 L). $BH_3$-$Me_2S$ (1.0 M in THF, 497 mL) was added dropwise to the reaction. The resultant mixture was stirred for 1 h at RT and then for 12 h at 50° C. After quenching the reaction mixture by the addition of MeOH (800 mL), $H_2O$ (1 L) was added. The aqueous phase was extracted with ethyl acetate (2×1 L). The combined organic phases were washed with brine (1×1 L) and further dried over sodium sulfate. Solvent was removed under reduced pressure and the crude product was purified by flash chromatography on silica gel (EtOAc/PE, 2-100%) to afford the title compound 15. MS (ESI): m/z calc'd for $C_7H_7ClFNO$ $[M+H]^+$: 176, found 176.

2-Amino-5-chloro-4-fluorobenzaldehyde (16)

A 3 L three-necked round bottom flask was charged with compound 15 (291 g, 1.66 mol) in dioxane (1.8 L). $MnO_2$ (432 g, 4.97 mol) was added to the reaction. The resultant suspension was stirred for 24 h at 80° C. The mixture was filtered, and the solvent removed under reduced pressure. The crude product was triturated with PE/MTBE=10/1 at 20° C. for 1 h and then filtered to afford the title compound 16. MS (ESI): m/z calc'd for $C_7H_5ClFNO$ $[M+H]^+$: 174, found 174.

6-Chloro-7-fluoroquinazolin-2-amine (17)

A 1 L three-necked round bottom flask was charged with compound 16 (20.0 g, 115 mmol) in DMA (500 mL). Guanidine carbonate (20.4 g, 346 mmol) was added to the reaction. The resultant mixture was stirred for 1 h at 150° C. $H_2O$ (30 L) was added to the reaction mixture. The resultant suspension was filtered and the solid collected. The crude product was triturated with MTBE (2×500 mL) at 20° C. for 0.5 h and then filtered to collect the solids. The resultant solid was then triturated with DCM/MeOH=10/1 (2×500 mL) at 20° C. for 0.5 h and then filtered to collect the solids. The resultant solid was then triturated with MeOH (2×500 mL) at 20° C. for 0.5 h and then filtered to obtain title compound 17. MS (ESI): m/z calc'd for $C_8H_5ClFN_3$ $[M+H]^+$: 198, found 198; $^1H$ NMR (400 MHz, DMSO-$d_6$, 25° C.) δ 9.09 (s, 1H), 8.12 (d, J=8.4 Hz, 1H), 7.35 (d, J=10.8 Hz, 1H), 7.18 (s, 2H).

Scheme 9. Synthesis of 7-fluoro-6-methylquinazolin-2-amine

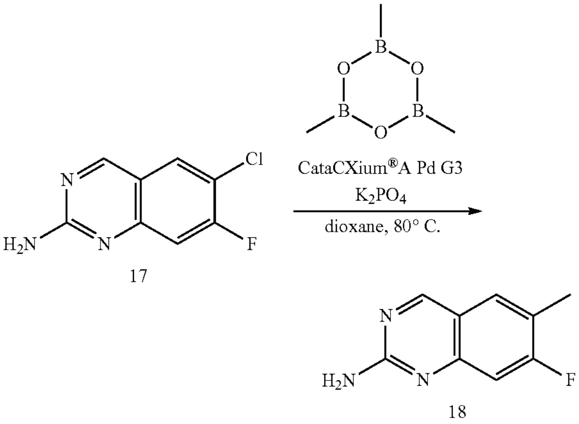

A flask was charged with 6-chloro-7-fluoroquinazolin-2-amine (10) (100 mg, 0.506 mmol), trimethylboroxine (0.424 mL, 3.04 mmol), CataCXium® A Pd G3 (92 mg, 0.13 mmol), and $K_3PO_4$ (430 mg, 2.02 mmol). Dioxane (5 mL) was added and the resultant solution was purged with nitrogen gas and stirred at 80° C. overnight. The reaction mixture was diluted with EtOAc (10 mL), filtered over Celite® washing with EtOAc, then concentrated under reduced pressure. The crude residue was subjected to flash chromatography over silica (MeOH/DCM, 0-10%) to afford the title compound 18. MS (ESI): m/z calc'd for $C_9H_8FN_3$ $[M+H]^+$: 178, found 178. $^1H$ NMR (500 MHz, DMSO-$d_6$, 25° C.) δ 9.00 (s, 1H), 7.71 (d, J=8.7 Hz, 1H), 7.09 (d, J=11.7 Hz, 1H), 6.85 (s, 2H), 2.30 (s, 3H).

Scheme 10. Synthesis of 2-amino-7-fluoroquinazoline-6-carbonitrile

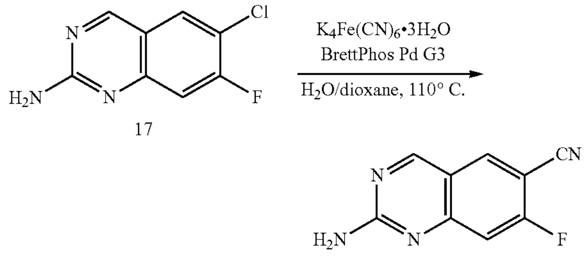

17

19

A flask was charged with 6-chloro-7-fluoroquinazolin-2-amine (17) (500 mg, 2.53 mmol), potassium hexacyanoferrate(II) trihydrate (3.2 g, 7.6 mmol) and BrettPhos Pd G3 (459 mg, 0.506 mmol). Dioxane (18 mL) and water (6 mL) were added and the resultant mixture was stirred at 110° C. for 24 h. The reaction mixture was poured into water (10 mL) and EtOAc (5 mL) was added. The organic phase was separated, and the aqueous phase was extracted with EtOAc (3x5 mL). The combined organic phases were washed with brine (3x10 mL), dried over sodium sulfate, and concentrated under reduced pressure to afford the crude product which was subjected to purification by flash chromatography over silica (EtOAc/PE, 0-80%) to afford the title compound 19. MS (ESI): m/z calc'd for $C_9H_5FN_4$ $[M+H]^+$: 189, found 189.

Scheme 11. Synthesis of 6-bromo-7-chloroisoquinolin-3-amine and 6-bromo-5-chloroisoquinolin-3-amine

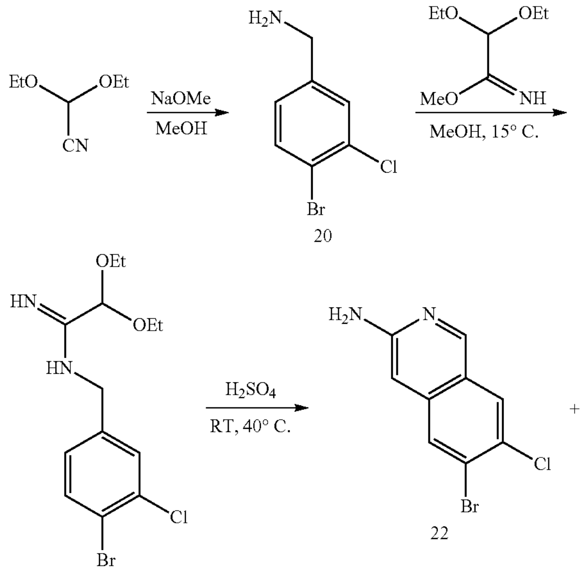

20

21

22

-continued

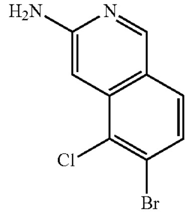

23

N-(4-bromo-3-chlorobenzyl)-2,2-diethoxyacetimidamide (20)

A 5 L round-bottom flask was charged with 2,2-diethoxyacetonitrile (250 g, 1.94 mol), and MeOH (1.50 L). Sodium methoxide (24.4 g, 135 mmol) was added to the mixture dropwise. The flask was evacuated and purged with $N_2$ three times. The resulting mixture was allowed to stir for 6 h at 25° C. The crude reaction mixture was adjusted to a pH of 8-9 using dry $CO_2$. The reaction was concentrated and then diluted with water (100 mL). The organic material was extracted out of the aqueous solution using ethyl acetate (2x250 mL). Four reactions of the same scale were combined for the following workup. The organic layers were combined and washed with water, dried over sodium sulfate. The solution was then concentrated under reduced pressure, to afford the title compound 20 which was carried onto the next step without purification.

N-(4-bromo-3-chlorobenzyl)-2,2-diethoxyacetimidamide (21)

A 500 mL round-bottom flask was charged with 4-bromo-3-chlorophenyl methanamine (1.00 kg, 4.56 mol) into MeOH (150 mL). Methyl 2,2-diethoxyacetimidate (918 g, 5.69 mol) was added to the mixture and stirred at 15° C. for 16 hours. The crude material was concentrated in vacuo to afford the title compound 21 which was used directly in a subsequent reaction without further purification.

6-Bromo-7-chloroisoquinolin-3-amine (22) and 6-bromo-5-chloroisoquinolin-3-amine (23)

A 5 L round-bottom flask was charged with N-(4-bromo-3-chlorobenzyl)-2,2-diethoxyacetimidamide (280 g, 800 mmol). Sulfuric acid (1.4 L) was added, and the reaction was stirred overnight at 40° C. The pH of the mixture was adjusted to pH 9 with ammonium hydroxide (3.5 L) to precipitate out the product. The precipitate was collected by filtration and washed with water, affording a mixture of two isomers. The crude product was purified by reverse phase HPLC, eluting with water (0.1% $NH_4OH$)-MeCN. Ammonium hydroxide was used to adjust to a pH=7-8. The solution was filtered and washed with water (100 mL). The organic layer was concentrated in vacuo to afford the title compounds 22 and 23. Data for 22: MS (ESI): m/z calc'd for $C_9H_6BrClN_2$ $[M+H]^+$: 257, found 257. $^1H$ NMR (400 MHz, DMSO-$d_6$, 25° C.) δ 8.79 (s, 1H), 8.06 (s, 1H), 8.05-8.08 (m, 1H), 8.02 (s, 1H), 6.55 (s, 1H), 6.23 (s, 2H).

Scheme 12. Synthesis of (R)- and (S)- 4-bromo-5-chloro-1-(2,2-difluorocyclopropyl)-1H-pyrazole

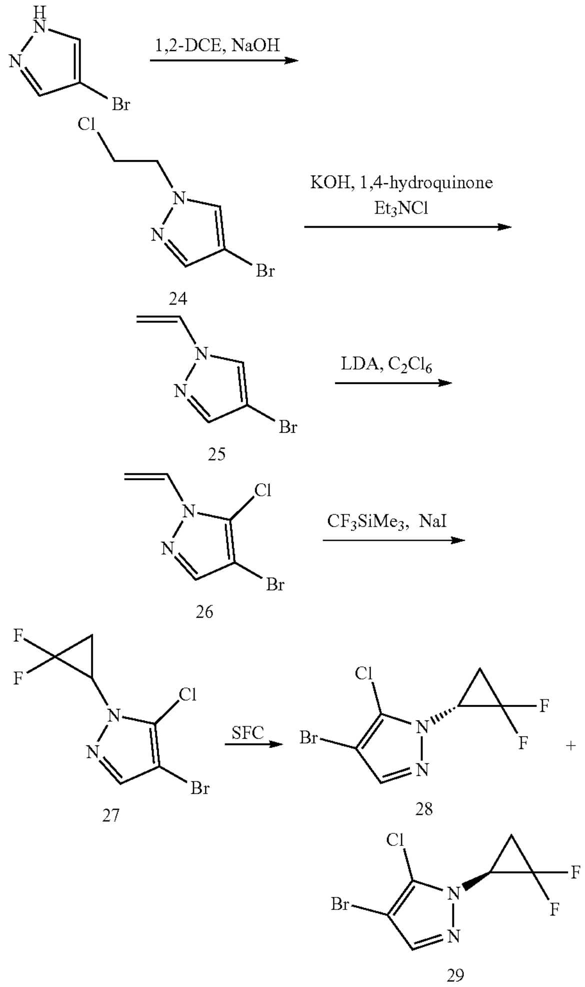

24

25

26

27

28

29

4-Bromo-1-(2-chloroethyl)-1H-pyrazole (24)

A 10-L 3-necked round-bottom flask was charged with a solution of NaOH (201 g, 5.03 mol) in $H_2O$ (1.2 L). DCE (1.73 kg, 17.4 mol), 4-bromopyrazole (493 g, 3.35 mol) and benzyl triethylammonium chloride (38.4 g, 0.28 mol) were then added at RT. The reaction mixture was warmed to 80° C. and stirred for 3 h at this temperature. On cooling to RT, the reaction mixture was poured into water (1.00 L) and layers were separated. The aqueous phase was extracted with DCM (3×1 L). The combined organic phase was washed with $H_2O$ (3×1 L) and brine (3×1 L), dried over anhydrous $Na_2SO_4$ and filtered. Solvent was removed from the collected filtrate under reduced pressure to afford the title compound 24.

4-Bromo-1-vinyl-1H-pyrazole (25)

A 10-L 3-necked round-bottom flask was charged with a solution of KOH (372 g, 6.6 mol) in $H_2O$ (800 mL). To the stirring mixture at RT were added 1,4-hydroquinone (62 g, 0.56 mol), benzyl triethylammonium chloride (23 g, 0.10 mol), and 4-bromo-1-(2-chloroethyl)-1H-pyrazole (23) (534 g, 2.55 mol). After stirring at RT for 3 h, the reaction mixture was warmed to 80° C. and stirred for an additional 3 h. The reaction mixture was poured into water (1 L) and layers were separated. The reaction mixture was extracted with ether (3×1 L). The combined organic phase was washed with HCl (1 N, 2×500 mL) and brine (2×500 mL), dried over anhydrous $Na_2SO_4$, and filtered. Solvent was removed from the collected filtrate under reduced pressure to afford a crude residue. The crude product was distilled in vacuum (70° C., 10 mmHg pressure) to afford the title compound 25.

4-Bromo-5-chloro-1-vinyl-1H-pyrazole (26)

A 10-L 3-necked round-bottom flask was charged with diisopropylamine (300 g, 2.9 mol) under inert atmosphere and cooled to −78° C. To the stirring mixture at this temperature was slowly added nBuLi (1.08 L, 2.5 M in hexanes, 2.69 mol), and the resultant mixture was stirred for 20 min at this temperature. A solution of 4-bromo-1-vinyl-1H-pyrazole 25 (343 g, 1.9 mol) in THF (1 L) was then slowly added, and on complete addition the solution was allowed to warm to RT. The resulting solution was stirred for 40 min at RT then cooled to −78° C., and hexachloroethane (558 g, 2.35 mol) was added. The mixture was stirred at −78° C. for 2 h. The reaction mixture was poured into sat. aq. $NH_4Cl$ (1 L) and extracted with ether (3×1.5 L). The combined organic phase was washed with HCl (1 N, 3×1.5 L), sat. aq. $NaHCO_3$(3×1 L) and brine (3×1 L). The collected organic phase was dried over $Na_2SO_4$ and filtered. Solvent was removed from the collected filtrate under reduced pressure to afford a crude residue. The crude residue was subjected to purification by flash chromatography over silica gel (100% PE) to afford the title compound 26.

(R)- and (S)-4-Bromo-5-chloro-1-(2,2-difluorocyclopropyl)-1H-pyrazole (28 and 29)

A 10-L 3-necked round-bottom flask was charged with 4-bromo-5-chloro-1-vinyl-1H-pyrazole 26 (288 g, 1.39 mol) and NaI (833 g, 5.56 mol) under inert atmosphere. MeCN (3 L) was added and the mixture was warmed to 80° C. To the stirring mixture at this temperature was added trifluoromethyltrimethylsilane (850 g, 5.97 mol) dropwise. The reaction mixture was stirred at 80° C. for 3 h. Upon cooling, the reaction mixture was filtered, and solvent was removed from the collected filtrate under reduced pressure. The crude residue was subjected to purification by flash chromatography over silica gel (1-10% EtOAc/PE) to afford the racemic title compound 27. The racemic material could be resolved to its component enantiomers by chiral preparative SFC (Column & dimensions: OD-5H, 4.6 mm×150 mm; Mobile phase A: $CO_2$; Mobile phase B: 1:1 n-heptane/IPA with 0.1% $NH_4OH$) to afford the title compounds 28 ($t_R$=3.6 min) and 29 ($t_R$×5.2 min). MS (ESI): m/z calc'd for $C_6H_5BrClF_2N_2$ $[M+H]^+$: 256, found 256; $^1H$ NMR (300 MHz, $CDCl_3$, 25° C.) δ: 7.55 (s, 1H), 3.98 (m, 1H), 2.47 (m, 1H), 2.16 (m, 1H).

Scheme 13. Synthesis of (R)- and (S)- 4-bromo-1-(2,2-difluorocyclopropyl)-5-methyl-1H-pyrazole

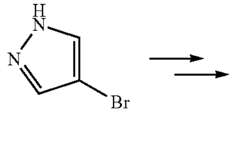

-continued

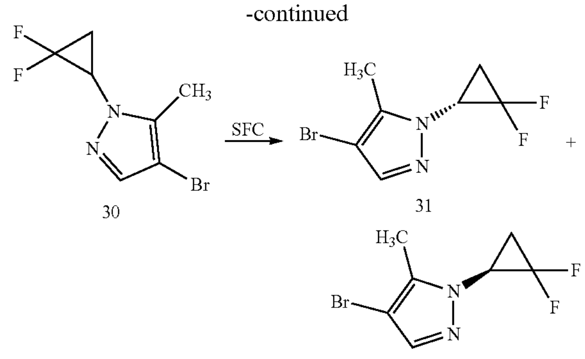

30

31

32

(R)- and (S)-4-bromo-1-(2,2-difluorocyclopropyl)-5-methyl-1H-pyrazole (31 and 32)

The title compounds were prepared analogously to compounds 28 and 28, substituting iodomethane for hexachloroethane. At the final reaction, the racemic title compound 29 was purified from the crude residue by recrystallization from petroleum ether. The racemic material could be resolved to its component enantiomers by chiral preparative SFC (Column & dimensions: AD, 50 mm×250 mm; Mobile phase A: $CO_2$; Mobile phase B: 1:1 n-heptane/IPA with 0.1% $NH_4OH$) to afford the title compounds 31 ($t_R$=3.5 min) and 32 ($t_R$=4.7 min). MS (ESI): m/z calc'd for $C_7H_8BrF_2N_2$ $[M+H]^+$: 237, found 237; $^1H$ NMR (400 MHz, $CDCl_3$, 25° C.) δ: 7.43 (s, 1H), 3.89-3.83 (m, 1H), 2.42-2.38 (m, 1H), 2.33 (s, 3H), 2.14-2.09 (m, 1H).

Scheme 14. Synthesis of 1-(3-methyloxetan-3-yl)piperazine

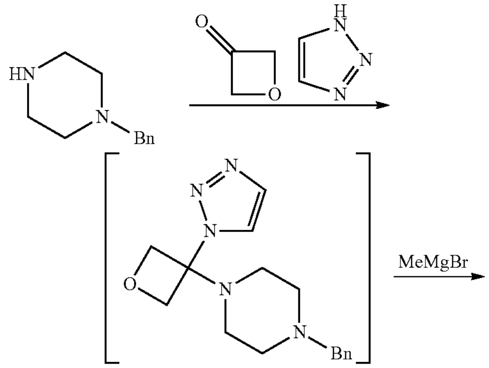

-continued

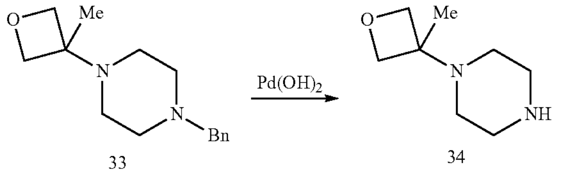

33

34

1-Benzyl-4-(3-methyloxetan-3-yl)piperazine (33)

A 1-L 3-necked round-bottom flask was charged with benzylpiperazine (50 g, 280 mmol) under inert atmosphere. Toluene (500 mL) was added, followed by 3-oxetanone (22.5 g, 312 mmol), and finally 1,2,3-triazole (23.5 g, 340 mmol). The resultant solution was warmed to 125° C. and stirred at this temperature for 2 h. The solution was allowed to cool to RT and the putative triazole adduct used directly in the subsequent step (vide infra).

A 1-L 3-necked round-bottom flask was charged with bromo(methyl)magnesium (250 mL, 3 M in $Et_2O$) and THF (250 mL) under inert atmosphere, and the solution was cooled to 10° C. The toluene solution from step 1 was then added dropwise to the stirring mixture at this temperature. The resultant solution was stirred for 30 min at 20° C., at which point it was quenched by the addition of ice water. This mixture was extracted with toluene, and the combined organic layers were dried over anhydrous $Na_2SO_4$. The solution was filtered and solvent was removed under reduced pressure to afford the title compound 33.

1-(3-Methyloxetan-3-yl)piperazine (34)

A 500-mL round-bottom flask was charged with 1-benzyl-4-(3-methyloxetan-3-yl)piperazine (18 g, 73 mmol), and Pd/C (11 g, 103 mmol) under inert atmosphere. After purging the headspace, EtOH (240 mL) was added. The inert atmosphere was then carefully exchanged for $H_2$ atmosphere (1 atm), and the resultant mixture was stirred for 5 h at RT. Solids were removed by filtration and the filter cake was quenched with water. Solvent was removed from the filtrate under reduced pressure to afford the title compound 34. MS (ESI): m/z calc'd for $C_8H_{17}N_2O$ $[M+H]^+$: 157, found 157. $^1H$ NMR (400 MHz, DMSO-$d_6$, 25° C.) δ 4.38 (d, J=5.5 Hz, 2H), 4.09 (d, J=5.5 Hz, 2H), 2.74-2.65 (m, 4H), 2.23-2.14 (m, 4H), 1.25 (s, 3H).

Scheme 15. Synthesis of (R)- and (S)- 4-((tert-butyldiphenylsilyl)oxy)dihydrofuran-3(2H)-one

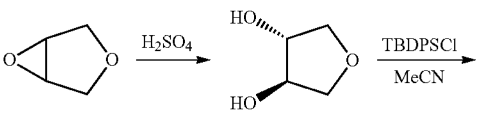

35

-continued

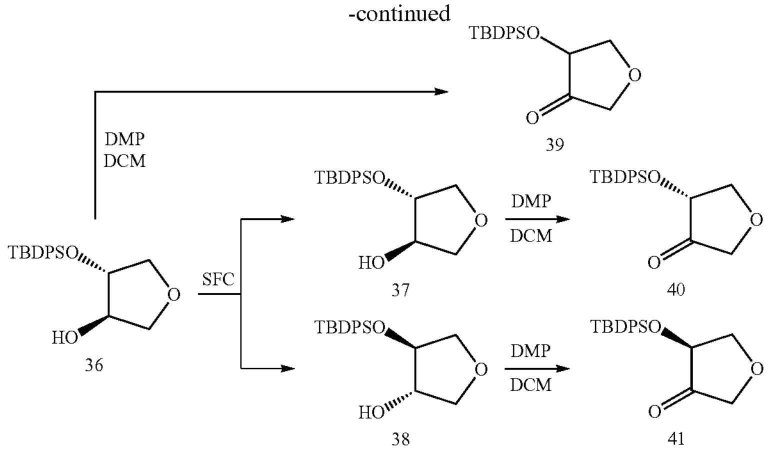

36 37 38 39 40 41 trans-tetrahydrofuran-3,4-diol (35)

A 10-L 4-necked round-bottom flask was charged with 3,6-dioxabicyclo[3.1.0]hexane (409 g, 4.75 mol). $H_2SO_4$ (4 L, 1.5 mol/L) was added, and the resulting solution was heated to reflux and stirred for 6 hrs. The reaction mixture was cooled to room temperature. The pH value of the solution was adjusted to 8 with $Na_2CO_3$. Solvent was removed under reduces pressure. The product was extracted with THF (5 L). THF was removed from the extract under reduced pressure to afford the title compound 35.

trans-4-((tert-butyldiphenylsilyl)oxy)tetrahydro-furan-3-ol (36)

A 3-L 4-necked round-bottom flask was charged with trans-tetrahydrofuran-3,4-diol 35 (52 g, 499 mmol), imidazole (51 g, 749 mmol), and TBDPSCl (137 g, 498 mmol) under inert atmosphere. MeCN (1.50 L) was added and the resultant solution was stirred for 4 hrs at 80° C. Solvent was removed under reduced pressure. The residue was taken up in EtOAc (1 L), and the organic phase was washed with water (2×500 mL), dried over $Na_2SO_4$, and filtered. Solvent was removed from the collected filtrate under reduced pressure. The crude residue was subjected to purification by flash chromatography over silica gel (0-3% EtOAc/PE) to afford the racemic title compound 36. (3S,4S) and (3R,4R) 4-((tert-butyldiphenylsilyl)oxy)tetrahydrofuran-3-ol (37 and 38)

The racemic material 36 could be resolved to its component enantiomers by chiral preparative SFC (Column & dimensions: AS-H, 50 mm×250 mm; Mobile phase A: $CO_2$; Mobile phase B: 2% DEA in IPA) to afford the title compounds 37 ($t_R$=2.9 min) and 38 ($t_R$=5.4 min). 4-((tert-butyldiphenylsilyl)oxy)dihydrofuran-3(2H)-one (39)

A 500-mL 4-necked round-bottom flask was charged with intermediate 36 (85.7 g, 250 mmol) under inert atmosphere. DCM (1.7 L) was added, and to the resulting solution was added Dess-Martin periodinane (117 g, 275 mmol) in portions at room temperature. The reaction mixture was stirred for 3 hrs at 30-35° C. The reaction was then quenched by the addition of 1.5 L of aqueous $NaHCO_3/Na_2S_2O_3$ (1:1). Phases were separated, and the aqueous phase was extracted with additional DCM (3×500 mL). The combined organic phase was then washed with brine (1×500 mL), dried over anhydrous $Na_2SO_4$, filtered, and solvent was removed from the collected filtrate under reduced pressure. The crude residue was subjected to purification by flash chromatography over silica gel (1% EtOAc/PE) to afford the title compound 39. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H). (R)- and (S)-4-((tert-butyldiphenylsilyl)oxy)dihydrofuran-3(2H)-one (40 and 41)

By substituting alcohol 37 in an identical procedure to that described above, the enantiopure compound 40 was prepared. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H).

By substituting alcohol 38 in an identical procedure to that described above, the enantiopure compound 41 was prepared. MS (ESI): m/z calc'd for $C_{20}H_{27}O_3Si$ $[M+H]^+$: 341, found 341; $^1H$ NMR (300 MHz, DMSO-$d_6$, 25° C.) δ: 7.66 (m, 4H), 7.56-7.36 (m, 6H), 4.35 (m, 1H), 4.18-3.85 (m, 3H), 3.71 (m, 1H), 1.03 (s, 9H).

Scheme 16. Synthesis of 1-(4-((tert-butyldiphenylsilyl)oxy)-3-methyltetrahydrofuran-3-yl)piperazine

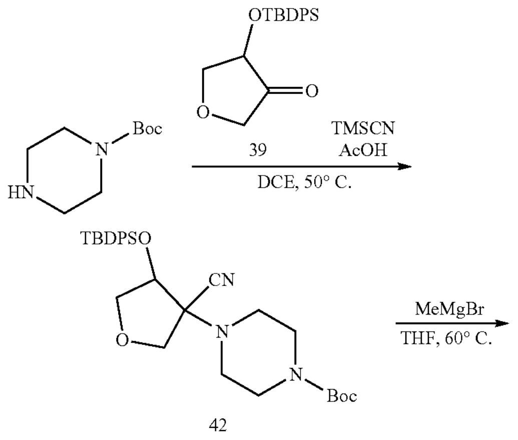

39 42

-continued

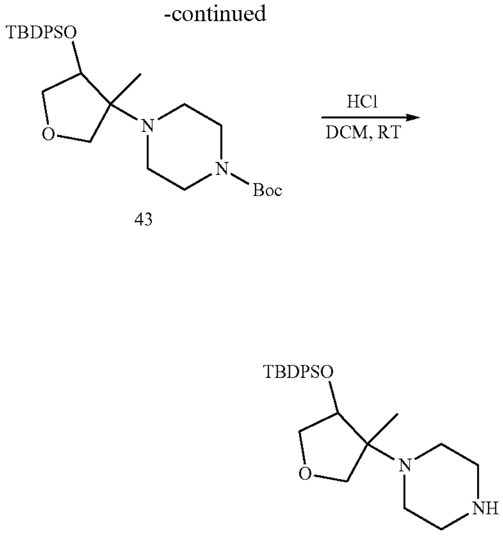

43

44

Tert-butyl4-(4-((tert-butyldiphenylsilyl)oxy)-3-cyanotetrahydrofuran-3-yl)piperazine-1-carboxylate (42)

A 3 L 3-necked round-bottom flask purged and maintained with an inert atmosphere of nitrogen was charged with tert-butyl piperazine-1-carboxylate (50.0 g, 268 mmol) in DCE (2.5 L). To this mixture was added 4-((tert-butyldiphenylsilyl)oxy)dihydrofuran-3(2H)-one 39 (119 g, 349 mmol), followed by acetic acid (24.2 g, 403 mmol) dropwise at 25° C. The reaction was stirred at 50° C. for 30 min at which time trimethylsilanecarbonitrile (39.9 g, 403 mmol) was added to the mixture. The resultant mixture was stirred at 50° C. for 12 h. The reaction was quenched by the addition of a sat. aq. solution of $NaHCO_3$(1 L). The aqueous phase was extracted with DCM (3×2.5 L) and the combined organic phases were dried over $Na_2SO_4$ and concentrated under reduced pressure. The resultant crude residue was subjected to purification by flash chromatography over silica gel (ethyl acetate/PE, 33%) affording the title compound 42. MS (EI): m/z calc'd for $C_{30}H_{41}N_3O_4Si$ $[M+H]^+$: 536, found 536.

Tert-butyl 4-(4-((tert-butyldiphenylsilyl)oxy)-3-methyltetrahydrofuran-3-yl) piperazine-1-carboxylate (43)

A 5 L 3-necked round-bottom flask purged and maintained with an inert atmosphere of nitrogen was charged with tert-butyl 4-(4-((tert-butyldiphenylsilyl)oxy)-3-cyanotetrahydrofuran-3-yl) piperazine-1-carboxylate 42 (73.0 g, 136 mmol). THF (3.7 L) followed by methylmagnesium bromide (227 mL, 681 mmol) was added at 0° C. under a stream of $N_2$. The resultant solution was stirred at 60° C. for 5 h. The reaction was quenched by the addition of a sat. aq. solution of $NaHCO_3$(1 L). The aqueous phase was extracted with ethyl acetate (3×3 L) and the combined organic phases were dried over $Na_2SO_4$ and concentrated under reduced pressure. The resultant crude residue was subjected to purification by flash chromatography over silica gel (EtOAc/PE, 5%) affording the title compound 43. MS (EI): m/z calc'd for $C_{30}H_{44}N_2O_4Si$ $[M+H]^+$: 525, found 525.

1-(4-((Tert-butyldiphenylsilyl)oxy)-3-methyltetrahydrofuran-3-yl)piperazine (44)

A 500 mL 3-necked round-bottom flask purged and maintained with an inert atmosphere of nitrogen was charged with tert-butyl 4-(4-((tert-butyldiphenylsilyl)oxy)-3-methyltetrahydrofuran-3-yl)piperazine-1-carboxylate 43 (32.1 g, 61.2 mmol). DCM (321 mL) was added followed by HCl (45.9 ml, 184 mmol, 4 N in EtOAc) at 0° C. under $N_2$. The resultant solution was stirred at 25° C. for 16 h. The solvent was evaporated under reduced pressure and water (300 mL) was added. To the mixture was added sat. aq. of $NaHCO_3$ to adjust the pH of the solution to 7-8. The aqueous phase was extracted with ethyl acetate (3×300 mL) and the organic layers were combined and dried over $Na_2SO_4$ and concentrated to afford the title compound 44. MS (ESI): m/z calc'd for $C_{25}H_{36}N_2O_2Si$ $[M+H]^+$: 425, found 425. $^1H$ NMR (400 MHz, DMSO-$d_6$, 25° C.) δ 9.49 (s, 1H), 7.73-7.71 (m, 2H), 7.71-7.62 (m, 2H), 7.49-7.36 (m, 6H), 4.00-3.97 (m, 2H), 3.89-3.83 (m, 2H), 3.61 (d, J=6.8 Hz, 1H), 3.02 (s, 4H), 2.72-2.58 (m, 4H), 1.03 (s, 9H), 0.94 (s, 3H).

Scheme 17. Synthesis of (3R,4R) or (3S,4S) 1-(4-((tert-butyldiphenylsilyl)oxy)-3-methyltetrahydrofuran-3-yl)piperazine (45 or 46)

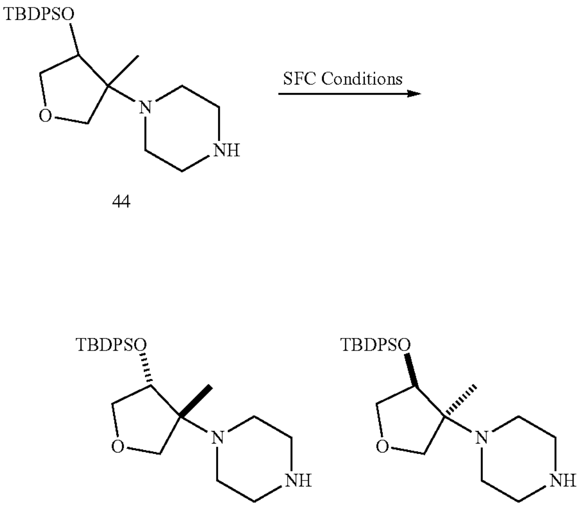

44

45 46

1-(4-((tert-butyldiphenylsilyl)oxy)-3-methyltetrahydrofuran-3-yl)piperazine 44 was synthesized according to Scheme 16 shown above. The component enantiomers were separated by chiral preparative SFC (Column & dimensions: Amylose-SC, 5 cm×25 cm; Mobile phase A: $CO_2$; Mobile phase B: MeOH (8 mmol/L $NH_3$·MeOH)) to afford the title compounds 45 ($t_R$=4.63 min) and 46 ($t_R$=5.30 min). MS (ESI): m/z calc'd for $C_{25}H_{36}N_2O_2Si$ $[M+H]^+$: 425, found 425. $^1H$ NMR (400 MHz, DMSO-$d_6$, 25° C.) δ 7.83-7.75 (m, 2H), 7.75-7.67 (m, 2H), 7.50-7.39 (m, 4H), 7.43-7.36 (m, 2H), 4.07 (m, 1H), 4.01 (m, 1H), 3.82 (m, 2H), 3.65 (m, 1H), 2.84 (m, 4H), 2.51 (m, 2H), 2.35 (m, 2H), 2.21 (s, 1H), 1.13 (m, 1H), 1.11 (s, 8H), 0.97-0.92 (m, 3H).

Scheme 18. Synthesis of (R or S)-1-(3-methyltetrahydrofuran-3-yl)piperazine (50)

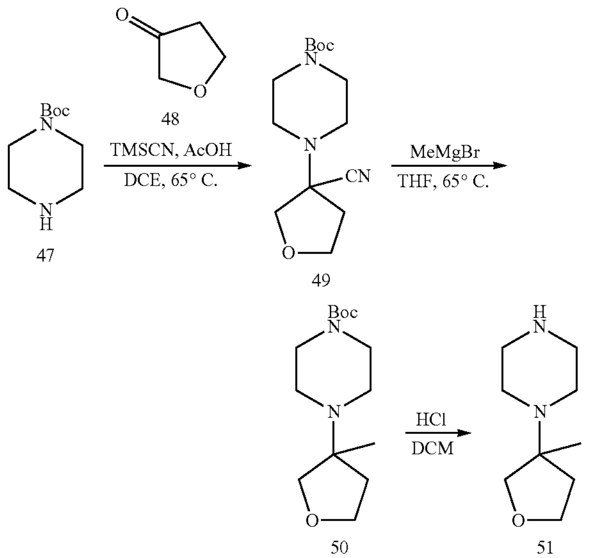

47 48 49 50 51

(R or S) tert-butyl 4-(3-cyanotetrahydrofuran-3-yl)piperazine-1-carboxylate (49) By substituting ketone 48 in an identical procedure to that described in Scheme 16 for the synthesis of 44, the racemic compound 49 was prepared. MS (ESI): m/z calc'd for $C_{14}H_{23}N_3O_3$ $[M+H]^+$: 282, found 282.

(R or S) tert-butyl 4-(3-methyltetrahydrofuran-3-yl)piperazine-1-carboxylate (50) By substituting piperazine 49 in an identical procedure to that described in Scheme 16 for the synthesis of 39, the racemic compound 50 was prepared. MS (ESI): m/z calc'd for $C_{14}H_{26}N_2O_3$ $[M+H]^+$: 271, found 271.

(R or S) 1-(3-methyltetrahydrofuran-3-yl)piperazine (51) By substituting piperazine 50 in an identical procedure to that described in Scheme 16 for the synthesis of 44, the racemic compound 51 was prepared. MS (ESI): m/z calc'd for $C_9H_{18}N_2O$ $[M+H]^+$: 172, found 172.

Scheme 19. Synthesis of (3R,4R) or (3S,4S) tert-butyl 1-(4-((tert-butyldiphenylsilyl)oxy)tetrahydrofuran-3-yl)piperazine (55 or 56)

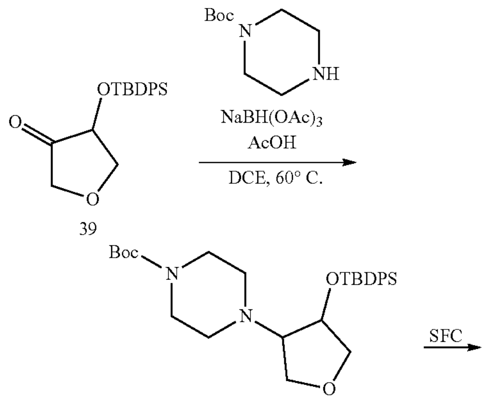

39 52

-continued

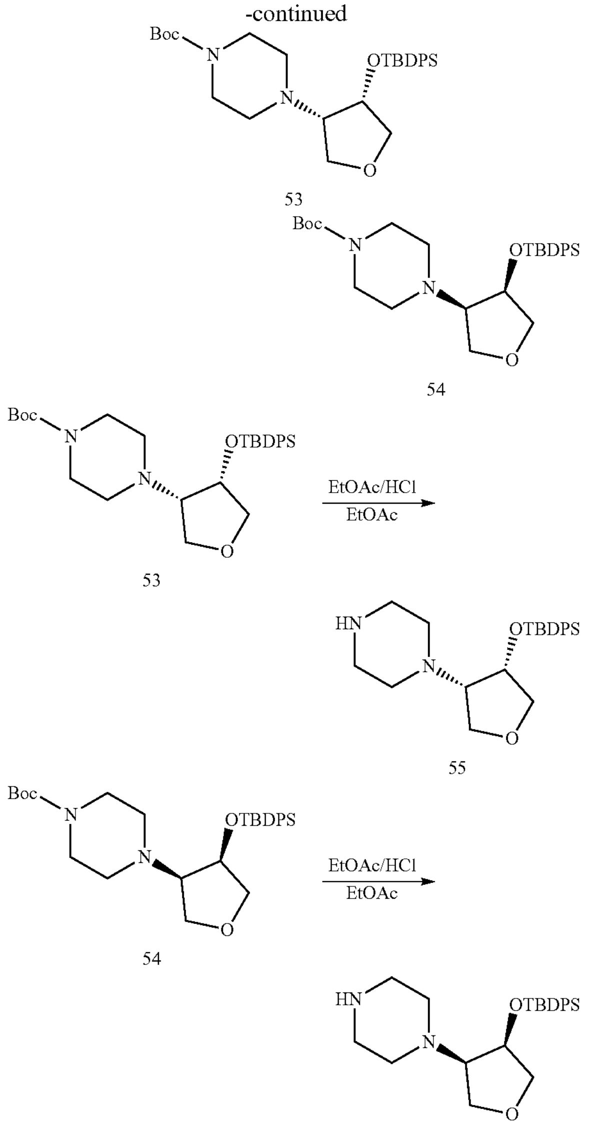

53 54 53 55 54 56

(3R,4R) or (3S,4S) 4-(-4-((tert-butyldiphenylsilyl)oxy)tetrahydrofuran-3-yl)piperazine-1-carboxylate (53 or 54)

A 5 L flask was charged with 4-((tert-butyldiphenylsilyl)oxy)dihydrofuran-3(2H)-one (260 g, 0.77 mol). DCE (2.0 L) was added followed by tert-butyl piperazine-1-carboxylate (215 g, 1.15 mol) and $NaBH(OAc)_3$ (330 g, 1.5 mol). Acetic acid (92 g, 1.5 mol) was added dropwise to the reaction mixture at RT and the resultant mixture was stirred at 60° C. for 2.5 h. The mixture was poured into vigorously stirring sat. aq. $NaHCO_3$(6.0 L). The aqueous phase was extracted with DCM (3×1 L) and the combined organic phases were concentrated under reduced pressure. The resultant crude residue was subjected to purification by flash chromatography over silica gel (ethyl acetate/PE, 0-100%) affording the title compound 52. $^1H$ NMR (400 MHz, $CDCl_3$, 25° C.) 7.39-7.79 (m, 10H), 4.27 (s, 1H), 3.93-4.02 (m, 2H), 3.68-3.83 (m, 2H), 3.37 (s, 4H), 2.59-2.60 (m, 1H), 2.34-2.41 (m, 4H), 1.46 (s, 9H), 1.09 (s, 9H). The racemic material could be resolved to its component enantiomers by chiral preparative SFC (DAICEL CHIRALCEL OJ (250 mm×50 mm); Mobile phase A: $CO_2$; Mobile phase B: EtOH with 0.1% $NH_4OH$) to afford the title compounds 53 ($t_R$=3.40 min) and 54 ($t_R$=4.61 min).

(3R,4R) or (3S,4S) 1-(-4-((tert-butyldiphenylsilyl)oxy) tetrahydrofuran-3-yl)piperazine (55 or 56) To a 5 L flask was added intermediate 53 (110 g, 220 mmol) and ethyl acetate (2.0 L). Hydrochloric acid (350 mL, 4 M in EtOAc) was added dropwise to the reaction mixture at 0° C. The reaction was warmed to 20° C. for 36 h. The reaction mixture was concentrated under reduced pressure and the crude residue was dissolved in ethyl acetate (0.3 L) and filtered. The filter cake was dissolved in water (500 mL) and the pH was adjusted to 8 with sat. aq. $NaHCO_3$. The aqueous solution was extracted with ethyl acetate (2×1.0 L). The organic layers were combined and washed with brine, dried over sodium sulfate and concentrated under reduced pressure. The residue was washed with MTBE (500 mL) and concentrated under reduced pressure to afford the title compound 55. An identical procedure could be used to prepare the enantiomeric title compound 56, substituting starting 54 for 53. MS (ESI): m/z calc'd for $C_{29}H_{42}N_2O_4Si$ $[M+H]^+$: 411, found 411. $^1H$ NMR (400 MHz, DMSO-$d_6$, 25° C.) δ 7.73 (d, J=6.8 Hz, 2H), 7.64 (d, J=6.8 Hz, 2H), 7.39-7.46 (m, 6H), 4.29 (s, 1H), 3.97-4.00 (m, 1H), 3.91-3.93 (m, 1H), 3.84 (m, 1H), 3.70-3.74 (m, 1H), 3.05 (s, 4H), 2.66-2.73 (m, 5H), 1.08 (s, 9H).

Scheme 20. Synthesis of (3R,4R) or (3S,4S) 4-(2,6-diazaspiro[3.3]heptan-2-yl)tetrahydrofuran-3-ol (59)

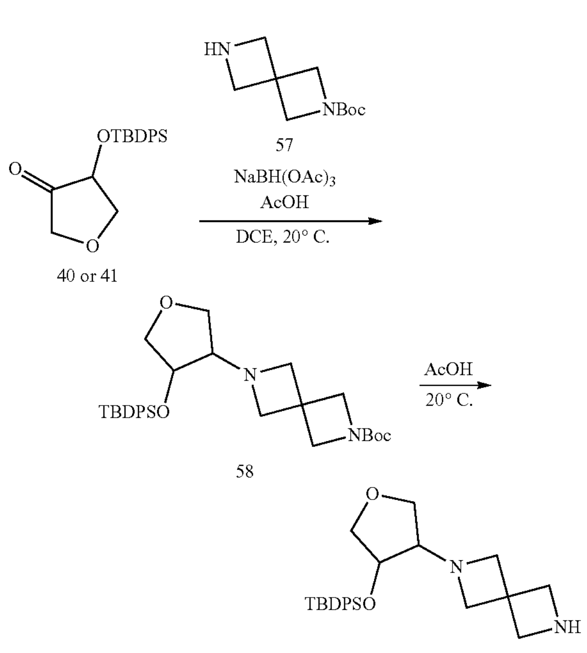

57

40 or 41

58

59

(3R,4R) or (3S,4S) Tert-butyl 6-(4-hydroxytetrahydrofuran-3-yl)-2,6-diazaspiro[3.3]heptane-2-carboxylate (58)

By substituting amine 57 in an identical procedure to that described in Scheme 19 for the synthesis of 52, the enantiopure compound 58 was prepared. MS (ESI): m/z calc'd for $C_{30}H_{42}N_2O_4Si$ $[M+H]^+$: 523, found 523.

(3R,4R) or (3S,4S) 4-(2,6-diazaspiro[3.3]heptan-2-yl)tetrahydrofuran-3-ol (59)

A solution of tert-butyl 6-(4-((tert-butyldiphenylsilyl) oxy)tetrahydrofuran-3-yl)-2,6-diazaspiro[3.3]heptane-2-carboxylate (58) (380 mg, 0.73 mmol) in HCOOH (5.0 mL) was stirred at 20° C. for 16 h. The mixture was concentrated in vacuo and sat. aq. $NaHCO_3$ solution was added to the mixture and stirred for 30 min. Water (10 mL) was added to the suspension. The mixture was extracted with EtOAc (3×10 mL). The combined organic layers were washed with brine (10 mL), dried over anhydrous $Na_2SO_4$ and filtered. The filtrate was concentrated in vauco to give crude 2-(4-((tert-butyldiphenylsilyl)oxy)tetrahydrofuran-3-yl)-2,6-diazaspiro [3.3]heptane (59) (250 mg, 0.53 mmol, 73% yield). MS (ESI): m/z calc'd for $C_{25}H_{34}N_2O_2Si$ $[M+H]^+$: 423, found 423.

Scheme 21. Synthesis of 6-chloro-7-(4-(3-methyloxetan-3-yl)piperazin-1-yl)quinazolin-2-amine

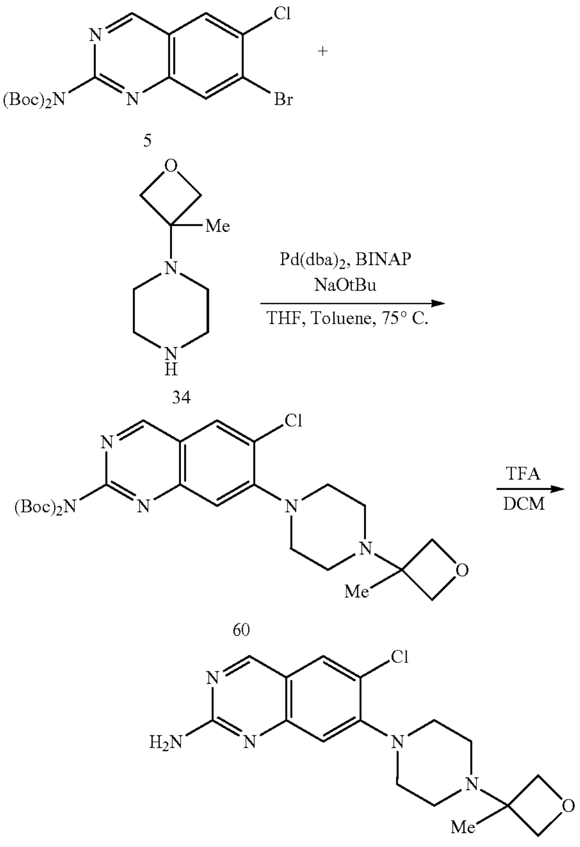

5

34

60

61

Tert-butyl (6-chloro-7-(4-(3-methyloxetan-3-yl)piperazin-1-yl)quinazolin-2-yl)carbamate (60)

A 3-L 3-necked round-bottom flask purged and maintained with an inert atmosphere of nitrogen was charged with tert-butyl N-(7-bromo-6-chloroquinazolin-2-yl)-N-(tert-butoxycarbonyl)carbamate 5 (50.0 g, 108 mmol). THF (500 mL, 6.2 mol), toluene (500 mL, 4.7 mol), 1-(3-methyloxetan-3-yl)piperazine 34 (22.1 g, 141 mmol), NaOtBu (20.9 g, 217 mmol), Pd(dba)$_2$ (6.3 g, 11 mmol), and BINAP (6.8 g, 11 mmol) were added. The resultant mixture was stirred at 75° C. for 18 h. The reaction mixture was quenched with $H_2O$ (500 mL) and the aqueous layer was extracted with ethyl acetate (3×250 mL). The organic phases were combined, dried over anhydrous sodium sulfate, and concentrated under reduced pressure. The crude product was re-crystallized from ethyl acetate:PE in the ratio of 1:5. The solids were collected by filtration to afford the title compound 60.

6-Chloro-7-(4-(3-methyloxetan-3-yl)piperazin-1-yl) quinazolin-2-amine (61)

A 5-L 3-necked round-bottom flask purged and maintained with an inert atmosphere of nitrogen was charged with tert-butyl N-[6-chloro-7-[4-(3-methyloxetan-3-yl)piperazin-1-yl]quinazolin-2-yl]carbamate 60 (110 g, 253 mmol). DCM (1.65 L, 26.0 mol) was added followed by the addition of trifluoroacetaldehyde (1.1 L) dropwise with stirring at 25° C. The resultant solution was stirred at 25° C. for 4 h. The reaction mixture was concentrated under reduced pressure and the residue was dissolved in $H_2O$. The pH of the solution was adjusted to 10 with $K_2CO_3$. The solids were collected by filtration to afford the title compound 61. MS (ESI): m/z calc'd for $C_{16}H_{20}ClN_5O$ $[M+H]^+$: 334, found 334. $^1$H NMR: (300 MHz, $CDCl_3$, 25° C.): δ 8.86 (s, 1H), 7.73 (s, 1H), 7.11 (s, 1H), 5.49 (s, 2H), 4.70 (d, J=5.6 Hz, 2H), 4.30 (d, J=5.7 Hz, 2H), 3.31 (s, 4H), 2.63 (t, J=4.8 Hz, 4H), 1.48 (s, 3H).

Scheme 22. Synthesis of (1R,5S,8R)-8-methyl-3-azabicyclo[3.2.1]octan-8-ol

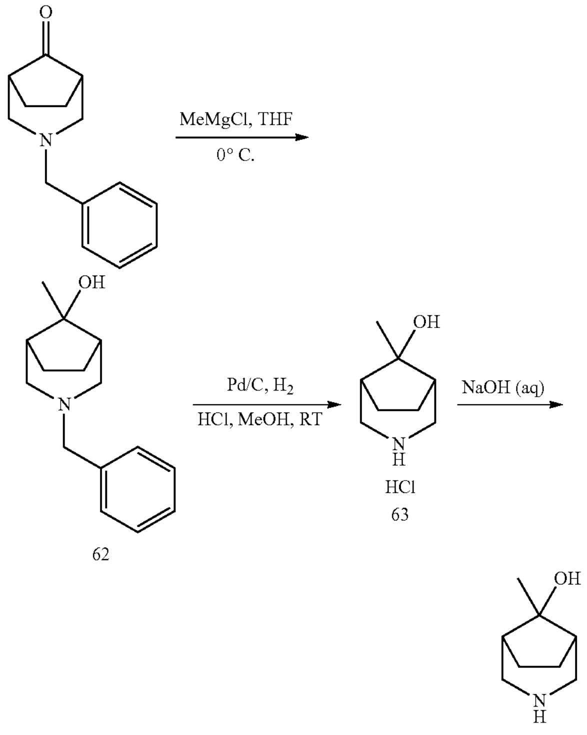

62

63

64

(1R,5S,8R)-3-benzyl-8-methyl-3-azabicyclo[3.2.1] octan-8-ol (62)

To a mixture of (1R,5S)-3-benzyl-3-azabicyclo[3.2.1]octan-8-one (220 g, 1.0 mol) in THF (2.2 L) was added MeMgCl (1.0 L, 3 M in THF) dropwise at 0° C. The resultant mixture was stirred at 0° C. for 30 min. The reaction was quenched by the addition of saturated $NH_4Cl$ solution (2.0 L), the solid was filtered out, and the filter cake was wash with ethyl acetate (2.0 L). The organic phase was separated and washed with brine (3×500 mL), dried over $Na_2SO_4$ and concentrated under reduced pressure. The resultant crude residue was subjected to purification by flash chromatography over silica gel (EtOAc/PE, 10%) affording the title compound 62. MS (ESI): m/z calc'd for $C_{15}H_{21}NO$ $[M+H]^+$: 232, found 232.

(1R,5S,8R)-8-methyl-3-azabicyclo[3.2.1]octan-8-ol hydrochloride (63)

To a solution of (1R,5S,8S)-3-benzyl-8-methyl-3-azabicyclo[3.2.1]octan-8-ol 63 (145 g, 630 mmol) in MeOH (1.5 L) was added Pd/C (70 g, 5 wt %) and HCl (145 mL) under $H_2$ atmosphere. The reaction was stirred at RT for 12 h. At this time the solid was filtered out and the filtrate was concentrated under reduced pressure. The crude residue was redissolved in ethyl acetate (145 mL) and filtered. The solids were collected by filtration to afford the title compound 63. MS (ESI): m/z calc'd for $CsH_{15}NO$ $[M+H]^+$: 142, found 142. $^1$H NMR: (300 MHz, $CD_3OD$, 25° C.) δ 3.68-3.64 (m, 2H), 3.00-2.96 (m, 2H), 2.06-1.93 (m, 4H), 1.85-1.78 (m, 2H), 1.32 (s, 3H).

(1R,5S,8R)-8-methyl-3-azabicyclo[3.2.1]octan-8-ol (64)

The free amino alcohol can be obtained by treating a solution of 8-methyl-3-azabicyclo[3.2.1]octan-8-ol hydrochloride 63 (1.38 g, 7.77 mmol) in 20 mL of water with sodium hydroxide (7.77 mL, 7.77 mmol, 1 M). The free amino alcohol was extracted with 4:1 chloroform/IPA (2×75 mL). The combined organic extracts were dried over sodium sulfate, filtered, and concentrated under reduced pressure to afford the title compound 64, which was used without further purification. MS (ESI): m/z calc'd for $C_8H_{15}NO$ $[M+H]^+$: 142, found 142.

Scheme 23. Synthesis of 1-(bycyclo[1.1.1]pentan-1-yl)-4-iodo-1-H-pyrazole

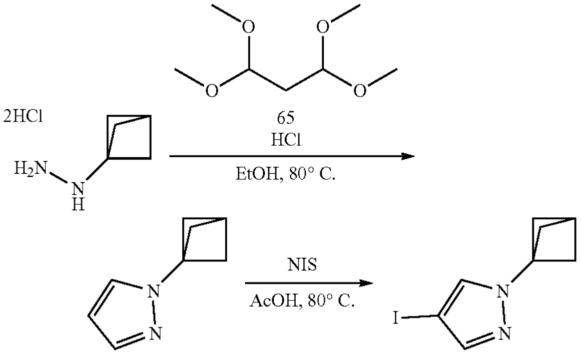

65

66

67

1-(Bicyclo[1.1.1]pentan-1-yl)-1H-pyrazole (66)

Bicyclo[1.1.1]pentan-1-ylhydrazine bis-HCl (20.0 g, 117 mmol), 1,1,3,3-tetramethoxypropane 65 (19.2 g, 117 mmol), and EtOH (140 mL) were added to a 250 mL three-necked round-bottom flask. Concentrated hydrogen chloride (36.9 g, 374 mmol) was added to the suspension in one portion, and the suspension stirred at 80° C. for 16 h. The reaction was cooled and quenched with $H_2O$ (500 mL), then extracted with DCM (5×200 mL). The combined organic phases were dried over $Na_2SO_4$ and concentrated carefully (product is volatile) under reduced pressure to afford the title compound 66. The crude product was carried on to the next step without further purification. $^1$H NMR: (400 MHz, DMSO-$d_6$, 25° C.) δ 7.72 (d, J=2.2 Hz, 1H), 7.45 (s, 1H), 6.25 (t, J=2.0 Hz, 1H), 2.60 (s, 1H), 2.21 (s, 6H). MS (EI): m/z calc'd for $C_8H_{10}N_2$ $[M-H]^-$: 133, found 133.

1-(Bicyclo[1.1.1]pentan-1-yl)-4-iodo-1H-pyrazole (67)

1-(Bicyclo[1.1.1]pentan-1-yl)-1H-pyrazole 66 (15.3 g, 114 mmol) and NIS (25.6 g, 114 mmol) were dissolved in acetic acid (381 mL). The resultant mixture was stirred at 80° C. for 2 h. The reaction mixture was cooled and concentrated under reduced pressure. The resultant crude residue was subjected to purification by flash chromatography over silica gel (3:1 EtOAc/PE, 0-70%) to afford the title compound 67. $^1$H NMR: (400 MHz, DMSO-$d_6$, 25° C.) δ 7.98 (s, 1H), 7.54 (s, 1H), 2.60 (s, 1H), 2.20 (s, 6H). MS (EI): m/z calc'd for $C_8H_9IN_2$ $[M+H]^+$: 261, found 261.

Scheme 24. Synthesis of 4-Bromo-1-(3-methoxymethyl)bicyclo[1.1.1]pentan-1-yl)-1H-pyrazole

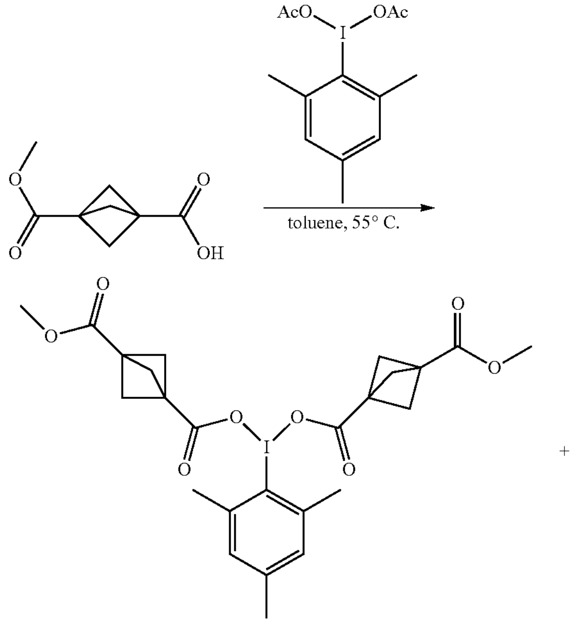

68

-continued

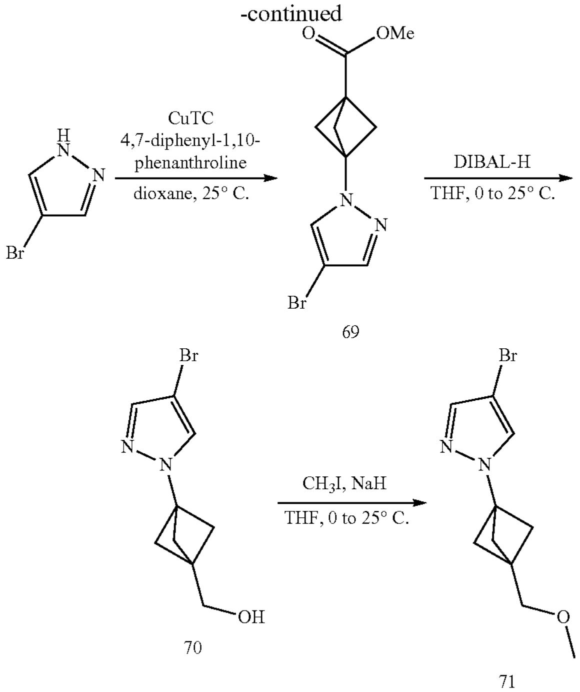

69

70

71

O'1,O1-(mesityl-13-iodanediyl) 3,3'-dimethyl bis (bicyclo[1.1.1]pentane-1,3-dicarboxylate) (68)

A 100 mL round-bottom flask was charged with iodomesitylene diacetate (475 mg, 1.30 mmol), 3-(methoxycarbonyl)bicyclo[1.1.1]pentane-1-carboxylic acid (460 mg, 2.70 mmol) and 25 mL toluene. The flask was attached to a rotary evaporator and a water bath heated to 55° C., and the solvent (and the generated acetic acid) was removed over a period of −10 min. A second 18.5 mL aliquot of toluene was added to the flask and the evaporation step was repeated. The evaporation step was repeated two more times with 12.5 mL toluene each time. After further removal of residual toluene under high vacuum, the title compound 68 was generated and used in next step directly. $^1$H NMR (500 MHz, $CDCl_3$, 25° C.): δ 7.08 (s, 2H), 3.65 (s, 6H), 2.69 (s, 6H), 2.38 (s, 3H), 2.20 (s, 12H).

Methyl 3-(4-bromo-1H-pyrazol-1-yl)bicyclo[1.1.1] pentane-1-carboxylate (69)

A flask was charged with 4-bromo-1H-pyrazole (100 g, 680 mmol), 55 (497 g, 850 mmol) and 4,7-diphenyl-1,10-phenanthroline (33.9 g, 102 mmol), followed by dioxane (3.00 L). Thiophene-2-carbonyloxycopper (38.9 g, 204 mmol) was then added and the reaction stirred at 25° C. for 16 h. The reaction was then filtered and concentrated under reduced pressure to give the crude product. The resultant crude residue was subjected to purification by flash chromatography over silica gel (EtOAc/PE, 5-100%) to afford the title compound 69. $^1$H NMR: (400 MHz, $CDCl_3$, 25° C.) δ 7.51 (s, 1H) 7.46 (s, 1H) 3.75 (s, 3H) 2.56 (s, 5H) 2.49-2.64 (m, 1H). MS (EI): m z calc'd for $C_{10}H_{11}BrN_2O_2$ $[M+H]^+$: 271, found 271.

(3-(4-Bromo-1H-pyrazol-1-yl)bicyclo[1.1.1.]pentan-1-yl)methanol (70)

To a solution of 69, (5.0 g, 18 mmol) in anhydrous THF (75 mL) cooled to 0° C. was added DIBAL-H (55.3 mL, 55.3 mmol 1 M in hexanes) via syringe and the resulting solution was stirred at 0° C. for 2 h. The reaction was quenched by slowly pouring into sat. aq. $NH_4Cl$ solution (100 mL) and allowed to stir vigorously at RT. The resultant mixture was then filtered through Celite® and the organic phases were separated. The mixture was then filtered and concentrated under reduced pressure. The resultant crude residue was subjected to purification by flash chromatography over silica gel (EtOAc/hexanes, 0-80%) to afford the title compound 70. MS (EI): m/z calc'd for $C_9H_{11}IN_2O$ $[M+H]^+$: 291, found 291.

4-Bromo-1-(3-(methoxymethyl)bicyclo[1.1.1]pentan-1-yl)-1H-pyrazole (71)

To a solution of 70 (1.00 g, 4.11 mmol) in anhydrous THF (20 mL) cooled to 0° C. was added in portions over 10 min NaH (200 mg, 5.00 mmol), and the resulting solution stirred for 30 min at 0° C. MeI (0.514 mL, 8.23 mmol) was added dropwise via syringe and the solution was stirred for an additional 2 h, allowing to warm to RT. The reaction was quenched with sat. aq. $NH_4Cl$ (25 mL) and diluted with ethyl acetate (25 mL). The organic phase was separated, dried over sodium sulfate, filtered, and concentrated under reduced pressure. The resultant crude residue was subjected to purification by flash chromatography over silica gel (EtOAc/hexanes, 0-50%) to afford the title compound 71. MS (EI): m/z calc'd for $C_{10}H_{13}BrN_2O$ $[M+H]^+$: 257, found 257.

Scheme 25. Synthesis of 1-(3-fluorobicyclo[1.1.1]pentan-1-yl)-4-iodo-1H-pyrazole

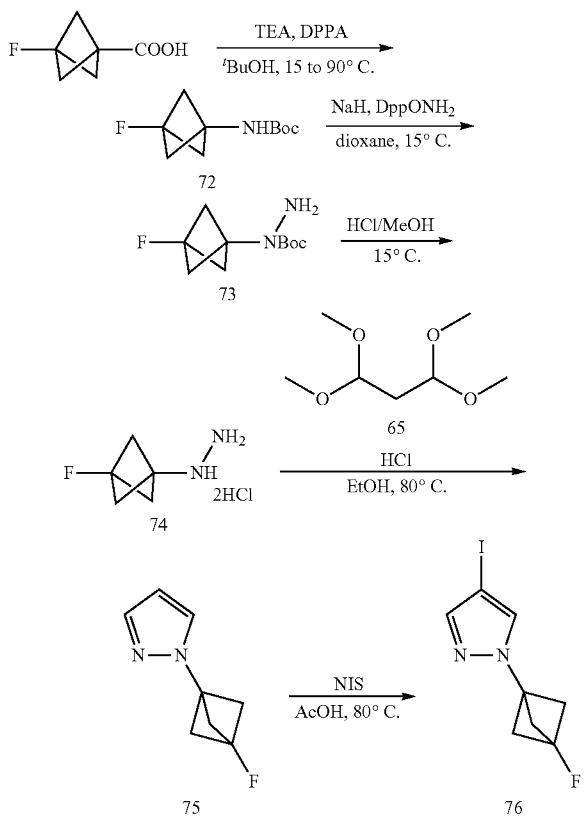

72

73

65

74

75

76

Tert-butyl (3-fluorobicyclo[1.1.1]pentan-1-yl)carbamate (72)

To a flask charged with triethylamine (2.04 g, 20.0 mmol) and fluorobicyclo[1.1.1]pentane-1-carboxylic acid (2.50 g, 19.2 mmol) in anhydrous t-BuOH (25 mL), was added diphenyl azidooxyphosphonate (5.71 g, 19.6 mmol) over 20 min. The resultant mixture was stirred at 15° C. for 2 h and then stirred at 90° C. for 3 h. The reaction mixture was concentrated under reduced pressure and the residue was diluted with MTBE. The resulting mixture was washed with sat. aq. $NaHCO_3$ solution (3×30 mL). The combined organic phases were dried over $Na_2SO_4$, filtered, and concentrated under reduced pressure. The crude residue was subjected to purification by flash chromatography over silica gel (EtOAc/PE, 30-100%) to afford the title compound 72. $^1$H NMR: (400 MHz, $CDCl_3$, 25° C.) δ 2.33 (s, 6H), 1.45 (s, 9H).

Tert-butyl 1-(3-fluorobicyclo[1.1.1]pentan-1-yl)hydrazine-1-carboxylate (73)

NaH (0.39 g, 9.9 mmol, 65% in mineral oil) was added to a solution of tert-butyl (3-fluorobicyclo[1.1.1]pentan-1-yl) carbamate 72 (1.0 g, 5.0 mmol) in dioxane (20 mL) at 15° C. The reaction mixture was stirred at 15° C. for 3 h at which point O-(diphenylphosphinyl)-hydroxylamine (1.51 g, 6.46 mmol) was added. The resulting mixture was stirred at 15° C. for 21 h. The reaction was quenched by the addition of $H_2O$ and the mixture was extracted with EtOAc (5×20 mL). The combined organic phases were dried over $Na_2SO_4$, filtered, and concentrated under reduced pressure. The residue was subjected to purification by flash chromatography over silica gel (EtOAc/PE, 30-100%) to afford the title compound 73. $^1$H NMR: (400 MHz, DMSO-$d_6$, 25° C.) δ 4.50 (s, 2H), 2.28 (d, J=2.1 Hz, 6H), 1.41 (s, 9H).

(3-Fluorobicyclo[1.1.1]pentan-1-yl)hydrazine, HCl salt (74)

To a flask containing tert-butyl 1-(3-fluorobicyclo[1.1.1]pentan-1-yl)hydrazine-1-carboxylate 73 (720 mg, 3.33 mmol) was added HCl (4 M solution in MeOH, 14.4 mL) at 15° C. The reaction was stirred at 15° C. for 6 h. The reaction mixture was concentrated under reduced pressure to afford crude 74 which was used directly in the next step without further purification. $^1$H NMR (400 MHz, DMSO-$d_6$, 25° C.) δ 2.18 (d, J=2.1 Hz, 6H).

1-(3-Fluorobicyclo[1.1.1]pentan-1-yl)-1H-pyrazole (75)

To a flask containing (3-fluorobicyclo[1.1.1]pentan-1-yl) hydrazine, HCl salt 61(500 mg, 2.64 mmol) and 1,1,3,3-tetramethoxypropane 65 (443 mg, 2.70 mmol) in EtOH (5 mL) was added HCl (834 mg, 8.46 mmol) at 15° C. The reaction mixture was stirred at 80° C. for 2 h, then quenched by the addition of $H_2O$, and the aqueous phase was extracted with DCM (5×10 mL). The combined organic phases were dried over $Na_2SO_4$, filtered, and concentrated under reduced pressure to afford the title compound 75. The crude residue was used directly in the next step without further purification. MS (EI): m/z calc'd for $C_8H_9FN_2$ $[M+H]^+$: 153, found 153.

1-(3-Fluorobicyclo[1.1.1]pentan-1-yl)-4-iodo-1H-pyrazole (76)

To a flask containing 1-(3-fluorobicyclo[1.1.1]pentan-1-yl)-1H-pyrazole 75 (400 mg, 8.87 mmol) in acetic acid (10 mL) at 15° C. was added NIS (2.00 g, 5.26 mmol). The resultant mixture was stirred at 80° C. for 16 h. The mixture was concentrated under reduced pressure and the residue was subjected to purification by flash chromatography over silica (EtOAc/PE, 20%) to give the title compound 76. MS (EI): m/z calc'd for $C_8H_8FIN_2$ $[M+H]^+$: 279, found 279; $^1H$ NMR: (400 MHz, DMSO-$d_6$, 25° C.) δ 8.05 (s, 1H), 7.62 (s, 1H), 2.61 (d, J=2.03 Hz, 6H).

Scheme 26. Synthesis of 3-(2-(2H-1,2,3-triazol-2-yl)propan-2-yl)-1-(methyl-d3)-1H-pyrazol-5-amine

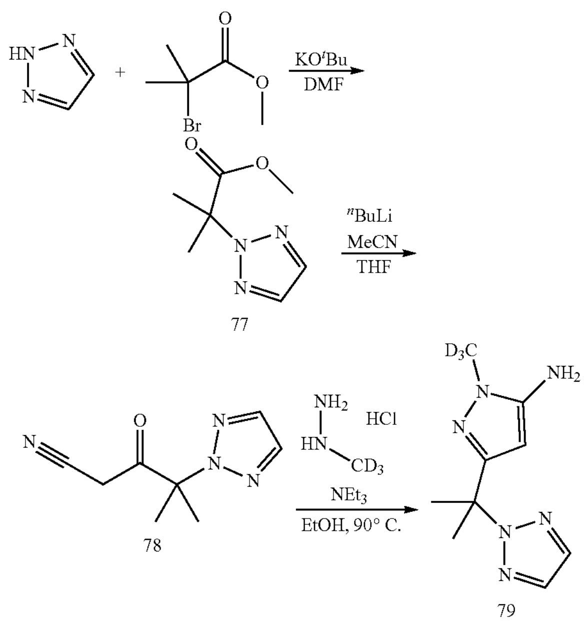

77

78

79

Methyl 2-methyl-2-(2H-1,2,3-triazol-2-yl)propanoate (77)

To a solution of 2H-1,2,3-triazole (10.0 g, 145 mmol) in anhydrous DMF (100 mL) was added potassium tert-butoxide (24.4 g, 217 mmol) at 0° C. under $N_2$. To the reaction mixture was added methyl 2-bromo-2-methylpropanoate (39.3 g, 217 mmol) dropwise and the resultant mixture was stirred at 25° C. for 3 h. The crude mixture was poured into ice-water (300 mL) and stirred for 5 min. The aqueous phase was extracted with EtOAc (3×100 mL) and the combined organic phases were washed with brine (2×100 mL), dried over $Na_2SO_4$, filtered, and concentrated under reduced pressure. The crude product was subjected to purification by flash chromatography over silica (EtOAc/PE, 0-3%) to afford the title compound 77. $^1H$ NMR (400 MHz, $CDCl_3$, 25° C.) δ=7.65 (s, 2H), 3.70 (s, 3H), 1.96 (s, 6H).

4-Methyl-3-oxo-4-(2H-1,2,3-triazol-2-yl)pentanenitrile (78)

To a solution of MeCN (1.1 mL, 22 mmol) in THF (50 mL) was added $^n$BuLi (8.51 mL, 21.3 mmol, 2.5 M) dropwise at −78° C. The resultant mixture was stirred at −78° C. for 50 min. To the mixture was added methyl 2-methyl-2-(2H-1,2,3-triazol-2-yl)propanoate 77 (3.0 g, 18 mmol) at −78° C. and the resultant mixture was stirred at −78° C. for 2 h, then quenched with ice-water and the pH was adjusted to pH 5-6 using HCl (1 N). The aqueous phase was extracted with EtOAc (3×30 mL). The combined organic phases were washed with water (3×10 mL), dried over $Na_2SO_4$, filtered and concentrated under reduced pressure. The crude product was subjected to purification by flash chromatography over silica (EtOAc/PE, 0-25%) to afford the title compound 78. MS (ESI): m/z calc'd for $C_8H_{10}N_4O$ $[M+H]^+$: 179, found 179.

3-(2-(2H-1,2,3-triazol-2-yl)propan-2-yl)-1-(methyl-d3)-1H-pyrazol-5-amine (79)

A flask was charged with 4-methyl-3-oxo-4-(2H-1,2,3-triazol-2-yl)pentanenitrile 78 (720 mg, 4.04 mmol), (methyl-d3)hydrazine hydrochloride (1.5 g, 12 mmol), triethylamine (3.94 mL, 28.3 mmol) and EtOH (40 mL). The resultant mixture was stirred at 90° C. for 3 h at which point the reaction mixture was concentrated under reduced pressure. The crude residue was diluted with water (20 mL) and extracted with EtOAc (3×20 mL). The combined organic layers were dried over $Na_2SO_4$, filtered, and concentrated under reduced pressure to afford the crude product 79 which was used directly in the next step without further purification. MS (ESI): m/z calc'd for $C_9H_{11}D_3N_6$ $[M+H]^+$: 210, found 210.

Scheme 27. Synthesis of 4-bromo-5-chloro-1-((4-dimethyloxetan-2-yl)methyl)-1H-pyrazole

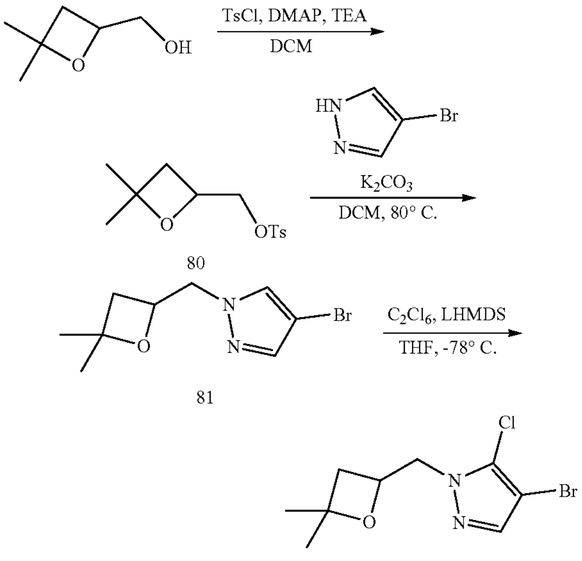

80

81

82

(4,4-Dimethyloxetan-2-yl)methyl 4-methylbenzenesulfonate (80)

A flask was charged with triethylamine (0.17 mL, 1.2 mmol), DMAP (7.4 mg, 0.060 mmol), TsCl (138 mg, 0.723 mmol) and DCM (1.0 mL). To the mixture was added (4,4-dimethyloxetan-2-yl)methanol (70 mg, 0.60 mmol), and the resultant mixture was stirred at 25° C. for 12 h. The reaction mixture was concentrated under reduced pressure and subjected to purification by preparative TLC ($SiO_2$, EtOAc/PE, 50%) to afford the title compound 80. $^1H$ NMR (400 MHz, $CDCl_3$, 25° C.) δ 7.82 (d, J=8.3 Hz, 2H), 7.35 (d, J=8.1 Hz, 2H), 4.72 (m, 1H), 4.10 (d, J=4.2 Hz, 2H), 2.45 (s, 3H), 2.36 (m, 2H), 1.45 (s, 3H), 1.36 (s, 3H).

4-Bromo-1-((4,4-dimethyloxetan-2-yl)methyl)-1H-pyrazole (81)

To a solution of (4,4-dimethyloxetan-2-yl)methyl 4-methylbenzenesulfonate 80 (100 mg, 0.370 mmol) and 4-bromo-1H-pyrazole (65.2 mg, 0.444 mmol) in DMF (2.0 mL) was added $K_2CO_3$ (153 mg, 1.11 mmol). The resultant mixture was stirred at 80° C. for 15 h under $N_2$. The mixture was poured into water (10 mL), and EtOAc (10 mL) was added. The aqueous phase was extracted with EtOAc (2×10 mL), and the combined layers were concentrated under reduced pressure and subjected to purification by preparative TLC ($SiO_2$, EtOAc/PE, 50%) to afford the title compound 81. MS (ESI): m/z calc'd for $C_9H_{13}BrN_2O$ $[M+H]^+$: 245, found 245; $^1H$ NMR (400 MHz, $CDCl_3$, 25° C.) δ 7.57 (s, 1H), 7.48 (s, 1H), 4.88 (m, 1H), 4.28 (d, J=4.4 Hz, 2H), 2.41-2.34 (m, 1H), 2.21 (m, 1H), 1.47 (s, 3H), 1.21 (s, 3H).

4-Bromo-5-chloro-1-((4,4-dimethyloxetan-2-yl)methyl)-1H-pyrazole (82)

To a solution of 4-bromo-1-((4,4-dimethyloxetan-2-yl)methyl)-1H-pyrazole 81 (80 mg, 0.33 mmol) in THF (5 mL) at −78° C. was added LHMDS (0.98 mL, 0.98 mmol, 1.0 M) dropwise. The resultant mixture was stirred at −78° C. for 30 min at which point perchloroethane (100 mg, 0.424 mmol) as a solution in THF (1 mL) was added. The reaction mixture was stirred at −78° C. for 1 h then allowed to warm to 25° C. and stir for 12 hours at that temperature. The resultant mixture was poured into water (10 mL), and the organic phase was separated. The aqueous phase was extracted with EtOAc (2×10 mL), and the combined organic layers were washed with brine (10 mL), dried over $Na_2SO_4$ and filtered. The filtrate was concentrated under reduced pressure to give the crude residue which was subjected to purification by preparative TLC ($SiO_2$, EtOAc/PE, 33%) to afford the title compound 82. MS (ESI): m/z calc'd for $C_9H_{12}BrClN_{20}$ $[M+H]^+$: 279, found 279; $^1H$ NMR (400 MHz, $CDCl_3$, 25° C.) δ 7.54 (s, 1H), 4.98-4.84 (m, 1H), 4.35 (d, J=5.5 Hz, 2H), 2.47-2.40 (m, 1H), 2.39-2.31 (m, 1H), 1.45 (s, 3H), 1.25 (s, 3H)

Scheme 28. Synthesis of 4-bromo-1-cyclopropyl-5-(difluoromethyl)-1H-pyrazole

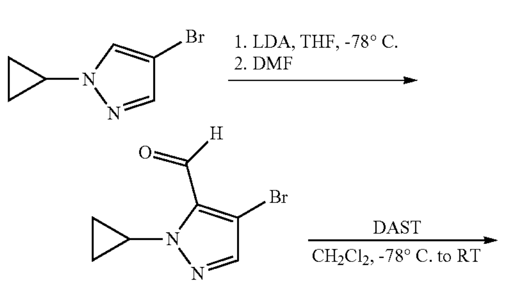

83

-continued

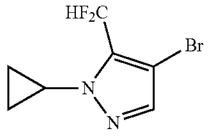

84

4-bromo-1-cyclopropyl-1H-pyrazole-5-carbaldehyde (83)

A 250-mL round-bottom flask was charged with 4-bromo-1-cyclopropyl-1H-pyrazole (2.50 g, 13.4 mmol) under inert atmosphere. THF (10 mL) was added, and the mixture was cooled to −78° C. with stirring. To the mixture at this temperature was slowly added lithium diisopropylamide (1 M in THF/hexanes, 20.0 mL). The mixture was held at this temperature with stirring for 1.5 hrs, at which point DMF (1.55 mL) was slowly added. The mixture was stirred overnight, allowing the dry ice bath to warm to RT. Water (20 mL) was added, and the mixture was stirred for 20 min. The mixture was then transferred to a separatory funnel where it was diluted into additional water (50 mL) and extracted with DCM (3×50 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 83. MS (ESI): m/z calc'd for $C_7H_8BrN_2O$ $[M+H]^+$: 215, found 215.

4-bromo-1-cyclopropyl-5-(difluoromethyl)-1H-pyrazole (84)

A 50-mL Corning™ Falcon™ tube was charged with 4-bromo-1-cyclopropyl-1H-pyrazole-5-carbaldehyde 83 (1.00 g, 4.65 mmol) under inert atmosphere. DCM (10 mL) was added, and the mixture was cooled to −78° C. To the mixture at this temperature was slowly added DAST (1 M in DCM, 14.0 mL). Upon complete addition, the reaction was stirred overnight, allowing the dry ice bath to warm to RT. Water (20 mL) was added and the mixture was transferred to a separatory funnel containing an excess of sat. aq. $NaHCO_3$. The phases were mixed vigorously, then separated. The aqueous phase was then extracted with additional DCM (2×40 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 84. MS (ESI): m/z calc'd for $C_7H_8BrF_2N_2$ $[M+H]^+$: 236, found 236.

General Synthetic Schemes and Preparative Examples

The compounds of the invention may be prepared by methods known in the art of organic synthesis as set forth in part by the following general synthetic schemes and specific preparative examples. Starting materials are available commercially or may be prepared by known methods.

General Scheme 1

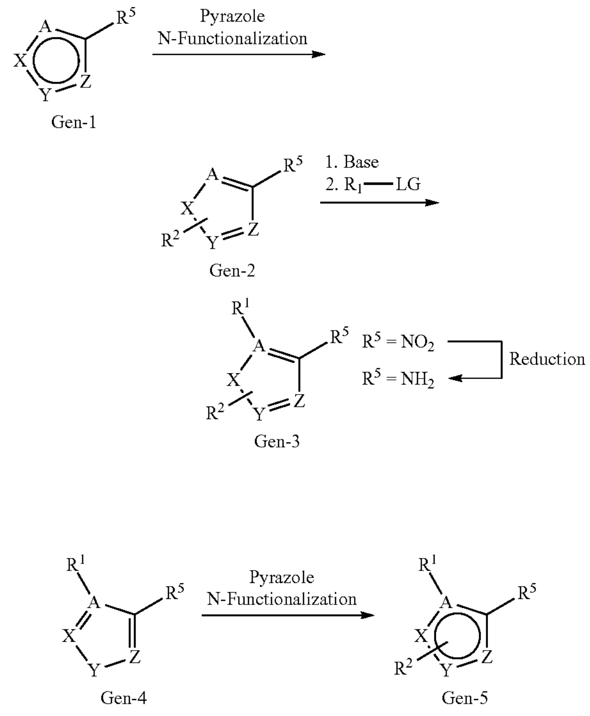

A= C, N
X = C, N
Y = C, N, S
Z = C, N, S
$R^1$ = Cl, H, Me
$R^2$ = alkyl
$R^5$ = Br, I, $NO_2$ In General Scheme 1, commercially available or synthetically prepared 4-substituted pyrazoles Gen-1 could be alkylated using a number of synthetic transformations commonly known to those skilled in the art, including, but not limited to, base-mediated alkylation, a Mitsunobu reaction, an epoxide-opening reaction, or a Chan-Lam coupling reaction to afford N-alkyl pyrazoles Gen-2. A number of intermediates of the form Gen-2 are available commercially, including isothiazoles of the depicted substitution pattern. Likewise, isothiazoles in this substitution pattern can be accessed synthetically by known methods. In cases where Gen-2 is a pyrazole, it could optionally be functionalized at the 5-position by treatment with strong base followed by reaction with an electrophile (chlorination or methylation, for example) to form Gen-3. In instances of Gen-3 where $R_1$=$NO_2$, reduction to the corresponding aniline was performed. In an alternate route, commercially available or synthetically prepared 3,4-disubstituted pyrazoles Gen-4 could be alkylated using similar transformations to those performed on Gen-1. These transformations typically afforded a mixture of 1,4,5-trisubstituted-pyrazoles (i.e. Gen-3), and 1,3,4-trisubstituted-pyrazoles, which together are represented as Gen-5. representative preparative examples from each sequence are described in more detail below.

Scheme 29. Synthesis of 5-chloro-1-((3R,4S)-3-methyl-1-(oxetan-3-yl)piperidin-4-yl)-1H-pyrazol-4-amine

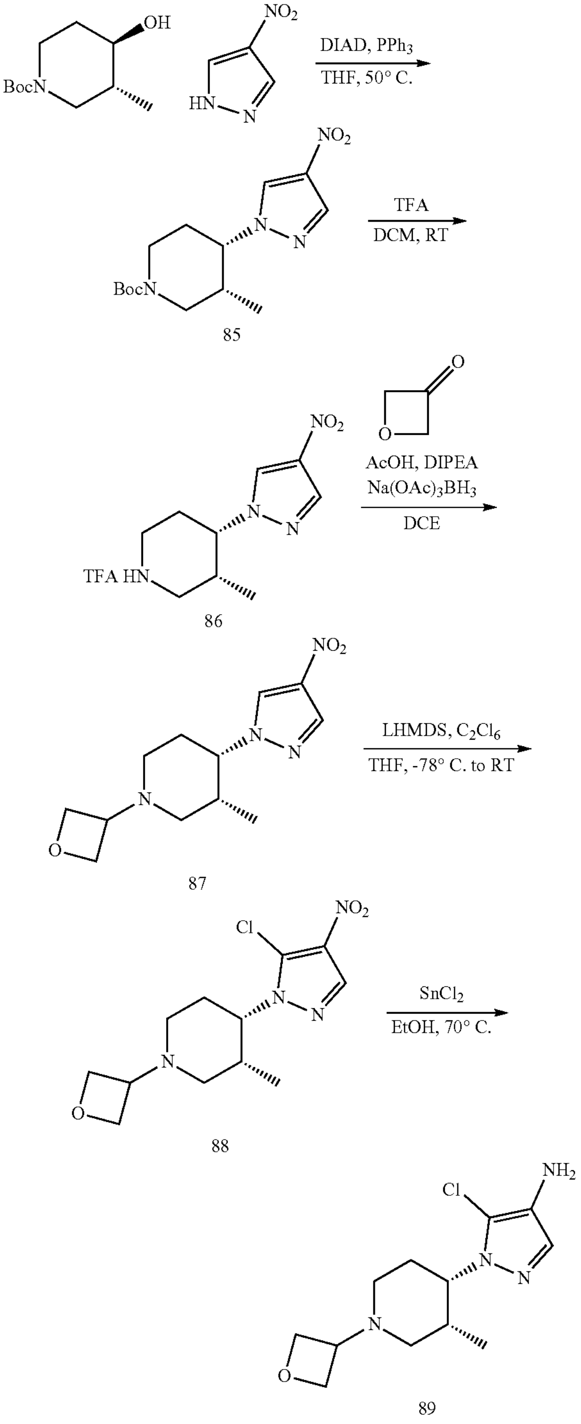

Tert-butyl (3R,4S)-3-methyl-4-(4-nitro-TH-pyrazol-1-yl)piperidine-1-carboxylate (85)

A microwave vial was charged with tert-butyl (3R,4R)-4-hydroxy-3-methylpiperidine-1-carboxylate (2.0 g, 9.3 mmol), 4-nitro-TH-pyrazole (1.05 g, 9.29 mmol), DIAD (3.21 g, 13.9 mmol), and triphenylphosphine (3.65 g, 13.9 mmol). The vial was sealed and purged with $N_2$. THF (12.4 mL) was added and the resultant mixture was stirred at 50° C. for 18 h. The mixture was transferred to a recovery flask and the solvent removed under reduced pressure. The crude residue was then extracted with ice cold diethyl ether, and the combined organic phases were filtered through a plug of silica. The filtrate was then concentrated under reduced pressure and subjected to purification by flash chromatography over silica gel (EtOAc/hexanes, 10-100%) to afford the title compound 85. Only the free N—H piperdine was detected by LC/MS. MS (ESI): m/z calc'd for $C_9H_{14}N_4O_2$ $[M+H]^+$: 211, found 211.

(3R,4S)-3-methyl-4-(4-nitro-TH-pyrazol-1-yl)piperidine TFA salt (86)

A vial was charged with tert-butyl (3R,4S)-3-methyl-4-(4-nitro-1H-pyrazol-1-yl)piperidine-1-carboxylate 85 (550 mg, 1.77 mmol). The vial was then evacuated and purged with $N_2$ (3×). Then, under a positive flow of $N_2$ anhydrous DCM (10 mL) and TFA (0.55 mL, 7.1 mmol) were added and the resultant mixture was stirred at RT for 5 h. DCM and TFA were removed under reduced pressure to afford the title compound 86 and the material was carried forward without purification.

(3R,4S)-3-methyl-4-(4-nitro-1H-pyrazol-1-yl)-1-(oxetan-3-yl)piperidine (87)

A vial containing 86 was dissolved in DCE (10 mL), and DIPEA (0.454 mL, 2.66 mmol) was added via syringe. The resultant mixture was stirred at RT for 15 min at which time oxetan-3-one (0.28 mL, 4.4 mmol) and sodium triacetoxyborohydride (750 mg, 3.5 mmol) were added. Finally, acetic acid (0.12 mL, 2.1 mmol) was added and the resultant mixture was stirred at 35° C. for 18 h. The reaction was diluted with DCM and quenched by pouring into sat. aq. $NaHCO_3$(100 mL). The phases were separated and the aqueous phase was extracted with DCM (1×50 mL). The combined organic phases were washed with brine, dried over $Na_2SO_4$, and the solvent removed under reduced pressure. The crude residue was subject to purification by flash chromatography over silica gel (EtOAc/hexanes, 10-100%) to afford the title compound 87. MS (ESI): m/z calc'd for $C_{12}H_{18}N_4O_3$ $[M+H]^+$: 267, found 267.

(3R,4S)-4-(5-chloro-4-nitro-1H-pyrazol-1-yl)-3-methyl-1-(oxetan-3-yl)piperidine (88)

A vial was charged with (3R,4S)-3-methyl-4-(4-nitro-1H-pyrazol-1-yl)-1-(oxetan-3-yl) piperidine 87 (170 mg, 0.64 mmol). The vial was then evacuated and purged with $N_2$ (3×). THF (4.5 mL) was added and the resultant mixture was stirred at −78° C. To the stirring mixture, LHMDS (0.77 mL, 0.77 mmol) was added via syringe and the resultant mixture was stirred at −78° C. under $N_2$ for 2 h. In a separate flask, a solution of perchloroethane (181 mg, 0.766 mmol) in anhydrous THF (1.5 mL) was prepared and transferred via syringe to the stirring solution of 87. The resultant mixture was stirred at −78° C. for 10 min, then the dry ice bath was removed, and the solution was allowed to slowly warm to RT and stir for an additional 2 h. The reaction mixture was carefully quenched by the addition of sat. aq. $NH_4Cl$ and diluted with EtOAc. The phases were separated and the aqueous phase was extracted with EtOAc (1×50 mL). The combined organic phases were washed with brine (50 mL), dried over $Na_2SO_4$, and the solvent removed under reduced pressure. The crude residue was subjected to purification by flash chromatography over silica gel (3:1 EtOAc:EtOH/hexanes, 20-100%) to afford the title compound 88. MS (ESI): m/z calc'd for $C_{12}H_{17}ClN_4O_3$ $[M+H]^+$: 301, found 301.

5-chloro-1-((3R,4S)-3-methyl-1-(oxetan-3-yl)piperidin-4-yl)-1H-pyrazol-4-amine (89)

A vial was charged with (3R,4S)-4-(5-chloro-4-nitro-1H-pyrazol-1-yl)-3-methyl-1-(oxetan-3-yl)piperidine 88 (17 mg, 0.057 mmol) and tin chloride (54 mg, 0.28 mmol). Ethanol (3 mL) was added, and the resultant mixture was stirred at 70° C. for 4 h, then allowed to cool to RT. The mixture was carefully poured onto ice and the pH adjusted to 7-8 by addition of sat. aq. $NaHCO_3$. The phases were separated, and the aqueous phase was extracted with EtOAc (2×50 mL). The combined organic phases were washed with brine (50 mL), dried over $Na_2SO_4$, and concentrated under reduced pressure to afford the title compound 89. This material was carried on directly without further purification. MS (ESI): m/z calc'd for $C_{12}H_{19}ClN_4O$ $[M+H]^+$: 271, found 271.

Scheme 30. Synthesis of 4-(4-bromo-5-chloro-1H-pyrazol-1-yl)-1-(3-methyloxetan-3-yl)piperidine

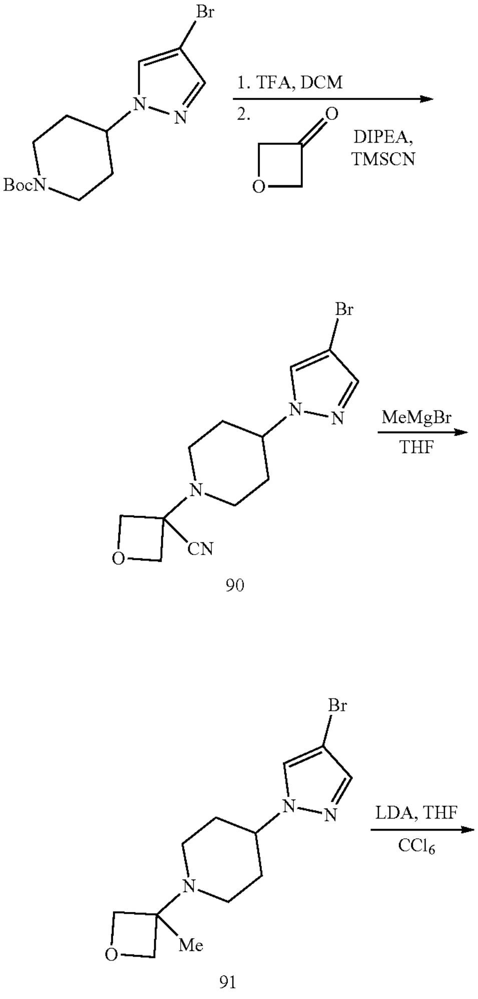

-continued

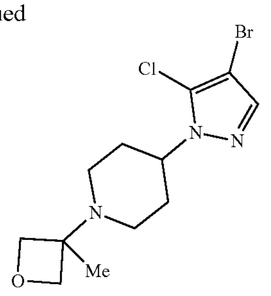

92

3-(4-(4-Bromo-1H-pyrazol-1-yl)piperidin-1-yl)oxetane-3-carbonitrile (90)

A 20 mL vial was charged with tert-butyl 4-(4-bromo-1H-pyrazol-1-yl)piperidine-1-carboxylate (1.5 g, 4.5 mmol). DCM (11.4 mL) and trifluoroacetic acid (0.30 mL, 3.9 mmol) were added, and the reaction mixture was stirred at RT for 4 h. The crude mixture was concentrated under reduced pressure. The crude product was diluted in DCE (11.4 mL) and DIPEA (3.96 mL, 22.7 mmol) and oxetan-3-one (0.665 mL, 11.4 mmol) was added. The reaction mixture was stirred at RT for 20 min after which trimethylsilanecarbonitrile (0.682 mL, 5.45 mmol), and acetic acid (0.312 mL, 5.45 mmol) were added. The reaction mixture was heated to 70° C., and the components were stirred overnight. The crude reaction mixture was concentrated, diluted in DCM (20 mL) and sat. aq. $NaHCO_3$ was added (100 mL). The aqueous layer was extracted with DCM (3x50 mL), and the organic layers were combined, dried, and concentrated under reduced pressure to afford the title compound 90. No further purification was performed, and the crude mixture was carried forward without any purification. MS (ESI): m/z calc'd for $C_{12}H_{16}BrN_4O$ $[M+H]^+$: 311, found 311.

4-(4-Bromo-1H-pyrazol-1-yl)-1-(3-methyloxetan-3-yl)piperidine (91)

A 20 mL vial was charged with 3-(4-(4-bromo-1H-pyrazol-1-yl)piperidin-1-yl)oxetane-3-carbonitrile 90 (700 mg, 2.25 mmol), and THF (5.2 mL) was added. To the stirring mixture was added MeMgBr (3.31 mL, 11.3 mmol, 3.4 M in 2-MeTHF) under $N_2$. The reaction mixture was stirred at 65° C. for 3 h under a positive pressure of $N_2$. The vial was removed from the heat and cooled to RT. The reaction was quenched with 1 M NaOH (20 mL) and extracted with DCM (3x50 mL). The combined organic layers were dried over $Na_2SO_4$, filtered, and concentrated under reduced pressure. The resultant crude residue was subjected to purification by flash chromatography over silica gel (ethyl acetate/hexanes, 0-100%) affording the title compound 91. MS (ESI): m/z calc'd for $C_{12}H_{19}BrN_3O$ $[M+H]^+$: 300, found 300.

4-(4-Bromo-5-chloro-1H-pyrazol-1-yl)-1-(3-methyloxetan-3-yl)piperidine (92)

LDA was freshly prepared by charging a round bottom flask with diisopropylamine (0.57 mL, 4.0 mmol) in THF (12 mL) and was chilled to −78° C. $^n$BuLi (2.3 ml, 3.7 mmol) was added dropwise and the reaction was stirred at −78° C. for 5 min. 4-(4-Bromo-1H-pyrazol-1-yl)-1-(3-methyloxetan-3-yl)piperidine 91 (1.0 g, 3.3 mmol) was dissolved in THF (3 mL) and was added dropwise to the solution of LDA. The resultant mixture was stirred at −78° C. for 15 min, then hexachloroethane (0.95 g, 4.0 mmol) in THF (2 mL) was added dropwise. The reaction was stirred at −78° C. for 15 min and then at RT for 3 h. The reaction mixture was quenched by the addition of sat. aq. $NH_4Cl$ solution. The aqueous phase was extracted with ethyl acetate (3x50 mL), dried over magnesium sulfate, and concentrated under reduced pressure. The resultant crude residue was subjected to purification by flash chromatography over silica gel (ethyl acetate/hexanes, 0-100%) affording the title compound 92. MS (ESI): m/z calc'd for $C_{12}H_{18}BrClN_3O$ $[M+H]^+$: 334, found 334.

Scheme 31. Synthesis of 5-chloro-1-(2,2-difluoroethyl)-1H-pyrazol-4-amine

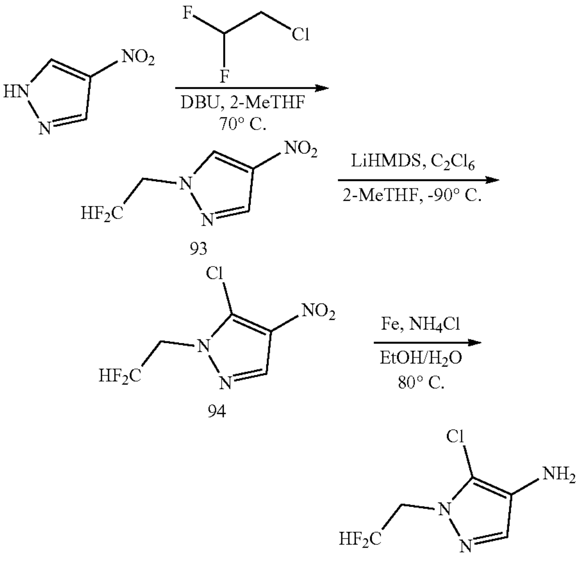

93

94

95

1-(2,2-Difluoroethyl)-4-nitro-1H-pyrazole (93)

A 10-L 4-necked round-bottom flask was charged with 4-nitropyrazole (300 g, 2.65 mol) under inert atmosphere. 2-MeTHF (3 L) was added, followed by DBU (808 g, 5.31 mol), and ultimately 2-chloro-1,1-difluoroethane (653 g, 7.96 mol). The resultant solution was warmed to 70° C. and stirred for 18 h at this temperature. Upon cooling to RT, the reaction was quenched by the addition of ice water. Phases were separated, and the aqueous phase was extracted with 2-MeTHF (2x1 L). The combined organic layers were dried over $MgSO_4$ and filtered. Solvent volume was reduced to under reduced pressure. This form of the title compound 93 was used directly in the next step without further purification.

5-Chloro-1-(2,2-difluoroethyl)-4-nitro-1H-pyrazole (94)

A 10-L 4-necked round-bottom flask was charged with a solution of 1-(2,2-difluoroethyl)-4-nitropyrazole 93 in 2-MeTHF (3.3 L) and hexachloroethane (529 g, 2.24 mol) under inert atmosphere. The solution was cooled to −90° C., and to the stirring mixture was added LHMDS (1 M, 2.23 L)

dropwise over 2 h. The resultant solution was stirred for an additional 1 h at this temperature, then quenched by the addition of sat. aq. $NH_4Cl$. Phases were separated, and the aqueous phase was extracted with 2-MeTHF (2×1 L). The combined organic layers were washed with $H_2O$ (2×1 L), dried over $MgSO_4$, and filtered. Solvent was removed under reduced pressure, and this form of the title compound 94 was used without further purification. MS (ESI):

m/z calc'd for $C_5H_5ClF_2N_3O_2$ $[M+H]^+$: 212, found 212; $^1$H NMR (400 MHz, $CDCl_3$, 25° C.) δ: 8.57 (s, 1H), 6.48 (m, 1H), 4.81 (m, 2H).

5-Chloro-1-(2,2-difluoroethyl)-1H-pyrazol-4-amine (95)

A 30-mL scintillation vial equipped with a magnetic stirrer was charged with 5-chloro-1-(2,2-difluoroethyl)-4-nitro-1H-pyrazole 94 (1.60 g, 7.56 mmol), iron dust (3.01 g, 54.0 mmol), and $NH_4Cl$ (2.89 g, 54.0 mmol). To the vial was added EtOH (10 mL) then water (2 mL), the vial was sealed with a pressure release cap, and the mixture was heated to 80° C. for 3 h. Upon cooling to RT, the reaction mixture was diluted into EtOAc, and the resultant mixture was treated with $Na_2SO_4$ to remove water. This mixture was then filtered first through a fritted pad to remove iron, and subsequently the filtrate was taken through a fritted Celite® pad to remove residual inorganics and water. Solvent was removed from the resultant filtrate under reduced pressure to afford the title compound 95. Note that 95 and related aminopyrazole intermediates were stable for a period of days under inert atmosphere and protected from light at 4° C., but typically were only prepared in quantities as needed. MS (ESI): m/z calc'd for $C_5H_7ClF_2N_3$ $[M+H]^+$: 181, found 181; $^1$H NMR (400 MHz, acetone-$d_6$, 25° C.) δ: 7.38 (s, 1H), 6.31 (m, 1H), 4.57 (m, 2H), 2.85 (br s, 2H).

Scheme 32. Synthesis of 2-(4-bromo-5-methyl-1H-pyrazol-1-y)-2-methylpropanenitrile

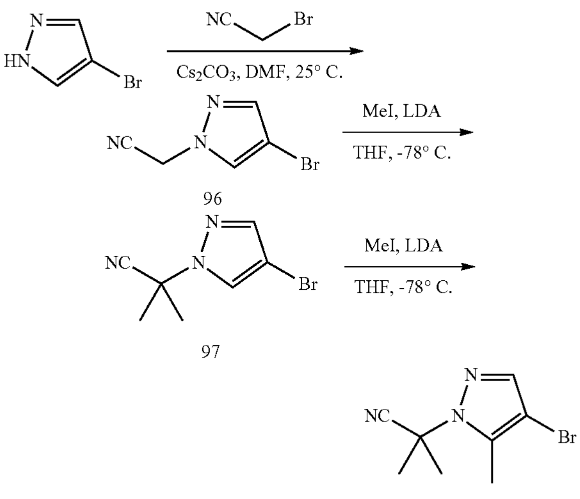

96

97

98

2-(4-Bromo-1H-pyrazol-1-yl)acetonitrile (96)

To a solution of 4-bromo-1H-pyrazole (2.00 g, 13.6 mmol) and $Cs_2CO_3$ (8.87 g, 27.2 mmol) in DMF (20 mL) was added 2-bromoacetonitrile (2.45 g, 20.4 mmol). The reaction was stirred at 25° C. for 4 h. The mixture was poured into $H_2O$ (20 mL), and EtOAc (20 mL) was added into the mixture. The organic phase was separated, and the aqueous phase was extracted with EtOAc (2×20 mL), dried over anhydrous $Na_2SO_4$, filtered, and the solvent was removed under reduced pressure. The resultant crude residue was subjected to purification by flash chromatography over silica gel (ethyl acetate/PE, 0-18%) affording the title compound 96. MS (ESI): m/z calc'd for $C_5H_4BrN_3$ $[M+H]^+$: 185, found 185.

2-(4-Bromo-1H-pyrazol-1-yl)-2-methylpropanenitrile (97)

To a mixture of 2-(4-bromo-1H-pyrazol-1-yl)acetonitrile 96 (200 mg, 1.08 mmol) in THF (1.5 mL) was added LDA (1.61 mL, 3.23 mmol, 2.0 M) at −78° C. under $N_2$. The mixture was stirred at this temperature for 10 min. MeI (0.34 mL, 5.4 mmol) was added into the mixture at −78° C., and the resultant mixture was stirred at this temperature for 2 h. The reaction mixture was quenched with $H_2O$ (10 mL), and the aqueous phase was extracted with EtOAc (3×10 mL). The combined organic phases were dried over anhydrous $Na_2SO_4$, filtered, and concentrated under reduced pressure. The crude residue was purified by preparative TLC ($SiO_2$, PE/EtOAc=3:1, v/v) to afford the title compound 97. MS (ESI): m/z calc'd for $C_7H_8BrN_3$ $[M+H]^+$: 213, found 213.

2-(4-Bromo-5-methyl-1H-pyrazol-1-yl)-2-methylpropanenitrile) (98)

To a mixture of 2-(4-bromo-1H-pyrazol-1-yl)-2-methylpropanenitrile 97 (160 mg, 0.75 mmol)) in THF (4.0 mL) at −78° C. was added LDA (0.75 mL, 1.5 mmol, 2.0 M) under $N_2$. The mixture was stirred at this temperature for 10 min. MeI (0.47 mL, 7.5 mmol) was added into the mixture at −78° C., and the resultant mixture was stirred at this temperature for 2 h. The reaction mixture was quenched with $H_2O$ (10 mL), and the aqueous phase was extracted with EtOAc (3×10 mL). The combined organic phases were dried over anhydrous $Na_2SO_4$, filtered, and concentrated under reduced pressure. The crude residue was purified by preparative TLC ($SiO_2$, PE/EtOAc=3:1, v/v) to afford the title compound 98. MS (ESI): m/z calc'd for $C_8H_{10}BrN_3$ $[M+H]^+$: 227, found 227.

Scheme 33. Synthesis of 4-bromo-1-((1R,2S)-2-methoxycyclobutyl)-5-methyl-1H-pyrazole

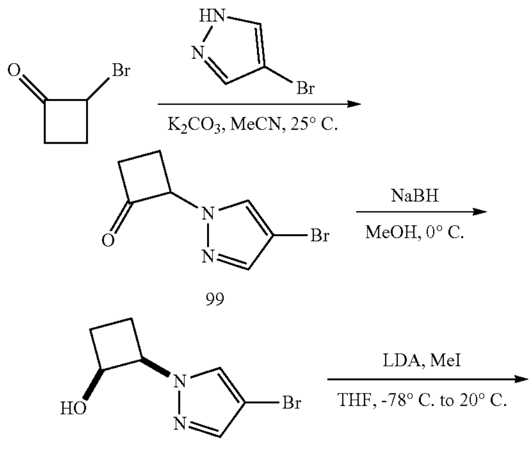

99

100

-continued

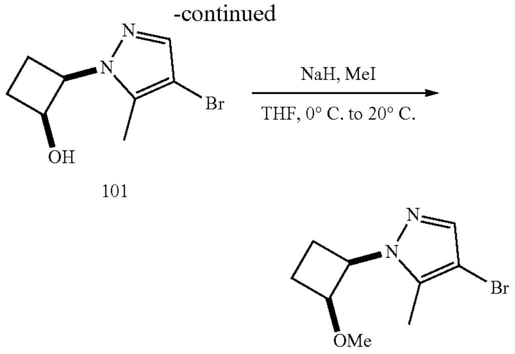

101

102

2-(4-Bromo-1H-pyrazol-1-yl)cyclobutan-1-one (99)

A mixture of 2-bromocyclobutanone (4.05 g, 27.2 mmol), 4-bromo-1H-pyrazole (2.00 g, 13.6 mmol) and $K_2CO_3$ (3.76 g, 27.2 mmol) in MeCN (30 mL) was stirred at 25° C. for 5 h. The reaction mixture was filtered, and the filtrate was concentrated under reduced pressure to give the crude compound 99 which was used in the next step without further purification.

(1S,2R)-2-(4-Bromo-1H-pyrazol-1-yl)cyclobutan-1-ol (100)

A mixture of 2-(4-bromo-1H-pyrazol-1-yl)cyclobutanone 99 (2.0 g, 9.3 mmol) and $NaBH_4$ (0.35 g, 9.3 mmol, 1.0 equiv) in MeOH (20 mL) was stirred at 20° C. for 2 h. The solvent was removed under reduced pressure, and the crude residue was dissolved in sat. aq. $NH_4Cl$ (20 mL) and EtOAc (20 mL). The organic phase was separated, the aqueous phase was extracted with EtOAc (3×10 mL), and the combined organic layers were washed with brine (50 mL), dried over anhydrous $Na_2SO_4$, filtered, and concentrated under reduced pressure. The crude residue was subjected to purification by flash chromatography over silica gel (ethyl acetate/PE, 0-30%) affording the title compound 100. MS (ESI): m/z calc'd for $C_7H_9BrN_2O$ $[M+H]^+$: 217, found 217.

(1S,2R)-2-(4-Bromo-5-methyl-1H-pyrazol-1-yl)cyclobutan-1-ol (101)

LDA (3.51 mL, 7.03 mmol) was added to a solution of 2-(4-bromo-1H-pyrazol-1-yl)cyclobutanol 100 (610 mg, 2.81 mmol) in THF (10 mL) at −78° C. After stirring for 0.5 h at −78° C., MeI (0.879 mL, 14.1 mmol) was added to the mixture at this temperature. The resultant mixture was allowed to warm to 20° C. with stirring for 90 min. The reaction mixture was quenched with sat. aq. $NH_4Cl$ (10 mL) and extracted with EtOAc (3×10 mL). The combined organic phases were washed with brine (50 mL), dried over anhydrous $Na_2SO_4$, filtered, and concentrated under reduced pressure to give crude 101 which was used in the next step without further purification. MS (ESI): m/z calc'd for $C_8H_{11}BrN_2O$ $[M+H]^+$: 231, found 231.

4-Bromo-1-((1R,2S)-2-methoxycyclobutyl)-5-methyl-1H-pyrazole (102)

NaH (228 mg, 5.71 mmol) was added to a solution of 2-(4-bromo-5-methyl-1H-pyrazol-1-yl)cyclobutanol 101 (660 mg, 2.86 mmol) in THF (10 mL) at 0° C. After stirring for 0.5 h at 0° C., MeI (0.536 mL, 8.57 mmol) was added to the mixture at 0° C. The resultant mixture was stirred at 20° C. for another 1 h. The reaction mixture was quenched with sat. aq. $NH_4Cl$ (20 mL) and extracted with EtOAc (3×15 mL). The combined organic phases were washed with brine (30 mL), dried over anhydrous $Na_2SO_4$, filtered, and concentrated under reduced pressure. The residue was purified by reverse phase HPLC, eluting with water (0.1% TFA)-MeCN to afford the title compound 102. MS (ESI): m/z calc'd for $C_9H_{13}BrN_{20}$ $[M+H]^+$: 245, found 245.

Scheme 34. Synthesis of 4-iodo-1-((1R,3R)-3-methoxycyclobutyl)-5-methyl-1H-pyrazole

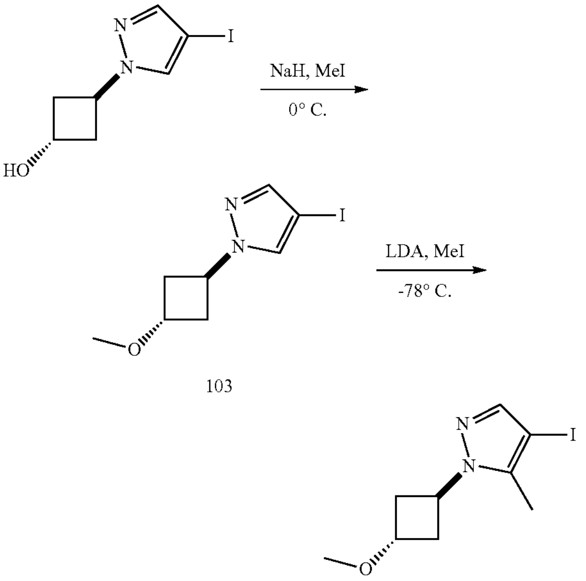

103

104

4-Iodo-1-((1R,3R)-3-methoxycyclobutyl)-1H-pyrazole (103)

To a solution of (1R,3R)-3-(4-iodo-1H-pyrazol-1-yl)cyclobutanol (200 mg, 0.757 mmol) in THF (2.0 mL) was added NaH (60.6 mg, 1.52 mmol). The resultant mixture was stirred for 0.5 h at 0° C. with stirring under $N_2$. MeI (0.237 mL, 3.79 mmol) was added into the solution and the mixture was stirred at this temperature for 2 h. The reaction was quenched by the addition of $H_2O$ (20 mL), and the aqueous phase was extracted with EtOAc (3×15 mL). The combined organic phases were dried over $Na_2SO_4$ and concentrated under reduced pressure. The crude residue was purified by preparative TLC ($SiO_2$; PE:EtOAc=3:1) to give the title compound 103. MS (ESI): m/z calc'd for $C_8H_{11}IN_{20}$ $[M+H]^+$: 279, found 279.

4-Iodo-1-((1R,3R)-3-methoxycyclobutyl)-5-methyl-1H-pyrazole (104)

To a solution of 4-iodo-1-((1R,3R)-3-methoxycyclobutyl)-1H-pyrazole 103 (31 mg, 0.11 mmol, 1.0 equiv) in THF (1.0 mL) was added LDA (0.17 mL, 0.33 mmol, 3.0 equiv) at −78° C. under $N_2$. The resultant mixture was allowed to stir at that temperature for 0.5 h. MeI (0.035 mL, 0.557 mmol) was added into the solution and the mixture was stirred at −78° C. for 2 h. The reaction was quenched by the addition of $H_2O$ (10 mL), and the aqueous phase was extracted with EtOAc (3×10 mL), the combined organic layers were dried over $Na_2SO_4$ and concentrated under reduced pressure. The crude residue was purified by preparative TLC ($SiO_2$; PE:EtOAc=3:1) to give the title compound 104. MS (ESI): m/z calc'd for $C_9H_{13}IN_{20}$ [M+H]$^+$: 293, found 293.

Scheme 35 Synthesis of 5-chloro-4-iodo-1-(1-(trifluoromethyl) cyclopropyl)-1H-pyrazole

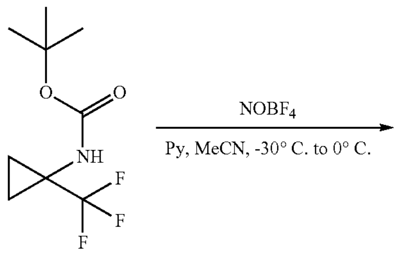

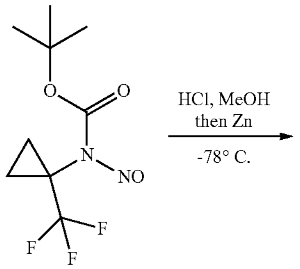

105

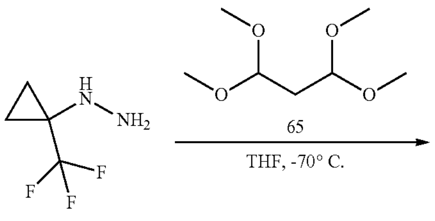

106

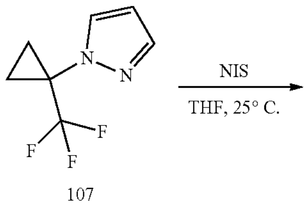

107

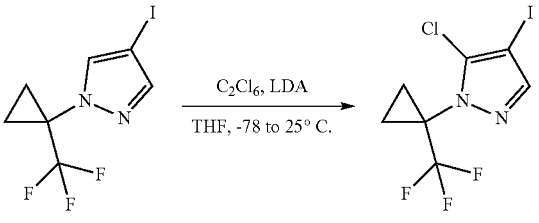

108

109

Tert-butyl nitroso(1-(trifluoromethyl)cyclopropyl)carbamate (105)

Nitrosonium tetrafluoroborate (2.3 g, 20 mmol) was added in several portions to a cooled solution of tert-butyl (1-(trifluoromethyl)cyclopropyl)carbamate (3.00 g, 13.3 mmol) at −30° C. in anhydrous pyridine (2 mL) and MeCN (20 mL). The solution was stirred at this temperature for 30 min then at 0° C. for 3 h. The reaction mixture was quenched by the addition of ice water and EtOAc. The organic phase was separated and washed with 1 N HCl (3×50 mL), 1 N $NaHCO_3$(1×50 mL), brine (1×50 mL), dried over $MgSO_4$, filtered, and concentrated under reduced pressure to afford the title compound 105 which was used for next step without further purification.

(1-(Trifluoromethyl)cyclopropyl)hydrazine (106)

To a mixture of tert-butyl nitroso(1-(trifluoromethyl)cyclopropyl)carbamate 105 (3.00 g, 11.8 mmol) in anhydrous MeOH (100 mL) stirred at −78° C. for 30 min was added HCl (9.69 mL, 118 mmol) and zinc (7.72 g, 118 mmol). The resultant mixture was stirred at −78° C. for 2 h. The mixture was filtered and concentrated under reduced pressure to afford the title compound 106 which was used for next step without further purification.

1-(1-(Trifluoromethyl)cyclopropyl)-1H-pyrazole (107)

A mixture of (1-(trifluoromethyl)cyclopropyl)hydrazine hydrochloride 106 (1.5 g, 10.7 mmol), 1,1,3,3-tetramethoxypropane 65 (2.09 g, 12.7 mmol) in THF (20 mL) was stirred at 70° C. for 1 h. LCMS of the reaction mixture showed the desired product 107 present. The reaction mixture was used for next step without further purification.

4-Iodo-1-(1-(trifluoromethyl)cyclopropyl)-1H-pyrazole (108)

To a mixture of 1-(1-(trifluoromethyl)cyclopropyl)-1H-pyrazole 107 (1.2 g, 6.8 mmol) in THF (30 mL) was added NIS (7.7 g, 34 mmol) at 25° C. The resultant mixture was stirred at 25° C. for 15 h. The reaction mixture was diluted with DCM (200 mL) and washed with sat. aq. $Na_2SO_3$ (3×100 mL). The mixture was concentrated under reduced pressure and the resultant crude residue was subjected to purification by flash chromatography over silica gel (EtOAc/PE, 10%) to afford the title compound 108. MS (ESI): m/z calc'd for $C_7H_6F_3IN_2$ [M+H]$^+$: 303, found 303.

5-Chloro-4-iodo-1-(1-(trifluoromethyl)cyclopropyl)-1H-pyrazole (109)

To a solution of 4-iodo-1-(1-(trifluoromethyl)cyclopropyl)-1H-pyrazole 108 (1.0 g, 3.3 mmol) in anhydrous THF (10 mL) was added LDA (3.3 mL, 6.6 mmol) at −78° C. The resultant mixture was stirred at this temperature for 30 min at which time perchloroethane (0.94 g, 4.0 mmol) in THF (2 mL) was added to the mixture dropwise at −78° C. under $N_2$. The resultant mixture was stirred at −78° C. for 1 h and then allowed to warm to RT and stir for an additional 1 h. The reaction mixture was quenched by pouring into sat. aq. $NaHCO_3$ solution (100 mL) and EtOAc (50 mL) was added into the mixture. The organic phase was separated, and the aqueous phase was extracted with EtOAc (2×50 mL). The combined organic phases were dried over anhydrous $Na_2SO_4$, filtered, and concentrated under reduced pressure. The resultant crude residue was subjected to purification by flash chromatography over silica gel (EtOAc/PE, 0-5%) to afford the title compound 109. MS (ESI): m/z calc'd for $C_7H_5ClF_3IN_2$ $[M+H]^+$: 337, found 337; $^1H$ NMR (400 MHz, $CDCl_3$, 25° C.) δ 7.59 (s, 1H), 1.72-1.69 (m, 2H), 1.56-1.50 (m, 2H).

Scheme 36. Synthesis of 4-bromo-5-chloro-1-(1-methylcyclopropyl)-1H-pyrazole

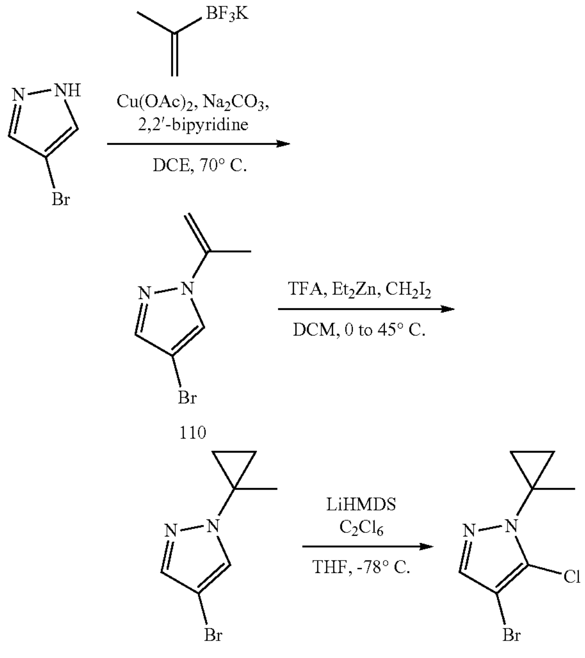

110

111

112

4-Bromo-1-(prop-1-en-2-yl)-1H-pyrazole (110)

A 20-L 4-necked round-bottom flask was charged with 4-bromo-1H-pyrazole (600 g, 4.08 mol), potassium isopropenyl trifluoroborate (1.03 kg, 6.94 mol), and $Na_2CO_3$ (865 g, 8.16 mol) under inert atmosphere. DCE (6 L) was added, and the solution was cooled to 15° C. A suspension of $Cu(OAc)_2$ (742 g, 4.08 mol) and 2,2'-bipyridine (956 g, 6.12 mol) in DCE (4 L) was then added to the reaction mixture at this temperature. Upon complete addition, the reaction was warmed to 70° C., and stirring was continued at this temperature for 5 h. The mixture was allowed to cool to RT and filtered to remove solids. Solvent was removed from the collected filtrate under reduced pressure, and the resultant crude residue was subjected to purification by flash chromatography over silica gel (EtOAc/PE, 0-10%) to afford the title compound 110.

4-Bromo-1-(1-methylcyclopropyl)-1H-pyrazole (111)

A 10-L 3-necked round-bottom flask was charged with DCM (1.2 L) under inert atmosphere. The solvent was cooled to 0° C., and $Et_2Zn$ (1 M, 1 L) was added. The mixture was again equilibrated to 0° C., and TFA (122 g, 1.07 mol) was carefully added. The resultant mixture was stirred at this temperature for 30 min, at which point a solution of $CH_2I_2$ (286 g, 1.07 mol) in DCM (500 mL) was added dropwise, maintaining the temperature at or below 5° C. Upon complete addition, the mixture was stirred for an additional 30 min, at which point a solution of 4-bromo-1-(prop-1-en-2-yl)-1H-pyrazole 110 (100 g, 535 mmol) in DCM (600 mL) was added. The reaction mixture was then warmed to 45° C. and stirred at this temperature for 72 h. The reaction was cooled to 15° C., and carefully quenched by the addition of sat. aq. $NH_4Cl$ (4 L). The phases were separated, and the aqueous phase extracted with EtOAc (3×2 L). The combined organic phases were washed with $H_2O$ (1 L), dried over $Na_2SO_4$, and the solvent removed under reduced pressure. The crude residue was subjected to purification by flash chromatography over silica gel (EtOAc/PE, 0-5%) to afford title compound 111.

4-Bromo-5-chloro-1-(1-methylcyclopropyl)-1H-pyrazole (112)

A 10-L 3-necked round-bottom flask was charged with 4-bromo-1-(1-methylcyclopropyl)-1H-pyrazole 111 (200 g, 995 mmol) under inert atmosphere. THF (1.2 L) was added, and the solution was cooled to −78° C. To the stirring mixture at this temperature was added LDA (2 M, 746 mL), and stirring was continued for 2 h at this temperature. A solution of hexachloroethane (283 g, 1.19 mol) in THF (800 mL) was then added dropwise at −78° C. over the course of 2 h. Upon complete addition, the mixture was allowed to warm to 15° C. and stirred at this temperature for 4 h. The mixture was quenched by pouring carefully into sat. aq. $NH_4Cl$ (2.5 L) at 0° C. The phases were separated, and the aqueous phase extracted with EtOAc (3×800 mL). The combined organic layers were washed with brine (2×800 mL), dried over $Na_2SO_4$, and filtered. Solvent was removed under reduced pressure and the crude residue was subjected to purification by flash chromatography over silica gel (EtOAc/PE, 0-10%) to afford the title compound 112. MS (ESI): m/z calc'd for $C_7H_9BrClN_2$ $[M+H]^+$: 235, found 235; $^1H$ NMR (400 MHz, DMSO-$d_6$, 25° C.) δ: 7.69 (s, 1H), 1.44 (s, 3H), 1.19-1.16 (m, 2H), 1.04-1.00 (m, 2H).

Scheme 37. Synthesis of 1-(4-bromo-5-chloro-1H-pyrazol-1-yl)-2-methylpropan-2-ol)

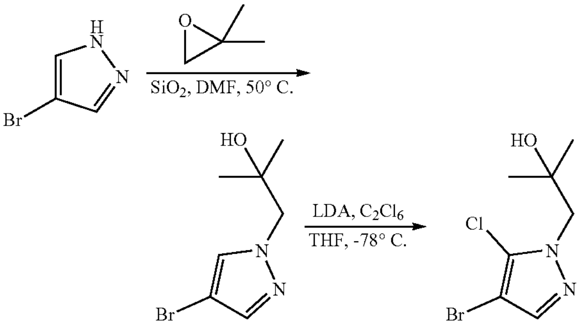

113

114

1-(4-Bromo-1H-pyrazol-1-yl)-2-methylpropan-2-ol (113)

A 10-L pressure vessel was charged with 4-bromo-1H-pyrazole (180 g, 1.22 mol), 2,2-dimethyloxirane (883 g, 12.3 mol), and $SiO_2$ (2.21 g, 36.7 mmol) under inert atmosphere.

DMF (900 mL) was added. The vessel was purged with inert atmosphere, and the pressure increased to 50 psi. The mixture was then warmed to 50° C. with stirring for 24 h. On completion, MTBE (200 mL) was added and the mixture slurried for 2 h, at which point the solid was collected by filtration and dried to afford the title compound 113.

1-(4-Bromo-5-chloro-1H-pyrazol-1-yl)-2-methylpropan-2-ol (114)

A 5-L 3-necked round-bottom flask was charged with 1-(4-bromo-1H-pyrazol-1-yl)-2-methylpropan-2-ol 113 (87.5 g, 399 mmol) under inert atmosphere. THF (613 mL) was added, and the stirring solution was cooled to −78° C. To the stirring mixture at this temperature LDA (2 M, 409 mL) was added dropwise. The reaction was stirred at −78° C. for 1 h, at which point a solution of hexachloroethane (114 g, 479 mmol) in THF (262 mL) was added dropwise. Upon complete addition, the reaction was allowed to stir for an additional 0.5 h. The mixture was then carefully quenched with sat. aq. $NH_4Cl$ (2.5 L), and extracted with MTBE (3×1.0 L). The organic phases were combined, and solvent was removed under reduced pressure. The resultant crude residue was subjected to purification by flash chromatography over silica gel (EtOAc/PE, 1-100%) to afford the title compound 114. MS (ESI): m/z calc'd for $C_7H_{11}BrClN_2O$ $[M+H]^+$: 252, found 252; $^1H$ NMR: (400 MHz, $CDCl_3$, 25° C.) δ: 7.50 (s, 1H), 4.05 (s, 2H), 3.62 (s, 1H), 1.11 (s, 6H).

Scheme 38. Synthesis of 1-(4-bromo-5-methyl-1H-pyrazol-1-yl)-2-methylpropan-2-ol

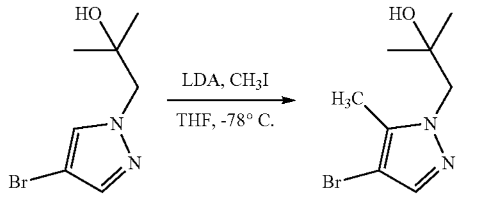

113 115

1-(4-Bromo-5-methyl-1H-pyrazol-1-yl)-2-methylpropan-2-ol (115)

A 20-mL scintillation vial was charged with 1-(4-bromo-1H-pyrazol-1-yl)-2-methylpropan-2-ol 113 (150 mg, 0.69 mmol) under inert atmosphere. THF (3.5 mL) was added, and the stirring solution was cooled to −78° C. To the stirring mixture at this temperature was added LDA (1.0 M, 1.6 mL) dropwise. The reaction was stirred at −78° C. for 1 h, at which point iodomethane (65 μL, 1.0 mmol) was added. The mixture was allowed to slowly warm to RT overnight, then carefully quenched by the addition of sat. aq. $NH_4Cl$ (20 mL). The mixture was extracted with EtOAc (3×20 mL), the combined organic phases dried over $Na_2SO_4$, and the solvent removed under reduced pressure. The resultant crude residue was subjected to purification by flash chromatography over silica gel (3:1 EtOAc/EtOH in hexanes, 0-80%) to afford the title compound 115. MS (ESI): m/z calc'd for $C_8H_{14}BrN_2O$ $[M+H]^+$: 233, found 233.

Scheme 39. Synthesis of 1-(3-(4-bromo-1H-pyrazol-1-yl)azetidin-1-yl)-2-methylpropan-2-ol

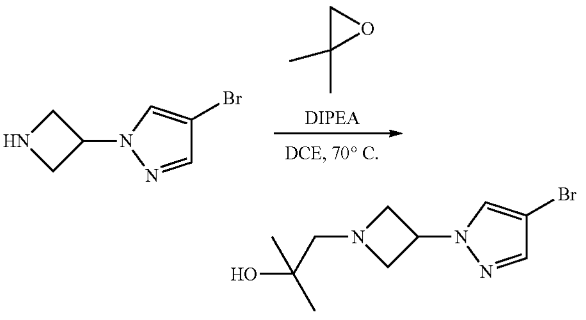

116

1-(3-(4-Bromo-TH-pyrazol-1-yl)azetidin-1-yl)-2-methylpropan-2-ol (116)

A solution of 1-(azetidin-3-yl)-4-bromo-TH-pyrazole (1.6 g, 2.9 mmol) in DCE (14.7 mL) and DIPEA (2.56 mL, 14.7 mmol) was stirred at RT for 1 h. 2,2-Dimethyloxirane (0.78 mL, 8.8 mmol) was added and the reaction mixture was stirred at 70° C. for 18 h. The reaction mixture was concentrated under reduced pressure and subjected to purification by flash chromatography over silica gel (3:1 EtOAc/EtOH in hexanes, 0-100%) to afford the title compound 116. MS (ESI): m/z calc'd for $C_{10}H_{16}BrN_3O$ $[M+H]^+$: 274, found 274.

Scheme 40. Synthesis of 4-bromo-1-cyclopropyl-5-(difluoromethyl)-1H-pyrazole

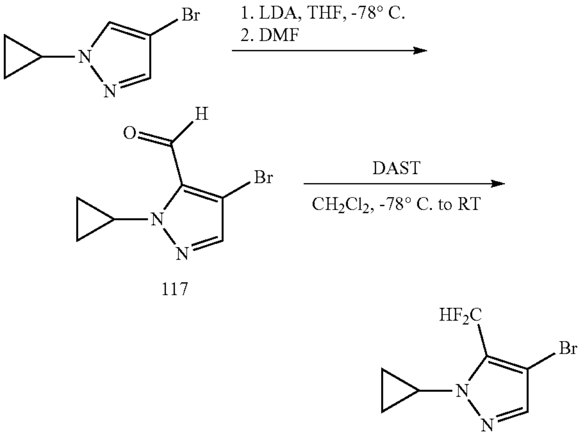

117

118

4-Bromo-1-cyclopropyl-1H-pyrazole-5-carbaldehyde (117)

A 250-mL round-bottom flask was charged with 4-bromo-1-cyclopropyl-1H-pyrazole (2.50 g, 13.4 mmol) under inert atmosphere. THF (10 mL) was added, and the mixture was cooled to −78° C. with stirring. To the mixture at this temperature was slowly added lithium diisopropylamide (1 M in THF/hexanes, 20.0 mL). The mixture was held at this temperature with stirring for 1.5 hrs, at which point DMF (1.55 mL) was slowly added. The mixture was stirred overnight, allowing the dry ice bath to warm to RT. Water (20 mL) was added, and the mixture was stirred for 20 min. The mixture was then transferred to a separatory funnel where it was diluted into additional water (50 mL) and extracted with DCM (3×50 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 117. MS (ESI): m/z calc'd for $C_7H_8BrN_2O$ $[M+H]^+$: 215, found 215.

4-bromo-1-cyclopropyl-5-(difluoromethyl)-1H-pyrazole (118)

A 50-mL Corning™ Falcon™ tube was charged with 4-bromo-1-cyclopropyl-1H-pyrazole-5-carbaldehyde 117 (1.00 g, 4.65 mmol) under inert atmosphere. DCM (10 mL) was added, and the mixture was cooled to −78° C. To the mixture at this temperature was slowly added DAST (1 M in DCM, 14.0 mL). Upon complete addition, the reaction was stirred overnight, allowing the dry ice bath to warm to RT. Water (20 mL) was added, and the mixture was transferred to a separatory funnel containing an excess of sat. aq. $NaHCO_3$. The phases were mixed vigorously, then separated. The aqueous phase was then extracted with additional DCM (2×40 mL). The combined organic layers were dried over anhydrous $Na_2SO_4$, filtered, and solvent was removed from the collected filtrate under reduced pressure. The crude residue was subjected to purification by flash chromatography over silica gel (0-50% $Et_2O$:hexanes) and collected by gentle evaporation (35° C., 150 mbar) to afford the title compound 118. MS (ESI): m/z calc'd for $C_7H_8BrF_2N_2$ $[M+H]^+$: 236, found 236.

The following substituted pyrazoles, 119 through 137 presented in Table 1 below were obtained using the procedures analogous to those described in General Scheme 1 but substituting appropriate starting materials that are either commercially available or prepared using procedures analogous to those described in Schemes 29 through 40.

TABLE 1

| Intermediate | Structure |
|---|---|
| 119 | 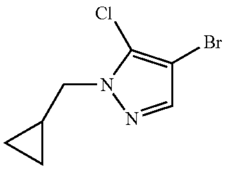 [SMILES: Clc1c(Br)cnn1CC1CC1] |
| 120 | 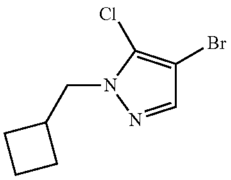 [SMILES: Clc1c(Br)cnn1CC1CCC1] |

TABLE 1-continued

| Intermediate | Structure |
|---|---|
| 121 | 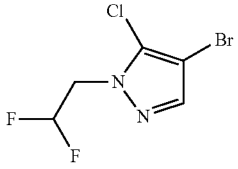 [SMILES: FC(F)Cn1ncc(Br)c1Cl] |
| 122 | 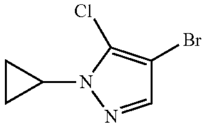 |
| 123 | 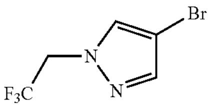 |
| 124 | 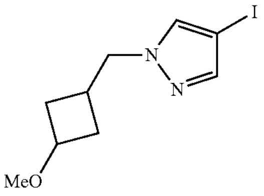 [SMILES: COC1CC(Cn2cc(I)cn2)C1] |
| 125 | 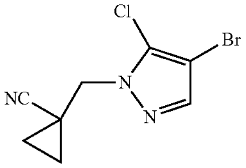 [SMILES: N#CC1(Cn2ncc(Br)c2Cl)CC1] |
| 126 | 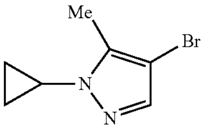 |
| 127 | 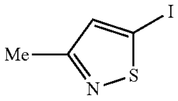 |
| 128 | 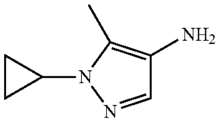 |
| 129 | 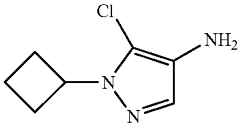 [SMILES: Nc1cnn(C2CCC2)c1Cl] |
| 130 | 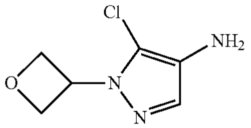 [SMILES: Nc1cnn(C2COC2)c1Cl] |

TABLE 1-continued
| Intermediate | Structure |
|---|---|
| 131 | 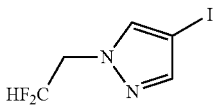 |
| 132 | 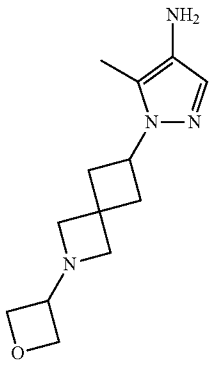 [SMILES: Cc1c(N)cnn1C1CC2(C1)CN(C1COC1)C2] |
| 133 | 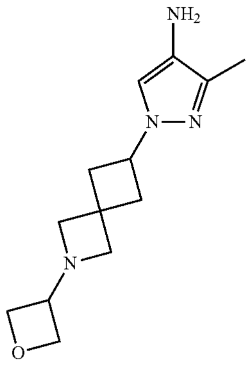 [SMILES: Cc1nn(C2CC3(C2)CN(C2COC2)C3)cc1N] |
| 134 | 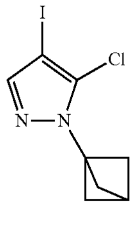 [SMILES: Clc1c(I)cnn1C12CC(C1)C2] |
| 135 | 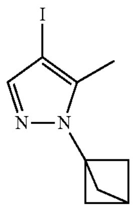 |
| 136 | 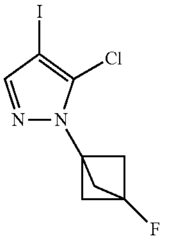 [SMILES: FC12CC(n3ncc(I)c3Cl)(C1)C2] |
| 137 | 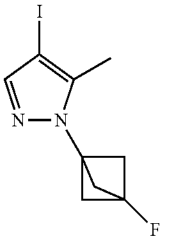 |
General Scheme 2
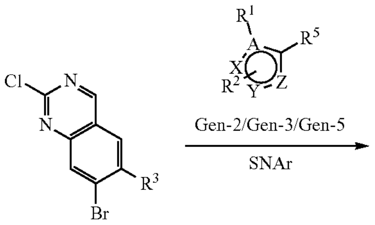
Gen-6
$R^3$ = H, Cl, Me
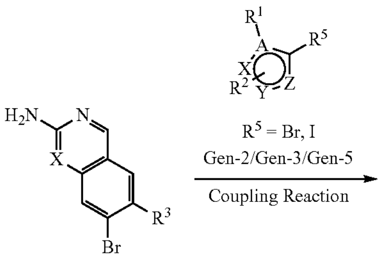
Gen-7

-continued

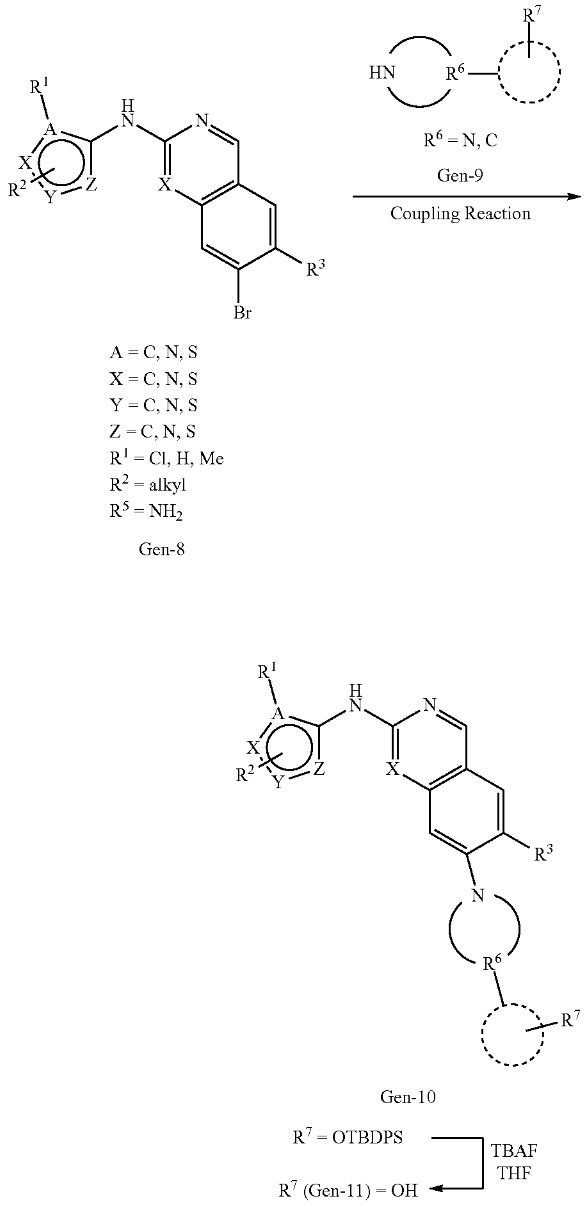

In General Scheme 2 commercially available or synthetically prepared intermediates Gen-6 and Gen-7 were coupled with commercially available or synthetically prepared halo or amino heterocycles Gen-2/Gen-3/Gen-5 through either $S_NAr$ chemistry (cf. Scheme 7) or a palladium or copper catalyzed coupling reaction to provide Gen-8. The aryl bromide Gen-8 could ultimately be transformed under palladium or copper catalyzed cross coupling with commercially available or synthetically prepared cyclic amines Gen-9, to afford elaborated compounds of the form Gen-10. In cases where $R^7$ represents a TBDPS protected alcohol a subsequent fluoride promoted deprotection reaction could be employed to generate compounds of the form Gen-11. The representative compounds are described in more detail below.

EXAMPLES

Preparation of Examples 1.1 and 1.2

Scheme 41. Synthesis of (3R,4R) or (3S,4S) 4-(4-(7-chloro-3-((1-cyclopropyl-5-methyl-1H-pyrazol-4-yl)amino)isoquinolin-6-yl)-piperazin-1-yl)-4-methyltetrahydrofuran-3-ol

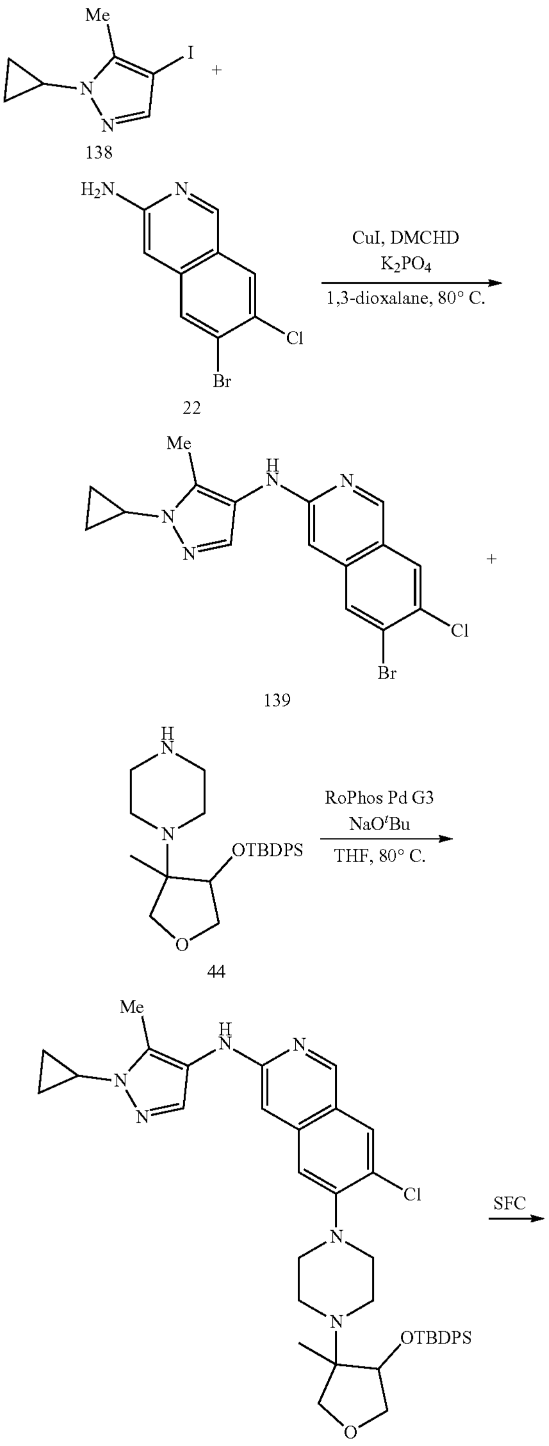

140

-continued

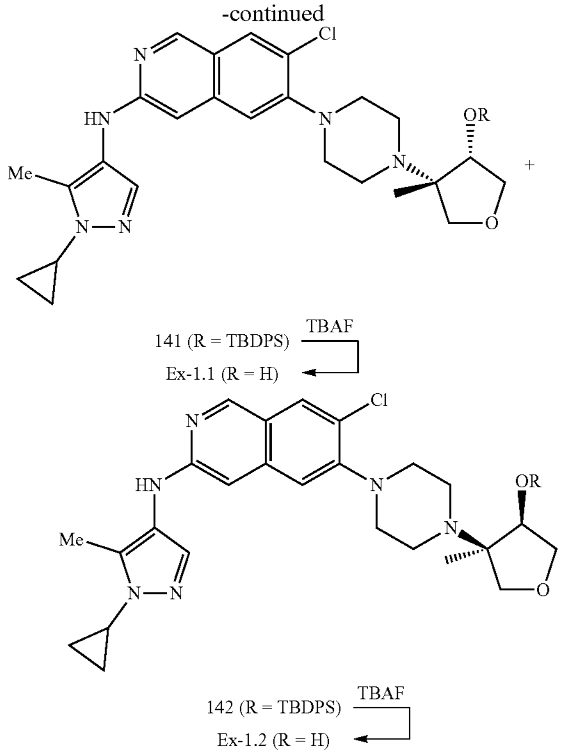

6-Bromo-7-chloro-N-(1-cyclopropyl-5-methyl-1H-pyrazol-4-yl)isoquinolin-3-amine (139)

A 20 mL scintillation vial was charged with copper (I) iodide (74 mg, 0.39 mmol) and trans-N,N-dimethylcyclohexane-1,2-diamine (92 μL, 0.58 mmol) under inert atmosphere. 1,3-dioxolane (9.7 mL) was added and the resulting mixture was allowed to stir for 5 min at RT. A separate 20 mL microwave vial was charged with 6-bromo-7-chloroisoquinolin-3-amine 22 (500 mg, 1.94 mmol), 1-cyclopropyl-4-iodo-5-methyl-1H-pyrazole 138 (963 mg, 3.88 mmol), and tribasic potassium phosphate (2.47 g, 11.7 mmol) under inert atmosphere. At this point, the catalyst mixture was added to the microwave vial. The resultant mixture was warmed to 80° C. and stirred at this temperature overnight. On cooling to RT, the reaction mixture was diluted with 3:1 (v/v) $CHCl_3$:IPA, washed with sat. aq. $NH_4Cl$ (2×50 mL), and brine (1×50 mL). The organic phase was dried over anhydrous $Na_2SO_4$, filtered, and solvent was removed under reduced pressure. The crude residue was subjected to purification by flash chromatography over silica gel (3:1 EtOAc:EtOH/hexanes, 0-100%) to afford the title compound 139. MS (ESI): m/z calc'd for $C_{16}H_{15}BrClN_4$ $[M+H]^+$: 377, found 377.

(3R,4R) or (3S,4S) 6-(4-(4-((tert-butyldiphenylsilyl)oxy)-3-methyltetrahydrofuran-3-yl)piperazin-1-yl)-7-chloro-N-(1-cyclopropyl-5-methyl-1H-pyrazol-4-yl)isoquinolin-3-amine (141) or (142)

A 5 mL microwave vial was charged with 6-bromo-7-chloro-N-(1-cyclopropyl-5-methyl-1H-pyrazol-4-yl)isoquinolin-3-amine 139 (100 mg, 0.265 mmol), 1-(4-((tert-butyldiphenylsilyl)oxy)-3-methyltetrahydrofuran-3-yl)piperazine (169 mg, 0.397 mmol), and RuPhos Pd G3 (44 mg, 0.05 mmol) under inert atmosphere. THF (1.3 mL) was added and the resultant mixture was warmed to 80° C. and stirred at this temperature for 4 h. Upon cooling to RT, the reaction mixture was diluted with EtOAc, washed with sat. aq. $NH_4Cl$ (2×50 mL), and brine (1×50 mL). The organic phase was dried over anhydrous $Na_2SO_4$, filtered, and solvent was removed from the collected filtrate under reduced pressure. The crude residue was subjected to purification by flash chromatography over silica gel (3:1 EtOAc:EtOH/hexanes, 0-100%) to afford the racemic title compound 140. This material was then resolved into its component enantiomers by chiral preparative SFC (Column & dimensions: CCA, 21 mm×250 mm; Mobile phase A: $CO_2$; Mobile phase B: MeOH with 0.1% $NH_4OH$) to afford 141 ($t_R$=4.7 min) and 142 ($t_R$=6.5 min). MS (ESI): m/z calc'd for $C_{41}H_{50}ClN_6O_2Si$ $[M+H]^+$: 721, found 721; MS (ESI): m/z calc'd for $C_{41}H_{50}ClN_6O_2Si$ $[M+H]^+$: 721, found 721.

(3R,4R) or (3S,4S) 4-(4-(7-chloro-3-((1-cyclopropyl-5-methyl-1H-pyrazol-4-yl)amino)isoquinolin-6-yl)piperazin-1-yl)-4-methyltetrahydrofuran-3-ol (Ex-1.1 and Ex-1.2)

A 2 dram scintillation vial was charged with either (3R,4R) or (3S,4S) 6-(4-(4-((tert-butyldiphenylsilyl)oxy)-3-methyltetrahydrofuran-3-yl)piperazin-1-yl)-7-chloro-N-(1-cyclopropyl-5-methyl-1H-pyrazol-4-yl)isoquinolin-3-amine 141 or 142 (32 mg, 0.044 mmol) under inert atmosphere. THF (887 μL) was added and the resultant solution was cooled to 0° C. TBAF (1 M in THF) (133 μL, 0.133 mmol) was added to the stirring mixture at this temperature. After 30 min, the ice bath was removed, and the reaction mixture was allowed to stir at RT for 6 h. The reaction mixture was diluted with 3:1 $CHCl_3$:IPA, washed with sat. aq. $NH_4Cl$ (2×50 mL), and brine (1×50 mL). The organic phase was dried over anhydrous $Na_2SO_4$, filtered, and solvent was removed from the collected filtrate under reduced pressure. The crude residue was subjected to purification by flash chromatography over silica gel (3:1 EtOAc:EtOH/hexanes, 0-100%) to afford each of the corresponding title compounds Ex-1.1 and Ex-1.2. MS (ESI): m z calc'd for $C_{25}H_{32}ClN_6O_2$ $[M+H]^+$: 483, found 483; $^1H$ NMR (400 MHz, DMSO-$d_6$, 25° C.) δ: 8.74 (s, 1H), 7.92 (s, 1H), 7.90 (s, 1H), 7.38 (s, 1H), 7.15 (s, 1H), 6.45 (s, 1H), 4.32 (br s, 1H), 3.97 (m, 1H), 3.80 (m, 1H), 3.70 (m, 1H), 3.64 (m, 1H), 3.54 (m, 1H), 3.51 (m, 1H), 3.10 (br s, 4H), 2.74 (m, 2H), 2.22 (s, 3H), 1.33 (s, 1H), 1.24 (s, 1H), 1.07-1.00 (m, overlap, 5H). MS (ESI): m/z calc'd for $C_{25}H_{32}ClN_{6O2}$ $[M+H]^+$: 483, found 483; $^1H$ NMR (400 MHz, DMSO-$d_6$, 25° C.) δ: 8.74 (s, 1H), 7.92 (s, 1H), 7.90 (s, 1H), 7.38 (s, 1H), 7.15 (s, 1H), 6.45 (s, 1H), 4.32 (br s, 1H), 3.97 (m, 1H), 3.80 (m, 1H), 3.70 (m, 1H), 3.64 (m, 1H), 3.54 (m, 1H), 3.51 (m, 1H), 3.10 (br s, 4H), 2.74 (m, 2H), 2.22 (s, 3H), 1.33 (s, 1H), 1.24 (s, 1H), 1.07-1.00 (m, overlap, 5H).

Scheme 42. Synthesis of 7-bromo-6-chloro-N-(1-(2-fluoroethyl)-5-methyl-1H-pyrazol-4-yl)quinazolin-2-amine

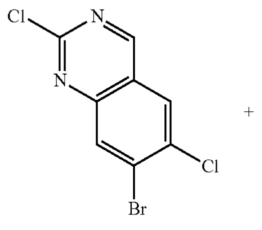

6

-continued

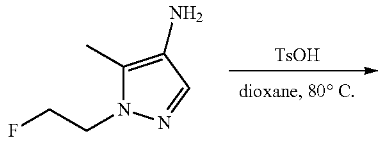

143

-continued

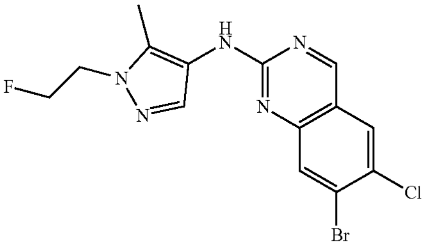

144

7-Bromo-2,6-dichloroquinazoline 6 (100 mg, 0.360 mmol), 1-(2-fluoroethyl)-5-methyl-1H-pyrazol-4-amine 143 (67.0 mg, 0.468 mmol), and TsOH (103 mg, 0.540 mmol) were added to a vial. Dioxane (1.8 mL) was added and the resultant mixture was stirred at 80° C. overnight. The precipitate was collected by vacuum filtration and dried to afford the title compound (144) which was carried forward without further purification.

Preparation of Example 1.3

Scheme 43. Synthesis of 6-chloro-N-(1-(2,2-difluoroethyl)-5-methyl-1H-pyrazol-4-yl)-7-(3,3,4-trimethylpiperazin-1-yl)quinazolin-2-amine

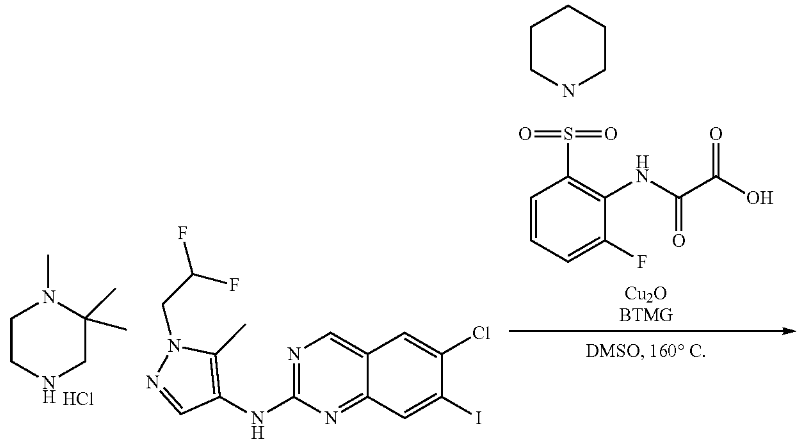

13

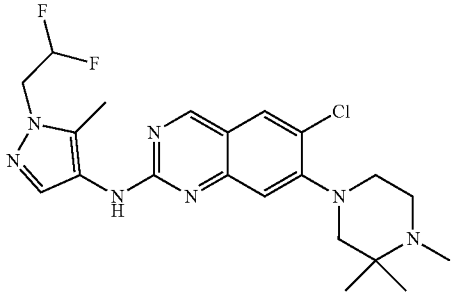

Ex-1.3

A vial was charged with 1,2,2-trimethylpiperazine hydrochloride (5.2 mg, 0.032 mmol) in a glovebox. To the stirring amine was added a stock solution of 6-chloro-N-(5-chloro-1-(2,2-difluoroethyl)-1H-pyrazol-4-yl)-7-iodoquinazolin-2-amine (9.9 mg, 0.021 mmol) in 0.1 mL of DMSO. Then $Cu_2O$ (0.08 mL, 0.2 M in DMSO) was added, followed by 2-fluoro-6-(piperidine-1-sulfonyl)anilino(oxo)acetic acid (0.02 mL, 0.75 M in DMSO) and BTMG (10.8 mg, 0.063 mmol). The reaction was stirred for 16 h at 100° C. in the glovebox. The reaction was cooled to room temperature, diluted with 1 mL of DMF, and filtered through a 0.45 micron syringe filter. The filtrate was subjected to purification by reverse phase HPLC, eluting with water (0.1% $NH_4OH$)-ACN to afford the title compound Ex-1.3. MS (ESI): m/z calc'd for $C_{21}H_{26}ClF_2N_7$ $[M+H]^+$: 450, found 450. $^1H$ NMR (500 MHz, DMSO-$d_6$, 25° C.) δ 9.46 (s, 1H), 9.23 (s, 1H), 8.20 (s, 1H), 8.15 (s, 1H), 8.06 (s, 1H), 6.51-6.29 (m, 1H), 4.65 (m, 2H), 3.47 (s, 3H), 3.45 (m, 9H, overlapping with HDO), 2.54 (s, 6H, overlapping with DMSO).

The following Examples, 1.4-1.48 were obtained using the procedure analogous to those in General Scheme 2 but substituting appropriate starting materials that are either commercially available or prepared using procedures analogous to those described in Schemes 41 through 43.

TABLE 2

| Ex | Structure | Name | Exact Mass [M + H]$^+$ |
|---|---|---|---|
| Ex-1.4 | 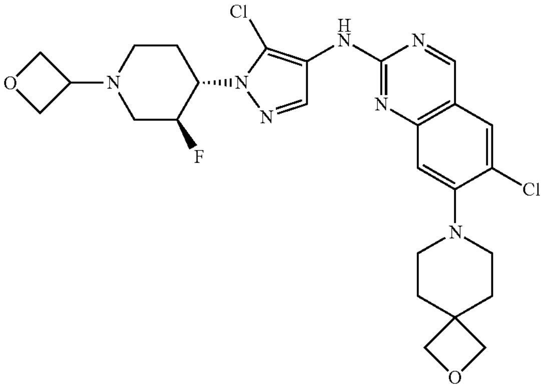 [SMILES: F[C@H]1CN(C2COC2)CC[C@@H]1n1ncc(Nc2ncc3cc(Cl)c(N4CCC5(CC4)COC5)cc3n2)c1Cl] | 6-chloro-N-{5-chloro-1-[(3S,4S)-3-fluoro-1-(oxetan-3-yl)piperidin-4-yl]-1H-pyrazol-4-yl}-7-(2-oxa-7-azaspiro[3.5]nonan-7-yl)quinazolin-2-amine | Calc'd 562.0, found 562 |
| Ex-1.5 | 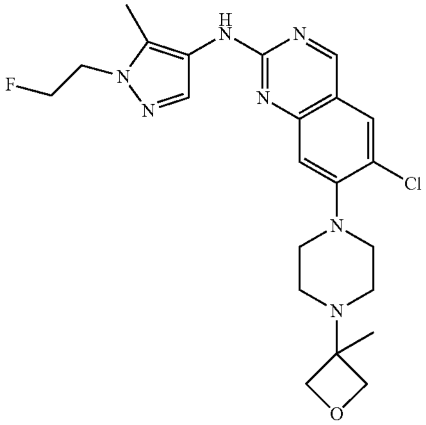 [SMILES: Cc1c(Nc2ncc3cc(Cl)c(N4CCN(C5(C)COC5)CC4)cc3n2)cnn1CCF] | 6-chloro-N-[1-(2-fluoroethyl)-5-methyl-1H-pyrazol-4-yl]-7-[4-(3-methyloxetan-3-yl)piperazin-1-yl]quinazolin-2-amine | Calc'd 460.0, found 460 |
| Ex-1.6 | 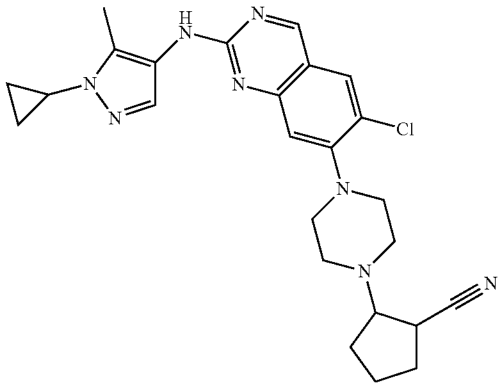 [SMILES: Cc1c(Nc2ncc3cc(Cl)c(N4CCN(C5CCCC5C#N)CC4)cc3n2)cnn1C1CC1] | (3S,4S or 3R,4R)-2-(4-{6-chloro-2-[(1-cyclopropyl-5-methyl-1H-pyrazol-4-yl)amino]quinazolin-7-yl}piperazin-1-yl)cyclopentane-1-carbonitrile | Calc'd 477.0, found 477 |

TABLE 2-continued

| Ex | Structure | Name | Exact Mass $[M + H]^+$ |
|---|---|---|---|
| Ex-1.7 | 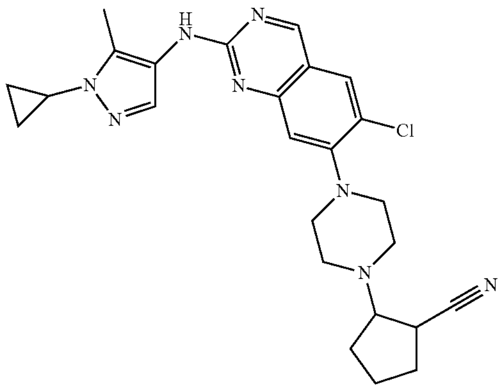 [SMILES: Cc1c(Nc2ncc3cc(Cl)c(N4CCN(C5CCCC5C#N)CC4)cc3n2)cnn1C1CC1] | (3S,4S or 3R,4R)-2-(4-{6-chloro-2-[(1-cyclopropyl-5-methyl-1H-pyrazol-4-yl)amino]quinazolin-7-yl}piperazin-1-yl)cyclopentane-1-carbonitrile | Calc'd 477.0, found 477 |
| Ex-1.8 | 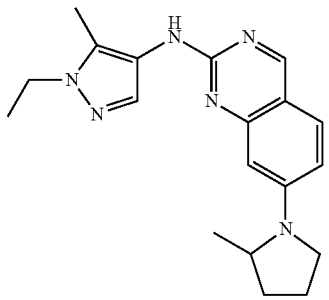 [SMILES: CCn1ncc(Nc2ncc3ccc(N4CCCC4C)cc3n2)c1C] | (S) or (R) N-(1-ethyl-5-methyl-1H-pyrazol-4-yl)-7-(2-methylpyrrolidin-1-yl)quinazolin-2-amine | Calc'd 337.0, found 377 |
| Ex-1.9 | 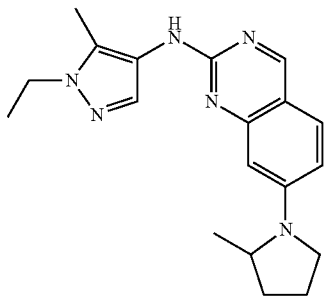 [SMILES: CCn1ncc(Nc2ncc3ccc(N4CCCC4C)cc3n2)c1C] | (S) or (R) N-(1-ethyl-5-methyl-1H-pyrazol-4-yl)-7-(2-methylpyrrolidin-1-yl)quinazolin-2-amine | Calc'd 337.0, found 377 |
| Ex-1.10 | 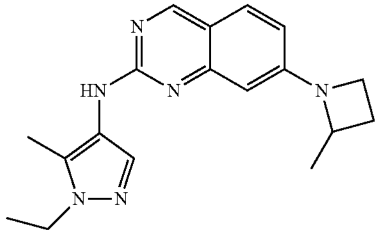 [SMILES: CCn1ncc(Nc2ncc3ccc(N4CCC4C)cc3n2)c1C] | (S) or (R) N-(1-ethyl-5-methyl-1H-pyrazol-4-yl)-7-(2-methylazetidin-1-yl)quinazolin-2-amine | Calc'd 323.0, found 323 |
| Ex-1.11 | 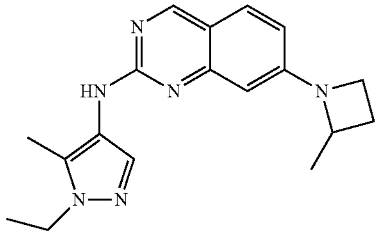 [SMILES: CCn1ncc(Nc2ncc3ccc(N4CCC4C)cc3n2)c1C] | (S) or (R) N-(1-ethyl-5-methyl-1H-pyrazol-4-yl)-7-(2-methylazetidin-1-yl)quinazolin-2-amine | Calc'd 323.0, found 323 |

TABLE 2-continued

| Ex | Structure | Name | Exact Mass [M + H]+ |
|---|---|---|---|
| Ex-1.12 | 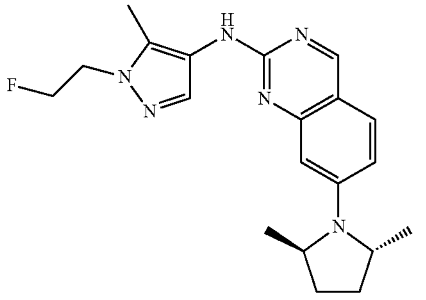 [SMILES: Cc1c(Nc2ncc3ccc(N4[C@H](C)CC[C@H]4C)cc3n2)cnn1CCF] | (2R,5S or 2,5R)-7-[2,5-dimethylpyrrolidin-1-yl]-N-[1-(2-fluoroethyl)-5-methyl-1H-pyrazol-4-yl]quinazolin-2-amine | Calc'd 369.0, found 369 |
| Ex-1.13 | 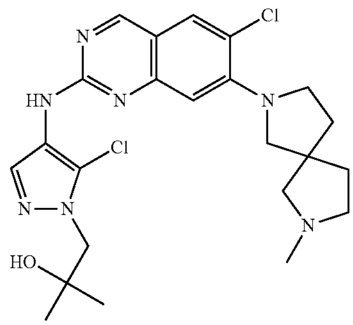 [SMILES: CN1CCC2(CCN(c3cc4nc(Nc5cnn(CC(C)(C)O)c5Cl)ncc4cc3Cl)C2)C1] | 1-(5-chloro-4-{[6-chloro-7-(7-methyl-2,7-diazaspiro[4.4]nonan-2-yl)quinazolin-2-yl]amino}-1H-pyrazol-1-yl)-2-methylpropan-2-ol | Calc'd 490.0, found 490 |
| Ex-1.14 | 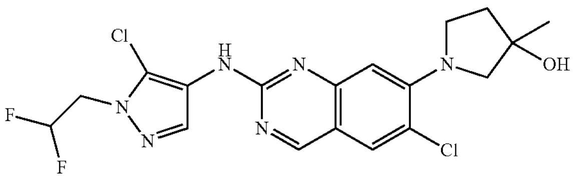 [SMILES: CC1(O)CCN(c2cc3nc(Nc4cnn(CC(F)F)c4Cl)ncc3cc2Cl)C1] | 1-(6-chloro-2-{[5-chloro-1-(2,2-difluoroethyl)-1H-pyrazol-4-yl]amino}quinazolin-7-yl)-3-methylpyrrolidin-3-ol | Calc'd 443.0, found 443 |
| Ex-1.15 | 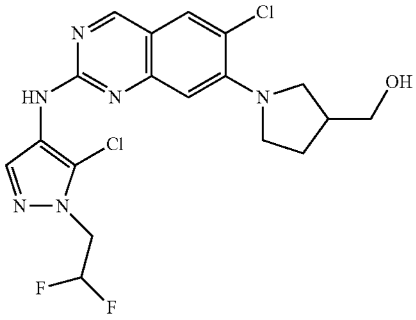 [SMILES: OCC1CCN(c2cc3nc(Nc4cnn(CC(F)F)c4Cl)ncc3cc2Cl)C1] | [1-(6-chloro-2-{[5-chloro-1-(2,2-difluoroethyl)-1H-pyrazol-4-yl]amino}quinazolin-7-yl)pyrrolidin-3-yl]methanol | Calc'd 443.0, found 443 |
| Ex-1.16 | 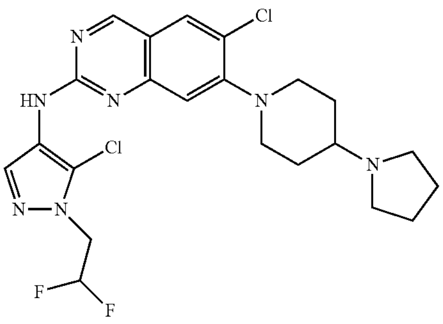 [SMILES: FC(F)Cn1ncc(Nc2ncc3cc(Cl)c(N4CCC(N5CCCC5)CC4)cc3n2)c1Cl] | 6-chloro-N-[5-chloro-1-(2,2-difluoroethyl)-1H-pyrazol-4-yl]-7-[4-(pyrrolidin-1-yl)piperidin-1-yl]quinazolin-2-amine | Calc'd 496.0, found 496 |

TABLE 2-continued

| Ex | Structure | Name | Exact Mass [M + H]+ |
|---|---|---|---|
| Ex-1.17 | 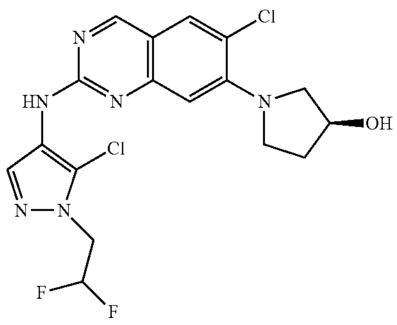 [SMILES: O[C@H]1CCN(c2cc3nc(Nc4cnn(CC(F)F)c4Cl)ncc3cc2Cl)C1] | (3S)-1-(6-chloro-2-{[5-chloro-1-(2,2-difluoroethyl)-1H-pyrazol-4-yl]amino}quinazolin-7-yl)pyrrolidin-3-ol | Calc'd 429.0, found 429 |
| Ex-1.18 | 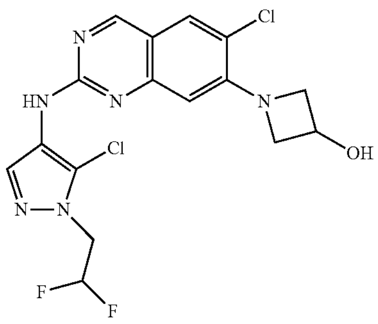 [SMILES: OC1CN(c2cc3nc(Nc4cnn(CC(F)F)c4Cl)ncc3cc2Cl)C1] | 1-(6-chloro-2-{[5-chloro-1-(2,2-difluoroethyl)-1H-pyrazol-4-yl]amino}quinazolin-7-yl)azetidin-3-ol | Calc'd 415.0, 415 |
| Ex-1.19 | 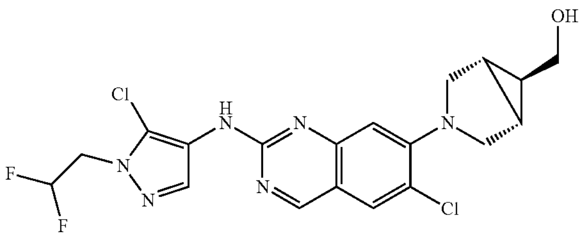 [SMILES: OC[C@@H]1[C@H]2CN(c3cc4nc(Nc5cnn(CC(F)F)c5Cl)ncc4cc3Cl)C[C@@H]12] | [(1R,5S,6R)-3-(6-chloro-2-{[5-chloro-1-(2,2-difluoroethyl)-1H-pyrazol-4-yl]amino}quinazolin-7-yl)-3-azabicyclo[3.1.0]hexan-6-yl]methanol | Calc'd 455.0, found 455 |
| Ex-1.20 | 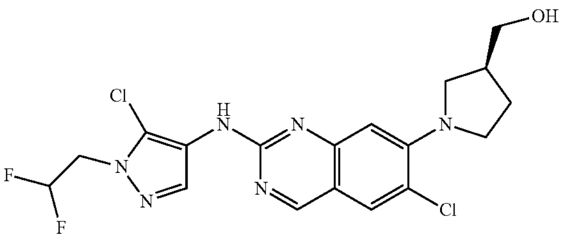 [SMILES: OC[C@H]1CCN(c2cc3nc(Nc4cnn(CC(F)F)c4Cl)ncc3cc2Cl)C1] | [(3S)-1-(6-chloro-2-{[5-chloro-1-(2,2-difluoroethyl)-1H-pyrazol-4-yl]amino}quinazolin-7-yl)pyrrolidin-3-yl]methanol | Calc'd 443.0, found 443 |
| Ex-1.21 | 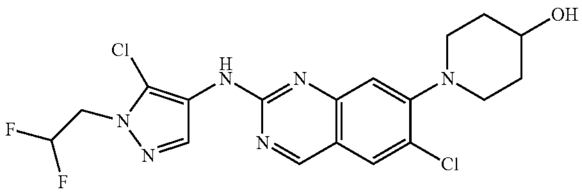 [SMILES: OC1CCN(c2cc3nc(Nc4cnn(CC(F)F)c4Cl)ncc3cc2Cl)CC1] | 1-(6-chloro-2-{[5-chloro-1-(2,2-difluoroethyl)-1H-pyrazol-4-yl]amino}quinazolin-7-yl)piperidin-4-ol | Calc'd 443.0, found 443 |

TABLE 2-continued

| Ex | Structure | Name | Exact Mass [M + H]+ |
|---|---|---|---|
| Ex-1.22 | 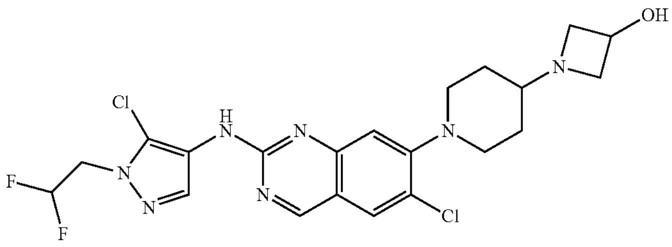 [SMILES: OC1CN(C2CCN(c3cc4nc(Nc5cnn(CC(F)F)c5Cl)ncc4cc3Cl)CC2)C1] | 1-[1-(6-chloro-2-{[5-chloro-1-(2,2-difluoroethyl)-1H-pyrazol-4-yl]amino}quinazolin-7-yl)piperidin-4-yl]azetidin-3-ol | Calc'd 498.0, found 498 |
| Ex-1.23 | 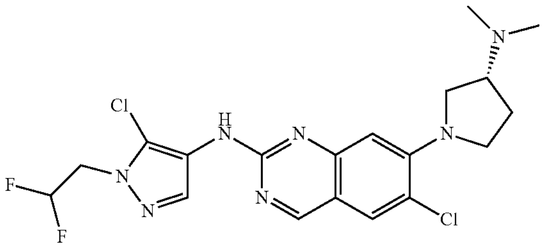 [SMILES: CN(C)[C@@H]1CCN(c2cc3nc(Nc4cnn(CC(F)F)c4Cl)ncc3cc2Cl)C1] | 6-chloro-N-[5-chloro-1-(2,2-difluoroethyl)-1H-pyrazol-4-yl]-7-[(3R)-3-(dimethylamino)pyrrolidin-1-yl]quinazolin-2-amine | Calc'd 456.0, found 456 |
| Ex-1.24 | 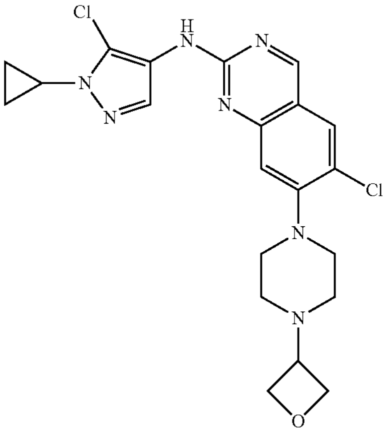 [SMILES: Clc1cc2cnc(Nc3cnn(C4CC4)c3Cl)nc2cc1N1CCN(C2COC2)CC1] | 6-chloro-N-(5-chloro-1-cyclopropyl-1H-pyrazol-4-yl)-7-[4-(oxetan-3-yl)piperazin-1-yl]quinazolin-2-amine | Calc'd 460.0, found 460 |
| Ex-1.25 | 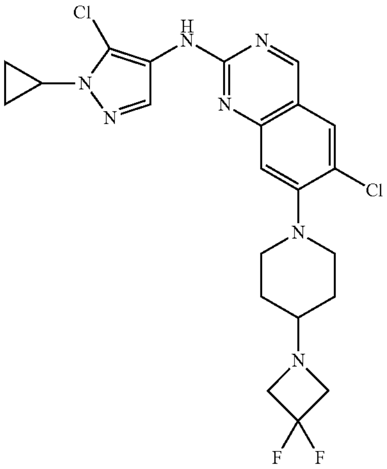 [SMILES: FC1(F)CN(C2CCN(c3cc4nc(Nc5cnn(C6CC6)c5Cl)ncc4cc3Cl)CC2)C1] | 6-chloro-N-(5-chloro-1-cyclopropyl-1H-pyrazol-4-yl)-7-[4-(3,3-difluoroazetidin-1-yl)piperidin-1-yl]quinazolin-2-amine | Calc'd 494.0, found 494 |

TABLE 2-continued

| Ex | Structure | Name | Exact Mass [M + H]+ |
|---|---|---|---|
| Ex-1.26 | 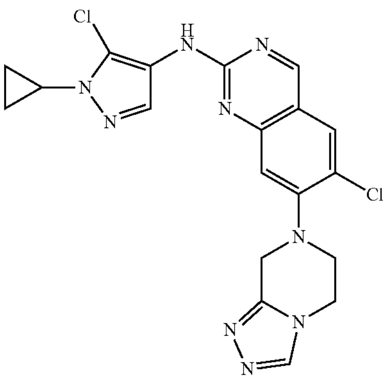 [SMILES: Clc1cc2cnc(Nc3cnn(C4CC4)c3Cl)nc2cc1N1CCn2cnnc2C1] | 6-chloro-N-(5-chloro-1-cyclopropyl-1H-pyrazol-4-yl)-7-(5,6-dihydro[1,2,4]triazolo[4,3-a]pyrazin-7(8H)-yl)quinazolin-2-amine | Calc'd 442.0, found 442 |
| Ex-1.27 | 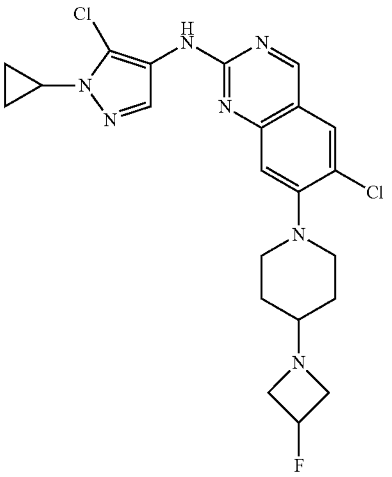 [SMILES: FC1CN(C2CCN(c3cc4nc(Nc5cnn(C6CC6)c5Cl)ncc4cc3Cl)CC2)C1] | 6-chloro-N-(5-chloro-1-cyclopropyl-1H-pyrazol-4-yl)-7-[4-(3-fluoroazetidin-1-yl)piperidin-1-yl]quinazolin-2-amine | Calc'd 476.0, found 476 |
| Ex-1.28 | 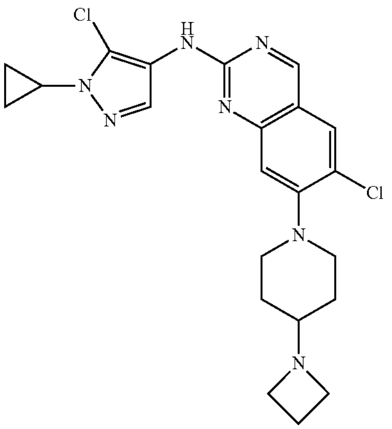 [SMILES: Clc1cc2cnc(Nc3cnn(C4CC4)c3Cl)nc2cc1N1CCC(N2CCC2)CC1] | 7-[4-(azetidin-1-yl)piperidin-1-yl]-6-chloro-N-(5-chloro-1-cyclopropyl-1H-pyrazol-4-yl)quinazolin-2-amine | Calc'd 458.0, found 458 |

TABLE 2-continued

| Ex | Structure | Name | Exact Mass [M + H]+ |
|---|---|---|---|
| Ex-1.29 | 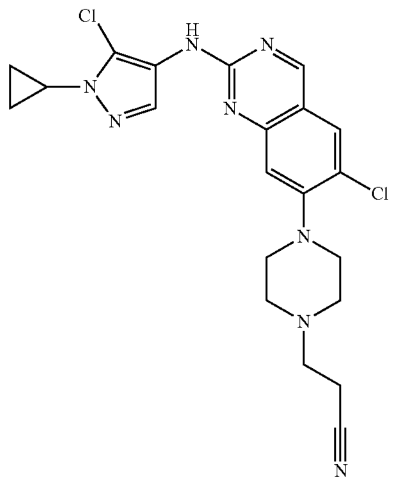 [SMILES: N#CCCN1CCN(c2cc3nc(Nc4cnn(C5CC5)c4Cl)ncc3cc2Cl)CC1] | 3-(4-{6-chloro-2-[(5-chloro-1-cyclopropyl-1H-pyrazol-4-yl)amino]quinazolin-7-yl}piperazin-1-yl)propanenitrile | Calc'd 457.0, found 457 |
| Ex-1.30 | 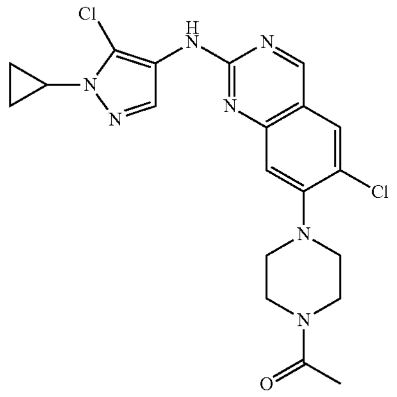 [SMILES: CC(=O)N1CCN(c2cc3nc(Nc4cnn(C5CC5)c4Cl)ncc3cc2Cl)CC1] | 1-(4-{6-chloro-2-[(5-chloro-1-cyclopropyl-1H-pyrazol-4-yl)amino]quinazolin-7-yl}piperazin-1-yl)ethan-1-one | Calc'd 446.0, found 446 |
| Ex-1.31 | 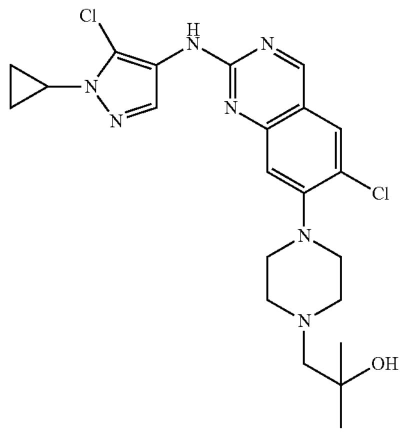 [SMILES: CC(C)(O)CN1CCN(c2cc3nc(Nc4cnn(C5CC5)c4Cl)ncc3cc2Cl)CC1] | 1-(4-{6-chloro-2-[(5-chloro-1-cyclopropyl-1H-pyrazol-4-yl)amino]quinazolin-7-yl}piperazin-1-yl)-2-methylpropan-2-ol | Calc'd 476.0, found 476 |

TABLE 2-continued

| Ex | Structure | Name | Exact Mass [M + H]$^+$ |
|---|---|---|---|
| Ex-1.32 | 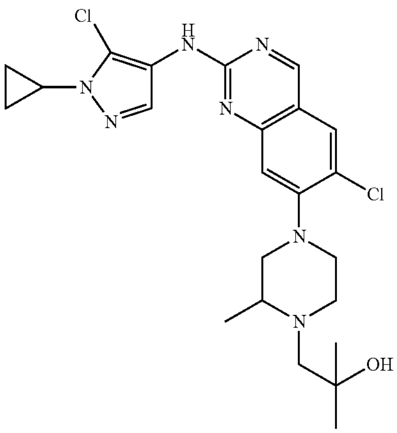 [SMILES: CC1CN(c2cc3nc(Nc4cnn(C5CC5)c4Cl)ncc3cc2Cl)CCN1CC(C)(C)O] | 1-(4-{6-chloro-2-[(5-chloro-1-cyclopropyl-1H-pyrazol-4-yl)amino]quinazolin-7-yl}-2-methylpiperazin-1-yl)-2-methylpropan-2-ol | Calc'd 490.0, found 490 |
| Ex-1.33 | 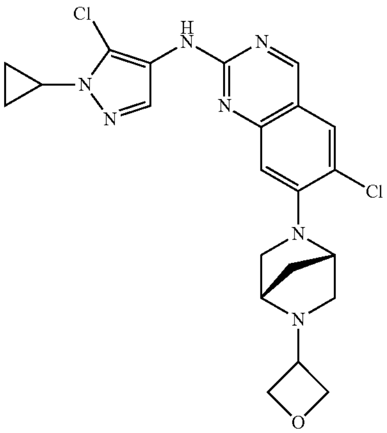 [SMILES: Clc1cc2cnc(Nc3cnn(C4CC4)c3Cl)nc2cc1N1C[C@@H]2C[C@H]1CN2C1COC1] | 6-chloro-N-(5-chloro-1-cyclopropyl-1H-pyrazol-4-yl)-7-[(1S,4S)-5-(oxetan-3-yl)-2,5-diazabicyclo[2.2.1]heptan-2-yl]quinazolin-2-amine | Calc'd 472.0, found 472 |
| Ex-1.34 | 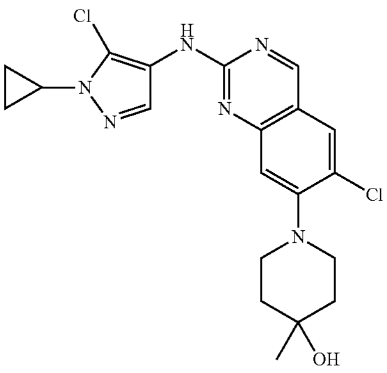 [SMILES: CC1(O)CCN(c2cc3nc(Nc4cnn(C5CC5)c4Cl)ncc3cc2Cl)CC1] | 1-{6-chloro-2-[(5-chloro-1-cyclopropyl-1H-pyrazol-4-yl)amino]quinazolin-7-yl}-4-methylpiperidin-4-ol | Calc'd 433.0, found 443 |

TABLE 2-continued

| Ex | Structure | Name | Exact Mass [M + H]+ |
|---|---|---|---|
| Ex-1.35 | 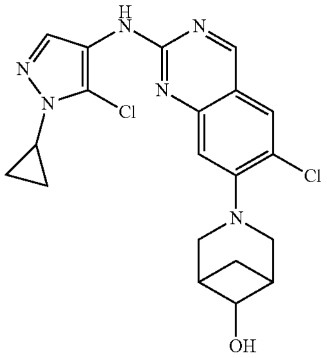 [SMILES: OC1C2CC1CN(c1cc3nc(Nc4cnn(C5CC5)c4Cl)ncc3cc1Cl)C2] | 3-{6-chloro-2-[(5-chloro-1-cyclopropyl-1H-pyrazol-4-yl)amino]quinazolin-7-yl}-3-azabicyclo[3.1.1]heptan-6-ol | Calc'd 431.0, found 431 |
| Ex-1.36 | 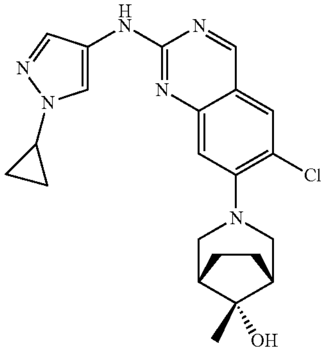 [SMILES: C[C@]1(O)[C@@H]2CC[C@H]1CN(c1cc3nc(Nc4cnn(C5CC5)c4)ncc3cc1Cl)C2] | (8-syn)-3-{6-chloro-2-[(1-cyclopropyl-1H-pyrazol-4-yl)amino]quinazolin-7-yl}-8-methyl-3-azabicyclo[3.2.1]octan-8-ol | Calc'd 425.0, found 425 |
| Ex-1.37 | 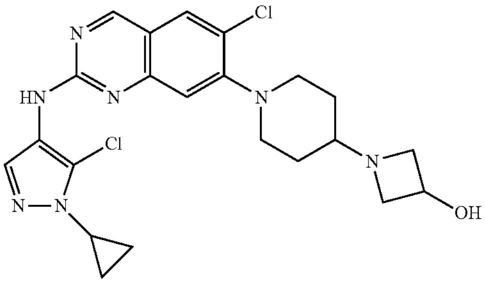 [SMILES: OC1CN(C2CCN(c3cc4nc(Nc5cnn(C6CC6)c5Cl)ncc4cc3Cl)CC2)C1] | 1-(1-{6-chloro-2-[(5-chloro-1-cyclopropyl-1H-pyrazol-4-yl)amino]quinazolin-7-yl}piperidin-4-yl)azetidin-3-ol | Calc'd 474.0, found 474 |
| Ex-1.38 | 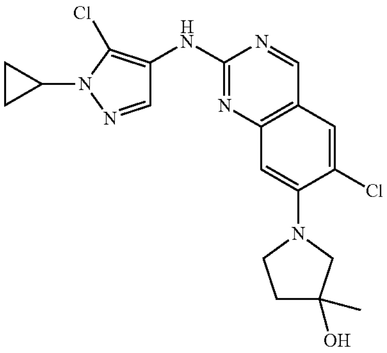 [SMILES: CC1(O)CCN(c2cc3nc(Nc4cnn(C5CC5)c4Cl)ncc3cc2Cl)C1] | 1-{6-chloro-2-[(5-chloro-1-cyclopropyl-1H-pyrazol-4-yl)amino]quinazolin-7-yl}-3-methylpyrrolidin-3-ol | Calc'd 419.0, found 419 |

TABLE 2-continued

| Ex | Structure | Name | Exact Mass [M + H]+ |
|---|---|---|---|
| Ex-1.39 | 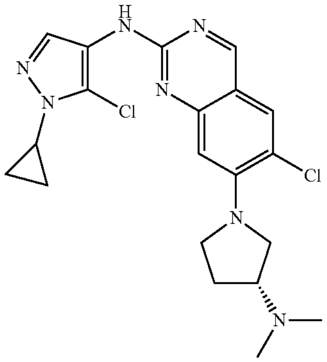 [SMILES: CN(C)[C@@H]1CCN(c2cc3nc(Nc4cnn(C5CC5)c4Cl)ncc3cc2Cl)C1] | (3R or 3S)-6-chloro-N-(5-chloro-1-cyclopropyl-1H-pyrazol-4-yl)-7-[3-(dimethylamino)pyrrolidin-1-yl]quinazolin-2-amine | Calc'd 432.0, found 432 |
| Ex-1.39 | 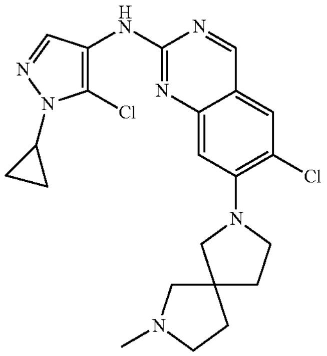 [SMILES: CN1CCC2(CCN(c3cc4nc(Nc5cnn(C6CC6)c5Cl)ncc4cc3Cl)C2)C1] | 6-chloro-N-(5-chloro-1-cyclopropyl-1H-pyrazol-4-yl)-7-(7-methyl-2,7-diazaspiro[4.4]nonan-2-yl)quinazolin-2-amine | Calc'd 458.0, found 458 |
| Ex-1.40 | 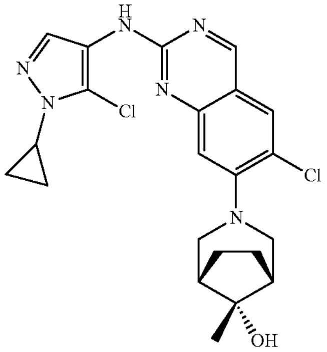 [SMILES: C[C@]1(O)[C@@H]2CC[C@H]1CN(c1cc3nc(Nc4cnn(C5CC5)c4Cl)ncc3cc1Cl)C2] | (8-syn)-3-{6-chloro-2-[(5-chloro-1-cyclopropyl-1H-pyrazol-4-yl)amino]quinazolin-7-yl}-8-methyl-3-azabicyclo[3.2.1]octan-8-ol | Calc'd 459.0, found 459 |
| Ex-1.41 | 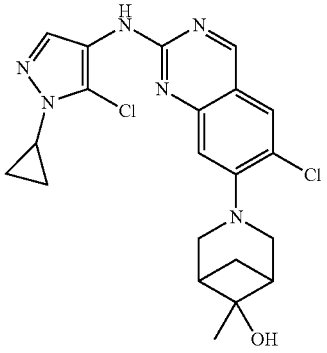 [SMILES: CC1(O)C2CC1CN(c1cc3nc(Nc4cnn(C5CC5)c4Cl)ncc3cc1Cl)C2] | 3-{6-chloro-2-[(5-chloro-1-cyclopropyl-1H-pyrazol-4-y)amino]quinazolin-7-yl}-6-methyl-3-azabicyclo[3.1.1]heptan-6-ol | Calc'd 445.0, found 445 |

TABLE 2-continued

| Ex | Structure | Name | Exact Mass [M + H]+ |
|---|---|---|---|
| Ex-1.42 | 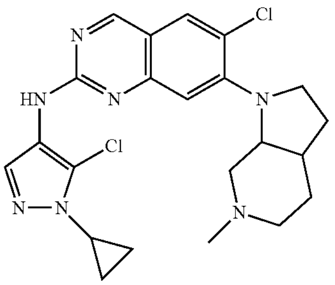 [SMILES: CN1CCC2CCN(c3cc4nc(Nc5cnn(C6CC6)c5Cl)ncc4cc3Cl)C2C1] | 6-chloro-N-(5-chloro-1-cyclopropyl-1H-pyrazol-4-yl)-7-(6-methyloctahydro-1H-pyrrolo[2,3-c]pyridin-1-yl)quinazolin-2-amine | Calc'd 458.0, found 458 |
| Ex-1.43 | 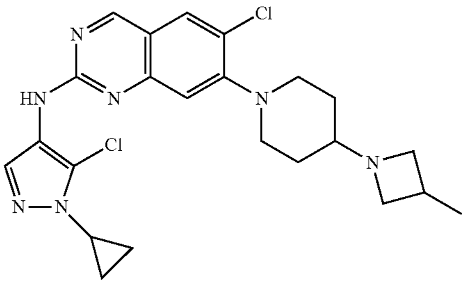 [SMILES: CC1CN(C2CCN(c3cc4nc(Nc5cnn(C6CC6)c5Cl)ncc4cc3Cl)CC2)C1] | 6-chloro-N-(5-chloro-1-cyclopropyl-1H-pyrazol-4-yl)-7-[4-(3-methylazetidin-1-yl)piperidin-1-yl]quinazolin-2-amine | Calc'd 472.0, found 472 |
| Ex-1.44 | 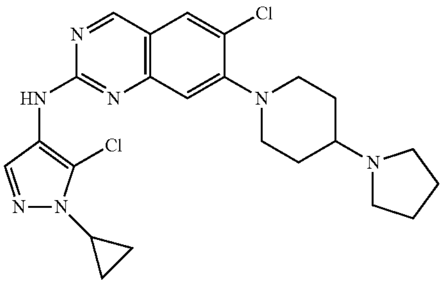 [SMILES: Clc1cc2cnc(Nc3cnn(C4CC4)c3Cl)nc2cc1N1CCC(N2CCCC2)CC1] | 6-chloro-N-(5-chloro-1-cyclopropyl-1H-pyrazol-4-yl)-7-[4-(pyrrolidin-1-yl)piperidin-1-yl]quinazolin-2-amine | Calc'd 472.0, found 472 |
| Ex-1.45 | 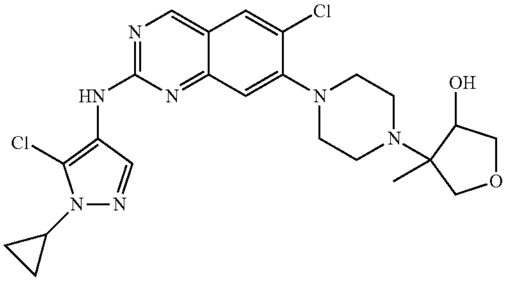 [SMILES: CC1(N2CCN(c3cc4nc(Nc5cnn(C6CC6)c5Cl)ncc4cc3Cl)CC2)COCC1O] | (3S,4S or 3R,4R)-4-(4-{6-chloro-2-[(5-chloro-1-cyclopropyl-1H-pyrazol-4-yl)amino]quinazolin-7-yl}piperazin-1-yl)-4-methyloxolan-3-ol | Calc'd 504.0, found 504 |
| Ex-1.46 | 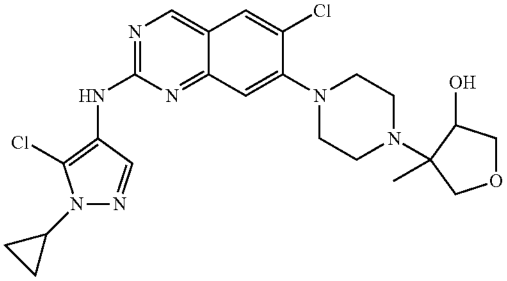 [SMILES: CC1(N2CCN(c3cc4nc(Nc5cnn(C6CC6)c5Cl)ncc4cc3Cl)CC2)COCC1O] | (3S,4S or 3R,4R)-4-(4-{6-chloro-2-[5-chloro-1-cyclopropyl-1H-pyrazol-4-yl)amino]quinazolin-7-yl}piperazin-1-yl)-4-methyloxolane-3-ol | Calc'd 504.0, found 504 |

TABLE 2-continued

| Ex | Structure | Name | Exact Mass [M + H]$^+$ |
|---|---|---|---|
| Ex-1.47 | 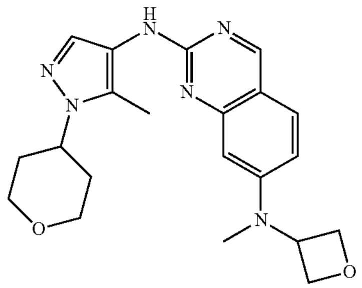 [SMILES: Cc1c(Nc2ncc3ccc(N(C)C4COC4)cc3n2)cnn1C1CCOCC1] | N-7-methyl-N-2-[5-methyl-1-(oxan-4-yl)-1H-pyrazol-4-yl]-N-7-(oxetan-3-yl)quinazoline-2,7-diamine | Calc'd 395.0, found 395 |
| Ex-1.48 | 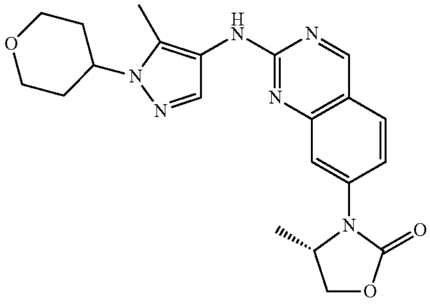 [SMILES: Cc1c(Nc2ncc3ccc(N4C(=O)OC[C@@H]4C)cc3n2)cnn1C1CCOCC1] | (4S)-4-methyl-3-(2-{[5-methyl-1-(oxan-4-yl)-1H-pyrazol-4-yl]amino}quinazolin-7-yl)-1,3-oxazolidin-2-one | Calc'd 409.0, found 409 |

General Scheme 3

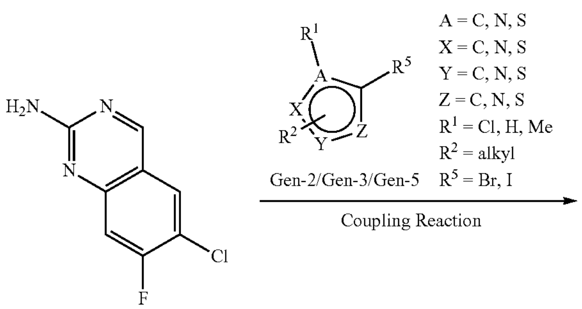

17

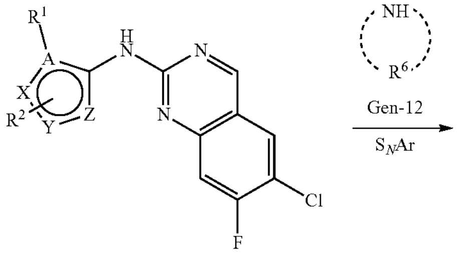

Gen-11

-continued

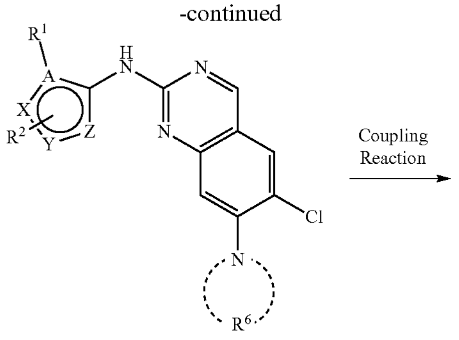

Gen-13

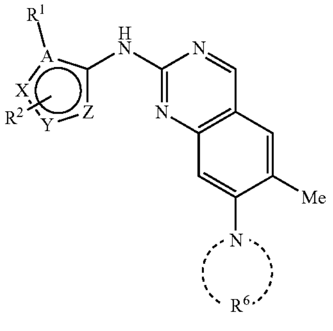

Gen-14

In General Scheme 3 synthetically prepared intermediate 17 was coupled with commercially available or synthetically prepared halo heterocycles Gen-2/Gen-3/Gen-5 through either a palladium or copper catalyzed coupling reaction to provide Gen-11. The alkyl or cyclic amine Gen-12 could ultimately be transformed under $S_NAr$ conditions to afford elaborated compounds of the form Gen-13. A palladium-catalyzed coupling reaction could be employed to generate compounds of the form Gen-14. The representative compounds are described in more detail below.

Preparation of Example 2.1

Scheme 44. Synthesis of (3R,4R)-4-(4-(6-chloro-2-((1,5-dimethyl-1H-pyrazol-4-yl)amino)quinazolin-7-yl)piperazin-1-yl)-4-methyltetrahydrofuran-3-ol

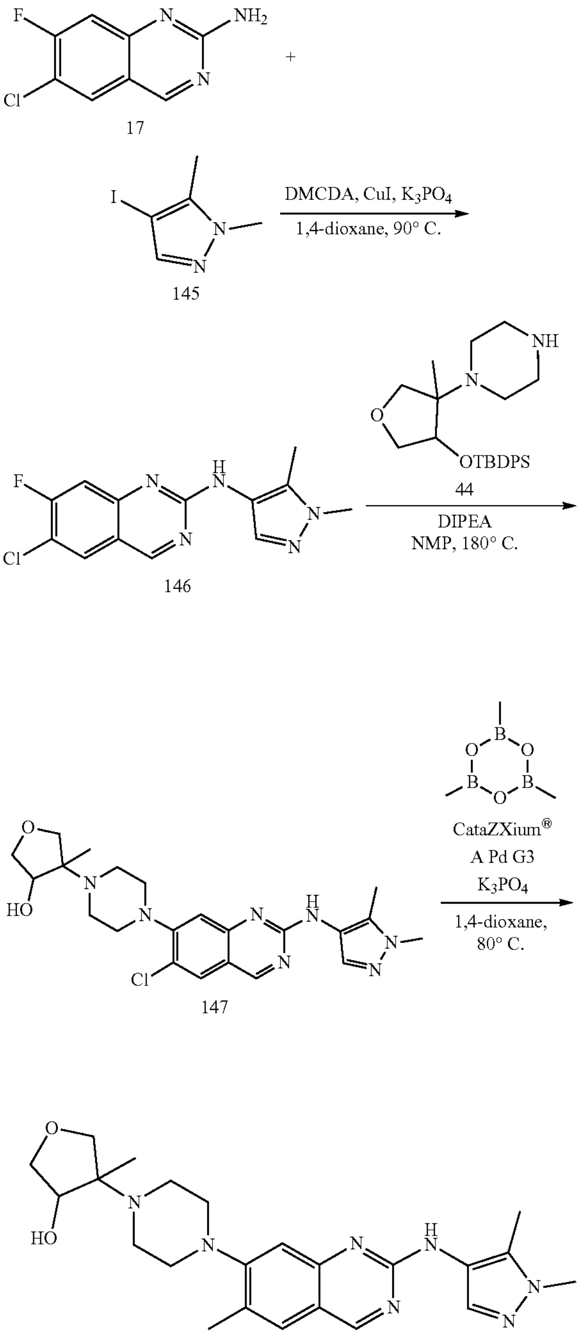

17

145

44

146

147

Ex-2.1

4-(4-(6-Chloro-2-((1,5-dimethyl-1H-pyrazol-4-yl)amino)quinazolin-7-yl)piperazin-1-yl)-4-methyltetrahydrofuran-3-ol (146)

Utilizing a comparative Cu-mediated coupling reaction sequence as demonstrated in Scheme 41 in the formation of 139, the title compound 146 was synthesized. MS (ESI): m/z calc'd for $C_{13}H_{11}ClFN_5$ $[M+H]^+$: 292, found 292.

(3R,4R)-4-(4-(6-Chloro-2-((1,5-dimethyl-1H-pyrazol-4-yl)amino)quinazolin-7-yl)piperazin-1-yl)-4-methyltetrahydrofuran-3-ol (147)

A microwave vial was charged with 6-chloro-N-(1,5-dimethyl-1H-pyrazol-4-yl)-7-fluoroquinazolin-2-amine 146 (43.8 mg, 0.15 mmol) and 1-((3R,4R)-4-((tert-butyldiphenylsilyl)oxy)tetrahydrofuran-3-yl)piperazine 44 (127 mg, 0.300 mmol). To this mixture was added NMP (150 μL) and DIPEA (105 μL, 0.600 mmol). The vial was sealed, evacuated and charged with nitrogen and then stirred at 180° C. for 6 h. The resultant mixture was then stirred at RT overnight. Heating was resumed at 180° C. for 3 h. The crude mixture was diluted in DCM and subjected to purification by flash chromatography over silica (3:1 EtOAc:EtOH/hexanes, 25-100%) to afford the title compound 147. MS (ESI): m/z calc'd for $C_{22}H_{27}ClN_7O_2$ $[M+H]^+$: 458, found 458.

(3R,4R)-4-(4-(2-((1,5-Dimethyl-1H-pyrazol-4-yl)amino)-6-methylquinazolin-7-yl)piperazin-1-yl)-4-methyltetrahydrofuran-3-ol, isomer 1 (Ex-2.1)

4-(4-(6-Chloro-2-((1,5-dimethyl-1H-pyrazol-4-yl)amino)quinazolin-7-yl)piperazin-1-yl)-4-methyltetrahydrofuran-3-ol 147 (0.057 g, 0.12 mmol), CataCXium© A Pd G3 (0.018 g, 0.025 mmol) and $K_3PO_4$ (0.106 g, 0.498 mmol) were added to a 0.5-2 ml microwave vial. The solids were purged with nitrogen 3 times, then dioxane (1.3 mL) and trimethylboroxine (0.087 mL, 0.62 mmol) were added and the reaction mixture was purged 3× with nitrogen. The resultant mixture was stirred at 80° C. overnight. The reaction mixture was diluted with 1 mL of DCM, filtered, and solvent removed under reduced pressure. The crude residue was subjected to purification by flash chromatography over silica gel (3:1 EtOAc:EtOH/hexanes, 50-100%) to afford the title compound Ex-2.1. MS (ESI): m/z calc'd for $C_{23}H_{31}N_7O_2$ $[M+H]^+$: 438, found 438; $^1H$ NMR (500 MHz, $CDCl_3$, 25° C.) δ: 8.86 (s, 1H), 7.75 (s, 1H), 7.48 (s, 1H), 7.10 (s, 1H), 6.49 (s, 1H), 4.44 (m, 1H), 4.11 (d, J=10 Hz, 1H), 4.01 (d, J=9 Hz, 1H), 3.86-3.81 (s, m, 5H), 3.74 (d, J=6.5 Hz, 1H), 3.64 (d, J=6.5 Hz, 1H), 3.12 (m, 2H), 2.83 (m, 2H), 2.62 (m, 2H), 2.41 (s, 3H), 2.25 (s, 3H), 1.19 (s, 3H). The isomeric intermediate tert-butyl 1-((3S,4S)-4-((tert-butyldiphenylsilyl)oxy)tetrahydrofuran-3-yl)piperazine (45) can be used as the amine coupling partner to provide the isomeric product Ex. 2.2.

The following Examples, 2.2-2.4 were obtained using the procedures analogous to those in General Scheme 3 but substituting appropriate starting materials that are either commercially available or prepared using procedures analogous to those described in Scheme 44.

TABLE 3

| Ex | Structure | Name | Exact Mass [M + H]+ |
|---|---|---|---|
| Ex-2.2 | 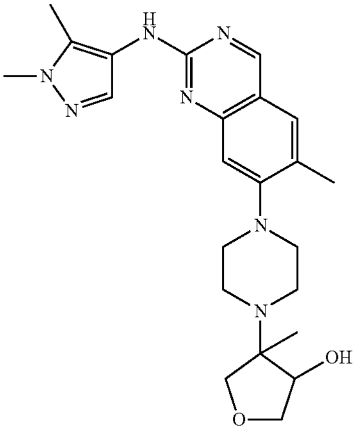 | (3S,4S or 3R,4R)-4-(4-{2-[(1,5-dimethyl-1H-pyrazol-4-yl)amino]-6-methylquinazolin-7-yl}piperazin-1-yl)-4-methyloxolane-3-ol | Calc'd 438.0, found 438 |
| Ex-2.3 | 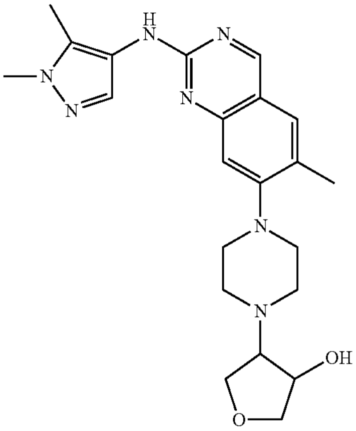 | (3S,4S or 3R,4R)-4-(4-{2-[(1,5-dimethyl-1H-pyrazol-4-yl)amino]-6-methylquinazolin-7-yl}piperazin-1-yl)oxolan-3-ol | Calc'd 424.0, found 424 |
| Ex-2.4 | 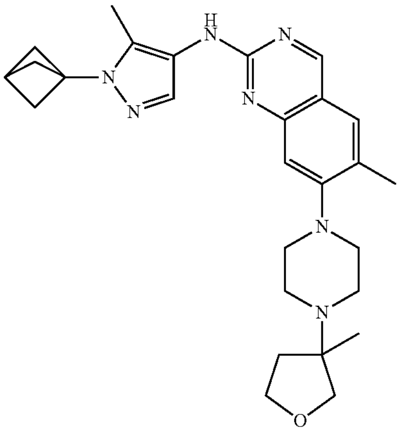 [SMILES: Cc1cc2cnc(Nc3cnn(C45CC(C4)C5)c3C)nc2cc1N1CCN(C2(C)CCOC2)CC1] | (3S,4S or 3R,4R)-N-(1-(bicyclo[1.1.1]pentan-1-yl)-5-methyl-1H-pyrazol-4-yl)-6-methyl-7-(4-(3-methyltetrahydrofuran-3-yl)piperazin-1-yl)quinazolin-2-amine | Calc'd 474.0, found 474 |

General Scheme 4

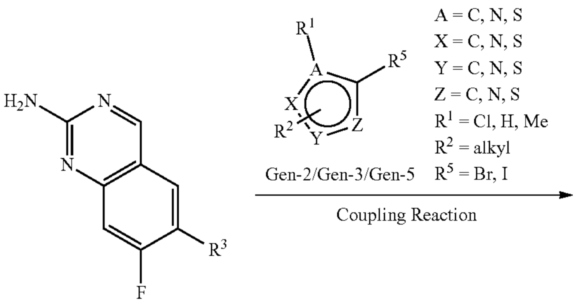

Gen-15

$R^3$ = H, Me, CN

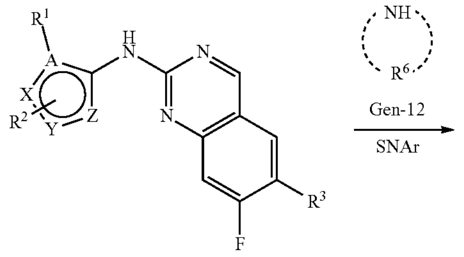

Gen-16

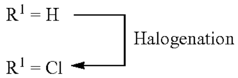

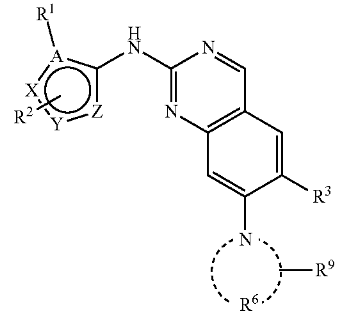

Gen-18

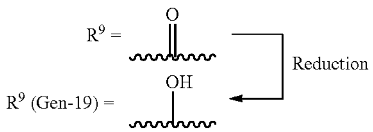

In General Scheme 4 synthetically prepared intermediate Gen-15 was coupled with commercially available or synthetically prepared halo heterocycles Gen-2/Gen-3/Gen-5 through either a palladium or copper catalyzed coupling reaction to provide Gen-16. A subsequent chlorination reaction employing Palau' Chlor® could be used to transform $R^1$ into a chlorine atom if $R^1$=H in pyrazoles Gen-2/Gen-3/Gen-5. The cyclic or acyclic amine Gen-12 could ultimately be used as a nucleophile in conjunction with Gen-12 under $S_NAr$ conditions to afford elaborated compounds of the form Gen-18. In cases where $R^9$ represents a ketone group, a subsequent reduction sequence could be performed to yield compounds of the form Gen-19. The representative compounds are described in more detail below.

Preparation of Example 3.1

Scheme 45. Synthesis of (endo)-3-(6-chloro-2-((5-chloro-1-(3-(methoxymethyl)bicyclo[1.1.1]pentan-1-yl)-1H-pyrazol-4-yl)amino)quinazolin-7-yl)-8-methyl-3-azabicyclo[3.2.1]octan-8-ol

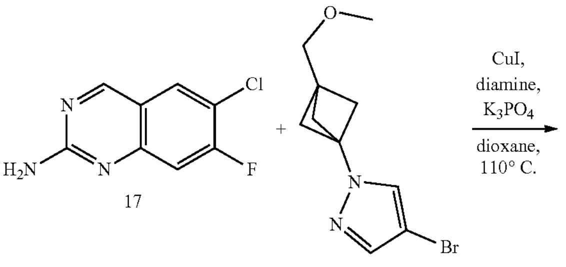

17

71

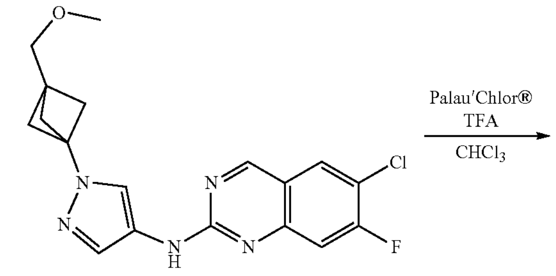

148

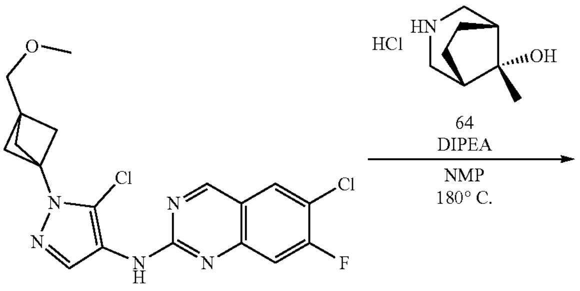

149

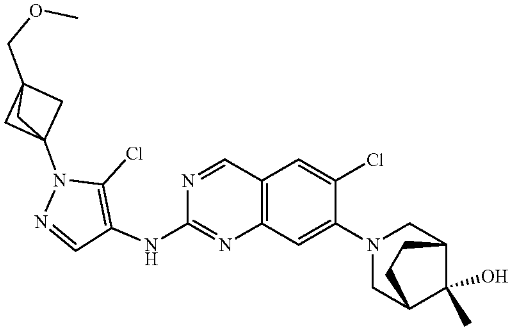

Ex-3.1

6-Chloro-7-fluoro-N-(1-(3-(methoxymethyl)bicyclo[1.1.1]pentan-1-yl)-1H-pyrazol-4-yl)quinazolin-2-amine (148)

A comparative Cu-mediated coupling reaction sequence as demonstrated in Scheme 41 in the formation of 139 was utilized with 4-bromo-1-(3-(methoxymethyl)bicyclo[1.1.1]pentan-1-yl)-1H-pyrazole 71 as coupling partner to 6-chloro-7-fluoroquinazolin-2-amine 17 to afford the title compound 148 MS (ESI): m/z calc'd for $C_{18}H_{17}ClFN_5O$ $[M+H]^+$: 374, found 374.

6-Chloro-N-(5-chloro-1-(3-(methoxymethyl)bicyclo[1.1.1]pentan-1-yl)-1H-pyrazol-4-yl)-7-fluoroquinazolin-2-amine (149)

A 4-mL vial was charged with 6-chloro-7-fluoro-N-(1-(3-(methoxymethyl)bicyclo[1.1.1]pentan-1-yl)-1H-pyrazol-4-yl)quinazolin-2-amine 148 (29 mg, 0.078 mmol) and dissolved in chloroform (776 μL). To the suspension was added Palau' Chlor® (16.3 mg, 0.0780 mmol) followed by TFA (17.9 μL, 0.233 mmol). The reaction mixture was allowed to stir for 20 min at which point LC/MS indicated the reaction was nearly complete. The reaction mixture was stirred another 15 min at which point the solvent was removed under reduced pressure. The resultant crude residue was subjected to purification by flash chromatography over silica gel (EtOAc/PE, 5-100%) to afford the title compound 149. MS (ESI): m/z calc'd for $C_{18}H_{16}Cl_2FN_5O$ $[M+H]^+$: 408, found 408.

(Endo)-3-(6-chloro-2-((5-chloro-1-(3-(methoxymethyl)bicyclo[1.1.1]pentan-1-yl)-1H-pyrazol-4-yl)amino)quinazolin-7-yl)-8-methyl-3-azabicyclo[3.2.1]octan-8-ol (Ex-3.1)

6-Chloro-N-(5-chloro-1-(3-(methoxymethyl)bicyclo[1.1.1]pentan-1-yl)-1H-pyrazol-4-yl)-7-fluoroquinazolin-2-amine 149 (0.022 μg, 0.054 mmol) and (endo)-8-methyl-3-azabicyclo[3.2.1]octan-8-ol hydrochloride 64 (0.038 g, 0.22 mmol) were added to a 0.5-2 mL microwave vial. NMP (0.054 mL) and DIPEA (0.094 mL, 0.54 mmol) were added, and the vial was sealed, then evacuated and backfilled with nitrogen. The resultant mixture was heated to 180° C. for 3 h. Upon cooling to RT the reaction mixture was diluted with DCM (1 mL), filtered, and subjected to purification by flash chromatography over silica gel (3:1 EtOAc:EtOH/hexanes, 30-75%) to afford the title compound Ex-3.1. MS (ESI): m/z calc'd for $C_{26}H_{30}Cl_2N_6O_2$ $[M+H]^+$: 529, found 529. $^1H$ NMR (500 MHz, $CDCl_3$, 25° C.) δ: 8.85 (s, 1H), 8.28 (s, 1H), 7.69 (s, 1H), 7.25 (s, 1H), 6.65 (s, 1H), 3.60 (s, 2H), 3.51 (d, J=11 Hz, 2H), 3.43 (s, 3H), 3.29 (d, J=11 Hz, 2H), 2.41 (s, 6H), 2.07 (m, 2H), 1.90 (m, 2H), 1.79 (m, 2H), 1.40 (m, 4H).

Preparation of Examples 3.2 and 3.3

Scheme 46. Synthesis of (R) or (S)-8-(6-chloro-2-((5-chloro-1-cyclopropyl-1H-pyrazol-4-yl)amino)quinazolin-7-yl)-2-oxa-8-azaspiro[4.5]decan-4-ol (Ex-3.2) and (R) or (S)-8-(6-chloro-2-((5-chloro-1-cyclopropyl-1H-pyrazol-4-yl)amino)quinazolin-7-yl)-2-oxa-8-azaspiro[4.5]decan-4-ol (Ex-3.3)

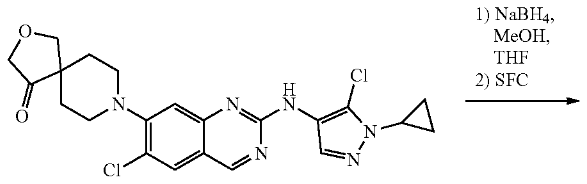

150

-continued

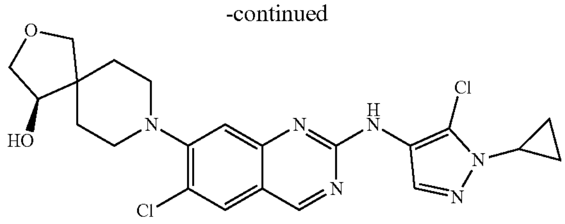

Ex-3.2

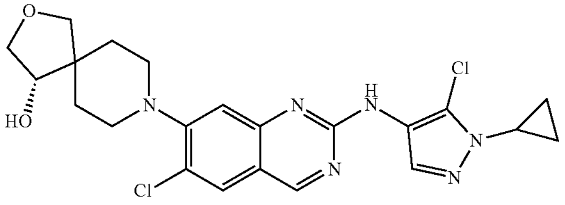

Ex-3.3

8-(6-Chloro-2-((5-chloro-1-cyclopropyl-1H-pyrazol-4-yl)amino)quinazolin-7-yl)-2-oxa-8-azaspiro[4.5]decan-4-one 150 (50.9 mg, 0.108 mmol) was dissolved in MeOH (1 mL) and the reaction mixture was cooled to 0° C. $NaBH_4$ (6.10 mg, 0.161 mmol) was added. The resultant mixture was stirred at 0° C. for 2.5 h, then quenched with 1-2 drops of 1 N HCl followed by the addition of sat. aq. $NH_4Cl$ (10 mL). The aqueous phase was extracted with EtOAc (3×20 mL). The combined organic phases were washed with sat. aq. $NaHCO_3$, dried over sodium sulfate, filtered, and the solvent removed under reduced pressure. The resultant crude residue was submitted to SFC chiral separation (Column OD-H, 4.6×250 mm; Mobile Phase A: $CO_2$; Mobile Phase B: EtOH+0.1% DIPEA) to afford the title compounds Example 3.2 ($t_R$=8.2 min) and Example 3.3 ($t_R$=9.7 min). Isomer 1 (Ex-3.2): MS (ESI): m/z calc'd for $C_{22}H_{24}C_{12}N_6O_2$ $[M+H]^+$: 475, found 475. $^1H$ NMR (500 MHz, $CDCl_3$, 25° C.) δ: 8.87 (s, 1H), 8.23 (s, 1H), 7.73 (s, 1H), 7.18 (s, 1H), 6.75 (s, 1H), 4.18 (m, 1H), 4.14 (m, 1H), 3.87 (d, J=8.5 Hz, 1H), 3.79 (m, 2H), 3.48 (m, 1H), 3.36 (m, 2H), 3.12 (m, 2H), 2.99 (m, 1H), 1.89-1.74 (m, 2H), 1.28 (m, 4H), 1.11 (d, J=6.5 Hz, 2H). Isomer 2 (Ex-3.3): MS (ESI): m/z calc'd for $C_{22}H_{24}C_{12}N_6O_2$ $[M+H]^+$: 475, found 475. $^1H$ NMR (500 MHz, $CDCl_3$, 25° C.) δ: 8.87 (s, 1H), 8.23 (s, 1H), 7.73 (s, 1H), 7.18 (s, 1H), 6.75 (s, 1H), 4.18 (m, 1H), 4.14 (m, 1H), 3.87 (d, J=8.5 Hz, 1H), 3.79 (m, 2H), 3.48 (m, 1H), 3.36 (m, 2H), 3.12 (m, 2H), 2.99 (m, 1H), 1.89-1.74 (m, 2H), 1.28 (m, 4H), 1.11 (d, J=6.5 Hz, 2H).

Preparation of Examples 3.4 and 3.5

Scheme 47. Synthesis of (R) or (S)-8-(6-chloro-2-((5-chloro-1-cyclopropyl-1H-pyrazol-4-yl)amino)quinazolin-7-yl)-4-methyl-2-oxa-8-azaspiro[4.5]decan-4-ol (Ex-3.4 and Ex-3.5)

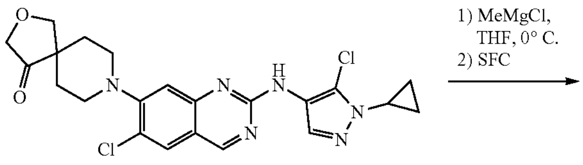

150

-continued

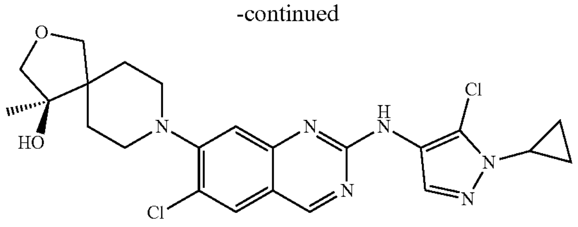

Ex-3.4

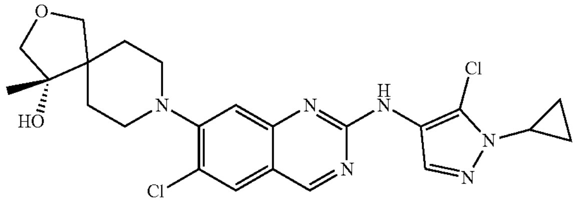

Ex-3.5

8-(6-Chloro-2-((5-chloro-1-cyclopropyl-1H-pyrazol-4-yl)amino)quinazolin-7-yl)-2-oxa-8-azaspiro[4.5]decan-4-one 150 (64.4 mg, 0.136 mmol) was dissolved in THF (907 μL) and the reaction mixture was cooled to 0° C. MeMgCl (3.0 M in THF, 0.25 mL, 0.75 mmol) was added. The resultant mixture was stirred at 0° C. overnight while slowly warming to RT. The resultant mixture was quenched by the addition of sat. aq. $NH_4Cl$ (10 mL). The aqueous phase was extracted with EtOAc (3×20 mL). The combined organic phases were washed with sat. aq. $NaHCO_3$, dried over magnesium sulfate, filtered, and the solvent removed under reduced pressure. The resultant crude residue was submitted to SFC chiral separation (Column AS-H, 21×250 mm; Mobile Phase A: $CO_2$; Mobile Phase B: 30% 1:1 MeOH: MeCN+0.2% DIPEA) to afford the title compounds Example 3.4 ($t_R$=4.7 min) and Example 3.5 ($t_R$=5.9 min). Isomer 1 (Ex-3.4): MS (ESI): m/z calc'd for $C_{23}H_{26}C_{12}N_6O_2$ $[M+H]^+$: 489, found 489. $^1$H NMR (500 MHz, $CDCl_3$, 25° C.) d 8.87 (s, 1H), 8.23 (s, 1H), 7.73 (s, 1H), 7.17 (s, 1H), 6.72 (s, 1H), 4.12 (d, J=8.7 Hz, 1H), 3.93 (m, 1H), 3.84 (s, 2H), 3.63 (m, 1H), 3.48 (m, 1H), 2.83, (m, 1H), 2.64 (m, 1H), 1.95 (m, 2H), 1.88 (m, 2H), 1.60 (m, 2H), 1.33 (s, 3H), 1.26 (m, 2H), 1.11 (m, 2H). Isomer 2 (Ex-3.5): MS (ESI): m/z calc'd for $C_{23}H_{26}C_{12}N_6O_2$ $[M+H]^+$: 489, found 489. $^1$H NMR (500 MHz, $CDCl_3$, 25° C.) d 8.87 (s, 1H), 8.23 (s, 1H), 7.73 (s, 1H), 7.17 (s, 1H), 6.72 (s, 1H), 4.12 (d, J=8.7 Hz, 1H), 3.93 (m, 1H), 3.84 (s, 2H), 3.63 (m, 1H), 3.48 (m, 1H), 2.83, (m, 1H), 2.64 (m, 1H), 1.95 (m, 2H), 1.88 (m, 2H), 1.60 (m, 2H), 1.33 (s, 3H), 1.25 (m, 2H), 1.11 (m, 2H).

The following Examples, 3.6-3.60 were obtained using the procedure analogous to those in General Scheme 4 but substituting appropriate starting materials that are either commercially available or prepared using procedures analogous to those described in Schemes 45 through 47.

TABLE 4

| Ex | Structure | Name | Exact Mass $[M + H]^+$ |
|---|---|---|---|
| Ex-3.6 | 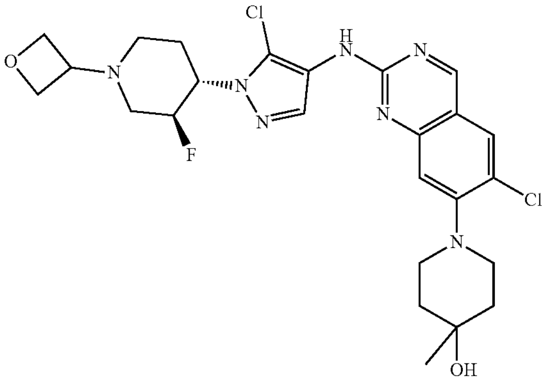 [SMILES: CC1(O)CCN(c2cc3nc(Nc4cnn([C@H]5CCN(C6COC6)C[C@@H]5F)c4Cl)ncc3cc2Cl)CC1] | 1-[6-chloro-2-({5-chloro-1-[(3S,4S)-3-fluoro-1-(oxetan-3-yl) piperidin-4-yl]-1H-pyrazol-4-yl} amino)quinazolin-7-yl]-4-methylpiperidin-4-ol | Calc'd 550.0, found 550 |
| Ex-3.7 | 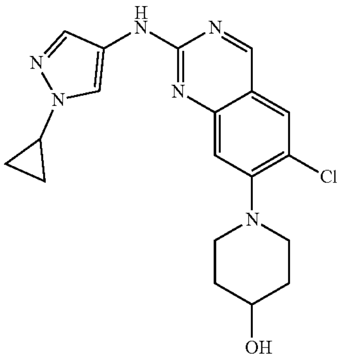 [SMILES: OC1CCN(c2cc3nc(Nc4cnn(C5CC5)c4)ncc3cc2Cl)CC1] | 1-{6-chloro-2-[(1-cyclopropyl-1H-pyrazol-4-yl)amino]quinazolin-7-yl} piperidin-4-ol | Calc'd 385.0, found 385 |

TABLE 4-continued

| Ex | Structure | Name | Exact Mass [M + H]+ |
|---|---|---|---|
| Ex-3.8 | 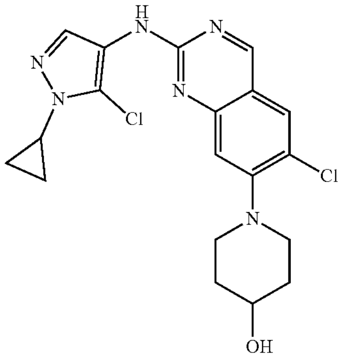 [SMILES: OC1CCN(c2cc3nc(Nc4cnn(C5CC5)c4Cl)ncc3cc2Cl)CC1] | 1-{6-chloro-2-[(5-chloro-1-cyclopropyl-1H-pyrazol-4-yl)amino]quinazolin-7-yl}piperidin-4-ol | Calc'd 419.0, found 419 |
| Ex-3.9 | 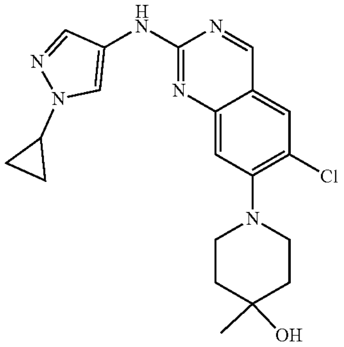 [SMILES: CC1(O)CCN(c2cc3nc(Nc4cnn(C5CC5)c4)ncc3cc2Cl)CC1] | 1-{6-chloro-2-[(1-cyclopropyl-1H-pyrazol-4-yl)amino]quinazolin-7-yl}-4-methylpiperidin-4-ol | Calc'd 399.0, found 399 |
| Ex-3.10 | 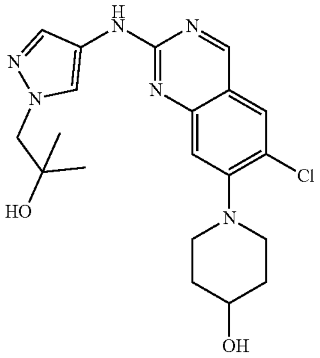 [SMILES: CC(C)(O)Cn1cc(Nc2ncc3cc(Cl)c(N4CCC(O)CC4)cc3n2)cn1] | 1-(6-chloro-2-{[1-(2-hydroxy-2-methylpropyl)-1H-pyrazol-4-yl]amino}quinazolin-7-yl)piperidin-4-ol | Calc'd 417.0, found 417 |
| Ex-3.11 | 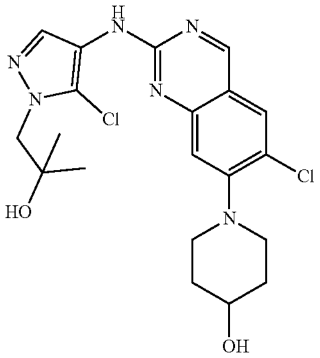 [SMILES: CC(C)(O)Cn1ncc(Nc2ncc3cc(Cl)c(N4CCC(O)CC4)cc3n2)c1Cl] | 1-(6-chloro-2-{[5-chloro-1-(2-hydroxy-2-methylpropyl)-1H-pyrazol-4-yl]amino}quinazolin-7-yl)piperidin-4-ol | Calc'd 451.0, found 451 |

TABLE 4-continued

| Ex | Structure | Name | Exact Mass [M + H]+ |
| --- | --- | --- | --- |
| Ex-3.12 | 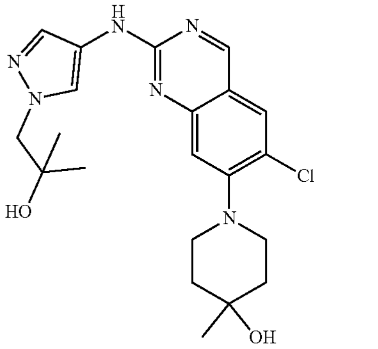 [SMILES: CC(C)(O)Cn1cc(Nc2ncc3cc(Cl)c(N4CCC(C)(O)CC4)cc3n2)cn1] | 1-(6-chloro-2-{[1-(2-hydroxy-2-methylpropyl)-1H-pyrazol-4-yl]amino}quinazolin-7-yl)-4-methyl-piperidin-4-ol | Calc'd 431.0, found 431 |
| Ex-3.13 | 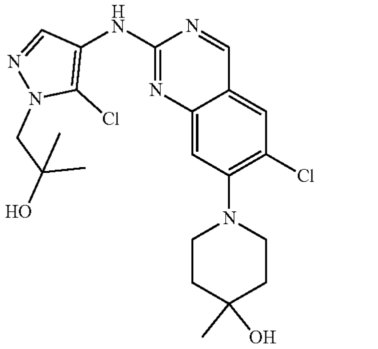 [SMILES: CC(C)(O)Cn1ncc(Nc2ncc3cc(Cl)c(N4CCC(C)(O)CC4)cc3n2)c1Cl] | 1-(6-chloro-2-{[5-chloro-1-(2-hydroxy-2-methylpropyl)-1H-pyrazol-4-yl]amino}quinazolin-7-yl)-4-methylpiperidin-4-ol | Calc'd 465.0, found 465 |
| Ex-3.14 | 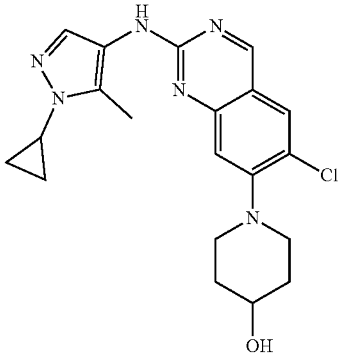 [SMILES: Cc1c(Nc2ncc3cc(Cl)c(N4CCC(O)CC4)cc3n2)cnn1C1CC1] | 1-{6-chloro-2-[(1-cyclopropyl-5-methyl-1H-pyrazol-4-yl)amino]quinazolin-7-yl}piperidin-4-ol | Calc'd 399.0, found 399 |
| Ex-3.15 | 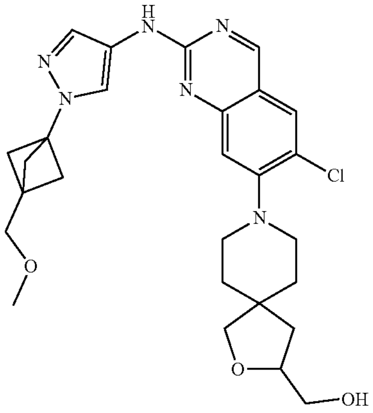 [SMILES: COCC12CC(n3cc(Nc4ncc5cc(Cl)c(N6CCC7(CC6)COC(CO)C7)cc5n4)cn3)(C1)C2] | {8-[6-chloro-2-({1-[3-(methoxymethyl)bicyclo[1.1.1]pentan-1-yl]-1H-pyrazol-4-yl}amino)quinazolin-7-yl]-2-oxa-8-azaspiro[4.5]decan-3-yl}methanol | Calc'd 525.0, found 525 |

TABLE 4-continued

| Ex | Structure | Name | Exact Mass [M + H]+ |
| --- | --- | --- | --- |
| Ex-3.16 | 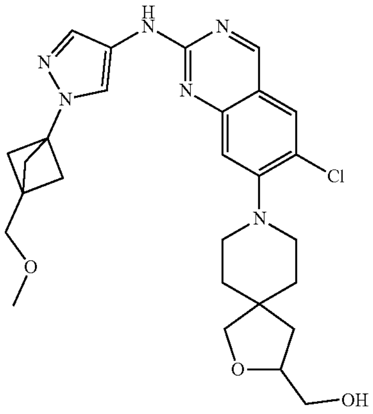 [SMILES: COCC12CC(n3cc(Nc4ncc5cc(Cl)c(N6CCC7(CC6)COC(CO)C7)cc5n4)cn3)(C1)C2] | (R) or (S)-{8-[6-chloro-2-({1-[3-(methoxymethyl)bicyclo[1.1.1]pentan-1-yl]-1H-pyrazol-4-yl}amino)quinazolin-7-yl]-2-oxa-8-azaspiro[4.5]decan-3-yl}methanol | Calc'd 525.0, found 525 |
| Ex-3.17 | 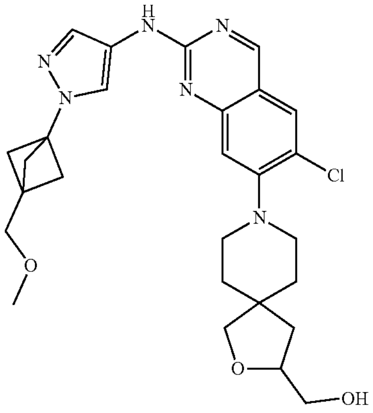 [SMILES: COCC12CC(n3cc(Nc4ncc5cc(Cl)c(N6CCC7(CC6)COC(CO)C7)cc5n4)cn3)(C1)C2] | (R) or (S)-{8-[6-chloro-2-({1-[3-(methoxymethyl)bicyclo[1.1.1]pentan-1-yl]-1H-pyrazol-4-yl}amino)quinazolin-7-yl]-2-oxa-8-azaspiro[4.5]decan-3-yl}methanol | Calc'd 525.0, found 525 |
| Ex-3.18 | 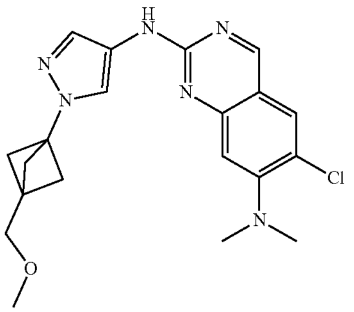 [SMILES: COCC12CC(n3cc(Nc4ncc5cc(Cl)c(N(C)C)cc5n4)cn3)(C1)C2] | 6-chloro-N-2-{1-[3-(methoxymethyl)bicyclo[1.1.1]pentan-1-yl]-1H-pyrazol-4-yl}-N-7-,N-7-dimethylquinazoline-2,7-diamine | Calc'd 399.0, found 399 |
| Ex-3.19 | 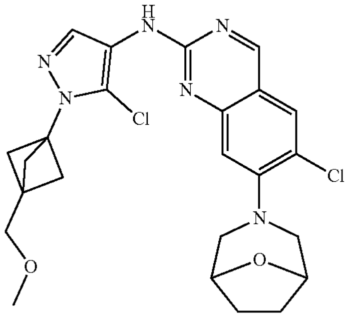 [SMILES: COCC12CC(n3ncc(Nc4ncc5cc(Cl)c(N6CC7CCC(C6)O7)cc5n4)c3Cl)(C1)C2] | 6-chloro-N-(5-chloro-1-cyclopropyl-1H-pyrazol-4-yl)-7-(8-oxa-3-azabicyclo[3.2.1]octan-3-yl)quinazolin-2-amine | Calc'd 431.0, found 431 |

TABLE 4-continued

| Ex | Structure | Name | Exact Mass [M + H]$^+$ |
|---|---|---|---|
| Ex-3.20 | 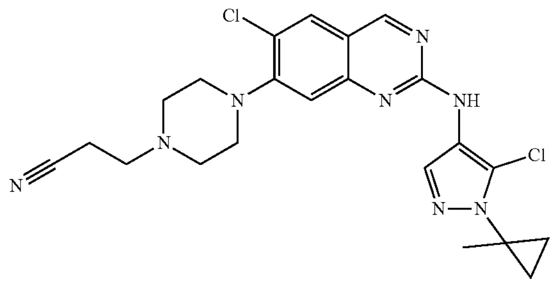 [SMILES: CC1(n2ncc(Nc3ncc4cc(Cl)c(N5CCN(CCC#N)CC5)cc4n3)c2Cl)CC1] | 3-[4-(6-chloro-2-{[5-chloro-1-(1-methylcyclopropyl)-1H-pyrazol-4-yl]amino}quinazolin-7-yl)piperazin-1-yl]propanenitrile | Calc'd 471.0, found 471 |
| Ex-3.21 | 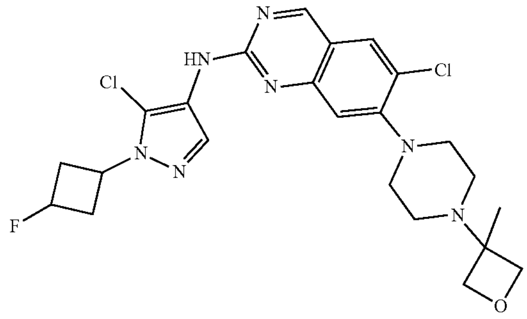 [SMILES: CC1(N2CCN(c3cc4nc(Nc5cnn(C6CC(F)C6)c5Cl)ncc4cc3Cl)CC2)COC1] | 6-chloro-N-[5-chloro-1-(3-fluorocyclobutyl)-1H-pyrazol-4-yl]-7-[4-(3-methyloxetan-3-yl) piperazin-1-yl]quinazolin-2-amine | Calc'd 506.0, found 506 |
| Ex-3.22 | 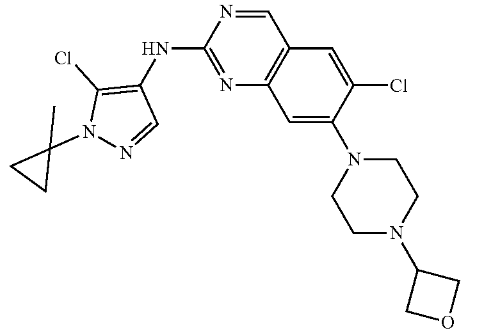 [SMILES: CC1(n2ncc(Nc3ncc4cc(Cl)c(N5CCN(C6COC6)CC5)cc4n3)c2Cl)CC1] | 6-chloro-N-[5-chloro-1-(1-methylcyclopropyl)-1H-pyrazol-4-yl]-7-[4-(oxetan-3-yl)piperazin-1-yl]quinazolin-2-amine | Calc'd 474.0, found 474 |
| Ex.3.23 | 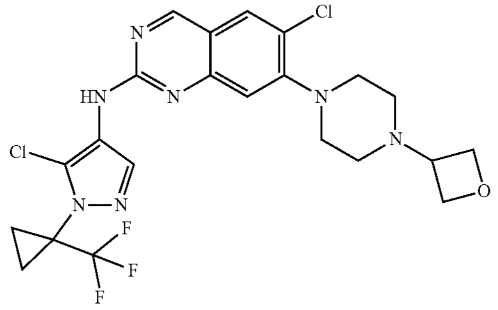 [SMILES: FC(F)(F)C1(n2ncc(Nc3ncc4cc(Cl)c(N5CCN(C6COC6)CC5)cc4n3)c2Cl)CC1] | 6-chloro-N-{5-chloro-1-[1-(trifluoromethyl)cyclopropyl]-1H-pyrazol-4-yl}-7-[4-(oxetan-3-yl)piperazin-1-yl]quinazolin-2-amine | Calc'd 528.0, found 528 |
| Ex-3.24 | 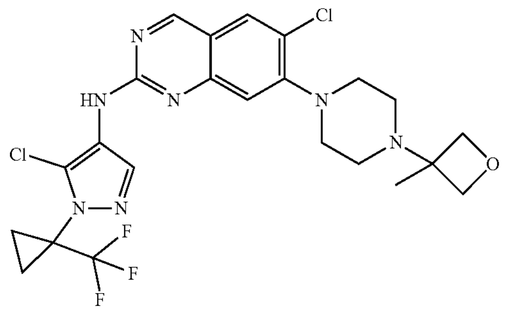 [SMILES: CC1(N2CCN(c3cc4nc(Nc5cnn(C6(C(F)(F)F)CC6)c5Cl)ncc4cc3Cl)CC2)COC1] | 6-chloro-N-{5-chloro-1-[1-(trifluoromethyl)cyclopropyl]-1H-pyrazol-4-yl}-7-[4-(3-methyloxetan-3-yl)piperazin-1-yl]quinazolin-2-amine | Calc'd 542.0, found 542 |

TABLE 4-continued

| Ex | Structure | Name | Exact Mass [M + H]+ |
|---|---|---|---|
| Ex-3.25 | 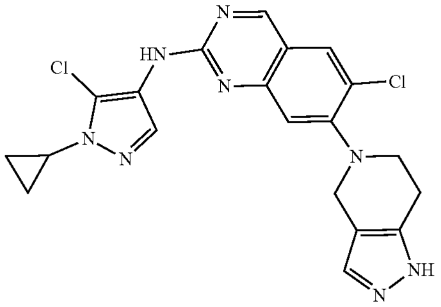 [SMILES: Clc1cc2cnc(Nc3cnn(C4CC4)c3Cl)nc2cc1N1CCc2[nH]ncc2C1] | 6-chloro-N-(5-chloro-1-cyclopropyl-1H-pyrazol-4-yl)-7-(1,4,6,7-tetrahydro-5H-pyrazolo[4,3-c]pyridin-5-yl) quinazolin-2-amine | Calc'd 441.0, found 441 |
| Ex-3.26 | 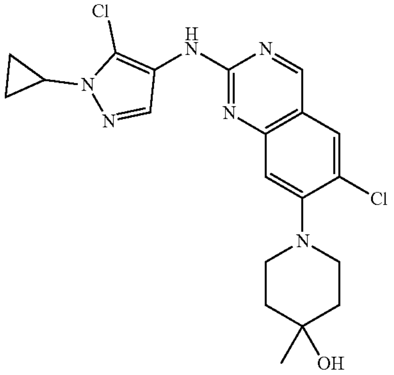 [SMILES: CC1(O)CCN(c2cc3nc(Nc4cnn(C5CC5)c4Cl)ncc3cc2Cl)CC1] | 1-{6-chloro-2-[(5-chloro-1-cyclopropyl-1H-pyrazol-4-yl) amino]quinazolin-7-yl}-4-methylpiperidin-4-ol | Calc'd 433.0, found 433 |
| Ex-3.27 | 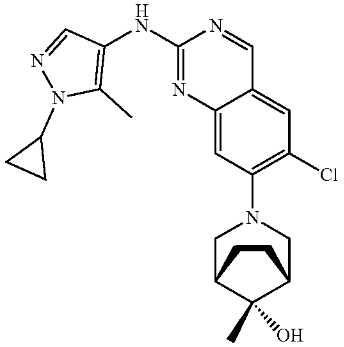 | (8-syn)-3-{6-chloro-2-[(1-cyclopropyl-5-methyl-1H-pyrazol-4-yl)amino]quinazolin-7-yl}-8-methyl-3-azabicyclo[3.2.1] octan-8-ol | Calc'd 439.0, found 439 |
| Ex-3.28 | 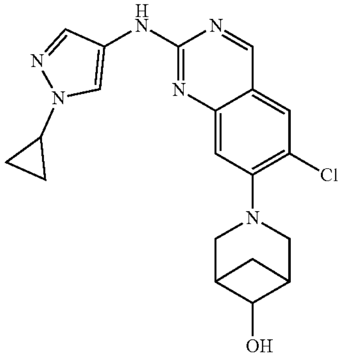 [SMILES: OC1C2CC1CN(c1cc3nc(Nc4cnn(C5CC5)c4)ncc3cc1Cl)C2] | 3-{6-chloro-2-[(1-cyclopropyl-1H-pyrazol-4-yl)amino] quinazolin-7-yl}-3-azabicyclo [3.1.1]heptan-6-ol | Calc'd 397.0, found 397 |

TABLE 4-continued

| Ex | Structure | Name | Exact Mass [M + H]$^+$ |
|---|---|---|---|
| Ex-3.29 | 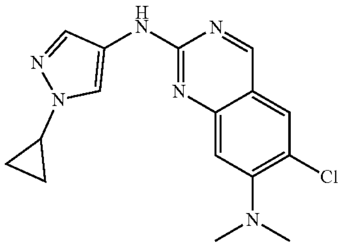 [SMILES: CN(C)c1cc2nc(Nc3cnn(C4CC4)c3)ncc2cc1Cl] | 6-chloro-N-2-(1-cyclopropyl-1H-pyrazol-4-yl)-N-7-,N-7-dimethylquinazoline-2,7-diamine | Calc'd 329.0, found 329 |
| Ex-3.30 | 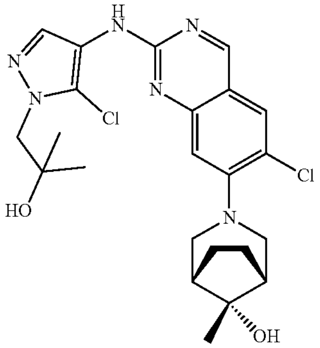 | (8-syn)-3-(6-chloro-2-{[5-chloro-1-(2-hydroxy-2-methylpropyl)-1H-pyrazol-4-yl]amino}quinazolin-7-yl)-8-methyl-3-azabicyclo[3.2.1]octan-8-ol | Calc'd 491.0, found 491 |
| Ex-3.31 | 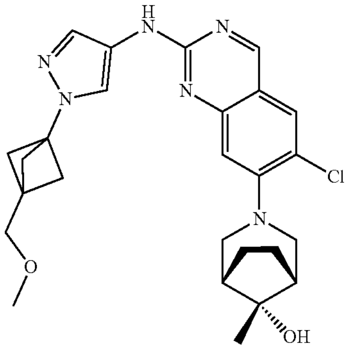 | (8-syn)-3-[6-chloro-2-({1-[3-(methoxymethyl)bicyclo[1.1.1]pentan-1-yl]-1H-pyrazol-4-yl}amino)quinazolin-7-yl]-8-methyl-3-azabicyclo[3.2.1]octan-8-ol | Calc'd 495.0, found 495 |
| Ex-3.32 | 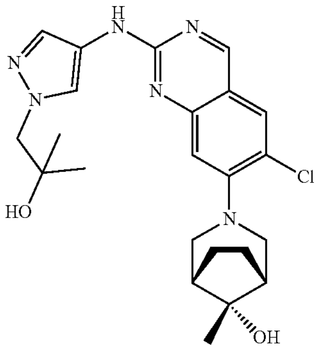 | (8-syn)-3-(6-chloro-2-{[1-(2-hydroxy-2-methylpropyl)-1H-pyrazol-4-yl]amino}quinazolin-7-yl)-8-methyl-3-azabicyclo[3.2.1]octan-8-ol | Calc'd 457.0, found 457 |

TABLE 4-continued

| Ex | Structure | Name | Exact Mass [M + H]$^+$ |
|---|---|---|---|
| Ex-3.33 | 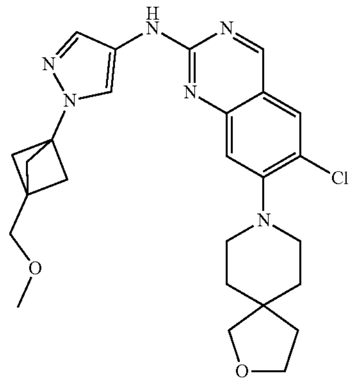 [SMILES: COCC12CC(n3cc(Nc4ncc5cc(Cl)c(N6CCC7(CCOC7)CC6)cc5n4)cn3)(C1)C2] | 6-chloro-N-{1-[3-(methoxymethyl) bicyclo[1.1.1]pentan-1-yl]-1H-pyrazol-4-yl}-7-(2-oxa-8-azaspiro [4.5]decan-8-yl)quinazolin-2-amine | Calc'd 495.0, found 495 |
| Ex-3.34 | 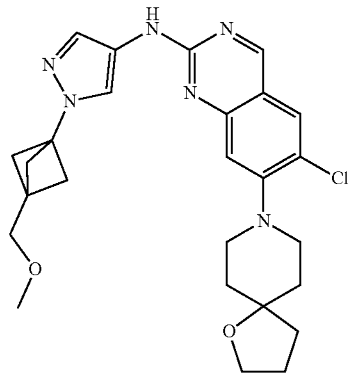 [SMILES: COCC12CC(n3cc(Nc4ncc5cc(Cl)c(N6CCC7(CCCO7)CC6)cc5n4)cn3)(C1)C2] | 6-chloro-N-{1-[3-(methoxymethyl) bicyclo[1.1.1]pentan-1-yl]-1H-pyrazol-4-yl}-7-(1-oxa-8-azaspiro [4.5]decan-8-yl)quinazolin-2-amine | Calc'd 495.0, found 495 |
| Ex-3.35 | 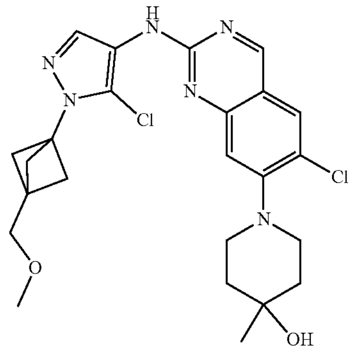 [SMILES: COCC12CC(n3ncc(Nc4ncc5cc(Cl)c(N6CCC(C)(O)CC6)cc5n4)c3Cl)(C1)C2] | 1-(2-{[1-(bicyclo[1.1.1]pentan-1-yl)-5-chloro-1H-pyrazol-4-yl]amino}-6-chloroquinazolin-7-yl)-4-methylpiperidin-4-ol | Calc'd 459.0, found 459 |
| Ex-3.36 | 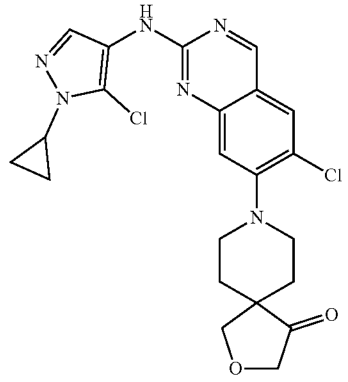 [SMILES: O=C1COCC12CCN(c1cc3nc(Nc4cnn(C5CC5)c4Cl)ncc3cc1Cl)CC2] | 8-{6-chloro-2-[(5-chloro-1-cyclopropyl-1H-pyrazol-4-yl)amino]quinazolin-7-yl}-2-oxa-8-azaspiro[4.5]decan-4-one | Calc'd 473.0, found 473 |

TABLE 4-continued

| Ex | Structure | Name | Exact Mass [M + H]+ |
|---|---|---|---|
| Ex-3.37 | 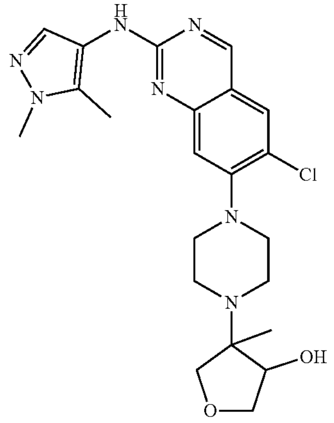 [SMILES: Cc1c(Nc2ncc3cc(Cl)c(N4CCN(C5(C)COCC5O)CC4)cc3n2)cnn1C] | (3R,4R) or (3S,4S) 4-(4-{6-chloro-2-[(1,5-dimethyl-1H-pyrazol-4-yl)amino]quinazolin-7-yl}piperazin-1-yl)-4-methyloxolan-3-ol | Calc'd 458.0, found 458 |
| Ex-3.38 | 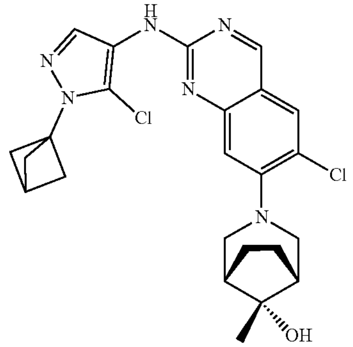 | (8-syn)-3-(2-{[1-(bicyclo[1.1.1]pentan-1-yl)-5-chloro-1H-pyrazol-4-yl]amino}-6-chloroquinazolin-7-yl)-8-methyl-3-azabicyclo[3.2.1]octan-8-ol | Calc'd 485.0, found 485 |
| Ex-3.39 | 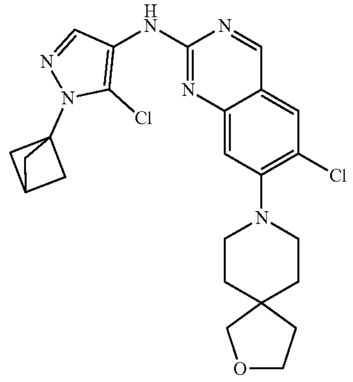 [SMILES: Clc1cc2cnc(Nc3cnn(C45CC(C4)C5)c3Cl)nc2cc1N1CCC2(CCOC2)CC1] | N-[1-(bicyclo[1.1.1]pentan-1-yl)-5-chloro-1H-pyrazol-4-yl]-6-chloro-7-(2-oxa-8-azaspiro[4.5]decan-8-yl)quinazolin-2-amine | Calc'd 485.0, found 485 |
| Ex-3.40 | 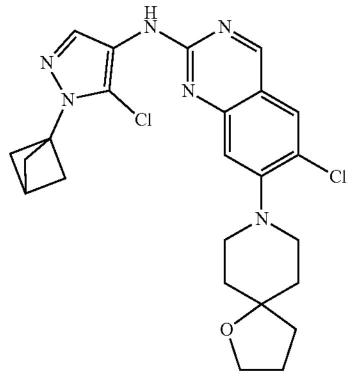 [SMILES: Clc1cc2cnc(Nc3cnn(C45CC(C4)C5)c3Cl)nc2cc1N1CCC2(CCCO2)CC1] | N-[1-(bicyclo[1.1.1]pentan-1-yl)-5-chloro-1H-pyrazol-4-yl]-6-chloro-7-(1-oxa-8-azaspiro[4.5]decan-8-yl)quinazolin-2-amine | Calc'd 485.0, found 485 |

TABLE 4-continued

| Ex | Structure | Name | Exact Mass [M + H]+ |
|---|---|---|---|
| Ex-3.41 | 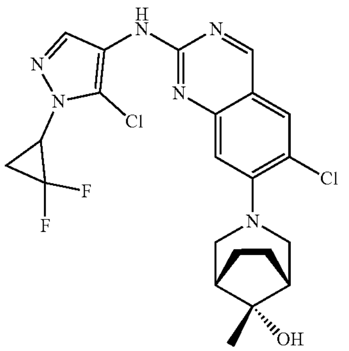 | (R) or (S) (8-syn)-3-(6-chloro-2-{[5-chloro-1-(2,2-difluorocyclopropyl)-1H-pyrazol-4-yl]amino}quinazolin-7-yl)-8-methyl-3-azabicyclo[3.2.1]octan-8-ol | Calc'd 495.0, found 495 |
| Ex-3.42 | 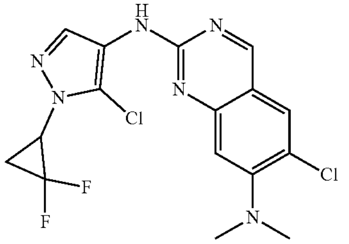 [SMILES: CN(C)c1cc2nc(Nc3cnn(C4CC4(F)F)c3Cl)ncc2cc1Cl] | (R) or (S) 6-chloro-N~2~-[5-chloro-1-(2,2-difluorocyclopropyl)-1H-pyrazol-4-yl]-N~7~,N~7~-dimethylquinazoline-2,7-diamine | Calc'd 399.0, found 399 |
| Ex-3.43 | 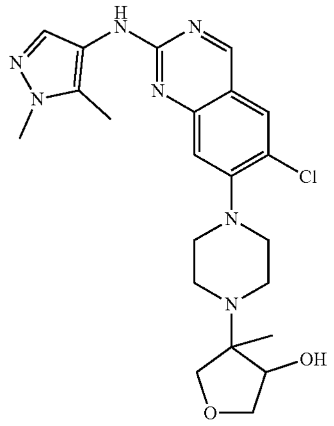 [SMILES: Cc1c(Nc2ncc3cc(Cl)c(N4CCN(C5(C)COCC5O)CC4)cc3n2)cnn1C] | (3R,4R) or (3S,4S) 4-(4-{6-chloro-2-[(1,5-dimethyl-1H-pyrazol-4-yl)amino]quinazolin-7-yl}piperazin-1-yl)-4-methyloxolan-3-ol | Calc'd 458.0, found 458 |
| Ex-3.44 | 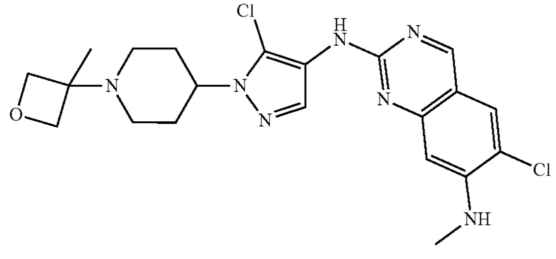 [SMILES: CNc1cc2nc(Nc3cnn(C4CCN(C5(C)COC5)CC4)c3Cl)ncc2cc1Cl] | 6-chloro-N~2~-{5-chloro-1-[1-(3-methyloxetan-3-yl)piperidin-4-yl]-1H-pyrazol-4-yl}-N~7~-methyl-quinazoline-2,7-diamine | Calc'd 462.0, found 462 |
| Ex-3.45 | 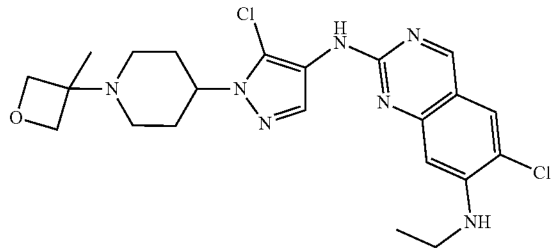 [SMILES: CCNc1cc2nc(Nc3cnn(C4CCN(C5(C)COC5)CC4)c3Cl)ncc2cc1Cl] | 6-chloro-N~2~-{5-chloro-1-[1-(3-methyloxetan-3-yl)piperidin-4-yl]-1H-pyrazol-4-yl}-N~7~-ethylquinazoline-2,7-diamine | Calc'd 476.0, found 476 |

TABLE 4-continued

| Ex | Structure | Name | Exact Mass [M + H]+ |
|---|---|---|---|
| Ex-3.46 | 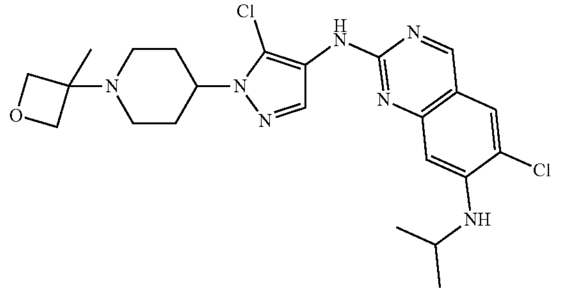 [SMILES: CC(C)Nc1cc2nc(Nc3cnn(C4CCN(C5(C)COC5)CC4)c3Cl)ncc2cc1Cl] | 6-chloro-N~2~-{5-chloro-1-[1-(3-methyloxetan-3-y])piperidin-4-yl]-1H-pyrazol-4-yl}-N~7~-(propan-2-yl)quinazoline-2,7-diamine | Calc'd 490.0, found 490 |
| Ex-3.47 | 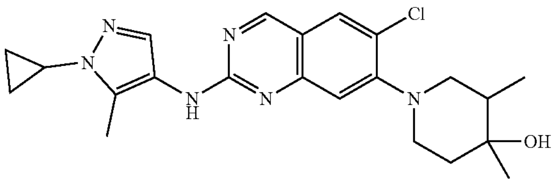 [SMILES: Cc1c(Nc2ncc3cc(Cl)c(N4CCC(C)(O)C(C)C4)cc3n2)cnn1C1CC1] | (3R,4R) or (3S,4S) or (3R,4S) or (3S,4R) 1-{6-chloro-2-[(1-cyclopropyl-5-methyl-1H-pyrazol-4-yl)amino]quinazolin-7-yl}-3,4-dimethylpiperidin-4-ol | Calc'd 427.0, found 427 |
| Ex-3.48 | 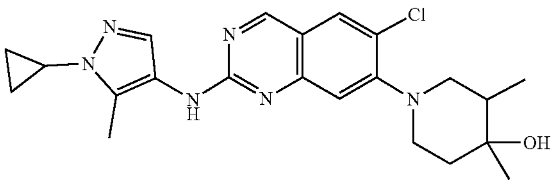 [SMILES: Cc1c(Nc2ncc3cc(Cl)c(N4CCC(C)(O)C(C)C4)cc3n2)cnn1C1CC1] | (3R,4R) or (3S,4S) or (3R,4S) or (3S,4R) 1-{6-chloro-2-[(1-cyclopropyl-5-methyl-1H-pyrazol-4-yl)amino] quinazolin-7-yl}-3,4-dimethylpiperidin-4-ol | Calc'd 427.0, found 427 |
| Ex-3.49 | 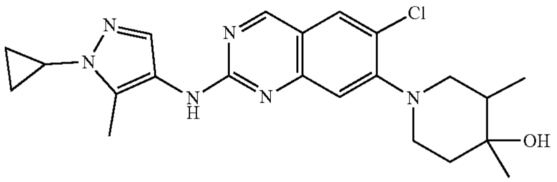 [SMILES: Cc1c(Nc2ncc3cc(Cl)c(N4CCC(C)(O)C(C)C4)cc3n2)cnn1C1CC1] | (3R,4R) or (3S,4S) or (3R,4S) or (3S,4R) 1-{6-chloro-2-[(1-cyclopropyl-5-methyl-1H-pyrazol-4-yl)amino] quinazolin-7-yl}-3,4-dimethylpiperidin-4-ol | Calc'd 427.0, found 427 |
| Ex-3.50 | 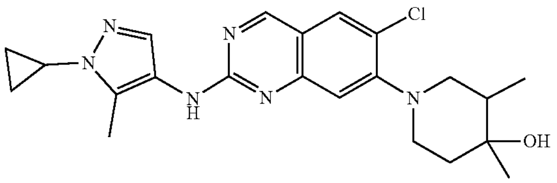 [SMILES: Cc1c(Nc2ncc3cc(Cl)c(N4CCC(C)(O)C(C)C4)cc3n2)cnn1C1CC1] | (3R,4R) or (3S,4S) or (3R,4S) or (3S,4R) 1-{6-chloro-2-[(1-cyclopropyl-5-methyl-1H-pyrazol-4-yl)amino] quinazolin-7-yl}-3,4-dimethylpiperidin-4-ol | Calc'd 427.0, found 427 |
| Ex-3.51 | 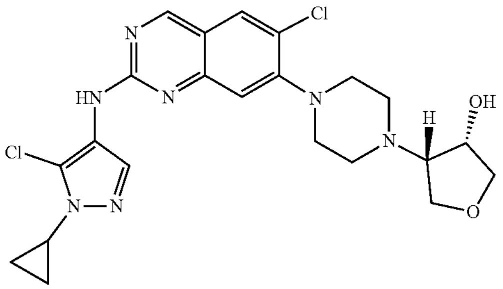 [SMILES: O[C@@H]1COC[C@@H]1N1CCN(c2cc3nc(Nc4cnn(C5CC5)c4Cl)ncc3cc2Cl)CC1] | (3R,4R) or (3S,4S) 4-(4-{6-chloro-2-[(5-chloro-1-cyclopropyl-1H-pyrazol-4-yl)amino]quinazolin-7-yl}piperazin-1-yl)oxolan-3-ol | Calc'd 490.0, found 490 |

TABLE 4-continued

| Ex | Structure | Name | Exact Mass [M + H]+ |
|---|---|---|---|
| Ex-3.52 | 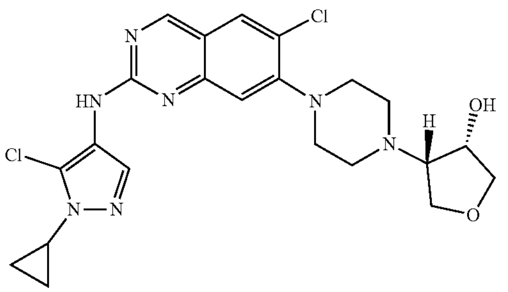 [SMILES: O[C@@H]1COC[C@@H]1N1CCN(c2cc3nc(Nc4cnn(C5CC5)c4Cl)ncc3cc2Cl)CC1] | (3R,4R) or (3S,4S) 4-(4-{6-chloro-2-[(5-chloro-1-cyclopropyl-1H-pyrazol-4-yl)amino]quinazolin-7-yl}piperazin-1-yl)oxolan-3-ol | Calc'd 490.0, found 490 |
| Ex-3.53 | 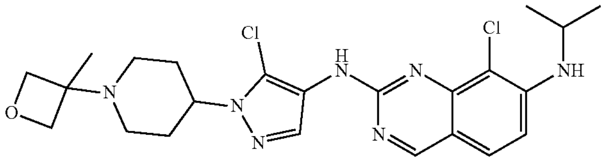 [SMILES: CC(C)Nc1ccc2cnc(Nc3cnn(C4CCN(C5(C)COC5)CC4)c3Cl)nc2c1Cl] | 8-chloro-N~2~-{5-chloro-1-[1-(3-methyloxetan-3-yl)piperidin-4-yl]-1H-pyrazol-4-yl}-N~7~-(propan-2-yl)quinazoline-2,7-diamine | Calc'd 490.0, found 490 |
| Ex-3.54 | 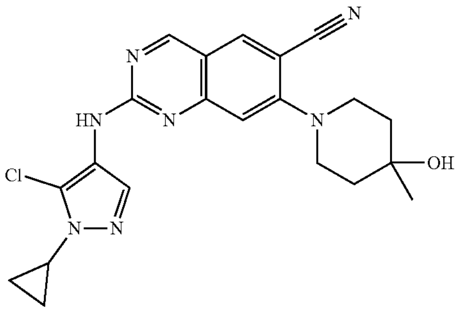 [SMILES: CC1(O)CCN(c2cc3nc(Nc4cnn(C5CC5)c4Cl)ncc3cc2C#N)CC1] | 2-[(5-chloro-1-cyclopropyl-1H-pyrazol-4-yl)amino]-7-(4-hydroxy-4-methylpiperidin-1-yl)quinazoline-6-carbonitrile | Calc'd 424.0, found 424 |
| Ex-3.55 | 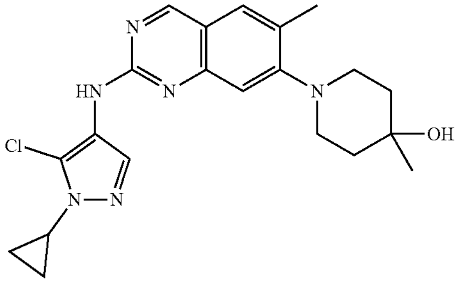 [SMILES: Cc1cc2cnc(Nc3cnn(C4CC4)c3Cl)nc2cc1N1CCC(C)(O)CC1] | 1-{2-[(5-chloro-1-cyclopropyl-1H-pyrazol-4-yl)amino]-6-methylquinazolin-7-yl}-4-methylpiperidin-4-ol | Calc'd 413.0, found 413 |
| Ex-3.56 | 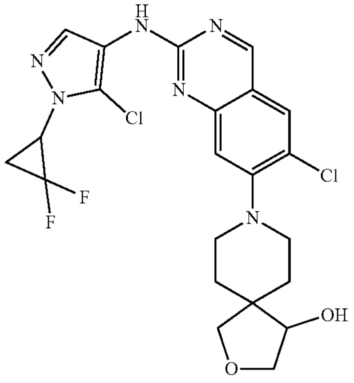 [SMILES: OC1COCC12CCN(c1cc3nc(Nc4cnn(C5CC5(F)F)c4Cl)ncc3cc1Cl)CC2] | (R) or (S)-8-(6-chloro-2-((1-((S) or (R)-2,2-difluorocyclopropyl)-5-methyl-1H-pyrazol-4-yl)amino)quinazolin-7-yl)-2-oxa-8-azaspiro[4.5]decan-4-ol | Calc'd 511.0, found 511 |

TABLE 4-continued

| Ex | Structure | Name | Exact Mass [M + H]$^+$ |
|---|---|---|---|
| Ex-3.57 | 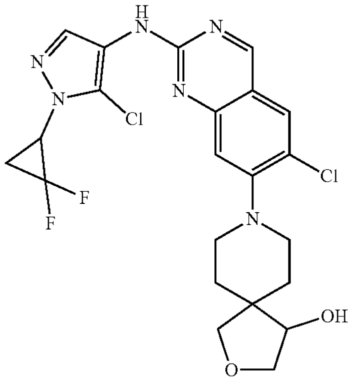 [SMILES: OC1COCC12CCN(c1cc3nc(Nc4cnn(C5CC5(F)F)c4Cl)ncc3cc1Cl)CC2] | (R) or (S)-8-(6-chloro-2-((1-((S) or (R)-2,2-difluorocyclopropyl)-5-methyl-1H-pyrazol-4-yl)amino)quinazolin-7-yl)-2-oxa-8-azaspiro[4.5]decan-4-ol | Calc'd 511.0, found 511 |
| Ex-3.58 | 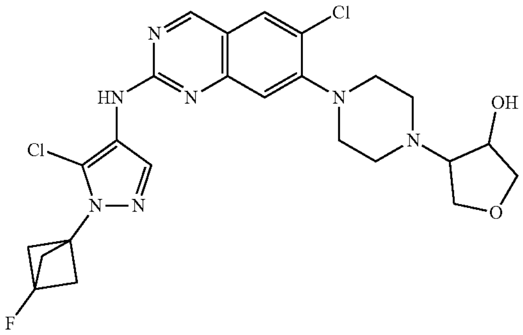 [SMILES: OC1COCC1N1CCN(c2cc3nc(Nc4cnn(C56CC(F)(C5)C6)c4Cl)ncc3cc2Cl)CC1] | (3R,4R) or (3S,4S) 4-(4-(6-chloro-2-((5-chloro-1-(3-fluorobicyclo[1.1.1]pentan-1-yl])-1H-pyrazol-4-yl)amino)quinazolin-7-yl)piperazin-1-yl)tetrahydrofuran-3-ol | Calc'd 534.0, found 534 |
| Ex-3.59 | 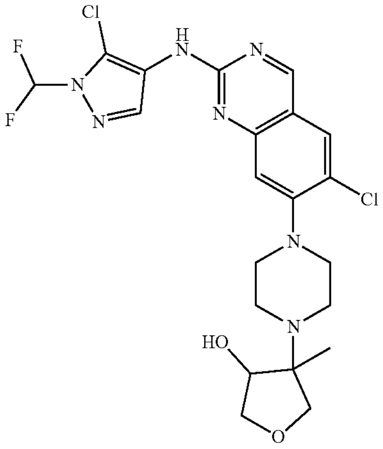 [SMILES: CC1(N2CCN(c3cc4nc(Nc5cnn(C(F)F)c5Cl)ncc4cc3Cl)CC2)COCC1O] | (3R,4R) or (3S,4S) 4-(4-(6-chloro-2-((5-chloro-1-(difluoromethyl)-1H-pyrazol-4-yl)amino)quinazolin-7-yl)piperazin-1-yl)-4-methyltetrahydrofuran-3-ol | Calc'd 514.0, found 514 |

TABLE 4-continued
| Ex | Structure | Name | Exact Mass $[M + H]^+$ |
|---|---|---|---|
| Ex-3.60 | 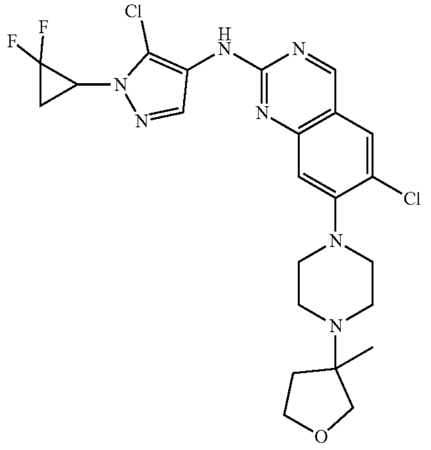 [SMILES: CC1(N2CCN(c3cc4nc(Nc5cnn(C6CC6(F)F)c5Cl)ncc4cc3Cl)CC2)CCOC1] | (R or S) 6-chloro-N-(5-chloro-1-((S) or (R) 2,2-difluorocyclopropyl)-1H-pyrazol-4-yl)-7-(4-(3-methyltetrahydrofuran-3-yl)piperazin-1-yl) quinazolin-2-amine | Calc'd 525.0, found 525 |
General Scheme 5
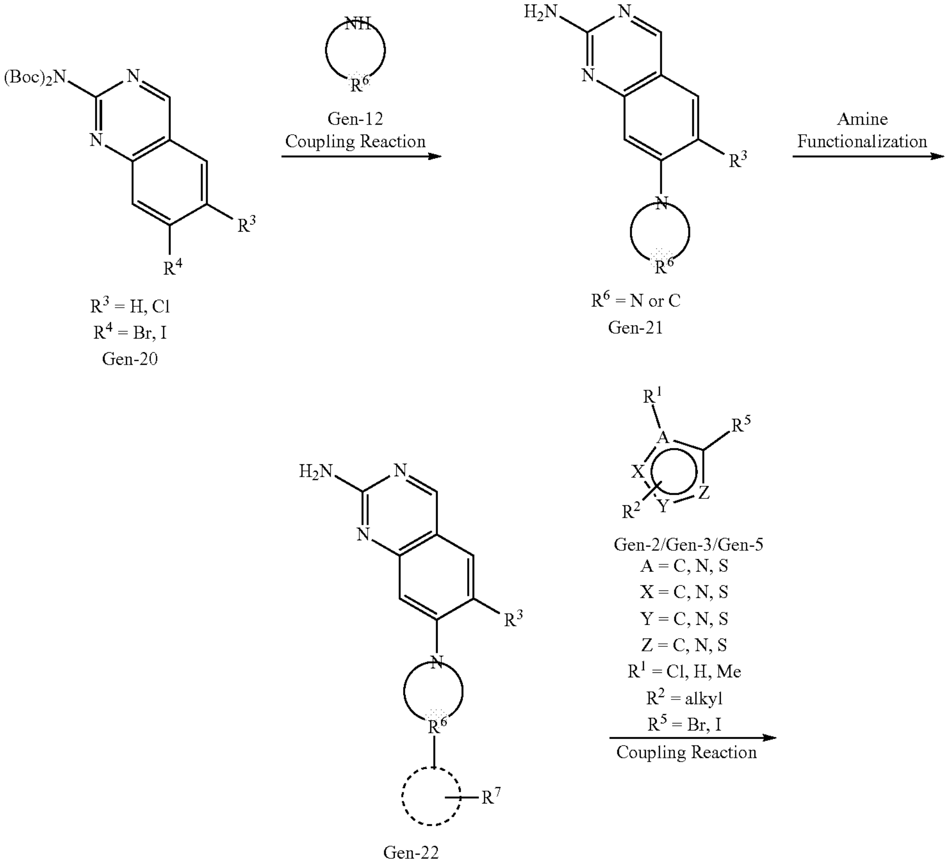

-continued

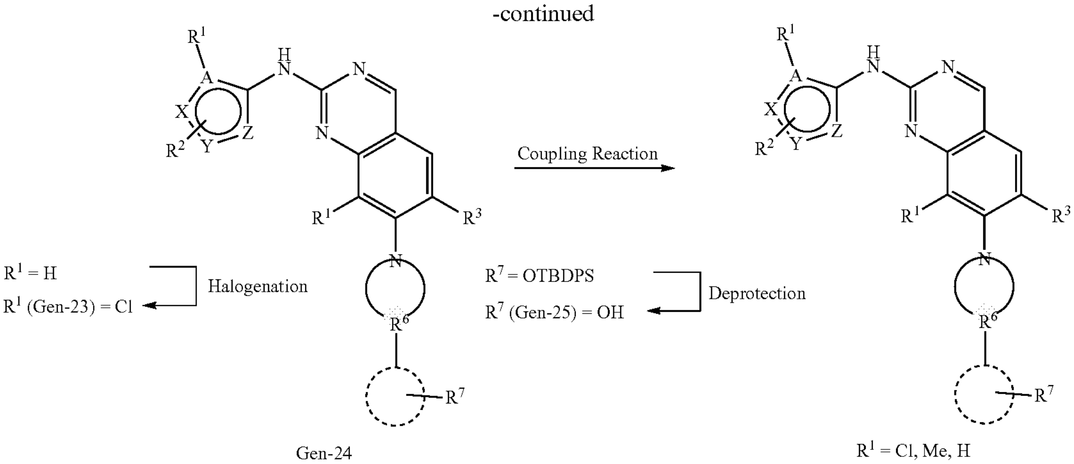

Gen-24

$R^1$ = Cl, Me, H
Gen-26

In General Scheme 5 synthetically prepared intermediate Gen-20 was coupled with commercially available or synthetically prepared cyclic amines (Gen-12) through either a palladium or copper catalyzed coupling reaction to provide Gen-21. An amine functionalization reaction such as reductive amination could be used to afford elaborated compounds of the form Gen-22. A palladium or copper-catalyzed coupling reaction utilizing halo-pyrazoles Gen-2/Gen-3/Gen-5 could be employed to generate compounds of the form Gen-24 which could undergo a subsequent halogenation reaction transforming $R^1$ into a chlorine atom (Gen-23) or a fluoride mediated deprotection to afford alcohol-containing compounds Gen-25. A final palladium-catalyzed coupling reaction could afford methyl containing compounds of the form Gen-26 (cf. Scheme 40, 132-Ex-2.1) The representative compounds are described in more detail below.

Preparation of Examples 4.1 and 4.2

Scheme 48. Synthesis of (3*S*,4*S*) or (3*R*,4*R*)-4-(4-(6-chloro-2-((1-cyclopropyl-5-methyl-1H-pyrazol-4-yl)amino)quinazolin-7-yl)piperazin-1-yl)tetrahydrofuran-3-ol

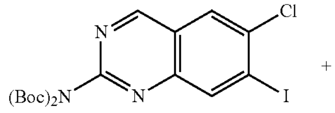

151

+

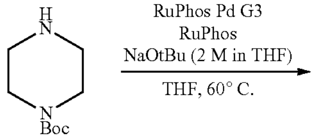

152

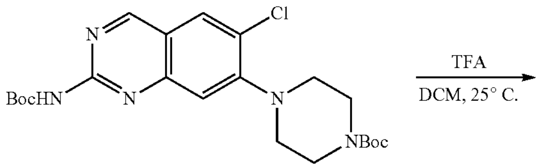

153

-continued

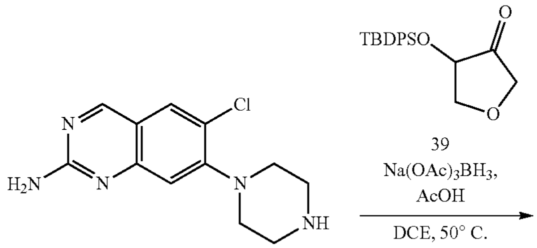

154

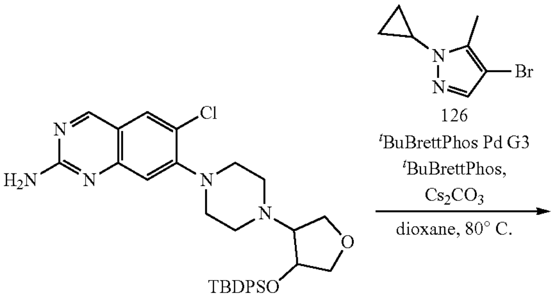

155

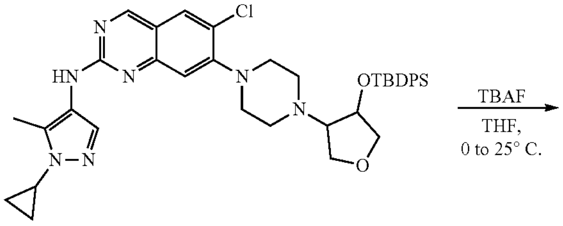

156

-continued

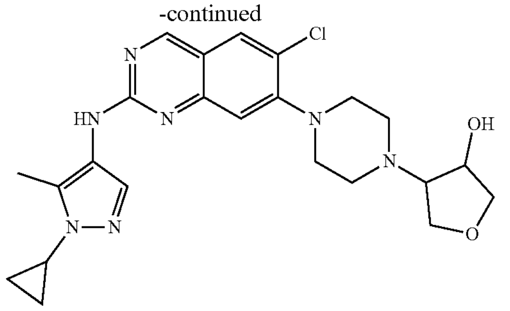

Ex-4.1

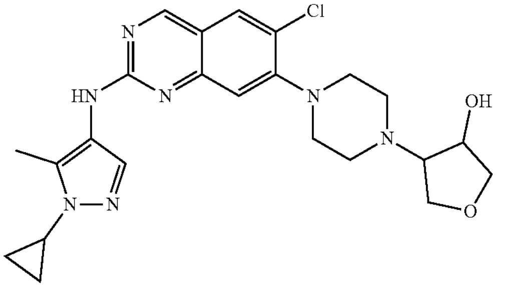

Ex-4.2

Tert-butyl 4-(2-((tert-butoxycarbonyl)amino)-6-chloroquinazolin-7-yl)piperazine-1-carboxylate (153)

A 250 mL round-bottom flask was charged with tert-butyl (tert-butoxycarbonyl)(6-chloro-7-iodoquinazolin-2-yl)carbamate 151 (5.00 g, 9.89 mmol), tert-butyl piperazine-1-carboxylate 152 (2.21 g, 11.9 mmol), sodium tert-butoxide (2.38 g, 24.7 mmol), and RuPhos Pd G3 (1.65 g, 1.98 mmol), RuPhos (0.923 g, 1.98 mmol) under inert atmosphere. THF (33 mL) was added and the resultant mixture was stirred at 80° C. for 12 h. The reaction was diluted in EtOAc (200 mL) and quenched by addition of sat. aq. $NH_4Cl$ (200 mL). The phases were separated and the aqueous phase extracted with EtOAc (3×100 mL). The combined organic phases were dried over $Na_2SO_4$, and the solvent removed under reduced pressure. The resultant crude residue was subjected to purification by silica gel chromatography (DCM in ethyl acetate, 0-100%) to afford tert-butyl 4-(2-((tert-butoxycarbonyl)amino)-6-chloroquinazolin-7-yl) piperazine-1-carboxylate 153. MS (ESI): m/z calc'd for $C_{22}H_{30}ClN_5O_4$ $[M+H]^+$: 464, found 464.

6-Chloro-7-(piperazin-1-yl)quinazolin-2-amine (154)

A 30 mL microwave vial was charged with tert-butyl 4-(2-((tert-butoxycarbonyl)amino)-6-chloroquinazolin-7-yl) piperazine-1-carboxylate 153 (2.3 g, 5.0 mmol) under inert atmosphere. DCM (49.6 mL) was added, and to the stirring mixture at RT was added TFA (5.73 mL, 74.4 mmol). The resultant mixture was stirred at rt for 2 h. The reaction was diluted with DCM (100 mL) and quenched by dropwise addition of sat. aq. $NaHCO_3$(100 mL). The phases were separated and the aqueous phase extracted with DCM (3×50 mL). The combined organic phases were washed with $H_2O$ (50 mL), dried over $Na_2SO_4$, and the solvent removed under reduced pressure to afford 6-chloro-7-(piperazin-1-yl)quinazolin-2-amine 154. MS (ESI): m/z calc'd for $C_{12}H_{14}ClN_5$ $[M+H]^+$: 264, found 264.

7-(4-(4-((Tert-butyldiphenylsilyl)oxy)tetrahydrofuran-3-yl)piperazin-1-yl)-6-chloroquinazolin-2-amine (155)

A 30 mL microwave vial was charged with 6-chloro-7-(piperazin-1-yl)quinazolin-2-amine 154 (295 mg, 1.12 mmol), 4-((tert-butyldiphenylsilyl)oxy)dihydrofuran-3(2H)-one 39 (476 mg, 1.40 mmol), sodium triacetoxyhydroborate (593 mg, 2.80 mmol), and 4 Å molecular sieves under inert atmosphere. DCE (11.2 mL) was added, and to the stirring mixture at RT was added acetic acid (0.160 mL, 2.80 mmol). The resultant mixture was stirred at 50° C. for 6 h. The reaction was diluted with DCM (50 mL), filtered, and quenched by dropwise addition of sat. aq. $NaHCO_3$(50 mL). The phases were separated and the aqueous phase extracted with DCM (3×50 mL). The combined organic phases were washed with $H_2O$ (50 mL), dried over $Na_2SO_4$, and the solvent removed under reduced pressure. The resultant crude residue was subjected to purification by silica gel chromatography (DCM in 20%-MeOH/DCM, 0-100%) to afford the title compound 155. MS (ESI): m/z calc'd for $C_{32}H_{38}ClN_5O_2Si$ $[M+H]^+$: 588, found 588.

7-(4-(4-((Tert-butyldiphenylsilyl)oxy)tetrahydrofuran-3-yl)piperazin-1-yl)-6-chloro-N-(1-cyclopropyl-5-methyl-1H-pyrazol-4-yl)quinazolin-2-amine (156)

A 20 mL scintillation vial was charged with 7-(4-(2-((tert-butyldiphenylsilyl)oxy)tetrahydrofuran-3-yl)piperazin-1-yl)-6-chloroquinazolin-2-amine 155 (150 mg, 0.255 mmol), 4-bromo-1-cyclopropyl-5-methyl-1H-pyrazole 126 (128 mg, 0.638 mmol), cesium carbonate (249 mg, 0.765 mmol), $^t$BuBrettPhos Pd G3 (55 mg, 0.064 mmol), and $^t$BuBrettPhos (31 mg, 0.064 mmol) under inert atmosphere. Dioxane (2.5 μL) was added and the resultant mixture was stirred at 80° C. for 12 h. The reaction was diluted with EtOAc (100 mL), filtered through Celite®, and and the solvent removed under reduced pressure. The resultant crude residue was subjected to purification by silica gel chromatography (DCM in 20%-MeOH/DCM, 0-100%) to afford the title compound 156. MS (ESI): m/z calc'd for $C_{39}H_{46}ClN_{702}Si$ $[M+H]^+$: 709, found 709.

(3S,4S) or (3R,4R)-4-(4-(6-chloro-2-((1-cyclopropyl-5-methyl-1H-pyrazol-4-yl)amino)quinazolin-7-yl)piperazin-1-yl)tetrahydrofuran-3-ol (Ex-4.1) and (3S, 4S) or (3R, 4R)-4-(4-(6-chloro-2-((1-cyclopropyl-5-methyl-1H-pyrazol-4-yl)amino)quinazolin-7-yl)piperazin-1-yl)tetrahydrofuran-3-ol (Ex-4.2)

A 30 mL scintillation vial was charged with 7-(4-(4-((tert-butyldiphenylsilyl)oxy)tetrahydrofuran-3-yl)piperazin-1-yl)-6-chloro-N-(1-cyclopropyl-5-methyl-1H-pyrazol-4-yl) quinazolin-2-amine 156 (99 mg, 0.14 mmol) under inert atmosphere. THF (2.8 mL) was added, and to the stirring mixture at RT was added TBAF (0.7 mL, 0.7 mmol). The resultant mixture was stirred at 25° C. for 12 h. The reaction was diluted with EtOAc (50 mL) and quenched by dropwise addition of brine (50 mL). The phases were separated, and the aqueous phase extracted with EtOAc (3×50 mL). The combined organic phases were washed with $H_2O$ (50 mL), dried over $Na_2SO_4$, and the solvent removed under reduced pressure. The resultant crude residue was subjected to purification by silica gel chromatography (DCM in 20%-MeOH/DCM, 0-100%) to afford the racemate. The racemic material was resolved to its component enantiomers by chiral preparative SFC (Column & dimensions: AS-H, 21 mm×250 mm; Mobile phase A: $CO_2$; Mobile phase B: MeOH with 0.1% $NH_4OH$) to afford (3S, 4S)-4-(4-(6-chloro-2-((1-cyclopropyl-5-methyl-1H-pyrazol-4-yl)amino)quinazolin-7-yl)piperazin-1-yl)tetrahydrofuran-3-ol Ex-4.1 ($t_R$=4.0 min) and (3R, 4R)-4-(4-(6-chloro-2-((1-cyclopropyl-5-methyl-1H-pyrazol-4-yl)amino)quinazolin-7-yl)piperazin-1-yl)tetrahydrofuran-3-ol Ex-4.2 ($t_R$=5.4 min). MS (ESI): m/z calc'd for $C_{23}H_{28}ClN_7O_2Si$ $[M+H]^+$: 709, found 709. $^1H$ NMR (400 MHz, DMSO-$d_6$, 25° C.) δ: 9.01 (s, 1H), 8.95 (s, 1H), 7.93 (s, 1H), 7.68 (s, 1H), 6.99 (s, 1H), 4.39 (d, J=3.5 Hz, 1H), 4.19 (d, J=3.5 Hz, 1H), 3.90-3.85 (m, 2H), 3.69 (d, J=9.5 Hz, 1H), 3.62 (dd, J=10.2, 7.4 Hz, 1H), 3.49 (tt, J=7.2, 3.9 Hz, 1H), 3.15 (s, 4H), 2.78 (s, 2H), 2.69 (ddd, J=10.9, 7.2, 4.2 Hz, 1H), 2.29 (s, 3H), 1.24 (s, 1H), 1.09-0.90 (m, 5H). MS (ESI) m/z calc'd for $C_{23}H_{28}ClN_7OdSi$ $[M+H]^+$: 709, found 709. $^1H$ NMR (400 MHz, DMSO-$d_6$, 25° C.) δ: 9.01 (s, 1H), 8.95 (s, 1H), 7.93 (s, 1H), 7.68 (s, 1H), 6.99 (s, 1H), 4.39 (d, J=3.4 Hz, 1H), 4.19 (d, J=3.5 Hz, 1H), 3.90-3.84 (m, 2H), 3.69 (d, J=9.5 Hz, 1H), 3.62 (dd, J=10.2, 7.4 Hz, 1H), 3.49 (tt, J=7.2, 3.8 Hz, 1H), 3.15 (s, 4H), 2.78 (s, 2H), 2.69 (ddd, J=10.9, 7.2, 4.2 Hz, 1H), 2.29 (s, 3H), 1.24 (s, 1H), 1.09-0.91 (m, 5H).

Preparation of Example 4.3

Scheme 49. Synthesis of 6-chloro-8-methyl-7-(4-(3-methyloxetan-3-yl)piperazin-1-yl)-N-(1-(2,2,2-trifluoroethyl)-1H-pyrazol-4-yl)quinazolin-2-amine

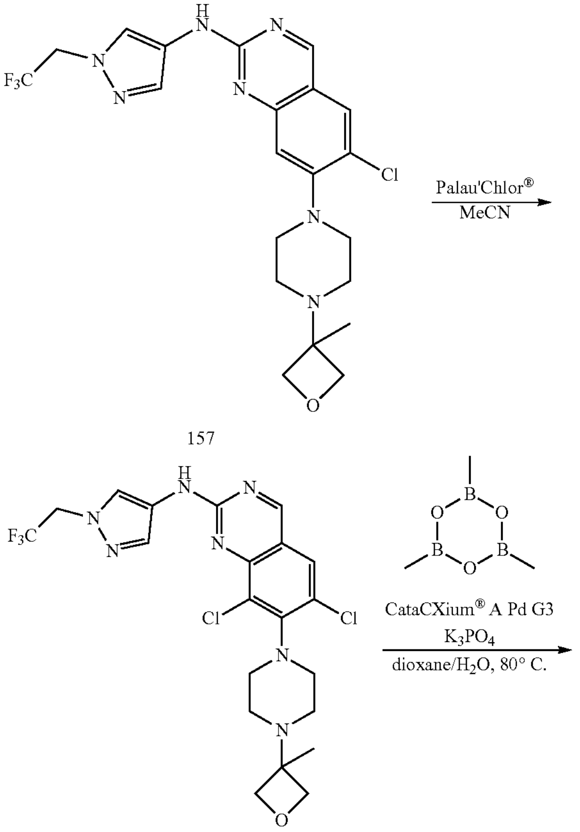

157

158

-continued

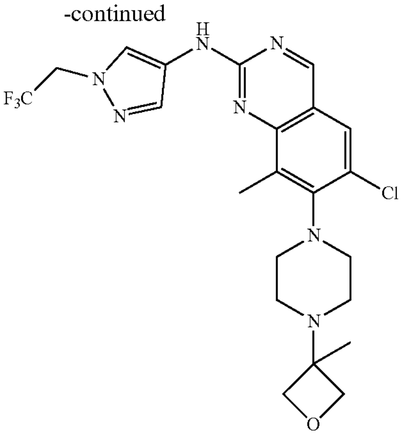

Ex-4.3

6,8-Dichloro-7-(4-(3-methyloxetan-3-yl)piperazin-1-yl)-N-(1-(2,2,2-trifluoroethyl)-1H-pyrazol-4-yl)quinazolin-2-amine (158)

A vial was charged with 6-chloro-7-(4-(3-methyloxetan-3-yl)piperazin-1-yl)-N-(1-(2,2,2-trifluoroethyl)-1H-pyrazol-4-yl)quinazolin-2-amine 157 (260 mg, 0.540 mmol) and acetonitrile (11 mL). Palau' Chlor® (209 mg, 0.998 mmol) was added and the reaction mixture was stirred at 25° C. for 3 h. The reaction mixture was concentrated under reduced pressure and the crude residue was purified by reverse phase HPLC, eluting with water (0.1% $NH_4OH$)-MeCN to afford the title compound 158. MS (ESI): m/z calc'd for $C_{21}H_{22}Cl_2F_3N_{70}$ $[M+H]^+$: 516, found 516.

6-Chloro-8-methyl-7-(4-(3-methyloxetan-3-yl)piperazin-1-yl)-N-(1-(2,2,2-trifluoroethyl)-1H-pyrazol-4-yl)quinazolin-2-amine (Ex-4.3)

A vial was charged with 6,8-dichloro-7-(4-(3-methyloxetan-3-yl)piperazin-1-yl)-N-(1-(2,2,2-trifluoroethyl)-1H-pyrazol-4-yl)quinazolin-2-amine 158 (25 mg, 0.048 mmol), CataCXium® A Pd G3 (7.05 mg, 9.68 μmol), and $K_3PO_4$ (41.1 mg, 0.194 mmol). The reaction vessel was purged with nitrogen three times. To the reaction mixture was added dioxane (440 μL), water (44 μL), and trimethyl boroxine (13 μL, 0.097 mmol) and the resultant mixture was stirred at 80° C. for 3 h. The reaction mixture was concentrated under reduced pressure and the crude residue was purified by reverse phase HPLC, eluting with water (0.1% TFA)-MeCN to afford the title compound Ex-4.3. MS (ESI): m/z calc'd for $C_{22}H_{25}ClF_3N_{70}$ $[M+H]^+$: 496, found 496. $^1H$ NMR (500 MHz, DMSO-$d_6$, 25° C.) δ 10.03 (s, 1H), 9.16 (s, 1H), 8.29 (s, 1H), 7.90 (s, 1H), 7.81 (s, 1H), 5.17 (q, J=9.0 Hz, 3H), 4.90 (d, J=7.5 Hz, 2H), 4.43 (d, J=7.5 Hz, 2H), 3.92 (bs, 1H), 3.47-3.09 (m, 6H), 2.66 (s, 3H), 1.72 (s, 3H).

The following Examples, 4.4-4.71 were obtained using the procedure analogous to those in General Scheme 5 but substituting appropriate starting materials that are either commercially available or prepared using procedures analogous to those described in Schemes 48 through 49. Table 5

TABLE 5

| Ex | Structure | Name | Exact Mass [M + H]+ |
|---|---|---|---|
| Ex-4.4 | 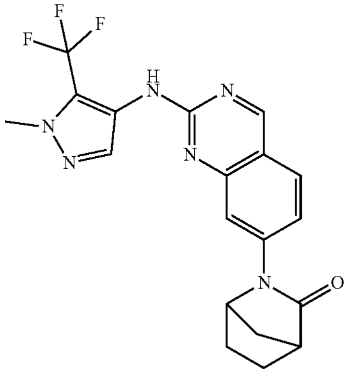 [SMILES: Cn1ncc(Nc2ncc3ccc(N4C(=O)C5CCC4C5)cc3n2)c1C(F)(F)F] | 2-(2-{[1-methyl-5-(trifluoromethyl)-1H-pyrazol-4-yl]amino}quinazolin-7-yl)-2-azabicyclo[2.2.1]heptan-3-one | Calc'd 403.0, found 403 |
| Ex-4.5 | 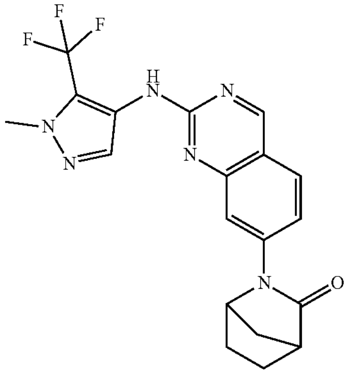 [SMILES: Cn1ncc(Nc2ncc3ccc(N4C(=O)C5CCC4C5)cc3n2)c1C(F)(F)F] | 2-(2-{[1-methyl-5-(trifluoromethyl)-1H-pyrazol-4-yl]amino}quinazolin-7-yl)-2-azabicyclo[2.2.1]heptan-3-one | Calc'd 403.0, found 403 |
| Ex-4.6 | 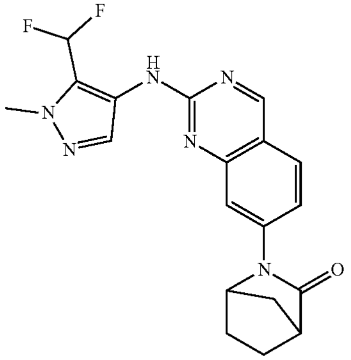 [SMILES: Cn1ncc(Nc2ncc3ccc(N4C(=O)C5CCC4C5)cc3n2)c1C(F)F] | 2-(2-{[5-(difluoromethyl)-1-methyl-1H-pyrazol-4-yl]amino}quinazolin-7-yl)-2-azabicyclo[2.2.1]heptan-3-one | Calc'd 385.0, found 385 |
| Ex-4.7 | 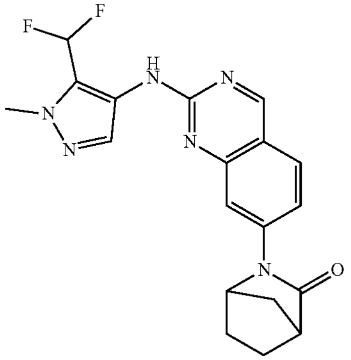 [SMILES: Cn1ncc(Nc2ncc3ccc(N4C(=O)C5CCC4C5)cc3n2)c1C(F)F] | 2-(2-{[5-(difluoromethyl)-1-methyl-1H-pyrazol-4-yl]amino}quinazolin-7-yl)-2-azabicyclo[2.2.1]heptan-3-one | Calc'd 385.0, found 385 |

TABLE 5-continued

| Ex | Structure | Name | Exact Mass [M + H]+ |
|---|---|---|---|
| Ex-4.8 | 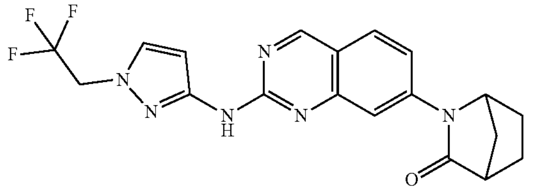 [SMILES: O=C1C2CCC(C2)N1c1ccc2cnc(Nc3ccn(CC(F)(F)F)n3)nc2c1] | 2-(2-{[1-(2,2,2-trifluoroethyl)-1H-pyrazol-3-yl]amino}quinazolin-7-yl)-2-azabicyclo[2.2.1]heptan-3-one | Calc'd 403.0, found 403 |
| Ex-4.9 | 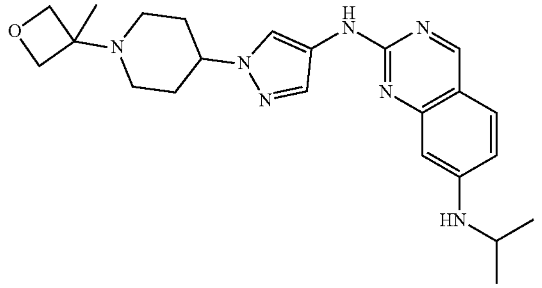 [SMILES: CC(C)Nc1ccc2cnc(Nc3cnn(C4CCN(C5(C)COC5)CC4)c3)nc2c1] | N~2~-{1-[1-(3-methyloxetan-3-yl)piperidin-4-yl]-1H-pyrazol-4-yl}-N~7~-(propan-2-yl)quinazoline-2,7-diamine | Calc'd 422.0, found 422 |
| Ex-4.10 | 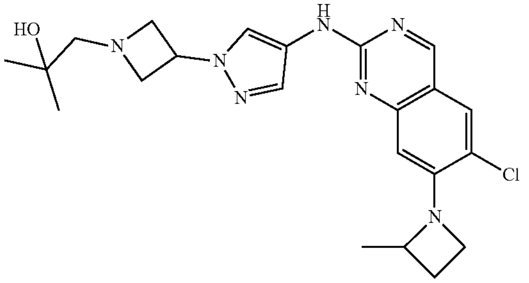 [SMILES: CC1CCN1c1cc2nc(Nc3cnn(C4CN(CC(C)(C)O)C4)c3)ncc2cc1Cl] | 1-[3-(4-{[6-chloro-7-(2-methylazetidin-1-yl)quinazolin-2-yl]amino}-1H-pyrazol-1-yl)azetidin-1-yl]-2-methylpropan-2-ol | Calc'd 442.0, found 442 |
| Ex-4.11 | 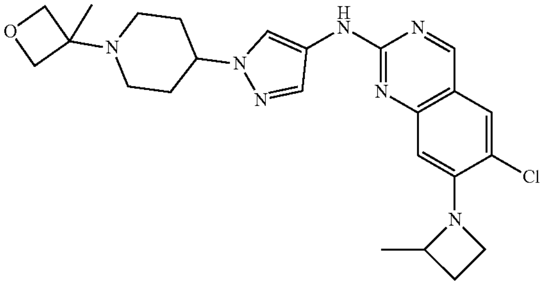 [SMILES: CC1CCN1c1cc2nc(Nc3cnn(C4CCN(C5(C)COC5)CC4)c3)ncc2cc1Cl] | 6-chloro-7-(2-methylazetidin-1-yl)-N-{1-[1-(3-methyloxetan-3-yl)piperidin-4-yl]-1H-pyrazol-4-yl}quinazolin-2-amine | Calc'd 468.0, found 468 |
| Ex-4.12 | 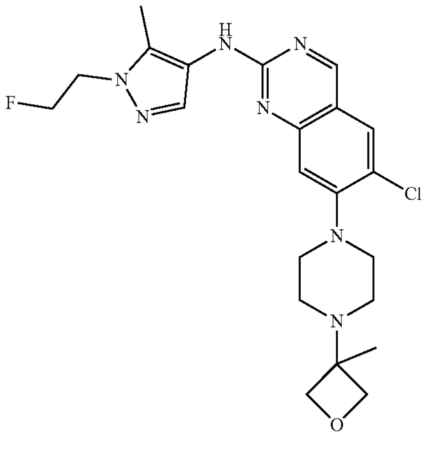 [SMILES: Cc1c(Nc2ncc3cc(Cl)c(N4CCN(C5(C)COC5)CC4)cc3n2)cnn1CCF] | 6-chloro-N-[1-(2-fluoroethyl)-5-methyl-1H-pyrazol-4-yl]-7-[4-(3-methyloxetan-3-yl)piperazin-1-yl]quinazolin-2-amine | Calc'd 460.0, found 460 |

TABLE 5-continued

| Ex | Structure | Name | Exact Mass [M + H]+ |
|---|---|---|---|
| Ex-4.13 | 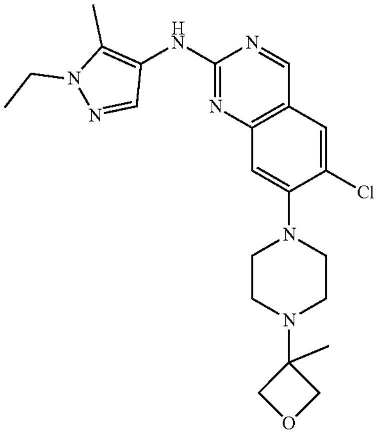 [SMILES: CCn1ncc(Nc2ncc3cc(Cl)c(N4CCN(C5(C)COC5)CC4)cc3n2)c1C] | 6-chloro-N-(1-ethyl-5-methyl-1H-pyrazol-4-yl)-7-[4-(3-methyloxetan-3-yl)piperazin-1-yl]quinazolin-2-amine | Calc'd 442.0, found 442 |
| Ex-4.14 | 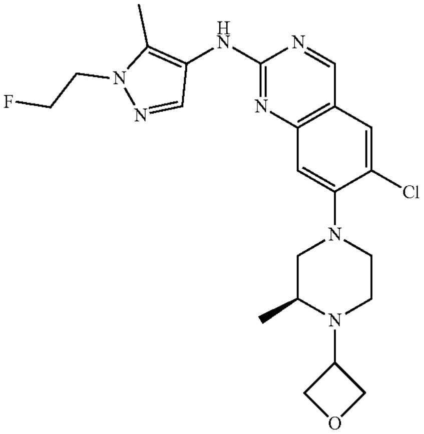 [SMILES: Cc1c(Nc2ncc3cc(Cl)c(N4CCN(C5COC5)[C@@H](C)C4)cc3n2)cnn1CCF] | 6-chloro-N-[1-(2-fluoroethyl)-5-methyl-1H-pyrazol-4-yl]-7-[(3S)-3-methyl-4-(oxetan-3-yl)piperazin-1-yl]quinazolin-2-amine | Calc'd 460.0, found 460 |
| Ex-4.15 | 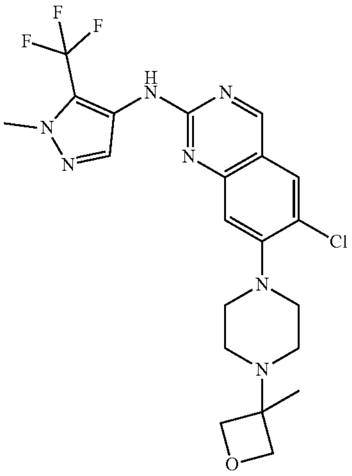 [SMILES: Cn1ncc(Nc2ncc3cc(Cl)c(N4CCN(C5(C)COC5)CC4)cc3n2)c1C(F)(F)F] | 6-chloro-7-[4-(3-methyloxetan-3-yl)piperazin-1-yl]-N-[1-methyl-5-(trifluoromethyl)-1H-pyrazol-4-yl]quinazolin-2-amine | Calc'd 482.0, found 482 |

TABLE 5-continued
| Ex | Structure | Name | Exact Mass [M + H]+ |
|---|---|---|---|
| Ex-4.16 | 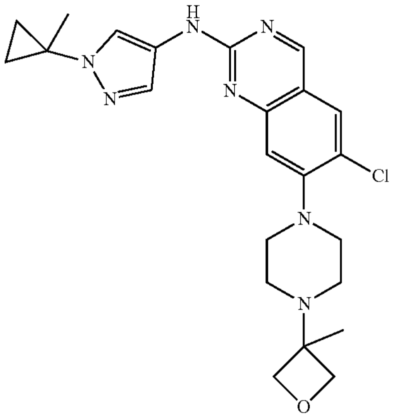 [SMILES: CC1(N2CCN(c3cc4nc(Nc5cnn(C6(C)CC6)c5)ncc4cc3Cl)CC2)COC1] | 6-chloro-N-[1-(1-methylcyclopropyl)-1H-pyrazol-4-yl]-7-[4-(3-methyloxetan-3-yl)piperazin-1-yl]quinazolin-2-amine | Calc'd 454.0, found 454 |
| Ex-4.17 | 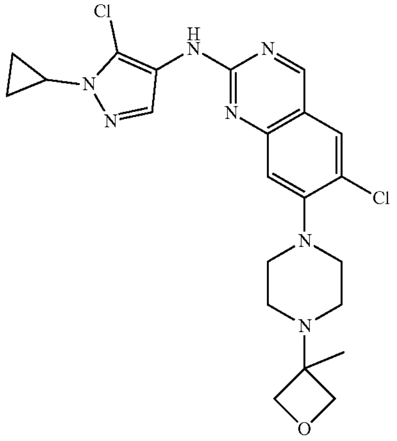 [SMILES: CC1(N2CCN(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-[4-(3-methyloxetan-3-yl)piperazin-1-yl]quinazolin-2-amine | Calc'd 474.0, found 474 |
| Ex-4.18 | 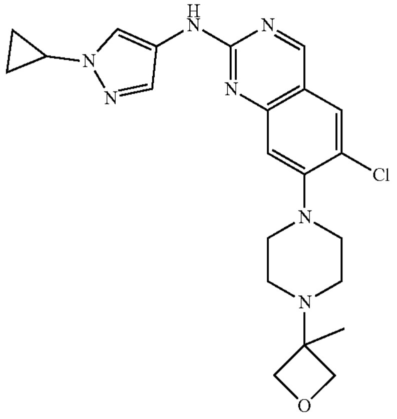 [SMILES: CC1(N2CCN(c3cc4nc(Nc5cnn(C6CC6)c5)ncc4cc3Cl)CC2)COC1] | 6-chloro-N-(1-cyclopropyl-1H-pyrazol-4-yl)-7-[4-(3-methyloxetan-3-yl)piperazin-1-yl]quinazolin-2-amine | Calc'd 440.0, found 440 |

TABLE 5-continued

| Ex | Structure | Name | Exact Mass [M + H]+ |
|---|---|---|---|
| Ex-4.19 | 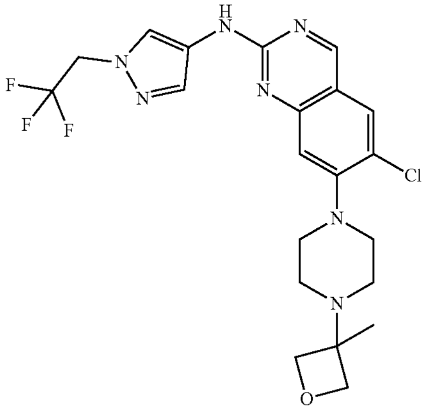 [SMILES: CC1(N2CCN(c3cc4nc(Nc5cnn(CC(F)(F)F)c5)ncc4cc3Cl)CC2)COC1] | 6-chloro-7-[4-(3-methyloxetan-3-yl)piperazin-1-yl]-N-[1-(2,2,2-trifluoroethyl)-1H-pyrazol-4-yl]quinazolin-2-amine | Calc'd 482.0, found 482 |
| Ex-4.20 | 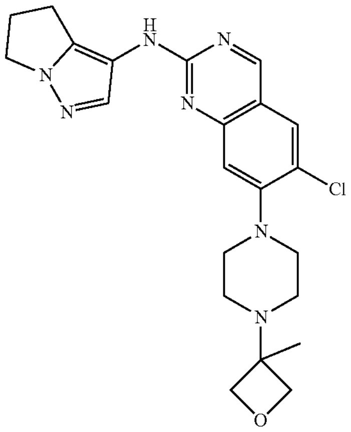 [SMILES: CC1(N2CCN(c3cc4nc(Nc5cnn6c5CCC6)ncc4cc3Cl)CC2)COC1] | 6-chloro-N-(5,6-dihydro-4H-pyrrolo[1,2-b]pyrazol-3-yl)-7-[4-(3-methyloxetan-3-yl)piperazin-1-yl]quinazolin-2-amine | Calc'd 440.0, found 440 |
| Ex-4.21 | 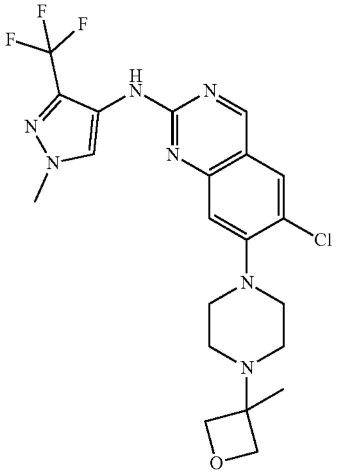 [SMILES: Cn1cc(Nc2ncc3cc(Cl)c(N4CCN(C5(C)COC5)CC4)cc3n2)c(C(F)(F)F)n1] | 6-chloro-7-[4-(3-methyloxetan-3-yl)piperazin-1-yl]-N-[1-methyl-3-(trifluoromethyl)-1H-pyrazol-4-yl]quinazolin-2-amine | Calc'd 482.0, found 482 |

TABLE 5-continued

| Ex | Structure | Name | Exact Mass $[M + H]^+$ |
|---|---|---|---|
| Ex-4.22 | 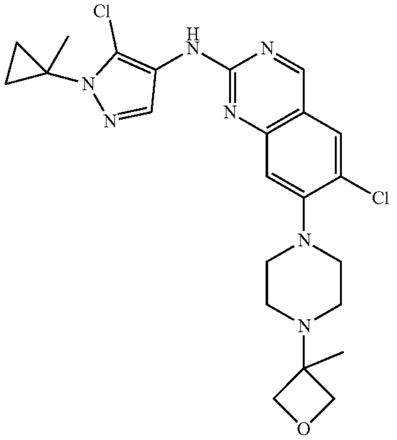 [SMILES: CC1(N2CCN(c3cc4nc(Nc5cnn(C6(C)CC6)c5Cl)ncc4cc3Cl)CC2)COC1] | 6-chloro-N-[5-chloro-1-(1-methylcyclopropyl)-1H-pyrazol-4-yl]-7-[4-(3-methyloxetan-3-yl)piperazin-1-yl]quinazolin-2-amine | Calc'd 488.0, found 488 |
| Ex-4.23 | 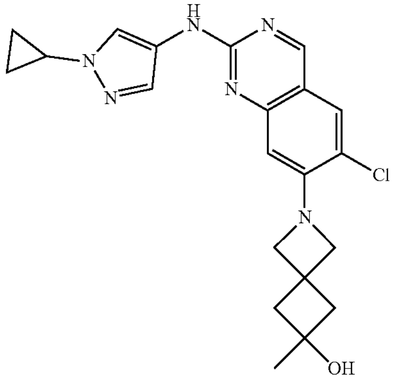 [SMILES: CC1(O)CC2(CN(c3cc4nc(Nc5cnn(C6CC6)c5)ncc4cc3Cl)C2)C1] | 2-{6-chloro-2-[(1-cyclopropyl-1H-pyrazol-4-yl)amino]quinazolin-7-yl}-6-methyl-2-azaspiro[3.3]heptan-6-ol | Calc'd 411.0, found 411 |
| Ex-4.24 | 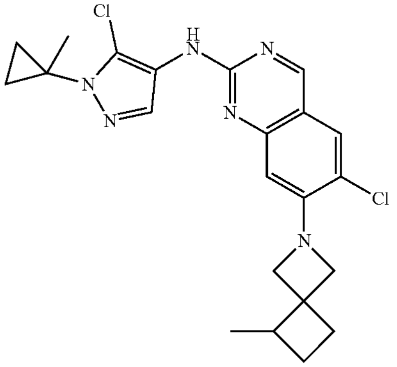 [SMILES: CC1CCC12CN(c1cc3nc(Nc4cnn(C5(C)CC5)c4Cl)ncc3cc1Cl)C2] | 6-chloro-N-[5-chloro-1-(1-methylcyclopropyl)-1H-pyrazol-4-yl]-7-(5-methyl-2-azaspiro[3.3]heptan-2-yl)quinazolin-2-amine | Calc'd 443.0, found 443 |
| Ex-4.25 | 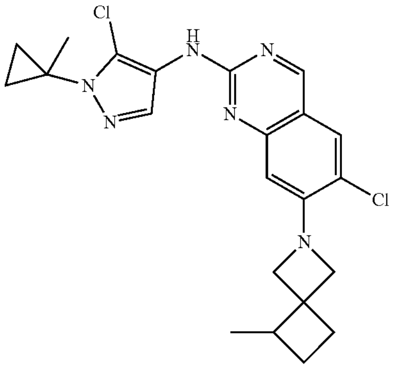 [SMILES: CC1CCC12CN(c1cc3nc(Nc4cnn(C5(C)CC5)c4Cl)ncc3cc1Cl)C2] | (R) or (S) 6-chloro-N-[5-chloro-1-(1-methylcyclopropyl)-1H-pyrazol-4-yl]-7-(5-methyl-2-azaspiro[3.3]heptan-2-yl)quinazolin-2-amine | Calc'd 443.0, found 443 |

TABLE 5-continued

| Ex | Structure | Name | Exact Mass [M + H]+ |
|---|---|---|---|
| Ex-4.26 | 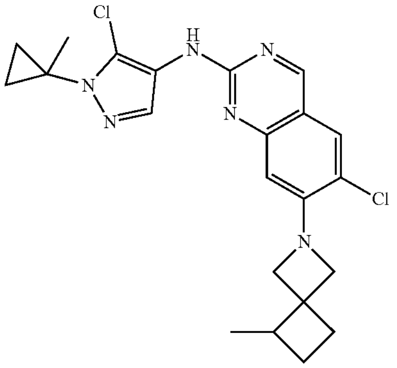 [SMILES: CC1CCC12CN(c1cc3nc(Nc4cnn(C5(C)CC5)c4Cl)ncc3cc1Cl)C2] | (R) or (S) 6-chloro-N-[5-chloro-1-(1-methylcyclopropyl)-1H-pyrazol-4-yl]-7-(5-methyl-2-azaspiro[3.3]heptan-2-yl)quinazolin-2-amine | Calc'd 443.0, found 443 |
| Ex-4.27 | 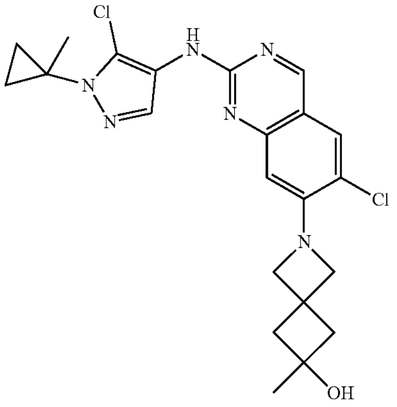 [SMILES: CC1(O)CC2(CN(c3cc4nc(Nc5cnn(C6(C)CC6)c5Cl)ncc4cc3Cl)C2)C1] | 2-(6-chloro-2-{[5-chloro-1-(1-methylcyclopropyl)-1H-pyrazol-4-yl]amino}quinazolin-7-yl)-6-methyl-2-azaspiro[3.3]heptan-6-ol | Calc'd 459.0, found 459.1 |
| Ex-4.28 | 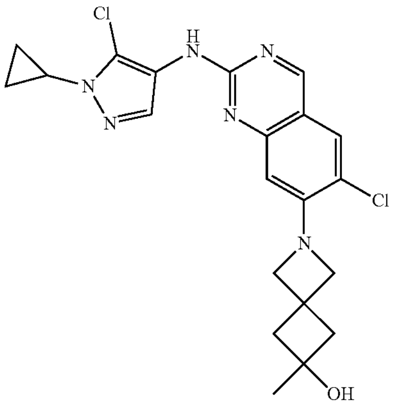 [SMILES: CC1(O)CC2(CN(c3cc4nc(Nc5cnn(C6CC6)c5Cl)ncc4cc3Cl)C2)C1] | 2-{6-chloro-2-[(5-chloro-1-cyclopropyl-1H-pyrazol-4-yl)amino]quinazolin-7-yl}-6-methyl-2-azaspiro[3.3]heptan-6-ol | Calc'd 445.0, found 445.1 |

TABLE 5-continued

| Ex | Structure | Name | Exact Mass [M + H]+ |
|---|---|---|---|
| Ex-4.29 | 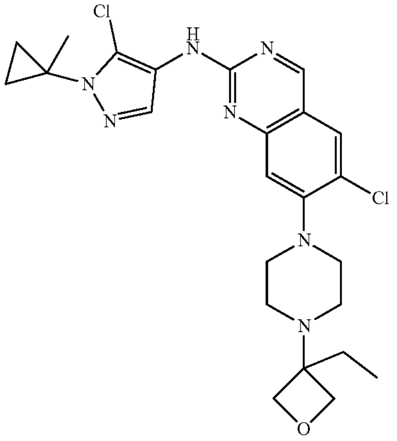 [SMILES: CCC1(N2CCN(c3cc4nc(Nc5cnn(C6(C)CC6)c5Cl)ncc4cc3Cl)CC2)COC1] | 6-chloro-N-[5-chloro-1-(1-methylcyclopropyl)-1H-pyrazol-4-yl]-7-[4-(3-ethyloxetan-3-yl)piperazin-1-yl]quinazolin-2-amine | Calc'd 502.0, found 502.1 |
| Ex-4.30 | 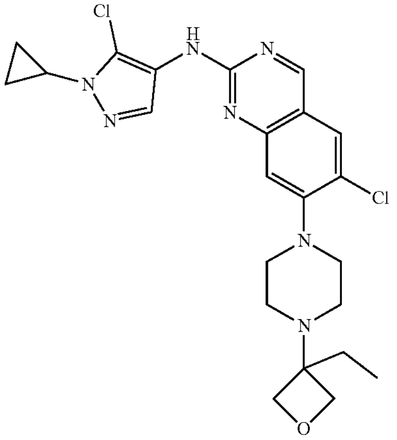 [SMILES: CCC1(N2CCN(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-[4-(3-ethyloxetan-3-yl)piperazin-1-yl]quinazolin-2-amine | Calc'd 488.0, found 488.1 |
| Ex-4.31 | 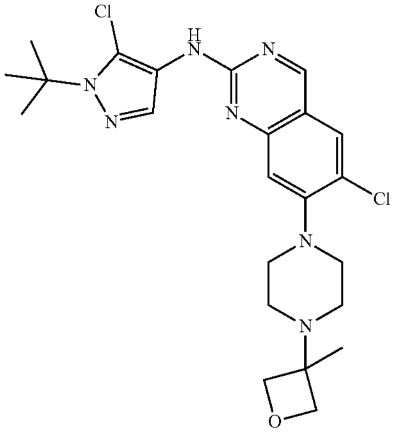 [SMILES: CC1(N2CCN(c3cc4nc(Nc5cnn(C(C)(C)C)c5Cl)ncc4cc3Cl)CC2)COC1] | N-(1-tert-butyl-5-chloro-1H-pyrazol-4-yl)-6-chloro-7-[4-(3-methyloxetan-3-yl)piperazin-1-yl]quinazolin-2-amine | Calc'd 490.0, found 490.1 |

TABLE 5-continued

| Ex | Structure | Name | Exact Mass [M + H]+ |
|---|---|---|---|
| Ex-4.32 | 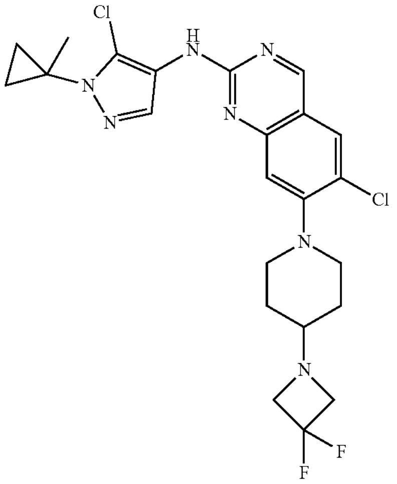 [SMILES: CC1(n2ncc(Nc3ncc4cc(Cl)c(N5CCC(N6CC(F)(F)C6)CC5)cc4n3)c2Cl)CC1] | 6-chloro-N-[5-chloro-1-(1-methylcyclopropyl)-1H-pyrazol-4-yl]-7-[4-(3,3-difluoroazetidin-1-yl)piperidin-1-yl]quinazolin-2-amine | Calc'd 508.0, found 508.1 |
| Ex-4.33 | 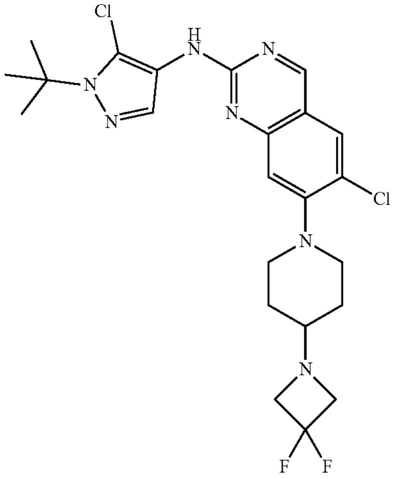 [SMILES: CC(C)(C)n1ncc(Nc2ncc3cc(Cl)c(N4CCC(N5CC(F)(F)C5)CC4)cc3n2)c1Cl] | N-(1-tert-butyl-5-chloro-1H-pyrazol-4-yl)-6-chloro-7-[4-(3,3-difluoroazetidin-1-yl)piperidin-1-yl]quinazolin-2-amine | Calc'd 510.0, found 510.1 |
| Ex-4.34 | 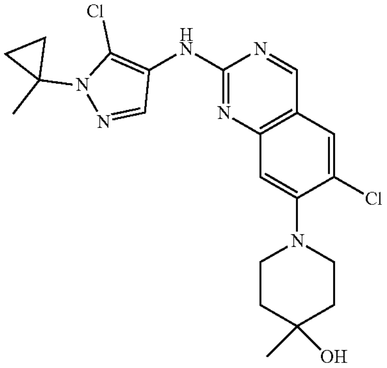 [SMILES: CC1(O)CCN(c2cc3nc(Nc4cnn(C5(C)CC5)c4Cl)ncc3cc2Cl)CC1] | 1-(6-chloro-2-{[5-chloro-1-(1-methylcyclopropyl)-1H-pyrazol-4-yl]amino}quinazolin-7-yl)-4-methylpiperidin-4-ol | Calc'd 447.0, found 447.1 |

TABLE 5-continued

| Ex | Structure | Name | Exact Mass [M + H]$^+$ |
|---|---|---|---|
| Ex-4.35 | 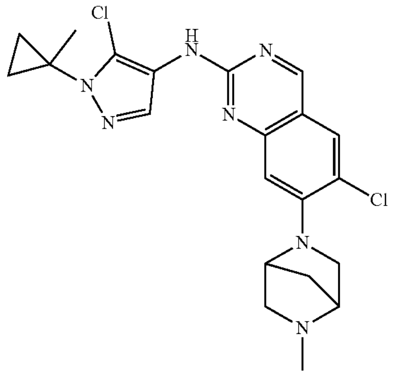 [SMILES: CN1CC2CC1CN2c1cc2nc(Nc3cnn(C4(C)CC4)c3Cl)ncc2cc1Cl] | 6-chloro-N-[5-chloro-1-(1-methylcyclopropyl)-1H-pyrazol-4-yl]-7-(5-methyl-2,5-diazabicyclo[2.2.1]heptan-2-yl)quinazolin-2-amine | Calc'd 444.0, found 444.2 |
| Ex-4.36 | 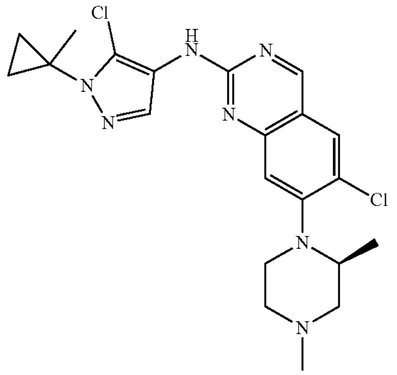 [SMILES: C[C@H]1CN(C)CCN1c1cc2nc(Nc3cnn(C4(C)CC4)c3Cl)ncc2cc1Cl] | 6-chloro-N-[5-chloro-1-(1-methylcyclopropyl)-1H-pyrazol-4-yl]-7-[(2S)-2,4-dimethylpiperazin-1-yl]quinazolin-2-amine | Calc'd 446.0, found 446.1 |
| Ex-4.37 | 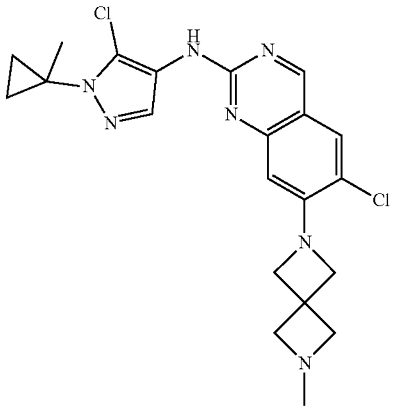 [SMILES: CN1CC2(C1)CN(c1cc3nc(Nc4cnn(C5(C)CC5)c4Cl)ncc3cc1Cl)C2] | 6-chloro-N-[5-chloro-1-(1-methylcyclopropyl)-1H-pyrazol-4-yl]-7-(6-methyl-2,6-diazaspiro[3.3.]heptan-2-yl)quinazolin-2-amine | Calc'd 444.0, found 444.1 |

TABLE 5-continued

| Ex | Structure | Name | Exact Mass [M + H]+ |
|---|---|---|---|
| Ex-4.38 | 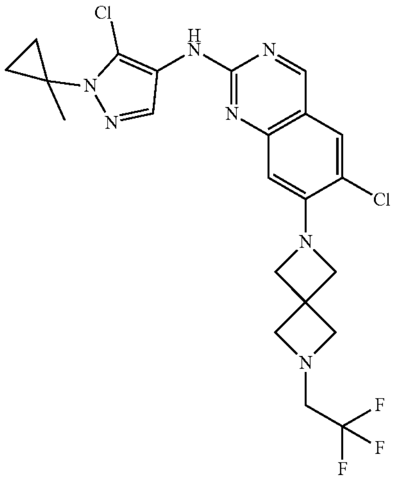 [SMILES: CC1(n2ncc(Nc3ncc4cc(Cl)c(N5CC6(CN(CC(F)(F)F)C6)C5)cc4n3)c2Cl)CC1] | 6-chloro-N-[5-chloro-1-(1-methylcyclopropyl)-1H-pyrazol-4-yl]-7-[6-(2,2,2-trifluoroethyl)-2,6-diazaspiro[3.3]heptan-2-yl]quinazolin-2-amine | Calc'd 512.0, found 512.2 |
| Ex-4.39 | 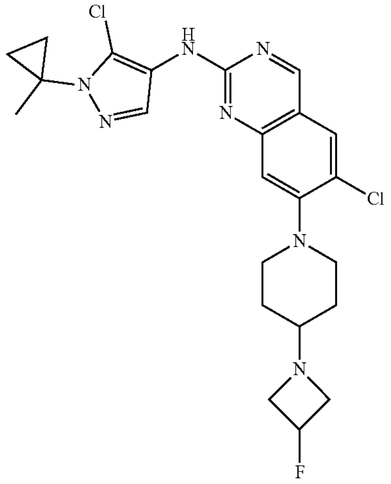 [SMILES: CC1(n2ncc(Nc3ncc4cc(Cl)c(N5CCC(N6CC(F)C6)CC5)cc4n3)c2Cl)CC1] | 6-chloro-N-[5-chloro-1-(1-methylcyclopropyl)-1H-pyrazol-4-yl]-7-[4-(3-fluoroazetidin-1-yl)piperidin-1-yl]quinazolin-2-amine | Calc'd 490.0, found 490.1 |
| Ex-4.40 | 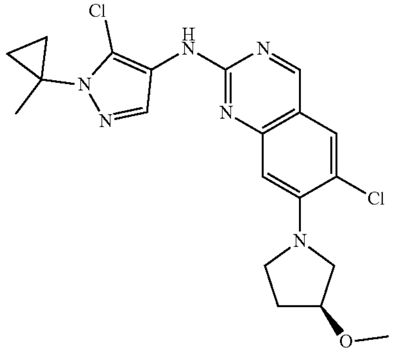 [SMILES: CO[C@H]1CCN(c2cc3nc(Nc4cnn(C5(C)CC5)c4Cl)ncc3cc2Cl)C1] | 6-chloro-N-[5-chloro-1-(1-methylcyclopropyl)-1H-pyrazol-4-yl]-7-[(3S)-3-methoxypyrrolidin-1-yl]quinazolin-2-amine | Calc'd 433.0, found 433.1 |

TABLE 5-continued

| Ex | Structure | Name | Exact Mass [M + H]+ |
|---|---|---|---|
| Ex-4.41 | 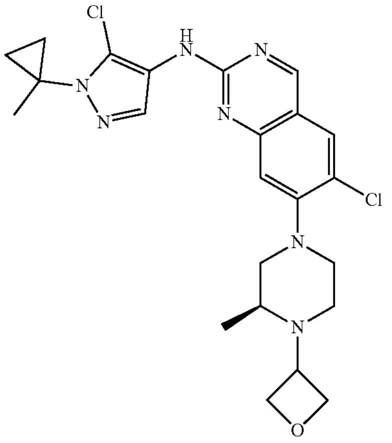 [SMILES: C[C@H]1CN(c2cc3nc(Nc4cnn(C5(C)CC5)c4Cl)ncc3cc2Cl)CCN1C1COC1] | 6-chloro-N-[5-chloro-1-(1-methylcyclopropyl)-1H-pyrazol-4-yl]-7-[(3S)-3-methyl-4-(oxetan-3-yl)piperazin-1-yl]quinazolin-2-amine | Calc'd 488.0, found 488.1 |
| Ex-4.42 | 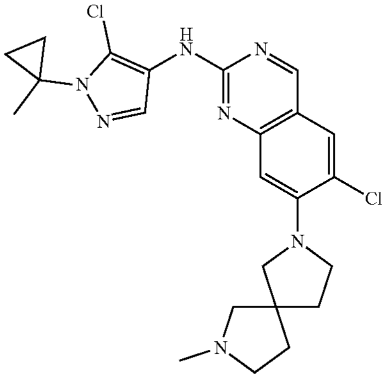 [SMILES: CN1CCC2(CCN(c3cc4nc(Nc5cnn(C6(C)CC6)c5Cl)ncc4cc3Cl)C2)C1] | 6-chloro-N-[5-chloro-1-(1-methylcyclopropyl)-1H-pyrazol-4-yl]-7-(7-methyl-2,7-diazaspiro[4.4]nonan-2-yl)quinazolin-2-amine | Calc'd 472.0, found 472.1 |
| Ex-4.43 | 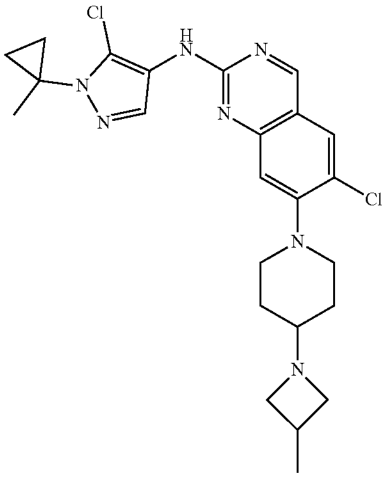 [SMILES: CC1CN(C2CCN(c3cc4nc(Nc5cnn(C6(C)CC6)c5Cl)ncc4cc3Cl)CC2)C1] | 6-chloro-N-[5-chloro-1-(1-methylcyclopropyl)-1H-pyrazol-4-yl]-7-[4-(3-methylazetidin-1-yl)piperidin-1-yl]quinazolin-2-amine | Calc'd 486.0, found 486.1 |

TABLE 5-continued

| Ex | Structure | Name | Exact Mass [M + H]+ |
|---|---|---|---|
| Ex-4.44 | 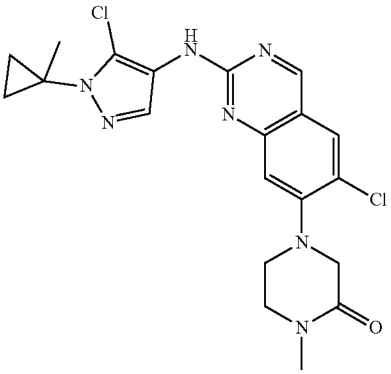 [SMILES: CN1CCN(c2cc3nc(Nc4cnn(C5(C)CC5)c4Cl)ncc3cc2Cl)CC1=O] | 4-(6-chloro-2-{[5-chloro-1-(1-methylcyclopropyl)-1H-pyrazol-4-yl]amino}quinazolin-7-yl)-1-methylpiperazin-2-one | Calc'd 446.0, found 446.1 |
| Ex-4.45 | 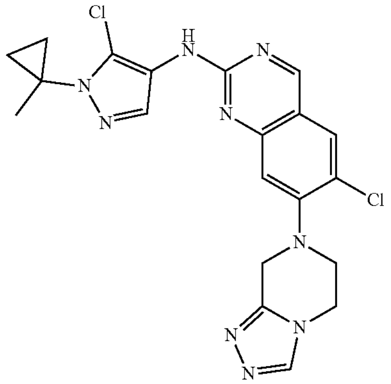 [SMILES: CC1(n2ncc(Nc3ncc4cc(Cl)c(N5CCn6cnnc6C5)cc4n3)c2Cl)CC1] | 6-chloro-N-[5-chloro-1-(1-methylcyclopropyl)-1H-pyrazol-4-yl]-7-(5,6-dihydro[1,2,4]triazolo[4,3-a]pyrazin-7(8H)-yl)quinazolin-2-amine | Calc'd 456.0 found 456.2 |
| Ex-4.46 | 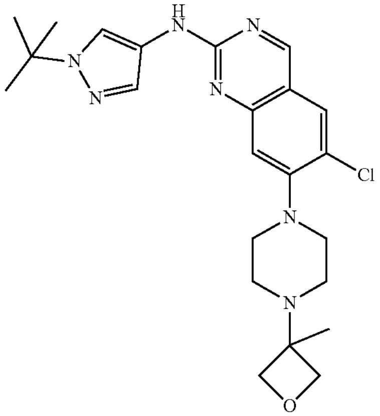 [SMILES: CC1(N2CCN(c3cc4nc(Nc5cnn(C(C)(C)C)c5)ncc4cc3Cl)CC2)COC1] | N-(1-tert-butyl-1H-pyrazol-4-yl)-6-chloro-7-[4-(3-methyloxetan-3-yl)piperazin-1-yl]quinazolin-2-amine | Calc'd 456.0, found 456.3 |

TABLE 5-continued

| Ex | Structure | Name | Exact Mass [M + H]+ |
|---|---|---|---|
| Ex-4.47 | 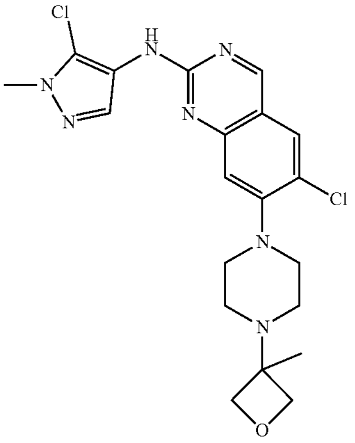 [SMILES: Cn1ncc(Nc2ncc3cc(Cl)c(N4CCN(C5(C)COC5)CC4)cc3n2)c1Cl] | 6-chloro-N-(5-chloro-1-methyl-1H-pyrazol-4-yl)-7-[4-(3-methyloxetan-3-yl)piperazin-1-yl]quinazolin-2-amine | Calc'd 448.0, found 448.1 |
| Ex-4.48 | 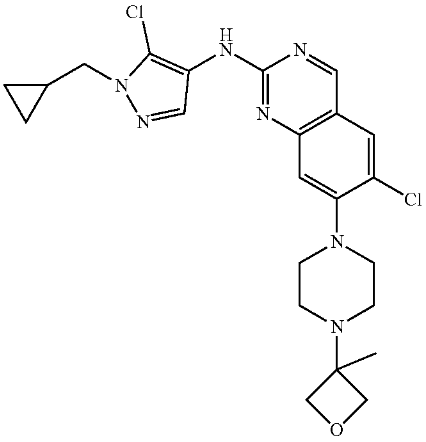 [SMILES: CC1(N2CCN(c3cc4nc(Nc5cnn(CC6CC6)c5Cl)ncc4cc3Cl)CC2)COC1] | 6-chloro-N-[5-chloro-1-(cyclopropylmethyl)-1H-pyrazol-4-yl]-7-[4-(3-methyloxetan-3-yl)piperazin-1-yl]quinazolin-2-amine | Calc'd 488.0, found 488.1 |
| Ex-4.49 | 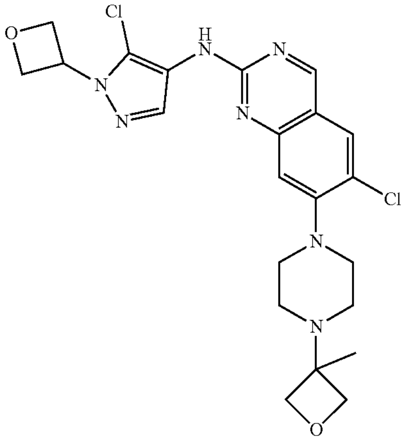 [SMILES: CC1(N2CCN(c3cc4nc(Nc5cnn(C6COC6)c5Cl)ncc4cc3Cl)CC2)COC1] | 6-chloro-N-[5-chloro-1-(oxetan-3-yl)-1H-pyrazol-4-yl]-7-[4-(3-methyloxetan-3-yl)piperazin-1-yl]quinazolin-2-amine | Calc'd 490.0, found 490.1 |

TABLE 5-continued

| Ex | Structure | Name | Exact Mass [M + H]+ |
|---|---|---|---|
| Ex-4.50 | 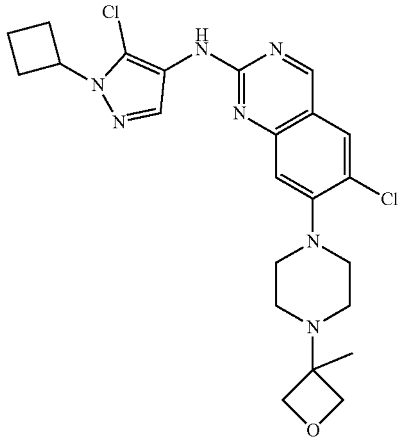 [SMILES: CC1(N2CCN(c3cc4nc(Nc5cnn(C6CCC6)c5Cl)ncc4cc3Cl)CC2)COC1] | 6-chloro-N-(5-chloro-1-cyclobutyl-1H-pyrazol-4-yl)-7-[4-(3-methyloxetan-3-yl)piperazin-1-yl]quinazolin-2-amine | Calc'd 488.0, found 488.1 |
| Ex-4.51 | 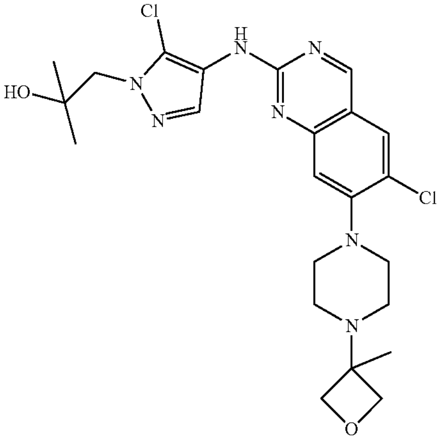 [SMILES: CC(C)(O)Cn1ncc(Nc2ncc3cc(Cl)c(N4CCN(C5(C)COC5)CC4)cc3n2)c1Cl] | 1-[5-chloro-4-({6-chloro-7-[4-(3-methyloxetan-3-yl)piperazin-1-yl]quinazolin-2-yl}amino)-1H-pyrazol-1-yl]-2-methylpropan-2-ol | Calc'd 506.0, found 506.1 |
| Ex-4.52 | 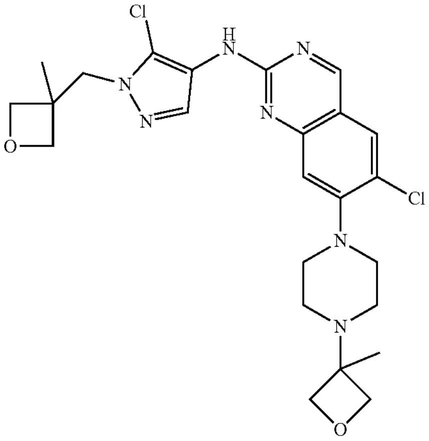 [SMILES: CC1(Cn2ncc(Nc3ncc4cc(Cl)c(N5CCN(C6(C)COC6)CC5)cc4n3)c2Cl)COC1] | 6-chloro-N-{5-chloro-1-[(3-methyloxetan-3-yl)methyl]-1H-pyrazol-4-yl}-7-[4-(3-methyloxetan-3-yl)piperazin-1-yl]quinazolin-2-amine | Calc'd 518.0, found 518.3 |

TABLE 5-continued

| Ex | Structure | Name | Exact Mass [M + H]+ |
| --- | --- | --- | --- |
| Ex-4.53 | 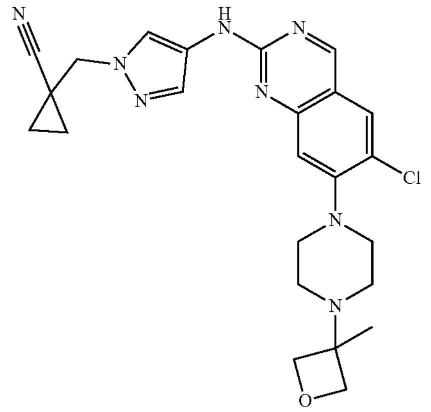 [SMILES: CC1(N2CCN(c3cc4nc(Nc5cnn(CC6(C#N)CC6)c5)ncc4cc3Cl)CC2)COC1] | 1-{[4-({6-chloro-7-[4-(3-methyloxetan-3-yl)piperazin-1-yl]quinazolin-2-yl}amino)-1H-pyrazol-1-yl]methyl}cyclopropane-1-carbonitrile | Calc'd 479.0, found 479.3 |
| Ex-4.54 | 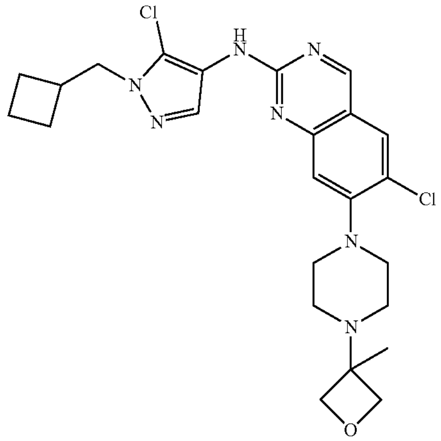 [SMILES: CC1(N2CCN(c3cc4nc(Nc5cnn(CC6CCC6)c5Cl)ncc4cc3Cl)CC2)COC1] | 6-chloro-N-[5-chloro-1-(cyclobutylmethyl)-1H-pyrazol-4-yl]-7-[4-(3-methyloxetan-3-yl)piperazin-1-yl]quinazolin-2-amine | Calc'd 502.0, found 502.1 |
| Ex-4.55 | 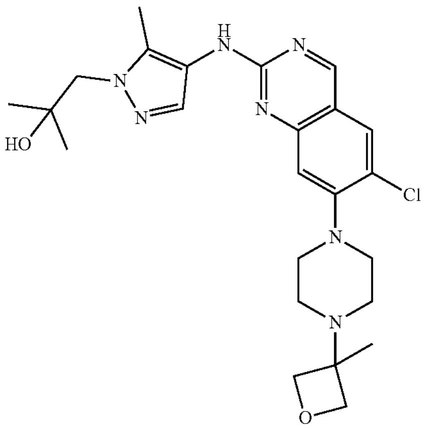 [SMILES: Cc1c(Nc2ncc3cc(Cl)c(N4CCN(C5(C)COC5)CC4)cc3n2)cnn1CC(C)(C)O] | 1-[4-({6-chloro-7-[4-(3-methyloxetan-3-yl)piperazin-1-yl]quinazolin-2-yl}amino)-5-methyl-1H-pyrazol-1-yl]-2-methylpropan-2-ol | Calc'd 486.0, found 486.3 |

TABLE 5-continued

| Ex | Structure | Name | Exact Mass [M + H]⁺ |
|---|---|---|---|
| Ex-4.56 | 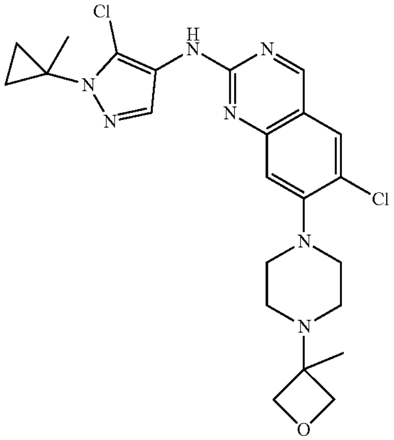 [SMILES: CC1(N2CCN(c3cc4nc(Nc5cnn(C6(C)CC6)c5Cl)ncc4cc3Cl)CC2)COC1] | 6-chloro-N-[5-chloro-1-(1-methylcyclopropyl)-1H-pyrazol-4-yl]-7-[4-(3-methyloxetan-3-yl)piperazin-1-yl]quinazolin-2-amine | Calc'd 488.0, found 488.1 |
| Ex-4.57 | 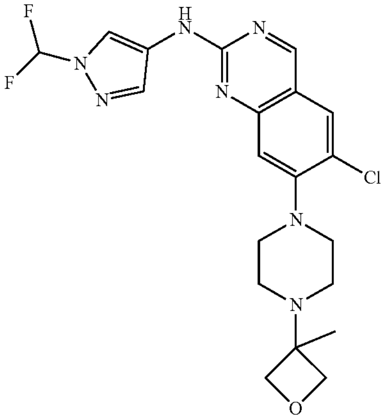 [SMILES: CC1(N2CCN(c3cc4nc(Nc5cnn(C(F)F)c5)ncc4cc3Cl)CC2)COC1] | 6-chloro-N-[1-(difluoromethyl)-1H-pyrazol-4-yl]-7-[4-(3-methyloxetan-3-yl)piperazin-1-yl]quinazolin-2-amine | Calc'd 450.0, found 450.1 |
| Ex-4.58 | 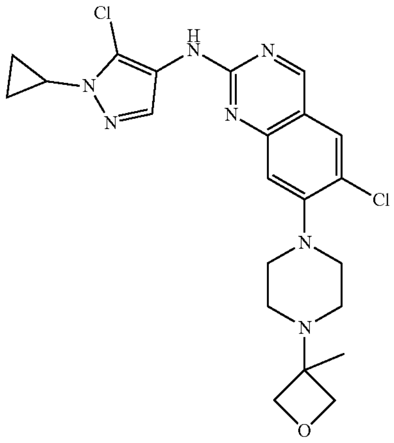 [SMILES: CC1(N2CCN(c3cc4nc(Nc5cnn(C6CC6)c5Cl)ncc4cc3Cl)CC2)COC1] | 6-chloro-N-(5-chloro-1-cyclopropyl-1H-pyrazol-4-yl)-7-[4-(3-methyloxetan-3-yl)piperazin-1-yl]quinazolin-2-amine | Calc'd 474.0, found 474.1 |

TABLE 5-continued

| Ex | Structure | Name | Exact Mass [M + H]+ |
|---|---|---|---|
| Ex-4.59 | 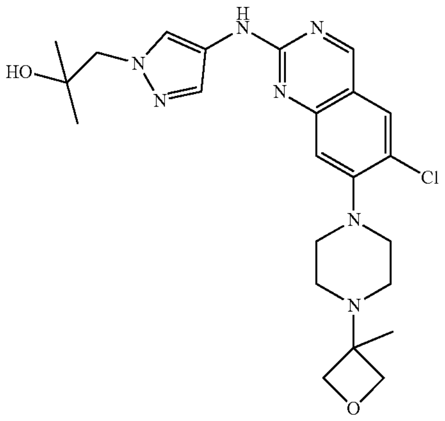 [SMILES: CC(C)(O)Cn1cc(Nc2ncc3cc(Cl)c(N4CCN(C5(C)COC5)CC4)cc3n2)cn1] | 1-[4-({6-chloro-7-[4-(3-methyloxetan-3-yl)piperazin-1-yl]quinazolin-2-yl}amino)-1H-pyrazol-1-yl]-2-methylpropan-2-ol | Calc'd 472.0, found 472.1 |
| Ex-4.60 | 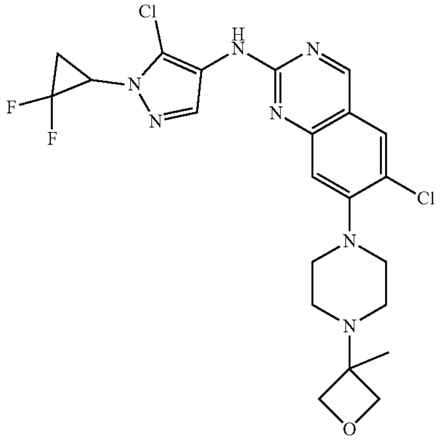 [SMILES: CC1(N2CCN(c3cc4nc(Nc5cnn(C6CC6(F)F)c5Cl)ncc4cc3Cl)CC2)COC1] | 6-chloro-N-[5-chloro-1-(2,2-(R) or (S) difluorocyclopropyl)-1H-pyrazol-4-yl]-7-[4-(3-methyloxetan-3-yl)piperazin-1-yl]quinazolin-2-amine | Calc'd 510.0, found 510.0 |
| Ex-4.61 | 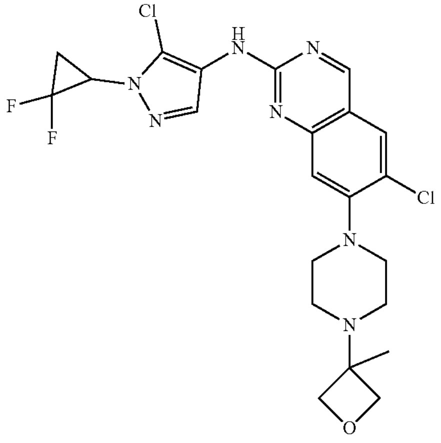 [SMILES: CC1(N2CCN(c3cc4nc(Nc5cnn(C6CC6(F)F)c5Cl)ncc4cc3Cl)CC2)COC1] | 6-chloro-N-[5-chloro-1-(2,2-(R) or (S) difluorocyclopropyl)-1H-pyrazol-4-yl]-7-[4-(3-methyloxetan-3-yl)piperazin-1-yl]quinazolin-2-amine | Calc'd 510.0, found 510.1 |

TABLE 5-continued

| Ex | Structure | Name | Exact Mass [M + H]+ |
|---|---|---|---|
| Ex-4.62 | 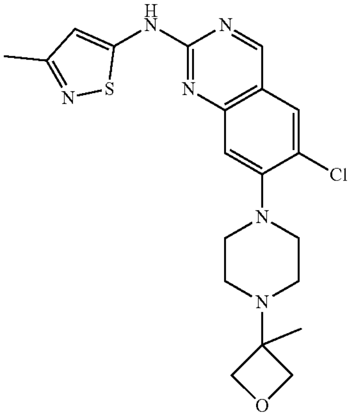 [SMILES: Cc1cc(Nc2ncc3cc(Cl)c(N4CCN(C5(C)COC5)CC4)cc3n2)sn1] | 6-chloro-7-[4-(3-methyloxetan-3-yl)piperazin-1-yl]-N-(3-methyl-1,2-thiazol-5-yl)quinazolin-2-amine | Calc'd 431.0, found 431.1 |
| Ex-4.63 | 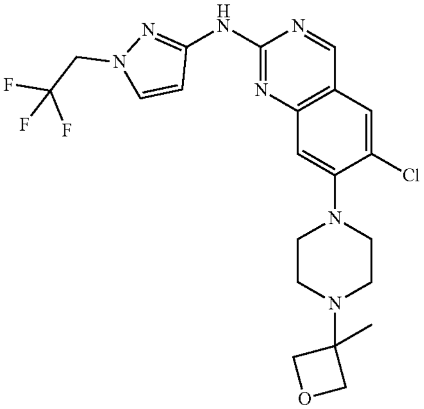 [SMILES: CC1(N2CCN(c3cc4nc(Nc5ccn(CC(F)(F)F)n5)ncc4cc3Cl)CC2)COC1] | 6-chloro-7-[4-(3-methyloxetan-3-yl)piperazin-1-yl]-N-[1-(2,2,2-trifluoroethyl)-1H-pyrazol-3-yl]quinazolin-2-amine | Calc'd 482.0, found 482.1 |
| Ex-4.64 | 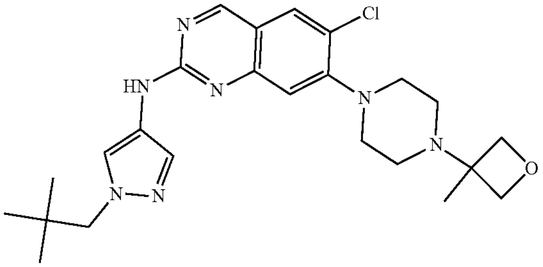 [SMILES: CC(C)(C)Cn1cc(Nc2ncc3cc(Cl)c(N4CCN(C5(C)COC5)CC4)cc3n2)cn1] | 6-chloro-N-[1-(2,2-dimethylpropyl)-1H-pyrazol-4-yl]-7-[4-(3-methyloxetan-3-yl)piperazin-1-yl]quinazolin-2-amine | Calc'd 470.0, found 470.6 |
| Ex-4.65 | 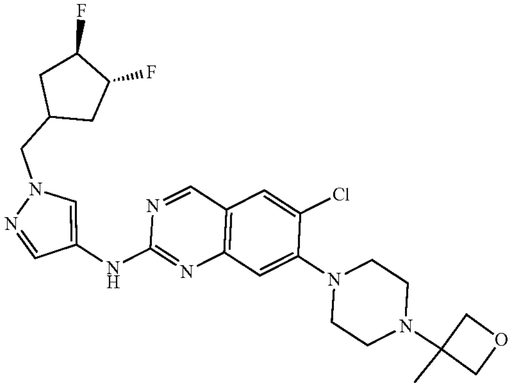 [SMILES: CC1(N2CCN(c3cc4nc(Nc5cnn(CC6C[C@@H](F)[C@H](F)C6)c5)ncc4cc3Cl)CC2)COC1] | 6-chloro-N-(1-{[(3R,4R)-3,4-difluorocyclopentyl]methyl}-1H-pyrazol-4-yl)-7-[4-(3-methyloxetan-3-yl)piperazin-1-yl]quinazolin-2-amine | Calc'd 518.0, found 518.5 |

TABLE 5-continued

| Ex | Structure | Name | Exact Mass [M + H]+ |
|---|---|---|---|
| Ex-4.66 | 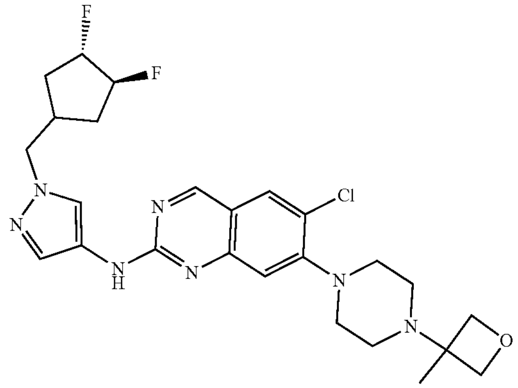 [SMILES: CC1(N2CCN(c3cc4nc(Nc5cnn(CC6C[C@H](F)[C@@H](F)C6)c5)ncc4cc3Cl)CC2)COC1] | 6-chloro-N-(1-{[(3S,4S)-3,4-difluorocyclopentyl]methyl}-1H-pyrazol-4-yl)-7-[4-(3-methyloxetan-3-yl)piperazin-1-yl]quinazolin-2-amine | Calc'd 518.0, found 518.5 |
| Ex-4.67 | 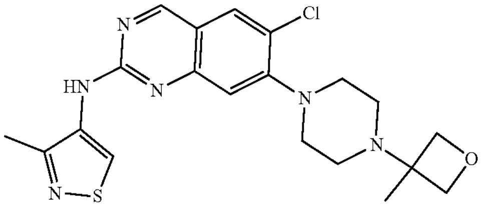 [SMILES: Cc1nscc1Nc1ncc2cc(Cl)c(N3CCN(C4(C)COC4)CC3)cc2n1] | 6-chloro-7-[4-(3-methyloxetan-3-yl)piperazin-1-yl]-N-(3-methyl-1,2-thiazol-4-yl)quinazolin-2-amine | Calc'd 431.0, found 431.5 |
| Ex-4.68 | 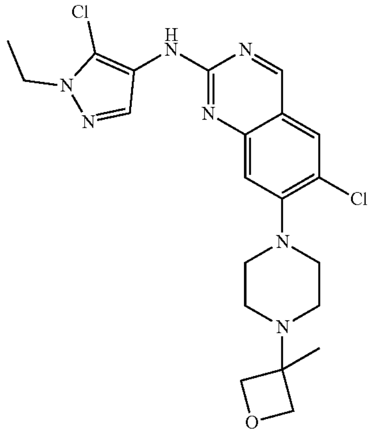 [SMILES: CCn1ncc(Nc2ncc3cc(Cl)c(N4CCN(C5(C)COC5)CC4)cc3n2)c1Cl] | 6-chloro-N-(5-chloro-1-ethyl-1H-pyrazol-4-yl)-7-[4-(3-methyloxetan-3-yl)piperazin-1-yl]quinazolin-2-amine | Calc'd 462.0, found 462.1 |
| Ex-4.69 | 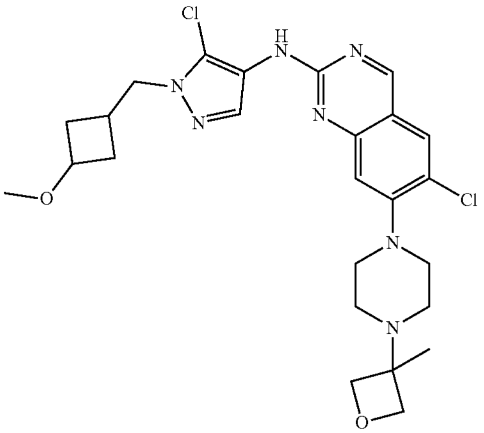 [SMILES: COC1CC(Cn2ncc(Nc3ncc4cc(Cl)c(N5CCN(C6(C)COC6)CC5)cc4n3)c2Cl)C1] | 6-chloro-N-{5-chloro-1-[(3-methoxycyclobutyl)methyl]-1H-pyrazol-4-yl}-7-[4-(3-methyloxetan-3-yl)piperazin-1-yl]quinazolin-2-amine | Calc'd 532.0, found 532.2 |

TABLE 5-continued
| Ex | Structure | Name | Exact Mass [M + H]+ |
|---|---|---|---|
| Ex-4.70 | 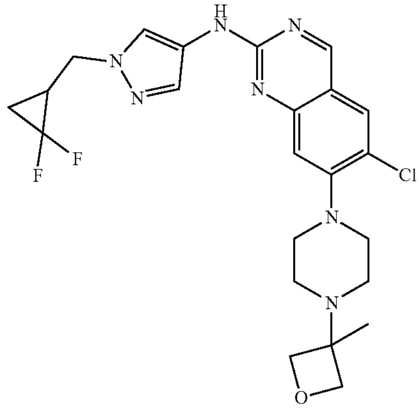 [SMILES: CC1(N2CCN(c3cc4nc(Nc5cnn(CC6CC6(F)F)c5)ncc4cc3Cl)CC2)COC1] | 6-chloro-N-{1-[(2,2-difluorocyclopropyl)methyl]-1H-pyrazol-4-yl}-7-[4-(3-methyloxetan-3-yl)piperazin-1-yl]quinazolin-2-amine | Calc'd 490.0, found 490 |
| Ex-4.71 | 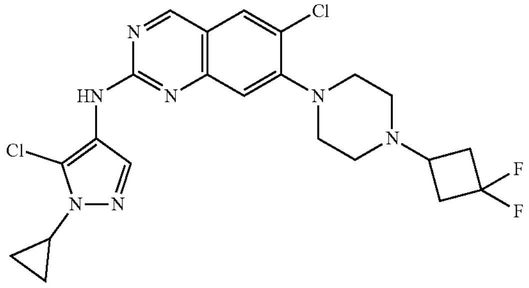 [SMILES: FC1(F)CC(N2CCN(c3cc4nc(Nc5cnn(C6CC6)c5Cl)ncc4cc3Cl)CC2)C1] | 6-chloro-N-(5-chloro-1-cyclopropyl-1H-pyrazol-4-yl)-7-(4-(3,3-difluorocyclobutyl)piperazin-1-yl)quinazolin-2-amine | Calc'd 494.0, found 494 |
General Scheme 6
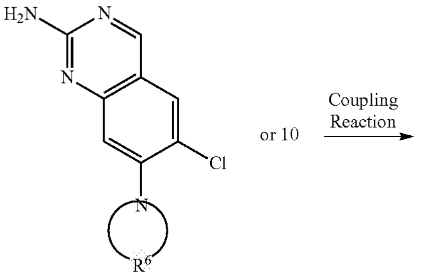
Gen-27
-continued
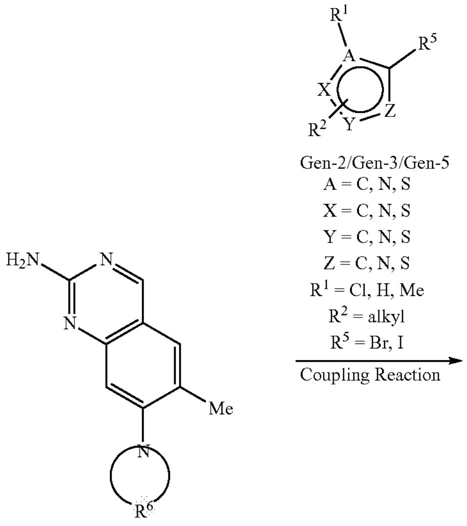
Gen-28

-continued

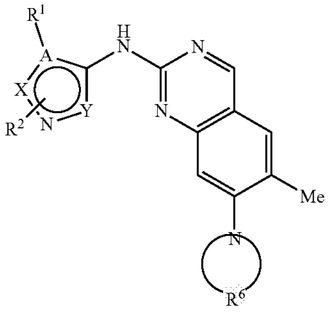

Gen-29

In General Scheme 6, synthetically prepared intermediate Gen-27 or intermediate 10 could undergo a coupling reaction to afford compounds of the form Gen-28. A palladium or copper-catalyzed reaction could be employed to couple Gen-28 with halo-pyrazoles Gen-2/Gen-3/Gen-5 to afford elaborated compounds of the form Gen-29. Representative preparative examples from each sequence are described in more detail below.

Preparation of Example 5.1

Scheme 50. Synthesis of (3S, 4S) or (3R, 4R) 4-(4-(2-((5-chloro-1-(2,2-(R) or (S) difluorocyclopropyl)-1H-pyrazol-4-yl)amino)-6-methylquinazolin-7-yl)piperazin-1-yl)tetrahydrofuran-3-ol

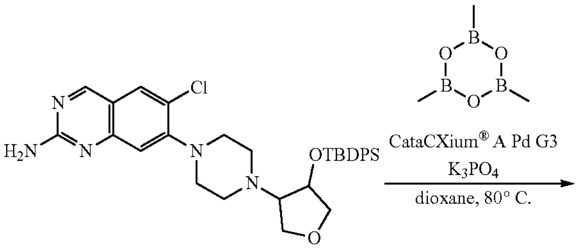

159

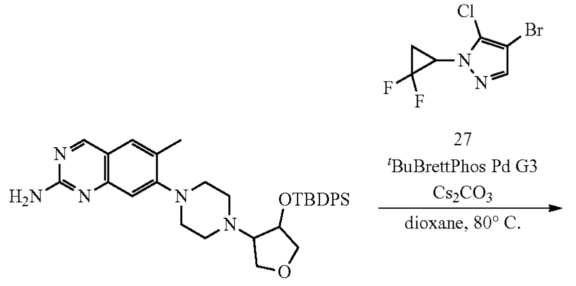

160

-continued

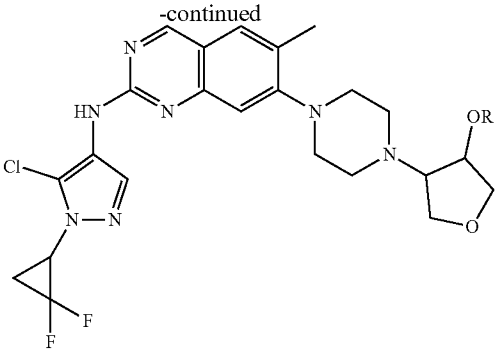

161 (R = TBDPS)
TBAF
Ex-5.1 (R = H)

(3S, 4S) or (3R, 4R) 7-(4-(4-((Tert-butyldiphenylsilyl)oxy)tetrahydrofuran-3-yl)piperazin-1-yl)-6-methylquinazolin-2-amine (160)

The title compound 160 was made through an analogus coupling reaction as demonstrated in Scheme 41 in the formation of 139. MS (ESI): m/z calc'd for $C_{33}H_{41}N_5O_2Si$ $[M+H]^+$: 568, found 568.

(3S, 4S) or (3R, 4R) 7-(4-(4-((Tert-butyldiphenylsilyl)oxy)tetrahydrofuran-3-yl)piperazin-1-yl)-N-(5-chloro-1-(2,2-(R) or (S) difluorocyclopropyl)-1H-pyrazol-4-yl)-6-methylquinazolin-2-amine (161)

The title compound 161 was made through an analogus coupling reaction as demonstrated in Scheme 48 in the formation of 156 using bromopyrazole 27 as the coupling partner. MS (ESI): m/z calc'd for $C_{39}H_{44}ClF_2N_7O_2Si$ $[M+H]^+$: 744, found 744. (3S, 4S) or (3R, 4R) 4-(4-(2-((5-Chloro-1-(2,2-(R) or (S) difluorocyclopropyl)-1H-pyrazol-4-yl)amino)-6-methylquinazolin-7-yl)piperazin-1-yl)tetrahydrofuran-3-ol (Ex-5.1) The title compound Ex-5.1 was made through an analogus TBAF promoted deprotection reaction as demonstrated in Scheme 48 and exemplified in the preparation of Example 4.1 and 4.2. MS (ESI): m/z calc'd for $C_{23}H_{26}ClF_2N_{7}O_2$ $[M+H]^+$: 506, found 506. $^1H$ NMR (500 MHz, DMSO-$d_6$, 25° C.) δ 8.99 (s, 1H), 8.94 (s, 1H), 8.02 (s, 1H), 7.62 (s, 1H), 6.94 (s, 1H), 4.52-4.45 (m, 1H), 4.37 (s, 1H), 4.19 (s, 1H), 3.92-3.80 (m, 2H), 3.69 (d, J=9.5 Hz, 1H), 3.63 (dd, J=10.1, 7.4 Hz, 1H), 3.31 (m, 1H, overlap with HDO) 3.03 (s, 4H), 2.77 (s, 2H), 2.72-2.66 (m, 1H), 2.46-2.38 (m, 2H), 2.34 (s, 3H), The following Examples, 5.2-5.16 were obtained using the procedure analogous to those in General Scheme 6 but substituting appropriate starting materials that are either commercially available or prepared using procedures analogous to those described in Scheme 45.

TABLE 6

| Ex | Structure | Name | Exact Mass $[M + H]^+$ |
|---|---|---|---|
| Ex-5.2 | 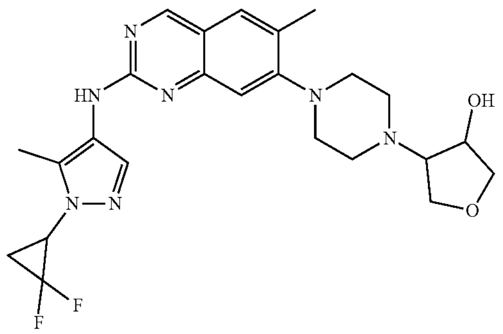 [SMILES: Cc1cc2cnc(Nc3cnn(C4CC4(F)F)c3C)nc2cc1N1CCN(C2COCC2O)CC1] | (3S,4S) or (3R,4R) 4-(4-(2-((1-(2,2-(R) or (S) difluorocyclopropyl)-5-methyl-1H-pyrazol-4-yl)amino)-6-methylquinazolin-7-yl)piperazin-1-yl)tetrahydrofuran-3-ol | Calc'd 486.0, found 486 |
| Ex-5.3 | 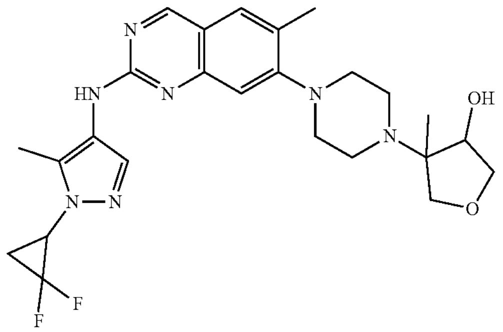 [SMILES: Cc1cc2cnc(Nc3cnn(C4CC4(F)F)c3C)nc2cc1N1CCN(C2(C)COCC2O)CC1] | (3S,4S) or (3R,4R) 4-(4-(2-((1-(2,2-(R) or (S) difluorocyclopropyl)-5-methyl-1H-pyrazol-4-yl)amino)-6-methylquinazolin-7-yl)piperazin-1-yl)-4-methyltetrahydrofuran-3-ol | Calc'd 500.0, found 500 |
| Ex-5.4 | 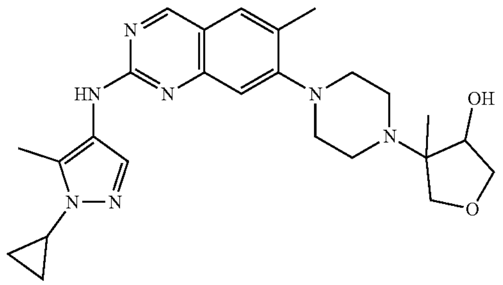 [SMILES: Cc1cc2cnc(Nc3cnn(C4CC4)c3C)nc2cc1N1CCN(C2(C)COCC2O)CC1] | (3S,4S) or (3R,4R) 4-(4-(2-((1-cyclopropyl-5-methyl-1H-pyrazol-4-yl)amino)-6-methylquinazolin-7-yl)piperazin-1-yl)-4-methyltetrahydrofuran-3-ol | Calc'd 464.0, found 464 |
| Ex-5.5 | 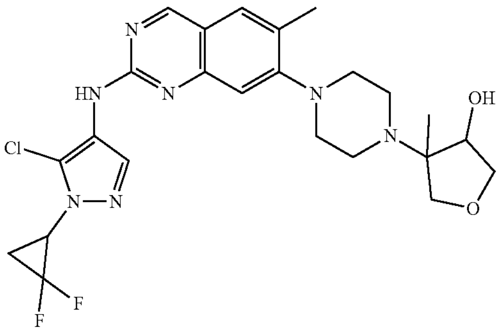 [SMILES: Cc1cc2cnc(Nc3cnn(C4CC4(F)F)c3Cl)nc2cc1N1CCN(C2(C)COCC2O)CC1] | (3S,4S) or (3R,4R) 4-(4-(2-((5-chloro-1-(2,2-(R) or (S) difluorocyclopropyl)-1H-pyrazol-4-yl)amino)-6-methylquinazolin-7-yl)piperazin-1-yl)-4-methyltetrahydrofuran-3-ol | Calc'd 520.0, found 520 |
| Ex-5.6 | 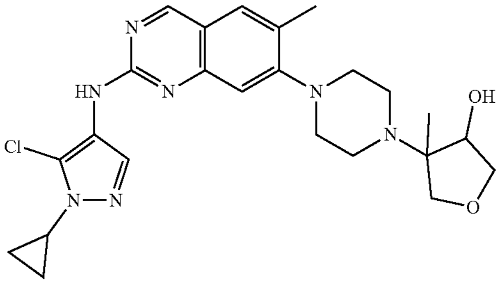 [SMILES: Cc1cc2cnc(Nc3cnn(C4CC4)c3Cl)nc2cc1N1CCN(C2(C)COCC2O)CC1] | (3S,4S) or (3R,4R) 4-(4-(2-((5-chloro-1-cyclopropyl-1H-pyrazol-4-yl)amino)-6-methylquinazolin-7-yl)piperazin-1-yl)-4-methyltetrahydrofuran-3-ol | Calc'd 484.0, found 484 |

TABLE 6-continued

| Ex | Structure | Name | Exact Mass [M + H]$^+$ |
|---|---|---|---|
| Ex-5.7 | 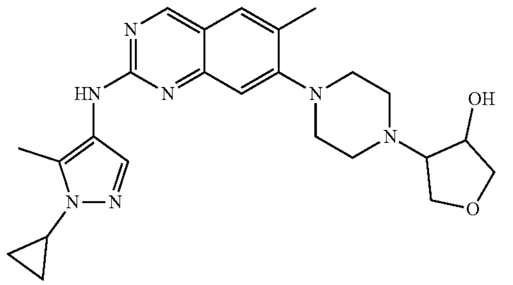 [SMILES: Cc1cc2cnc(Nc3cnn(C4CC4)c3C)nc2cc1N1CCN(C2COCC2O)CC1] | (3S,4S) or (3R,4R) 4-(4-{2-[(1-cyclopropyl-5-methyl-1H-pyrazol-4-yl)amino]-6-methylquinazolin-7-yl}piperazin-1-yl)oxolan-3-ol | Calc'd 450.0, found 450 |
| Ex-5.8 | 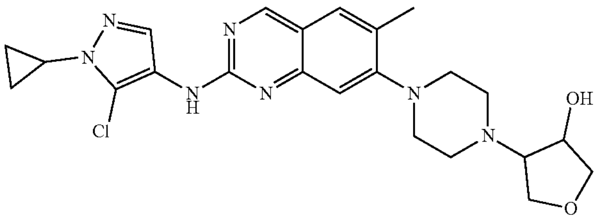 [SMILES: Cc1cc2cnc(Nc3cnn(C4CC4)c3Cl)nc2cc1N1CCN(C2COCC2O)CC1] | (3S,4S) or (3R,4R) 4-(4-{2-[(5-chloro-1-cyclopropyl-1H-pyrazol-4-yl)amino]-6-methylquinazolin-7-yl}piperazin-1-yl)oxolan-3-ol | Calc'd 470.0, found 470 |
| Ex-5.9 | 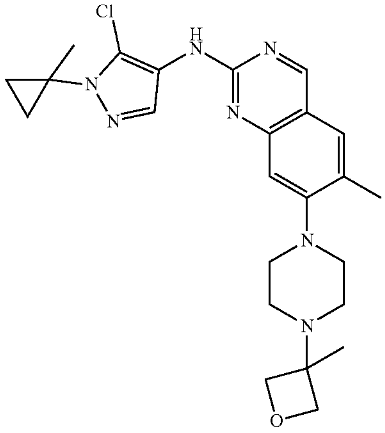 [SMILES: Cc1cc2cnc(Nc3cnn(C4(C)CC4)c3Cl)nc2cc1N1CCN(C2(C)COC2)CC1] | N-[5-chloro-1-(1-methylcyclopropyl)-1H-pyrazol-4-yl]-6-methyl-7-[4-(3-methyloxetan-3-yl)piperazin-1-yl]quinazolin-2-amine | Calc'd 468.0, found 468 |
| Ex-5.10 | 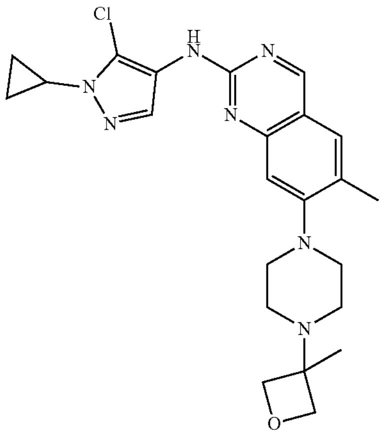 [SMILES: Cc1cc2cnc(Nc3cnn(C4CC4)c3Cl)nc2cc1N1CCN(C2(C)COC2)CC1] | N-(5-chloro-1-cyclopropyl-1H-pyrazol-4-yl)-6-methyl-7-[4-(3-methyloxetan-3-yl)piperazin-1-yl]quinazolin-2-amine | Calc'd 454.0, found 454 |

TABLE 6-continued

| Ex | Structure | Name | Exact Mass [M + H]+ |
|---|---|---|---|
| Ex-5.11 | 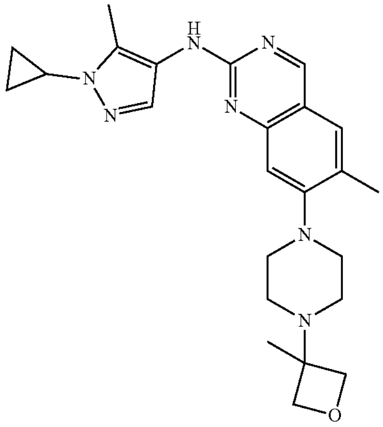 [SMILES: Cc1cc2cnc(Nc3cnn(C4CC4)c3C)nc2cc1N1CCN(C2(C)COC2)CC1] | N-(1-cyclopropyl-5-methyl-1H-pyrazol-4-yl)-6-methyl-7-[4-(3-methyloxetan-3-yl)piperazin-1-yl]quinazolin-2-amine | Calc'd 434.0, found 434 |
| Ex-5.12 | 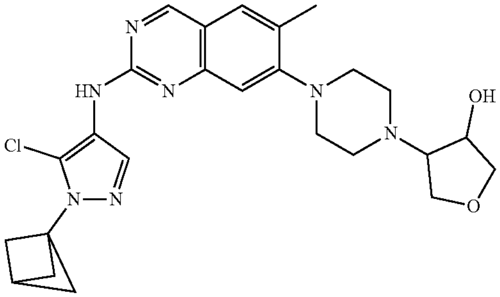 [SMILES: Cc1cc2cnc(Nc3cnn(C45CC(C4)C5)c3Cl)nc2cc1N1CCN(C2COCC2O)CC1] | (3S,4S) or (3R,4R) 4-(4-(2-((1-(bicyclo[1.1.1]pentan-1-yl)-5-chloro-1H-pyrazol-4-yl)amino)-6-methylquinazolin-7-yl)piperazin-1-yl)tetrahydrofuran-3-ol | Calc'd 496.0, found 496 |
| Ex-5.13 | 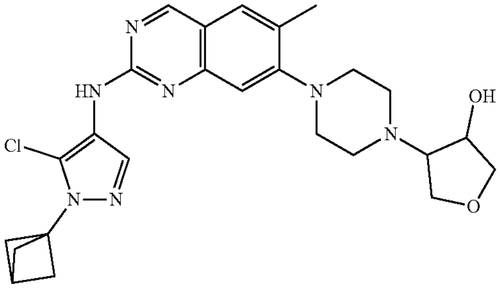 [SMILES: Cc1cc2cnc(Nc3cnn(C45CC(C4)C5)c3Cl)nc2cc1N1CCN(C2COCC2O)CC1] | (3S,4S) or (3R,4R) 4-(4-(2-((1-(bicyclo[1.1.1]pentan-1-yl)-5-chloro-1H-pyrazol-4-yl)amino)-6-methylquinazolin-7-yl)piperazin-1-yl)tetrahydrofuran-3-ol | Calc'd 496.0, found 496 |
| Ex-5.14 | 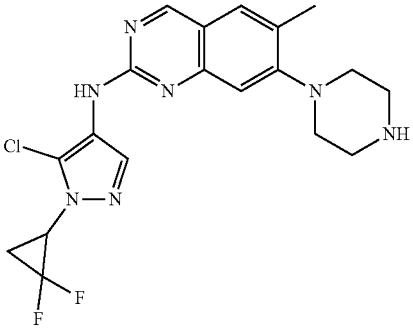 [SMILES: Cc1cc2cnc(Nc3cnn(C4CC4(F)F)c3Cl)nc2cc1N1CCNCC1] | N-(5-chloro-1-(2,2-difluorocyclopropyl)-1H-pyrazol-4-yl)-6-methyl-7-(piperazin-1-yl)quinazolin-2-amine | Calc'd 420.0, found 420 |

TABLE 6-continued

| Ex | Structure | Name | Exact Mass [M + H]+ |
|---|---|---|---|
| Ex-5.15 | 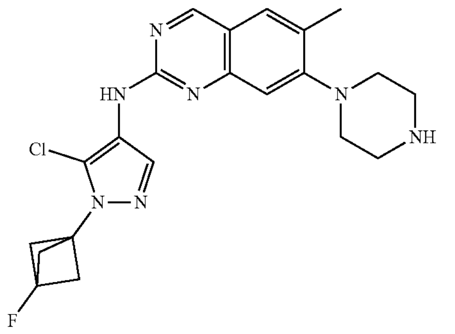 [SMILES: Cc1cc2cnc(Nc3cnn(C45CC(F)(C4)C5)c3Cl)nc2cc1N1CCNCC1] | N-(5-chloro-1-(3-fluorobicyclo[1.1.1]pentan-1-yl)-1H-pyrazol-4-yl)-6-methyl-7-(piperazin-1-yl)quinazolin-2-amine | Calc'd 428.0, found 428 |
| Ex-5.16 | 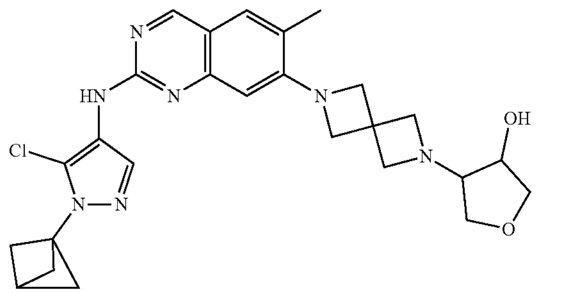 [SMILES: Cc1cc2cnc(Nc3cnn(C45CC(C4)C5)c3Cl)nc2cc1N1CC2(C1)CN(C1COCC1O)C2] | (3R,4R) or (3S,4S) 4-(6-(2-((1-(bicyclo[1.1.1]pentan-1-yl)-5-chloro-1H-pyrazol-4-yl)amino)-6-methylquinazolin-7-yl)-2,6-diazaspiro[3.3]heptan-2-yl)tetrahydrofuran-3-ol | Calc'd 508.0, found 508 |

General Scheme 7

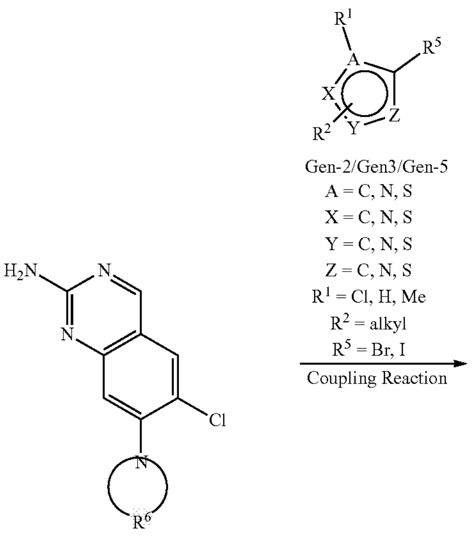

Gen-27

-continued

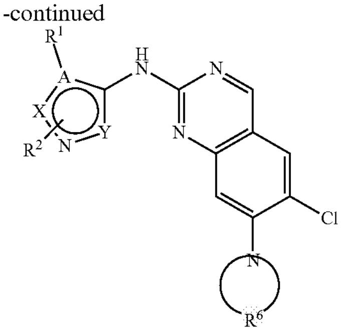

Gen-30

In General Scheme 7, synthetically prepared intermediate Gen-27 could undergo a palladium or copper-catalyzed reaction to couple Gen-27 with Gen-2/Gen-3/Gen-5 to afford elaborated compounds of the form Gen-30. Representative preparative examples from each sequence are described in more detail below.

Preparation of Example 6.1

Scheme 51. Synthesis of 6-chloro-N-(1-(2,2-difluoroethyl)-1H-pyrazol-4-yl)-7-(4-(3-methyloxetan-3-yl)piperazin-1-yl)quinazolin-2-amine

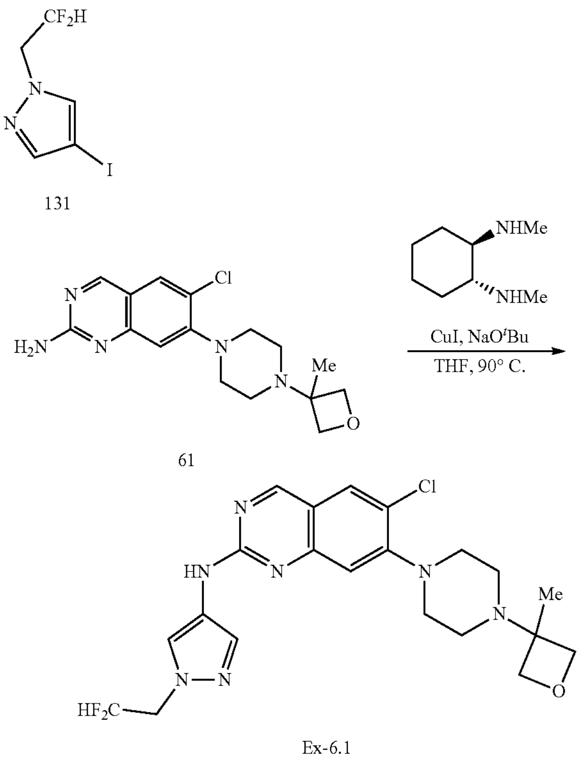

131

61

Ex-6.1

A 2-dram vial was charged with copper(I) iodide (11 mg, 0.060 mmol) and (1S,2S)-N1,N2-dimethylcyclohexane-1,2-diamine (14 μL, 0.090 mmol) under inert atmosphere. Dioxane (456 μL) was added, and this mixture was stirred to complex the copper and ligand for 10 min. A 5 mL microwave vial was charged with 1-(2,2-difluoroethyl)-4-iodo-1H-pyrazole 131 (85 mg, 0.33 mmol), 6-chloro-7-(4-(3-methyloxetan-3-yl)piperazin-1-yl)quanzolin-2-amine 61 (100 mg, 0.300 mmol) and potassium phosphate tribasic (190 mg, 0.90 mmol) under inert atmosphere. Dioxane (400 Ex) was added, and to the stirring mixture at RT was added the copper complex solution. The resultant mixture was stirred at 90° C. for 4 h. The reaction was quenched by the addition of water (5 mL). The phases were separated and the aqueous phase extracted with EtOAc (3×25 mL). The combined organic phases were washed with $H_2O$ (50 mL), dried over $Na_2SO_4$, and the solvent removed under reduced pressure. The crude residue was subject to purification by reverse phase HPLC, eluting with water (0.100 $NH_4OH$)-MeCN to afford 6-chloro-N-(1-(2,2-difluoroethyl)-1H-pyrazol-4-yl)-7-(4-(3-methyloxetan-3-yl)piperazin-1-yl)quinazolin-2-amine Ex-6.1. MS (ESI): m/z calc'd for $C_{21}H_{24}ClFN_7O$ $[M+H]^+$: 464, found 464.

The following Examples, 6.2-6.56 were obtained using the procedure analogous to those in General Scheme 7 but substituting appropriate starting materials that are either commercially available or prepared using procedures analogous to those described in Scheme 51.

TABLE 7

| Ex | Structure | Name | Exact Mass $[M + H]^+$ |
|---|---|---|---|
| Ex-6.2 | 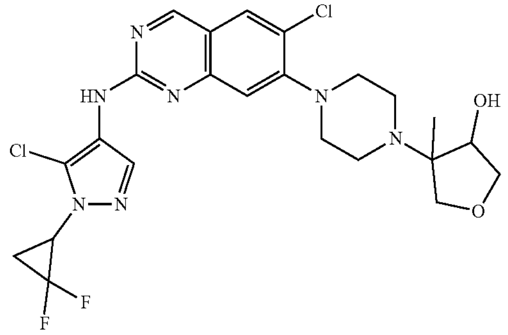 [SMILES: CC1(N2CCN(c3cc4nc(Nc5cnn(C6CC6(F)F)c5Cl)ncc4cc3Cl)CC2)COCC1O] | (3S,4S) or (3R,4R) 4-(4-(6-chloro-2-((5-chloro-1-(2,2-(R) or (S) difluorocyclopropyl)-1H-pyrazol-4-yl)amino)quinazolin-7-yl)piperazin-1-yl)-4-methyltetrahydrofuran-3-ol | Calc'd 540.0, found 540 |

TABLE 7-continued

| Ex | Structure | Name | Exact Mass [M + H]+ |
|---|---|---|---|
| Ex-6.3 | 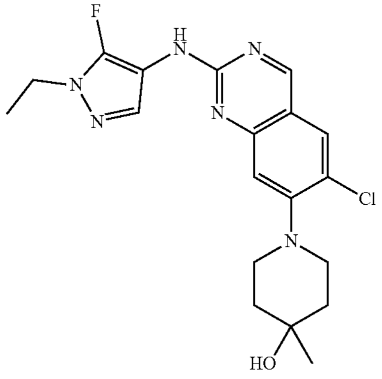 [SMILES: CCn1ncc(Nc2ncc3cc(Cl)c(N4CCC(C)(O)CC4)cc3n2)c1F] | 1-{6-chloro-2-[(1-ethyl-5-fluoro-1H-pyrazol-4-yl)amino]quinazolin-7-yl}-4-methylpiperidin-4-ol | Calc'd 405.0, found 405 |
| Ex-6.4 | 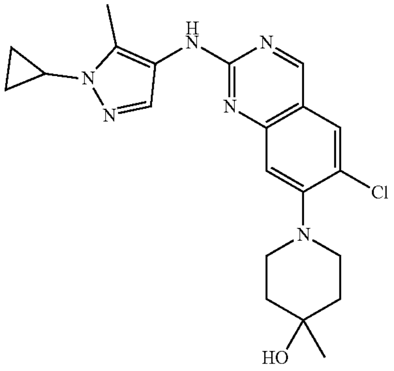 [SMILES: Cc1c(Nc2ncc3cc(Cl)c(N4CCC(C)(O)CC4)cc3n2)cnn1C1CC1] | 1-{6-chloro-2-[(1-cyclopropyl-5-methyl-1H-pyrazol-4-yl)amino}quinazolin-7-yl}-4-methylpiperidin-4-ol | Calc'd 413.0, found 413 |
| Ex-6.5 | 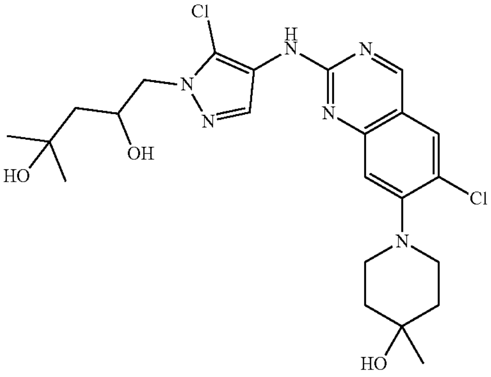 [SMILES: CC(C)(O)CC(O)Cn1ncc(Nc2ncc3cc(Cl)c(N4CCC(C)(O)CC4)cc3n2)c1Cl] | 1-(5-chloro-4-{[6-chloro-7-(4-hydroxy-4-methylpiperidin-1-yl)quinazolin-2-yl]amino}-1H-pyrazol-1-yl)-4-methylpentane-2,4-diol | Calc'd 509.0, found 509 |
| Ex-6.6 | 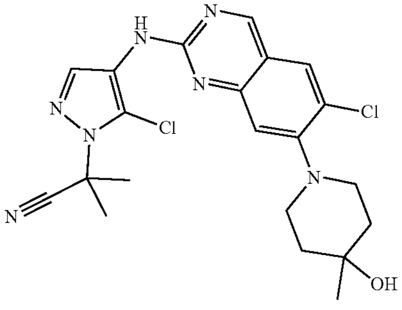 [SMILES: CC1(O)CCN(c2cc3nc(Nc4cnn(C(C)(C)C#N)c4Cl)ncc3cc2Cl)CC1] | 2-(5-chloro-4-{[6-chloro-7-(4-hydroxy-4-methylpiperidin-1-yl)quinazolin-2-yl]amino}-1H-pyrazol-1-yl)-2-methylpropanenitrile | Calc'd 460.0, found 460 |

TABLE 7-continued

| Ex | Structure | Name | Exact Mass [M + H]$^+$ |
|---|---|---|---|
| Ex-6.7 | 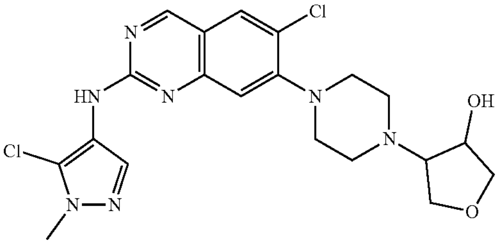 [SMILES: Cn1ncc(Nc2ncc3cc(Cl)c(N4CCN(C5COCC5O)CC4)cc3n2)c1Cl] | (3S,4S) or (3R,4R) 4-(4-{6-chloro-2-[(5-chloro-1-methyl-1H-pyrazol-4-yl)amino]quinazolin-7-yl}piperazin-1-yl)oxolan-3-ol | Calc'd 464.0, found 464 |
| Ex-6.8 | 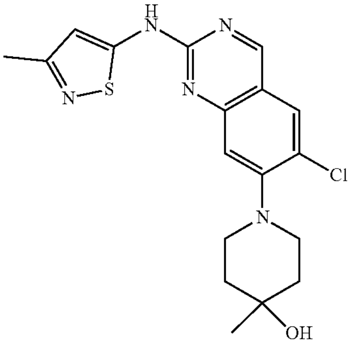 [SMILES: Cc1cc(Nc2ncc3cc(Cl)c(N4CCC(C)(O)CC4)cc3n2)sn1] | 1-{6-chloro-2-[(3-methyl-1,2-thiazol-5-yl)amino]quinazolin-7-yl}-4-methylpiperidin-4-ol | Calc'd 390.0, found 390 |
| Ex-6.9 | 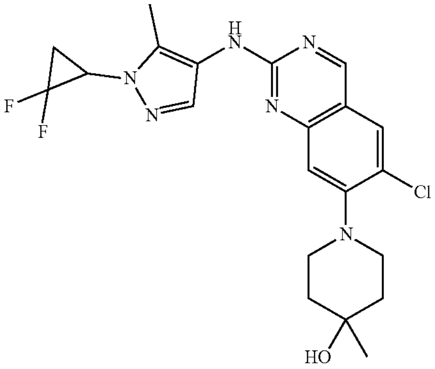 [SMILES: Cc1c(Nc2ncc3cc(Cl)c(N4CCC(C)(O)CC4)cc3n2)cnn1C1CC1(F)F] | 1-(6-chloro-2-{[1-(2,2-(R) or (S) difluorocyclopropyl)-5-methyl-1H-pyrazol-4-yl]amino}quinazolin-7-yl)-4-methylpiperidin-4-ol | Calc'd 449.0, found 449 |
| Ex-6.10 | 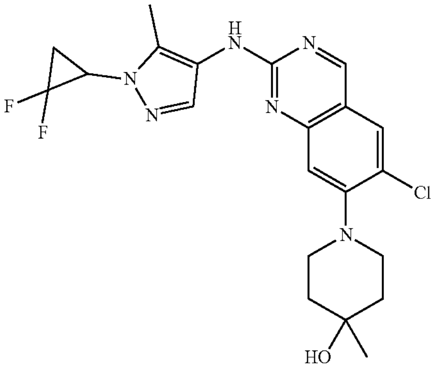 [SMILES: Cc1c(Nc2ncc3cc(Cl)c(N4CCC(C)(O)CC4)cc3n2)cnn1C1CC1(F)F] | 1-(6-chloro-2-{[1-(2,2-(R) or (S) difluorocyclopropyl)-5-methyl-1H-pyrazol-4-yl]amino}quinazolin-7-yl)-4-methylpiperidin-4-ol | Calc'd 449.0, found 449 |

TABLE 7-continued

| Ex | Structure | Name | Exact Mass [M + H]+ |
|---|---|---|---|
| Ex-6.11 | 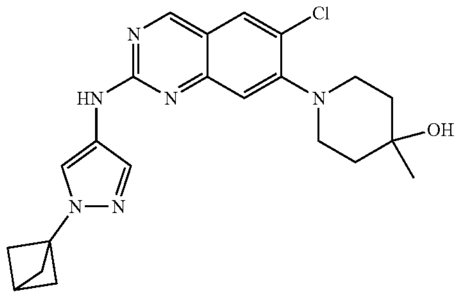 [SMILES: CC1(O)CCN(c2cc3nc(Nc4cnn(C56CC(C5)C6)c4)ncc3cc2Cl)CC1] | 1-(2-{[1-(bicyclo[1.1.1]pentan-1-yl)-1H-pyrazol-4-yl]amino}-6-chloroquinazolin-7-yl)-4-methylpiperidin-4-ol | Calc'd 425.0, found 425 |
| Ex-6.12 | 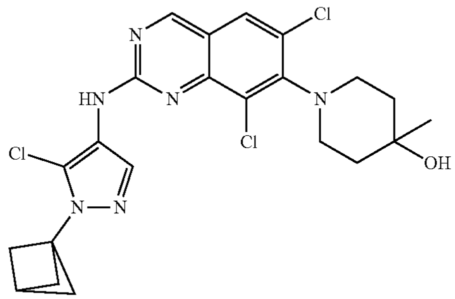 [SMILES: CC1(O)CCN(c2c(Cl)cc3cnc(Nc4cnn(C56CC(C5)C6)c4Cl)nc3c2Cl)CC1] | 1-(2-{[1-(bicyclo[1.1.1]pentan-1-yl)-5-chloro-1H-pyrazol-4-yl]amino}-6,8-dichloroquinazolin-7-yl)-4-methylpiperidin-4-ol | Calc'd 493.0, found 493 |
| Ex-6.13 | 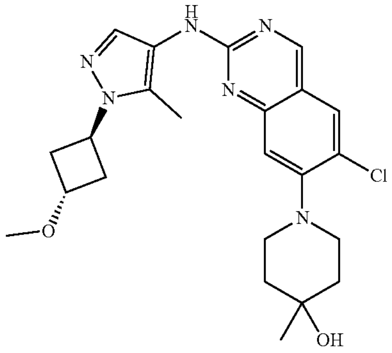 [SMILES: CO[C@H]1C[C@H](n2ncc(Nc3ncc4cc(Cl)c(N5CCC(C)(O)CC5)cc4n3)c2C)C1] | 1-(6-chloro-2-{[1-(trans-3-methoxycyclobutyl)-5-methyl-1H-pyrazol-4-yl]amino}quinazolin-7-yl)-4-methylpiperidin-4-ol | Calc'd 457.0, found 457 |
| Ex-6.14 | 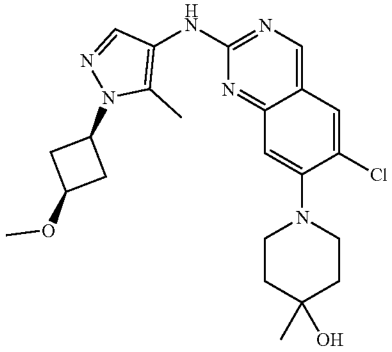 [SMILES: CO[C@H]1C[C@@H](n2ncc(Nc3ncc4cc(Cl)c(N5CCC(C)(O)CC5)cc4n3)c2C)C1] | 1-(6-chloro-2-{[1-(cis-3-methoxycyclobutyl)-5-methyl-1H-pyrazol-4-yl]amino}quinazolin-7-yl)-4-methylpiperidin-4-ol | Calc'd 457.0, found 457 |
| Ex-6.15 | 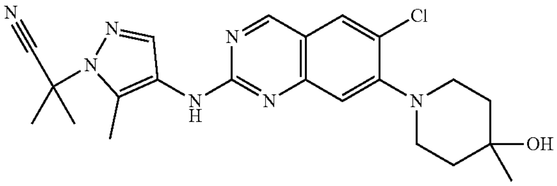 [SMILES: Cc1c(Nc2ncc3cc(Cl)c(N4CCC(C)(O)CC4)cc3n2)cnn1C(C)(C)C#N] | 2-(4-{[6-chloro-7-(4-hydroxy-4-methylpiperidin-1-yl)quinazolin-2-yl]amino}-5-methyl-1H-pyrazol-1-yl)-2-methylpropanenitrile | Calc'd 440.0, found 440 |

TABLE 7-continued

| Ex | Structure | Name | Exact Mass [M + H]+ |
|---|---|---|---|
| Ex-6.16 | 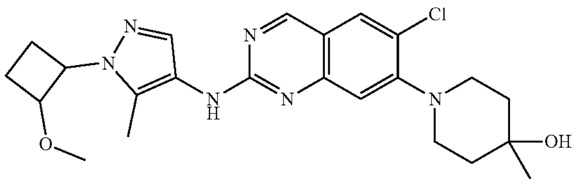 [SMILES: COC1CCC1n1ncc(Nc2ncc3cc(Cl)c(N4CCC(C)(O)CC4)cc3n2)c1C] | 1-(6-chloro-2-((1-((1R,2S) or (1S,2R)-2-methoxycyclobutyl)-5-methyl-1H-pyrazol-4-yl)amino)quinazolin-7-yl)-4-methylpiperidin-4-ol | Calc'd 457.0, found 457 |
| Ex-6.17 | 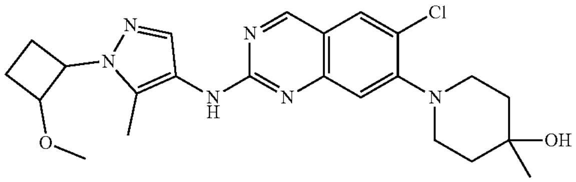 [SMILES: COC1CCC1n1ncc(Nc2ncc3cc(Cl)c(N4CCC(C)(O)CC4)cc3n2)c1C] | 1-[6-chloro-2-({1-[(1R,2S) or (1S,2R)-2-methoxycyclobutyl]-5-methyl-1H-pyrazol-4-yl}amino)quinazolin-7-yl]-4-methylpiperidin-4-ol | Calc'd 457.0, found 457 |
| Ex-6.18 | 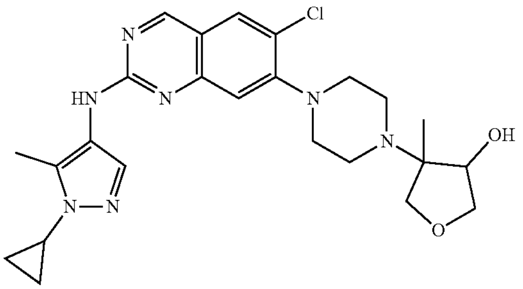 [SMILES: Cc1c(Nc2ncc3cc(Cl)c(N4CCN(C5(C)COCC5O)CC4)cc3n2)cnn1C1CC1] | (3S,4S) or (3R,4R) 4-(4-{6-chloro-2-[(1-cyclopropyl-5-methyl-1H-pyrazol-4-yl)amino]quinazolin-7-yl}piperazin-1-yl)-4-methyloxolan-3-ol | Calc'd 484.0, found 484 |
| Ex-6.19 | 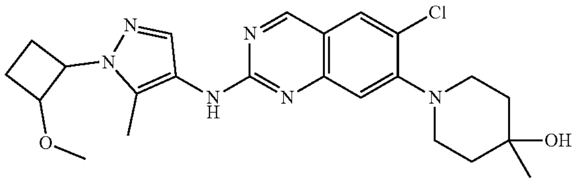 [SMILES: COC1CCC1n1ncc(Nc2ncc3cc(Cl)c(N4CCC(C)(O)CC4)cc3n2)c1C] | 1-[6-chloro-2-({1-[(1R,2R) or (1S,2S)-2-methoxycyclobutyl]-5-methyl-1H-pyrazol-4-yl}amino)quinazolin-7-yl]-4-methylpiperidin-4-ol | Calc'd 457.0, found 457 |
| Ex-6.20 | 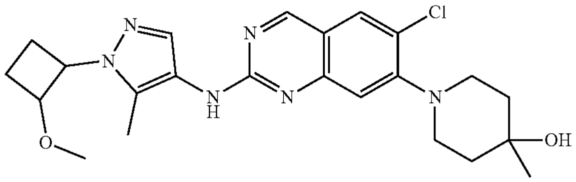 [SMILES: COC1CCC1n1ncc(Nc2ncc3cc(Cl)c(N4CCC(C)(O)CC4)cc3n2)c1C] | 1-[6-chloro-2-({1-[(1R,2R) or (1S,2S)-2-methoxycyclobutyl]-5-methyl-1H-pyrazol-4-yl}amino)quinazolin-7-yl]-4-methylpiperidin-4-ol | Calc'd 457.0, found 457 |
| Ex-6.21 | 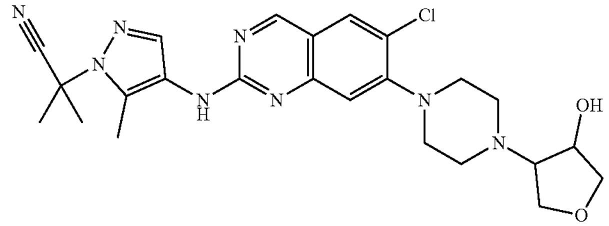 [SMILES: Cc1c(Nc2ncc3cc(Cl)c(N4CCN(C5COCC5O)CC4)cc3n2)cnn1C(C)(C)C#N] | (3S,4S) or (3R,4R) 2-[4-({6-chloro-7-[4-(4-hydroxyoxolan-3-yl)piperazin-1-yl]quinazolin-2-yl}amino)-5-methyl-1H-pyrazol-1-yl]-2-methylpropanenitrile | Calc'd 497.0, found 497 |
| Ex-6.22 | 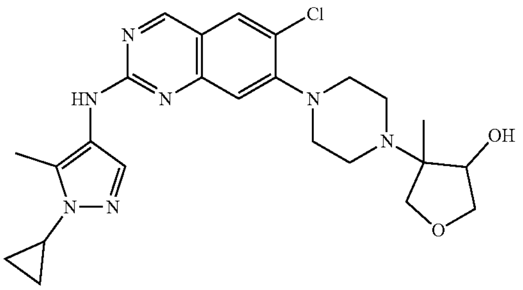 [SMILES: Cc1c(Nc2ncc3cc(Cl)c(N4CCN(C5(C)COCC5O)CC4)cc3n2)cnn1C1CC1] | (3S,4S) or (3R,4R) 4-(4-{6-chloro-2-[(1-cyclopropyl-5-methyl-1H-pyrazol-4-yl)amino]quinazolin-7-yl}piperazin-1-yl)-4-methyloxolan-3-ol | Calc'd 484.0, found 484 |

TABLE 7-continued

| Ex | Structure | Name | Exact Mass [M + H]$^+$ |
|---|---|---|---|
| Ex-6.23 | 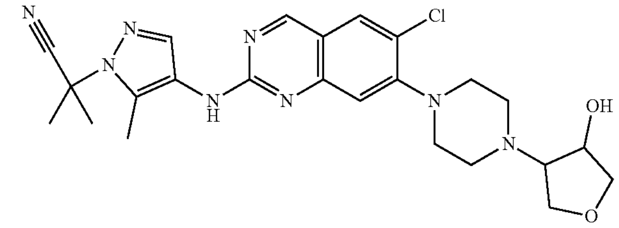 [SMILES: Cc1c(Nc2ncc3cc(Cl)c(N4CCN(C5COCC5O)CC4)cc3n2)cnn1C(C)(C)C#N] | (3S,4S) or (3R,4R) 2-[4-({6-chloro-7-[4-(4-hydroxyoxolan-3-yl)piperazin-1-yl]quinazolin-2-yl}amino)-5-methyl-1H-pyrazol-1-yl]-2-methylpropanenitrile | Calc'd 497.0, found 497 |
| Ex-6.24 | 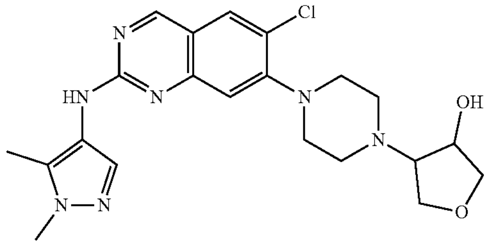 [SMILES: Cc1c(Nc2ncc3cc(Cl)c(N4CCN(C5COCC5O)CC4)cc3n2)cnn1C] | (3S,4S) or (3R,4R) 4-(4-{6-chloro-2-[(1,5-dimethyl-1H-pyrazol-4-yl)amino]quinazolin-7-yl}piperazin-1-yl)oxolan-3-ol | Calc'd 444.0, found 444 |
| Ex-6.25 | 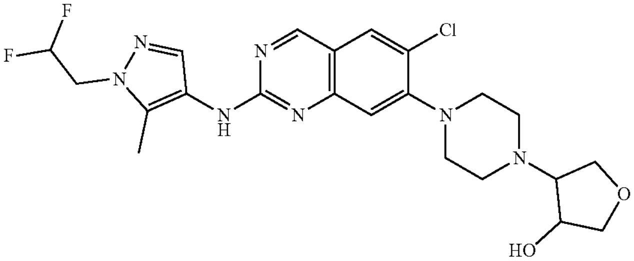 [SMILES: Cc1c(Nc2ncc3cc(Cl)c(N4CCN(C5COCC5O)CC4)cc3n2)cnn1CC(F)F] | (3S,4S) or (3R,4R) 4-[4-(6-chloro-2-{[1-(2,2-difluoroethyl)-5-methyl-1H-pyrazol-4-yl]amino}quinazolin-7-yl)piperazin-1-yl]oxolan-3-ol | Calc'd 494.0, found 494 |
| Ex-6.26 | 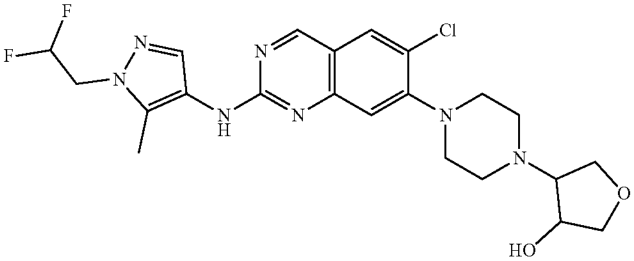 [SMILES: Cc1c(Nc2ncc3cc(Cl)c(N4CCN(C5COCC5O)CC4)cc3n2)cnn1CC(F)F] | (3S,4S) or (3R,4R) 4-[4-(6-chloro-2-{[1-(2,2-difluoroethyl)-5-methyl-1H-pyrazol-4-yl]amino}quinazolin-7-yl)piperazin-1-yl]oxolan-3-ol | Calc'd 494.0, found 494 |
| Ex-6.27 | 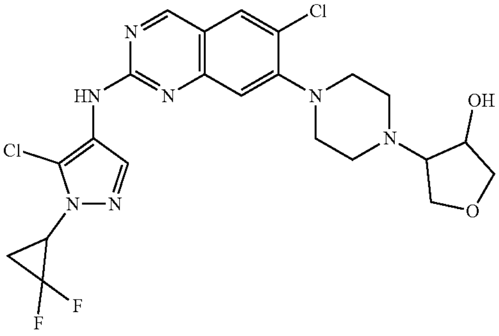 [SMILES: OC1COCC1N1CCN(c2cc3nc(Nc4cnn(C5CC5(F)F)c4Cl)ncc3cc2Cl)CC1] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]oxolan-3-ol | Calc'd 526.0, found 526 |

TABLE 7-continued

| Ex | Structure | Name | Exact Mass [M + H]+ |
|---|---|---|---|
| Ex-6.28 | 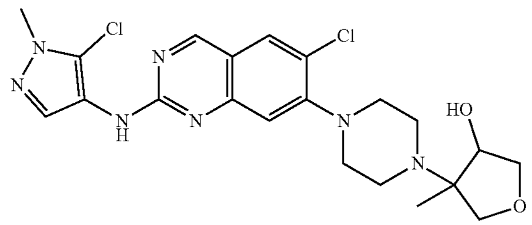 [SMILES: Cn1ncc(Nc2ncc3cc(Cl)c(N4CCN(C5(C)COCC5O)CC4)cc3n2)c1Cl] | (3S,4S) or (3R,4R) 4-(4-{6-chloro-2-[(5-chloro-1-methyl-1H-pyrazol-4-yl)amino]quinazolin-7-yl}piperazin-1-yl)-4-methyloxolan-3-ol | Calc'd 478.0, found 478 |
| Ex-6.29 | 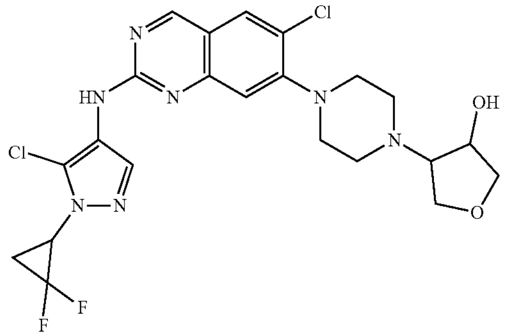 [SMILES: OC1COCC1N1CCN(c2cc3nc(Nc4cnn(C5CC5(F)F)c4Cl)ncc3cc2Cl)CC1] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl)oxolan-3-ol | Calc'd 526.0, found 526 |
| Ex-6.30 | 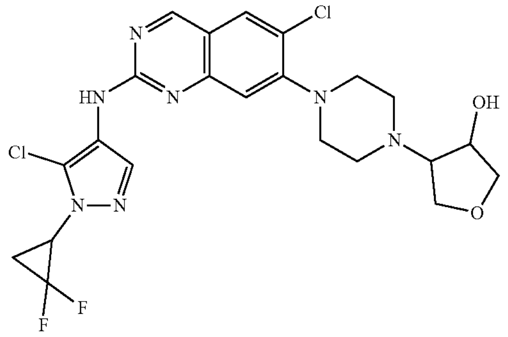 [SMILES: OC1COCC1N1CCN(c2cc3nc(Nc4cnn(C5CC5(F)F)c4Cl)ncc3cc2Cl)CC1] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]oxolan-3-ol | Calc'd 526.0, found 526 |
| Ex-6.31 | 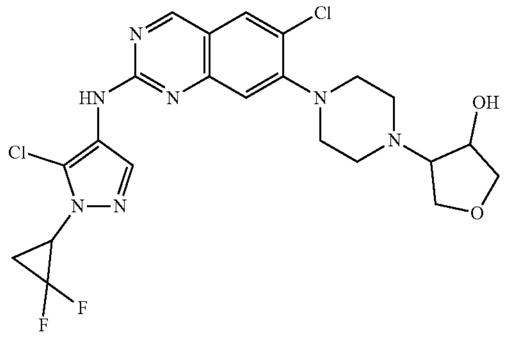 [SMILES: OC1COCC1N1CCN(c2cc3nc(Nc4cnn(C5CC5(F)F)c4Cl)ncc3cc2Cl)CC1] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]oxolan-3-ol | Calc'd 526.0, found 526 |
| Ex-6.32 | 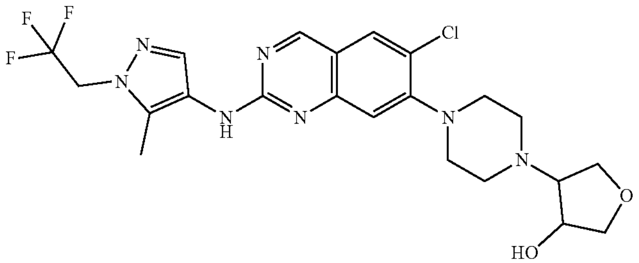 [SMILES: Cc1c(Nc2ncc3cc(Cl)c(N4CCN(C5COCC5O)CC4)cc3n2)cnn1CC(F)(F)F] | (3S,4S) or (3R,4R) 4-[4-(6-chloro-2-{[5-methyl-1-(2,2,2-trifluoroethyl)-1H-pyrazol-4-yl]amino}quinazolin-7-yl)piperazin-1-yl]oxolan-3-ol | Calc'd 512.0, found 512 |

TABLE 7-continued

| Ex | Structure | Name | Exact Mass [M + H]$^+$ |
|---|---|---|---|
| Ex-6.33 | 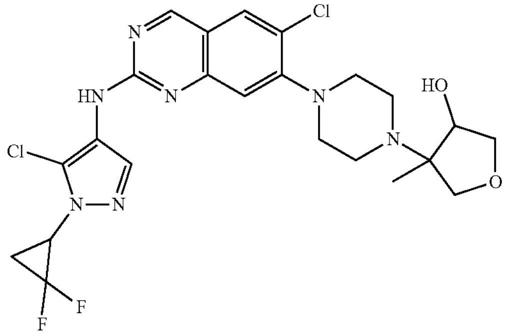 [SMILES: CC1(N2CCN(c3cc4nc(Nc5cnn(C6CC6(F)F)c5Cl)ncc4cc3Cl)CC2)COCC1O] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]-4-methyloxolan-3-ol | Calc'd 540.0, found 540 |
| Ex-6.34 | 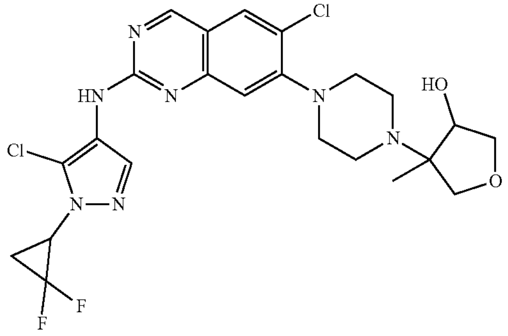 [SMILES: CC1(N2CCN(c3cc4nc(Nc5cnn(C6CC6(F)F)c5Cl)ncc4cc3Cl)CC2)COCC1O] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]-4-methyloxolan-3-ol | Calc'd 540.0, found 540.1 |
| Ex-6.35 | 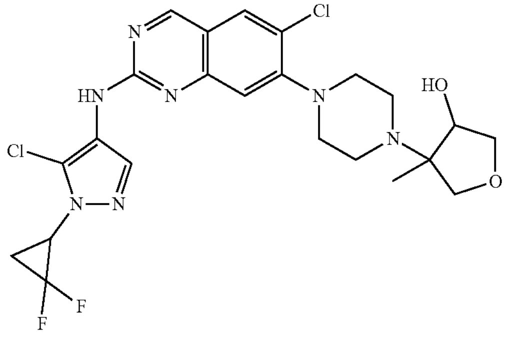 [SMILES: CC1(N2CCN(c3cc4nc(Nc5cnn(C6CC6(F)F)c5Cl)ncc4cc3Cl)CC2)COCC1O] | (3S,4S) or (3R,4R) 4-[4-(6-chloro-2-{[5-chloro-1-(2,2-(R) or (S) difluorocyclopropyl)-1H-pyrazol-4-yl]amino}quinazolin-7-yl)piperazin-1-yl]-4-methyloxolan-3-ol | Calc'd 540.0, found 540.1 |
| Ex-6.36 | 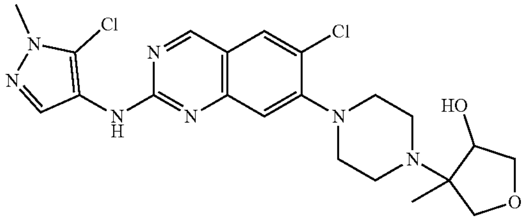 [SMILES: Cn1ncc(Nc2ncc3cc(Cl)c(N4CCN(C5(C)COCC5O)CC4)cc3n2)c1Cl] | (3S,4S) or (3R,4R) 4-[4-{6-chloro-2-[(5-chloro-1-methyl-1H-pyrazol-4-yl)amino]quinazolin-7-yl}piperazin-1-yl)-4-methyloxolan-3-ol | Calc'd 478.0, found 478.2 |
| Ex-6.37 | 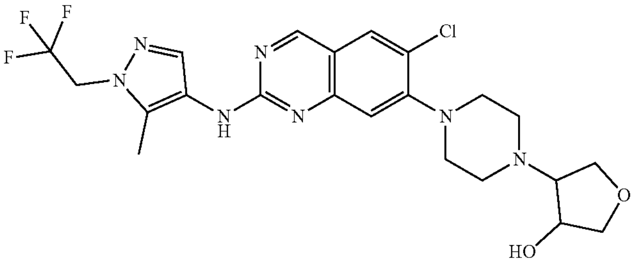 [SMILES: Cc1c(Nc2ncc3cc(Cl)c(N4CCN(C5COCC5O)CC4)cc3n2)cnn1CC(F)(F)F] | (3S,4S) or (3R,4R) 4-[4-(6-chloro-2-{[5-methyl-1-(2,2,2-trifluoroethyl)-1H-pyrazol-4-yl]amino}quinazolin-7-yl)piperazin-1-yl]oxolan-3-ol | Calc'd 512.0, found 512.1 |

TABLE 7-continued

| Ex | Structure | Name | Exact Mass [M + H]+ |
|---|---|---|---|
| Ex-6.38 | 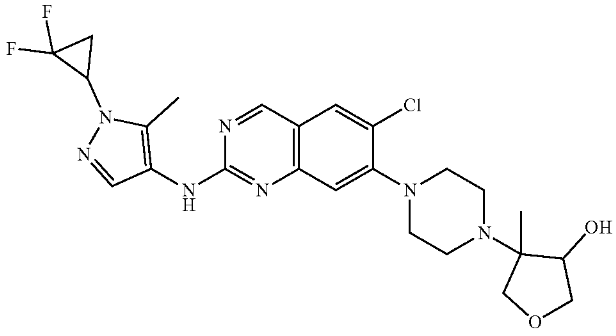 [SMILES: Cc1c(Nc2ncc3cc(Cl)c(N4CCN(C5(C)COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]-4-methyloxolan-3-ol | Calc'd 520.0, found 520.2 |
| Ex-6.39 | 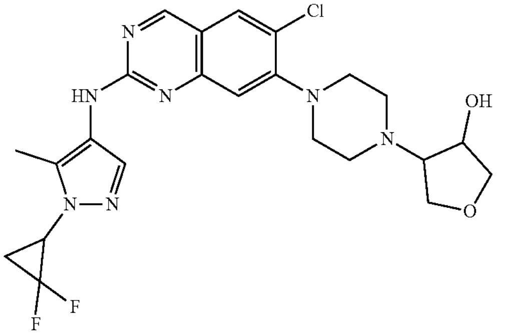 [SMILES: Cc1c(Nc2ncc3cc(Cl)c(N4CCN(C5COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]oxolan-3-ol | Calc'd 506.0, found 506.2 |
| Ex-6.40 | 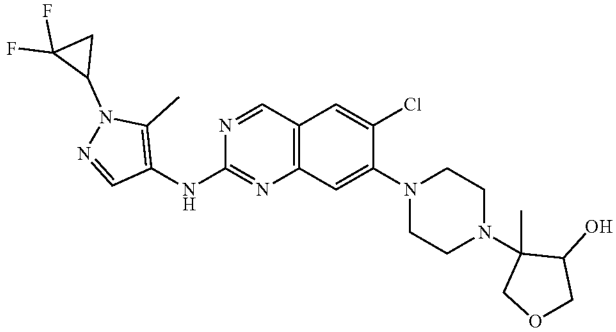 [SMILES: Cc1c(Nc2ncc3cc(Cl)c(N4CCN(C5(C)COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]-4-methyloxolan-3-ol | Calc'd 520.0, found 520.2 |
| Ex-6.41 | 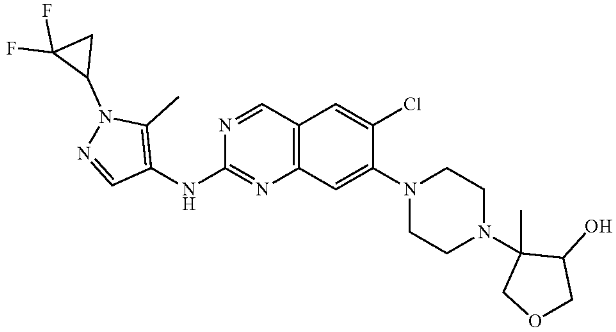 [SMILES: Cc1c(Nc2ncc3cc(Cl)c(N4CCN(C5(C)COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]-4-methyloxolan-3-ol | Calc'd 520.0, found 520.2 |

TABLE 7-continued

| Ex | Structure | Name | Exact Mass [M + H]$^+$ |
|---|---|---|---|
| Ex-6.42 | 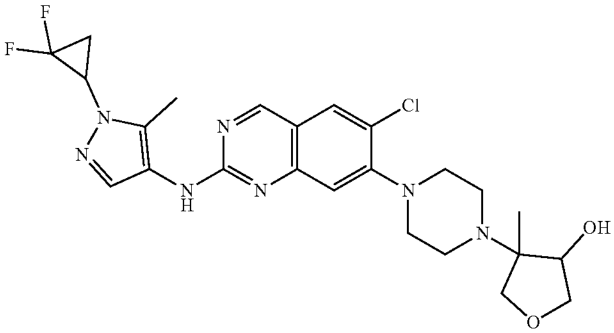 [SMILES: Cc1c(Nc2ncc3cc(Cl)c(N4CCN(C5(C)COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]-4-methyloxolan-3-ol | Calc'd 520.0, found 520.2 |
| Ex-6.43 | 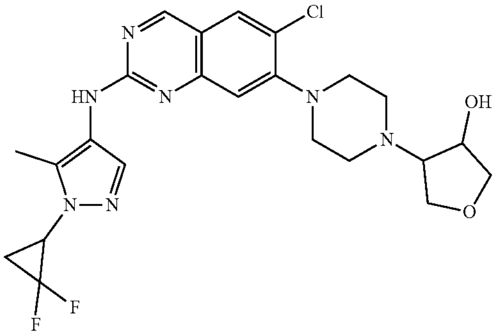 [SMILES: Cc1c(Nc2ncc3cc(Cl)c(N4CCN(C5COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]oxolan-3-ol | Calc'd 506.0, found 506.2 |
| Ex-6.44 | 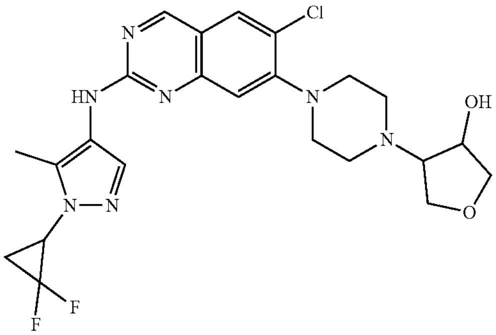 [SMILES: Cc1c(Nc2ncc3cc(Cl)c(N4CCN(C5COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]oxolan-3-ol | Calc'd 506.0, found 506.2 |
| Ex-6.45 | 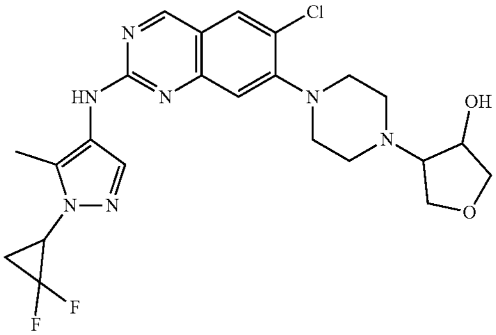 [SMILES: Cc1c(Nc2ncc3cc(Cl)c(N4CCN(C5COCC5O)CC4)cc3n2)cnn1C1CC1(F)F] | (3S,4S) or (3R,4R) 4-[4-(6-chloro-2-{[1-(2,2-(R) or (S) difluorocyclopropyl)-5-methyl-1H-pyrazol-4-yl]amino}quinazolin-7-yl)piperazin-1-yl]oxolan-3-ol | Calc'd 506.0, found 506.2 |

TABLE 7-continued

| Ex | Structure | Name | Exact Mass [M + H]+ |
|---|---|---|---|
| Ex-6.46 | 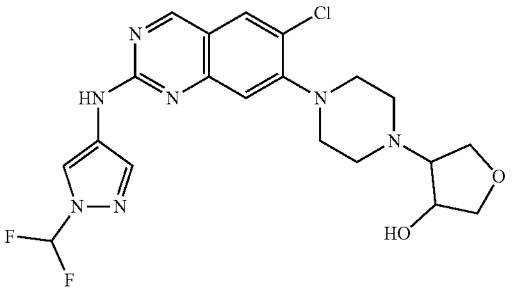 [SMILES: OC1COCC1N1CCN(c2cc3nc(Nc4cnn(C(F)F)c4)ncc3cc2Cl)CC1] | (3S,4S) or (3R,4R) 4-(4-(6-chloro-2-((1-(difluoromethyl)-1H-pyrazol-4-yl)amino)quinazolin-7-yl)piperazin-1-yl)tetrahydrofuran-3-ol | Calc'd 466.0, found 466 |
| Ex-6.47 | 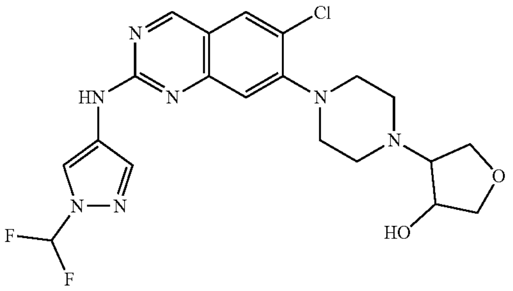 [SMILES: OC1COCC1N1CCN(c2cc3nc(Nc4cnn(C(F)F)c4)ncc3cc2Cl)CC1] | (3S,4S) or (3R,4R) 4-(4-(6-chloro-2-((1-(difluoromethyl)-1H-pyrazol-4-yl)amino)quinazolin-7-yl)piperazin-1-yl)tetrahydrofuran-3-ol | Calc'd 466.0, found 466 |
| Ex-6.48 | 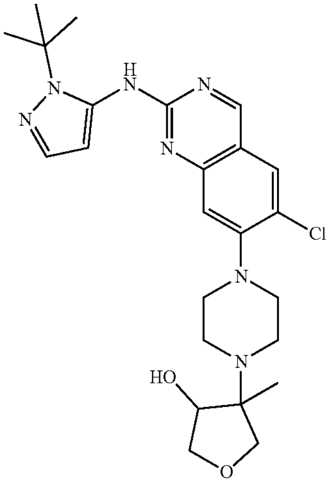 [SMILES: CC1(N2CCN(c3cc4nc(Nc5ccnn5C(C)(C)C)ncc4cc3Cl)CC2)COCC1O] | (3S,4S) or (3R,4R) 4-(4-(2-((1-(tert-butyl)-1H-pyrazol-5-yl)amino)-6-chloroquinazolin-7-yl)piperazin-1-yl)-4-methyltetrahydrofuran-3-ol | Calc'd 486.0, found 486 |
| Ex-6.49 | 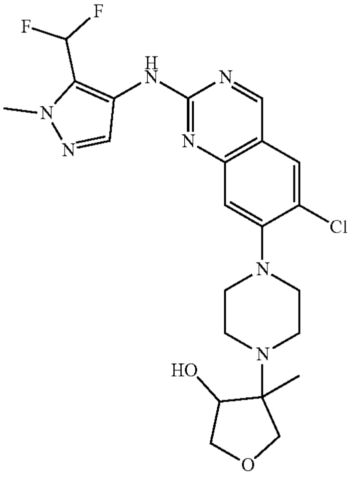 [SMILES: Cn1ncc(Nc2ncc3cc(Cl)c(N4CCN(C5(C)COCC5O)CC4)cc3n2)c1C(F)F] | (3S,4S) or (3R,4R) 4-(4-(6-chloro-2-((5-(difluoromethyl)-1-methyl-1H-pyrazol-4-yl)amino)quinazolin-7-yl)piperazin-1-yl)-4-methyltetrahydrofuran-3-ol | Calc'd 494.0, found 494 |

TABLE 7-continued

| Ex | Structure | Name | Exact Mass [M + H]+ |
|---|---|---|---|
| Ex-6.50 | 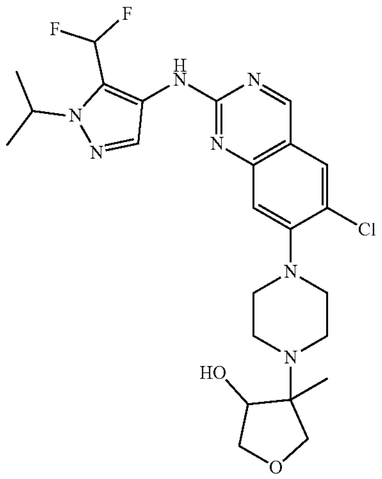 [SMILES: CC(C)n1ncc(Nc2ncc3cc(Cl)c(N4CCN(C5(C)COCC5O)CC4)cc3n2)c1C(F)F] | (3S,4S) or (3R,4R) 4-(4-(6-chloro-2-((5-(difluoromethyl)-1-isopropyl-1H-pyrazol-4-yl)amino)quinazolin-7-yl)piperazin-1-yl)-4-methyltetrahydrofuran-3-ol | Calc'd 522.0, found 522 |
| Ex-6.51 | 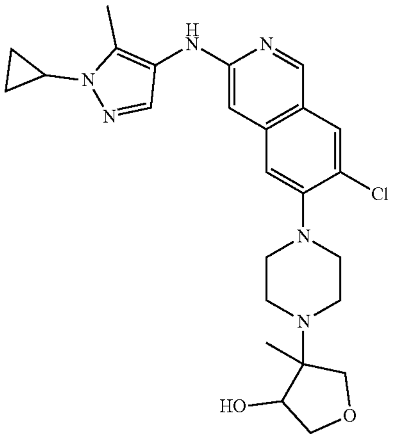 [SMILES: Cc1c(Nc2cc3cc(N4CCN(C5(C)COCC5O)CC4)c(Cl)cc3cn2)cnn1C1CC1] | (3S,4S) or (3R,4R) 4-(4-(7-chloro-3-((1-cyclopropyl-5-methyl-1H-pyrazol-4-yl)amino)isoquinolin-6-yl)piperazin-1-yl)-4-methyltetrahydrofuran-3-ol | Calc'd 483.0, found 483 |
| Ex-6.52 | 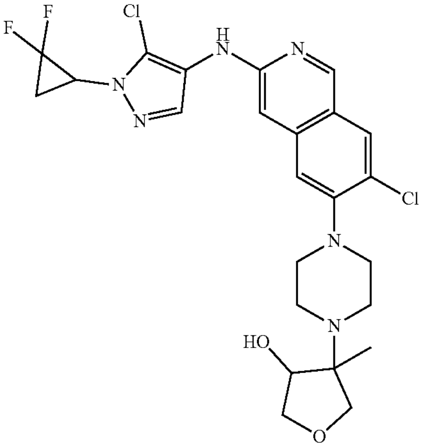 [SMILES: CC1(N2CCN(c3cc4cc(Nc5cnn(C6CC6(F)F)c5Cl)ncc4cc3Cl)CC2)COCC1O] | (3S,4S) or (3R,4R) 4-(4-(7-chloro-3-((5-chloro-1-(2,2-difluorocyclopropyl)-1H-pyrazol-4-yl)amino)isoquinolin-6-yl)piperazin-1-yl)-4-methyltetrahydrofuran-3-ol | Calc'd 539.0, found 539 |

TABLE 7-continued

| Ex | Structure | Name | Exact Mass [M + H]+ |
|---|---|---|---|
| Ex-6.53 | 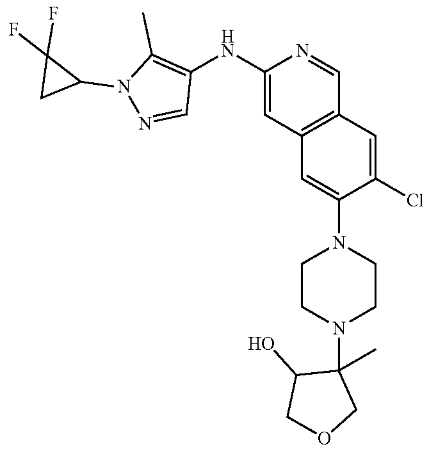 [SMILES: Cc1c(Nc2cc3cc(N4CCN(C5(C)COCC5O)CC4)c(Cl)cc3cn2)cnn1C1CC1(F)F] | (3S,4S) or (3R,4R) 4-(4-(7-chloro-3-((1-(2,2-difluorocyclopropyl)-5-methyl-1H-pyrazol-4-yl)amino)isoquinolin-6-yl)piperazin-1-yl)-4-methyltetrahydrofuran-3-ol | Calc'd 519.0, found 519 |
| Ex-6.54 | 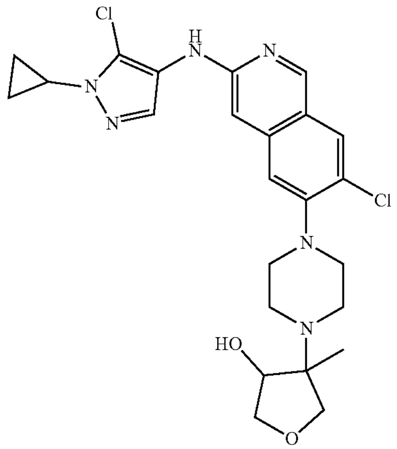 [SMILES: CC1(N2CCN(c3cc4cc(Nc5cnn(C6CC6)c5Cl)ncc4cc3Cl)CC2)COCC1O] | (3S,4S) or (3R,4R) 4-(4-(7-chloro-3-((5-chloro-1-cyclopropyl-1H-pyrazol-4-yl)amino)isoquinolin-6-yl)piperazin-1-yl)-4-methyltetrahydrofuran-3-ol | Calc'd 503.0, found 503 |
| Ex-6.55 | 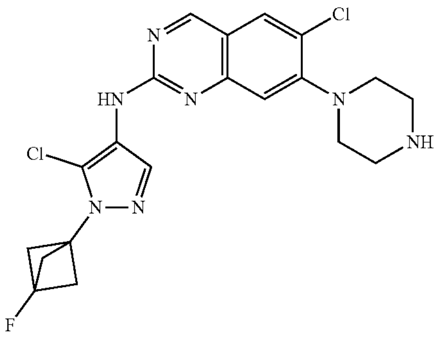 [SMILES: FC12CC(n3ncc(Nc4ncc5cc(Cl)c(N6CCNCC6)cc5n4)c3Cl)(C1)C2] | 6-chloro-N-(5-chloro-1-(3-fluorobicyclo[1.1.1]pentan-1-yl)-1H-pyrazol-4-yl)-7-(piperazin-1-yl)quinazolin-2-amine | Calc'd 448.0, found 448 |
| Ex-6.56 | 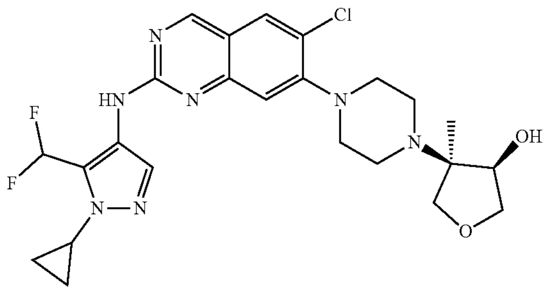 [SMILES: C[C@@]1(N2CCN(c3cc4nc(Nc5cnn(C6CC6)c5C(F)F)ncc4cc3Cl)CC2)COC[C@@H]1O] | (3R,4R)-4-(4-(6-chloro-2-((1-cyclopropyl-5-(difluoromethyl)-1H-pyrazol-4-yl)amino)quinazolin-7-yl)piperazin-1-yl)-4-methyltetrahydrofuran-3-ol | Calc'd 520.0, found 520 |

General Scheme 8

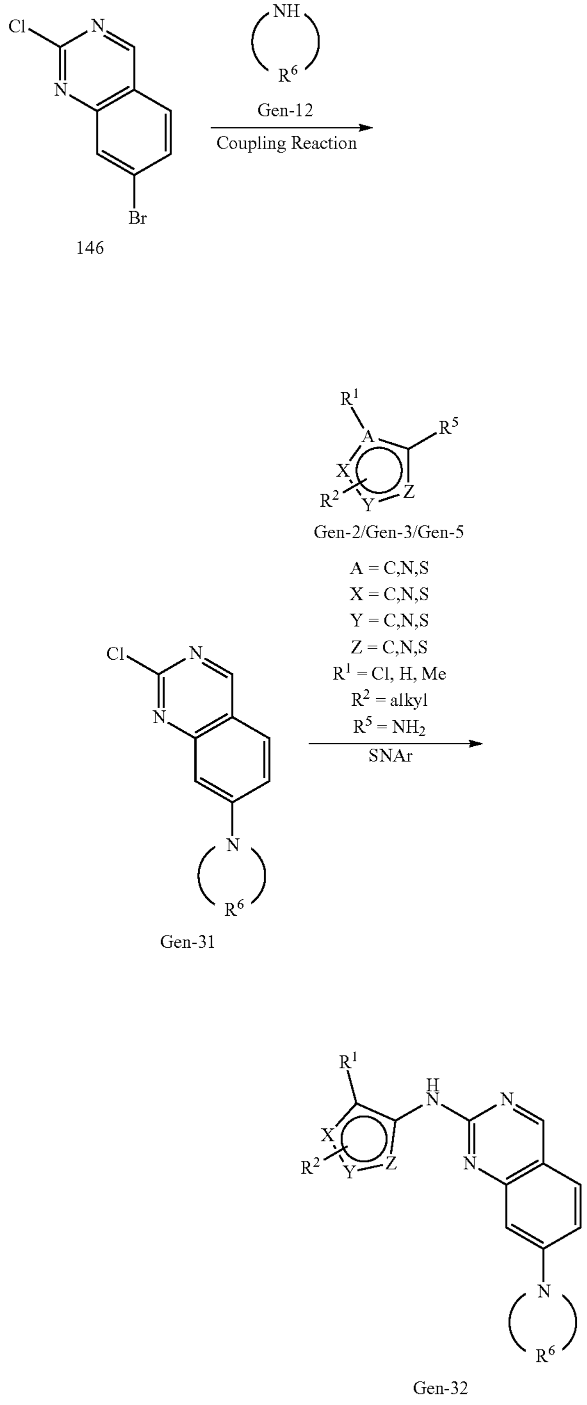

In General Scheme 8, commercially available intermediate 146 could undergo a palladium-catalyzed coupling reaction with cyclic amine Gen-12 to afford compounds of the form Gen-31. Subsequent $S_NAr$ chemistry could be performed utilizing amino pyrazoles Gen-2/Gen-3/Gen-5 to afford elaborated compounds of the form Gen-32. Representative preparative examples from each sequence are described in more detail below.

Preparation of Example 7.1

Scheme 52. Synthesis of (*S*)-3-(2-((1-ethyl-5-methyl-1H-pyrazol-4-yl)amino)quinazolin-7-yl)-4-methyloxazolidin-2-one

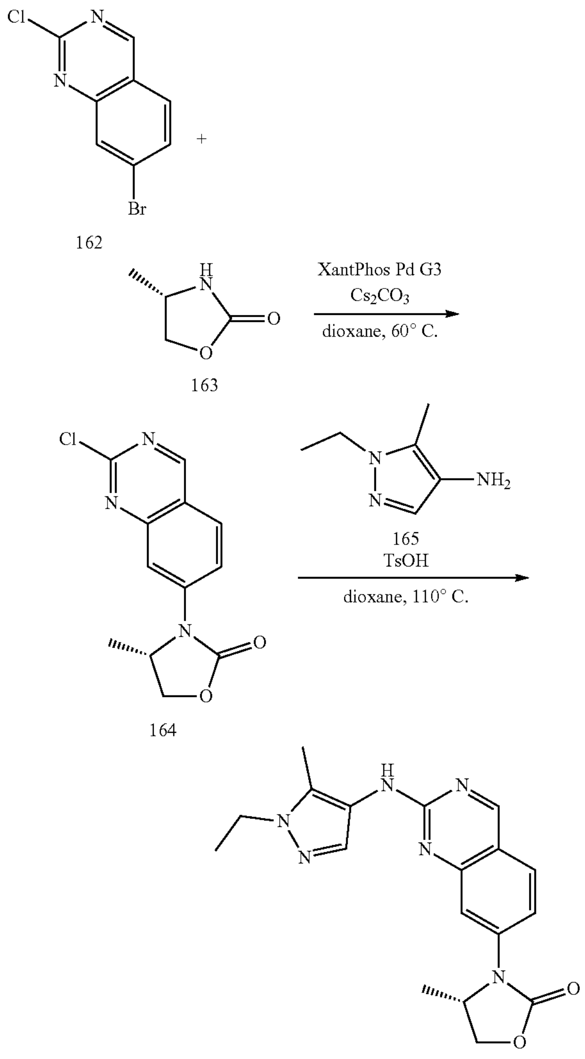

Ex-7.1

(S)-3-(2-chloroquinazolin-7-yl)-4-methyloxazolidin-2-one (164)

7-Bromo-2-chloroquinazoline 162 (100 mg, 0.411 mmol), (S)-4-methyloxazolidin-2-one 163 (45.7 mg, 0.452 mmol), 3rd Gen Xantphos pre-catalyst (39 mg, 0.041 mmol), and cesium carbonate (268 mg, 0.821 mmol) were added to a vial. The vial was sealed and its contents were placed under an inert atmosphere by performing 3 vacuum/nitrogen cycles. Dioxane (2053 μL) was added through the septum and the resulting mixture was allowed to stir at 60° C. for 8 h. The residue was purified by flash column chromatography over silica (3:1 EtOAc:EtOH/hexane, 0-100%). The desired fractions were pooled and concentrated under reduced pressure to afford the title compound 164. MS (ESI): m/z calc'd for $C_{12}H_{10}ClN_3O_2$ $[M+H]^+$: 264, found 264.

(S)-3-(2-((1-ethyl-5-methyl-1H-pyrazol-4-yl)amino) quinazolin-7-yl)-4-methyloxazolidin-2-one (Ex-7.1)

(S)-3-(2-chloroquinazolin-7-yl)-4-methyloxazolidin-2-one 164 (40.0 mg, 0.152 mmol), 1-ethyl-5-methyl-1H-pyrazol-4-amine 165 (22.8 mg, 0.182 mmol), 4-methylbenzenesulfonic acid (39.2 mg, 0.228 mmol), and dioxane (758 μL) were added to a vial. The resulting mixture was allowed to stir overnight at 110° C. The crude residue was subject to purification by reverse phase HPLC, eluting with water (0.1% $NH_4OH$)-MeCN to afford the title compound Ex-7.1. MS (ESI): m/z calc'd for $C_{18}H_{20}N_6O_2$ $[M+H]^+$: 353, found 353. $^1H$ NMR (500 MHz, DMSO-$d_6$, 25° C.) δ 9.10 (s, 1H), 8.89 (s, 1H), 7.86 (d, J=8.8 Hz, 1H), 7.70 (s, 1H), 7.58 (dd, J=8.8, 2.0 Hz, 1H), 7.52 (s, 1H), 4.89-4.81 (m, 1H), 4.58 (t, J=8.3 Hz, 1H), 4.12-4.03 (m, 3H), 2.22 (s, 3H), 1.34-1.28 (m, 6H).

The following Examples, 7.2-7.21 were obtained using the procedure analogous to those in General Scheme 8 but substituting appropriate starting materials that are either commercially available or prepared using procedures analogous to those described in Scheme 52.

TABLE 8

| Ex | Structure | Name | Exact Mass $[M + H]^+$ |
|---|---|---|---|
| Ex-7.2 | 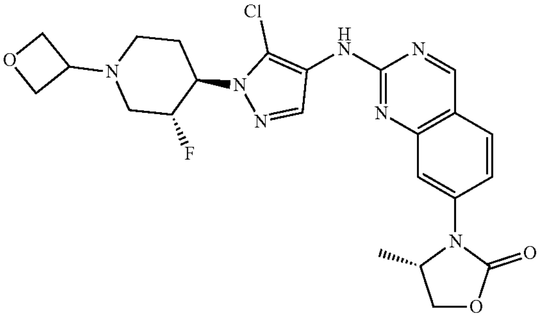 [SMILES: C[C@H]1COC(=O)N1c1ccc2cnc(Nc3cnn([C@@H]4CCN(C5COC5)C[C@H]4F)c3Cl)nc2c1] | (4S)-3-[2-({5-chloro-1-[(3R,4R)-3-fluoro-1-(oxetan-3-yl)piperidin-4-yl]-1H-pyrazol-4-yl}amino)quinazolin-7-yl]-4-methyl-1,3-oxazolidin-2-one | Calc'd 502.0 found 502.1 |
| Ex-7.3 | 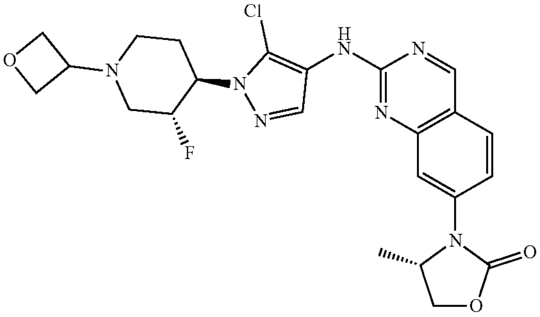 [SMILES: C[C@H]1COC(=O)N1c1ccc2cnc(Nc3cnn([C@@H]4CCN(C5COC5)C[C@H]4F)c3Cl)nc2c1] | (4S)-3-[2-({5-chloro-1-[(3S,4S)-3-fluoro-1-(oxetan-3-yl)piperidin-4-yl]-1H-pyrazol-4-yl}amino)quinazolin-7-yl]-4-methyl-1,3-oxazolidin-2-one | Calc'd 502.0, found 502.1 |
| Ex-7.4 | 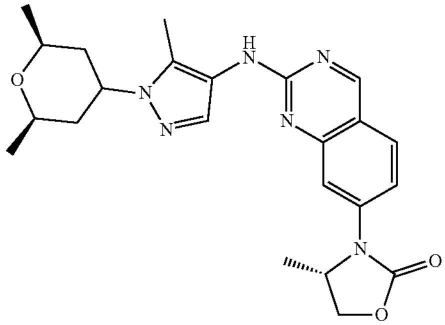 [SMILES: Cc1c(Nc2ncc3ccc(N4C(=O)OC[C@@H]4C)cc3n2)cnn1C1C[C@@H](C)O[C@@H](C)C1] | (4S)-3-[2-({1-[(2R,6S)-2,6-dimethyloxan-4-yl]-5-methyl-1H-pyrazol-4-yl}amino)quinazolin-7-yl]-4-methyl-1,3-oxazolidin-2-one | Calc'd 437.0, found 437.3 |
| Ex-7.5 | 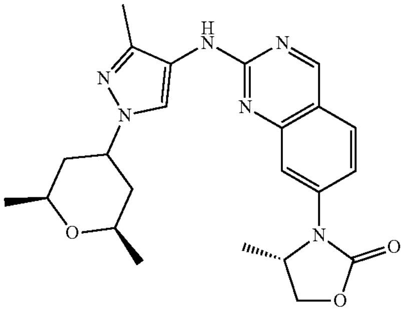 [SMILES: Cc1nn(C2C[C@@H](C)O[C@@H](C)C2)cc1Nc1ncc2ccc(N3C(=O)OC[C@@H]3C)cc2n1] | (4S)-3-[2-({1-[(2R,6S)-2,6-dimethyloxan-4-yl]-3-methyl-1H-pyrazol-4-yl}amino)quinazolin-7-yl]-4-methyl-1,3-oxazolidin-2-one | Calc'd 437.0, found 437.3 |

TABLE 8-continued

| Ex | Structure | Name | Exact Mass [M + H]+ |
|---|---|---|---|
| Ex-7.6 | 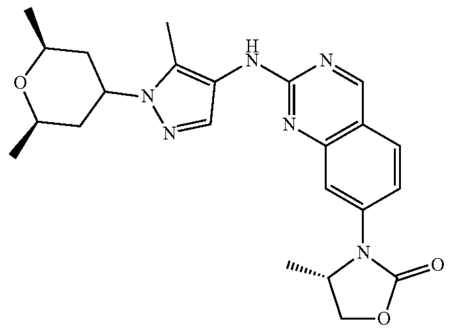 [SMILES: Cc1c(Nc2ncc3ccc(N4C(=O)OC[C@@H]4C)cc3n2)cnn1C1C[C@@H](C)O[C@@H](C)C1] | (4S)-3-[2-({1-[(2R,6S)-2,6-dimethyloxan-4-yl]-5-methyl-1H-pyrazol-4-yl}amino)quinazolin-7-yl]-4-methyl-1,3-oxazolidin-2-one | Calc'd 437.0, found 437.3 |
| Ex-7.7 | 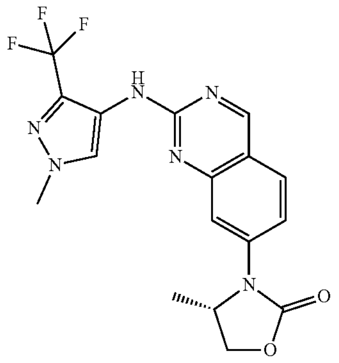 [SMILES: C[C@H]1COC(=O)N1c1ccc2cnc(Nc3cn(C)nc3C(F)(F)F)nc2c1] | (4S)-4-methyl-3-(2-{[1-methyl-3-(trifluoromethyl)-1H-pyrazol-4-yl]amino}quinazolin-7-yl)-1,3-oxazolidin-2-one | Calc'd 393.0, found 393.1 |
| Ex-7.8 | 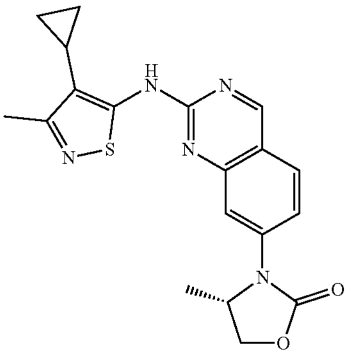 [SMILES: Cc1nsc(Nc2ncc3ccc(N4C(=O)OC[C@@H]4C)cc3n2)c1C1CC1] | (4S)-3-{2-[(4-cyclopropyl-3-methyl-1,2-thiazol-5-yl)amino]quinazolin-7-yl}-4-methyl-1,3-oxazolidin-2-one | Calc'd 382.0, found 382.1 |
| Ex-7.9 | 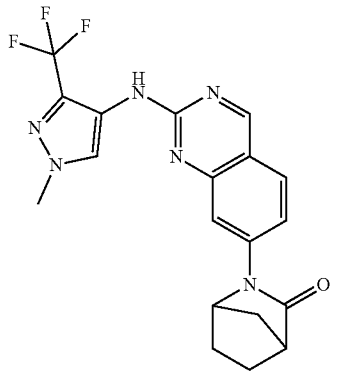 [SMILES: Cn1cc(Nc2ncc3ccc(N4C(=O)C5CCC4C5)cc3n2)c(C(F)(F)F)n1] | 2-(2-{[1-methyl-3-(trifluoromethyl)-1H-pyrazol-4-yl]amino}quinazolin-7-yl)-2-azabicyclo[2.2.1]heptan-3-one | Calc'd 403.0, found 403.1 |

TABLE 8-continued

| Ex | Structure | Name | Exact Mass [M + H]+ |
|---|---|---|---|
| Ex-7.10 | 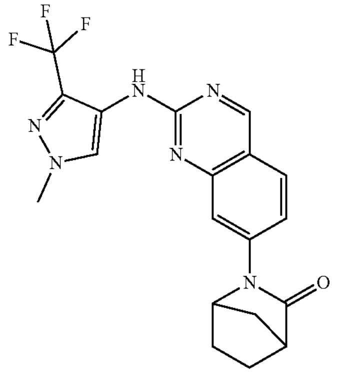 [SMILES: Cn1cc(Nc2ncc3ccc(N4C(=O)C5CCC4C5)cc3n2)c(C(F)(F)F)n1] | 2-(2-{[1-methyl-3-(trifluoromethyl)-1H-pyrazol-4-yl]amino}quinazolin-7-yl)-2-azabicyclo[2.2.1]heptan-3-one | Calc'd 403.0, found 403.1 |
| Ex-7.11 | 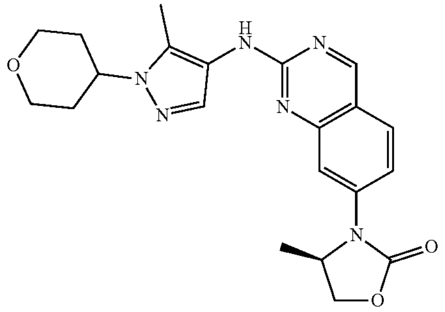 [SMILES: Cc1c(Nc2ncc3ccc(N4C(=O)OC[C@H]4C)cc3n2)cnn1C1CCOCC1] | (4R)-4-methyl-3-(2-{[5-methyl-1-(oxan-4-yl)-1H-pyrazol-4-yl]amino}quinazolin-7-yl)-1,3-oxazolidin-2-one | Calc'd 409.0, found 409.3 |
| Ex-7.12 | 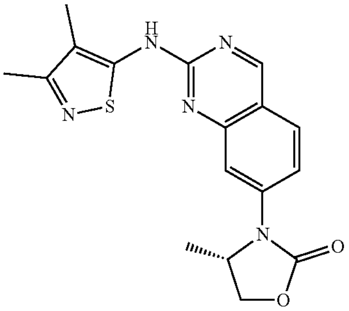 [SMILES: Cc1nsc(Nc2ncc3ccc(N4C(=O)OC[C@@H]4C)cc3n2)c1C] | (4S)-3-{2-[(3,4-dimethyl-1,2-thiazol-5-yl)amino]quinazolin-7-yl}-4-methyl-1,3-oxazolidin-2-one | Calc'd 356.0, found 356.1 |
| Ex-7.13 | 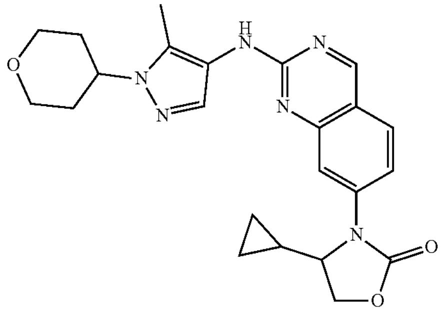 [SMILES: Cc1c(Nc2ncc3ccc(N4C(=O)OCC4C4CC4)cc3n2)cnn1C1CCOCC1] | (R) or (S) 4-cyclopropyl-3-(2-{[5-methyl-1-(oxan-4-yl)-1H-pyrazol-4-yl]amino}quinazolin-7-yl)-1,3-oxazolidin-2-one | Calc'd 435.0, found 435.1 |

TABLE 8-continued

| Ex | Structure | Name | Exact Mass [M + H]$^+$ |
|---|---|---|---|
| Ex-7.14 | 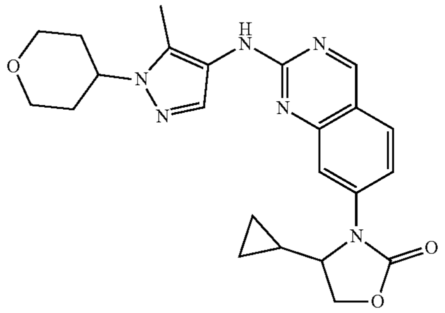 [SMILES: Cc1c(Nc2ncc3ccc(N4C(=O)OCC4C4CC4)cc3n2)cnn1C1CCOCC1] | (R) or (S) 4-cyclopropyl-3-(2-{[5-methyl-1-(oxan-4-yl)-1H-pyrazol-4-yl]amino}quinazolin-7-yl)-1,3-oxazolidin-2-one | Calc'd 435.0, found 435.3 |
| Ex-7.15 | 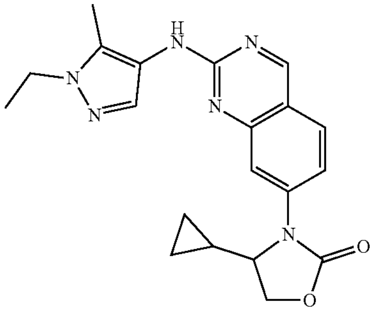 [SMILES: CCn1ncc(Nc2ncc3ccc(N4C(=O)OCC4C4CC4)cc3n2)c1C] | (R) or (S) 4-cyclopropyl-3-{2-[(1-ethyl-5-methyl-1H-pyrazol-4-yl)amino]quinazolin-7-yl}-1,3-oxazolidin-2-one | Calc'd 379.0, found 379.2 |
| Ex-7.16 | 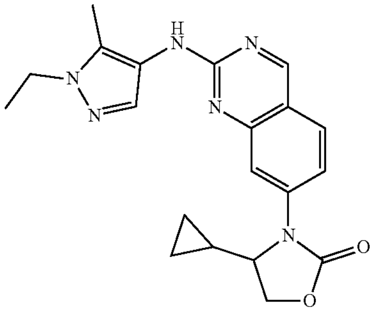 [SMILES: CCn1ncc(Nc2ncc3ccc(N4C(=O)OCC4C4CC4)cc3n2)c1C] | (R) or (S) 4-cyclopropyl-3-{2-[(1-ethyl-5-methyl-1H-pyrazol-4-yl)amino]quinazolin-7-yl}-1,3-oxazolidin-2-one | Calc'd 379.0, found 379.3 |
| Ex-7.17 | 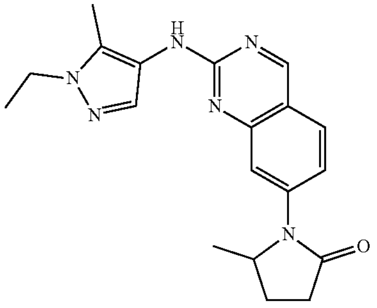 [SMILES: CCn1ncc(Nc2ncc3ccc(N4C(=O)CCC4C)cc3n2)c1C] | (R) or (S) 1-{2-[(1-ethyl-5-methyl-1H-pyrazol-4-yl)amino]quinazolin-7-yl}-5-methylpyrrolidin-2-one | Calc'd 351.0, found 351.1 |
| Ex-7.18 | 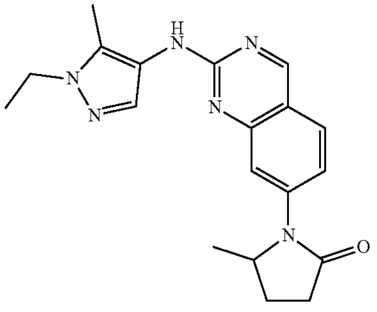 [SMILES: CCn1ncc(Nc2ncc3ccc(N4C(=O)CCC4C)cc3n2)c1C] | (R) or (S) 1-{2-[(1-ethyl-5-methyl-1H-pyrazol-4-yl)amino]quinazolin-7-yl}-5-methylpyrrolidin-2-one | Calc'd 351.0, found 351.2 |

TABLE 8-continued
| Ex | Structure | Name | Exact Mass [M + H]+ |
|---|---|---|---|
| Ex-7.19 | 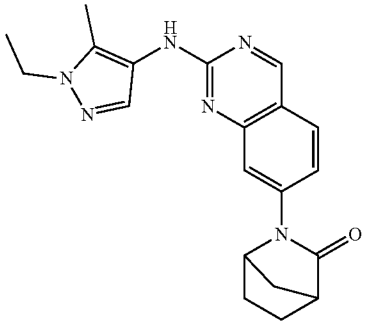 [SMILES: CCn1ncc(Nc2ncc3ccc(N4C(=O)C5CCC4C5)cc3n2)c1C] | 2-{2-[(1-ethyl-5-methyl-1H-pyrazol-4-yl)amino]quinazolin-7-yl}-2-azabicyclo[2.2.1]heptan-3-one | Calc'd 363.0, found 363.2 |
| Ex-7.20 | 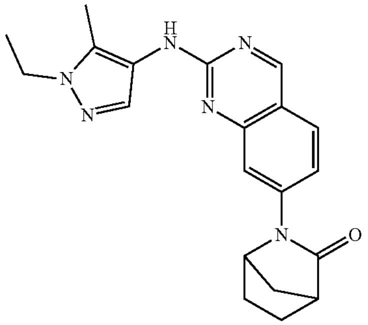 [SMILES: CCn1ncc(Nc2ncc3ccc(N4C(=O)C5CCC4C5)cc3n2)c1C] | 2-{2-[(1-ethyl-5-methyl-1H-pyrazol-4-yl)amino]quinazolin-7-yl}-2-azabicyclo[2.2.1]heptan-3-one | Calc'd 363.0, found 363.2 |
| Ex-7.21 | 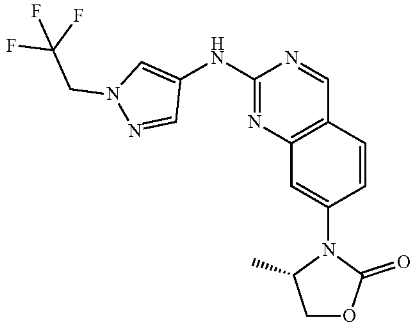 [SMILES: C[C@H]1COC(=O)N1c1ccc2cnc(Nc3cnn(CC(F)(F)F)c3)nc2c1] | (4S)-4-methyl-3-(2-{[1-(2,2,2-trifluoroethyl)-1H-pyrazol-4-yl]amino}quinazolin-7-yl)-1,3-oxazolidin-2-one | Calc'd 393.0 found 393.1 |

General Scheme 9

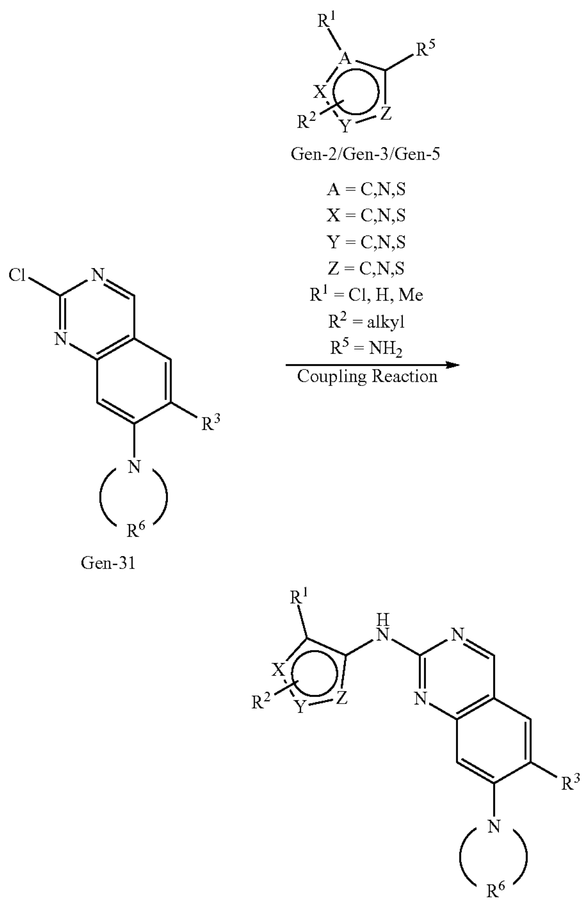

Gen-2/Gen-3/Gen-5

Gen-31

Gen-32

In General Scheme 9, synthetically prepared intermediates of the type Gen-31 could undergo a palladium catalyzed coupling reaction utilizing amino pyrazoles Gen-2/Gen-3/Gen-5 to afford elaborated compounds of the form Gen-32. Representative preparative examples from each sequence are described in more detail below.

Scheme 53. Synthesis of (1S,4R or 1R,4S)-2-(2-chloroquinazolin-7-yl)-2-azabicyclo[2.2.1]heptane-3-one (166) and (1R,4S or 1S, 4R)-2-(2-chloroquinazolin-7-yl)-2-azabicyclo[2.2.1]heptan-3-one (167)

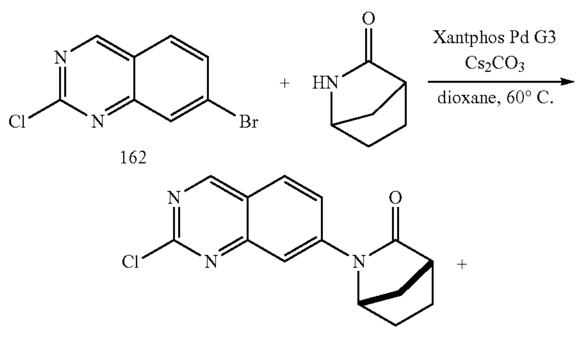

162

166

-continued

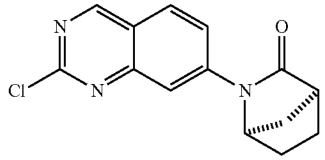

167

A vial was charged with 7-bromo-2-chloroquinazoline 162 (500 mg, 2.05 mmol), 2-azabicyclo[2.2.1]heptan-3-one (251 mg, 2.26 mmol), Xantphos Pd G3 (195 mg, 0.205 mmol), and $Cs_2CO_3$ (1.34 g, 4.11 mmol) under inert atmosphere. Dioxane (10.3 mL) was added and the resultant mixture was stirred at 60° C. overnight. The reaction mixture was diluted with EtOAc and washed with sat. aq. $NaHCO_3$ (2×50 mL) and with brine (1×50 mL). The combined organic layers were dried over anhydrous $MgSO_4$, filtered, and concentrated under reduced pressure. The residue was purified by flash chromatography over silica (3:1 EtOAc:EtOH/hexane, 0-100%). The desired fractions were pooled and concentrated under reduced pressure to afford the desired product as a racemic mixture. This product was submitted to SFC chiral separation (CCA, 21×250 mm; Mobile phase A: $CO_2$; Mobile phase B: MeOH with 0.1% $NH_4OH$) to afford (1S,4R or 1R,4S)-2-(2-chloroquinazolin-7-yl)-2-azabicyclo[2.2.1]heptan-3-one 166 ($t_R$=5.5 min) and (1S,4R or 1R,4S)-2-(2-chloroquinazolin-7-yl)-2-azabicyclo[2.2.1]heptan-3-one 167 ($t_R$=7.4 min).

Preparation of Examples 8.1

Scheme 54. Synthesis of (1S,4R or 1R, 4S)-2-(2-((5-methyl-1-(2-oxetan-3-yl)-2-azaspiro[3.3]heptan-6-yl)-1H-pyrazol-4-yl)amino-quinazolin-7-yl-2-azabicyclo[2.2.1]heotan-3-one (Ex-8.1)

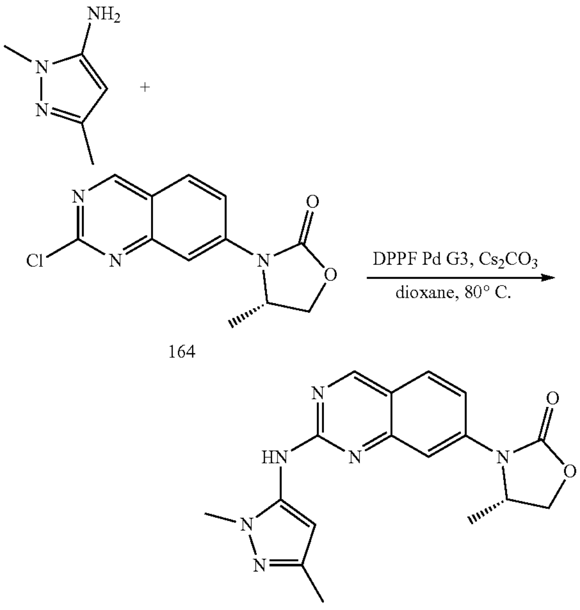

164

Ex-8.1

(4S)-3-{2-[(1,3-dimethyl-1H-pyrazol-5-yl)amino]quinazolin-7-yl}-4-methyl-1,3-oxazolidin-2-one (Ex-8.1)

A 5 mL microwave vial was charged with (S)-3-(2-chloroquinazolin-7-yl)-4-methyloxazolidin-2-one (30 mg, 0.11 mmol), 1,3-dimethyl-1H-pyrazol-5-amine (15.2 mg, 0.137 mmol), DPPF-Pd-G3 (10.5 mg, 0.0110 mmol), and $Cs_2CO_3$ (111 mg, 0.341 mmol). The vial was then sealed then evacuated and purged with $N_2$ (3×). The mixture was then dissolved in anhydrous dioxane (1 mL) which had been degassed by sparging. The vial was sealed and the solution was allowed to stir at 80° C. overnight. The reaction mixture was diluted in EtOAc, filtered through Celite®, and concentrated under reduced pressure. The crude residue was subject to purification by reverse phase HPLC, eluting with water (0.1% TFA)-MeCN to afford the title compound Ex-8.1. MS (ESI): m/z calc'd for $C_{17}H_8N_6O_2$ $[M+H]^+$: 339, found 339. $^1H$ NMR (600 MHz, DMSO-$d_6$. 25° C.) δ 9.67 (s, 1H), 9.23 (s, 1H), 7.96 (d, J=8.8 Hz, 1H), 7.70 (dd, J=8.8, 2.1 Hz, 1H), 7.65 (d, J=1.7 Hz, 1H), 6.24 (s, 1H), 4.88 (dq, J=12.4, 6.1 Hz, 1H), 4.59 (t, J=8.2 Hz, 1H), 4.11 (dd, J=8.4, 4.6 Hz, 1H), 3.64 (s, 3H), 2.16 (s, 3H), 1.29 (d, J=6.2 Hz, 3H).

Preparation of Example 8.2

Scheme 55. Synthesis of (Ex-8.2)

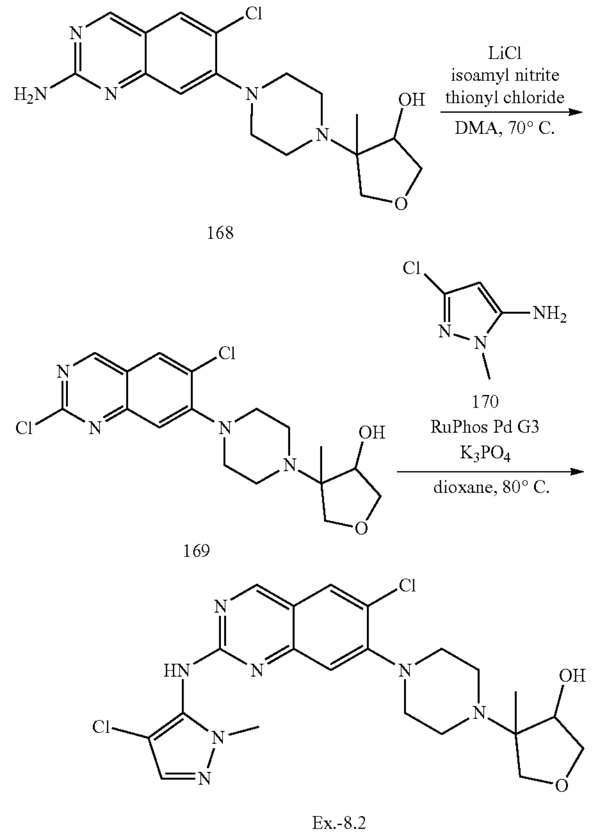

168

170

169

Ex.-8.2

(3S,4S) or (3R, 4R) 4-(4-(2,6-dichloroquinazolin-7-yl)piperazin-1-yl)-4-methyltetrahydrofuran-3-ol (169)

A 40-mL vial was charged with lithium chloride (58 mg, 1.4 mmol) and suspended in DMA (6871 μl). The mixture was heated to 70° C. to dissolve the lithium chloride. The solution was cooled to RT and 4-(4-(2-amino-6-chloroquinazolin-7-yl)piperazin-1-yl)-4-methyltetrahydrofuran-3-ol (169) (500 mg, 1.37 mmol) was added followed by isoamyl nitrite (278 μl, 2.06 mmol). The vial was cooled to 0° C. and to the mixture was added thionyl chloride (110 μl, 1.51 mmol). The reaction mixture was allowed to warm slowly to RT overnight. The reaction mixture was poured into sat. aq. $NaHCO_3$ and extracted with EtOAc (3×20 mL). The combined organic layers were washed with brine (1×50 mL) and concentrated in vacuo. The crude reaction mixture was purified by flash chromatography over silica (3:1 EtOAc: EtOH/hexane, 0-100%) to afford 4-(4-(2,6-dichloroquinazolin-7-yl)piperazin-1-yl)-4-methyltetrahydrofuran-3-ol (122 mg, 0.318 mmol, 23.12% yield). MS (ESI): m/z calc'd for $C_{17}H_{20}Cl_2N_4O_2$ $[M+H]^+$: 383, found 383.

(3S,4S) or (3R, 4R) 4-(4-(6-chloro-2-((4-chloro-1-methyl-1H-pyrazol-5-yl)amino)quinazolin-7-yl)piperazin-1-yl)-4-methyltetrahydrofuran-3-ol (Ex-8.2)

A vial was charged with 3-chloro-1-methyl-1H-pyrazol-5-amine (170) (25.7 mg, 0.196 mmol), 4-(4-(2,6-dichloroquinazolin-7-yl)piperazin-1-yl)-4-methyltetrahydrofuran-3-ol (169) (30 mg, 0.078 mmol), RuPhos Pd G3 (20. mg, 0.023 mmol) and K3P04 (83 mg, 0.39 mmol). Dioxane (391 μl) was added and the vial was purged with nitrogen (3×). The resultant mixture was stirred at 80° C. overnight. The crude mixture was diluted in DCM, filtered, concentrated, and purified by flash chromatography over silica (3:1 EtOAc: EtOH/hexane, 0-100%) to afford 4-(4-(6-chloro-2-((3-chloro-1-methyl-1H-pyrazol-5-yl)amino)quinazolin-7-yl)piperazin-1-yl)-4-methyltetrahydrofuran-3-ol (Ex-8.2) (13. mg, 0.028 mmol, 36% yield). MS (ESI): m/z calc'd for $C_{21}H_{25}Cl_2N_7O_2$ $[M+H]^+$: 478, found 478. $^1H$ NMR (500 MHz, DMSO-$d_6$) δ 9.92 (s, 1H), 9.17 (s, 1H), 8.07 (s, 1H), 7.17 (s, 1H), 6.55 (s, 1H), 5.47 (s, 3H), 5.25 (s, 1H), 4.33 (s, 1H), 3.98 (dd, J=9.6, 3.3 Hz, 1H), 3.81 (s, 1H), 3.71 (d, J=7.1 Hz, 3H), 3.45 (s, 4H), 3.22 (s, 1H), 2.75 (d, J=4.9 Hz, 1H), 1.41 (d, J=4.7 Hz, 2H), 1.06 (s, 2H).

Preparation of Example 8.3

Scheme 56. Synthesis of (3*S*,4*S*) or (3*R*,4*R*) 4-(4-(2-((5-chloro-1-(2,2-(*R*) or (*S*) difluorocyclopropyl)-1H-pyrazol-4-yl)amino)-6-ethylquinazolin-7-yl)piperazin-1-yl)-4-methyltetrahydrofuran-3-ol (Ex-8.3)

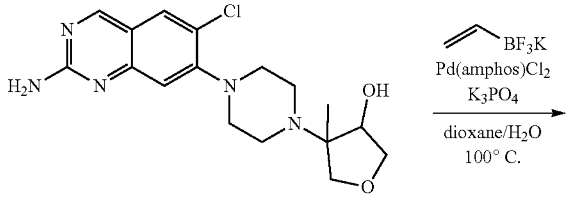

168

-continued

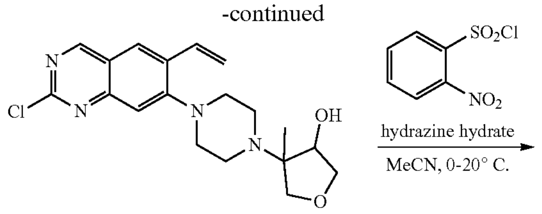

171

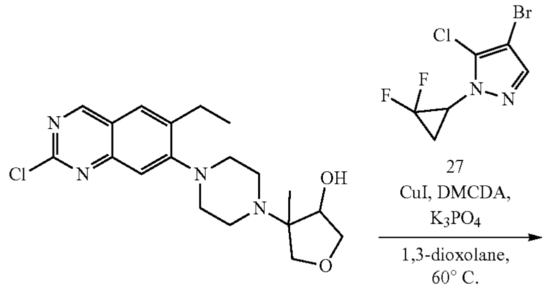

172

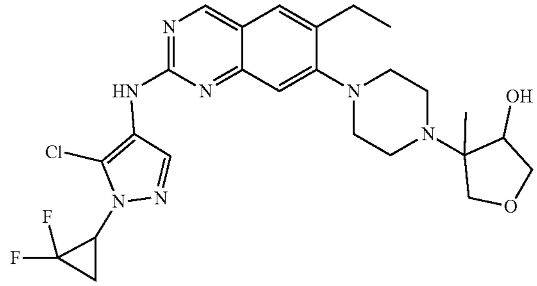

Ex-8.3

(3S,4S) or (3R, 4R) 4-(4-(2-chloro-6-vinylquinazolin-7-yl)piperazin-1-yl)-4-methyltetrahydrofuran-3-ol (171)

A vial was charged with 4-(4-(2-amino-6-chloroquinazolin-7-yl)piperazin-1-yl)-4-methyltetrahydrofuran-3-ol 168 (450 mg, 1.24 mmol), potassium trifluoro(vinyl)borate (331 mg, 2.47 mmol), Pd(amphos)$Cl_2$ (263 mg, 0.371 mmol), and $K_3PO_4$ (525 mg, 2.47 mmol). Dioxane (10 mL) and water (2 mL) was added and the resultant mixture was heated to 100° C. and stirred at this temperature for 2 hours. The reaction mixture was concentrated in vacuo and subjected to purification by reverse phase HPLC, eluting with water (0.1% TFA)-MeCN to afford 4-(4-(2-amino-6-vinylquinazolin-7-yl)piperazin-1-yl)-4-methyltetrahydrofuran-3-ol (171) (350 mg, 0.99 mmol, 80% yield). MS (ESI): m/z calc'd for $C_{19}H_{23}N_5O_2$ $[M+H]^+$: 374, found 374.

(3S,4S) or (3R,4R) 4-(4-(2-chloro-6-ethylquinazolin-7-yl)piperazin-1-yl)-4-methyltetrahydrofuran-3-ol (172)

To a solution of (3S,4S) or (3R, 4R) 4-(4-(2-amino-6-vinylquinazolin-7-yl)piperazin-1-yl)-4-methyltetrahydrofuran-3-ol (171) (180 mg, 0.506 mmol) and 2-nitrobenzenesulfonyl chloride (1.1 g, 5.1 mmol) in MeCN (5 mL) at 0° C. was added hydrazine hydrate (1.26 mL, 25.3 mmol). The resulting mixture was stirred at 20° C. for 2 hours. The reaction mixture was quenched with $H_2O$ (50 mL) and extracted with EtOAc (3×50 mL). The combined organic phases were washed with brine (50 mL), dried over anhydrous $Na_2SO_4$, filtered, and concentrated under reduced pressure. The residue was subjected to purification by reverse phase HPLC, eluting with water (0.1% TFA)-MeCN to give 172 (3S,4S) or (3R, 4R) 4-(4-(2-amino-6-ethylquinazolin-7-yl)piperazin-1-yl)-4-methyltetrahydrofuran-3-ol (90 mg, 0.25 mmol, 49% yield). MS (ESI): m z calc'd for $C_{19}H_{25}N_5O_2$ $[M+H]^+$: 376, found 376.

(3S,4S) or (3R,4R) 4-(4-(2-((5-chloro-1-(2,2-(R) or (S) difluorocyclopropyl)-1H-pyrazol-4-yl)amino)-6-ethylquinazolin-7-yl)piperazin-1-yl)-4-methyltetrahydrofuran-3-ol (Ex-8.3)

A comparative Cu-mediated coupling reaction sequence as demonstrated in Scheme 41 in the formation of 139 was utilized with 4-bromo-5-chloro-1-(2,2-difluorocyclopropyl)-1H-pyrazole 27 as coupling partner to (3S,4S) or (3R, 4R) 4-(4-(2-chloro-6-ethylquinazolin-7-yl)piperazin-1-yl)-4-methyltetrahydrofuran-3-ol 172 to afford the title compound Ex-8.3 MS (ESI): m/z calc'd for $C_{25}H_{30}ClF_2N_7O_2$ $[M+H]^+$: 534, found 534. $^1$H NMR (400 MHz, $CDCl_3$) δ 9.10 (s, 1H), 7.85 (s, 1H), 7.73 (s, 1H), 7.37 (s, 1H), 4.25 (d, J=16.8 Hz, 3H), 4.03-3.89 (m, 2H), 3.80-3.69 (m, 3H), 3.57 (s, 3H), 3.30 (s, 2H), 2.81-2.70 (m, 3H), 2.52-2.40 (m, 1H), 2.15 (td, J=10.0, 19.2 Hz, 1H), 1.48 (s, 3H), 1.37 (t, J=7.2 Hz, 3H).

The following Examples, 8.4-8.16 were obtained using the procedure analogous to those in General Scheme 9 but substituting appropriate starting materials that are either commercially available or prepared using procedures analogous to those described in Schemes 53-56.

TABLE 9

| Ex | Structure | Name | Exact Mass [M + H]+ |
|---|---|---|---|
| Ex-8.4 | 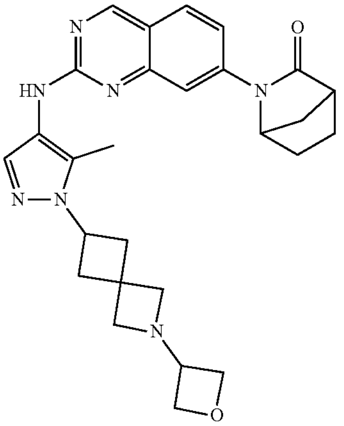 [SMILES: Cc1c(Nc2ncc3ccc(N4C(=O)C5CCC4C5)cc3n2)cnn1C1CC2(C1)CN(C1COC1)C2] | (1R,4S) or (1S,4R)-2-(2-((3-methyl-1-(2-(oxetan-3-yl)-2-azaspiro[3.3]heptan-6-yl)-1H-pyrazol-4-yl)amino)quinazolin-7-yl)-2-azabicyclo[2.2.1]heptan-3-one | Calc'd 486.0, found 486.3 |
| Ex-8.5 | 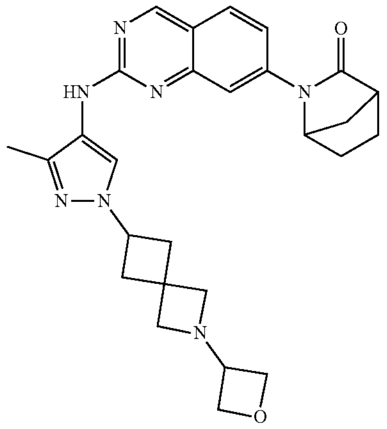 [SMILES: Cc1nn(C2CC3(C2)CN(C2COC2)C3)cc1Nc1ncc2ccc(N3C(=O)C4CCC3C4)cc2n1] | (1R,4S) or (1S,4R)-2-(2-((3-methyl-1-(2-(oxetan-3-yl)-2-azaspiro[3.3]heptan-6-yl)-1H-pyrazol-4-yl)amino)quinazolin-7-yl)-2-azabicyclo[2.2.1]heptan-3-one | Calc'd 486.0, found 486.3 |
| Ex-8.6 | 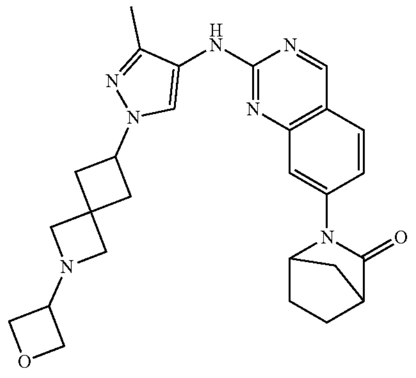 [SMILES: Cc1nn(C2CC3(C2)CN(C2COC2)C3)cc1Nc1ncc2ccc(N3C(=O)C4CCC3C4)cc2n1] | (1R,4S) or (1S,4R)-2-[2-({3-methyl-1-[2-(oxetan-3-yl)-2-azaspiro[3.3]heptan-6-yl]-1H-pyrazol-4-yl} amino)quinazolin-7-yl]-2-azabicyclo[2.2.1]heptan-3-one | Calc'd 486.0, found 486.3 |
| Ex-8.7 | 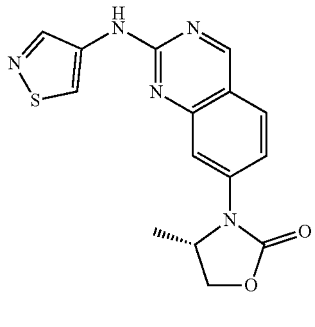 [SMILES: C[C@H]1COC(=O)N1c1ccc2cnc(Nc3cnsc3)nc2c1] | (4S)-4-methyl-3-{2-[(1,2-thiazol-4-yl)amino]quinazolin-7-yl}-1,3-oxazolidin-2-one | Calc'd 328.0, found 328.0 |

TABLE 9-continued

| Ex | Structure | Name | Exact Mass [M + H]+ |
|---|---|---|---|
| Ex-8.8 | 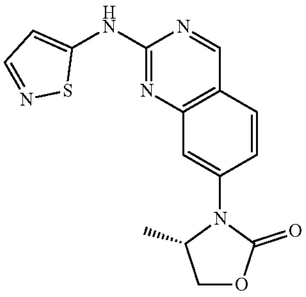 [SMILES: C[C@H]1COC(=O)N1c1ccc2cnc(Nc3ccns3)nc2c1] | (4S)-4-methyl-3-{2-[(1,2-thiazol-5-yl)amino]quinazolin-7-yl}-1,3-oxazolidin-2-one | Calc'd 328.0, found 328.1 |
| Ex-8.9 | 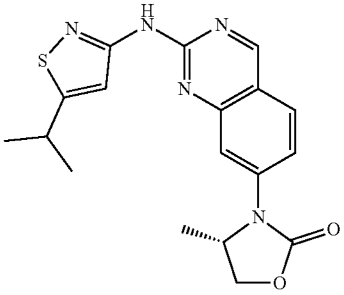 [SMILES: CC(C)c1cc(Nc2ncc3ccc(N4C(=O)OC[C@@H]4C)cc3n2)ns1] | (4S)-4-methyl-3-(2-{[5-(propan-2-yl)-1,2-thiazol-3-yl]amino}quinazolin-7-yl)-1,3-oxazolidin-2-one | Calc'd 370.0, found 370.1 |
| Ex-8.10 | 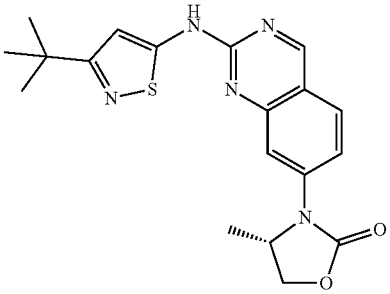 [SMILES: C[C@H]1COC(=O)N1c1ccc2cnc(Nc3cc(C(C)(C)C)ns3)nc2c1] | (4S)-3-{2-[(3-tert-butyl-1,2-thiazol-5-yl)amino]quinazolin-7-yl}-4-methyl-1,3-oxazolidin-2-one | Calc'd 384.0, found 384.2 |
| Ex-8.11 | 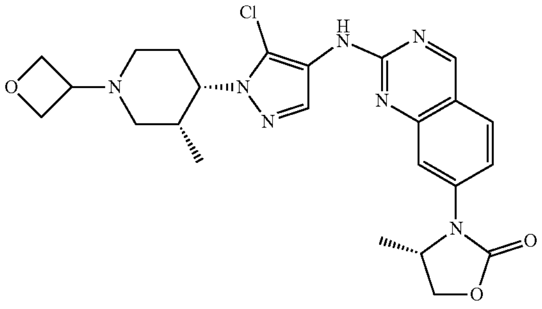 [SMILES: C[C@@H]1CN(C2COC2)CC[C@@H]1n1ncc(Nc2ncc3ccc(N4C(=O)OC[C@@H]4C)cc3n2)c1Cl] | (4.5)-3-[2-({5-chloro-1-[(3R,4S)-3-methyl-1-(oxetan-3-yl)piperidin-4-yl]-1H-pyrazol-4-yl}amino)quinazolin-7-yl]-4-methyl-1,3-oxazolidin-2-one | Calc'd 498.0, found 498.1 |
| Ex-8.12 | 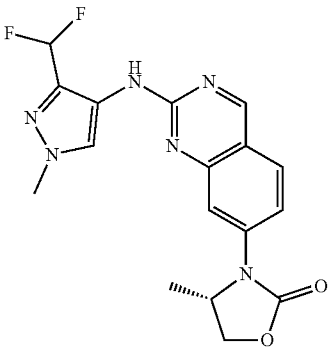 [SMILES: C[C@H]1COC(=O)N1c1ccc2cnc(Nc3cn(C)nc3C(F)F)nc2c1] | (4S)-3-(2-{[3-(difluoromethyl)-1-methyl-1H-pyrazol-4-yl]amino}quinazolin-7-yl)-4-methyl-1,3-oxazolidin-2-one | Calc'd 375.0, found 375.1 |

TABLE 9-continued

| Ex | Structure | Name | Exact Mass [M + H]+ |
|---|---|---|---|
| Ex-8.13 | 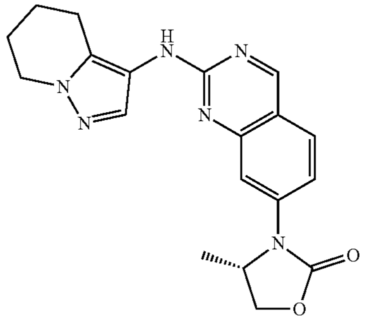 [SMILES: C[C@H]1COC(=O)N1c1ccc2cnc(Nc3cnn4c3CCCC4)nc2c1] | (4S)-4-methyl-3-{2-[(4,5,6,7-tetrahydropyrazolo[1,5-a]pyridin-3-yl)amino]quinazolin-7-yl}-1,3-oxazolidin-2-one | Calc'd 365.0, found 365.1 |
| Ex-8.14 | 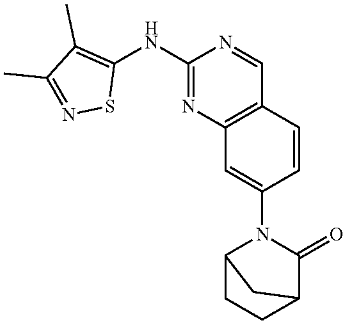 [SMILES: Cc1nsc(Nc2ncc3ccc(N4C(=O)C5CCC4C5)cc3n2)c1C] | 2-{2-[(3,4-dimethyl-1,2-thiazol-5-yl)amino]quinazolin-7-yl}-2-azabicyclo[2.2.1]heptan-3-one | Calc'd 366.0, found 366.1 |
| Ex-8.15 | 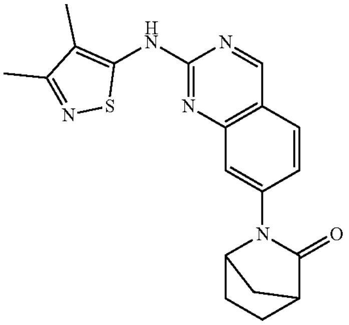 [SMILES: Cc1nsc(Nc2ncc3ccc(N4C(=O)C5CCC4C5)cc3n2)c1C] | 2-{2-[(3,4-dimethyl-1,2-thiazol-5-yl)amino]quinazolin-7-yl}-2-azabicyclo[2.2.1]heptan-3-one | Calc'd 366.0, found 366.1 |
| Ex-8.16 | 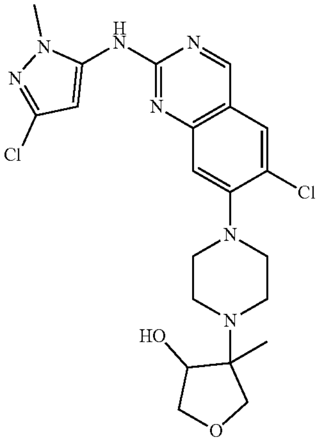 [SMILES: Cn1nc(Cl)cc1Nc1ncc2cc(Cl)c(N3CCN(C4(C)COCC4O)CC3)cc2n1] | 4-(4-(6-chloro-2-((3-chloro-1-methyl-1H-pyrazol-5-yl)amino)quinazolin-7-yl)piperazin-1-yl)-4-methyltetrahydrofuran-3-ol | Calc'd 478.0, found 478.0 |

Preparation of Examples 9.1 and 9.2

Scheme 57. Synthesis of (2*R*,4*S* or 2*S*,4*R*, or 2*S*,4*S*, or 2*R*,4*R*)-1-(6-chloro-2-((1-cyclopropyl-5-methyl-1H-pyrazol-4-yl)amino)quinazolin-7-yl)-2,4-dimethylpiperidin-4-ol (Ex-9.1) and (2*R*,4*S* or 2*S*,4*R*, or 2*S*,4*S*, or 2*R*,4*R*)-1-(6-chloro-2-((1-cyclopropyl-5-methyl-1H-pyrazol-4-yl)amino)quinazolin-7-yl)-2,4-dimethylpiperidin-4-ol (Ex-9.2)

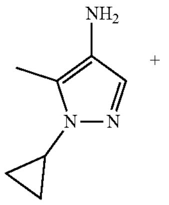

128

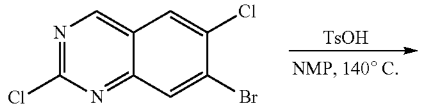

6

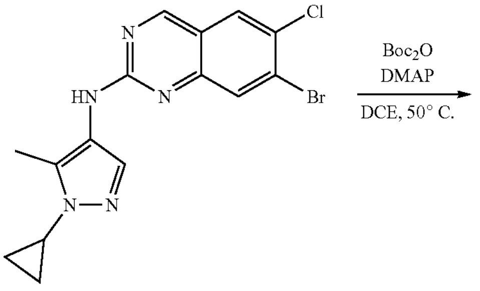

173

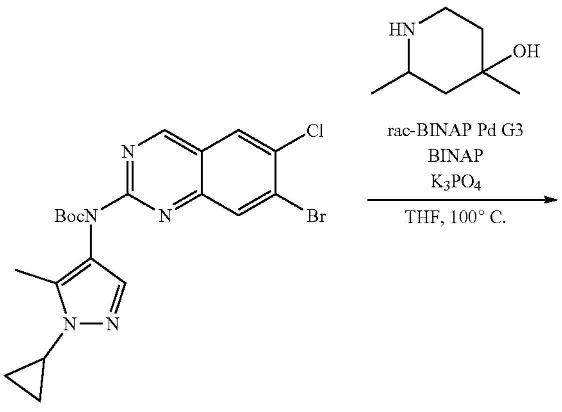

174

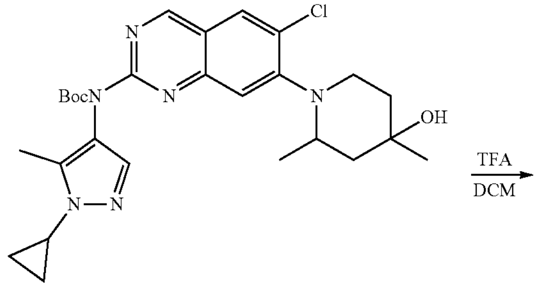

175

-continued

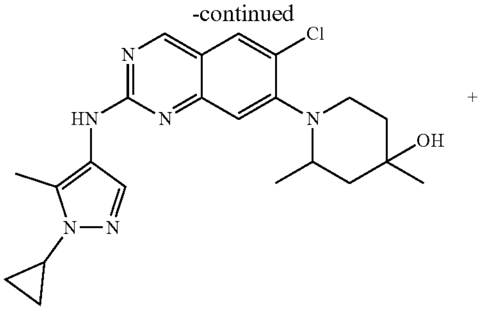

Ex-9.1

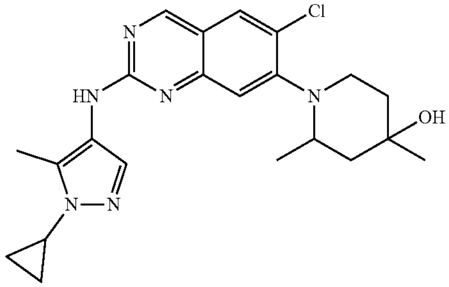

Ex-9.2

7-Bromo-6-chloro-N-(1-cyclopropyl-5-methyl-1H-pyrazol-4-yl)quinazolin-2-amine (173)

The title compound 173 was made through an analogous $S_NAr$ reaction as demonstrated in Scheme 52 and exemplified in the preparation of Example 7.1 utilizing amino pyrazole 128 and chloroquinazoline 6. MS (ESI): m/z calc'd for $C_{15}H_{13}BrClN_5$ $[M+H]^+$: 378, found 378.

Tert-butyl (7-bromo-6-chloroquinazolin-2-yl)(1-cyclopropyl-5-methyl-1H-pyrazol-4-yl)carbamate (174)

A 100 mL round bottomed flask was charged with 7-bromo-6-chloro-N-(1-cyclopropyl-5-methyl-1H-pyrazol-4-yl)quinazolin-2-amine 173 (682 mg, 1.80 mmol), DMAP (55.0 mg, 0.450 mmol), and di-tert-butyl carbonate (0.827 mL, 3.60 mmol). Under a positive flow of argon, anhydrous DCE (18 mL) was added and the reaction mixture was stirred at 50° C. for 1 h. The reaction mixture was diluted with DCM and poured into sat. aq. $NaHCO_3$. The aqueous phase was extracted with DCM (1×20 mL). The combined organic phases were dried over $Na_2SO_4$, filtered, and concentrated under reduced pressure. The crude residue was subjected to flash chromatography over silica (EtOAc/DCM, 0-100%) to afford the title compound 174. MS (ESI): m/z calc'd for $C_{20}H_{21}BrClN_5O_2$ $[M+H]^+$: 478, found 478.

(2R,4S or 2S,4R, or 2S,4S, or 2R,4R)-Tert-butyl (6-chloro-7-(4-hydroxy-2,4-dimethylpiperidin-1-yl)quinazolin-2-yl)(1-cyclopropyl-5-methyl-1H-pyrazol-4-yl)carbamate (175)

The title compound 175 was made through an analogus Pd-catalyzed coupling reaction as demonstrated in Scheme 41 and exemplified in the preparation of 139. MS (ESI): m/z calc'd for $C_{27}H_{35}ClN_{603}$ $[M+H]^+$: 527, found 527.

(2R,4S or 2S,4R, or 2S,4S, or 2R,4R)-1-(6-Chloro-2-((1-cyclopropyl-5-methyl-1H-pyrazol-4-yl)amino)quinazolin-7-yl)-2,4-dimethylpiperidin-4-ol isomer 1 (Ex-9.1) isomer 2 (Ex-9.2)

The title compounds Ex-9.1 and Ex-9.2 were made through an analogus TFA deprotection as demonstrated in Scheme 48 exemplified in the preparation of 154. The racemic material could be resolved to its component enantiomers by chiral preparative SFC (Column & dimensions: AD-3, 50 mm×4.6 mm; Mobile phase A: $CO_2$; Mobile phase B: EtOH with 0.05% DEA) to afford the title compounds Ex-9.1 ($t_R$=1.07 min) and Ex-9.2 ($t_R$=1.76 min). Isomer 1 (Ex-9.1) MS (ESI): m/z calc'd for $C_{22}H_{27}ClN_6O$ $[M+H]^+$: 427, found 427; $^1H$ NMR (400 MHz, $CDCl_3$, 25° C.) δ 8.81 (s, 1H), 7.73 (s, 1H), 7.66 (s, 1H), 7.16 (s, 1H), 6.67 (s, 1H), 3.75-3.66 (m, 1H), 3.45 (J=3.9, 7.7, 12.1 Hz, 1H), 3.34 (J=3.7, 7.2 Hz, 1H), 2.75 (J=4.0, 7.4, 12.0 Hz, 1H), 2.30 (s, 3H), 1.93 (J=4.0, 13.3 Hz, 1H), 1.84-1.76 (m, 2H), 1.72 (s, 2H), 1.63 (J=6.4, 13.2 Hz, 1H), 1.50-1.38 (m, 1H), 1.32 (s, 3H), 1.20-1.14 (m, 2H), 1.08 (d, J=6.4 Hz, 3H). Isomer 2 (Ex-9.2) MS (ESI): m/z calc'd for $C_{22}H_{27}ClN_{60}$ $[M+H]^+$: 427, found 427; $^1H$ NMR (400 MHz, $CDCl_3$, 25° C.) δ 8.78 (s, 1H), 7.64 (s, 2H), 7.19 (s, 1H), 7.10 (s, 1H), 3.79 (s, 1H), 3.47 (s, 1H), 3.29 (d, J=3.2 Hz, 1H), 2.83 (s, 1H), 2.28 (s, 3H), 1.88 (J=4.4, 13.4 Hz, 1H), 1.76 (s, 2H), 1.59 (J=5.3, 13.3 Hz, 1H), 1.27 (s, 3H), 1.21-1.08 (m, 6H), 0.98 (d, J=6.1 Hz, 2H).

Preparation of Example 10.1

(S)-3-(2-((3-Chloro-1H-pyrazol-4-yl)amino)quinazolin-7-yl)-4-methyloxazolidin-2-one (177)

A microwave vial was charged with (S)-3-(2-chloroquinazolin-7-yl)-4-methyloxazolidin-2-one 164 (50 mg, 0.19 mmol), 3-chloro-1H-pyrazol-4-amine, HCl 176 (36.5 mg, 0.237 mmol), Pd PEPPSI IPent (15 mg, 0.019 mmol), and potassium phosphate (161 mg, 0.758 mmol). The vial was then sealed with a septum cap and further sealed with an inverted rubber septum. The vial was then evacuated and purged with $N_2$ on the manifold (3×). Under a positive flow of $N_2$ anhydrous $^t$BuOH (1.9 mL) was added. The rubber septum was exchanged for a microwave cap under a blanket of nitrogen, and the reaction mixture was stirred at 100° C. for 7 h. The reaction was then transferred to a 65° C. block where it was stirred overnight. The reaction mixture was allowed to cool to RT, diluted with EtOAc, and filtered through Celite®. The organic phase was washed with water (2×10 mL), brine (10 mL), dried over $Na_2SO_4$, then filtered and concentrated under reduced pressure. The crude residue was subjected to purification by flash chromatography over silica (MeOH/DCM, 0-10%) to afford the title compound 177. MS (ESI): m/z calc'd for $C_{15}H_{13}ClN_6O_2$ $[M+H]^+$: 345, found 345.

(S)-3-(2-((3-Chloro-1-cyclohexyl-1H-pyrazol-4-yl)amino)quinazolin-7-yl)-4-methyloxazolidin-2-one (Ex-10.1)

In a ventilated balance enclosure, an 8 mL vial equipped with a magnetic stirrer was charged with (S)-3-(2-((3-chloro-1H-pyrazol-4-yl)amino)quinazolin-7-yl)-4-methyl- Scheme 58. Synthesis of (S)-3-(2-((3-chloro-1-cyclohexyl-1H-pyrazol-4-yl)amino)quinolin-7-yl)-4-methyloxazolidin-2-one

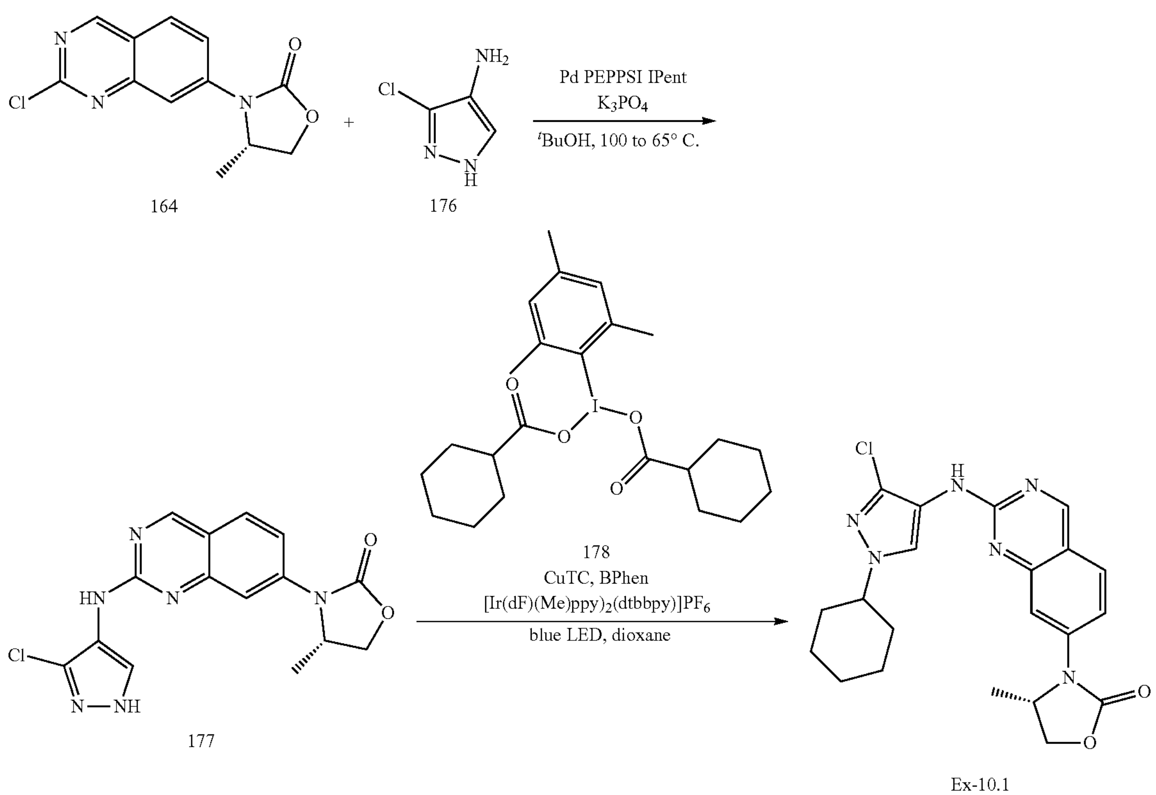

164

176

178

177

Ex-10.1 oxazolidin-2-one 177 (28 mg, 0.081 mmol), mesityl-13-iodanediyl dicyclohexanecarboxylate 178 (81 mg, 0.16 mmol), ((thiophene-2-carbonyl)oxy)copper (3.10 mg, 0.016 mmol), 4,7-diphenyl-1,10-phenanthroline (8.10 mg, 0.024 mmol), and Iridium(III) bis[2-(2,4-difluorophenyl)-5-methylpyridine-N,$C_{20}$]-4,40-di-tert-butyl-2,20-bipyridine hexafluorophosphate (1.312 mg, 1.624 μmol). The vial was then sealed with a septum cap and evacuated and purged with $N_2$ on the manifold (3×). Then, under a positive flow of $N_2$ anhydrous dioxane (1.3 mL), was added and the mixture was degassed by sparging for 5-10 min. The nitrogen inlet was then removed and the reaction was placed on the Penn® PhD Photoreactor M2 for 1 hr (100% LED intensity, 700 rpm stir rate, nearly maximum fan setting). At this point the mixture was diluted with EtOAc and filtered through Celite®. The filtrate was concentrated to dryness under reduced pressure. The crude residue was subject to purification by reverse phase HPLC, eluting with water (0.1% TFA)-MeCN. The resultant TFA salt was dissolved in EtOAc (10 mL) and washed with sat. aq. $Na_2CO_3$ (3×20 mL), brine (1×20 mL), dried over anhydrous $Na_2SO_4$, filtered, and solvent removed from the collected filtrate under reduced pressure to afford the title compound Ex-10.1. MS (ESI): m/z calc'd for $C_{21}H_{24}ClN_6O_2$ $[M+H]^+$: 427, found 427; $^1H$ NMR (500 MHz, $CDCl_3$, 25° C.) δ: 8.99 (s, 1H), 8.32 (s, 1H), 7.75 (m, 1H), 7.72-7.57 (br m, 2H), 7.01 (s, 1H), 4.71 (m, 1H), 4.64 (dd, J=8.2, 8.2 Hz, 1H), 4.12 (dd, J=8.2, 4.8 Hz, 1H), 4.07 (tt, J=11.7, 3.9 Hz, 1H), 2.17 (m, 2H), 1.93 (m, 2H), 1.82 (m, 2H), 1.74 (m, 1H), 1.59 (br m, 2H) 1.47 (d, J=5.9 Hz, 3H), 1.43 (m, 1H).

Preparation of Example 11.1

Scheme 59. Synthesis of 6-chloro-N-(5-chloro-1-methyl-1H-pyrazol-4-yl)-7-(4-methylpiperazin-1-yl)quinazolin-2-amine

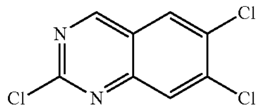

179

+

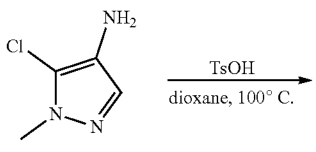

180

-continued

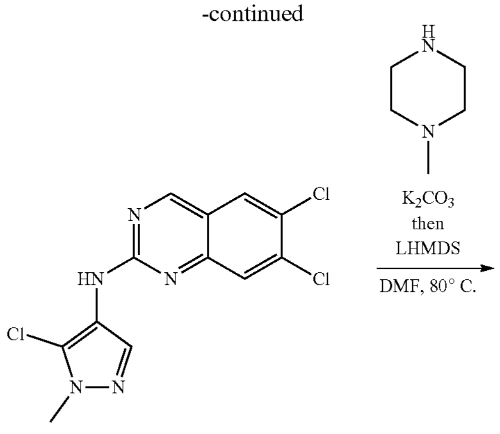

181

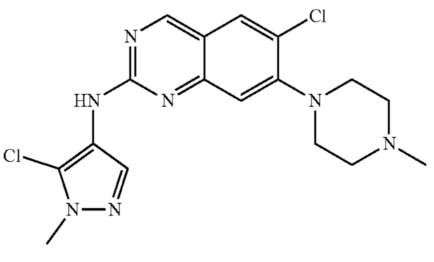

Ex-11.1

6-Chloro-N-(5-chloro-1-methyl-1H-pyrazol-4-yl)-7-(4-methylpiperazin-1-yl)quinazolin-2-amine (181)

The title compound 181 was made through an analogus $S_NAr$ reaction as demonstrated in Scheme 52 and exemplified in the preparation of Example 7.1. MS (ESI): m/z calc'd for $C_{12}H_8C_{13}N_5$ $[M+H]^+$: 328, found 328.

6-Chloro-N-(5-chloro-1-methyl-1H-pyrazol-4-yl)-7-(4-methylpiperazin-1-yl)quinazolin-2-amine (Ex-11.1)

A vial was charged with 6,7-dichloro-N-(5-chloro-1-methyl-1H-pyrazol-4-yl)quinazolin-2-amine 181 (33 mg, 0.10 mmol) and $K_2CO_3$ (139 mg, 1.00 mmol). The flask was evacuated and back filled with nitrogen (3×). The solids were dissolved in DMF (1.0 mL) and 1-methylpiperazine (55.7 μL, 0.502 mmol) was added. The resultant mixture was stirred at 80° C. overnight. Due to incomplete conversion, LHMDS (502 μL, 0.502 mmol 1.0 M) was added and the reaction was stirred at 80° C. overnight. The crude residue was subject to purification by reverse phase HPLC, eluting with water (0.1% TFA)-MeCN to afford the title compound Ex-11.1. MS (ESI): m/z calc'd for $C_{17}H_{19}Cl_2N_7$ $[M+H]^+$: 392, found 392; $^1H$ NMR (600 MHz, DMSO-$d_6$, 25° C.) δ 9.86 (s, 1H), 9.17 (s, 1H), 9.11 (s, 1H), 8.04 (s, 1H), 7.90 (s, 1H), 3.82 (s, 3H), 3.67 (d, J=12.8 Hz, 2H), 3.57 (d, J=11.6 Hz, 2H), 3.33-3.20 (m, 2H), 3.09 (t, J=12.1 Hz, 2H), 2.91 (d, J=3.1 Hz, 3H).

General Scheme 10

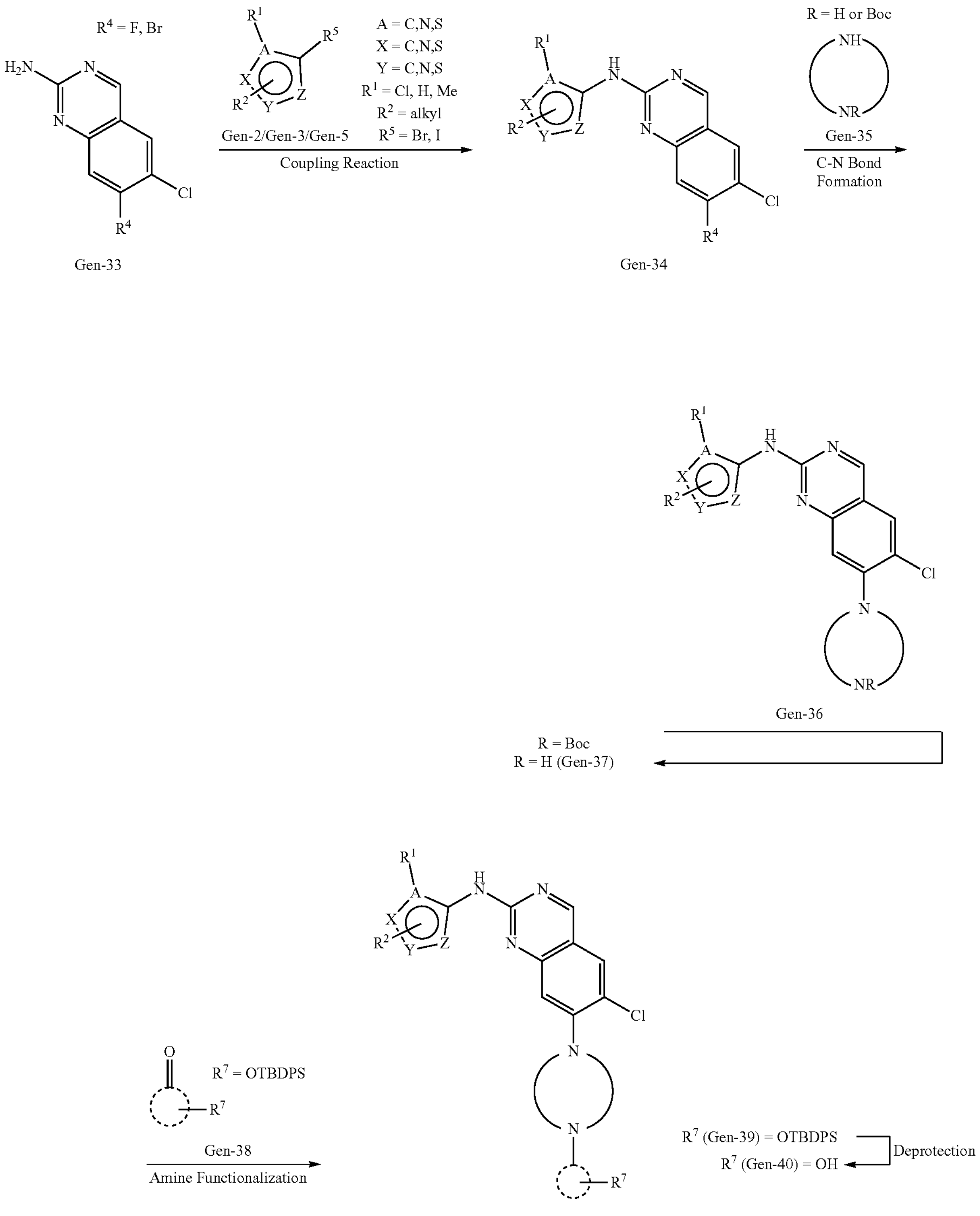

In General Scheme 10, synthetically commercially available or prepared intermediate Gen-33 could undergo a palladium-catalyzed coupling reaction with halo-pyrazoles Gen-2/Gen-3/Gen-5 to afford compounds of the form Gen-34. Subsequent C—N bond formation using a Pd-catalyzed coupling (c.f. Scheme 37, 123-124) or $S_NAr$ (c.f. Scheme 40, 131-132) reaction could be performed utilizing intermediates of the form Gen-35 to afford elaborated compounds of the form Gen-36. In the cases where R=Boc, a deprotection reaction could be performed to form Gen-37. A final amine functionalization reaction such as a reductive amination could be performed using ketones of the form Gen-38 to afford elaborated compounds of the form Gen-39 which could then undergo a subsequent deprotection reaction to afford free alcohol compounds of the form Gen-40. Representative preparative examples from each sequence are described in more detail below.

Scheme 60. Synthesis of 6-chloro-N-(5-chloro-1-cyclopropyl-1H-pyrazol-yl)-7-(piperazin-1-yl)quinazolin-2-amine

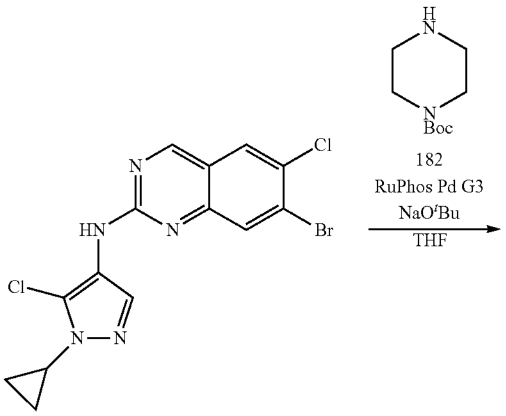

8

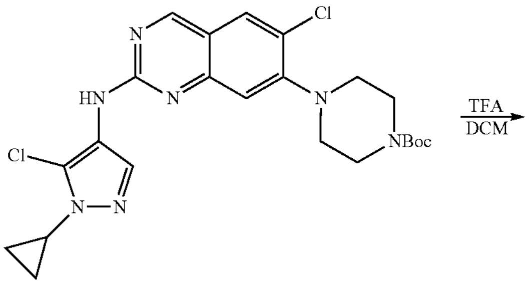

183

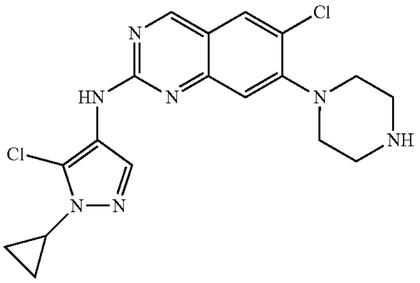

184

Tert-butyl 4-(6-chloro-2-((5-chloro-1-cyclopropyl-1H-pyrazol-4-yl)amino)quinazolin-7-yl)piperazine-1-carboxylate (183)

The title compound 162 was made using coupling partner 161 through an analogus Pd-coupling reaction as detailed in Scheme 41 to form 139. MS (ESI): m/z calc'd for $C_{23}H_{27}C_{12}N_7O_2$ [M+H]$^+$: 504, found 504.

6-Chloro-N-(5-chloro-1-cyclopropyl-TH-pyrazol-4-yl)-7-(piperazin-1-yl)quinazolin-2-amine (184)

Tert-butyl 4-(6-chloro-2-((5-chloro-1-cyclopropyl-TH-pyrazol-4-yl)amino)quinazolin-7-yl)piperazine-1-carboxylate 183 (7.0 mg, 0.014 mmol) was taken up in a vial and TFA (1.0 mL, 13 mmol) was added followed by DCM (3 mL). The resultant mixture was allowed to stir at RT overnight. The crude residue was subject to purification by reverse phase HPLC, eluting with water (0.1% TFA)-MeCN to afford the title compound 184. $^1$H NMR (500 MHz, DMSO-$d_6$, 25° C.) δ 9.20-9.06 (m, 2H), 8.83 (s, 2H), 8.04 (d, J=2.5 Hz, 1H), 7.14 (s, 1H), 3.62 (d, J=3.5 Hz, 1H), 3.32 (s, 7H), 1.24 (s, 1H), 1.09 (s, 4H).

Preparation of Example 12.1

Scheme 61. Synthesis of 6-chloro-N-(1-cyclopropyl-5-methyl-1H-pyrazol-4-yl)-7-(4-(5,5-dimethyltetrahydrofuran-3-yl)piperazin-1-yl)quinazolin-2-amine

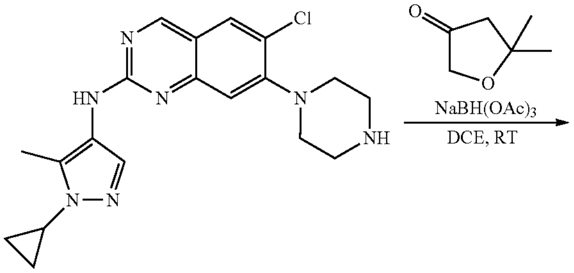

185

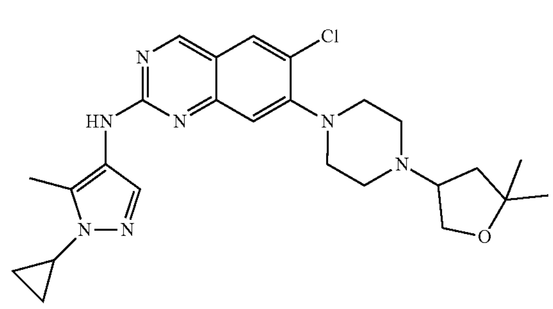

Ex-12.1

To a mixture of 6-chloro-N-(1-cyclopropyl-5-methyl-1H-pyrazol-4-yl)-7-(piperazin-1-yl)quinazolin-2-amine (50 mg, 0.13 mmol), 5,5-dimethyldihydrofuran-3(2H)-one (22.3 mg, 0.195 mmol) in DCE (2 mL) was added sodium triacetoxy-borohydride (41.4 mg, 0.195 mmol). The resultant mixture was stirred at 25° C. for 3 h. The crude reaction mixture was subject to purification by reverse phase HPLC, eluting with water (0.1% TFA)-MeCN to afford the title compound Ex-12.1. MS (ESI): m/z calc'd for $C_{25}H_{32}ClN_7O$ [M+H]$^+$: 482 found 482. $^1$H NMR (400 MHz, $CDCl_3$, 25° C.) δ=9.02 (s, 1H), 7.85 (s, 1H), 7.70 (s, 1H), 7.21 (s, 1H), 4.23 (dd, J=5.1, 10.6 Hz, 1H), 4.12-4.06 (m, 1H), 3.94 (s, 1H), 3.69 (s, 3H), 3.41-3.29 (m, 3H), 2.41 (s, 3H), 2.20 (s, 2H), 1.42 (s, 3H), 1.26 (s, 3H), 1.18 (s, 2H), 1.11-1.04 (m, 2H).

Preparation of Examples 12.2 and 12.3

Scheme 62. Synthesis of (3*S*, 4*S*) or (3*R*, 4*R*) 6-chloro-N-(1-cyclopropyl-5-methyl-1H-pyrazol-4-yl)-7-(4-(3,5,5-trimethyltetrahydrofuran-3-yl)piperazin-1-yl)quinazolin-2-amine (Ex-12.2) and (3*S*, 4*S*) or (3*R*, 4*R*) 6-chloro-N-(1-cyclopropyl-5-methyl-1H-pyrazol-4-yl)-7-(4-(3,5,-trimethyltetrahydrofuran-3-yl) piperazin-1-yl)quinazolin-2-amine (Ex-12.3)

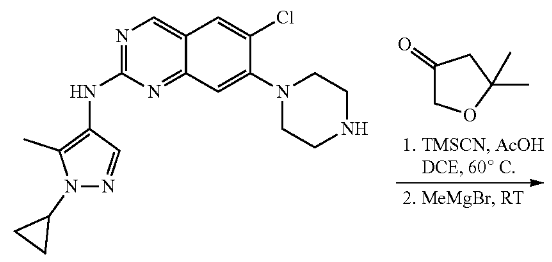

186

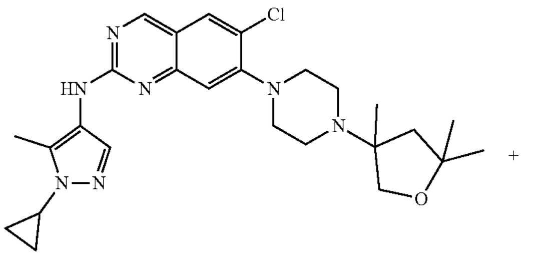

Ex-12.2

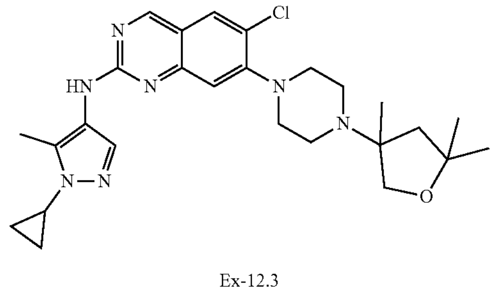

Ex-12.3

The title compounds were made through a reductive amination sequence analogous to that exemplified in the preparation of 43 in Scheme 16. The racemic material could be resolved to its component enantiomers by chiral preparative SFC (Column & dimensions: Chiralcel OJ-3, 250 mmx30 mm; Mobile phase A: $CO_2$; Mobile phase B: EtOH with base) to afford Ex-12.2 ($t_R$ 0.91 min) and Ex-12.3 ($t_R$=1.17 min). Isomer 1 (Ex-12.2) MS (ESI): m/z calc'd for $C_{26}H_{34}ClN_7O$ $[M+H]^+$: 496, found 496; $^1H$ NMR (400 MHz, $CDCl_3$, 25° C.): 6=8.82 (s, 1H), 7.78-7.64 (m, 2H), 7.09 (s, 1H), 6.51 (s, 1H), 3.79 (s, 1H), 3.67 (s, 1H), 3.36 (s, 1H), 3.20 (s, 4H), 2.85-2.49 (m, 4H), 2.32 (s, 3H), 1.94 (s, 1H), 1.70 (d, J=12.9 Hz, 1H), 1.58 (s, 3H), 1.27-1.17 (m, 6H), 1.06 (d, J=5.1 Hz, 2H), 0.82 (bs, 2H). Isomer 2 (Ex-12.3) MS (ESI): m/z calc'd for $C_{26}H_{34}ClN_7O$ $[M+H]^+$: 496, found 496; $^1H$ NMR (400 MHz, $CDCl_3$, 25° C.): δ=8.83 (s, 1H), 7.76-7.63 (m, 2H), 7.10 (s, 1H), 6.53 (s, 1H), 3.68-3.50 (m, 2H), 3.36 (d, J=3.5 Hz, 1H), 3.21 (s, 4H), 2.85-2.51 (m, 4H), 2.35 (s, 3H) 1.94 (s, 1H), 1.78-1.56 (m, 4H), 1.33 (s, 3H), 1.25 (s, 3H), 1.20 (s, 2H), 1.09-1.03 (m, 2H)

Preparation of Example 12.4

Scheme 61. Synthesis of 6-chloro-N-(1-cyclopropyl-5-methyl-1H-pyrazol-4-yl)-7-(4-(5,5-dimethyltetrahydrofuran-3-yl)piperazin-1-yl)quinazolin-2-amine

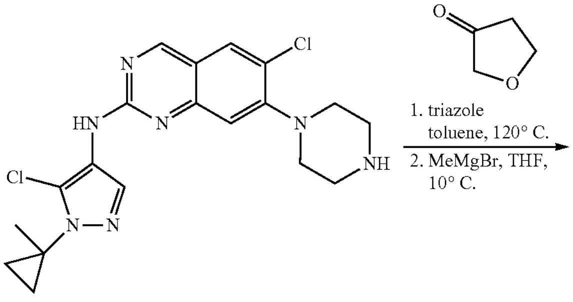

187

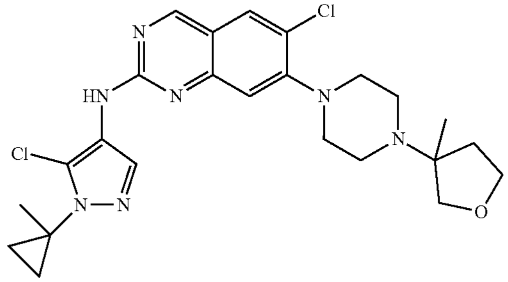

Ex-12.4

6-Chloro-N-(5-chloro-1-cyclopropyl-1H-pyrazol-4-yl)-7-(4-(3-methyltetrahydrofuran-3-yl)piperazin-1-yl)quinazolin-2-amine (Ex-12.4)

To a solution of 6-chloro-N-(5-chloro-1-(1-methylcyclopropyl)-1H-pyrazol-4-yl)-7-(piperazin-1-yl)quinazolin-2-amine 187 (10 mg, 0.024 mmol) in anhydrous toluene (3 mL) was added 1H-1,2,3-triazole (24.8 mg, 0.359 mmol) and dihydrofuran-3(2H)-one (30.9 mg, 0.359 mmol) The resulting mixture was stirred at 120° C. under $N_2$ for 2 h, then cooled to 15° C. and slowly added directly to a flask charged with methylmagnesium bromide (0.117 mL, 0.351 mmol) in THF (1.0 mL) at 0'° C. The resultant mixture was stirred at 15° C. for 30 min. The crude mixture was concentrated under reduced pressure and was subject to purification by reverse phase HPLC, eluting with water (0.2 TFA)-MeCN to afford the title compound Ex-12.4. MS (ESI): m/z calc'd for $C_{24}H_{29}Cl_2N_{70}$ $[M+H]^+$: 502 found 502. $^1H$ NMR (400 MHz, $CDCl_3$, 25° C.): δ 8.79 (s, 1H), 8.83-8.70 (m, 1H), 8.17 (s, 1H), 7.64 (d, J=1.2 Hz, 1H), 7.09 (s, 1H), 6.67 (s, 1H), 4.03-3.82 (m, 2H), 3.74-3.54 (m, 2H), 3.21 (s, 2H), 2.85-2.53 (m, 3H), 2.20-2.11 (m, 1H), 2.01-1.88 (m, 2H), 1.50-1.46 (m, 1H), 1.49 (s, 3H), 1.49-1.45 (m, 1H), 1.30-1.25 (m, 3H), 0.96-0.91 (m, 2H), 0.83-0.77 (in, 2H).

The following Examples, 12.5-12.10 were obtained using the procedure analogous to those in General Scheme 10 but substituting appropriate starting materials that are either commercially available or prepared using procedures analogous to those described in Schemes 60 through 63.

| | | | |
|---|---|---|---|
| Ex-12.5 | 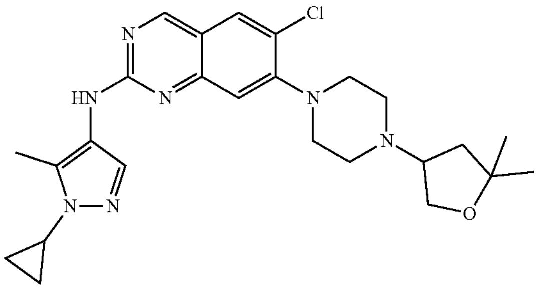 [SMILES: Cc1c(Nc2ncc3cc(Cl)c(N4CCN(C5COC(C)(C)C5)CC4)cc3n2)cnn1C1CC1] | 6-chloro-N-(1-cyclopropyl-5-methyl-1H-pyrazol-4-yl)-7-(4-(5,5-dimethyltetrahydrofuran-3-yl)piperazin-1-yl)quinazolin-2-amine | Calc'd 482.0, found 482 |
| Ex-12.6 | 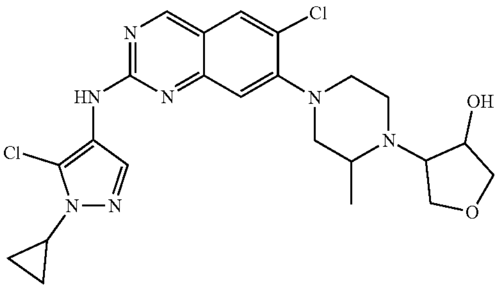 [SMILES: CC1CN(c2cc3nc(Nc4cnn(C5CC5)c4Cl)ncc3cc2Cl)CCN1C1COCC1O] | (3S,4S) or (3R, 4R)-4-((R) or (S)-4-(4-(6-chloro-2-((5-chloro-1-cyclopropyl-1H-pyrazol-4-yl)amino)quinazolin-7-yl)-2-methylpiperazin-1-yl)tetrahydrofuran-3-ol | Calc'd 504.0, found 504 |
| Ex-12.7 | 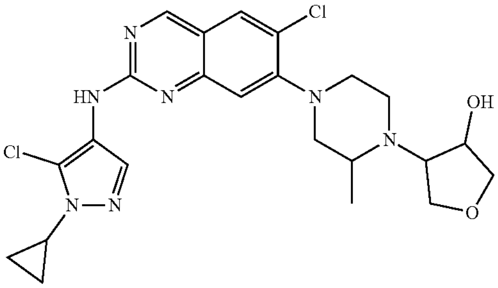 [SMILES: CC1CN(c2cc3nc(Nc4cnn(C5CC5)c4Cl)ncc3cc2Cl)CCN1C1COCC1O] | (3S,4S) or (3R, 4R)-4-((R) or (S)-4-(4-(6-chloro-2-((5-chloro-1-cyclopropyl-1H-pyrazol-4-yl)amino)quinazolin-7-yl)-2-methylpiperazin-1-yl)tetrahydrofuran-3-ol | Calc'd 504.0, 5 found 504 |
| Ex-12.8 | 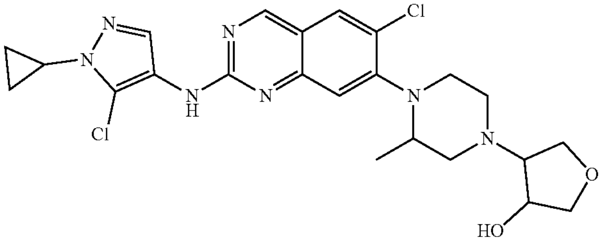 [SMILES: CC1CN(C2COCC2O)CCN1c1cc2nc(Nc3cnn(C4CC4)c3Cl)ncc2cc1Cl] | (3S,4S) or (3R, 4R)-4-((R) or (S)-4-(6-chloro-2-((5-chloro-1-cyclopropyl-1H-pyrazol-4-yl)amino)quinazolin-7-yl)-3-methylpiperazin-1-yl)tetrahydrofuran-3-ol | Calc'd 504.0, found 504 |
| Ex-12.9 | 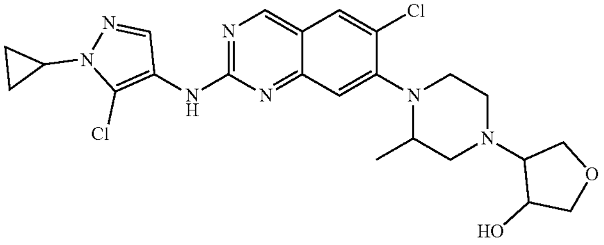 [SMILES: CC1CN(C2COCC2O)CCN1c1cc2nc(Nc3cnn(C4CC4)c3Cl)ncc2cc1Cl] | (3S,4S) or (3R, 4R)-4-((R) or (S)-4-(6-chloro-2-((5-chloro-1-cyclopropyl-1H-pyrazol-4-yl)amino)quinazolin-7-yl)-3-methylpiperazin-1-yl)tetrahydrofuran-3-ol | Calc'd 504.0, found 504 |

-continued

| | | | |
|---|---|---|---|
| Ex-12.10 | 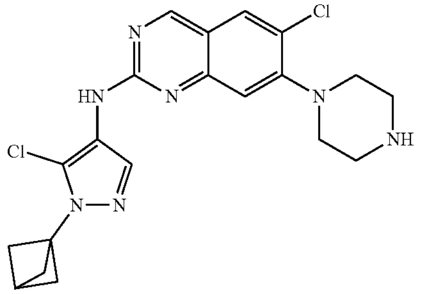 [SMILES: Clc1cc2cnc(Nc3cnn(C45CC(C4)C5)c3Cl)nc2cc1N1CCNCC1] | N-(1-(bicyclo[1.1.1]pentan-1-yl)-5-chloro-1H-pyrazol-4-yl)-6-chloro-7-(piperazin-1-yl)quinazolin-2-amine | Calc'd 430.0, found 430 |

General Scheme 11

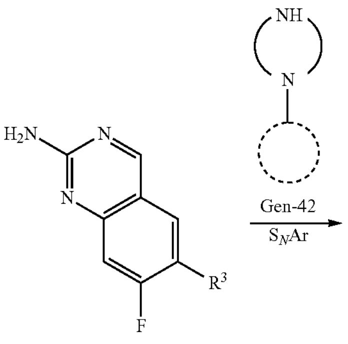

$R^3$ = Cl, Me

Gen-41

-continued

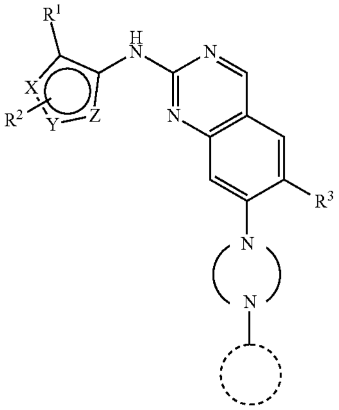

Gen-44

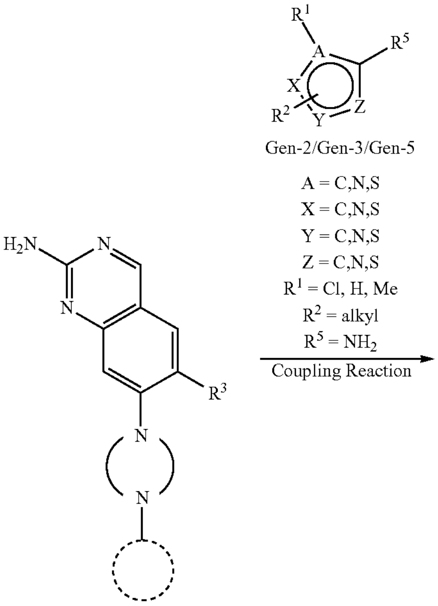

Gen-43

In General Scheme 11, synthetically commercially available or prepared intermediate Gen-41 could undergo $S_NAr$ chemistry utilizing amine partners Gen-42 to afford elaborated compounds of the form Gen-43. A subsequent palladium or copper-catalyzed coupling reaction with halo-pyrazoles Gen-2/Gen-3/Gen-5 could be performed to afford compounds of the form Gen-44. Representative preparative examples from each sequence are described in more detail below.

Preparation of Example 13.1 and 13.2

Scheme 64. Synthesis of (3S,4S) or (3R,4R)-4-(4-(2-((1-bicyclo[1.1.1]pentan-1-yl)-5-chloro-1H-pyrazol-4-yl)amino)-6-chloroquinazolin-7-yl)piperazin-1-yl)tetrahydrofuran-3-ol

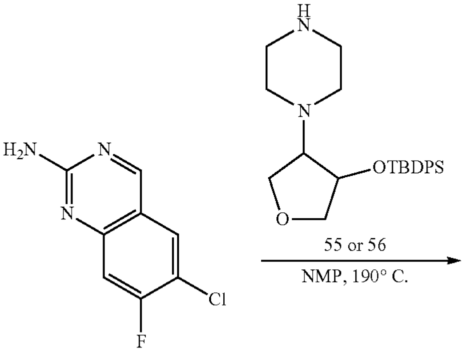

17

-continued

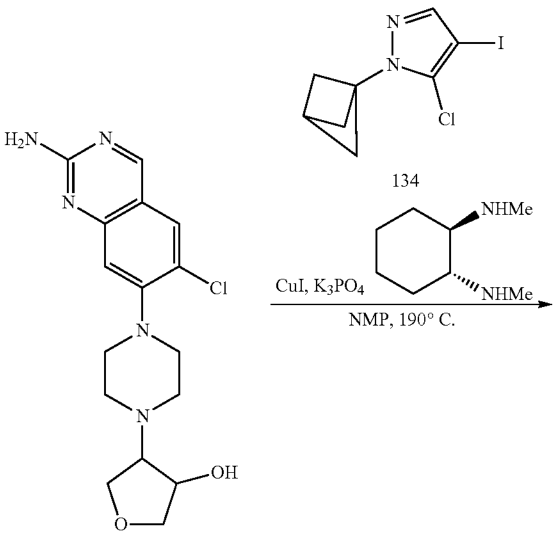

134

188

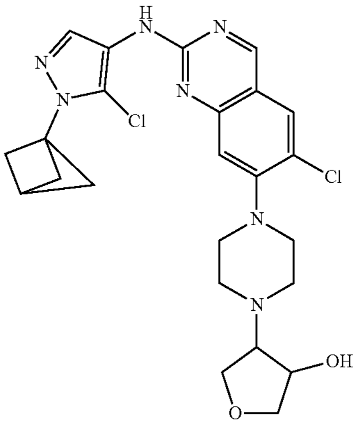

Ex-13.1

-continued

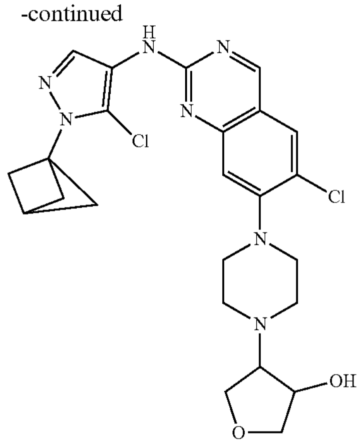

Ex-13.2

(3S,4S) or (3R,4R)-4-(4-(2-amino-6-chloroquinazolin-7-yl)piperazin-1-yl)tetrahydrofuran-3-ol (166)

The title compound 188 was made using the amine partner either 55 or 56 through an analogous $S_N$Ar reaction as detailed in Scheme 52 and exemplified in the preparation of Example 7.1 without using DIPEA. MS (ESI): m/z calc'd for $C_{23}H_{27}C_{12}N_7O_2$ $[M+H]^+$: 350, found 350.

(3S,4S) or (3R,4R)-4-(4-(2-((1-(bicyclo[1.1.1]pentan-1-yl)-5-chloro-1H-pyrazol-4-yl)amino)-6-chloroquinazolin-7-yl)piperazin-1-yl)tetrahydrofuran-3-ol (Ex-13.1)

The title compound Ex-13.1 was made using the coupling partner 134 through an analogous Cu-catalyzed coupling reaction as detailed in Scheme 51 in the preparation of Ex-6.1. MS (ESI): m/z calc'd for $C_{23}H_{27}C_{12}N_7O_2$ $[M+H]^+$: 516, found 516. $^1$H NMR (400 MHz, $CDCl_3$, 25° C.) δ=8.88 (br s, 1H), 8.24 (s, 1H), 7.72 (s, 1H), 7.15 (s, 1H), 6.73 (br s, 1H), 4.31-4.27 (m, 1H), 4.04-3.98 (m, 3H), 3.82 (br t, J=8.8 Hz, 1H), 3.28 (br s, 4H), 3.02-2.88 (m, 3H), 2.71-2.59 (m, 3H), 2.44 (s, 6H).

Utilizing the isomeric form of 55 which is 56, the enantiomer of Ex-13.1 could be made in an analogous fashion (Ex-13.2). MS (ESI): m/z calc'd for $C_{23}H_{27}C_{12}N_7O_2$ $[M+H]^+$: 516, found 516. The following Examples, 13.3-13.9 were obtained using the procedure analogous to those in General Scheme 11 but substituting appropriate starting materials that are either commercially available or prepared using procedures analogous to those described in Scheme 64.

TABLE 11

| | | | |
|---|---|---|---|
| Ex-13.3 | 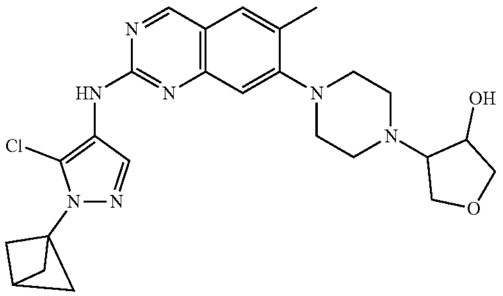 [SMILES: Cc1cc2cnc(Nc3cnn(C45CC(C4)C5)c3Cl)nc2cc1N1CCN(C2COCC2O)CC1] | (3S,4S) or (3R, 4R)-4-(4-(2-((1-(bicyclo[1.1.1]pentan-1-yl)-5-chloro-1H-pyrazol-4-yl)amino)-6-methylquinazolin-7-yl)piperazin-1-yl)tetrahydrofuran-3-ol | Calc'd 496.0, found 496 |

TABLE 11-continued

| | | | |
|---|---|---|---|
| Ex-13.4 | 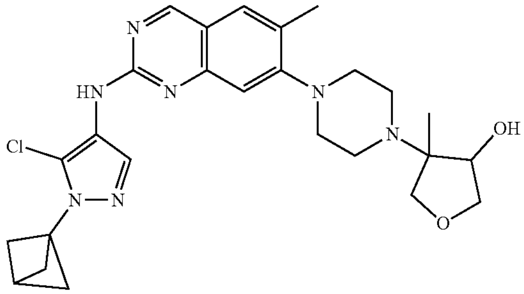 [SMILES: Cc1cc2cnc(Nc3cnn(C45CC(C4)C5)c3Cl)nc2cc1N1CCN(C2(C)COCC2O)CC1] | (3S,4S) or (3R, 4R)-4-(4-(2-((1-(bicyclo[1.1.1]pentan-1-yl)-5-chloro-1H-pyrazol-4-yl)amino)-6-methylquinazolin-7-yl)piperazin-1-yl)-4-methyltetrahydrofuran-3-ol | Calc'd 510.0, found 510 |
| Ex-13.5 | 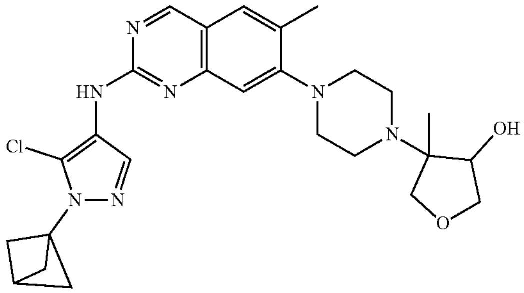 [SMILES: Cc1cc2cnc(Nc3cnn(C45CC(C4)C5)c3Cl)nc2cc1N1CCN(C2(C)COCC2O)CC1] | (3S,4S) or (3R, 4R)-4-(4-(2-((1-(bicyclo[1.1.1]pentan-1-yl)-5-chloro-1H-pyrazol-4-yl)amino)-6-methylquinazolin-7-yl)piperazin-1-yl)-4-methyltetrahydrofuran-3-ol | Calc'd 510.0, found 510 |
| Ex-13.6 | 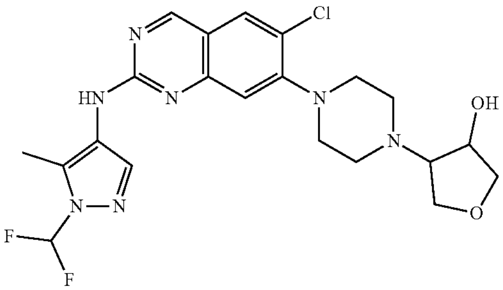 [SMILES: Cc1c(Nc2ncc3cc(Cl)c(N4CCN(C5COCC5O)CC4)cc3n2)cnn1C(F)F] | (3S,4S) or (3R,4R)-4-(4-(6-chloro-2-((1-(difluoromethyl)-5-methyl-1H-pyrazol-4-yl)amino)quinazolin-7-yl)piperazin-1-yl)tetrahydrofuran-3-ol | Calc'd 480.0, found 480 |
| Ex-13.7 | 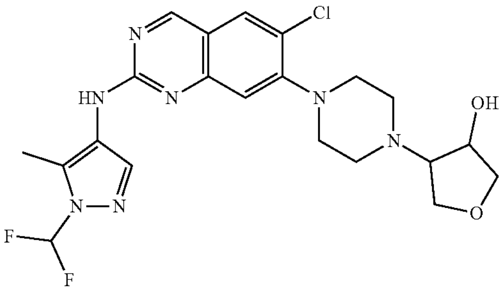 [SMILES: Cc1c(Nc2ncc3cc(Cl)c(N4CCN(C5COCC5O)CC4)cc3n2)cnn1C(F)F] | (3S,4S) or (3R, 4R)-4-(4-(6-chloro-2-((1-(difluoromethyl)-5-methyl-1H-pyrazol-4-yl)amino)quinazolin-7-yl)piperazin-1-yl)tetrahydrofuran-3-ol | Calc'd 480.0, found 480 |
| Ex-13.8 | 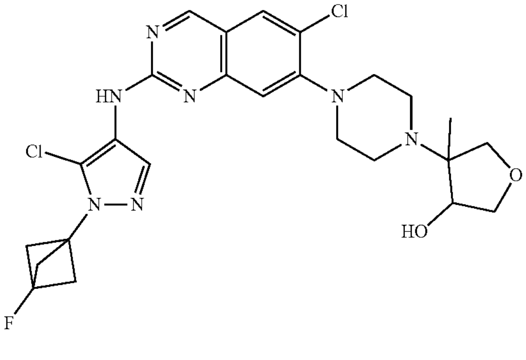 [SMILES: CC1(N2CCN(c3cc4nc(Nc5cnn(C67CC(F)(C6)C7)c5Cl)ncc4cc3Cl)CC2)COCC1O] | (3S,4S) or (3R,4R)4-(4-(6-chloro-2-((5-chloro-1-(3-fluorobicyclo[1.1.1]pentan-1-yl)-1H-pyrazol-4-yl)amino)quinazolin-7-yl)piperazin-1-yl)-4-methyltetrahydrofuran-3-ol | Calc'd 548.0, found 548 |

TABLE 11-continued

| | | | |
|---|---|---|---|
| Ex-13.9 | 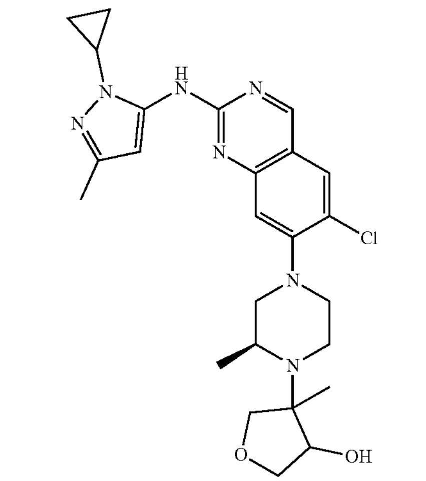 [SMILES: Cc1cc(Nc2ncc3cc(Cl)c(N4CCN(C5(C)COCC5O)[C@@H](C)C4)cc3n2)n(C2CC2)n1] | 4-((S or R) (3S,4S) or (3R,4R)-4-(6-chloro-2-((1-cyclopropyl-3-methyl-1H-pyrazol-5-yl)amino)quinazolin-7-yl)-2-methylpiperazin-1-yl)-4-methyltetrahydrofuran-3-ol | Calc'd 498.0, found 498 |

Preparation of Example 14.1

Scheme 65. Synthesis of 1-(2-((3-(2-(2H-1,2,3-triazol-2-yl)propan-2-yl)-1-(methyl-d3)-1H-pyrazol-5-yl)amino)-6-chloroquinazolin-7-yl)-4-methylpipetidin-4-ol

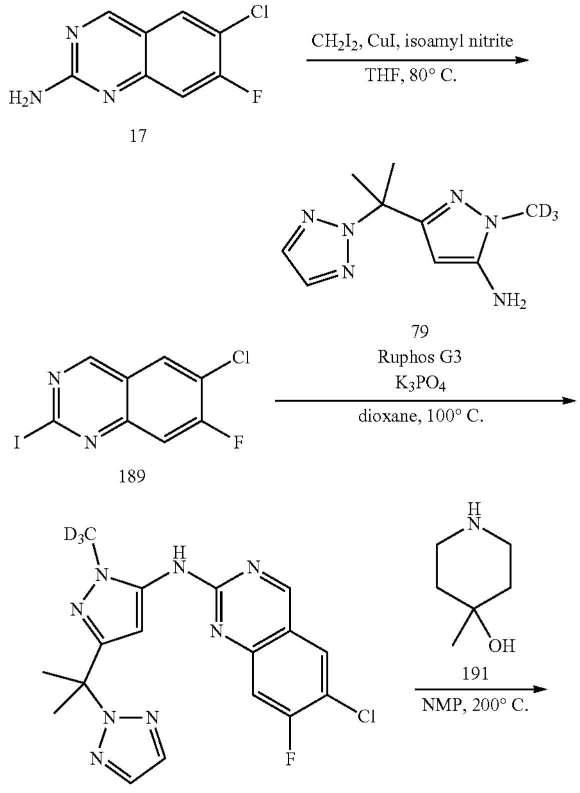

-continued

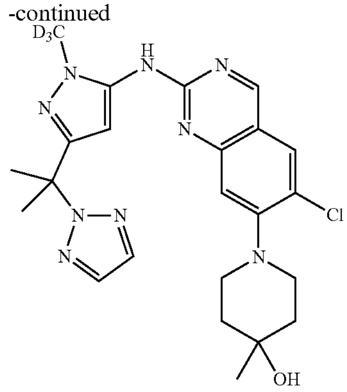

Ex-14.1

6-Chloro-7-fluoro-2-iodoquinazoline (189)

To a solution of 6-chloro-7-fluoroquinazolin-2-amine 17 (200 mg, 1.01 mmol) and diiodomethane (1.36 g, 5.06 mmol) in THF (2 mL) was added copper(I) iodide (193 mg, 1.01 mmol) and isoamyl nitrite (0.409 mL, 3.04 mmol). The resultant mixture was stirred at 80° C. for 16 h under $N_2$, then quenched by the addition of sat. aq. $NH_4OH$ (1 mL). The aqueous phase was extracted with ethyl acetate (3×5 mL). The combined organic layers were washed with brine (10 mL), dried over $Na_2SO$, and filtered to afford the title compound 189 which was used in next step directly without further purification. MS (ESI): m/z calc'd for $C_8H_3ClFIN_2$ $[M+H]^+$: 309, found 309.

N-(3-(2-(2H-1,2,3-Triazol-2-yl)propan-2-yl)-1-(methyl-$d_3$)-1H-pyrazol-5-yl)-6-chloro-7-fluoroquinazolin-2-amine (190)

To a solution of 6-chloro-7-fluoro-2-iodoquinazoline 189 (150 mg, 0.486 mmol) and 3-(2-(2H-1,2,3-triazol-2-yl)propan-2-yl)-1-(methyl-$d_3$)-1H-pyrazol-5-amine 79 (102 mg, 0.486 mmol) in 1,4-dioxane (1 mL) was added $K_3PO_4$ (310 mg, 1.46 mmol) and RuPhos Pd G3 (81 mg, 0.097 mmol) at 25° C. The mixture was degassed with $N_2$ three times. The mixture was stirred at 100° C. for 16 h. The reaction mixture was poured into water (5 mL) and extracted with EtOAc (3×5 mL). The combined organic phases were washed with water (3×5 mL) and dried over $Na_2SO_4$. After filtration and concentration under reduced pressure, the crude product was purified by preparative TLC ($SiO_2$, PE:EtOAc=1:1) to afford the title compound 190. MS (ESI): m/z calc'd for $C_{17}H_{13}D_3ClFN_8$ $[M+H]^+$: 390, found 390.

1-(2-((3-(2-(2H-1,2,3-Triazol-2-yl)propan-2-yl)-1-(methyl-d3)-1H-pyrazol-5-yl)amino)-6-chloroquinazolin-7-yl)-4-methylpiperidin-4-ol (Ex-14.1)

The title compound Ex-14.1 was made using the amine partner 191 through an analogous $S_NAr$ reaction as detailed in Scheme 52 in the preparation of Ex-7.1 without using DIPEA. MS (ESI): m/z calc'd for $C_{23}H_{25}D_3ClN_{90}$ $[M+H]^+$: 485, found 485; $^1H$ NMR (400 MHz, $CDCl_3$, 25° C.) δ: 8.91 (s, 1H), 7.81 (s, 1H), 7.61 (s, 2H), 7.19 (s, 1H), 6.13 (s, 1H), 3.51 (d, J=12.2 Hz, 2H), 3.40-3.30 (m, 2H), 2.09 (s, 6H), 1.90-1.83 (m, 2H), 1.80-1.73 (m, 2H), 1.36 (s, 3H).

-continued

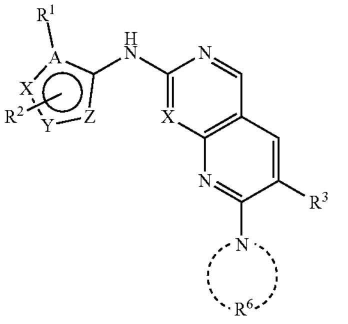

Gen-47

TABLE 12

| | | | |
|---|---|---|---|
| Ex-14.1 | 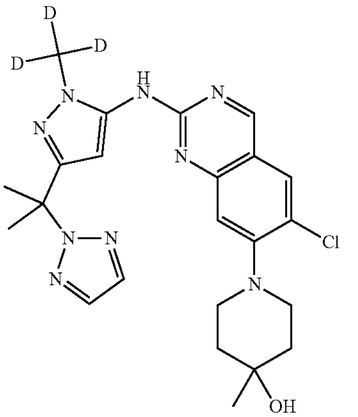 [SMILES: [2H]C([2H])([2H])n1nc(C(C)(C)n2nccn2)cc1Nc1ncc2cc(Cl)c(N3CCC(C)(O)CC3)cc2n1] | 1-[6-chloro-2-({1-(2-H-3-) methyl-3-[2-(2H-1,2,3-triazol-2-yl)propan-2-yl]-1H-pyrazol-5-yl} amino)quinazolin-7-yl]-4-methylpiperidin-4-ol | Calc'd 485.0, found |

General Scheme 12

$R^3$ = H, Cl, Br, F

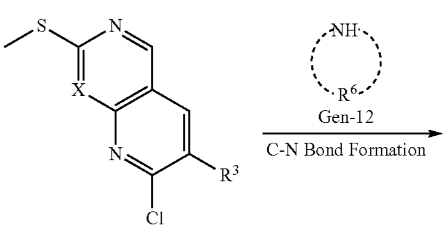

Gen-45

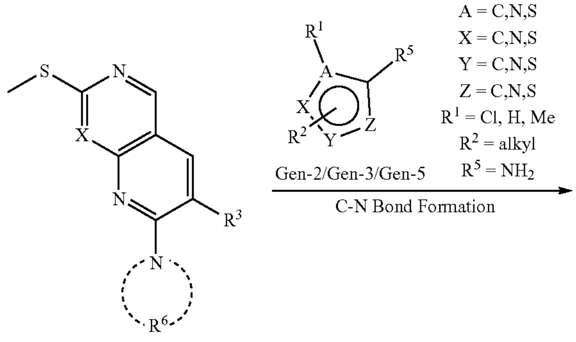

Gen-46

In General Scheme 12, commercially available or prepared intermediate Gen-45 could undergo a C—N bond formation reaction involving a Pd-catalyzed coupling reaction or $S_NAr$ reaction to afford elaborated compounds of the form Gen-46. A subsequent oxidation of Gen-46 followed by $S_NAr$ reaction with amino pyrazoles Gen-2/Gen-3/Gen-5 could be performed to afford compounds of the form Gen-47. Representative preparative examples from each sequence are described in more detail below.

Preparation of Example 15.1

Scheme 66. 1-(4-((6-bromo-7-((cyclopropylmethyl)amino)pyrido[2,3-d]pyrimidin-2-yl)amino)-5-chloro-1H-pyrazol-1-yl)-2-methylpropan-2-ol

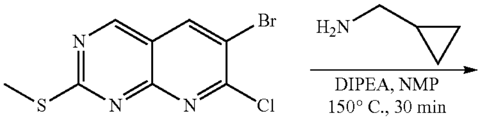

191

-continued

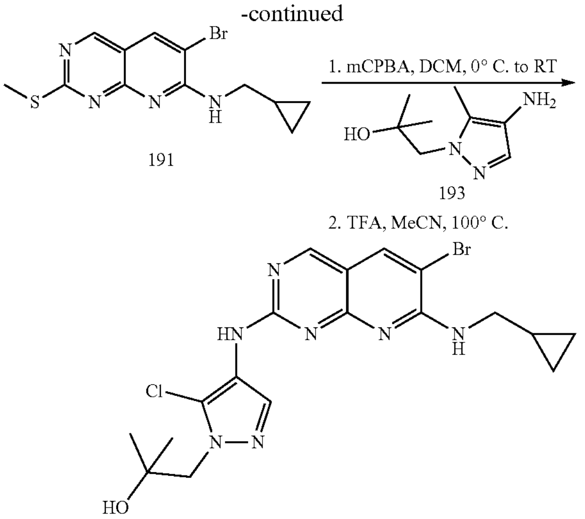

191

193

Ex-15.1

6-Bromo-N-(cyclopropylmethyl)-2-(methylthio) pyrido[2,3-d]pyrimidin-7-amine (192)

A microwave vial was charged with 6-bromo-7-chloro-2-(methylthio)pyrido[2,3-d]pyrimidine 191 (100 mg, 0.344 mmol) and cyclopropylmethanamine (0.119 mL, 1.38 mmol). The vial was sealed and purged with argon gas (3×). Then, under a positive flow of argon anhydrous NMP (1.5 ml) and DIPEA (0.240 mL, 1.38 mmol) were added. The mixture was then heated to 150° C. in the microwave for 30 min. Upon cooling, the reaction mixture was diluted with EtOAc, then partitioned between EtOAc/$H_2O$. The phases were separated and the aqueous phase extracted with EtOAc (1×20 mL). The combined organic layers were then washed with $H_2O$, then brine, dried over $Na_2SO_4$, and concentrated under reduced pressure. The residue was purified by flash chromatography over silica (EtOAc:DCM, 0-15%) to afford the title compound 192. MS (ESI): m/z calc'd for $C_{12}H_{13}BrN_4S$ [M+H]$^+$: 324, found 324.

1-[4-({6-Bromo-7-[(cyclopropylmethyl)amino] pyrido[2,3-d]pyrimidin-2-yl}amino)-5-chloro-1H-pyrazol-1-yl]-2-methylpropan-2-ol (Ex-15.1)

A 20 mL vial was charged with 6-bromo-N-(cyclopropylmethyl)-2-(methylthio)pyrido[2,3-d]pyrimidin-7-amine 192 (37 mg, 0.11 mmol). Under a positive flow of argon anhydrous DCM (3 mL) was added and the resultant mixture was cooled to 0° C. At this temperature, mCPBA (65.4 mg, 0.284 mmol) was added and the resultant mixture was stirred at 0° C. for 45 min at which time the ice bath was removed, and the reaction was allowed to slowly warm to RT. After stirring at RT for 4 h the reaction mixture was quenched by the addition of sat. aq. $Na_2S_2O_5$. The mixture was stirred for several minutes at RT then added to sat. aq. $NaHCO_3$. The layers were separated, and the aqueous phase was extracted with DCM (1×20 mL). The combined organic layers were dried over $Na_2SO_4$, filtered, and concentrated under reduced pressure. This crude residue was dissolved in MeCN (1.5 mL) and added to a 5 mL microwave vial containing 1-(4-amino-5-chloro-1H-pyrazol-1-yl)-2-methylpropan-2-ol 193 (86 mg, 0.46 mmol). To this mixture was added TFA (0.018 mL, 0.23 mmol). The resultant mixture was stirred overnight at 100° C. The reaction mixture was allowed to cool to room temperature, diluted with EtOAc, and filtered. The filtrate was then concentrated under reduced pressure. The residue was purified by reverse phase HPLC, eluting with water (0.1% $NH_4OH$)-MeCN to afford the title compound Ex-15.1. MS (ESI): m/z calc'd for $C_{18}H_{21}BrClN_7O$ [M+H]$^+$: 466, found 466. $^1H$ NMR (600 MHz, DMSO-$d_6$, 25° C.) δ 8.97 (s, 1H), 8.73 (s, 1H), 8.23 (s, 1H), 7.85 (s, 1H), 7.36 (s, 1H), 4.74 (s, 1H), 4.02 (s, 2H), 1.15 (s, 9H), 0.52-0.24 (m, 4H).

The following Examples, 15.2-15.5 were obtained using the procedure analogous to those in General Scheme 12 but substituting appropriate starting materials that are either commercially available or prepared using procedures analogous to those described in Scheme 66.

TABLE 13

| Ex | Structure | Name | Exact Mass [M + H]$^+$ |
|---|---|---|---|
| Ex-15.2 | 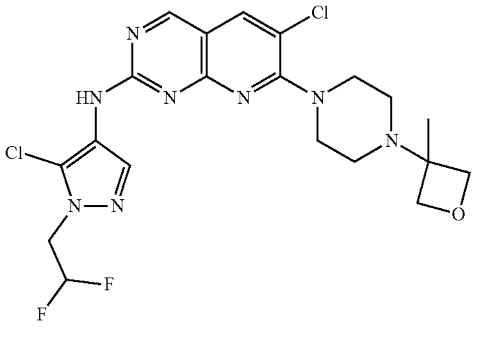 [SMILES: CC1(N2CCN(c3nc4nc(Nc5cnn(CC(F)F)c5Cl)ncc4cc3Cl)CC2)COC1] | 6-chloro-N-[5-chloro-1-(2,2-difluoroethyl)-1H-pyrazol-4-yl]-7-[4-(3-methyloxetan-3-yl)piperazin-1-yl]pyrido[2,3-d]pyrimidin-2-amine | Calc'd 499.0, found 499 |

TABLE 13-continued

| Ex | Structure | Name | Exact Mass [M + H]+ |
|---|---|---|---|
| Ex-15.3 | 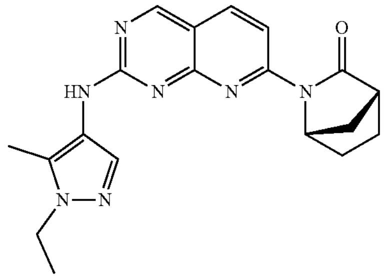 [SMILES: CCn1ncc(Nc2ncc3ccc(N4C(=O)[C@@H]5CC[C@H]4C5)nc3n2)c1C] | (1S,4R) or (1R,4S)-2-{2-[(1-ethyl-5-methyl-1H-pyrazol-4-yl)amino]pyrido[2,3-d]pyrimidin-7-yl}-2-azabicyclo[2.2.1]heptan-3-one | Calc'd 364.0, found 364 |
| Ex-15.4 | 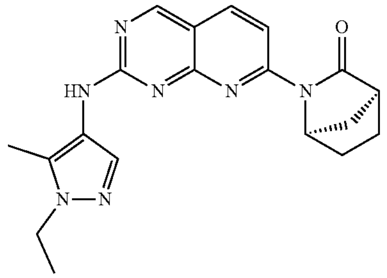 [SMILES: CCn1ncc(Nc2ncc3ccc(N4C(=O)[C@H]5CC[C@@H]4C5)nc3n2)c1C] | (1S,4R) or (1R,4S)-2-{2-[(1-ethyl-5-methyl-1H-pyrazol-4-yl)amino]pyrido[2,3-d]pyrimidin-7-yl}-2-azabicyclo[2.2.1]heptan-3-one | Calc'd 364.0, found 364 |
| Ex-15.5 | 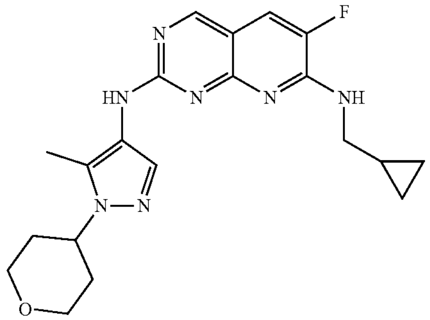 [SMILES: Cc1c(Nc2ncc3cc(F)c(NCC4CC4)nc3n2)cnn1C1CCOCC1] | N-7-(cyclopropylmethyl)-6-fluoro-N-2-[5-methyl-1-(oxan-4-yl)-1H-pyrazol-4-yl]pyrido[2,3-d]pyrimidine-2,7-diamine | Calc'd 398.0, found 398 |

General Scheme 13

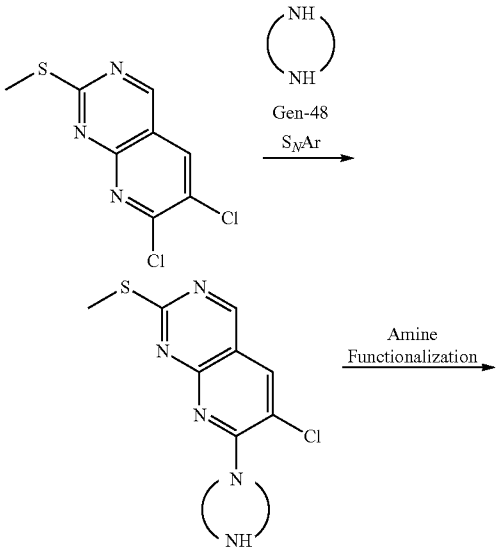

Gen-49

-continued

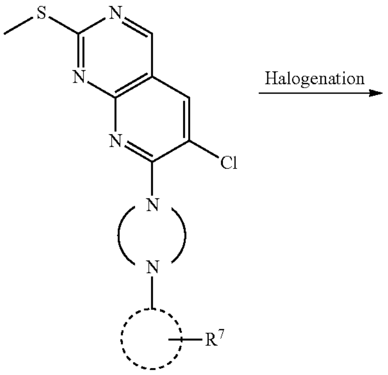

Gen-50

-continued

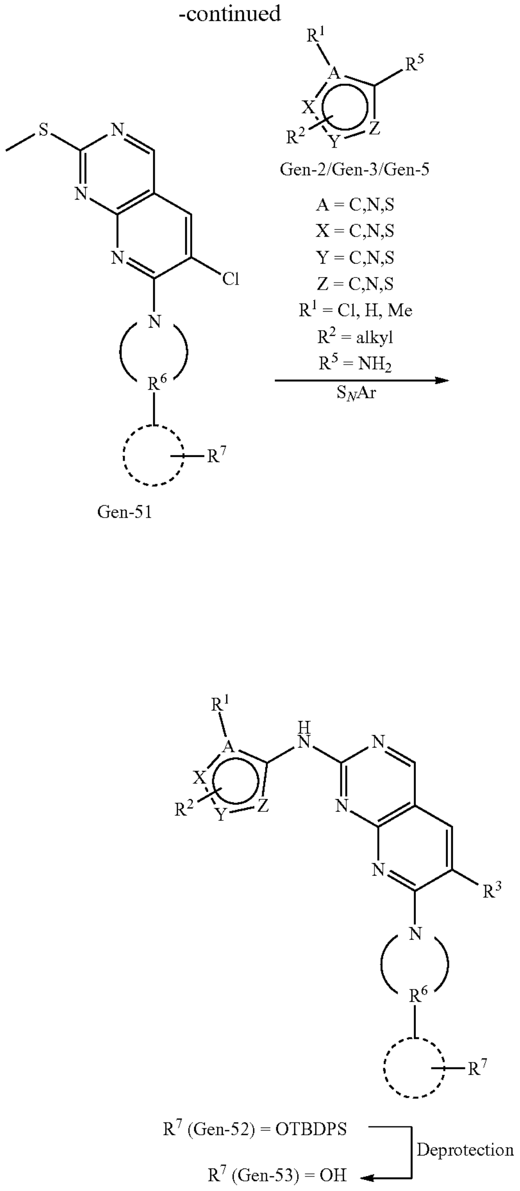

In General Scheme 13, commercially available intermediate 194 could undergo an $S_NAr$ reaction with cyclic amine Gen-48 to afford elaborated compounds of the form Gen-49. A subsequent amine functionalization reaction including but not limited to a reductive amination of Gen-49 could be performed to afford compounds of the form Gen-50. A halogenation reaction could be performed to afford compounds of the form Gen-51. An $S_NAr$ reaction utilizing amino pyrazoles Gen-2/Gen-3/Gen-5 could be performed to afford compounds of the form Gen-52. A subsequent deprotection of Gen-52 could be performed to afford compounds of the form Gen-53. Representative preparative examples from each sequence are described in more detail below.

Preparation of Examples 16.1 and 16.2

Scheme 67. Synthesis of (3S,4S) or (3R,4R)-4-(4-(6-Chloro-2-((5-chloro-1-cyclopropyl-1H-pyrazol-4-yl)amino)pyrido[2,3-d]pyrimidin-7-yl)tetrahydrofuran-3-ol

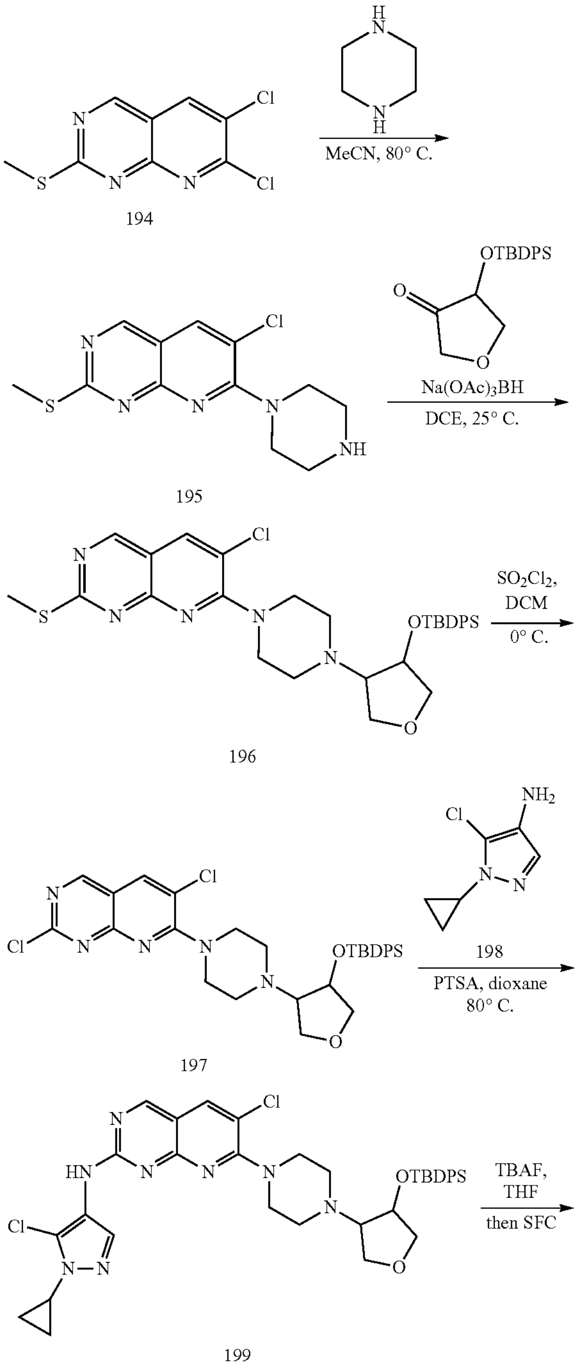

-continued

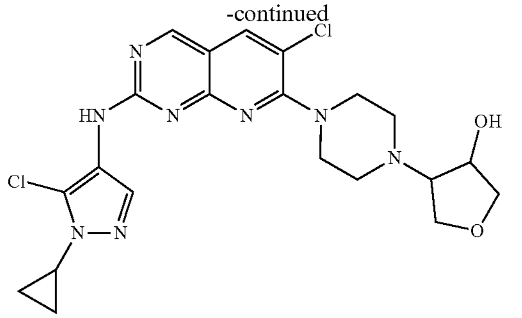

+

Ex-16.1

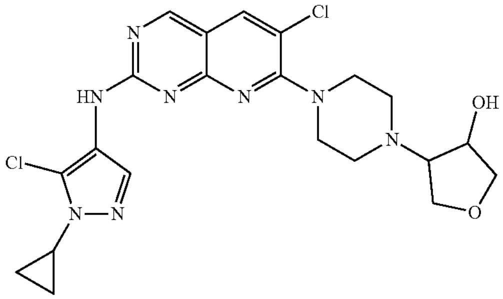

Ex-16.2

6-Chloro-2-(methylthio)-7-(piperazin-1-yl)pyrido[2,3-d]pyrimidine (195)

A flask was charged with piperazine (1.05 g, 12.2 mmol), 6,7-dichloro-2-(methylthio)pyrido[2,3-d]pyrimidine 194 (600 mg, 2.44 mmol), and MeCN (1 mL). The resultant mixture was stirred at 80° C. for 2 h. The crude mixture was filtered and concentrated under reduced pressure. The residue was purified by reverse phase HPLC, eluting with water (0.1% TFA)-MeCN to afford the title compound 195. MS (ESI): m/z calc'd for $C_{12}H_{14}ClN_5S$ $[M+H]^+$: 296, found 296.

(3S,4S) or (3R, 4R)-7-(4-(4-((Tert-butyldiphenylsilyl)oxy)tetrahydrofuran-3-yl)piperazin-1-yl)-6-chloro-2-(methylthio)pyrido[2,3-d]pyrimidine (196)

To a solution of 6-chloro-2-(methylthio)-7-(piperazin-1-yl)pyrido[2,3-d]pyrimidine 195 (300 mg, 1.01 mmol) and 4-((tert-butyldiphenylsilyl)oxy)dihydrofuran-3(2H)-one (518 mg, 1.52 mmol) in DCE (5 mL) was added $MgSO_4$ (244 mg, 2.03 mmol) and sodium triacetoxyborohydride (645 mg, 3.04 mmol). The resultant mixture was stirred at 25° C. for 2.5 h. The reaction was quenched by the addition of sat. aq. $Na_2CO_3$ solution (3 mL), carefully at first, and the mixture was stirred for 1 h (pH=9). The layers were separated, and the aqueous layer was extracted with DCM (3×10 mL). The combined organic layers were washed with brine (10 mL), dried over $MgSO_4$, filtered, and concentrated under reduced pressure. The crude product was purified by preparative TLC ($SiO_2$, PE:EtOAc=2:1) to give the title compound 196. MS (ESI): m/z calc'd for $C_{32}H_{38}ClN_5O_2SSi$ $[M+H]^+$: 620, found 620.

(3S,4S) or (3R, 4R)-7-(4-(4-((Tert-butyldiphenylsilyl)oxy)tetrahydrofuran-3-yl)piperazin-1-yl)-2,6-dichloropyrido[2,3-d]pyrimidine (197)

To a solution of 7-(4-(4-((tert-butyldiphenylsilyl)oxy)tetrahydrofuran-3-yl)piperazin-1-yl)-6-chloro-2-(methylthio)pyrido[2,3-d]pyrimidine 196 (100 mg, 0.161 mmol) in MeCN (2 mL) at 0° C. was added sulfuryl dichloride (218 mg, 1.61 mmol) in DCM (1 mL). The resultant mixture was stirred at 0° C. for 1 h. The reaction mixture was quenched by the addition of sat. aq. $NaHCO_3$ solution (1 mL). The layers were separated, and the aqueous layer was extracted with EtOAc (3×5 mL). The combined organic layers were washed with brine (10 mL), dried over $MgSO_4$, filtered, and concentrated under reduced pressure. The crude residue was purified by preparative TLC (PE:EtOAc=1:1) to afford the title compound 197. MS (ESI): m/z calc'd for $C_{31}H_{35}Cl_2N_5O_2Si$ $[M+H]^+$: 608, found 608.

(3S,4S) or (3R, 4R)-7-(4-(4-((Tert-butyldiphenylsilyl)oxy)tetrahydrofuran-3-yl)piperazin-1-yl)-6-chloro-N-(5-chloro-1-cyclopropyl-1H-pyrazol-4-yl)pyrido[2,3-d]pyrimidin-2-amine (199)

To a solution of 7-(4-(4-((tert-butyldiphenylsilyl)oxy)tetrahydrofuran-3-yl)piperazin-1-yl)-2,6-dichloropyrido[2,3-d]pyrimidine 197 (50 mg, 0.16 mmol) and 5-chloro-1-cyclopropyl-1H-pyrazol-4-amine 198 (52 mg, 0.33 mmol) in 1,4-dioxane (1 mL) was added 4-methylbenzenesulfonic acid (5.7 mg, 0.030 mmol). The resultant mixture was stirred at 80° C. for 16 h. The reaction mixture was poured into water (5 mL) and extracted with EtOAc (3×5 mL). The combined organic layers were washed with brine (10 mL), dried over $Na_2SO_4$, filtered, and concentrated under reduced pressure. The crude residue containing 199 was carried forward to the next step without purification. MS (ESI): m/z calc'd for $C_{37}H_{42}C_{12}N_8O_2Si$ $[M+H]^+$: 729, found 729.

(3S,4S) or (3R, 4R)-4-(4-(6-Chloro-2-((5-chloro-1-cyclopropyl-1H-pyrazol-4-yl)amino)pyrido[2,3-d]pyrimidin-7-yl)piperazin-1-yl)tetrahydrofuran-3-ol (Ex-16.1 and Ex-16.2)

To a solution of 7-(4-(4-((tert-butyldiphenylsilyl)oxy)tetrahydrofuran-3-yl)piperazin-1-yl)-6-chloro-N-(5-chloro-1-cyclopropyl-1H-pyrazol-4-yl)pyrido[2,3-d]pyrimidin-2-amine 199 (70 mg, 0.14 mmol) in THF (2 mL) was added TBAF (0.16 mL, 0.16 mmol, 1.0 M in THF). The resultant mixture was stirred at 50° C. for 1 h. The reaction mixture was filtered and concentrated under reduced pressure and the crude product was purified by reverse phase HPLC, eluting with water (0.1% TFA)-MeCN to afford the racemic mixture of compounds. The racemic mixture was submitted to SFC chiral separation (Column OD-3, 4.6×50 mm; Mobile Phase A: $CO_2$; Mobile Phase B: EtOH+0.05% DEA) to afford the title compounds Ex-16.1 ($t_R$=0.975 min) and Ex-16.2 ($t_R$=1.21 min). Isomer 1 (Ex-16.1): MS (ESI): m/z calc'd for $C_{21}H_{24}Cl_2N_8O_2$ $[M+H]^+$: 491, found 491. $^1$H NMR (400 MHz, $CDCl_3$, 25° C.) δ 8.85 (s, 1H), 8.08 (s, 1H), 7.94-7.81 (m, 1H), 7.88 (s, 1H), 4.30 (t, J=3.5 Hz, 1H), 4.03-3.94 (m, 2H), 3.87 (d, J=9.8 Hz, 1H), 3.79 (m, 1H), 3.74 (s, 3H), 3.54 (m, 1H), 2.88-2.75 (m, 3H), 2.61-2.52 (m, 2H), 1.28 (s, 1H), 1.22-1.15 (m, 2H), 1.15-1.09 (m, 2H). Isomer 2 (Ex-16.2): MS (ESI): m/z calc'd for $C_{21}H_{24}Cl_2N_8O_2$ $[M+H]^+$: 491, found 491. $^1$H NMR (400 MHz, $CDCl_3$, 25° C.) δ 8.76 (s, 1H), 7.99 (s, 1H), 7.78 (s, 1H), 4.21 (t, J=3.5 Hz, 1H), 3.95-3.86 (m, 2H), 3.79-3.74 (m, 1H), 3.70 (m, 1H), 3.64 (s, 3H), 3.43 (m, 1H), 3.23-3.18 (m, 2H), 2.82-2.70 (m, 3H), 2.54-2.47 (m, 2H), 1.18 (s, 1H), 1.11-1.06 (m, 2H), 1.05-0.98 (m, 2H).

The following Examples, 16.3-16.4 were obtained using the procedure analogous to those in General Scheme 13 but substituting appropriate starting materials that are either commercially available or prepared using procedures analogous to those described in Scheme 67.

TABLE 14

| Ex | Structure | Name | Exact Mass $[M + H]^+$ |
|---|---|---|---|
| Ex-16.3 | 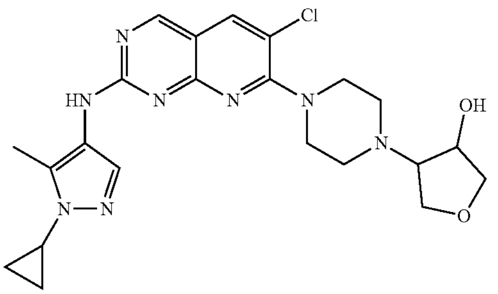 | (3S,4S) or (3R,4R)-4-(4-{6-chloro-2-[(1-cyclopropyl-5-methyl-1H-pyrazol-4-yl)amino]pyrido[2,3-d]pyrimidin-7-yl}piperazin-1-yl)oxolan-3-ol | Calc'd 471.0, found 471 |
| Ex-16.4 | 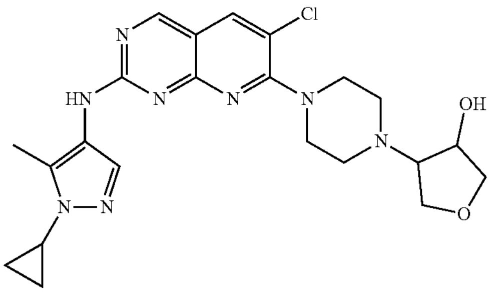 [SMILES: Cc1c(Nc2ncc3cc(Cl)c(N4CCN(C5COCC5O)CC4)nc3n2)cnn1C1CC1] | (3S,4S) or (3R,4R)-4-(4-{6-chloro-2-[(1-cyclopropyl-5-methyl-1H-pyrazol-4-yl)amino]pyrido[2,3-d]pyrimidin-7-yl}piperazin-1-yl)oxolan-3-ol | Calc'd 471.0, found 471 |

The compounds in Table 15, surprisingly and advantageously, exhibit exceptional potency as inhibitors of LRRK2 kinase. The $IC_{50}$ values reported herein were measured as follows.

Biological Assay: LRRK2 Km ATP LanthaScreen™ Assay

The LRRK2 kinase activity reported herein as IC50 values was determined with LanthaScreen™ technology from Life Technologies Corporation (Carlsbad, CA) using GST-tagged truncated human mutant G2019S LRRK2 in the presence of the fluorescein-labeled peptide substrate LRRKtide, also from Life Technologies. The data presented for the Km ATP LanthaScreen™ Assay represents mean $IC_{50}$ values based on several test results and may have reasonable deviations depending on the specific conditions and reagents used. Assays were performed in the presence of 134 μM ATP (Km ATP). Upon completion, the assay was stopped and phosphorylated substrate detected with a terbium (Tb)-labeled anti-pERM antibody (cat. no. PV4898). The compound dose response was prepared by diluting a 10 mM stock of compound to a maximum concentration of 9.99 μM in 100% dimethylsulfoxide followed by custom fold serial dilution in dimethylsulfoxide nine times. Twenty nanoliters of each dilution was spotted via a Labcyte Echo onto a 384-well black-sided plate (Corning 3575) followed by 15 μl of a 1.25 nM enzyme solution in 1× assay buffer (50 mM Tris pH 8.5, 10 mM MgCl2, 0.01% Brij-35, 1 mM EGTA, 2 mM dithiothreitol, 0.05 mM sodium orthovanadate). Following a 15-minute incubation at room temperature, the kinase reaction was started with the addition of 5 μl of 400 nM fluorescein-labeled LRRKtide peptide substrate and 134 μM ATP solution in 1× assay buffer. The reaction was allowed to progress at ambient temperature for 90 minutes. The reaction was then stopped by the addition of 20 μl of TR-FRET Dilution Buffer (Life Technologies, Carlsbad, CA) containing 2 nM Tb-labeled anti-phospho LRRKtide antibody and 10 mM EDTA (Life Technologies, Carlsbad, CA). After an incubation of 1 hour at room temperature, the plate was read on an EnVision multimode plate reader (Perkin Elmer, Waltham, MA) with an excitation wavelength of 337 nm (Laser) and a reading emission at both 520 and 495 nm. Compound IC50s were interpolated from nonlinear regression best fits of the log of the final compound concentration, plotted as a function of the 520/495-nm emission ratio using Activity base. Abase uses a 4 parameter (4P) logistic fit based on the Levenberg-Marquardt algorithm.

TABLE 15

| Ex. | LRRK2 pIC50 (nM) |
|---|---|
| Ex-1.1 | 0.7159 |
| Ex-1.2 | 8.413 |
| Ex-1.3 | 180.2 |
| Ex-1.4 | 1.543 |
| Ex-1.5 | 0.625 |
| Ex-1.6 | 1.894 |
| Ex-1.7 | 6.913 |
| Ex-1.8 | 15.95 |
| Ex-1.9 | 36.06 |
| Ex-1.10 | 13.32 |
| Ex-1.11 | 33.2 |
| Ex-1.12 | 20.24 |
| Ex-1.13 | 20.97 |
| Ex-1.14 | 4.705 |
| Ex-1.15 | 5.49 |
| Ex-1.16 | 16.03 |
| Ex-1.17 | 9.256 |
| Ex-1.18 | 18.92 |
| Ex-1.19 | 4.866 |
| Ex-1.20 | 8.228 |
| Ex-1.21 | 6.092 |
| Ex-1.22 | 6.936 |
| Ex-1.23 | 32.61 |
| Ex-1.24 | 2.594 |
| Ex-1.25 | 4.326 |
| Ex-1.26 | 1.492 |

TABLE 15-continued

| Ex. | LRRK2 pIC50 (nM) |
|---|---|
| Ex-1.27 | 0.7783 |
| Ex-1.28 | 3.309 |
| Ex-1.29 | 2.783 |
| Ex-1.30 | 7.163 |
| Ex-1.31 | 10.12 |
| Ex-1.32 | 5.488 |
| Ex-1.33 | 26.12 |
| Ex-1.34 | 1.392 |
| Ex-1.35 | 3.477 |
| Ex-1.36 | 6.716 |
| Ex-1.37 | 1.712 |
| Ex-1.38 | 9.772 |
| Ex-1.39 | 37.94 |
| Ex-1.39 | 11.09 |
| Ex-1.40 | 11.24 |
| Ex-1.41 | 8.929 |
| Ex-1.42 | 25.6 |
| Ex-1.43 | 12.65 |
| Ex-1.44 | 22.27 |
| Ex-1.45 | 21.27 |
| Ex-1.46 | 0.625 |
| Ex-1.47 | 38.81 |
| Ex-1.48 | 0.625 |
| Ex-2.1 | 0.5762 |
| Ex-2.2 | 35.98 |
| Ex-2.3 | 1.774 |
| Ex-2.4 | 0.279 |
| Ex-3.1 | 0.09295 |
| Ex-3.2 | 1.061 |
| Ex-3.3 | 17.22 |
| Ex-3.4 | 19.9 |
| Ex-3.5 | 1.54 |
| Ex-3.6 | 0.625 |
| Ex-3.7 | 1.435 |
| Ex-3.8 | 2.532 |
| Ex-3.9 | 5.901 |
| Ex-3.10 | 0.4069 |
| Ex-3.11 | 0.4876 |
| Ex-3.12 | 0.2208 |
| Ex-3.13 | 1.537 |
| Ex-3.14 | 0.1061 |
| Ex-3.15 | 0.2274 |
| Ex-3.16 | 0.2183 |
| Ex-3.17 | 2.281 |
| Ex-3.18 | 1.949 |
| Ex-3.19 | 5.771 |
| Ex-3.20 | 1.075 |
| Ex-3.21 | 4.015 |
| Ex-3.22 | 0.9539 |
| Ex.3.23 | 3.453 |
| Ex-3.24 | 3.682 |
| Ex-3.25 | 1.21 |
| Ex-3.26 | 5.63 |
| Ex-3.27 | 0.4864 |
| Ex-3.28 | 4.516 |
| Ex-3.29 | 8.786 |
| Ex-3.30 | 5.086 |
| Ex-3.31 | 2.075 |
| Ex-3.32 | 0.3933 |
| Ex-3.33 | 1.148 |
| Ex-3.34 | 0.594 |
| Ex-3.35 | 1.414 |
| Ex-3.36 | 3.023 |
| Ex-3.37 | 29.92 |
| Ex-3.38 | 6.619 |
| Ex-3.39 | 3.232 |
| Ex-3.40 | 9.759 |
| Ex-3.41 | 22.99 |
| Ex-3.42 | 7.369 |
| Ex-3.43 | 0.4378 |
| Ex-3.44 | 19.48 |
| Ex-3.45 | 23.52 |
| Ex-3.46 | 15.02 |
| Ex-3.47 | 10.19 |
| Ex-3.48 | 1.457 |
| Ex-3.49 | 1.329 |
| Ex-3.50 | 0.8205 |
| Ex-3.51 | 16.29 |

TABLE 15-continued

| Ex. | LRRK2 pIC50 (nM) |
|---|---|
| Ex-3.52 | 0.8866 |
| Ex-3.53 | 6.885 |
| Ex-3.54 | 8.428 |
| Ex-3.55 | 12.08 |
| Ex-3.56 | 3.561 |
| Ex-3.57 | 23.07 |
| Ex-3.58 | 0.44 |
| Ex-3.59 | 0.178 |
| Ex-3.60 | 0.20 |
| Ex-4.1 | 10.99 |
| Ex-4.2 | 0.625 |
| Ex-4.3 | 3.358 |
| Ex-4.4 | 24.57 |
| Ex-4.5 | 7.263 |
| Ex-4.6 | 34.88 |
| Ex-4.7 | 3.187 |
| Ex-4.8 | 8.946 |
| Ex-4.9 | 9.163 |
| Ex-4.10 | 34.29 |
| Ex-4.11 | 35.33 |
| Ex-4.12 | 0.625 |
| Ex-4.13 | 6.825 |
| Ex-4.14 | 0.9694 |
| Ex-4.15 | 19.32 |
| Ex-4.16 | 1.124 |
| Ex-4.17 | 2.32 |
| Ex-4.18 | 2.39 |
| Ex-4.19 | 3.031 |
| Ex-4.20 | 2.589 |
| Ex-4.21 | 36.82 |
| Ex-4.22 | 0.625 |
| Ex-4.23 | 2.473 |
| Ex-4.24 | 218 |
| Ex-4.25 | 570 |
| Ex-4.26 | 9.087 |
| Ex-4.27 | 1.602 |
| Ex-4.28 | 1.051 |
| Ex-4.29 | 5.282 |
| Ex-4.30 | 15.67 |
| Ex-4.31 | 1.008 |
| Ex-4.32 | 2.025 |
| Ex-4.33 | 4.754 |
| Ex-4.34 | 0.625 |
| Ex-4.35 | 4.907 |
| Ex-4.36 | 6.059 |
| Ex-4.37 | 1.241 |
| Ex-4.38 | 29.37 |
| Ex-4.39 | 0.625 |
| Ex-4.40 | 15.18 |
| Ex-4.41 | 1.907 |
| Ex-4.42 | 6.555 |
| Ex-4.43 | 3.52 |
| Ex-4.44 | 20 |
| Ex-4.45 | 1.268 |
| Ex-4.46 | 0.7921 |
| Ex-4.47 | 8.558 |
| Ex-4.48 | 0.625 |
| Ex-4.49 | 1.87 |
| Ex-4.50 | 4.614 |
| Ex-4.51 | 2.758 |
| Ex-4.52 | 1.886 |
| Ex-4.53 | 1.821 |
| Ex-4.54 | 2.871 |
| Ex-4.55 | 11.05 |
| Ex-4.56 | 0.625 |
| Ex-4.57 | 4.132 |
| Ex-4.58 | 2.322 |
| Ex-4.59 | 5.26 |
| Ex-4.60 | 3.241 |
| Ex-4.61 | 7.3 |
| Ex-4.62 | 0.7933 |
| Ex-4.63 | 28.3 |
| Ex-4.64 | 9.727 |
| Ex-4.65 | 23.86 |
| Ex-4.66 | 8.883 |
| Ex-4.67 | 23.8 |
| Ex-4.68 | 3.381 |
| Ex-4.69 | 3.225 |

TABLE 15-continued

| Ex. | LRRK2 pIC50 (nM) |
|---|---|
| Ex-4.70 | 4.931 |
| Ex-4.71 | 11.11 |
| Ex-5.1 | 0.1053 |
| Ex-5.2 | 0.45 |
| Ex-5.3 | 0.31 |
| Ex-5.4 | 0.18 |
| Ex-5.5 | 0.42 |
| Ex-5.6 | 0.403 |
| Ex-5.7 | 0.197 |
| Ex-5.8 | 0.17 |
| Ex-5.9 | 0.64 |
| Ex-5.10 | 5.67 |
| Ex-5.11 | 2.822 |
| Ex-5.12 | 5.165 |
| Ex-5.13 | 1.052 |
| Ex-5.14 | 11.63 |
| Ex-5.15 | 25.1 |
| Ex-5.16 | 20.95 |
| Ex-6.1 | 5.676 |
| Ex-6.2 | 0.08 |
| Ex-6.3 | 10.29 |
| Ex-6.4 | 1.921 |
| Ex-6.5 | 27.26 |
| Ex-6.6 | 4.023 |
| Ex-6.7 | 1.586 |
| Ex-6.8 | 16.34 |
| Ex-6.9 | 1.788 |
| Ex-6.10 | 0.1996 |
| Ex-6.11 | 0.8078 |
| Ex-6.12 | 1.24 |
| Ex-6.13 | 0.9761 |
| Ex-6.14 | 1.651 |
| Ex-6.15 | 3.574 |
| Ex-6.16 | 1.571 |
| Ex-6.17 | 10.52 |
| Ex-6.18 | 0.3224 |
| Ex-6.19 | 2.17 |
| Ex-6.20 | 2.533 |
| Ex-6.21 | 0.3232 |
| Ex-6.22 | 33.5 |
| Ex-6.23 | 13.15 |
| Ex-6.24 | 0.6025 |
| Ex-6.25 | 0.4179 |
| Ex-6.26 | 11.53 |
| Ex-6.27 | 0.2703 |
| Ex-6.28 | 0.3807 |
| Ex-6.29 | 15.19 |
| Ex-6.30 | 0.9 |
| Ex-6.31 | 17.89 |
| Ex-6.32 | 0.6076 |
| Ex-6.33 | 0.2116 |
| Ex-6.34 | 10.6 |
| Ex-6.35 | 20.81 |
| Ex-6.36 | 11.21 |
| Ex-6.37 | 6.354 |
| Ex-6.38 | 0.835 |
| Ex-6.39 | 0.6503 |
| Ex-6.40 | 0.3525 |
| Ex-6.41 | 32.95 |
| Ex-6.42 | 21.45 |
| Ex-6.43 | 7.921 |
| Ex-6.44 | 6.891 |
| Ex-6.45 | 0.8429 |
| Ex-6.46 | 18.38 |
| Ex-6.47 | 0.85 |
| Ex-6.48 | 11.43 |
| Ex-6.49 | 2.07 |
| Ex-6.50 | 0.08 |
| Ex-6.51 | 1.35 |
| Ex-6.52 | 3.119 |
| Ex-6.53 | 0.522 |
| Ex-6.54 | 1.207 |
| Ex-6.55 | 2.11 |
| Ex-6.56 | 0.080 |
| Ex-7.1 | 0.9888 |
| Ex-7.2 | 0.625 |
| Ex-7.3 | 0.9757 |
| Ex-7.4 | 6.746 |
| Ex-7.5 | 33.7 |
| Ex-7.6 | 1.572 |
| Ex-7.7 | 1.919 |
| Ex-7.8 | 10.97 |
| Ex-7.9 | 34 |
| Ex-7.10 | 5.142 |
| Ex-7.11 | 9.346 |
| Ex-7.12 | 0.625 |
| Ex-7.13 | 11.39 |
| Ex-7.14 | 0.7492 |
| Ex-7.15 | 9.26 |
| Ex-7.16 | 0.625 |
| Ex-7.17 | 54.9 |
| Ex-7.18 | 8.733 |
| Ex-7.19 | 2.532 |
| Ex-7.20 | 11.26 |
| Ex-7.21 | 0.625 |
| Ex-8.1 | 4.409 |
| Ex-8.2 | 5.97 |
| Ex-8.3 | 0.745 |
| Ex-8.4 | 25.87 |
| Ex-8.5 | 0.625 |
| Ex-8.6 | 4.855 |
| Ex-8.7 | 5.197 |
| Ex-8.8 | 5.083 |
| Ex-8.9 | 8.029 |
| Ex-8.10 | 0.625 |
| Ex-8.11 | 1.591 |
| Ex-8.12 | 1.634 |
| Ex-8.13 | 0.625 |
| Ex-8.14 | 7.792 |
| Ex-8.15 | 2.59 |
| Ex-8.16 | 5.97 |
| Ex-9.1 | 4.68 |
| Ex-9.2 | 1.06 |
| Ex-10.1 | 7.01 |
| Ex-11.1 | 11.7 |
| Ex-12.1 | 2.93 |
| Ex-12.2 | 0.721 |
| Ex-12.3 | 186 |
| Ex-12.4 | 3.04 |
| Ex-12.5 | 0.56 |
| Ex-12.6 | 13.6 |
| Ex-12.7 | 4.36 |
| Ex-12.8 | 0.088 |
| Ex-12.9 | 8.64 |
| Ex-12.10 | 2.128 |
| Ex-13.1 | 0.116 |
| Ex-13.2 | 3.808 |
| Ex-13.3 | 6.98 |
| Ex-13.4 | 0.267 |
| Ex-13.5 | 9.89 |
| Ex-13.6 | 0.668 |
| Ex-13.7 | 31.63 |
| Ex-13.8 | 1.69 |
| Ex-13.9 | 97.5 |
| Ex-14.1 | 4.105 |
| Ex-15.1 | 36.74 |
| Ex-15.2 | 60.82 |
| Ex-15.3 | 4.428 |
| Ex-15.4 | 12.47 |
| Ex-15.5 | 32.57 |
| Ex-16.1 | 15.56 |
| Ex-16.2 | 125.5 |
| Ex-16.3 | 4.552 |
| Ex-16.4 | 83.79 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound having a structural Formula (I):

(I)

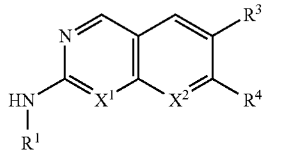

or a pharmaceutically acceptable salt thereof, wherein:

$X^1$ is N or CH;

$X^2$ is N or $CR^2$;

R1 is selected from:

(i)

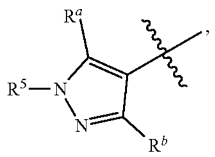

(ii)

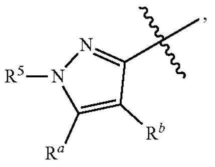

(iii)

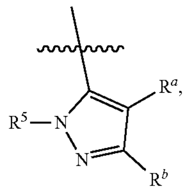

(iv)

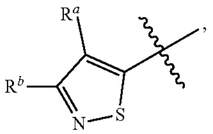

(v)

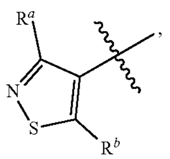

and

-continued (vi)

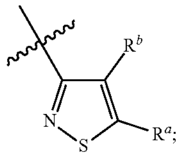

$R^2$ is selected from H, $C_{1-6}$ alkyl, and Cl, $R^3$ is selected from H, Cl, CN, and $C_{1-6}$ alkyl;

$R^4$ represents NRR', or an N-linked $C_{4-10}$ heterocyclyl, said heterocyclyl optionally substituted with 1 to 3 groups of $R^d$, each R represents H, or $C_{1-6}$ alkyl;

R' is selected from H, $C_{1-6}$ alkyl, $C_{3-6}$ cycloalkyl, and $C_{4-10}$ heterocyclyl, said alkyl, cycloalkyl and heterocyclyl are optionally substituted with 1 to 3 groups of $R^e$;

$R^5$ is selected from hydrogen, $C_{1-6}$ alkyl, $C_{1-6}$ alkylOR, $C_{1-3}$ haloalkyl, —$(CH_2)$nC4-10 heterocyclyl, —$(CH_2)$nC3-10 cycloalkyl, —$(CH_2)$nC5-10 heteroaryl, said alkyl, cycloalkyl, heteroaryl, and heterocyclyl are optionally substituted with 1 to 3 groups of $R^c$;

$R^a$ and $R^b$ are independently selected from hydrogen, halogen, $C_{1-6}$ alkyl, $C_{1-3}$ haloalkyl, —$(CH_2)$nC5-10 heteroaryl, and $C_{3-6}$cycloalkyl, or $R^5$ and $R^a$ in (i) and (ii) of $R^1$ can combine with the nitrogen and carbon atoms to which they are attached, respectively, to form a six membered ring;

$R^c$ is selected from OR, halogen, $(CH_2)_n$CN, $C_{1-3}$ haloalkyl, $C_{1-6}$ alkyl, $C_{1-6}$ alkylOR, $C_{1-3}$ haloalkyl, and $C_{4-10}$heterocyclyl, said alkyl and heterocyclyl are optionally substituted with 1 to 3 groups of $C_{1-6}$ alkyl or CN;

$R^d$ is selected from oxo, OR, $C_{1-6}$ alkyl, $C_{1-6}$ alkylOR, $CH_2CF_3$, $C_{4-10}$heterocyclyl, —$(CH_2)$nC3-10 cycloalkyl, C(O) $C_{1-6}$ alkyl, and NRR, said alkyl, heterocyclyl and cycloalkyl are optionally substituted with 1 to 3 groups of $R^e$;

$R^c$ is selected from OR, $C_{1-6}$ alkyl, CN, and fluorine; and

Each n is independently 1, 2, 3, or 4.

2. The compound according to claim 1 wherein $X^1$ is N, $X^2$ is CH.

3. The compound according to claim 1 wherein $R^1$ is structural formula (i).

4. The compound according to claim 1 wherein $R^1$ is structural formula (ii).

5. The compound according to claim 1 wherein $R^1$ is structural formula (iii).

6. The compound according to claim 1 wherein $R^1$ is structural formula (iv).

7. The compound according to claim 1 wherein $R^1$ is selected from structural formula (v), and (vi).

8. The compound according to claim 1 wherein $R^5$ of $R^1$ is selected from the group consisting of $CH_3$, $CH_2CH_3$, $CH_2CHF_2$, $(CH_2)_2F$, $CH_2CF_3$, $CHF_2$, $(CH_2)_nC(CH_3)_3$, $CH_2C(CH_3)_2OH$, $CH_2CH(OH)CH_2C(CH_3)_2OH$, $C(CH_3)_2CN$, $(CH_2)_2CN$, $(CH_2)_n$cyclopropyl, $(CH_2)_n$cyclobutyl, $(CH_2)_n$cyclopentyl, $(CH_2)_n$cyclohexyl, $(CH_2)_n$oxetanyl, azetidinyl, piperazinyl, piperidinyl, oxanyl, bicyclopentanyl, dihydropyrrolopyrazolo, azaspiroheptanyl, and tetrahydropyrazolopyridinyl, said cyclopropyl, cyclobutyl, cyclopentyl, cyclohexyl, oxetanyl, azetidinyl, piperazinyl, piperidinyl, oxanyl, bicyclopentanyl, dihydropyrrolopyrazolo, azaspiroheptanyl, and tetrahydropyrazolopyridinyl are optionally substituted with 1 to 3 groups of $R^c$.

9. The compound of claim 1 wherein $R^3$ is selected from the group consisting of hydrogen, chlorine, CN and methyl.

10. The compound of claim 1 wherein $R^4$ is selected from the group consisting of N-linked piperazinyl, oxetanylpiperidinyl, pyrrolidinyl, azetidinyl, diazaspirononanyl, piperidinyl, azabicyclohexanyl, dihydrotriazolopyrazinyl, diazabicycloheptanyl, azabicycloheptanyl, azabicyclooctanyl, pyrrolopyridinyl, oxazolidinonyl, azaspirodecanyl, pyrazolopyridinyl, oxaazaspirodecanonyl, azabicycloheptanonyl, azaspiroheptanyl, diazaspiroheptanyl, piperazinonyl, piperazinyltetrahydrofuranyl, oxazolidinonyl, and azabicycloheptanonyl, said group optionally substituted with 1 to 3 groups of $R^d$ selected from $C_{1-6}$ alkyl, $CH_2$ $(CH_3)$ 2OH, OH, $OCH_3$, $CH_2OH$, $CH_2CF_3$, $N(CH_3)_2$, $(CH_2)_2CN$, $C(O)CH_3$, oxo, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl are optionally substituted with 1 to 3 groups of $R^e$.

11. The compound according to claim 1 wherein $R^4$ is NRR' selected from the group consisting of $N(CH_3)$ 2, $NHCH_3$, $NHCH_2CH_3$, $NHCH(CH_3)$ 2, $NHCH_2$cyclopropyl, and $N(CH_3)$ oxetanyl.

12. The compound according to claim 1 wherein $R^a$ and $R^b$ are independently selected from the group consisting of hydrogen, chloro, fluoro, methyl, ethyl, isopropyl, t-butyl, $CF_3$, $CHF_2$, cyclopropyl, and $C(CH_3)_2$-triazolyl.

13. The compound according to claim 12 wherein at least one of $R^a$ and $R^b$ is hydrogen and the other is selected from the group consisting of chlorine, methyl, $CF_3$, $CHF_2$, and cyclopropyl.

14. The compound according to claim 1 represented by structural Formula II:

II

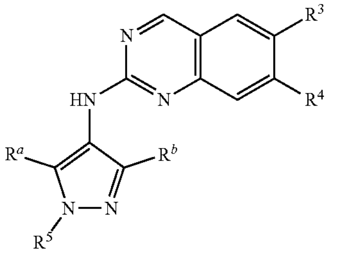

or a pharmaceutically acceptable salt thereof, wherein $R^a$ and $R^b$ are independently selected from the group consisting of hydrogen, chlorine, methyl, $CF_3$, $CHF_2$, and cyclopropyl, $R^3$ is selected from the group consisting of $CH_3$, chlorine, fluorine, bromine, hydrogen, and CN, $R^4$ is selected from the group consisting of a1

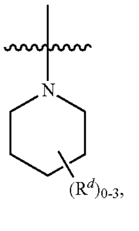

-continued a2

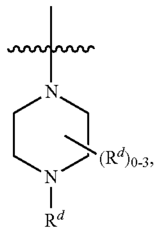

a3

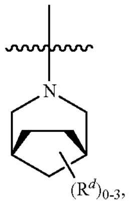

a4

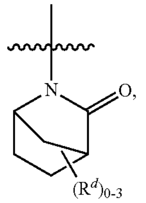

a5

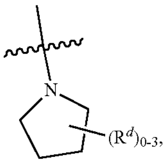

a6

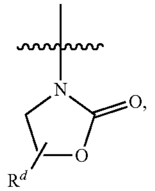

and a7

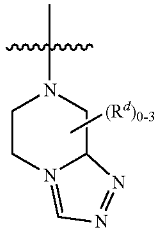

wherein $R^d$ is selected from the group consisting of $C_{1-6}$ alkyl, $CH_2(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl are optionally substituted with 1 to 3 groups of $R^e$, and $R^5$ is selected from the group consisting of $CH_3$, $CH_2CH_3$, $(CH_2)$ 2F, $CH_2CF_3$, $CHF_2$, $CH_2C(CH_3)_2OH$, $(CH_2)_n$cyclopropyl, $(CH_2)_n$oxetanyl, piperazinyl, piperidinyl, and bicyclopentanyl, said cyclopropyl, oxetanyl, piperazinyl, piperidinyl, and bicyclopentanyl are optionally substituted with 1 to 3 groups of $R^c$.

15. The compound according to claim 1 represented by structural Formula III:

Formula III

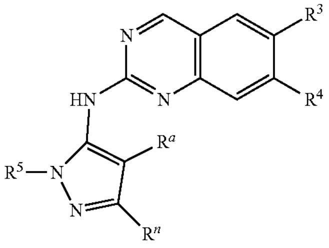

or a pharmaceutically acceptable salt thereof, wherein $R^a$ and $R^b$ are independently selected from the group consisting of hydrogen, chlorine, methyl, $CF_3$, $CHF_2$, and cyclopropyl, $R^3$ is selected from the group consisting of $CH_3$, chlorine, fluorine bromine, hydrogen, and CN, $R^4$ is selected from the group consisting of a1

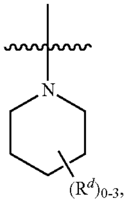

a2

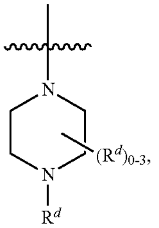

a3

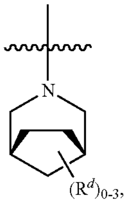

a4

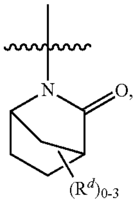

a5

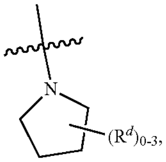

-continued a6

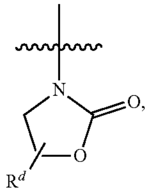

and a7

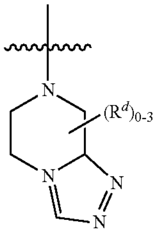

wherein $R^d$ is selected from the group consisting of $C_{1-6}$ alkyl, $CH_2$ $(CH_3)_2OH$, OH, $OCH_3$, $CH_2OH$, $CH_2CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl are optionally substituted with 1 to 3 groups of $R^e$, and $R^5$ is selected from the group consisting of $CH_3$, $CH_2CH_3$, $(CH_2)_2F$, $CH_2CF_3$, $CHF_2$, $CH_2C(CH_3)_2OH$, $(CH_2)$cyclopropyl, $(CH_2)_n$oxetanyl, piperazinyl, piperidinyl, and bicyclopentanyl, said cyclopropyl, oxetanyl, piperazinyl, piperidinyl, and bicyclopentanyl are optionally substituted with 1 to 3 groups of $R^c$.

16. The compound according to claim 1 represented by structural Formula IV:

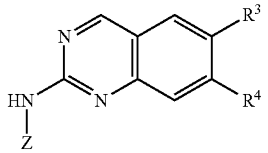

Z is

Formula IV (v)

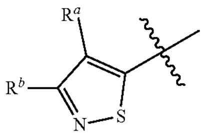

(vi)

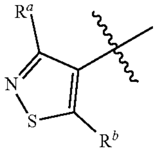

or

-continued (vii)

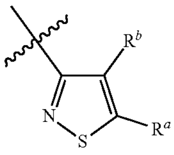

or a pharmaceutically acceptable salt thereof, wherein $R^a$ and $R^b$ are independently selected from the group consisting of hydrogen, chlorine, methyl, $CF_3$, $CHF_2$, and cyclopropyl, $R^3$ is selected from the group consisting of $CH_3$, chlorine, fluorine, bromine, hydrogen, and CN, $R^4$ is selected from the group consisting of:

a1

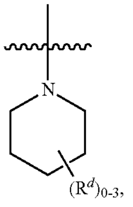

a2

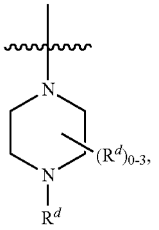

a3

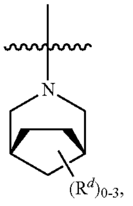

-continued a4

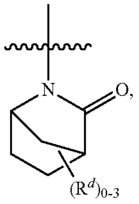

a5

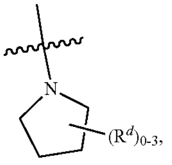

a6

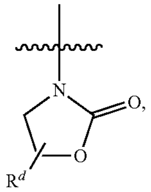

and a7

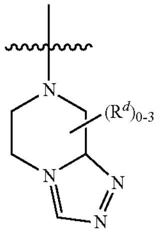

wherein $R^d$ is selected from the group consisting of $C_{1-6}$ alkyl, $CH_2(CH_3)_2OH$, OH, $OCH_3$, $CH_2OH$, $CH_3CF_3$, $N(CH_3)_2$, $(CH_2)_2CN$, $C(O)CH_3$, cyclopropyl, cyclopentanyl, azetidinyl, oxetanyl, oxolanyl, pyrrolidinyl, and tetrahydrofuranyl, said alkyl, cyclopropyl, cyclopentanyl, azetidinyl, oxetanyl, oxolanyl, pyrrolidinyl, and tetrahydrofuranyl are optionally substituted with 1 to 3 groups of $R^e$.

17. The compound of claim 1, or a pharmaceutically acceptable salt thereof, wherein said compound is selected from the group consisting of:

| Ex | Structure |
|---|---|
| Ex-1.1 | 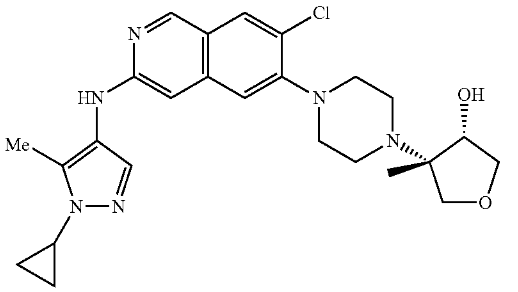 [SMILES: Cc1c(Nc2cc3cc(N4CCN([C@@]5(C)COC[C@H]5O)CC4)c(Cl)cc3cn2)cnn1C1CC1] |

-continued
| Ex | Structure |
| --- | --- |
| Ex-1.2 | 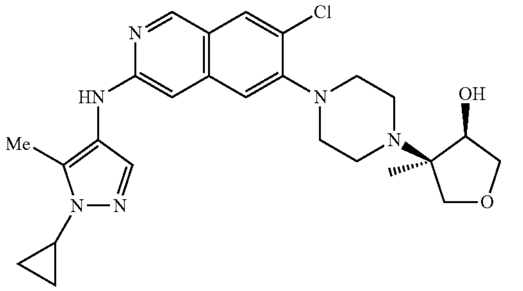 [SMILES: Cc1c(Nc2cc3cc(N4CCN([C@]5(C)COC[C@@H]5O)CC4)c(Cl)cc3cn2)cnn1C1CC1] |
| Ex-1.3 | 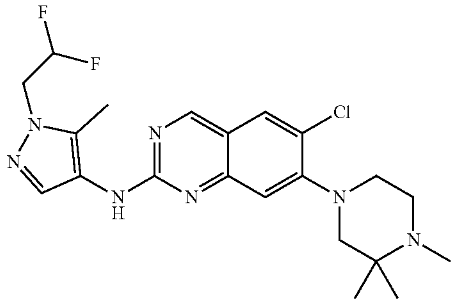 [SMILES: Cc1c(Nc2ncc3cc(Cl)c(N4CCN(C)C(C)(C)C4)cc3n2)cnn1CC(F)F] |
| Ex-1.4 | 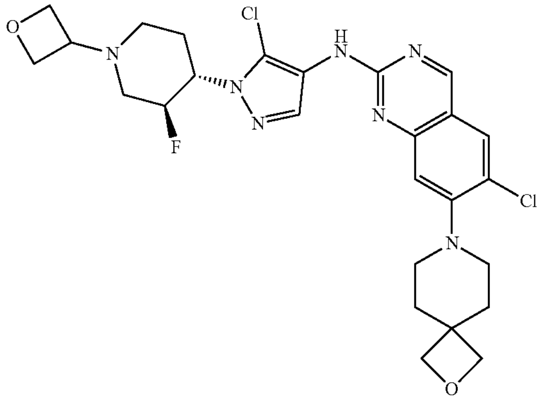 [SMILES: F[C@H]1CN(C2COC2)CC[C@@H]1n1ncc(Nc2ncc3cc(Cl)c(N4CCC5(CC4)COC5)cc3n2)c1Cl] |
| Ex-1.5 | 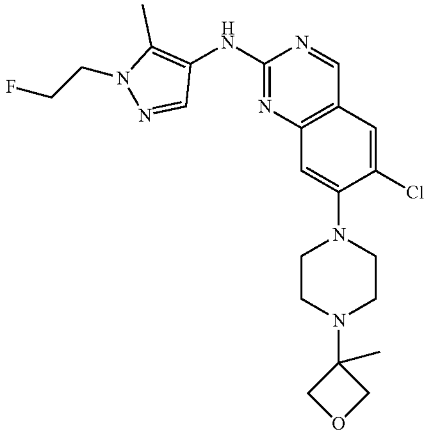 [SMILES: Cc1c(Nc2ncc3cc(Cl)c(N4CCN(C5(C)COC5)CC4)cc3n2)cnn1CCF] |

-continued
| Ex | Structure |
|---|---|
| Ex-1.6 | 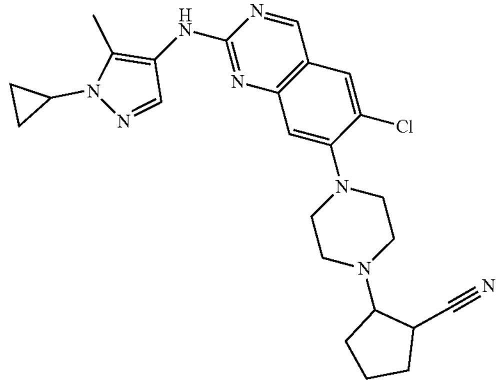 [SMILES: Cc1c(Nc2ncc3cc(Cl)c(N4CCN(C5CCCC5C#N)CC4)cc3n2)cnn1C1CC1] |
| Ex-1.7 | 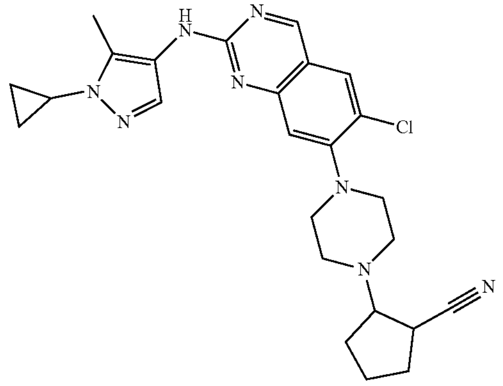 [SMILES: Cc1c(Nc2ncc3cc(Cl)c(N4CCN(C5CCCC5C#N)CC4)cc3n2)cnn1C1CC1] |
| Ex-1.8 | 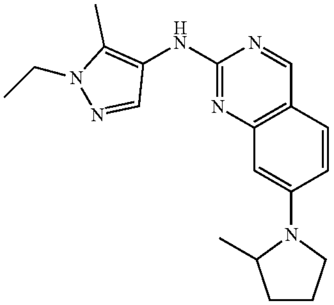 [SMILES: CCn1ncc(Nc2ncc3ccc(N4CCCC4C)cc3n2)c1C] |
| Ex-1.9 | 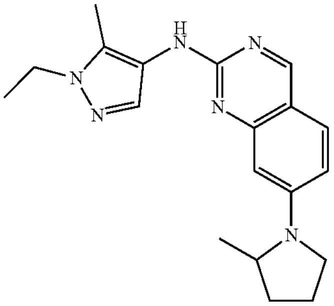 [SMILES: CCn1ncc(Nc2ncc3ccc(N4CCCC4C)cc3n2)c1C] |

-continued
| Ex | Structure |
| --- | --- |
| Ex-1.10 | 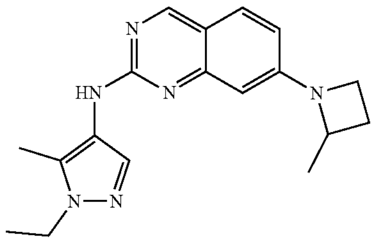 [SMILES: CCn1ncc(Nc2ncc3ccc(N4CCC4C)cc3n2)c1C] |
| Ex-1.11 | 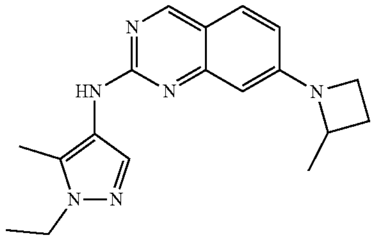 [SMILES: CCn1ncc(Nc2ncc3ccc(N4CCC4C)cc3n2)c1C] |
| Ex-1.12 | 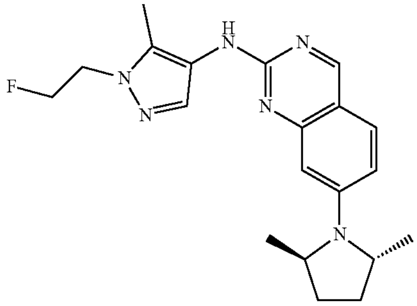 [SMILES: Cc1c(Nc2ncc3ccc(N4[C@H](C)CC[C@H]4C)cc3n2)cnn1CCF] |
| Ex-1.13 | 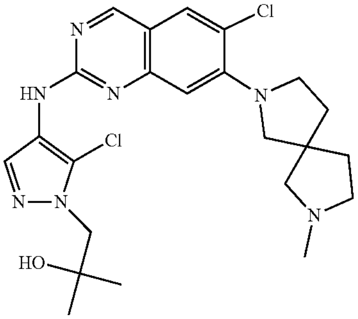 [SMILES: CN1CCC2(CCN(c3cc4nc(Nc5cnn(CC(C)(C)O)c5Cl)ncc4cc3Cl)C2)C1] |
| Ex-1.14 | 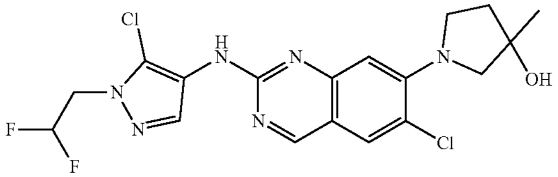 [SMILES: CC1(O)CCN(c2cc3nc(Nc4cnn(CC(F)F)c4Cl)ncc3cc2Cl)C1] |

-continued
| Ex | Structure |
|---|---|
| Ex-1.15 | 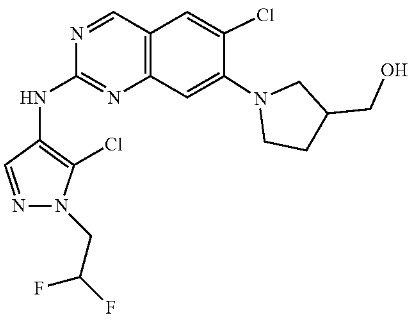 [SMILES: OCC1CCN(c2cc3nc(Nc4cnn(CC(F)F)c4Cl)ncc3cc2Cl)C1] |
| Ex-1.16 | 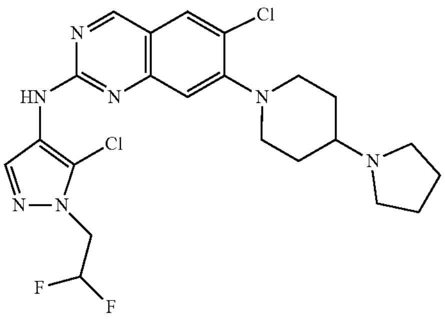 [SMILES: FC(F)Cn1ncc(Nc2ncc3cc(Cl)c(N4CCC(N5CCCC5)CC4)cc3n2)c1Cl] |
| Ex-1.17 | 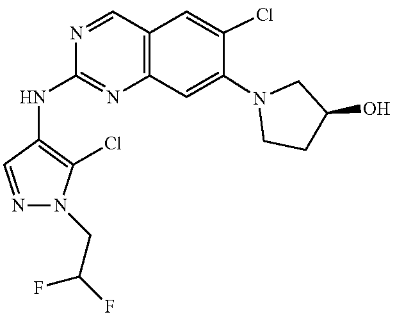 [SMILES: O[C@H]1CCN(c2cc3nc(Nc4cnn(CC(F)F)c4Cl)ncc3cc2Cl)C1] |
| Ex-1.18 | 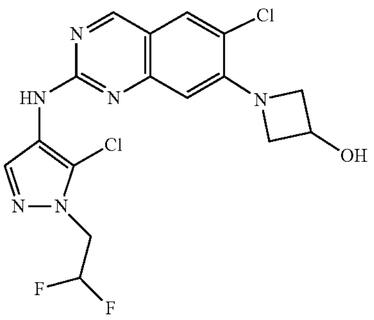 [SMILES: OC1CN(c2cc3nc(Nc4cnn(CC(F)F)c4Cl)ncc3cc2Cl)C1] |
| Ex-1.19 | 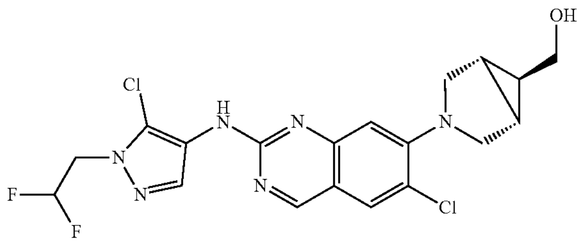 [SMILES: OC[C@@H]1[C@H]2CN(c3cc4nc(Nc5cnn(CC(F)F)c5Cl)ncc4cc3Cl)C[C@@H]12] |

-continued
| Ex | Structure |
|---|---|
| Ex-1.20 | 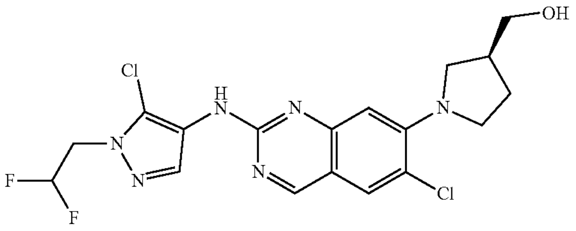 [SMILES: OC[C@H]1CCN(c2cc3nc(Nc4cnn(CC(F)F)c4Cl)ncc3cc2Cl)C1] |
| Ex-1.21 | 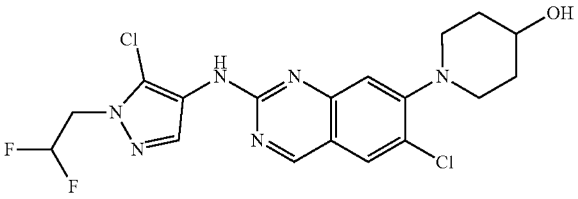 [SMILES: OC1CCN(c2cc3nc(Nc4cnn(CC(F)F)c4Cl)ncc3cc2Cl)CC1] |
| Ex-1.22 | 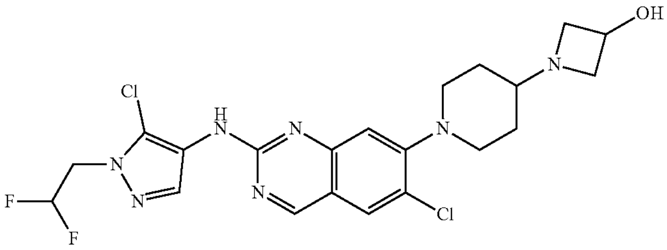 [SMILES: OC1CN(C2CCN(c3cc4nc(Nc5cnn(CC(F)F)c5Cl)ncc4cc3Cl)CC2)C1] |
| Ex-1.23 | 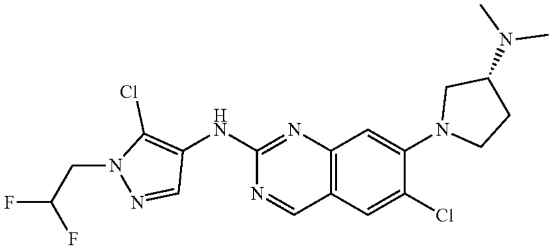 [SMILES: CN(C)[C@@H]1CCN(c2cc3nc(Nc4cnn(CC(F)F)c4Cl)ncc3cc2Cl)C1] |
| Ex-1.24 | 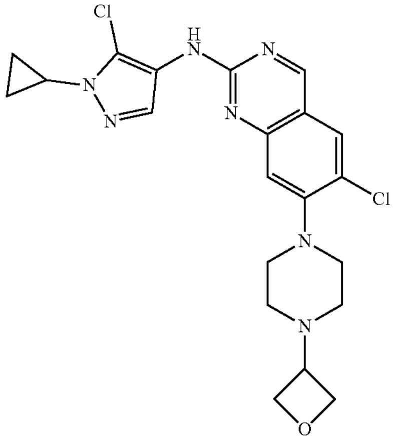 [SMILES: Clc1cc2cnc(Nc3cnn(C4CC4)c3Cl)nc2cc1N1CCN(C2COC2)CC1] |

-continued
| Ex | Structure |
|---|---|
| Ex-1.25 | 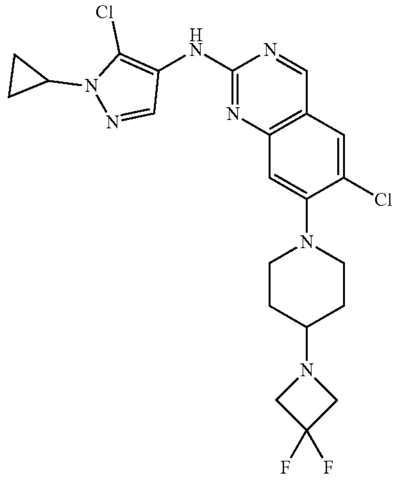 [SMILES: FC1(F)CN(C2CCN(c3cc4nc(Nc5cnn(C6CC6)c5Cl)ncc4cc3Cl)CC2)C1] |
| Ex-1.26 | 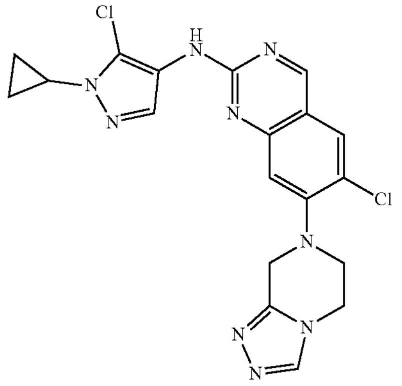 [SMILES: Clc1cc2cnc(Nc3cnn(C4CC4)c3Cl)nc2cc1N1CCn2cnnc2C1] |
| Ex-1.27 | 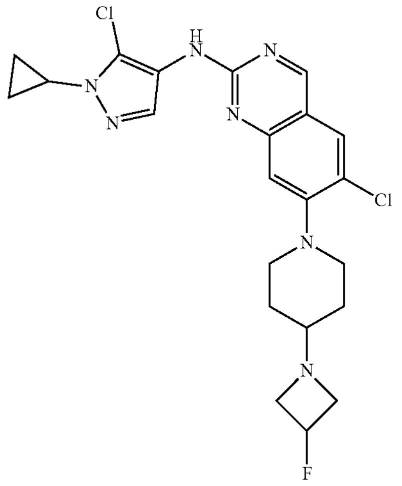 [SMILES: FC1CN(C2CCN(c3cc4nc(Nc5cnn(C6CC6)c5Cl)ncc4cc3Cl)CC2)C1] |

-continued
| Ex | Structure |
|---|---|
| Ex-1.28 | 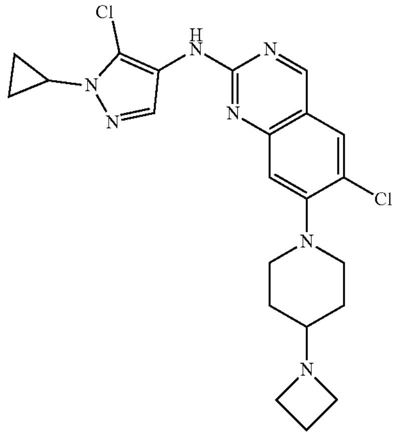 [SMILES: Clc1cc2cnc(Nc3cnn(C4CC4)c3Cl)nc2cc1N1CCC(N2CCC2)CC1] |
| Ex-1.29 | 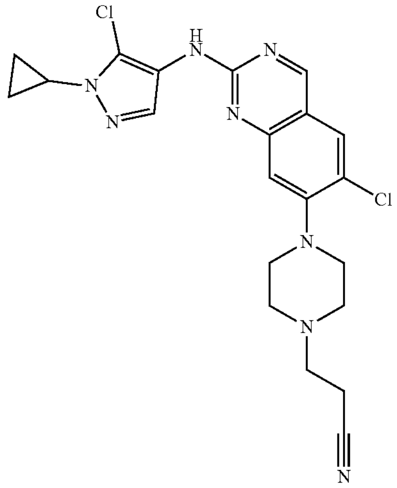 [SMILES: N#CCCN1CCN(c2cc3nc(Nc4cnn(C5CC5)c4Cl)ncc3cc2Cl)CC1] |
| Ex-1.30 | 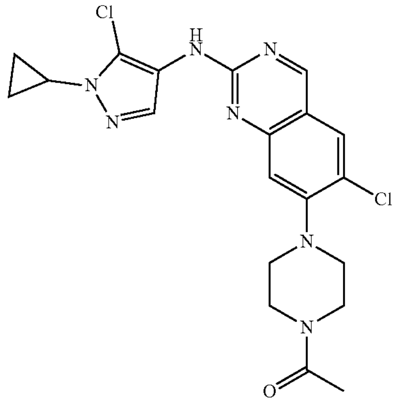 [SMILES: CC(=O)N1CCN(c2cc3nc(Nc4cnn(C5CC5)c4Cl)ncc3cc2Cl)CC1] |

-continued
| Ex | Structure |
| --- | --- |
| Ex-1.31 | 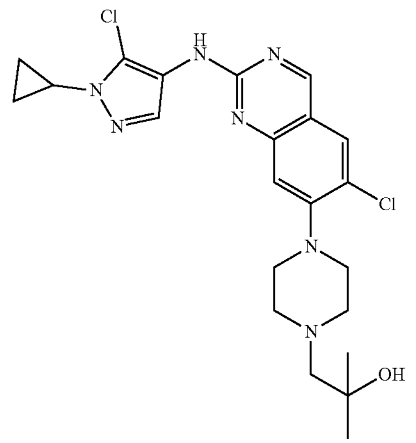 [SMILES: CC(C)(O)CN1CCN(c2cc3nc(Nc4cnn(C5CC5)c4Cl)ncc3cc2Cl)CC1] |
| Ex-1.32 | 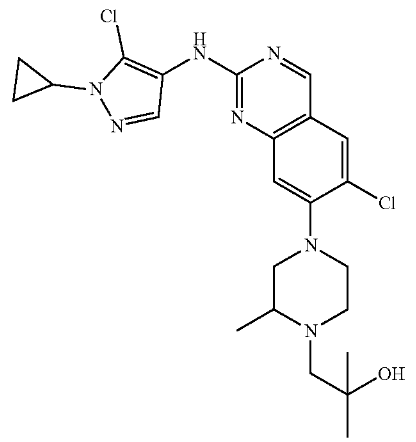 |
| Ex-1.33 | 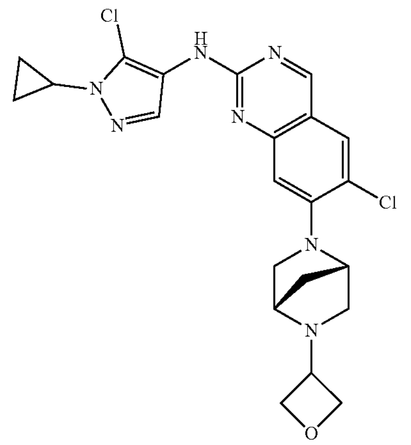 [SMILES: Clc1cc2cnc(Nc3cnn(C4CC4)c3Cl)nc2cc1N1C[C@@H]2C[C@H]1CN2C1COC1] |

-continued
| Ex | Structure |
| --- | --- |
| Ex-1.34 | 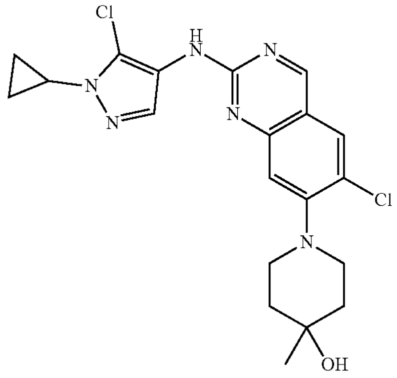 [SMILES: CC1(O)CCN(c2cc3nc(Nc4cnn(C5CC5)c4Cl)ncc3cc2Cl)CC1] |
| Ex-1.35 | 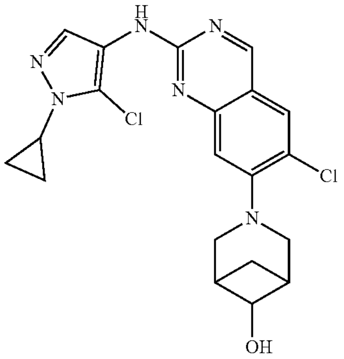 [SMILES: OC1C2CC1CN(c1cc3nc(Nc4cnn(C5CC5)c4Cl)ncc3cc1Cl)C2] |
| Ex-1.36 | 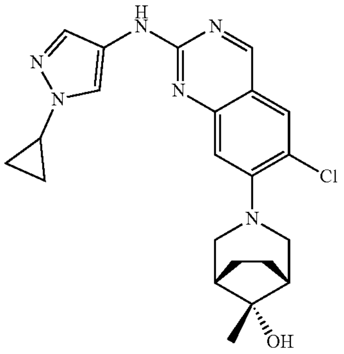 [SMILES: C[C@]1(O)[C@@H]2CC[C@H]1CN(c1cc3nc(Nc4cnn(C5CC5)c4)ncc3cc1Cl)C2] |
| Ex-1.37 | 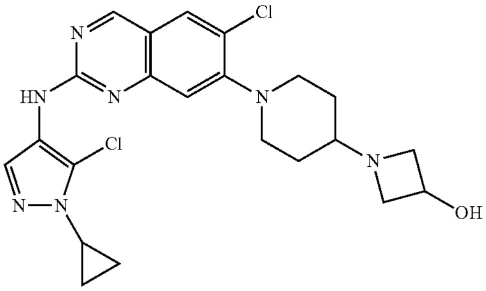 [SMILES: OC1CN(C2CCN(c3cc4nc(Nc5cnn(C6CC6)c5Cl)ncc4cc3Cl)CC2)C1] |

-continued
| Ex | Structure |
|---|---|
| Ex-1.38 | 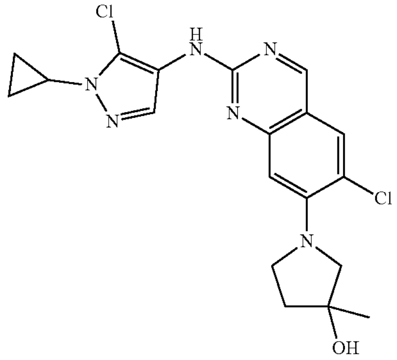 [SMILES: CC1(O)CCN(c2cc3nc(Nc4cnn(C5CC5)c4Cl)ncc3cc2Cl)C1] |
| Ex-1.39 | 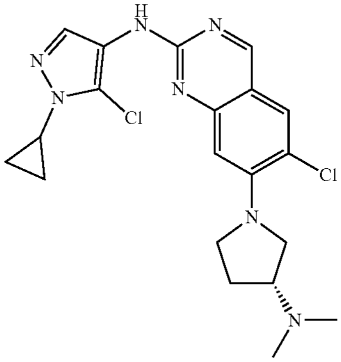 [SMILES: CN(C)[C@@H]1CCN(c2cc3nc(Nc4cnn(C5CC5)c4Cl)ncc3cc2Cl)C1] |
| Ex-1.39 | 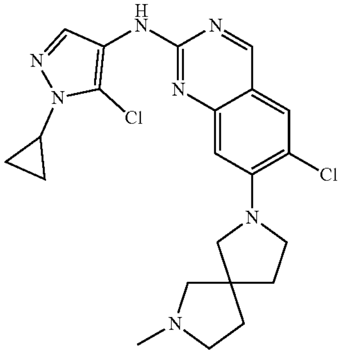 [SMILES: CN1CCC2(CCN(c3cc4nc(Nc5cnn(C6CC6)c5Cl)ncc4cc3Cl)C2)C1] |
| Ex-1.40 | 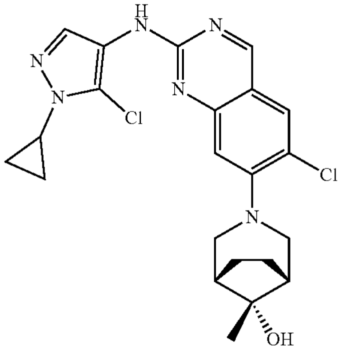 [SMILES: C[C@]1(O)[C@@H]2CC[C@H]1CN(c1cc3nc(Nc4cnn(C5CC5)c4Cl)ncc3cc1Cl)C2] |

-continued
| Ex | Structure |
|---|---|
| Ex-1.41 | 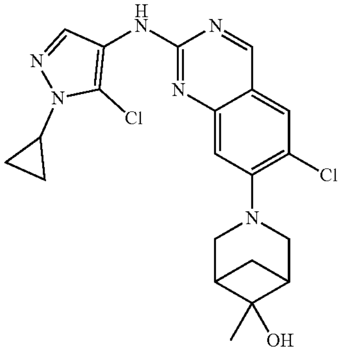 [SMILES: CC1(O)C2CC1CN(c1cc3nc(Nc4cnn(C5CC5)c4Cl)ncc3cc1Cl)C2] |
| Ex-1.42 | 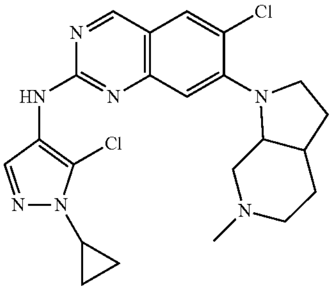 [SMILES: CN1CCC2CCN(c3cc4nc(Nc5cnn(C6CC6)c5Cl)ncc4cc3Cl)C2C1] |
| Ex-1.43 | 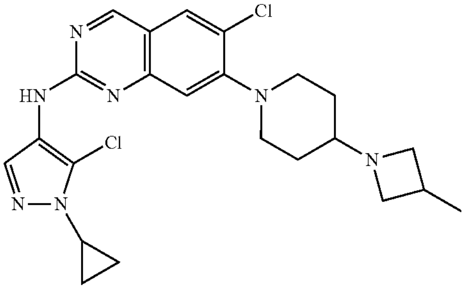 [SMILES: CC1CN(C2CCN(c3cc4nc(Nc5cnn(C6CC6)c5Cl)ncc4cc3Cl)CC2)C1] |
| Ex-1.44 | 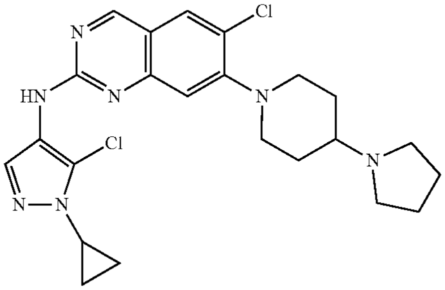 [SMILES: Clc1cc2cnc(Nc3cnn(C4CC4)c3Cl)nc2cc1N1CCC(N2CCCC2)CC1] |
| Ex-1.45 | 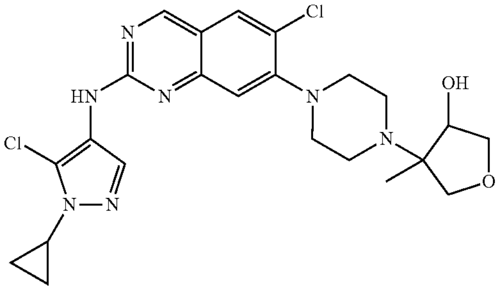 [SMILES: CC1(N2CCN(c3cc4nc(Nc5cnn(C6CC6)c5Cl)ncc4cc3Cl)CC2)COCC1O] |

-continued
| Ex | Structure |
|---|---|
| Ex-1.46 | 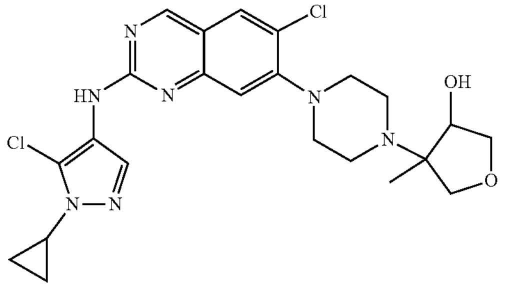 [SMILES: CC1(N2CCN(c3cc4nc(Nc5cnn(C6CC6)c5Cl)ncc4cc3Cl)CC2)COCC1O] |
| Ex-1.47 | 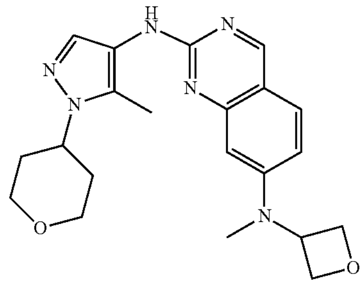 [SMILES: Cc1c(Nc2ncc3ccc(N(C)C4COC4)cc3n2)cnn1C1CCOCC1] |
| Ex-1.48 | 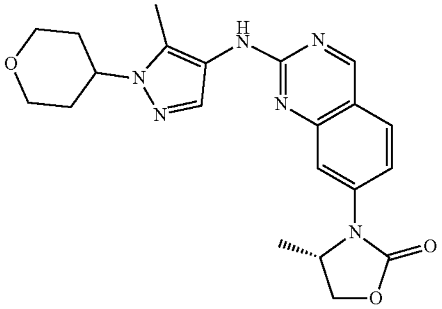 [SMILES: Cc1c(Nc2ncc3ccc(N4C(=O)OC[C@@H]4C)cc3n2)cnn1C1CCOCC1] |
| Ex-2.1 | 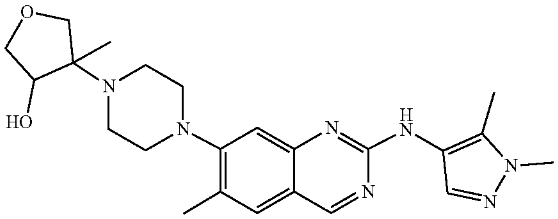 [SMILES: Cc1cc2cnc(Nc3cnn(C)c3C)nc2cc1N1CCN(C2(C)COCC2O)CC1] |
| Ex-2.2 | 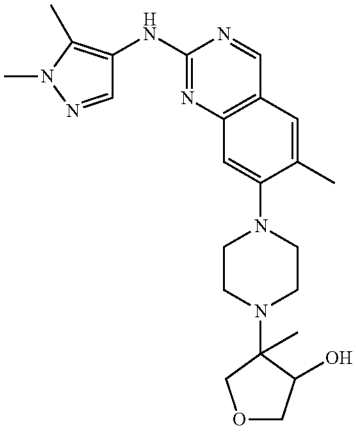 |

-continued
| Ex | Structure |
|---|---|
| Ex-2.3 | 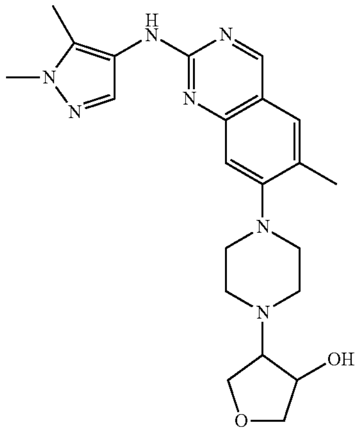 |
| Ex-2.4 | 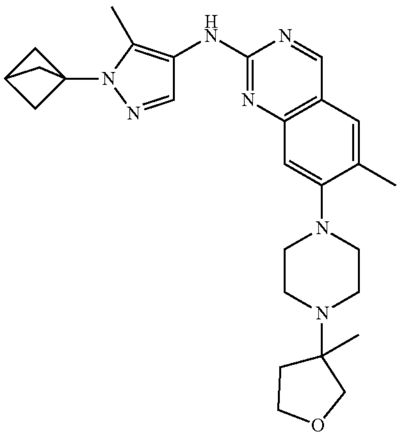 [SMILES: Cc1cc2cnc(Nc3cnn(C45CC(C4)C5)c3C)nc2cc1N1CCN(C2(C)CCOC2)CC1] |
| Ex-3.1 | 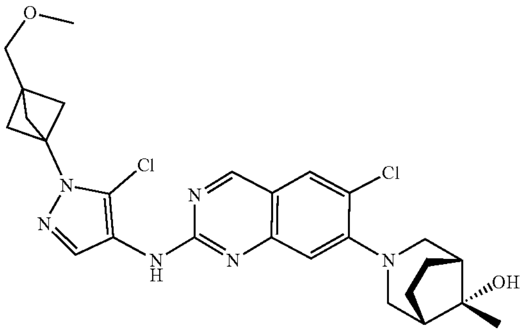 |
| Ex-3.2 | 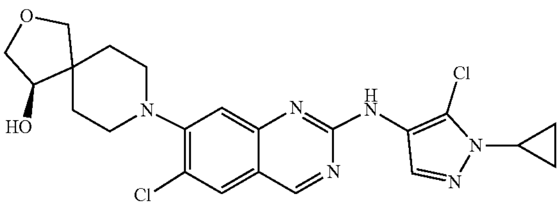 [SMILES: O[C@H]1COCC12CCN(c1cc3nc(Nc4cnn(C5CC5)c4Cl)ncc3cc1Cl)CC2] |

-continued
| Ex | Structure |
|---|---|
| Ex-3.3 | 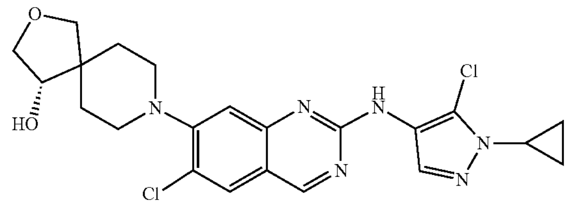 [SMILES: O[C@@H]1COCC12CCN(c1cc3nc(Nc4cnn(C5CC5)c4Cl)ncc3cc1Cl)CC2] |
| Ex-3.4 | 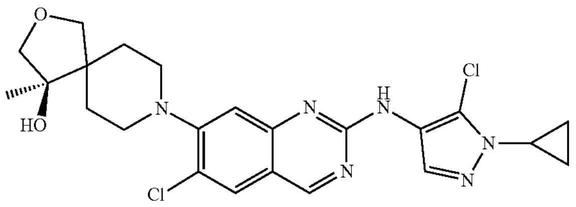 [SMILES: C[C@]1(O)COCC12CCN(c1cc3nc(Nc4cnn(C5CC5)c4Cl)ncc3cc1Cl)CC2] |
| Ex-3.5 | 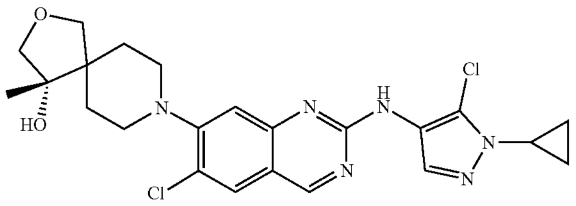 [SMILES: C[C@@]1(O)COCC12CCN(c1cc3nc(Nc4cnn(C5CC5)c4Cl)ncc3cc1Cl)CC2] |
| Ex-3.6 | 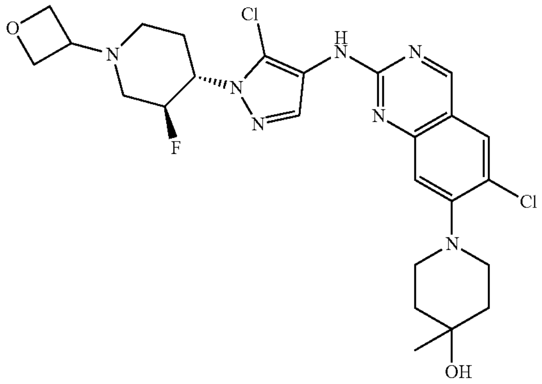 [SMILES: CC1(O)CCN(c2cc3nc(Nc4cnn([C@H]5CCN(C6COC6)C[C@@H]5F)c4Cl)ncc3cc2Cl)CC1] |
| Ex-3.7 | 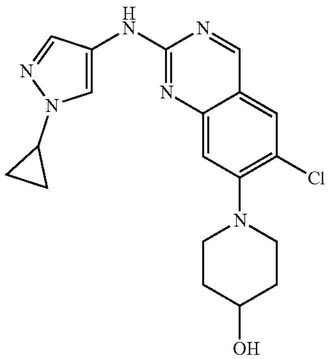 [SMILES: OC1CCN(c2cc3nc(Nc4cnn(C5CC5)c4)ncc3cc2Cl)CC1] |

-continued
| Ex | Structure |
|---|---|
| Ex-3.8 | 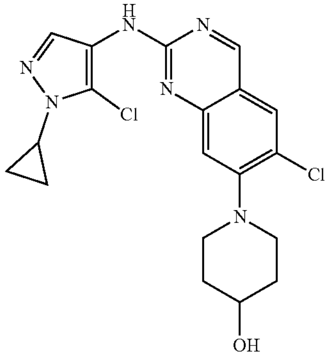 [SMILES: OC1CCN(c2cc3nc(Nc4cnn(C5CC5)c4Cl)ncc3cc2Cl)CC1] |
| Ex-3.9 | 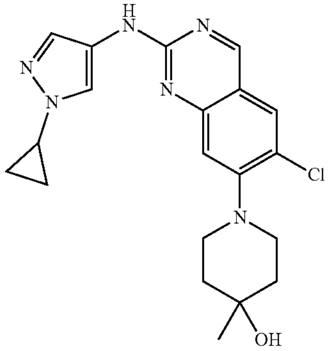 [SMILES: CC1(O)CCN(c2cc3nc(Nc4cnn(C5CC5)c4)ncc3cc2Cl)CC1] |
| Ex-3.10 | 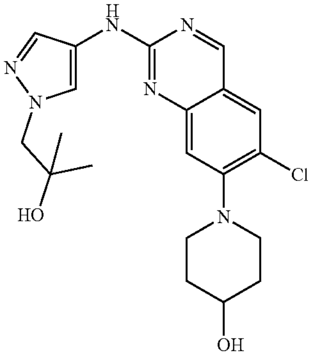 [SMILES: CC(C)(O)Cn1cc(Nc2ncc3cc(Cl)c(N4CCC(O)CC4)cc3n2)cn1] |
| Ex-3.11 | 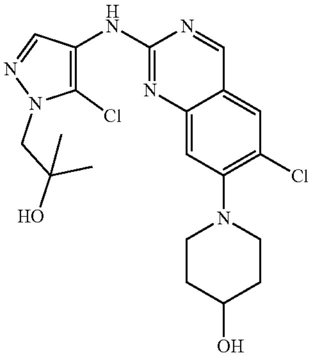 [SMILES: CC(C)(O)Cn1ncc(Nc2ncc3cc(Cl)c(N4CCC(O)CC4)cc3n2)c1Cl] |

-continued
| Ex | Structure |
|---|---|
| Ex-3.11 | 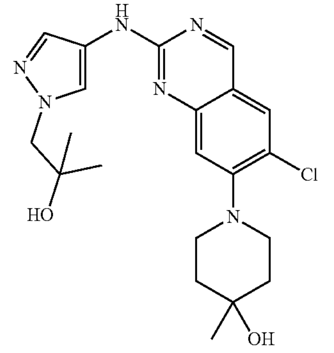 [SMILES: CC(C)(O)Cn1cc(Nc2ncc3cc(Cl)c(N4CCC(C)(O)CC4)cc3n2)cn1] |
| Ex-3.13 | 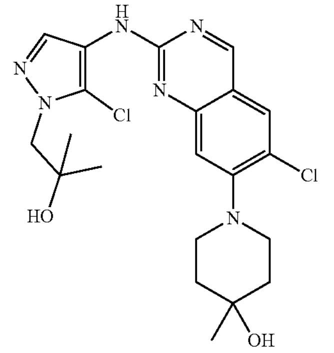 [SMILES: CC(C)(O)Cn1ncc(Nc2ncc3cc(Cl)c(N4CCC(C)(O)CC4)cc3n2)c1Cl] |
| Ex-3.14 | 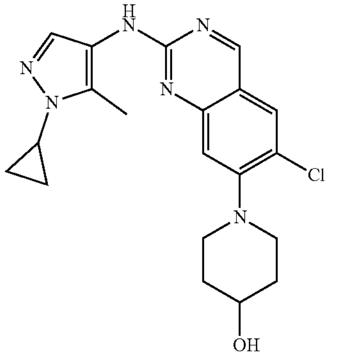 [SMILES: Cc1c(Nc2ncc3cc(Cl)c(N4CCC(O)CC4)cc3n2)cnn1C1CC1] |
| Ex-3.15 | 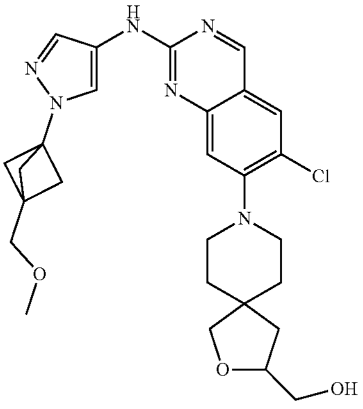 [SMILES: COCC12CC(n3cc(Nc4ncc5cc(Cl)c(N6CCC7(CC6)COC(CO)C7)cc5n4)cn3)(C1)C2] |

-continued
| Ex | Structure |
|---|---|
| Ex-3.16 | 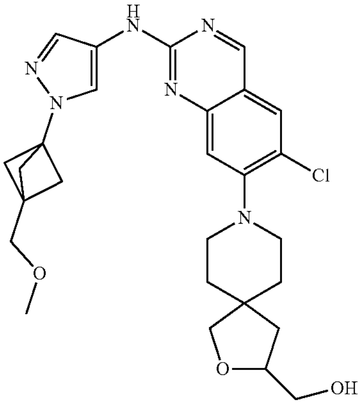 [SMILES: COCC12CC(n3cc(Nc4ncc5cc(Cl)c(N6CCC7(CC6)COC(CO)C7)cc5n4)cn3)(C1)C2] |
| Ex-3.17 | 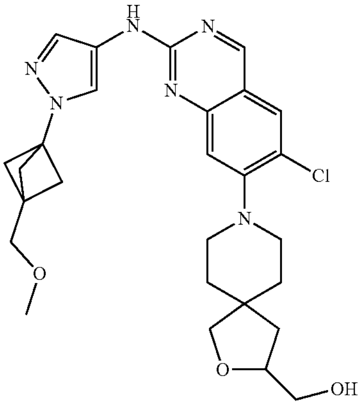 [SMILES: COCC12CC(n3cc(Nc4ncc5cc(Cl)c(N6CCC7(CC6)COC(CO)C7)cc5n4)cn3)(C1)C2] |
| Ex-3.18 | 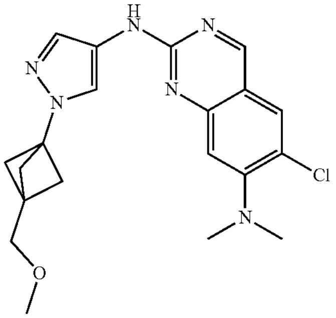 [SMILES: COCC12CC(n3cc(Nc4ncc5cc(Cl)c(N(C)C)cc5n4)cn3)(C1)C2] |
| Ex-3.19 | 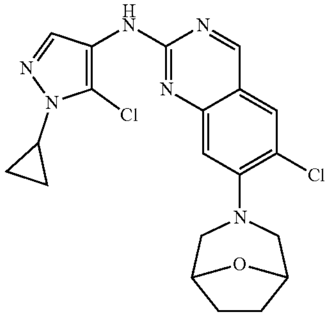 [SMILES: Clc1cc2cnc(Nc3cnn(C4CC4)c3Cl)nc2cc1N1CC2CCC(C1)O2] |

-continued
| Ex | Structure |
|---|---|
| Ex-3.20 | 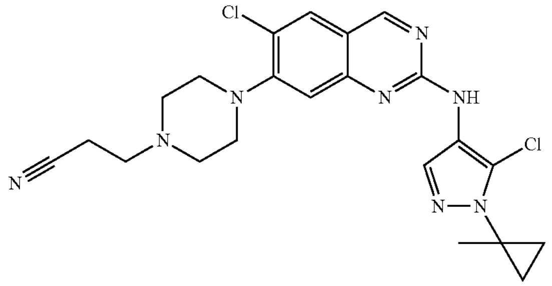 [SMILES: CC1(n2ncc(Nc3ncc4cc(Cl)c(N5CCN(CCC#N)CC5)cc4n3)c2Cl)CC1] |
| Ex-3.21 | 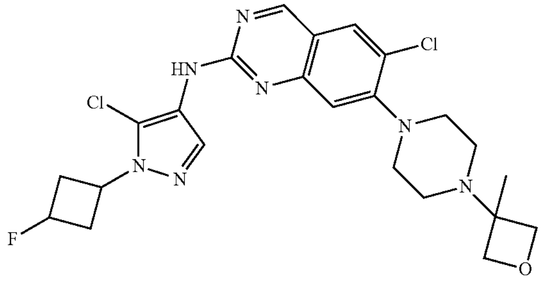 [SMILES: CC1(N2CCN(c3cc4nc(Nc5cnn(C6CC(F)C6)c5Cl)ncc4cc3Cl)CC2)COC1] |
| Ex-3.22 | 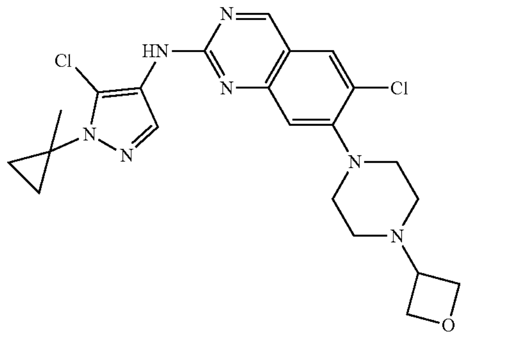 [SMILES: CC1(n2ncc(Nc3ncc4cc(Cl)c(N5CCN(C6COC6)CC5)cc4n3)c2Cl)CC1] |
| Ex.3.23 | 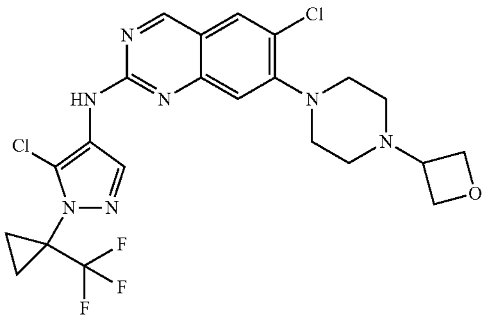 [SMILES: FC(F)(F)C1(n2ncc(Nc3ncc4cc(Cl)c(N5CCN(C6COC6)CC5)cc4n3)c2Cl)CC1] |
| Ex-3.24 | 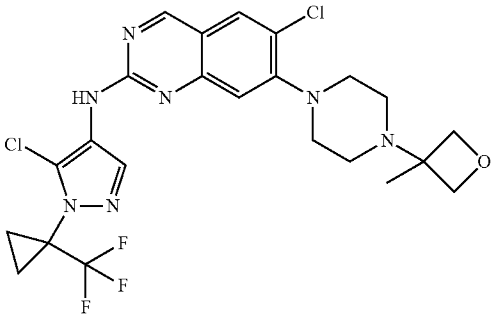 [SMILES: CC1(N2CCN(c3cc4nc(Nc5cnn(C6(C(F)(F)F)CC6)c5Cl)ncc4cc3Cl)CC2)COC1] |

-continued
| Ex | Structure |
|---|---|
| Ex-3.25 | 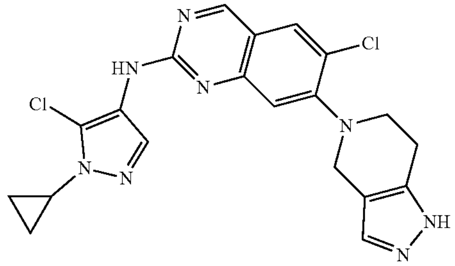 [SMILES: Clc1cc2cnc(Nc3cnn(C4CC4)c3Cl)nc2cc1N1CCc2[nH]ncc2C1] |
| Ex-3.26 | 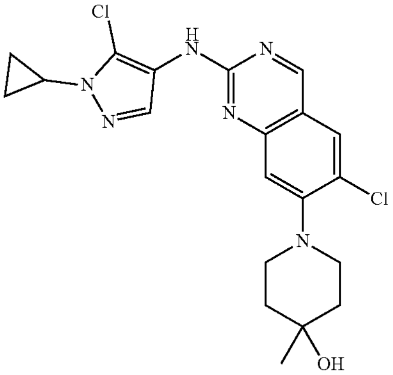 [SMILES: CC1(O)CCN(c2cc3nc(Nc4cnn(C5CC5)c4Cl)ncc3cc2Cl)CC1] |
| Ex-3.27 | 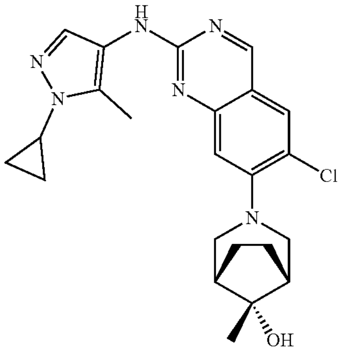 [SMILES: Cc1c(Nc2ncc3cc(Cl)c(N4C[C@H]5CC[C@@H](C4)[C@@]5(C)O)cc3n2)cnn1C1CC1] |
| Ex-3.28 | 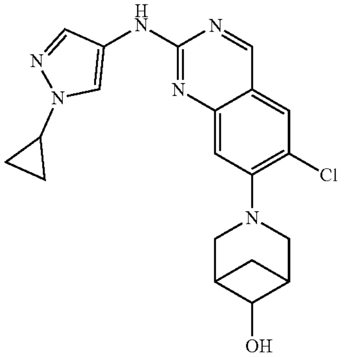 [SMILES: OC1C2CC1CN(c1cc3nc(Nc4cnn(C5CC5)c4)ncc3cc1Cl)C2] |

-continued
| Ex | Structure |
| --- | --- |
| Ex-3.29 | 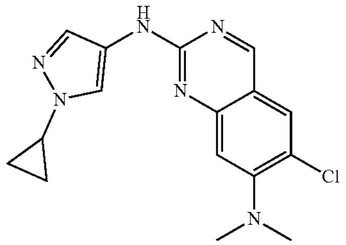 [SMILES: CN(C)c1cc2nc(Nc3cnn(C4CC4)c3)ncc2cc1Cl] |
| Ex-3.30 | 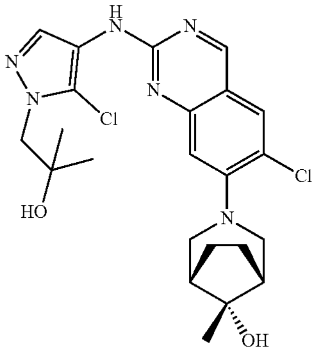 [SMILES: CC(C)(O)Cn1ncc(Nc2ncc3cc(Cl)c(N4C[C@H]5CC[C@@H](C4)[C@@]5(C)O)cc3n2)c1Cl] |
| Ex-3.31 | 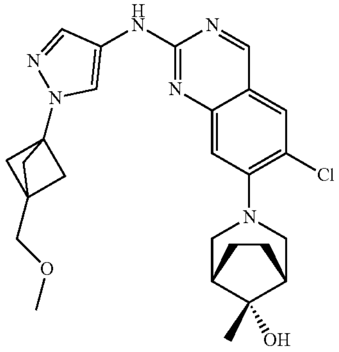 [SMILES: COCC12CC(n3cc(Nc4ncc5cc(Cl)c(N6C[C@H]7CC[C@@H](C6)[C@@]7(C)O)cc5n4)cn3)(C1)C2] |
| Ex-3.32 | 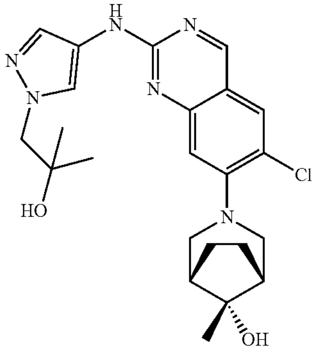 [SMILES: CC(C)(O)Cn1cc(Nc2ncc3cc(Cl)c(N4C[C@H]5CC[C@@H](C4)[C@@]5(C)O)cc3n2)cn1] |

-continued
| Ex | Structure |
|---|---|
| Ex-3.33 | 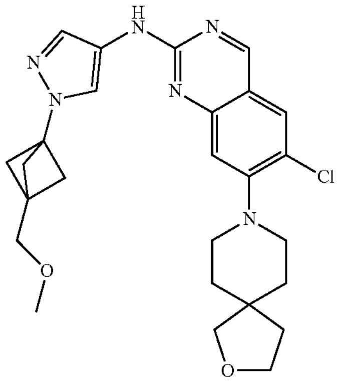 [SMILES: COCC12CC(n3cc(Nc4ncc5cc(Cl)c(N6CCC7(CCOC7)CC6)cc5n4)cn3)(C1)C2] |
| Ex-3.34 | 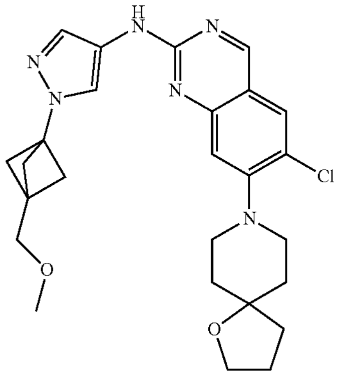 [SMILES: COCC12CC(n3cc(Nc4ncc5cc(Cl)c(N6CCC7(CCCO7)CC6)cc5n4)cn3)(C1)C2] |
| Ex-3.35 | 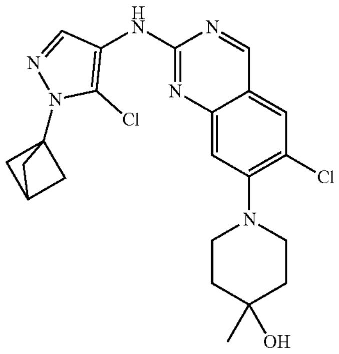 [SMILES: CC1(O)CCN(c2cc3nc(Nc4cnn(C56CC(C5)C6)c4Cl)ncc3cc2Cl)CC1] |
| Ex-3.36 | 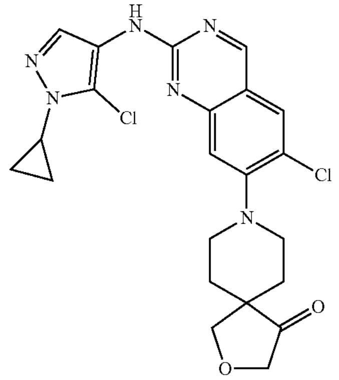 [SMILES: O=C1COCC12CCN(c1cc3nc(Nc4cnn(C5CC5)c4Cl)ncc3cc1Cl)CC2] |

-continued
| Ex | Structure |
| --- | --- |
| Ex-3.37 | 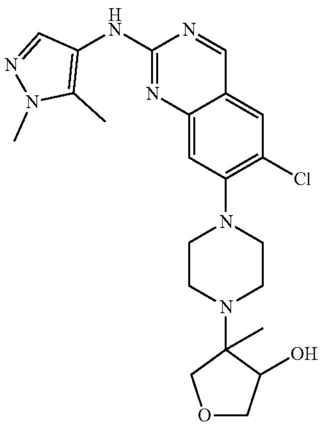 [SMILES: Cc1c(Nc2ncc3cc(Cl)c(N4CCN(C5(C)COCC5O)CC4)cc3n2)cnn1C] |
| Ex-3.38 | 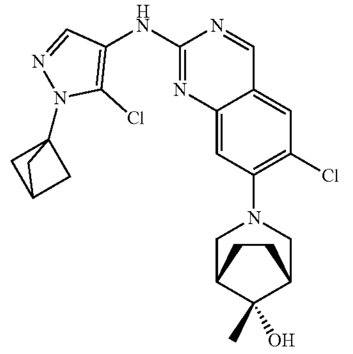 [SMILES: C[C@]1(O)[C@@H]2CC[C@H]1CN(c1cc3nc(Nc4cnn(C56CC(C5)C6)c4Cl)ncc3cc1Cl)C2] |
| Ex-3.39 | 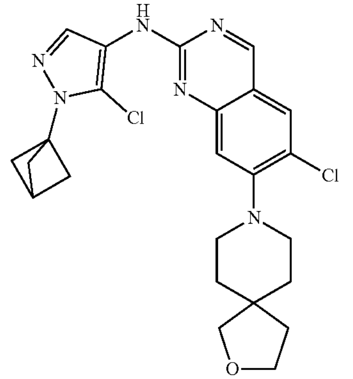 [SMILES: Clc1cc2cnc(Nc3cnn(C45CC(C4)C5)c3Cl)nc2cc1N1CCC2(CCOC2)CC1] |
| Ex-3.40 | 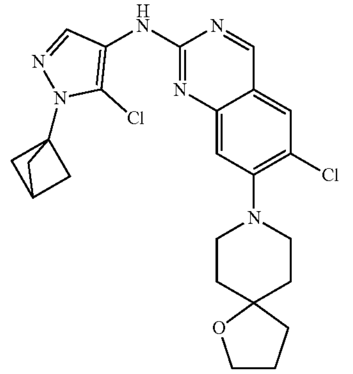 [SMILES: Clc1cc2cnc(Nc3cnn(C45CC(C4)C5)c3Cl)nc2cc1N1CCC2(CCCO2)CC1] |

-continued
| Ex | Structure |
|---|---|
| Ex-3.41 | 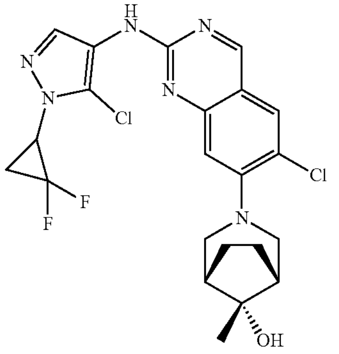 [SMILES: C[C@]1(O)[C@@H]2CC[C@H]1CN(c1cc3nc(Nc4cnn(C5CC5(F)F)c4Cl)ncc3cc1Cl)C2] |
| Ex-3.42 | 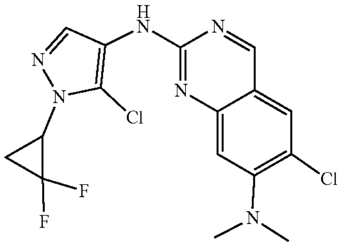 [SMILES: CN(C)c1cc2nc(Nc3cnn(C4CC4(F)F)c3Cl)ncc2cc1Cl] |
| Ex-3.43 | 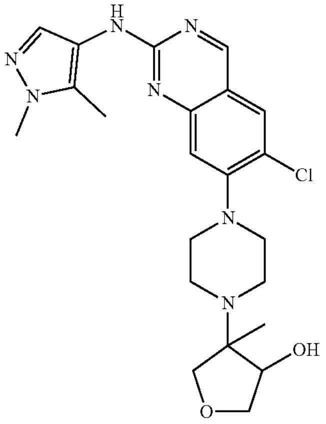 [SMILES: Cc1c(Nc2ncc3cc(Cl)c(N4CCN(C5(C)COCC5O)CC4)cc3n2)cnn1C] |
| Ex-3.44 | 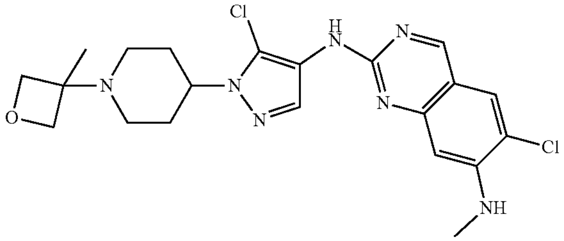 [SMILES: CNc1cc2nc(Nc3cnn(C4CCN(C5(C)COC5)CC4)c3Cl)ncc2cc1Cl] |
| Ex-3.45 | 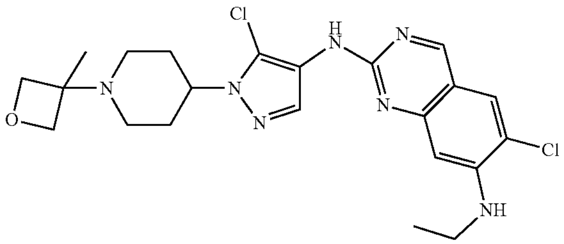 [SMILES: CCNc1cc2nc(Nc3cnn(C4CCN(C5(C)COC5)CC4)c3Cl)ncc2cc1Cl] |

-continued
| Ex | Structure |
| --- | --- |
| Ex-3.46 | 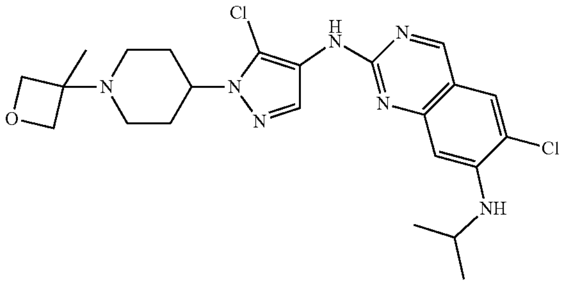 [SMILES: CC(C)Nc1cc2nc(Nc3cnn(C4CCN(C5(C)COC5)CC4)c3Cl)ncc2cc1Cl] |
| Ex-3.47 | 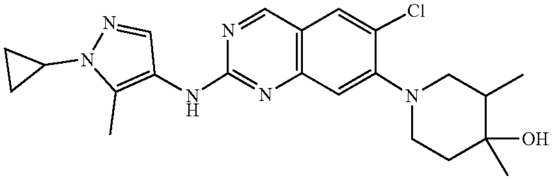 [SMILES: Cc1c(Nc2ncc3cc(Cl)c(N4CCC(C)(O)C(C)C4)cc3n2)cnn1C1CC1] |
| Ex-3.48 | 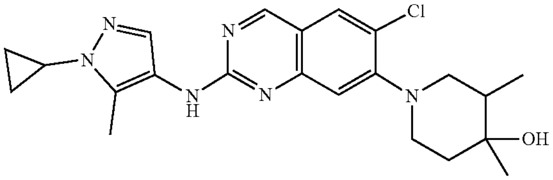 [SMILES: Cc1c(Nc2ncc3cc(Cl)c(N4CCC(C)(O)C(C)C4)cc3n2)cnn1C1CC1] |
| Ex-3.49 | 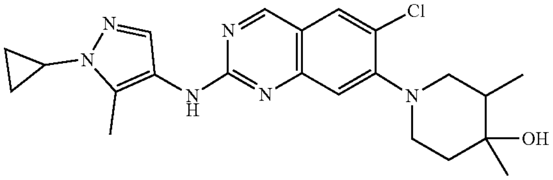 [SMILES: Cc1c(Nc2ncc3cc(Cl)c(N4CCC(C)(O)C(C)C4)cc3n2)cnn1C1CC1] |
| Ex-3.50 | 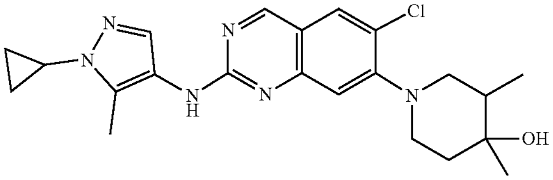 [SMILES: Cc1c(Nc2ncc3cc(Cl)c(N4CCC(C)(O)C(C)C4)cc3n2)cnn1C1CC1] |
| Ex-3.51 | 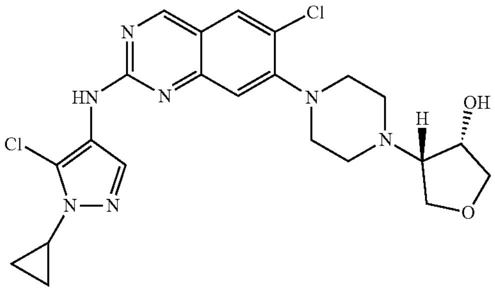 [SMILES: O[C@@H]1COC[C@@H]1N1CCN(c2cc3nc(Nc4cnn(C5CC5)c4Cl)ncc3cc2Cl)CC1] |

-continued
| Ex | Structure |
|---|---|
| Ex-3.52 | 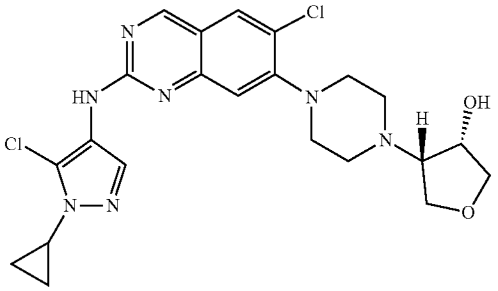 [SMILES: O[C@@H]1COC[C@@H]1N1CCN(c2cc3nc(Nc4cnn(C5CC5)c4Cl)ncc3cc2Cl)CC1] |
| Ex-3.53 | 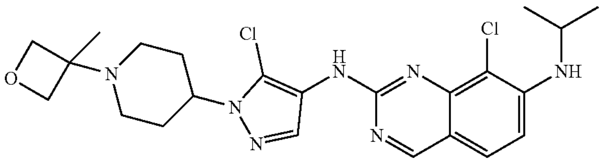 [SMILES: CC(C)Nc1ccc2cnc(Nc3cnn(C4CCN(C5(C)COC5)CC4)c3Cl)nc2c1Cl] |
| Ex-3.54 | 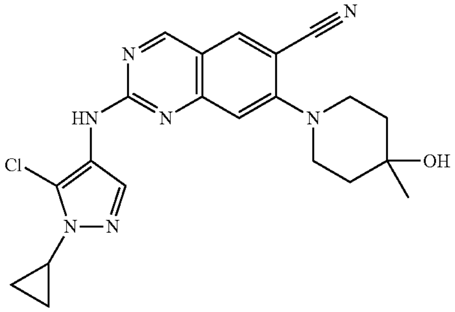 [SMILES: CC1(O)CCN(c2cc3nc(Nc4cnn(C5CC5)c4Cl)ncc3cc2C#N)CC1] |
| Ex-3.55 | 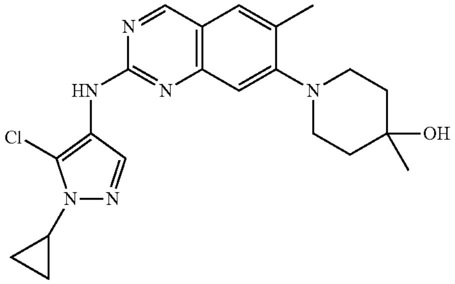 [SMILES: Cc1cc2cnc(Nc3cnn(C4CC4)c3Cl)nc2cc1N1CCC(C)(O)CC1] |
| Ex-3.56 | 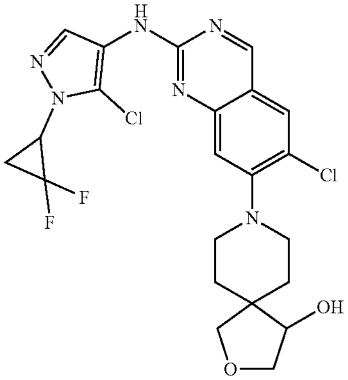 [SMILES: OC1COCC12CCN(c1cc3nc(Nc4cnn(C5CC5(F)F)c4Cl)ncc3cc1Cl)CC2] |

-continued
| Ex | Structure |
|---|---|
| Ex-3.57 | 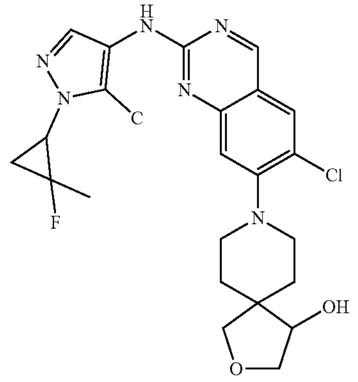 [SMILES: Cc1c(Nc2ncc3cc(Cl)c(N4CCC5(CC4)COCC5O)cc3n2)cnn1C1CC1(C)F] |
| Ex-3.58 | 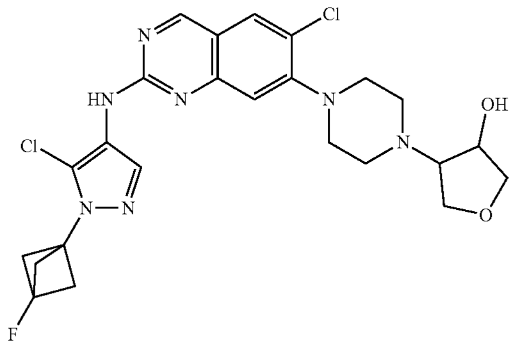 [SMILES: OC1COCC1N1CCN(c2cc3nc(Nc4cnn(C56CC(F)(C5)C6)c4Cl)ncc3cc2Cl)CC1] |
| Ex-3.59 | 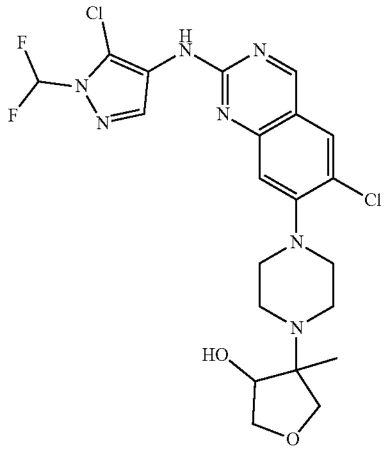 [SMILES: CC1(N2CCN(c3cc4nc(Nc5cnn(C(F)F)c5Cl)ncc4cc3Cl)CC2)COCC1O] |

-continued
| Ex | Structure |
| --- | --- |
| Ex-3.60 | 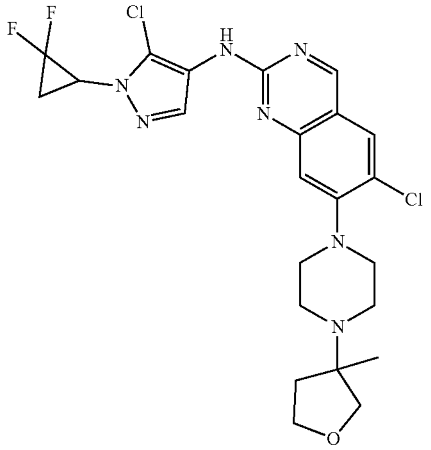 [SMILES: CC1(N2CCN(c3cc4nc(Nc5cnn(C6CC6(F)F)c5Cl)ncc4cc3Cl)CC2)CCOC1] |
| Ex-4.1 | 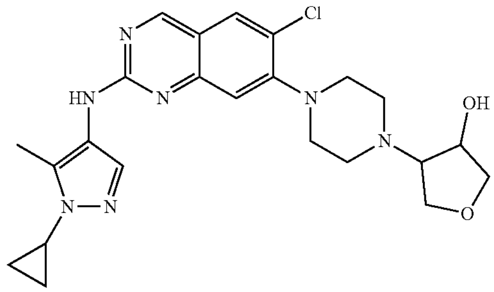 [SMILES: Cc1c(Nc2ncc3cc(Cl)c(N4CCN(C5COCC5O)CC4)cc3n2)cnn1C1CC1] |
| Ex-4.2 | 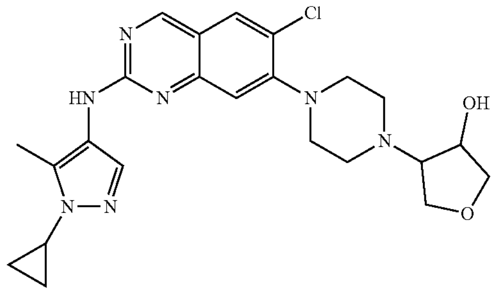 [SMILES: Cc1c(Nc2ncc3cc(Cl)c(N4CCN(C5COCC5O)CC4)cc3n2)cnn1C1CC1] |
| Ex-4.3 | 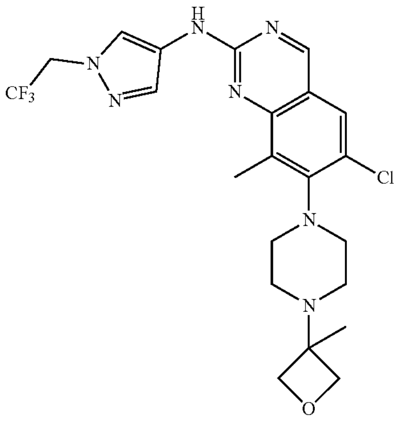 [SMILES: Cc1c(N2CCN(C3(C)COC3)CC2)c(Cl)cc2cnc(Nc3cnn(CC(F)(F)F)c3)nc12] |

-continued
| Ex | Structure |
|---|---|
| Ex-4.4 | 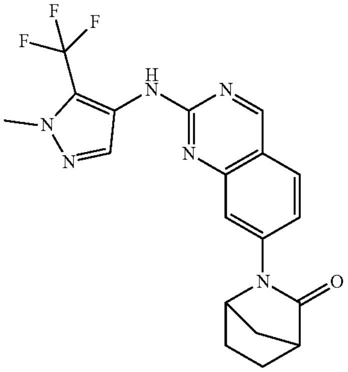 [SMILES: Cn1ncc(Nc2ncc3ccc(N4C(=O)C5CCC4C5)cc3n2)c1C(F)(F)F] |
| Ex-4.5 | 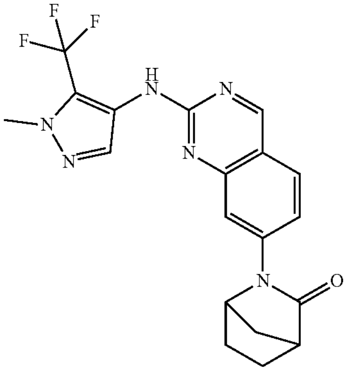 [SMILES: Cn1ncc(Nc2ncc3ccc(N4C(=O)C5CCC4C5)cc3n2)c1C(F)(F)F] |
| Ex-4.6 | 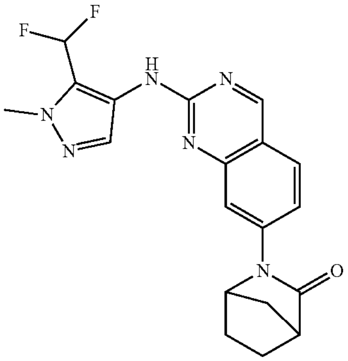 [SMILES: Cn1ncc(Nc2ncc3ccc(N4C(=O)C5CCC4C5)cc3n2)c1C(F)F] |
| Ex-4.7 | 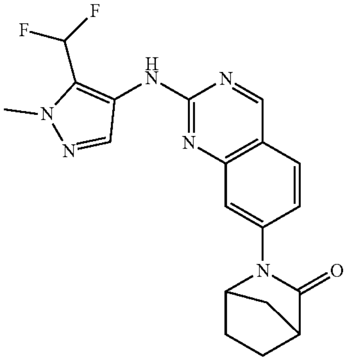 [SMILES: Cn1ncc(Nc2ncc3ccc(N4C(=O)C5CCC4C5)cc3n2)c1C(F)F] |

-continued
| Ex | Structure |
|---|---|
| Ex-4.8 | 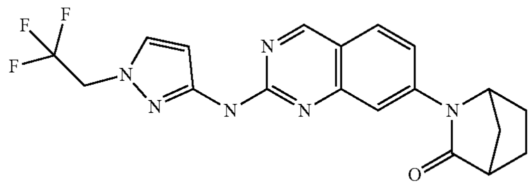 [SMILES: O=C1C2CCC(C2)N1c1ccc2cnc(Nc3ccn(CC(F)(F)F)n3)nc2c1] |
| Ex-4.9 | 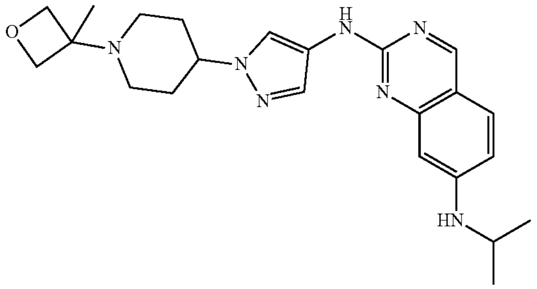 [SMILES: CC(C)Nc1ccc2cnc(Nc3cnn(C4CCN(C5(C)COC5)CC4)c3)nc2c1] |
| Ex-4.10 | 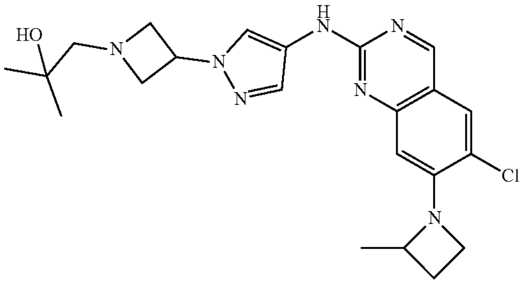 [SMILES: CC1CCN1c1cc2nc(Nc3cnn(C4CN(CC(C)(C)O)C4)c3)ncc2cc1Cl] |
| Ex-4.11 | 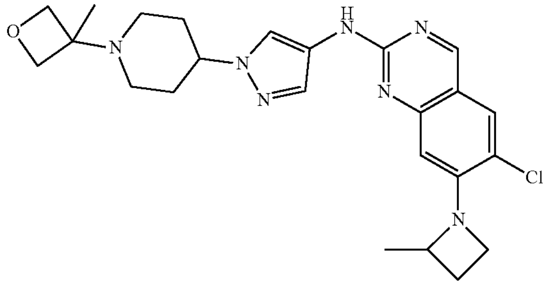 [SMILES: CC1CCN1c1cc2nc(Nc3cnn(C4CCN(C5(C)COC5)CC4)c3)ncc2cc1Cl] |
| Ex-4.12 | 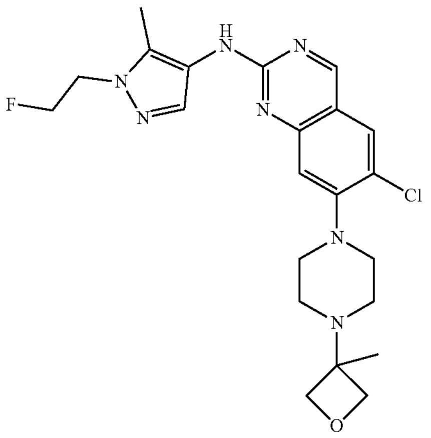 [SMILES: Cc1c(Nc2ncc3cc(Cl)c(N4CCN(C5(C)COC5)CC4)cc3n2)cnn1CCF] |

-continued
| Ex | Structure |
|---|---|
| Ex-4.13 | 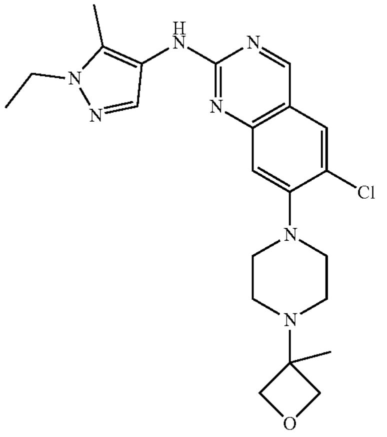 [SMILES: CCn1ncc(Nc2ncc3cc(Cl)c(N4CCN(C5(C)COC5)CC4)cc3n2)c1C] |
| Ex-4.14 | 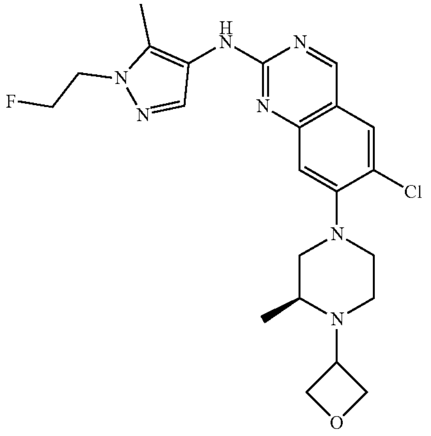 [SMILES: Cc1c(Nc2ncc3cc(Cl)c(N4CCN(C5COC5)[C@@H](C)C4)cc3n2)cnn1CCF] |
| Ex-4.15 | 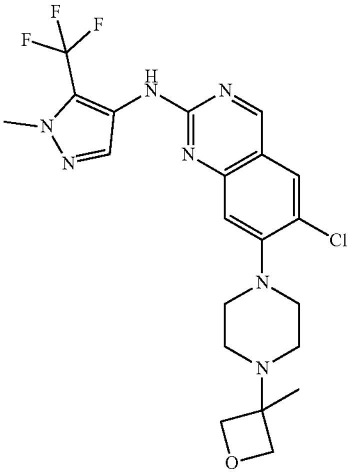 [SMILES: Cn1ncc(Nc2ncc3cc(Cl)c(N4CCN(C5(C)COC5)CC4)cc3n2)c1C(F)(F)F] |

-continued
| Ex | Structure |
|---|---|
| Ex-4.16 | 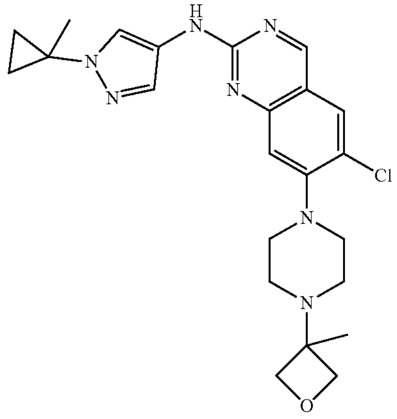 [SMILES: CC1(N2CCN(c3cc4nc(Nc5cnn(C6(C)CC6)c5)ncc4cc3Cl)CC2)COC1] |
| Ex-4.17 | 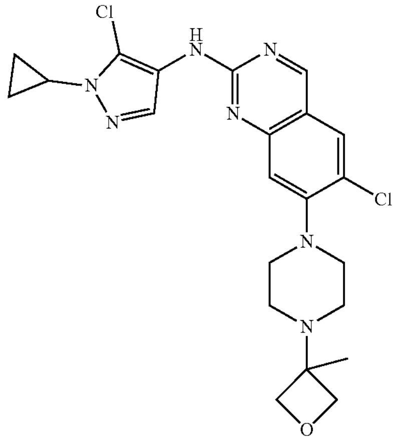 [SMILES: CC1(N2CCN(c3cc4nc(Nc5cnn(C6CC6)c5Cl)ncc4cc3Cl)CC2)COC1] |
| Ex-4.18 | 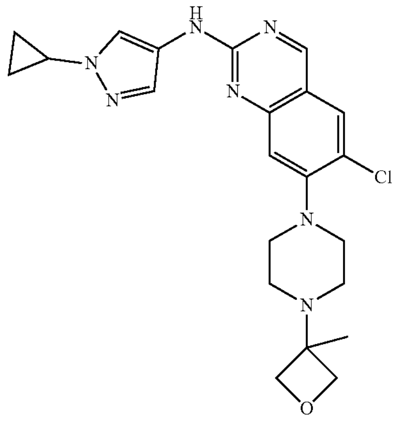 [SMILES: CC1(N2CCN(c3cc4nc(Nc5cnn(C6CC6)c5)ncc4cc3Cl)CC2)COC1] |

-continued
| Ex | Structure |
| --- | --- |
| Ex-4.19 | 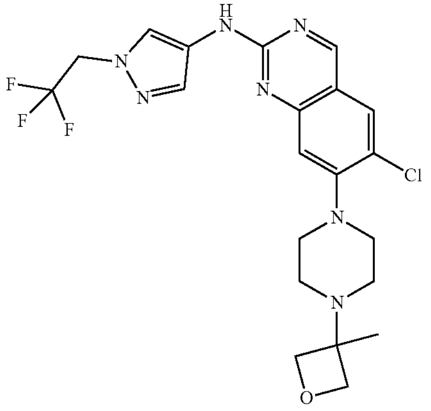 [SMILES: CC1(N2CCN(c3cc4nc(Nc5cnn(CC(F)(F)F)c5)ncc4cc3Cl)CC2)COC1] |
| Ex-4.20 | 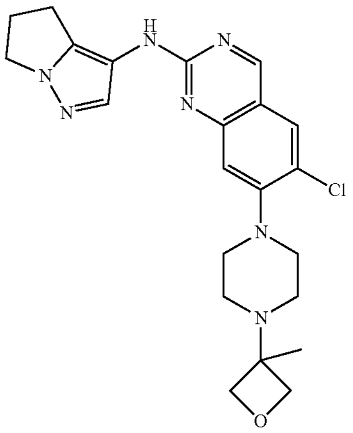 [SMILES: CC1(N2CCN(c3cc4nc(Nc5cnn6c5CCC6)ncc4cc3Cl)CC2)COC1] |
| Ex-4.21 | 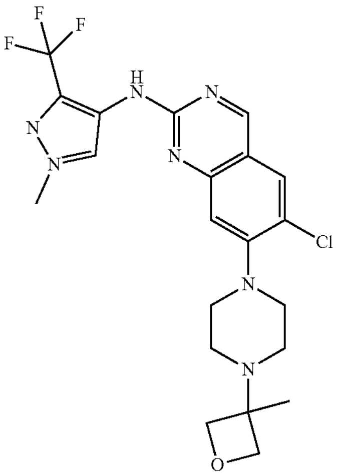 |

-continued
| Ex | Structure |
|---|---|
| Ex-4.22 | 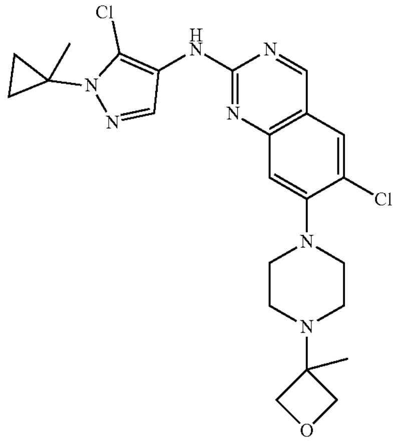 [SMILES: CC1(N2CCN(c3cc4nc(Nc5cnn(C6(C)CC6)c5Cl)ncc4cc3Cl)CC2)COC1] |
| Ex-4.23 | 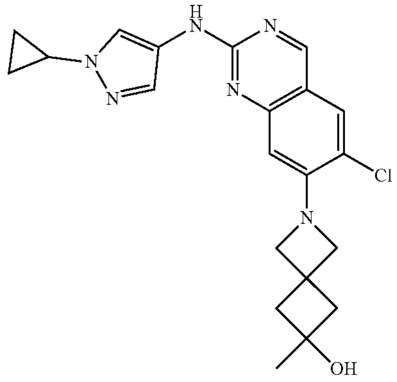 [SMILES: CC1(O)CC2(CN(c3cc4nc(Nc5cnn(C6CC6)c5)ncc4cc3Cl)C2)C1] |
| Ex-4.24 | 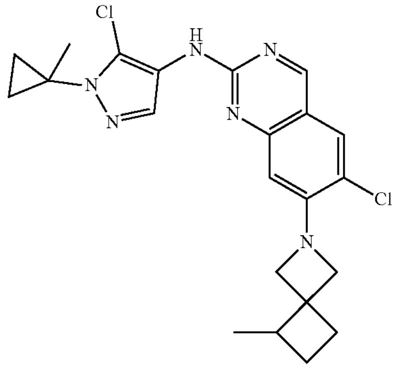 [SMILES: CC1CCC12CN(c1cc3nc(Nc4cnn(C5(C)CC5)c4Cl)ncc3cc1Cl)C2] |
| Ex-4.25 | 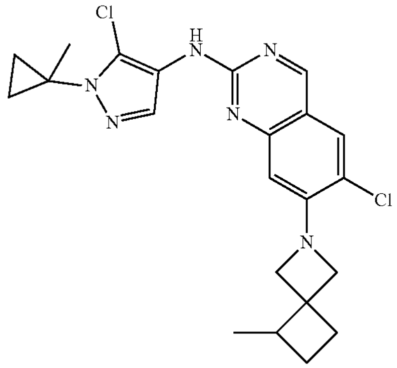 [SMILES: CC1CCC12CN(c1cc3nc(Nc4cnn(C5(C)CC5)c4Cl)ncc3cc1Cl)C2] |

-continued
| Ex | Structure |
|---|---|
| Ex-4.26 | 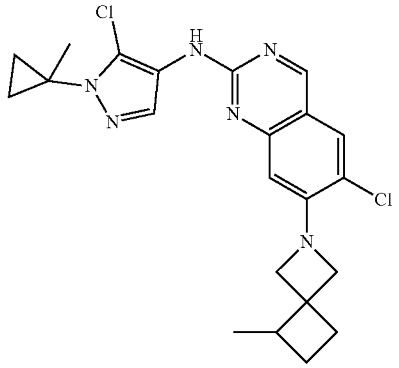 [SMILES: CC1CCC12CN(c1cc3nc(Nc4cnn(C5(C)CC5)c4Cl)ncc3cc1Cl)C2] |
| Ex-4.27 | 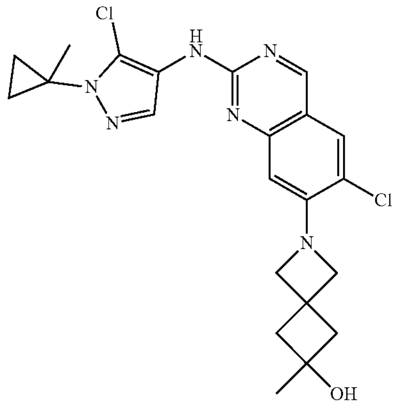 [SMILES: CC1(O)CC2(CN(c3cc4nc(Nc5cnn(C6(C)CC6)c5Cl)ncc4cc3Cl)C2)C1] |
| Ex-4.28 | 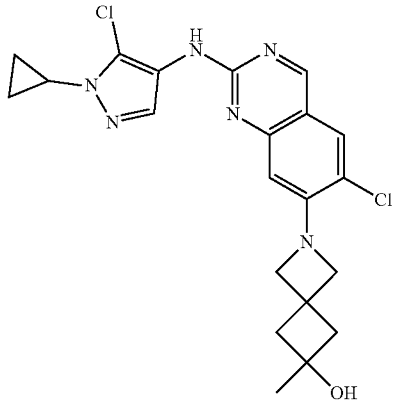 [SMILES: CC1(O)CC2(CN(c3cc4nc(Nc5cnn(C6CC6)c5Cl)ncc4cc3Cl)C2)C1] |

-continued
| Ex | Structure |
|---|---|
| Ex-4.29 | 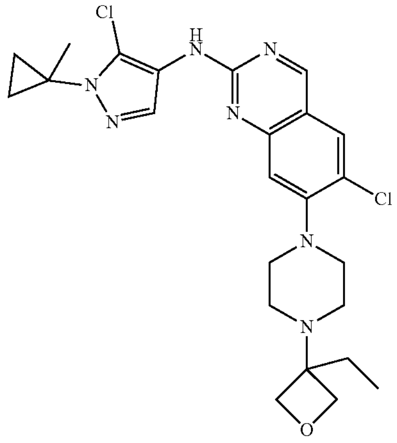 [SMILES: CCC1(N2CCN(c3cc4nc(Nc5cnn(C6(C)CC6)c5Cl)ncc4cc3Cl)CC2)COC1] |
| Ex-4.30 | 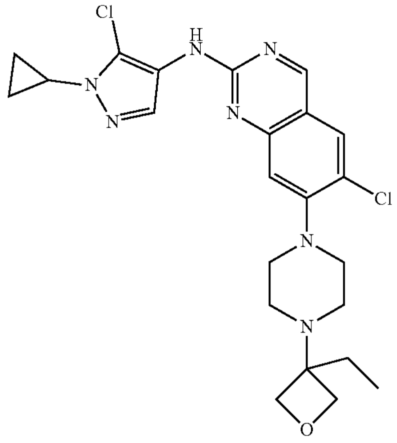 [SMILES: CCC1(N2CCN(c3cc4nc(Nc5cnn(C6CC6)c5Cl)ncc4cc3Cl)CC2)COC1] |
| Ex-4.31 | 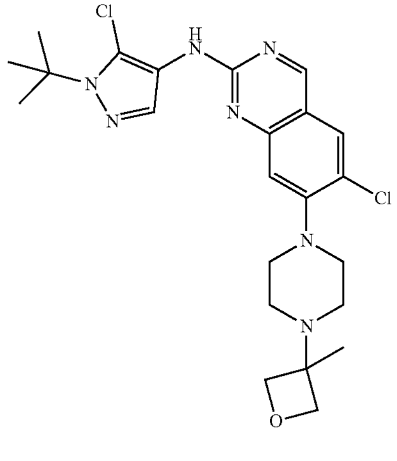 [SMILES: CC1(N2CCN(c3cc4nc(Nc5cnn(C(C)(C)C)c5Cl)ncc4cc3Cl)CC2)COC1] |

-continued
| Ex | Structure |
|---|---|
| Ex-4.32 | 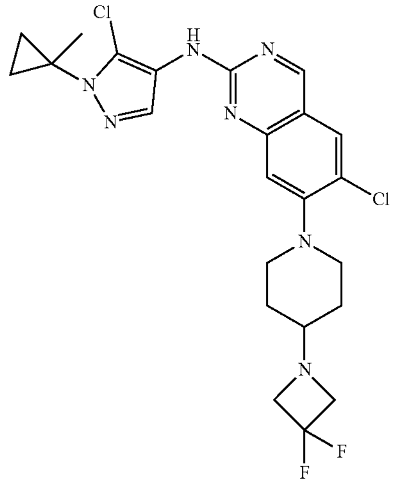 [SMILES: CC1(n2ncc(Nc3ncc4cc(Cl)c(N5CCC(N6CC(F)(F)C6)CC5)cc4n3)c2Cl)CC1] |
| Ex-4.33 | 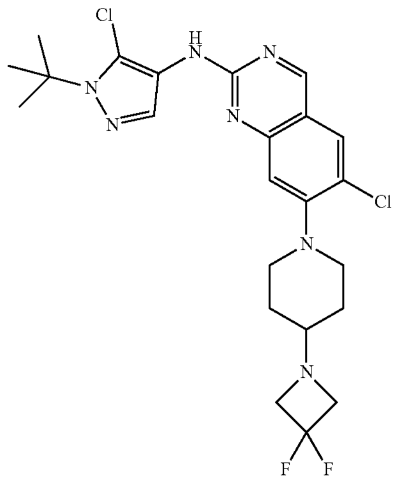 [SMILES: CC(C)(C)n1ncc(Nc2ncc3cc(Cl)c(N4CCC(N5CC(F)(F)C5)CC4)cc3n2)c1Cl] |
| Ex-4.34 | 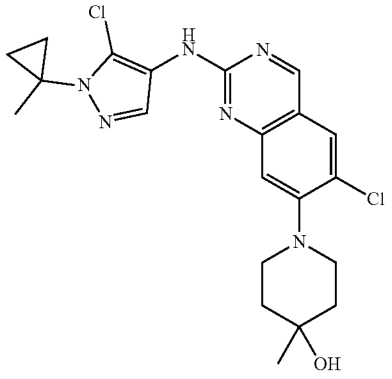 [SMILES: CC1(O)CCN(c2cc3nc(Nc4cnn(C5(C)CC5)c4Cl)ncc3cc2Cl)CC1] |

-continued
| Ex | Structure |
|---|---|
| Ex-4.35 | 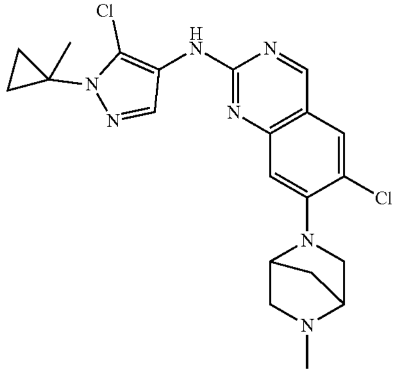 [SMILES: CN1CC2CC1CN2c1cc2nc(Nc3cnn(C4(C)CC4)c3Cl)ncc2cc1Cl] |
| Ex-4.36 | 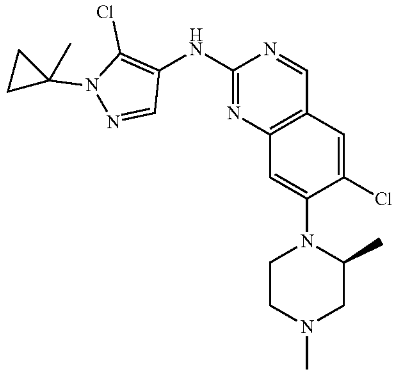 [SMILES: C[C@H]1CN(C)CCN1c1cc2nc(Nc3cnn(C4(C)CC4)c3Cl)ncc2cc1Cl] |
| Ex-4.37 | 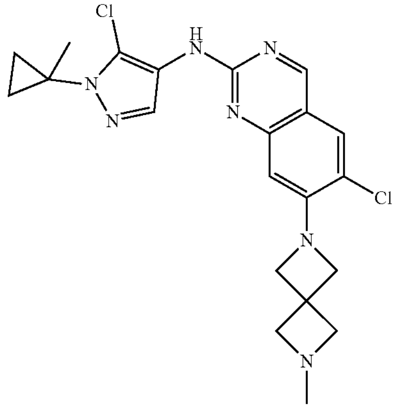 [SMILES: CN1CC2(C1)CN(c1cc3nc(Nc4cnn(C5(C)CC5)c4Cl)ncc3cc1Cl)C2] |

-continued
| Ex | Structure |
| --- | --- |
| Ex-4.38 | 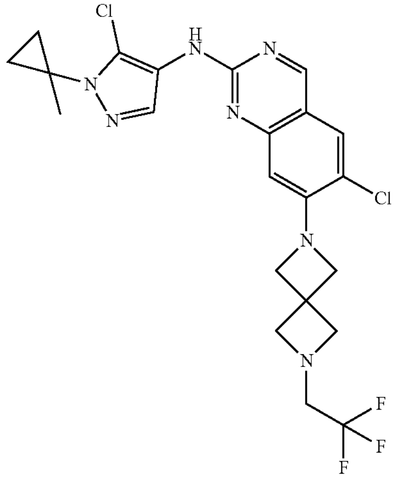 [SMILES: CC1(n2ncc(Nc3ncc4cc(Cl)c(N5CC6(CN(CC(F)(F)F)C6)C5)cc4n3)c2Cl)CC1] |
| Ex-4.39 | 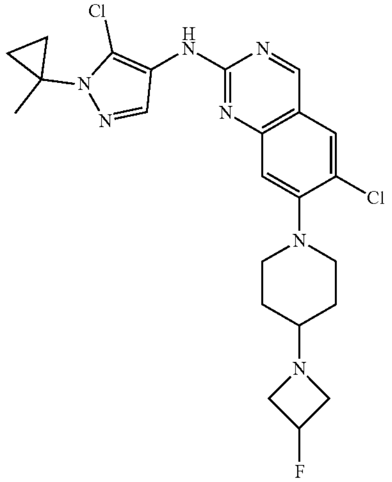 [SMILES: CC1(n2ncc(Nc3ncc4cc(Cl)c(N5CCC(N6CC(F)C6)CC5)cc4n3)c2Cl)CC1] |
| Ex-4.40 | 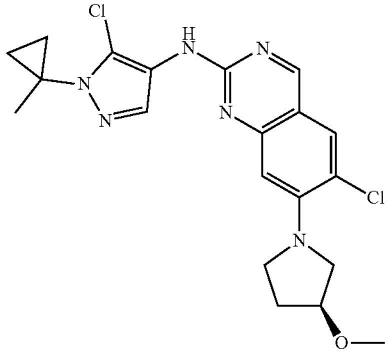 [SMILES: CO[C@H]1CCN(c2cc3nc(Nc4cnn(C5(C)CC5)c4Cl)ncc3cc2Cl)C1] |

-continued
| Ex | Structure |
|---|---|
| Ex-4.41 | 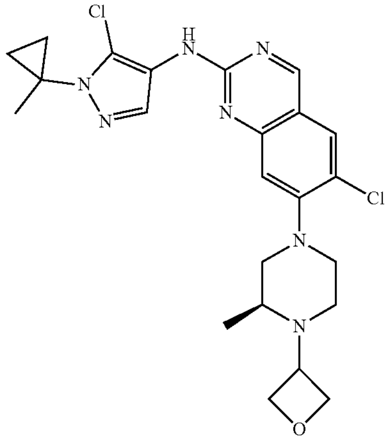 [SMILES: C[C@H]1CN(c2cc3nc(Nc4cnn(C5(C)CC5)c4Cl)ncc3cc2Cl)CCN1C1COC1] |
| Ex-4.42 | 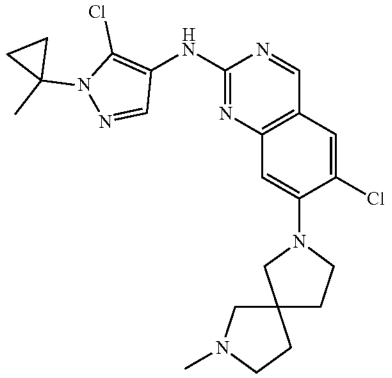 [SMILES: CN1CCC2(CCN(c3cc4nc(Nc5cnn(C6(C)CC6)c5Cl)ncc4cc3Cl)C2)C1] |
| Ex-4.43 | 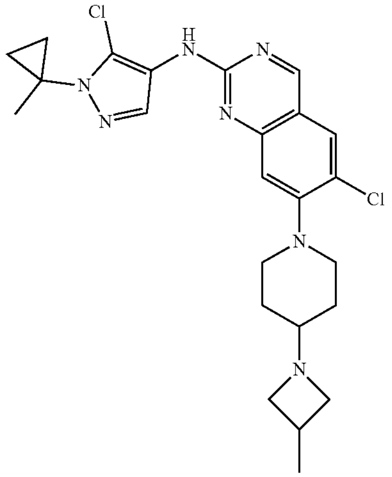 [SMILES: CC1CN(C2CCN(c3cc4nc(Nc5cnn(C6(C)CC6)c5Cl)ncc4cc3Cl)CC2)C1] |

-continued
| Ex | Structure |
|---|---|
| Ex-4.44 | 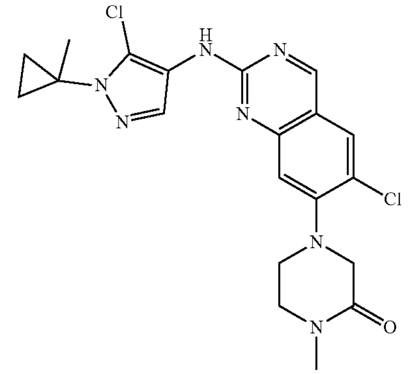 [SMILES: CN1CCN(c2cc3nc(Nc4cnn(C5(C)CC5)c4Cl)ncc3cc2Cl)CC1=O] |
| Ex-4.45 | 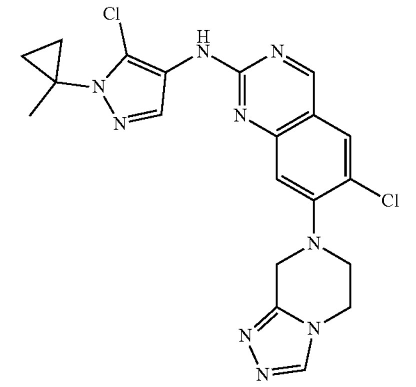 [SMILES: CC1(n2ncc(Nc3ncc4cc(Cl)c(N5CCn6cnnc6C5)cc4n3)c2Cl)CC1] |
| Ex-4.46 | 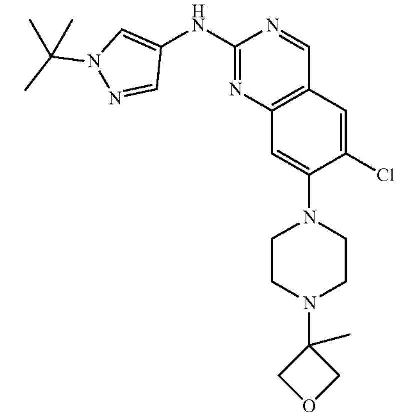 [SMILES: CC1(N2CCN(c3cc4nc(Nc5cnn(C(C)(C)C)c5)ncc4cc3Cl)CC2)COC1] |

-continued
| Ex | Structure |
|---|---|
| Ex-4.47 | 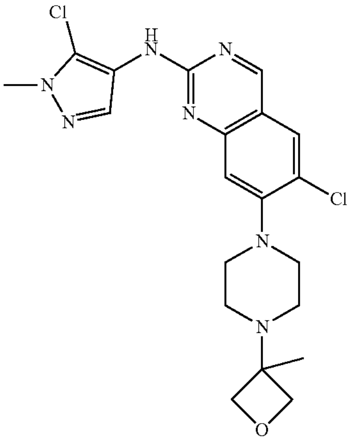 [SMILES: Cn1ncc(Nc2ncc3cc(Cl)c(N4CCN(C5(C)COC5)CC4)cc3n2)c1Cl] |
| Ex-4.48 | 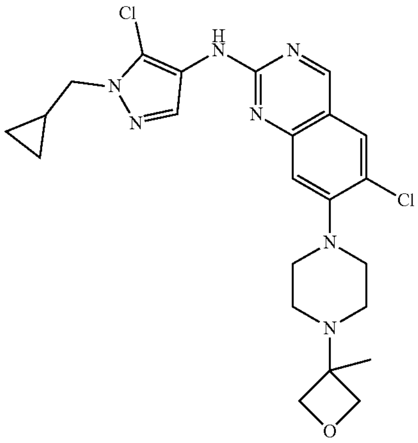 [SMILES: CC1(N2CCN(c3cc4nc(Nc5cnn(CC6CC6)c5Cl)ncc4cc3Cl)CC2)COC1] |
| Ex-4.49 | 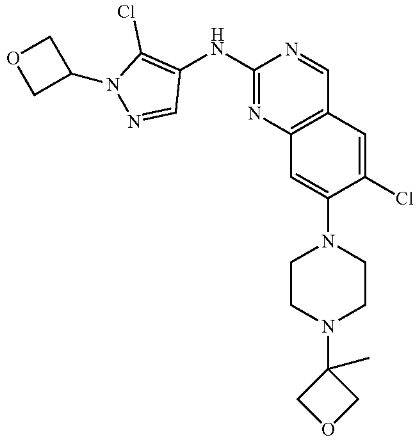 [SMILES: CC1(N2CCN(c3cc4nc(Nc5cnn(C6COC6)c5Cl)ncc4cc3Cl)CC2)COC1] |

-continued
| Ex | Structure |
|---|---|
| Ex-4.50 | 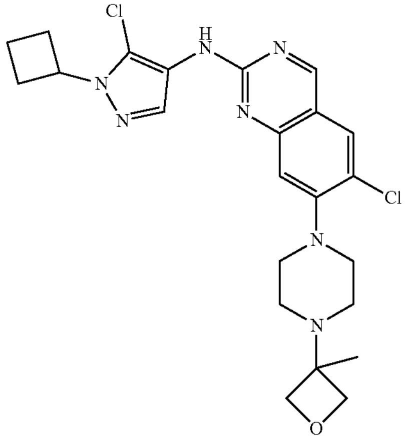 [SMILES: CC1(N2CCN(c3cc4nc(Nc5cnn(C6CCC6)c5Cl)ncc4cc3Cl)CC2)COC1] |
| Ex-4.51 | 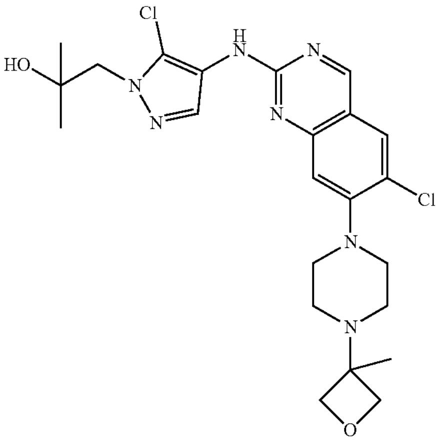 [SMILES: CC(C)(O)Cn1ncc(Nc2ncc3cc(Cl)c(N4CCN(C5(C)COC5)CC4)cc3n2)c1Cl] |
| Ex-4.52 | 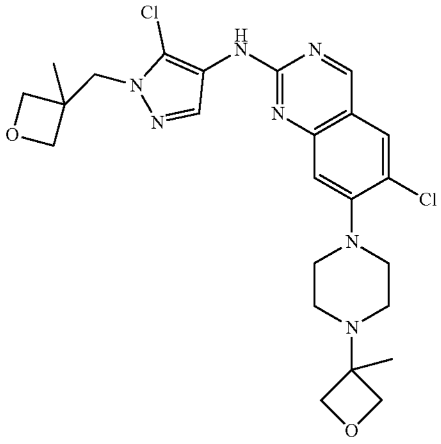 [SMILES: CC1(Cn2ncc(Nc3ncc4cc(Cl)c(N5CCN(C6(C)COC6)CC5)cc4n3)c2Cl)COC1] |

-continued
| Ex | Structure |
|---|---|
| Ex-4.53 | 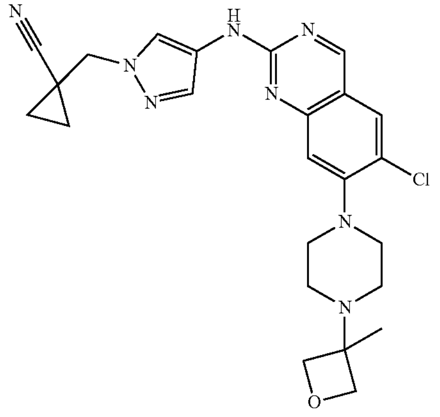 [SMILES: CC1(N2CCN(c3cc4nc(Nc5cnn(CC6(C#N)CC6)c5)ncc4cc3Cl)CC2)COC1] |
| Ex-4.54 | 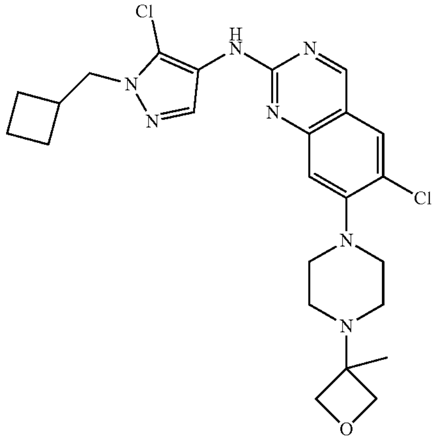 [SMILES: CC1(N2CCN(c3cc4nc(Nc5cnn(CC6CCC6)c5Cl)ncc4cc3Cl)CC2)COC1] |
| Ex-4.55 | 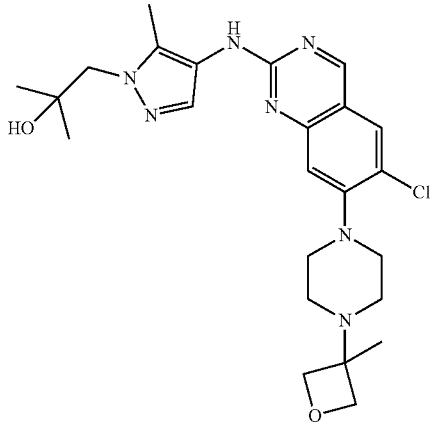 [SMILES: Cc1c(Nc2ncc3cc(Cl)c(N4CCN(C5(C)COC5)CC4)cc3n2)cnn1CC(C)(C)O] |

-continued
| Ex | Structure |
| --- | --- |
| Ex-4.56 | 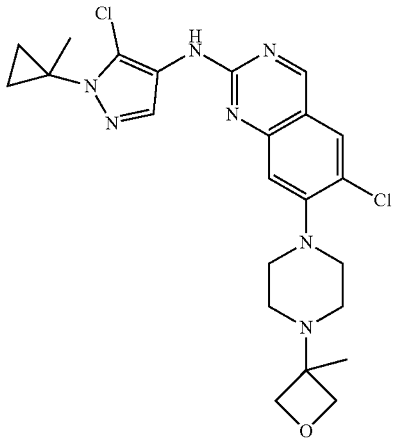 [SMILES: CC1(N2CCN(c3cc4nc(Nc5cnn(C6(C)CC6)c5Cl)ncc4cc3Cl)CC2)COC1] |
| Ex-4.57 | 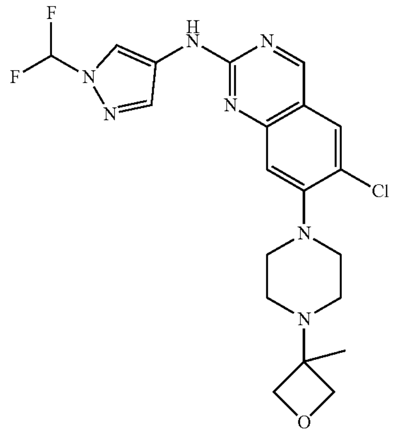 [SMILES: CC1(N2CCN(c3cc4nc(Nc5cnn(C(F)F)c5)ncc4cc3Cl)CC2)COC1] |
| Ex-4.58 | 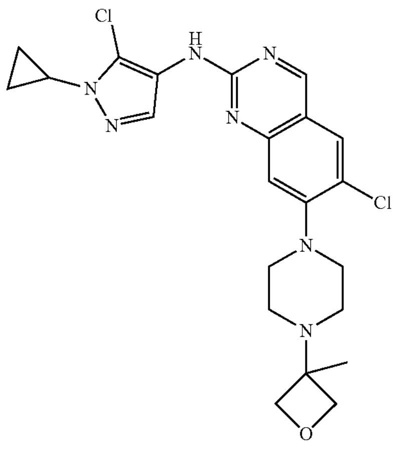 [SMILES: CC1(N2CCN(c3cc4nc(Nc5cnn(C6CC6)c5Cl)ncc4cc3Cl)CC2)COC1] |

-continued
| Ex | Structure |
|---|---|
| Ex-4.59 | 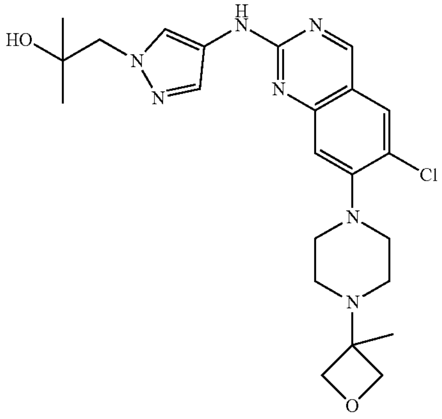 [SMILES: CC(C)(O)Cn1cc(Nc2ncc3cc(Cl)c(N4CCN(C5(C)COC5)CC4)cc3n2)cn1] |
| Ex-4.60 | 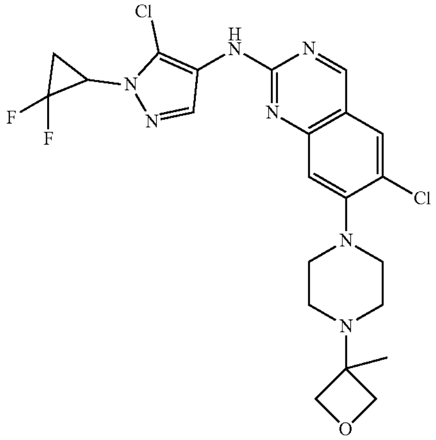 [SMILES: CC1(N2CCN(c3cc4nc(Nc5cnn(C6CC6(F)F)c5Cl)ncc4cc3Cl)CC2)COC1] |
| Ex-4.61 | 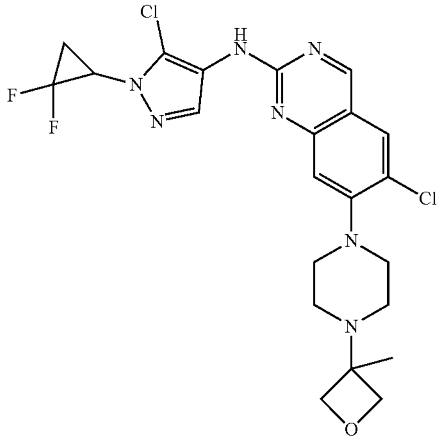 [SMILES: CC1(N2CCN(c3cc4nc(Nc5cnn(C6CC6(F)F)c5Cl)ncc4cc3Cl)CC2)COC1] |

-continued
| Ex | Structure |
|---|---|
| Ex-4.62 | 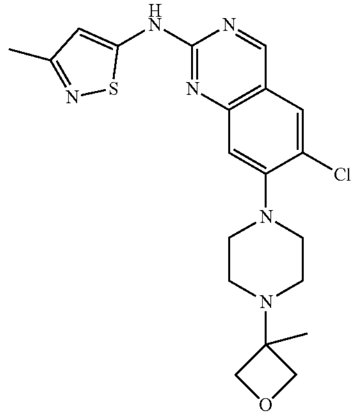 [SMILES: Cc1cc(Nc2ncc3cc(Cl)c(N4CCN(C5(C)COC5)CC4)cc3n2)sn1] |
| Ex-4.63 | 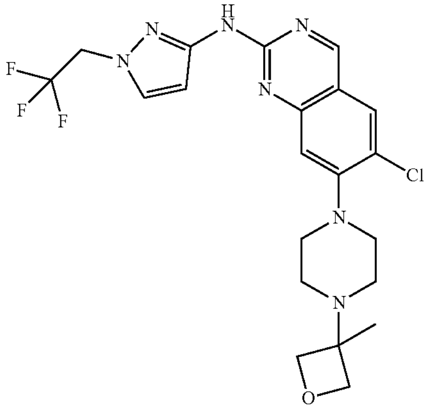 [SMILES: CC1(N2CCN(c3cc4nc(Nc5ccn(CC(F)(F)F)n5)ncc4cc3Cl)CC2)COC1] |
| Ex-4.64 | 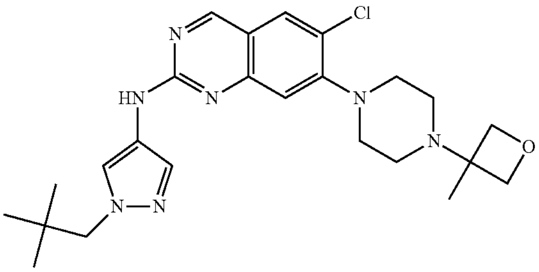 [SMILES: CC(C)(C)Cn1cc(Nc2ncc3cc(Cl)c(N4CCN(C5(C)COC5)CC4)cc3n2)cn1] |
| Ex-4.65 | 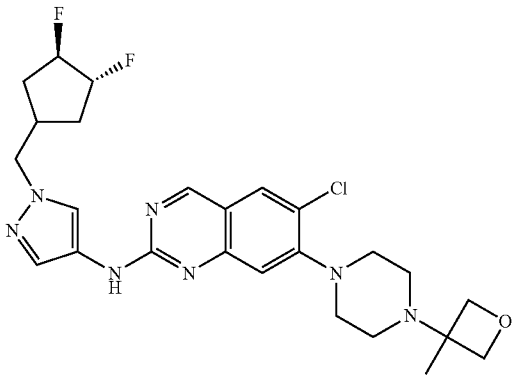 [SMILES: CC1(N2CCN(c3cc4nc(Nc5cnn(CC6C[C@@H](F)[C@H](F)C6)c5)ncc4cc3Cl)CC2)COC1] |

-continued
| Ex | Structure |
|---|---|
| Ex-4.66 | 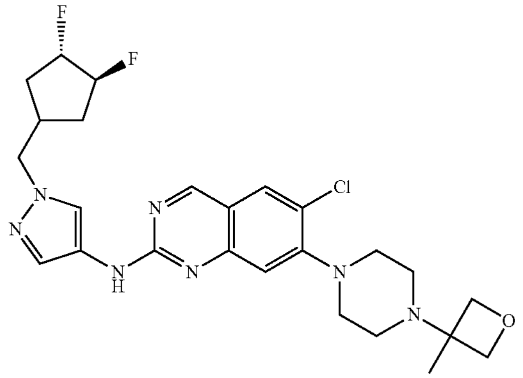 [SMILES: CC1(N2CCN(c3cc4nc(Nc5cnn(CC6C[C@H](F)[C@@H](F)C6)c5)ncc4cc3Cl)CC2)COC1] |
| Ex-4.67 | 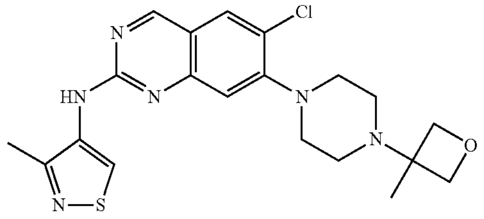 [SMILES: Cc1nscc1Nc1ncc2cc(Cl)c(N3CCN(C4(C)COC4)CC3)cc2n1] |
| Ex-4.68 | 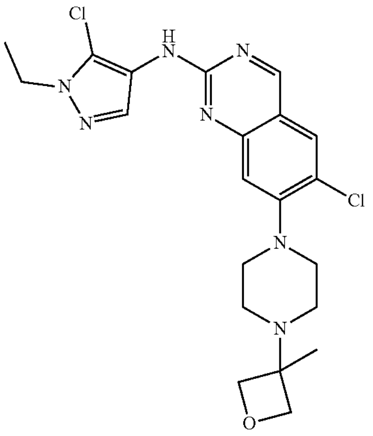 [SMILES: CCn1ncc(Nc2ncc3cc(Cl)c(N4CCN(C5(C)COC5)CC4)cc3n2)c1Cl] |
| Ex-4.69 | 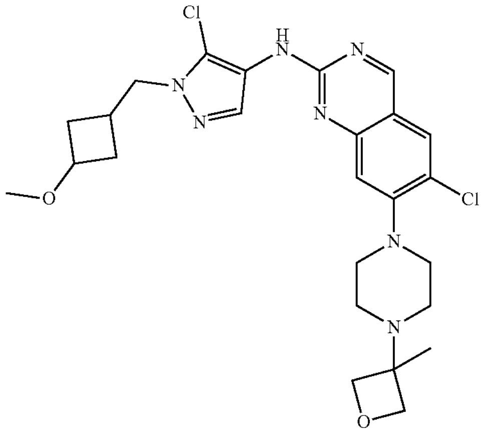 [SMILES: COC1CC(Cn2ncc(Nc3ncc4cc(Cl)c(N5CCN(C6(C)COC6)CC5)cc4n3)c2Cl)C1] |

-continued
| Ex | Structure |
| --- | --- |
| Ex-4.70 | 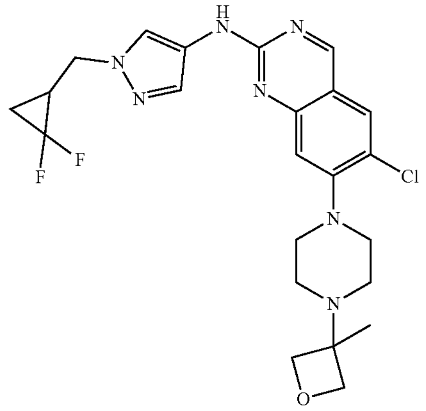 [SMILES: CC1(N2CCN(c3cc4nc(Nc5cnn(CC6CC6(F)F)c5)ncc4cc3Cl)CC2)COC1] |
| Ex-4.71 | 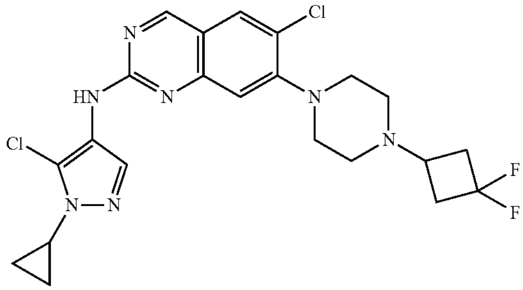 [SMILES: FC1(F)CC(N2CCN(c3cc4nc(Nc5cnn(C6CC6)c5Cl)ncc4cc3Cl)CC2)C1] |
| Ex-5.1 | 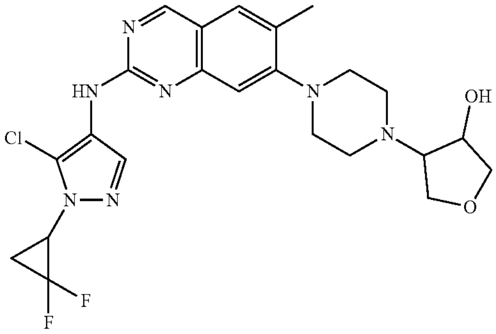 [SMILES: Cc1cc2cnc(Nc3cnn(C4CC4(F)F)c3Cl)nc2cc1N1CCN(C2COCC2O)CC1] |
| Ex-5.2 | 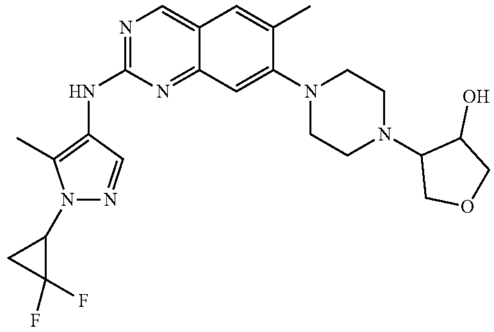 [SMILES: Cc1cc2cnc(Nc3cnn(C4CC4(F)F)c3C)nc2cc1N1CCN(C2COCC2O)CC1] |

-continued
| Ex | Structure |
|---|---|
| Ex-5.3 | 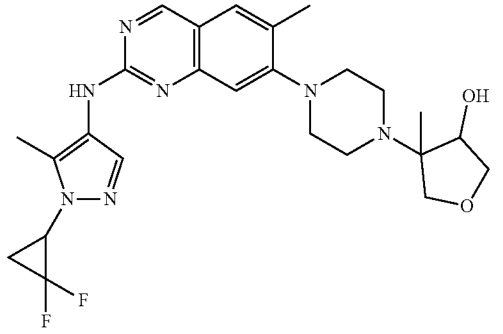 [SMILES: Cc1cc2cnc(Nc3cnn(C4CC4(F)F)c3C)nc2cc1N1CCN(C2(C)COCC2O)CC1] |
| Ex-5.4 | 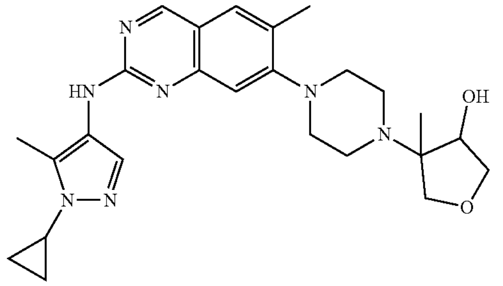 [SMILES: Cc1cc2cnc(Nc3cnn(C4CC4)c3C)nc2cc1N1CCN(C2(C)COCC2O)CC1] |
| Ex-5.5 | 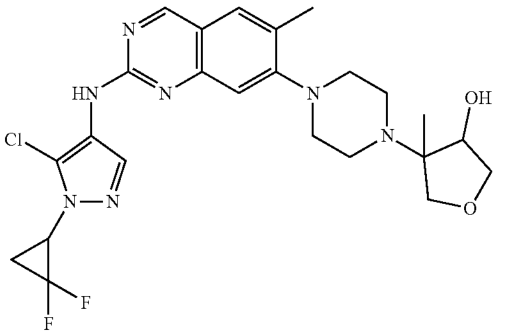 [SMILES: Cc1cc2cnc(Nc3cnn(C4CC4(F)F)c3Cl)nc2cc1N1CCN(C2(C)COCC2O)CC1] |
| Ex-5.6 | 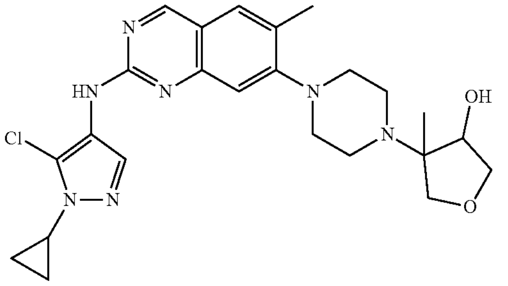 [SMILES: Cc1cc2cnc(Nc3cnn(C4CC4)c3Cl)nc2cc1N1CCN(C2(C)COCC2O)CC1] |
| Ex-5.7 | 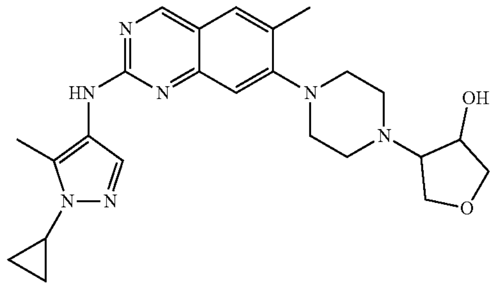 [SMILES: Cc1cc2cnc(Nc3cnn(C4CC4)c3C)nc2cc1N1CCN(C2COCC2O)CC1] |

-continued
| Ex | Structure |
| --- | --- |
| Ex-5.8 | 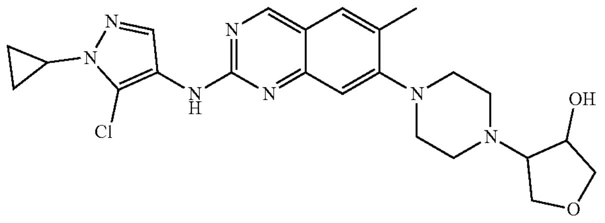 [SMILES: Cc1cc2cnc(Nc3cnn(C4CC4)c3Cl)nc2cc1N1CCN(C2COCC2O)CC1] |
| Ex-5.9 | 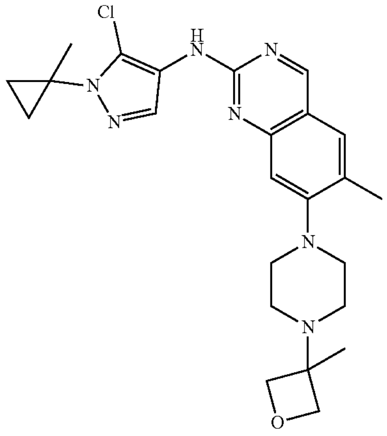 [SMILES: Cc1cc2cnc(Nc3cnn(C4(C)CC4)c3Cl)nc2cc1N1CCN(C2(C)COC2)CC1] |
| Ex-5.10 | 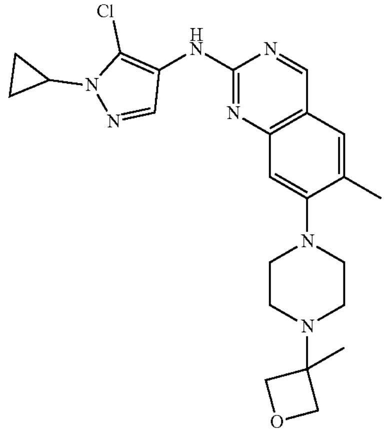 [SMILES: Cc1cc2cnc(Nc3cnn(C4CC4)c3Cl)nc2cc1N1CCN(C2(C)COC2)CC1] |
| Ex-5.11 | 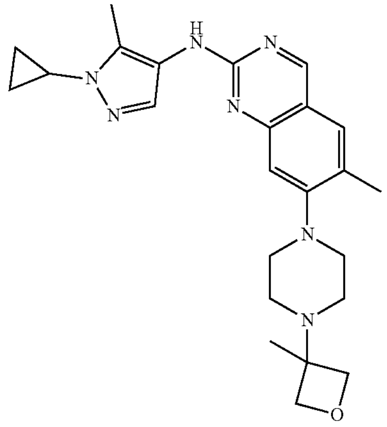 [SMILES: Cc1cc2cnc(Nc3cnn(C4CC4)c3C)nc2cc1N1CCN(C2(C)COC2)CC1] |

-continued
| Ex | Structure |
|---|---|
| Ex-5.12 | 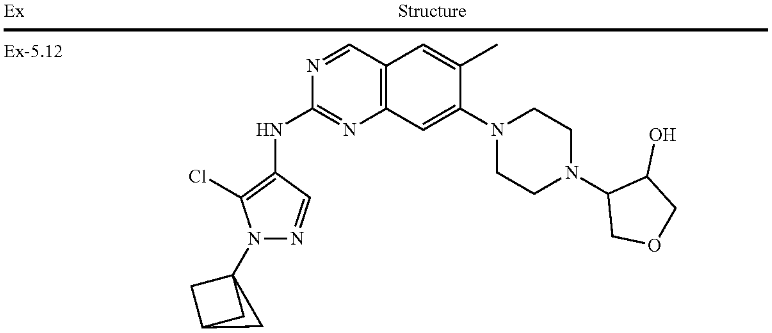 |
| Ex-5.13 | 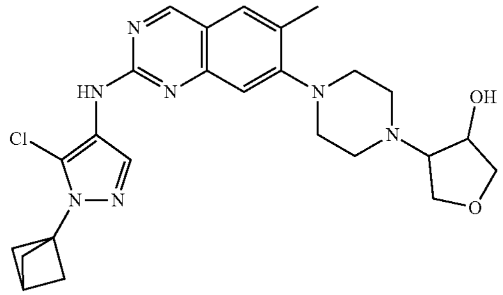 [SMILES: Cc1cc2cnc(Nc3cnn(C45CC(C4)C5)c3Cl)nc2cc1N1CCN(C2COCC2O)CC1] |
| Ex-5.14 | 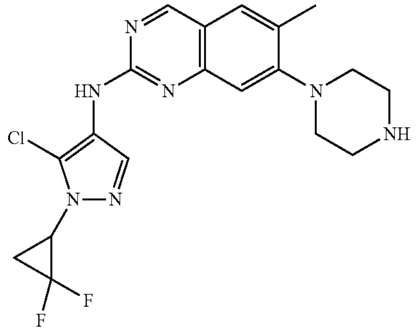 [SMILES: Cc1cc2cnc(Nc3cnn(C4CC4(F)F)c3Cl)nc2cc1N1CCNCC1] |
| Ex-5.15 | 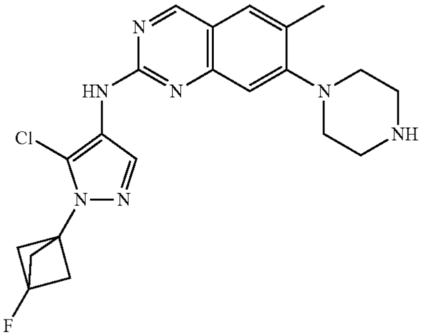 [SMILES: Cc1cc2cnc(Nc3cnn(C45CC(F)(C4)C5)c3Cl)nc2cc1N1CCNCC1] |
| Ex-5.16 | 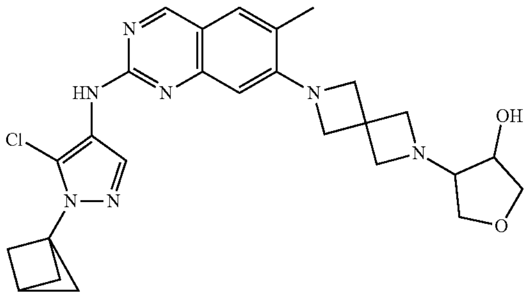 [SMILES: Cc1cc2cnc(Nc3cnn(C45CC(C4)C5)c3Cl)nc2cc1N1CC2(C1)CN(C1COCC1O)C2] |

-continued
| Ex | Structure |
|---|---|
| Ex-6.1 | 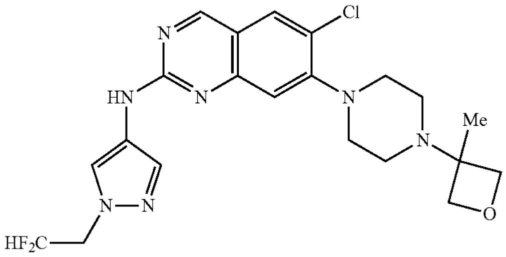 |
| Ex-6.2 | 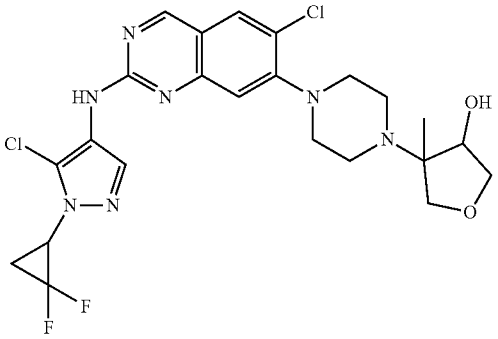 [SMILES: CC1(N2CCN(c3cc4nc(Nc5cnn(C6CC6(F)F)c5Cl)ncc4cc3Cl)CC2)COCC1O] |
| Ex-6.3 | 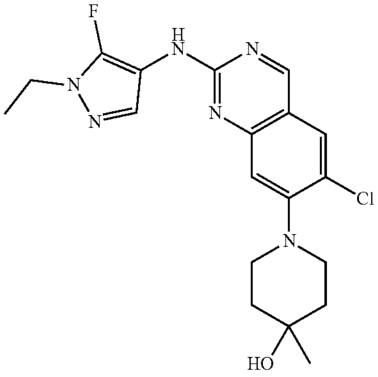 [SMILES: CCn1ncc(Nc2ncc3cc(Cl)c(N4CCC(C)(O)CC4)cc3n2)c1F] |
| Ex-6.4 | 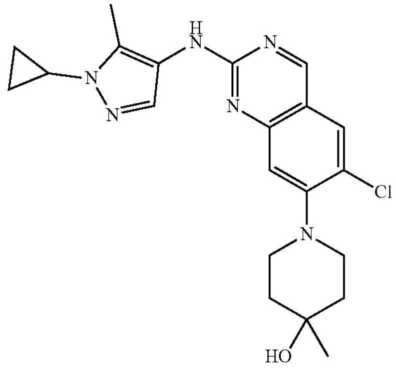 [SMILES: Cc1c(Nc2ncc3cc(Cl)c(N4CCC(C)(O)CC4)cc3n2)cnn1C1CC1] |

-continued
| Ex | Structure |
|---|---|
| Ex-6.5 | 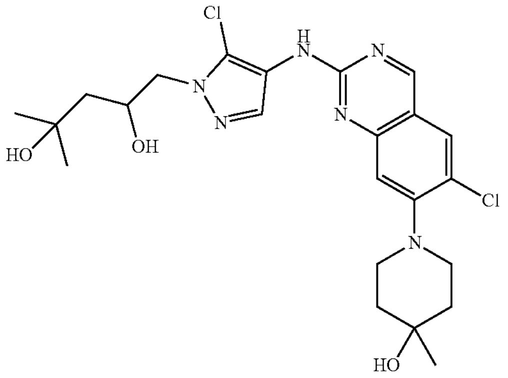 [SMILES: CC(C)(O)CC(O)Cn1ncc(Nc2ncc3cc(Cl)c(N4CCC(C)(O)CC4)cc3n2)c1Cl] |
| Ex-6.6 | 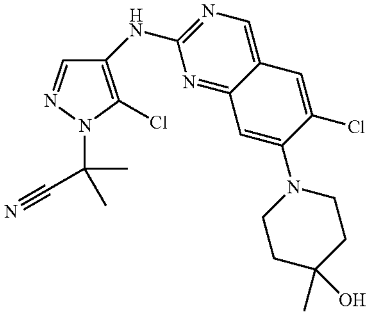 [SMILES: CC1(O)CCN(c2cc3nc(Nc4cnn(C(C)(C)C#N)c4Cl)ncc3cc2Cl)CC1] |
| Ex-6.7 | 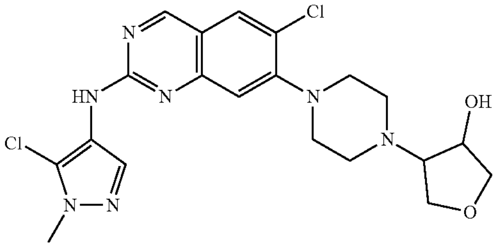 [SMILES: Cn1ncc(Nc2ncc3cc(Cl)c(N4CCN(C5COCC5O)CC4)cc3n2)c1Cl] |
| Ex-6.8 | 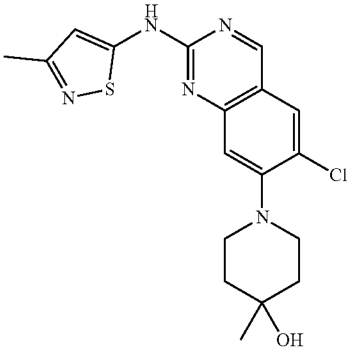 [SMILES: Cc1cc(Nc2ncc3cc(Cl)c(N4CCC(C)(O)CC4)cc3n2)sn1] |

-continued
| Ex | Structure |
| --- | --- |
| Ex-6.9 | 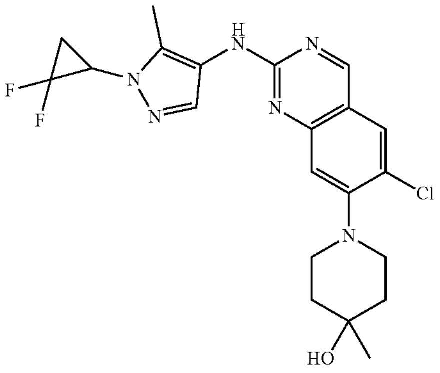 [SMILES: Cc1c(Nc2ncc3cc(Cl)c(N4CCC(C)(O)CC4)cc3n2)cnn1C1CC1(F)F] |
| Ex-6.10 | 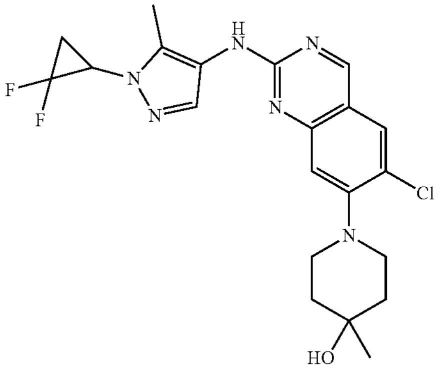 [SMILES: Cc1c(Nc2ncc3cc(Cl)c(N4CCC(C)(O)CC4)cc3n2)cnn1C1CC1(F)F] |
| Ex-6.11 | 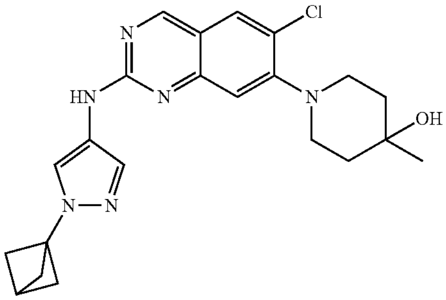 [SMILES: CC1(O)CCN(c2cc3nc(Nc4cnn(C56CC(C5)C6)c4)ncc3cc2Cl)CC1] |
| Ex-6.12 | 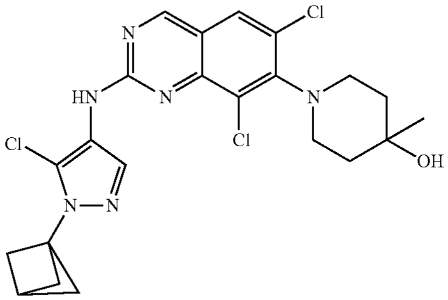 [SMILES: CC1(O)CCN(c2c(Cl)cc3cnc(Nc4cnn(C56CC(C5)C6)c4Cl)nc3c2Cl)CC1] |

-continued
| Ex | Structure |
|---|---|
| Ex-6.13 | 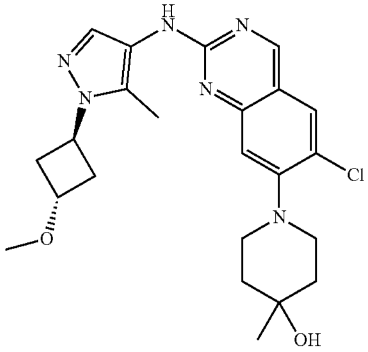 [SMILES: CO[C@H]1C[C@H](n2ncc(Nc3ncc4cc(Cl)c(N5CCC(C)(O)CC5)cc4n3)c2C)C1] |
| Ex-6.14 | 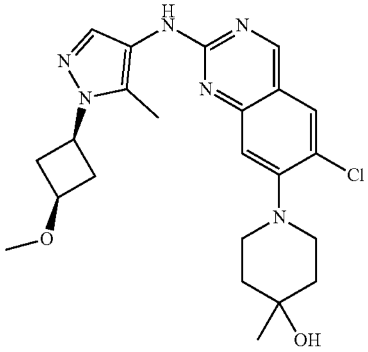 [SMILES: CO[C@H]1C[C@@H](n2ncc(Nc3ncc4cc(Cl)c(N5CCC(C)(O)CC5)cc4n3)c2C)C1] |
| Ex-6.15 | 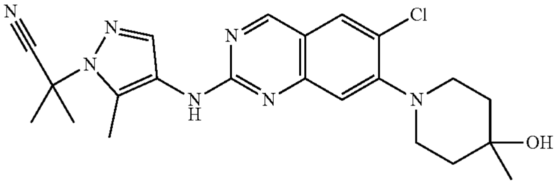 [SMILES: Cc1c(Nc2ncc3cc(Cl)c(N4CCC(C)(O)CC4)cc3n2)cnn1C(C)(C)C#N] |
| Ex-6.16 | 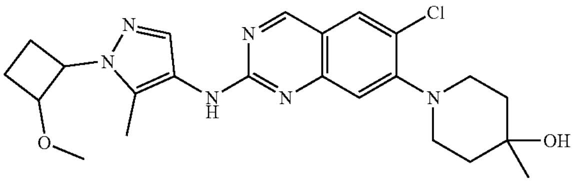 [SMILES: COC1CCC1n1ncc(Nc2ncc3cc(Cl)c(N4CCC(C)(O)CC4)cc3n2)c1C] |
| Ex-6.17 | 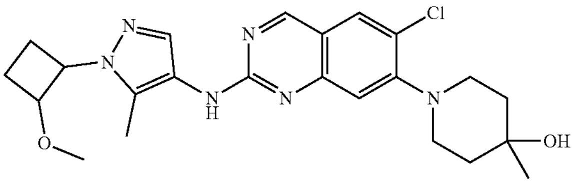 [SMILES: COC1CCC1n1ncc(Nc2ncc3cc(Cl)c(N4CCC(C)(O)CC4)cc3n2)c1C] |
| Ex-6.18 | 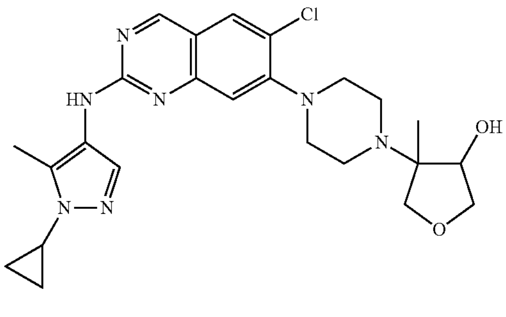 [SMILES: Cc1c(Nc2ncc3cc(Cl)c(N4CCN(C5(C)COCC5O)CC4)cc3n2)cnn1C1CC1] |

-continued
| Ex | Structure |
|---|---|
| Ex-6.19 | 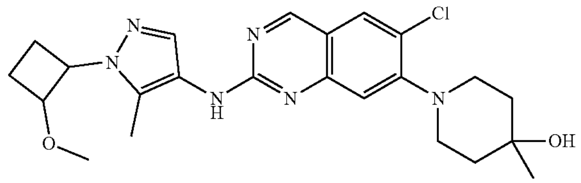 [SMILES: COC1CCC1n1ncc(Nc2ncc3cc(Cl)c(N4CCC(C)(O)CC4)cc3n2)c1C] |
| Ex-6.20 | 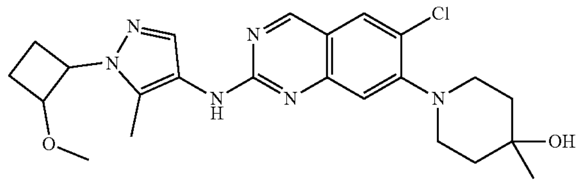 [SMILES: COC1CCC1n1ncc(Nc2ncc3cc(Cl)c(N4CCC(C)(O)CC4)cc3n2)c1C] |
| Ex-6.21 | 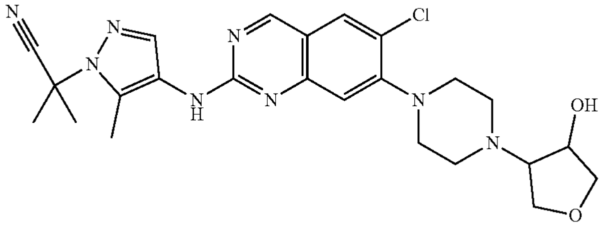<br>9874 |
| Ex-6.22 | 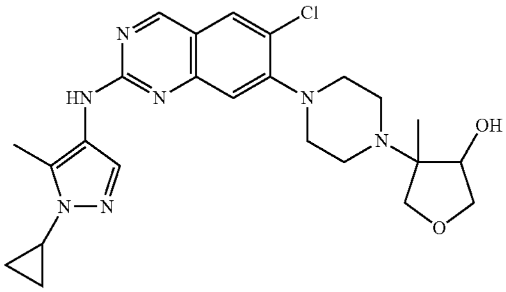 [SMILES: Cc1c(Nc2ncc3cc(Cl)c(N4CCN(C5(C)COCC5O)CC4)cc3n2)cnn1C1CC1] |
| Ex-6.23 | 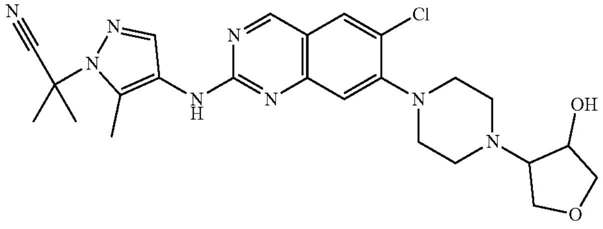 [SMILES: Cc1c(Nc2ncc3cc(Cl)c(N4CCN(C5COCC5O)CC4)cc3n2)cnn1C(C)(C)C#N] |
| Ex-6.24 | 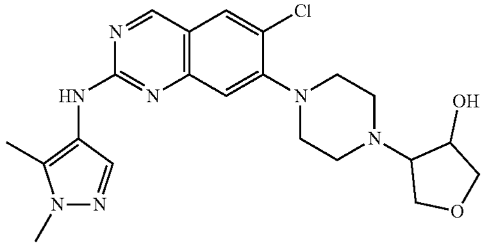 [SMILES: Cc1c(Nc2ncc3cc(Cl)c(N4CCN(C5COCC5O)CC4)cc3n2)cnn1C] |

-continued
| Ex | Structure |
|---|---|
| Ex-6.25 | 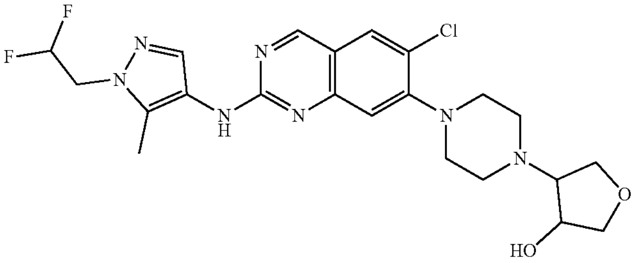 [SMILES: Cc1c(Nc2ncc3cc(Cl)c(N4CCN(C5COCC5O)CC4)cc3n2)cnn1CC(F)F] |
| Ex-6.26 | 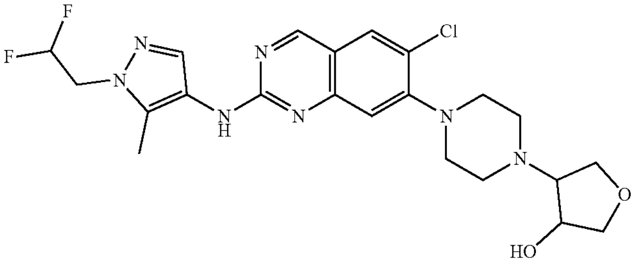 [SMILES: Cc1c(Nc2ncc3cc(Cl)c(N4CCN(C5COCC5O)CC4)cc3n2)cnn1CC(F)F] |
| Ex-6.27 | 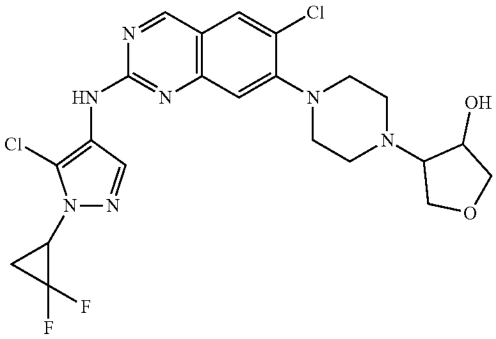 [SMILES: OC1COCC1N1CCN(c2cc3nc(Nc4cnn(C5CC5(F)F)c4Cl)ncc3cc2Cl)CC1] |
| Ex-6.28 | 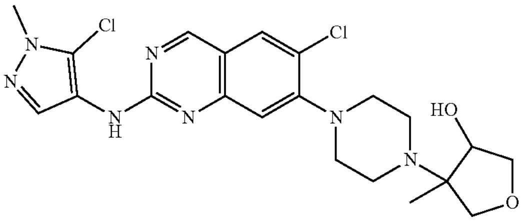 [SMILES: Cn1ncc(Nc2ncc3cc(Cl)c(N4CCN(C5(C)COCC5O)CC4)cc3n2)c1Cl] |
| Ex-6.29 | 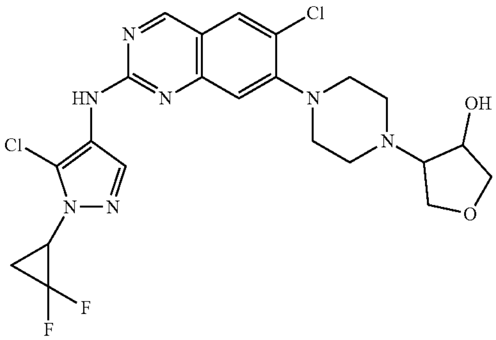 [SMILES: OC1COCC1N1CCN(c2cc3nc(Nc4cnn(C5CC5(F)F)c4Cl)ncc3cc2Cl)CC1] |

-continued
| Ex | Structure |
|---|---|
| Ex-6.30 | 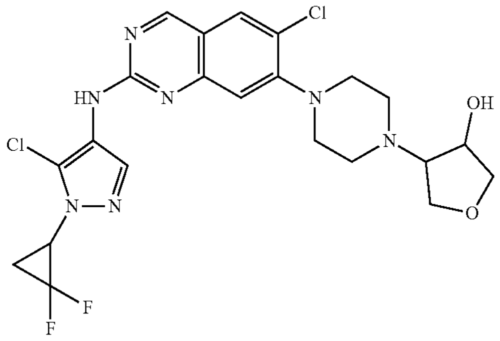 [SMILES: OC1COCC1N1CCN(c2cc3nc(Nc4cnn(C5CC5(F)F)c4Cl)ncc3cc2Cl)CC1] |
| Ex-6.31 | 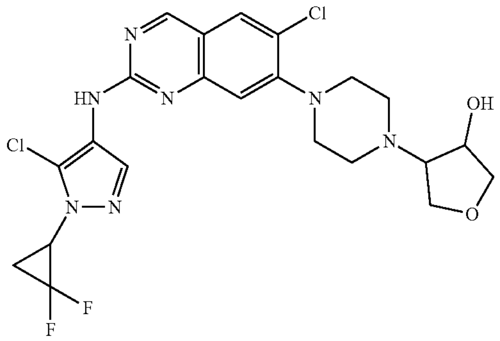 [SMILES: OC1COCC1N1CCN(c2cc3nc(Nc4cnn(C5CC5(F)F)c4Cl)ncc3cc2Cl)CC1] |
| Ex-6.32 | 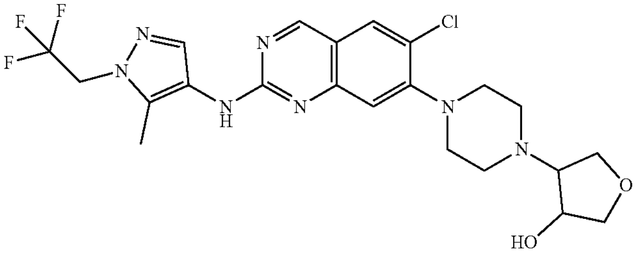 [SMILES: Cc1c(Nc2ncc3cc(Cl)c(N4CCN(C5COCC5O)CC4)cc3n2)cnn1CC(F)(F)F] |
| Ex-6.33 | 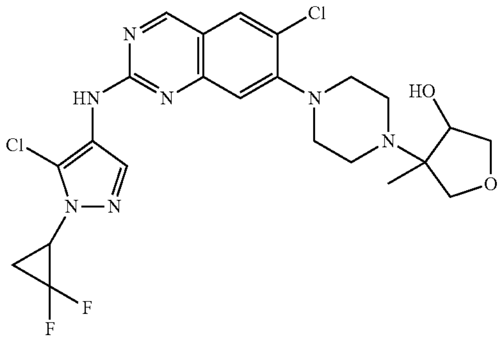 [SMILES: CC1(N2CCN(c3cc4nc(Nc5cnn(C6CC6(F)F)c5Cl)ncc4cc3Cl)CC2)COCC1O] |

-continued
| Ex | Structure |
| --- | --- |
| Ex-6.34 | 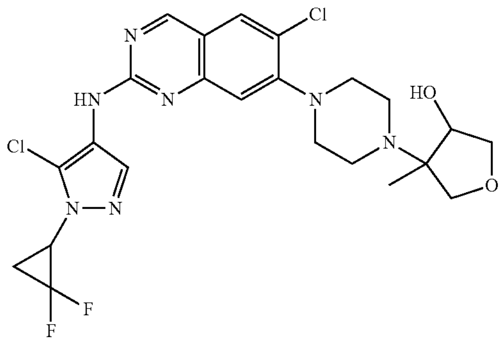 [SMILES: CC1(N2CCN(c3cc4nc(Nc5cnn(C6CC6(F)F)c5Cl)ncc4cc3Cl)CC2)COCC1O] |
| Ex-6.35 | 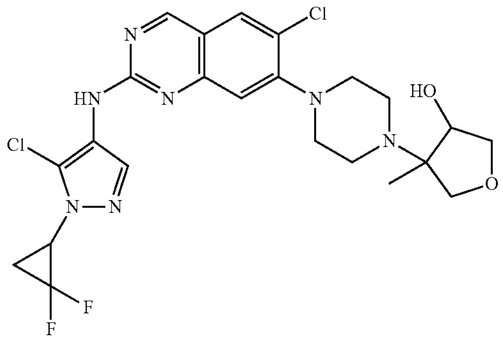 [SMILES: CC1(N2CCN(c3cc4nc(Nc5cnn(C6CC6(F)F)c5Cl)ncc4cc3Cl)CC2)COCC1O] |
| Ex-6.36 | 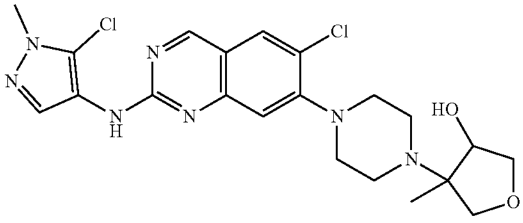 [SMILES: Cn1ncc(Nc2ncc3cc(Cl)c(N4CCN(C5(C)COCC5O)CC4)cc3n2)c1Cl] |
| Ex-6.37 | 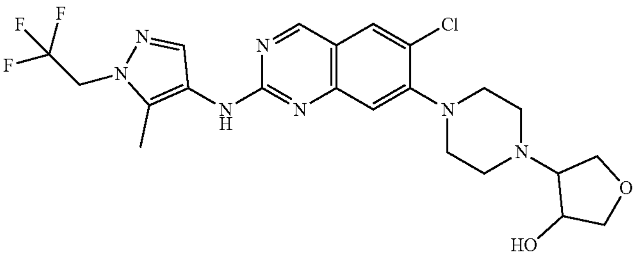 [SMILES: Cc1c(Nc2ncc3cc(Cl)c(N4CCN(C5COCC5O)CC4)cc3n2)cnn1CC(F)(F)F] |
| Ex-6.38 | 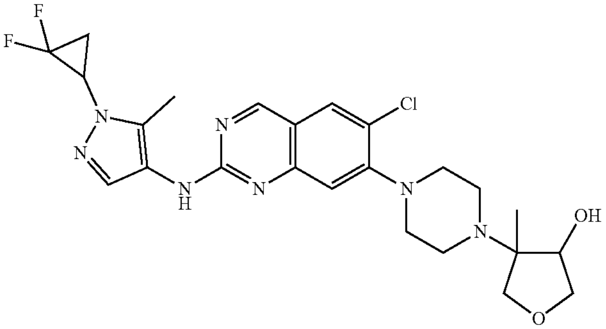 [SMILES: Cc1c(Nc2ncc3cc(Cl)c(N4CCN(C5(C)COCC5O)CC4)cc3n2)cnn1C1CC1(F)F] |

-continued
| Ex | Structure |
|---|---|
| Ex-6.39 | 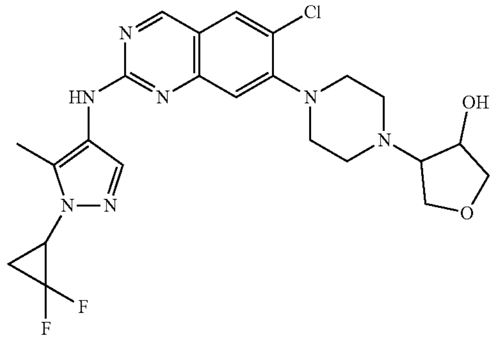 [SMILES: Cc1c(Nc2ncc3cc(Cl)c(N4CCN(C5COCC5O)CC4)cc3n2)cnn1C1CC1(F)F] |
| Ex-6.40 | 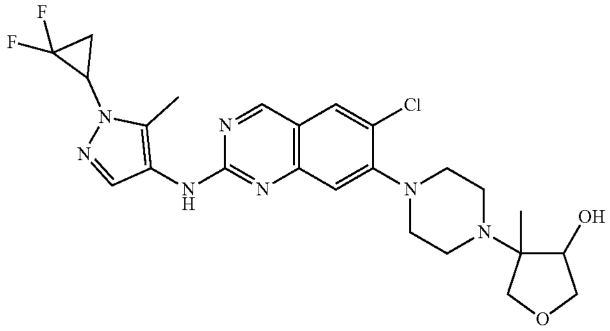 [SMILES: Cc1c(Nc2ncc3cc(Cl)c(N4CCN(C5(C)COCC5O)CC4)cc3n2)cnn1C1CC1(F)F] |
| Ex-6.41 | 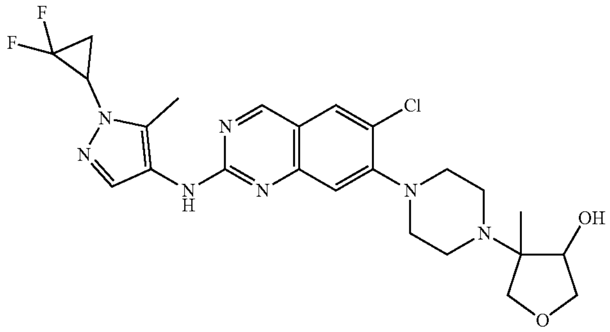 [SMILES: Cc1c(Nc2ncc3cc(Cl)c(N4CCN(C5(C)COCC5O)CC4)cc3n2)cnn1C1CC1(F)F] |
| Ex-6.42 | 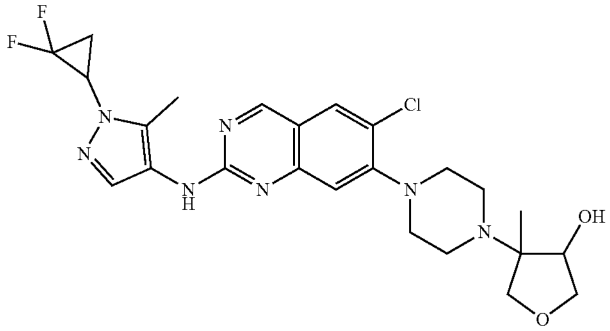 [SMILES: Cc1c(Nc2ncc3cc(Cl)c(N4CCN(C5(C)COCC5O)CC4)cc3n2)cnn1C1CC1(F)F] |

-continued
| Ex | Structure |
| --- | --- |
| Ex-6.43 | 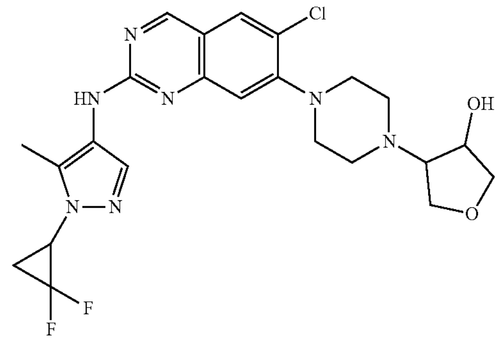 [SMILES: Cc1c(Nc2ncc3cc(Cl)c(N4CCN(C5COCC5O)CC4)cc3n2)cnn1C1CC1(F)F] |
| Ex-6.44 | 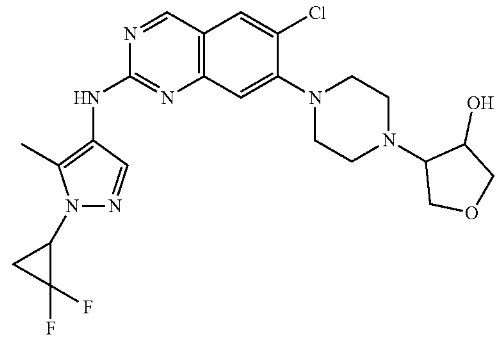 [SMILES: Cc1c(Nc2ncc3cc(Cl)c(N4CCN(C5COCC5O)CC4)cc3n2)cnn1C1CC1(F)F] |
| Ex-6.45 | 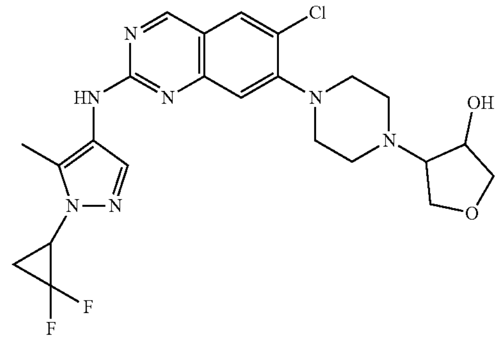 [SMILES: Cc1c(Nc2ncc3cc(Cl)c(N4CCN(C5COCC5O)CC4)cc3n2)cnn1C1CC1(F)F] |
| Ex-6.46 | 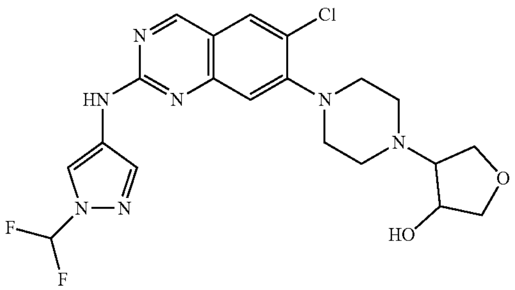 [SMILES: OC1COCC1N1CCN(c2cc3nc(Nc4cnn(C(F)F)c4)ncc3cc2Cl)CC1] |

-continued
| Ex | Structure |
|---|---|
| Ex-6.47 | 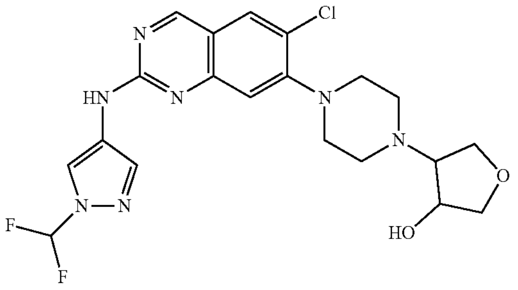 [SMILES: OC1COCC1N1CCN(c2cc3nc(Nc4cnn(C(F)F)c4)ncc3cc2Cl)CC1] |
| Ex-6.48 | 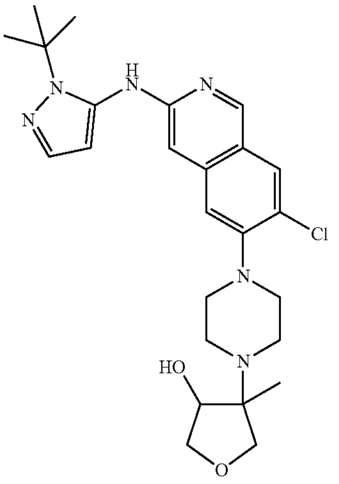 [SMILES: CC1(N2CCN(c3cc4cc(Nc5ccnn5C(C)(C)C)ncc4cc3Cl)CC2)COCC1O] |
| Ex-6.49 | 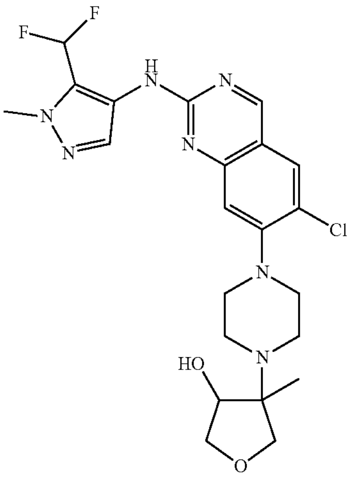 [SMILES: Cn1ncc(Nc2ncc3cc(Cl)c(N4CCN(C5(C)COCC5O)CC4)cc3n2)c1C(F)F] |

-continued
| Ex | Structure |
| --- | --- |
| Ex-6.50 | 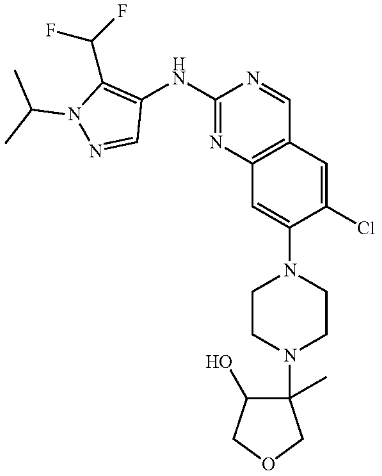 [SMILES: CC(C)n1ncc(Nc2ncc3cc(Cl)c(N4CCN(C5(C)COCC5O)CC4)cc3n2)c1C(F)F] |
| Ex-6.51 | 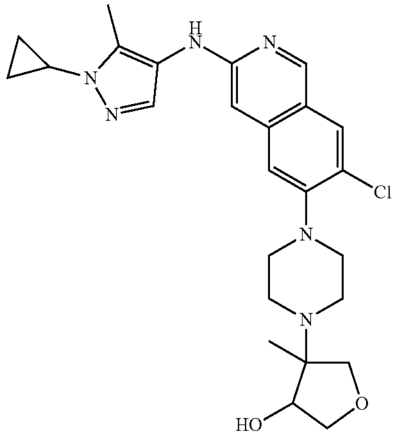 [SMILES: Cc1c(Nc2cc3cc(N4CCN(C5(C)COCC5O)CC4)c(Cl)cc3cn2)cnn1C1CC1] |
| Ex-6.52 | 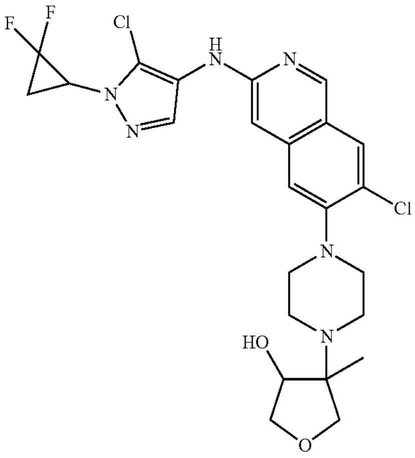 [SMILES: CC1(N2CCN(c3cc4cc(Nc5cnn(C6CC6(F)F)c5Cl)ncc4cc3Cl)CC2)COCC1O] |

-continued
| Ex | Structure |
|---|---|
| Ex-6.53 | 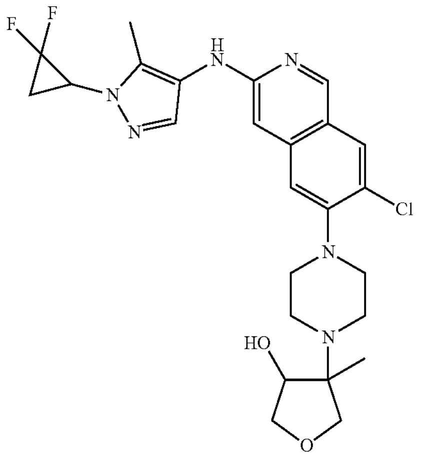 [SMILES: Cc1c(Nc2cc3cc(N4CCN(C5(C)COCC5O)CC4)c(Cl)cc3cn2)cnn1C1CC1(F)F] |
| Ex-6.54 | 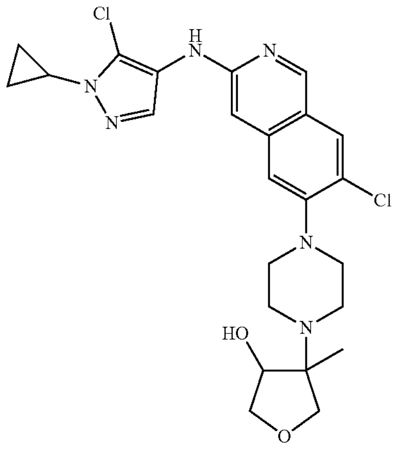 [SMILES: CC1(N2CCN(c3cc4cc(Nc5cnn(C6CC6)c5Cl)ncc4cc3Cl)CC2)COCC1O] |
| Ex-6.55 | 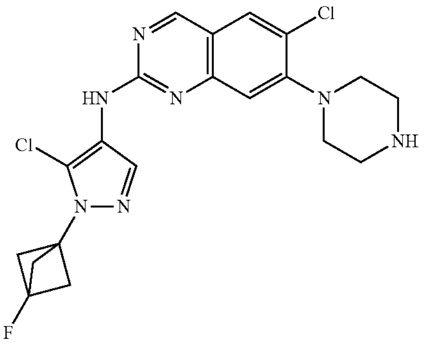 [SMILES: FC12CC(n3ncc(Nc4ncc5cc(Cl)c(N6CCNCC6)cc5n4)c3Cl)(C1)C2] |
| Ex-6.56 | 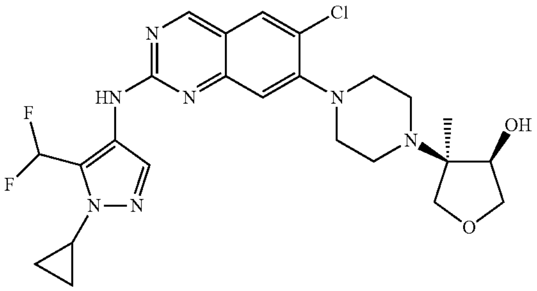 [SMILES: C[C@@]1(N2CCN(c3cc4nc(Nc5cnn(C6CC6)c5C(F)F)ncc4cc3Cl)CC2)COC[C@@H]1O] |

-continued
| Ex | Structure |
|---|---|
| Ex-7.1 | 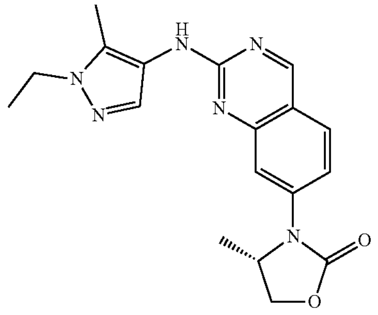 [SMILES: CCn1ncc(Nc2ncc3ccc(N4C(=O)OC[C@@H]4C)cc3n2)c1C] |
| Ex-7.2 | 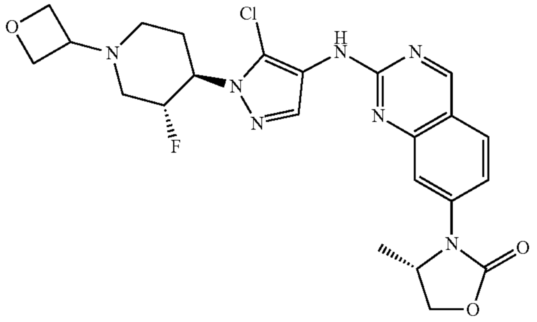 [SMILES: C[C@H]1COC(=O)N1c1ccc2cnc(Nc3cnn([C@@H]4CCN(C5COC5)C[C@H]4F)c3Cl)nc2c1] |
| Ex-7.3 | 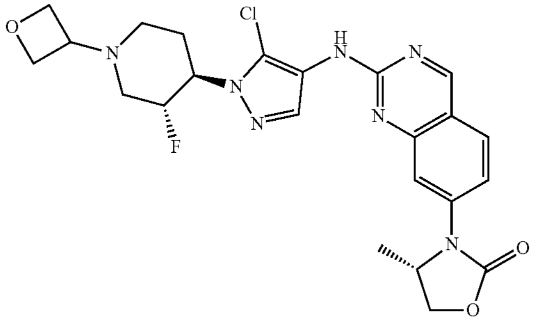 [SMILES: C[C@H]1COC(=O)N1c1ccc2cnc(Nc3cnn([C@@H]4CCN(C5COC5)C[C@H]4F)c3Cl)nc2c1] |
| Ex-7.4 | 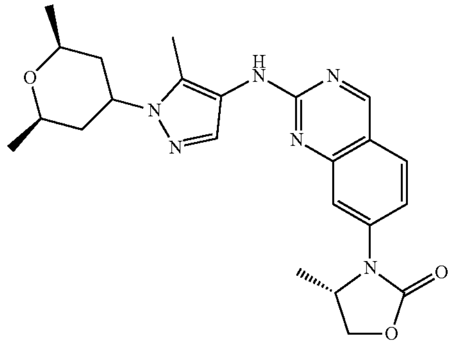 [SMILES: Cc1c(Nc2ncc3ccc(N4C(=O)OC[C@@H]4C)cc3n2)cnn1C1C[C@@H](C)O[C@@H](C)C1] |

-continued
| Ex | Structure |
|---|---|
| Ex-7.5 | 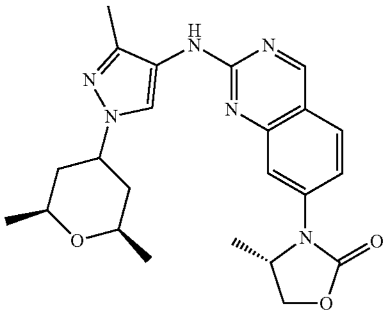 [SMILES: Cc1nn(C2C[C@@H](C)O[C@@H](C)C2)cc1Nc1ncc2ccc(N3C(=O)OC[C@@H]3C)cc2n1] |
| Ex-7.6 | 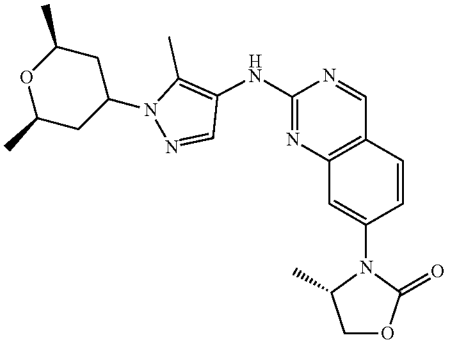 [SMILES: Cc1c(Nc2ncc3ccc(N4C(=O)OC[C@@H]4C)cc3n2)cnn1C1C[C@@H](C)O[C@@H](C)C1] |
| Ex-7.7 | 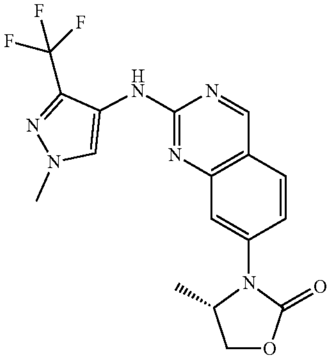 [SMILES: C[C@H]1COC(=O)N1c1ccc2cnc(Nc3cn(C)nc3C(F)(F)F)nc2c1] |
| Ex-7.8 | 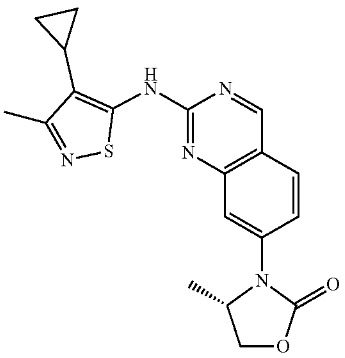 [SMILES: Cc1nsc(Nc2ncc3ccc(N4C(=O)OC[C@@H]4C)cc3n2)c1C1CC1] |

-continued
| Ex | Structure |
|---|---|
| Ex-7.9 | 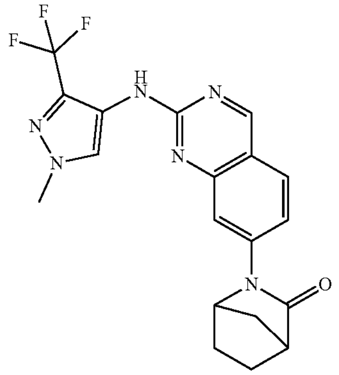 [SMILES: Cn1cc(Nc2ncc3ccc(N4C(=O)C5CCC4C5)cc3n2)c(C(F)(F)F)n1] |
| Ex-7.10 | 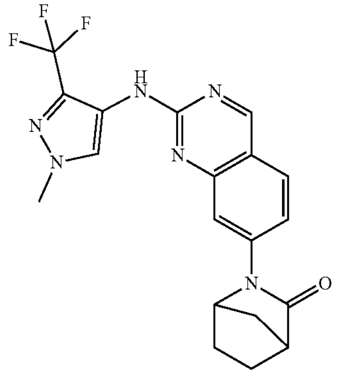 [SMILES: Cn1cc(Nc2ncc3ccc(N4C(=O)C5CCC4C5)cc3n2)c(C(F)(F)F)n1] |
| Ex-7.11 | 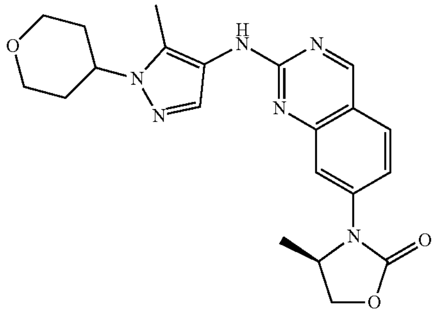 [SMILES: Cc1c(Nc2ncc3ccc(N4C(=O)OC[C@H]4C)cc3n2)cnn1C1CCOCC1] |
| Ex-7.12 | 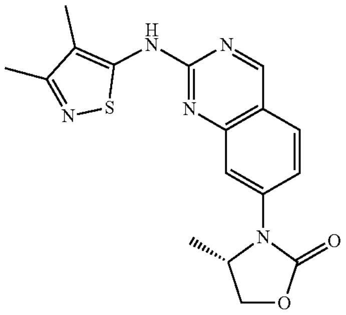 [SMILES: Cc1nsc(Nc2ncc3ccc(N4C(=O)OC[C@@H]4C)cc3n2)c1C] |

-continued
| Ex | Structure |
| --- | --- |
| Ex-7.13 | 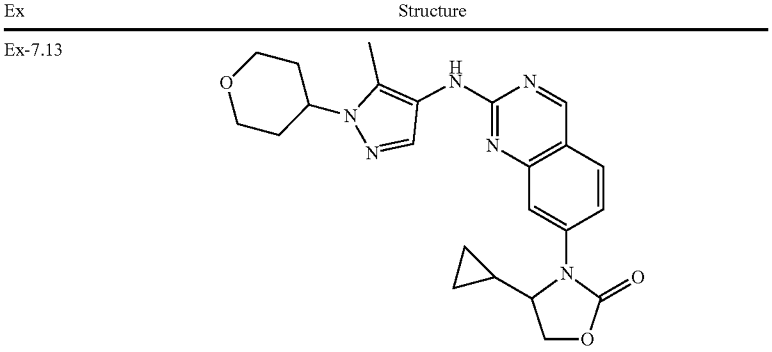 |
| Ex-7.14 | 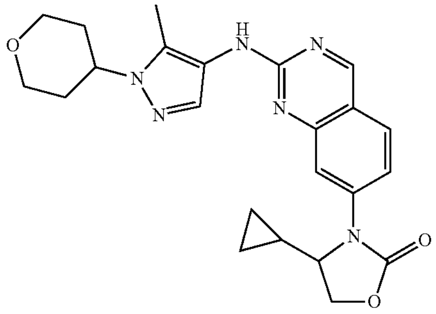 [SMILES: Cc1c(Nc2ncc3ccc(N4C(=O)OCC4C4CC4)cc3n2)cnn1C1CCOCC1] |
| Ex-7.15 | 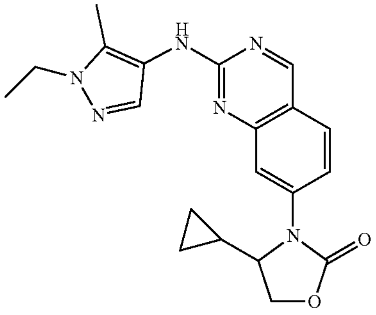 [SMILES: CCn1ncc(Nc2ncc3ccc(N4C(=O)OCC4C4CC4)cc3n2)c1C] |
| Ex-7.16 | 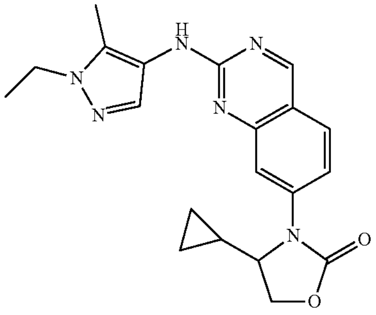 [SMILES: CCn1ncc(Nc2ncc3ccc(N4C(=O)OCC4C4CC4)cc3n2)c1C] |
| Ex-7.17 | 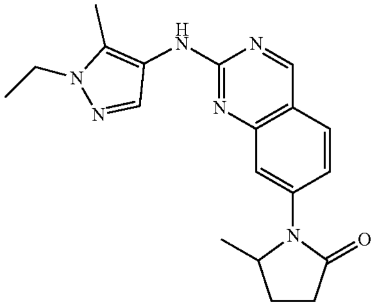 [SMILES: CCn1ncc(Nc2ncc3ccc(N4C(=O)CCC4C)cc3n2)c1C] |

-continued
| Ex | Structure |
| --- | --- |
| Ex-7.18 | 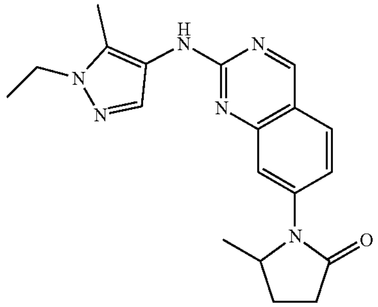 [SMILES: CCn1ncc(Nc2ncc3ccc(N4C(=O)CCC4C)cc3n2)c1C] |
| Ex-7.19 | 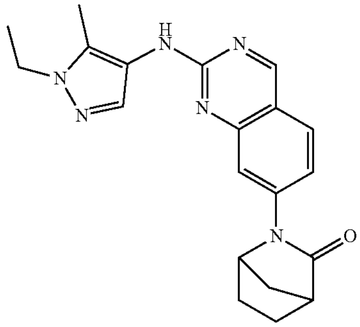 [SMILES: CCn1ncc(Nc2ncc3ccc(N4C(=O)C5CCC4C5)cc3n2)c1C] |
| Ex-7.20 | 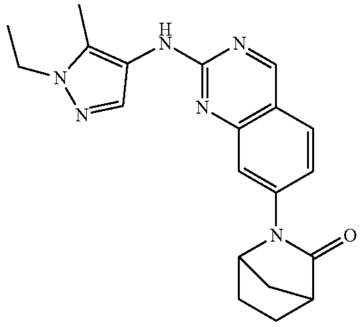 [SMILES: CCn1ncc(Nc2ncc3ccc(N4C(=O)C5CCC4C5)cc3n2)c1C] |
| Ex-7.21 | 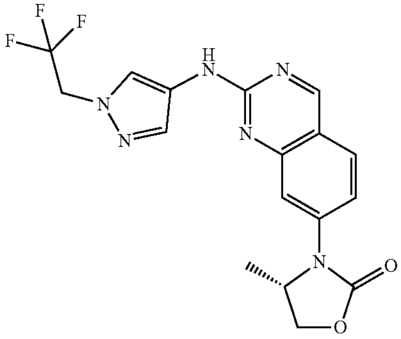 [SMILES: C[C@H]1COC(=O)N1c1ccc2cnc(Nc3cnn(CC(F)(F)F)c3)nc2c1] |
| Ex-8.1 | 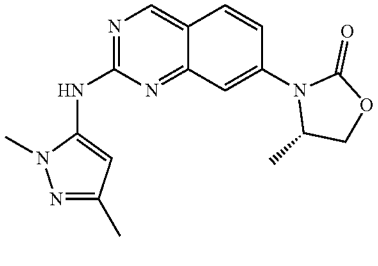 [SMILES: Cc1cc(Nc2ncc3ccc(N4C(=O)OC[C@@H]4C)cc3n2)n(C)n1] |

-continued
| Ex | Structure |
|---|---|
| Ex-8.2 | 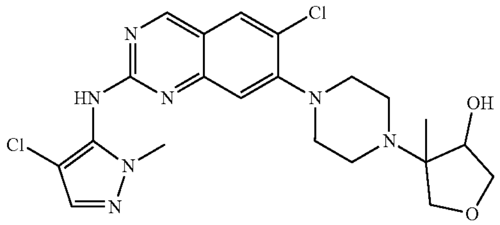 [SMILES: Cn1ncc(Cl)c1Nc1ncc2cc(Cl)c(N3CCN(C4(C)COCC4O)CC3)cc2n1] |
| Ex-8.3 | 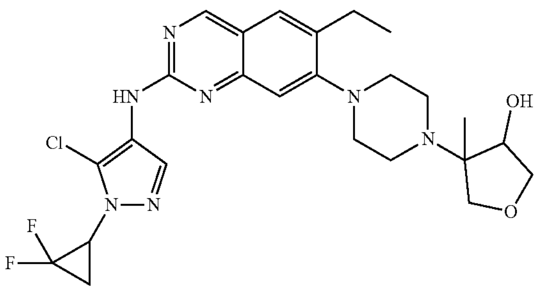 [SMILES: CCc1cc2cnc(Nc3cnn(C4CC4(F)F)c3Cl)nc2cc1N1CCN(C2(C)COCC2O)CC1] |
| Ex-8.4 | 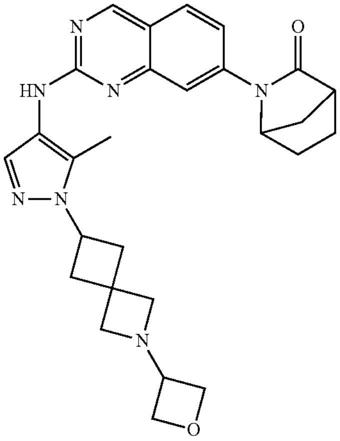 [SMILES: Cc1c(Nc2ncc3ccc(N4C(=O)C5CCC4C5)cc3n2)cnn1C1CC2(C1)CN(C1COC1)C2] |
| Ex-8.5 | 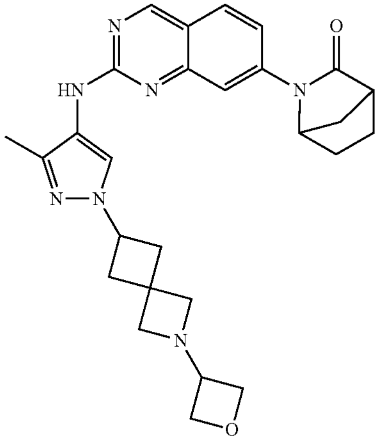 [SMILES: Cc1nn(C2CC3(C2)CN(C2COC2)C3)cc1Nc1ncc2ccc(N3C(=O)C4CCC3C4)cc2n1] |

-continued
| Ex | Structure |
|---|---|
| Ex-8.6 | 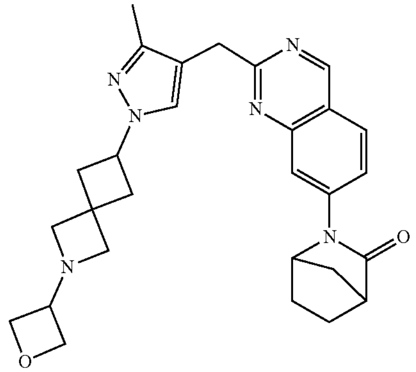 [SMILES: Cc1nn(C2CC3(C2)CN(C2COC2)C3)cc1Cc1ncc2ccc(N3C(=O)C4CCC3C4)cc2n1] |
| Ex-8.7 | 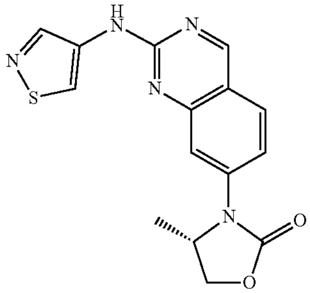 [SMILES: C[C@H]1COC(=O)N1c1ccc2cnc(Nc3cnsc3)nc2c1] |
| Ex-8.8 | 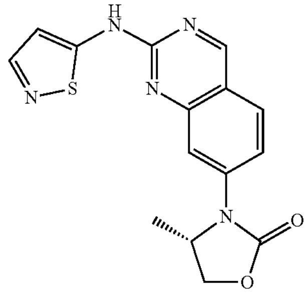 [SMILES: C[C@H]1COC(=O)N1c1ccc2cnc(Nc3ccns3)nc2c1] |
| Ex-8.9 | 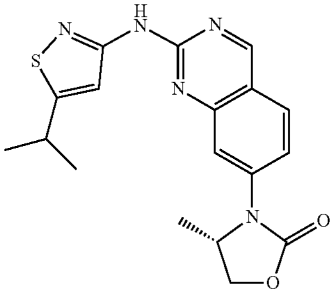 [SMILES: CC(C)c1cc(Nc2ncc3ccc(N4C(=O)OC[C@@H]4C)cc3n2)ns1] |
| Ex-8.10 | 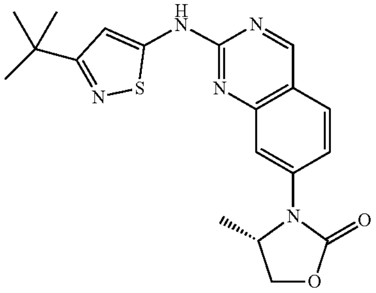 [SMILES: C[C@H]1COC(=O)N1c1ccc2cnc(Nc3cc(C(C)(C)C)ns3)nc2c1] |

-continued
| Ex | Structure |
|---|---|
| Ex-8.11 | 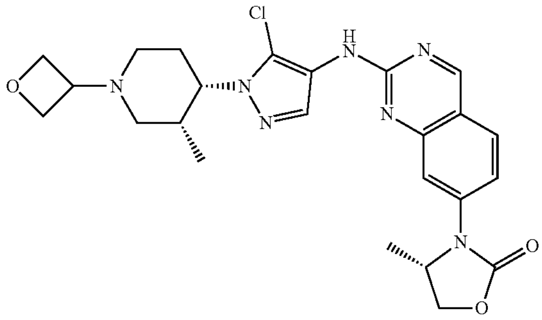 [SMILES: C[C@@H]1CN(C2COC2)CC[C@@H]1n1ncc(Nc2ncc3ccc(N4C(=O)OC[C@@H]4C)cc3n2)c1Cl] |
| Ex-8.12 | 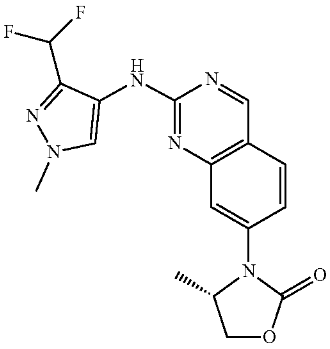 [SMILES: C[C@H]1COC(=O)N1c1ccc2cnc(Nc3cn(C)nc3C(F)F)nc2c1] |
| Ex-8.13 | 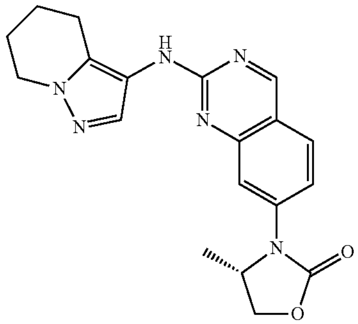 [SMILES: C[C@H]1COC(=O)N1c1ccc2cnc(Nc3cnn4c3CCCC4)nc2c1] |
| Ex-8.14 | 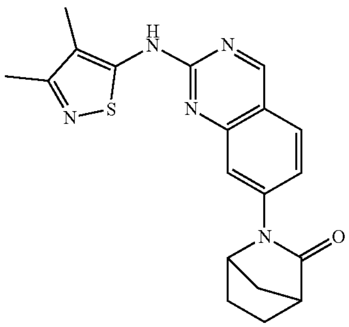 [SMILES: Cc1nsc(Nc2ncc3ccc(N4C(=O)C5CCC4C5)cc3n2)c1C] |

-continued
| Ex | Structure |
|---|---|
| Ex-8.15 | 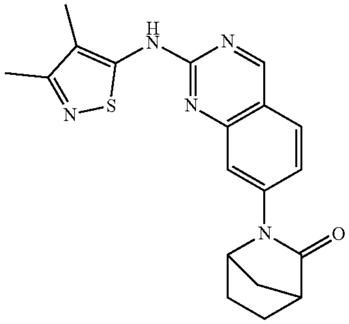 [SMILES: Cc1nsc(Nc2ncc3ccc(N4C(=O)C5CCC4C5)cc3n2)c1C] |
| Ex-8.16 | 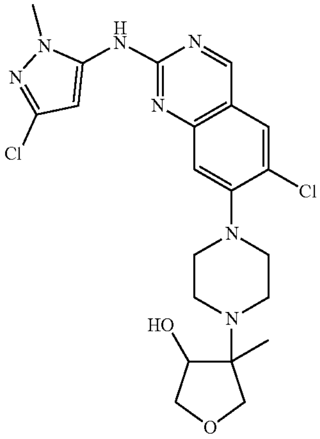 [SMILES: Cn1nc(Cl)cc1Nc1ncc2cc(Cl)c(N3CCN(C4(C)COCC4O)CC3)cc2n1] |
| Ex-9.1 | 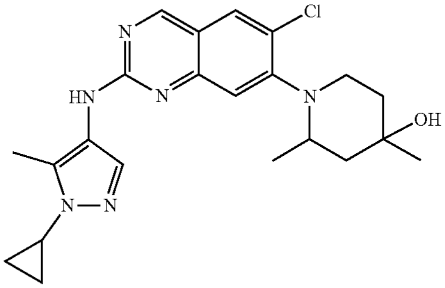 [SMILES: Cc1c(Nc2ncc3cc(Cl)c(N4CCC(C)(O)CC4C)cc3n2)cnn1C1CC1] + |
| Ex-9.2 | 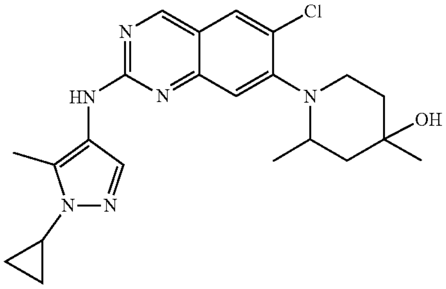 |

-continued
| Ex | Structure |
| --- | --- |
| Ex-10.1 | 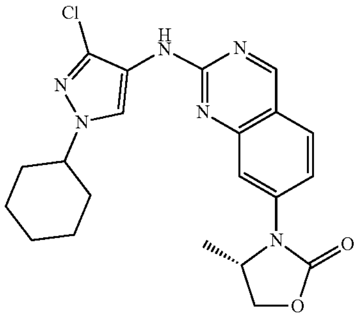 [SMILES: C[C@H]1COC(=O)N1c1ccc2cnc(Nc3cn(C4CCCCC4)nc3Cl)nc2c1] |
| Ex-11.1 | 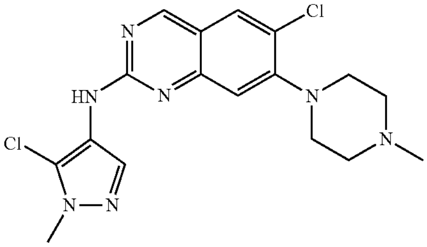 [SMILES: CN1CCN(c2cc3nc(Nc4cnn(C)c4Cl)ncc3cc2Cl)CC1] |
| Ex-12.1 | 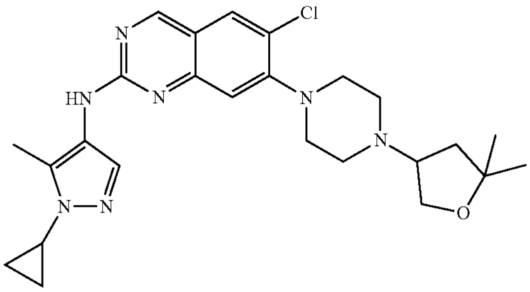 [SMILES: Cc1c(Nc2ncc3cc(Cl)c(N4CCN(C5COC(C)(C)C5)CC4)cc3n2)cnn1C1CC1] |
| Ex-12.2 | 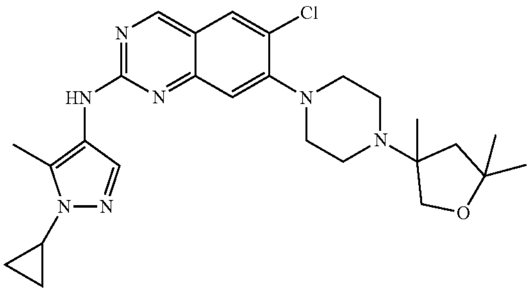 [SMILES: Cc1c(Nc2ncc3cc(Cl)c(N4CCN(C5(C)COC(C)(C)C5)CC4)cc3n2)cnn1C1CC1] |
| Ex-12.3 | 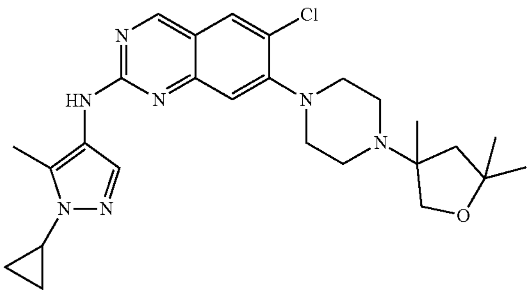 [SMILES: Cc1c(Nc2ncc3cc(Cl)c(N4CCN(C5(C)COC(C)(C)C5)CC4)cc3n2)cnn1C1CC1] |

-continued
| Ex | Structure |
|---|---|
| Ex-12.4 | 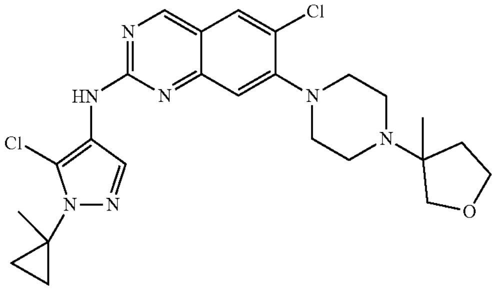 [SMILES: CC1(N2CCN(c3cc4nc(Nc5cnn(C6(C)CC6)c5Cl)ncc4cc3Cl)CC2)CCOC1] |
| Ex-12.5 | 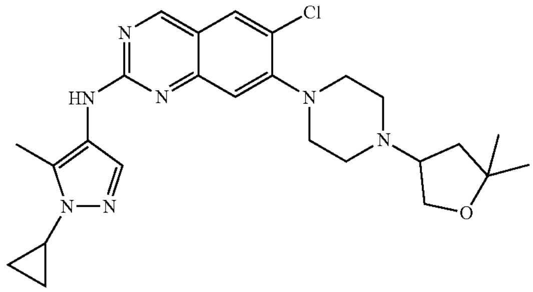 [SMILES: Cc1c(Nc2ncc3cc(Cl)c(N4CCN(C5COC(C)(C)C5)CC4)cc3n2)cnn1C1CC1] |
| Ex-12.6 | 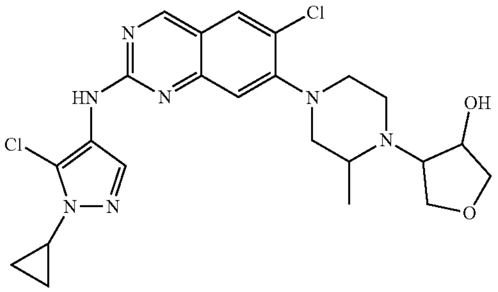 [SMILES: CC1CN(c2cc3nc(Nc4cnn(C5CC5)c4Cl)ncc3cc2Cl)CCN1C1COCC1O] |
| Ex-12.7 | 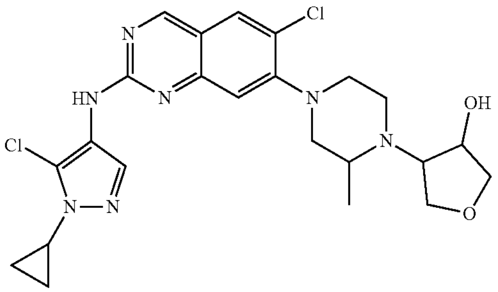 [SMILES: CC1CN(c2cc3nc(Nc4cnn(C5CC5)c4Cl)ncc3cc2Cl)CCN1C1COCC1O] |
| Ex-12.8 | 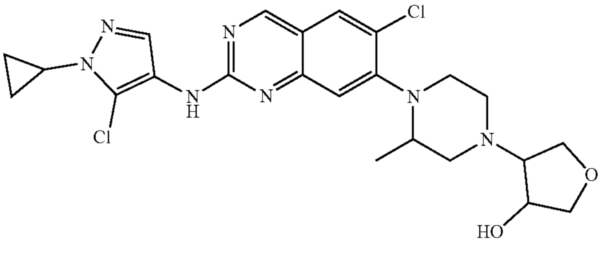 [SMILES: CC1CN(C2COCC2O)CCN1c1cc2nc(Nc3cnn(C4CC4)c3Cl)ncc2cc1Cl] |

-continued
| Ex | Structure |
| --- | --- |
| Ex-12.9 | 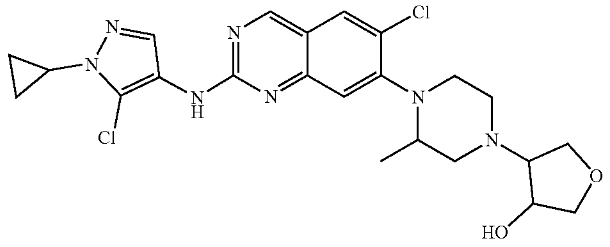 [SMILES: CC1CN(C2COCC2O)CCN1c1cc2nc(Nc3cnn(C4CC4)c3Cl)ncc2cc1Cl] |
| Ex-12.10 | 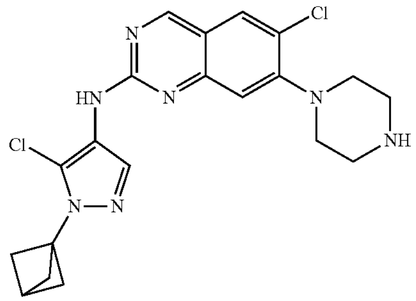 [SMILES: Clc1cc2cnc(Nc3cnn(C45CC(C4)C5)c3Cl)nc2cc1N1CCNCC1] |
| Ex-13.1 | 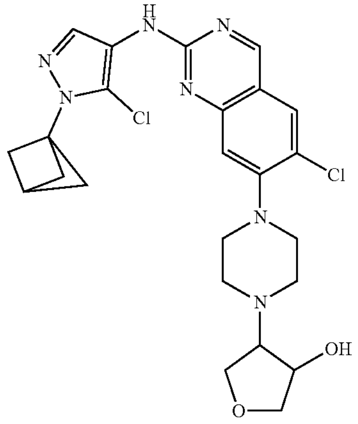 [SMILES: OC1COCC1N1CCN(c2cc3nc(Nc4cnn(C56CC(C5)C6)c4Cl)ncc3cc2Cl)CC1] |
| Ex-13.2 | 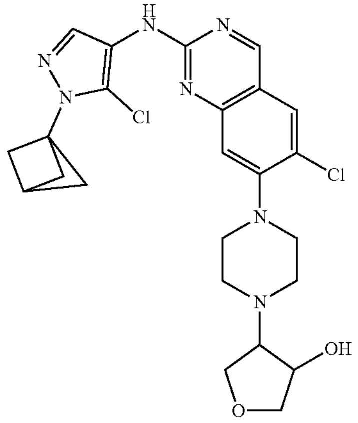 [SMILES: OC1COCC1N1CCN(c2cc3nc(Nc4cnn(C56CC(C5)C6)c4Cl)ncc3cc2Cl)CC1] |

-continued
| Ex | Structure |
| --- | --- |
| Ex-13.3 | 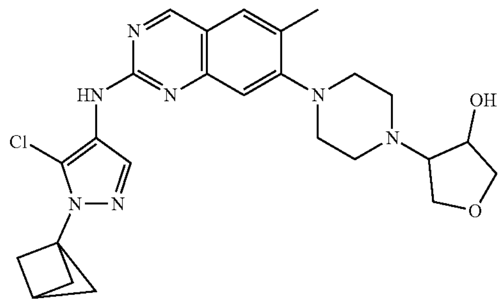 [SMILES: Cc1cc2cnc(Nc3cnn(C45CC(C4)C5)c3Cl)nc2cc1N1CCN(C2COCC2O)CC1] |
| Ex-13.4 | 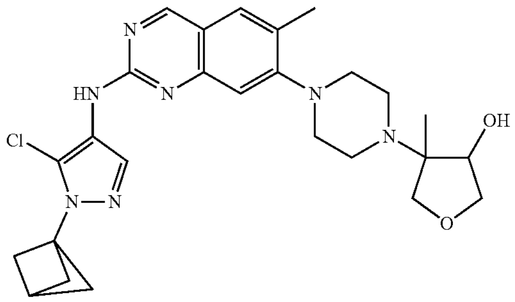 [SMILES: Cc1cc2cnc(Nc3cnn(C45CC(C4)C5)c3Cl)nc2cc1N1CCN(C2(C)COCC2O)CC1] |
| Ex-13.5 | 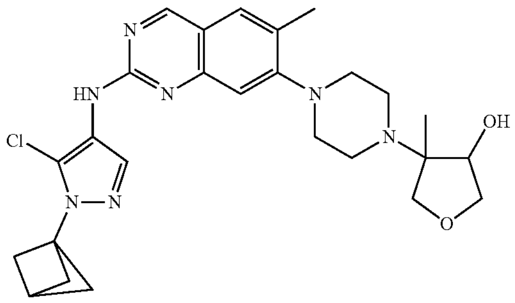 [SMILES: Cc1cc2cnc(Nc3cnn(C45CC(C4)C5)c3Cl)nc2cc1N1CCN(C2(C)COCC2O)CC1] |
| Ex-13.6 | 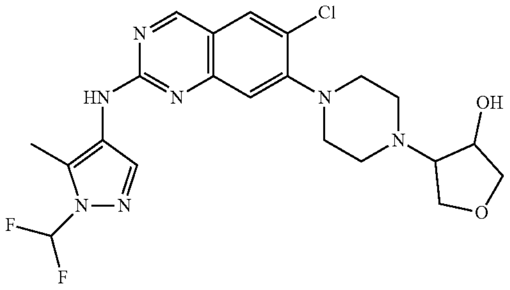 [SMILES: Cc1c(Nc2ncc3cc(Cl)c(N4CCN(C5COCC5O)CC4)cc3n2)cnn1C(F)F] |
| Ex-13.7 | 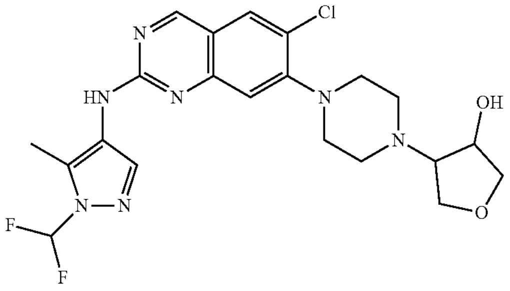 [SMILES: Cc1c(Nc2ncc3cc(Cl)c(N4CCN(C5COCC5O)CC4)cc3n2)cnn1C(F)F] |

-continued
| Ex | Structure |
|---|---|
| Ex-13.8 | 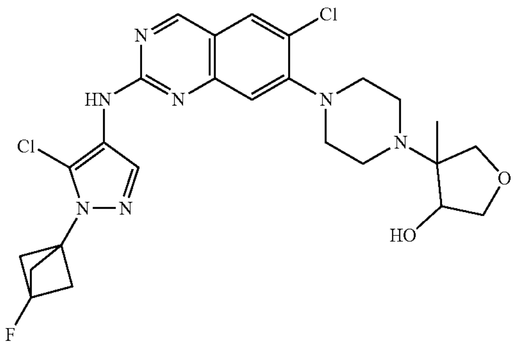 [SMILES: CC1(N2CCN(c3cc4nc(Nc5cnn(C67CC(F)(C6)C7)c5Cl)ncc4cc3Cl)CC2)COCC1O] |
| Ex-13.9 | 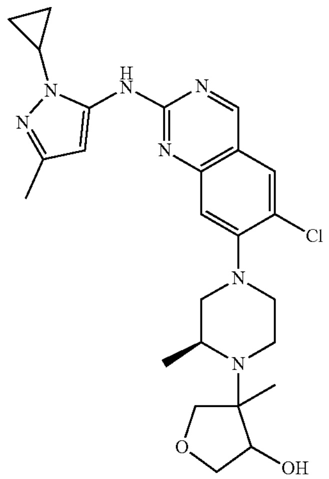 [SMILES: Cc1cc(Nc2ncc3cc(Cl)c(N4CCN(C5(C)COCC5O)[C@@H](C)C4)cc3n2)n(C2CC2)n1] |
| Ex-14.1 | 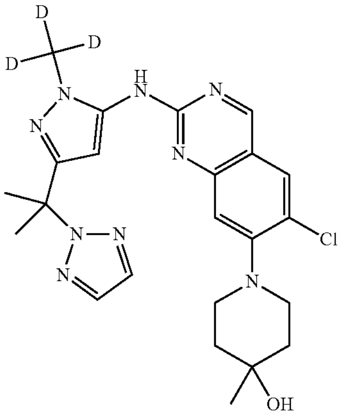 [SMILES: [2H]C([2H])([2H])n1nc(C(C)(C)n2nccn2)cc1Nc1ncc2cc(Cl)c(N3CCC(C)(O)CC3)cc2n1] |
| Ex-15.1 | 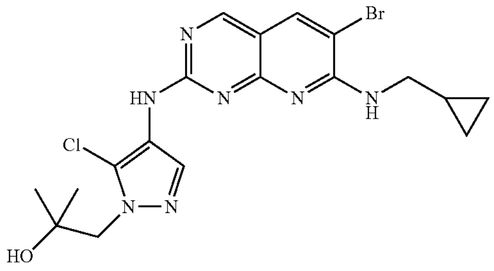 [SMILES: CC(C)(O)Cn1ncc(Nc2ncc3cc(Br)c(NCC4CC4)nc3n2)c1Cl] |

-continued
| Ex | Structure |
|---|---|
| Ex-15.2 | 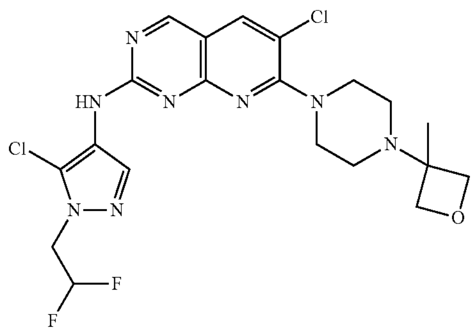 [SMILES: CC1(N2CCN(c3nc4nc(Nc5cnn(CC(F)F)c5Cl)ncc4cc3Cl)CC2)COC1] |
| Ex-15.3 | 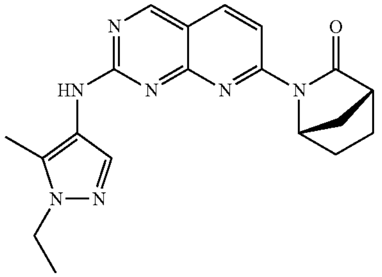 [SMILES: CCn1ncc(Nc2ncc3ccc(N4C(=O)[C@@H]5CC[C@H]4C5)nc3n2)c1C] |
| Ex-15.4 | 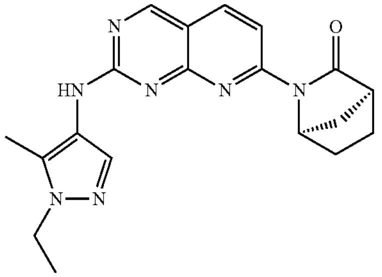 [SMILES: CCn1ncc(Nc2ncc3ccc(N4C(=O)[C@H]5CC[C@@H]4C5)nc3n2)c1C] |
| Ex-15.5 | 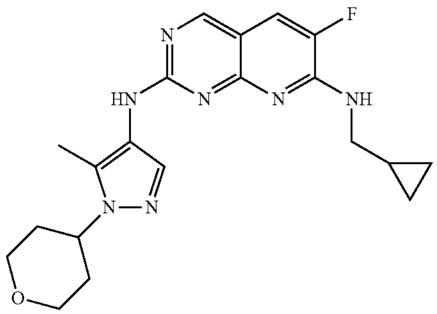 [SMILES: Cc1c(Nc2ncc3cc(F)c(NCC4CC4)nc3n2)cnn1C1CCOCC1] |
| Ex-16.1 | 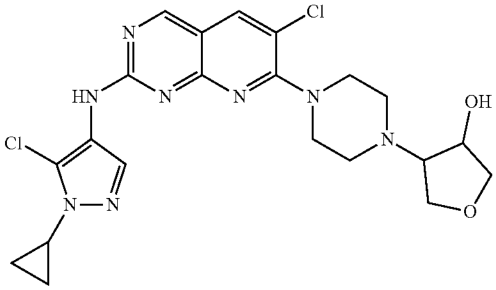 [SMILES: OC1COCC1N1CCN(c2nc3nc(Nc4cnn(C5CC5)c4Cl)ncc3cc2Cl)CC1] |

-continued

| Ex | Structure |
| --- | --- |
| Ex-16.2 | 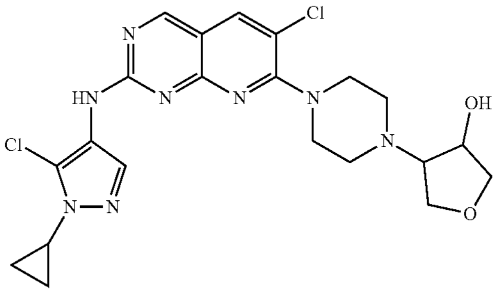 [SMILES: OC1COCC1N1CCN(c2nc3nc(Nc4cnn(C5CC5)c4Cl)ncc3cc2Cl)CC1] |
| Ex-16.3 | 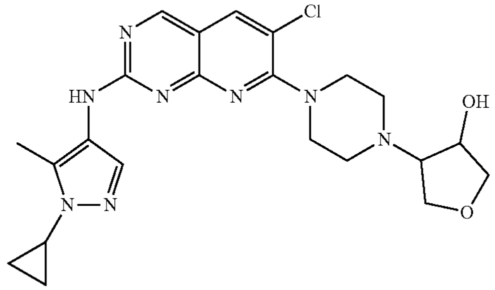 [SMILES: Cc1c(Nc2ncc3cc(Cl)c(N4CCN(C5COCC5O)CC4)nc3n2)cnn1C1CC1] |
| Ex-16.4 | 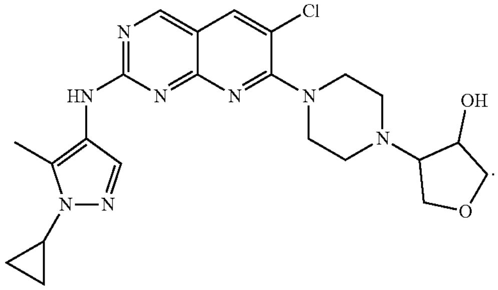 [SMILES: Cc1c(Nc2ncc3cc(Cl)c(N4CCN(C5COCC5O)CC4)nc3n2)cnn1C1CC1 ; "."] |

18. A pharmaceutical composition comprising a compound of claim 1, and a pharmaceutically acceptable carrier.

19. A method of treating Parkinson's Disease comprising administering an effective amount of a compound of claim 1, or a pharmaceutically acceptable salt thereof, to a person in need thereof.

20. A method for the treatment or prophylaxis of an indication in which LRRK2 kinase is involved comprising administering to a subject in need thereof an effective amount of a compound according to claim 1, or a pharmaceutically acceptable salt thereof, said indication selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17, neuroinflammation associated with of microglial inflammatory responses associated with multiple sclerosis, HIV-induced dementia, ALS, ischemic stroke, traumatic brain injury and spinal cord injury, lymphomas, leukemias, multiple sclerosis, rheumatoid arthritis, systemic lupus erythematosus, autoimmune hemolytic anemia, pure red cell aplasia, idiopathic thrombocytopenia pupura (ITP), Evans Syndrome, vasculitis, bullous skin disorder, type I diabetes mellitus, Sjorgen's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

* * * * *